United States Patent
Ruminski et al.

(10) Patent No.: US 6,831,199 B1
(45) Date of Patent: *Dec. 14, 2004

(54) PYRIMIDINE COMPOUNDS AND DERIVATIVES THEREOF

(75) Inventors: Peter Gerrard Ruminski, Ballwin, MO (US); Michael Clare, Skokie, IL (US); Paul Waddell Collins, Deerfield, IL (US); Bipinchandra Nanubhai Desai, Vernon Hills, IL (US); Richard John Lindmark, St. Louis, MO (US); Joseph Gerace Rico, Ballwin, MO (US); Thomas Edward Rogers, Ballwin, MO (US); Mark Andrew Russell, Gurnee, IL (US)

(73) Assignee: G. D. Searle & Co., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/215,229

(22) Filed: Dec. 18, 1998

Related U.S. Application Data

(62) Division of application No. 08/713,555, filed on Aug. 27, 1996, now Pat. No. 6,028,223.
(60) Provisional application No. 60/003,277, filed on Aug. 30, 1995.

(51) Int. Cl.[7] ............................................. C07C 211/00
(52) U.S. Cl. ....................................... 564/322; 564/322
(58) Field of Search ................................. 544/322, 324; 514/256

(56) References Cited

U.S. PATENT DOCUMENTS

| | | | |
|---|---|---|---|
| 4,677,111 A | 6/1987 | Haga et al. | 514/274 |
| 5,256,812 A | 10/1993 | Alig et al. | 560/35 |
| 5,273,995 A | 12/1993 | Alig et al. | 514/315 |
| 5,444,061 A * | 8/1995 | Bisset et al. | 514/259 |
| 5,518,735 A | 5/1996 | Sturzebecher et al. | 424/449 |
| 5,561,133 A * | 10/1996 | Bisset et al. | 514/259 |
| 5,681,820 A * | 10/1997 | Ruminski | 514/18 |
| 5,753,230 A | 5/1998 | Brooks et al. | 424/158.1 |
| 5,766,591 A | 6/1998 | Brooks et al. | 424/184.1 |
| 5,773,646 A * | 6/1998 | Chandrakumar et al. | 562/439 |
| 5,831,094 A * | 11/1998 | Van Dorsselaer et al. | 544/578 |
| 5,952,381 A * | 9/1999 | Chen et al. | 514/565 |
| 6,013,651 A * | 1/2000 | Rogers et al. | 514/269 |
| 6,100,423 A * | 8/2000 | Collins et al. | 560/42 |
| 6,251,944 B1 * | 6/2001 | Chen et al. | 514/565 |
| 6,372,719 B1 * | 4/2002 | Cunningham et al. | 514/34 |

FOREIGN PATENT DOCUMENTS

| | | | |
|---|---|---|---|
| AU | AU-A-57984/94 | 10/1994 | C07K/7/08 |
| AU | AU-A-79090/94 | 6/1995 | C07D/309/12 |
| CA | 2059857 | 7/1992 | C07D/211/34 |
| CA | 2134418 | 4/1995 | C07K/7/10 |
| DE | 43 38 944 A1 | 5/1995 | C07K/5/06 |
| EP | 0343893 A1 | 11/1989 | C07D/277/82 |
| EP | 0343894 A1 | 11/1989 | C07D/235/30 |
| EP | 0478328 A1 | 4/1992 | C07C/271/22 |
| EP | 0478363 A2 | 4/1992 | C07D/211/22 |
| EP | 0 643072 A1 | 3/1995 | C07K/5/08 |
| WO | WO 93/08823 | 5/1993 | A61K/37/02 |
| WO | WO94/18981 | 9/1994 | A61K/31/55 |
| WO | WO 95/14714 | 6/1995 | C07K/14/75 |
| WO | WO 95/28426 | 10/1995 | C07K/14/75 |
| WO | WO 95/32710 | 12/1995 | A61K/31/18 |
| WO | WO 96/00574 | 1/1996 | A61K/31/55 |
| WO | WO 96/00730 | 1/1996 | C07D/519/00 |
| WO | WO 96/26190 | 8/1996 | C07D/243/24 |
| ZA | 94/0435 | 1/1994 | |
| ZA | 94/2124 | 3/1994 | |
| ZA | 94/9017 | 11/1994 | |

OTHER PUBLICATIONS

Jackman A.L. et al. (CA 122:418, abstract of Adv. Exp. Med. Biol. (1993), 338 (Chem. and Biol. of Pteridines and Folates), 593–6), 1993.*
Bavestsias, V. et al. (CA 121:271415, abstract of Adv. Exp. Med. Biol. (1993), 338 (Chem. and Biol. of Pteridines and Folates)593–596, 1993.*
Derwent Abstract #00305 K/01.
Derwent Abstract #57918 B/1.
Derwent Abstract #77105 E/37.
Derwent Abstract #87–009150/02.
Derwent Abstract #87–065042/10.

(List continued on next page.)

*Primary Examiner*—Sabiha Qazi
(74) *Attorney, Agent, or Firm*—Rachel A. Polster

(57) ABSTRACT

The present invention relates to a class of compounds represented by the Formula I

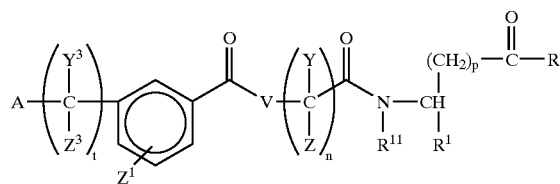

or a pharmaceutically acceptable salt thereof, wherein A is

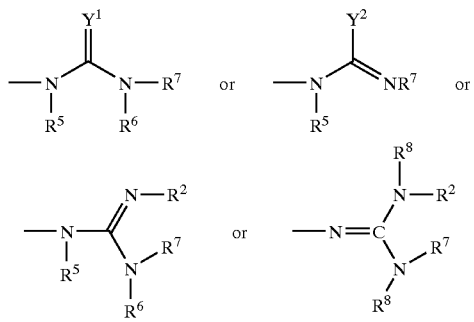

pharmaceutical compositions thereof and methods of using such compounds and compositions as $\alpha_v\beta_3$ antagonists.

20 Claims, No Drawings

OTHER PUBLICATIONS

Derwent Abstract #89–055466/08.
Derwent Abstract #89–349943/48.
Derwent Abstract #92–398070/48.
Derwent Abstract #93–060253/08.
Derwent Abstract #93–08363/11.
Derwent Abstract #93–127579/16.

Adamis, Anthony P., "Increased Vascular Endothelial Growth Factor Levels in the Vitreous of Eyes With Proliferative Diabetic Retinopathy", *American Journal of Opthamology*, vol. 118, pp. 445–450 (Oct. 1994).

Brooks, Peter C. et al., "Requirement for Vascular Integrin $\alpha_{v-3}$ for Angiogenesis", *Science*, vol. 264, pp. 569–571 (Apr. 22, 1994).

Brooks, Peter C. et al., "Integrin $\alpha_v\beta_3$ Antagonists Promote Tumor Regression by Inducing Apoptosis of Angiogenic Blood Vessels", *Cell*, vol. 79, pp. 1157–1164 (Dec. 30, 1994).

Choi, Eric T., et al., "Inhibition of Neointimal Hyperplasia by Blocking $\alpha_v\beta_3$ Integrin with a Small Peptide Antagonist GpenGRDSPCA", *Journal of Vascular Surgery*, vol. 19 (1), pp. 125–133.

Clyman, Ronald I. et al., "$\beta_1$ and $\beta_3$ Integrins Have Different Roles in the Adhesion and Migration of Vascular Smooth Muscle Cells on Extracellular Matrix", *Experimental Cell Research*, vol. 200, pp. 272–284 (1992).

Liaw, Lucy et al., "The Adhesive and Migratory Effects of Osteopontin Are Mediated via Distinct Cell Surface Integrins: Role of $\alpha_v\beta_3$ in Smooth Muscle Migration to Osteopontin in Vitro", *Journal of Clinical Investigation*, vol. 95, pp. 713–724 (Feb. 1995).

Peacock, Derek J. et al., "Anglogenesis Inhibition Suppresses Collagen Arthritis", *Journal of Experimental Medicine*, vol. 175, pp. 1135–1138 (Apr. 1992).

Seftor, Richard E. B. et al., "Role of the $\alpha_v\beta_3$ Integrin in Human Melanoma Cell Invasion", *Proceedings of the National Academy of Sciences U.S.A.*, vol. 89, pp. 1557–1561 (Mar. 1992).

Schnur, Rodney C. et al., "N–(5–Fluorobenzothiazaol–2–yl)–2–guanidinothiazole–4–carboxamide. A Novel, Systemically Active Antitumor Agent Effective Against 3LL Lewis Lung Carcinoma", *Journal of Medicinal Chemistry*, vol. 34 (3), pp. 914–918 (1991).

Schnur, Rodney C. et al., "Quantitative Structure–Activity Relationships of Antitumor Guanidinothiazolecarboxamides with Survival Enhancement for Therapy in the 3LL Lewis Lung Carcinoma Model", *Journal of Medicinal Chemistry*, vol. 34 (7), pp. 1975–1982 (1991).

Smith, Jeffery W. et al., "Interactions of Integrins $\alpha_v\beta_3$ and GlycoProtein IIb–IIa with Fibrinogen", *Journal of Biological Chemistry*, vol. 265 (21), pp. 12267–12271 (Jul. 25, 1990).

White, Judith M., "Integrins as Virus Receptors", *Current Biology*, vol. 3 (9), pp. 596–599 9 (1993).

Yue, Tian–Li, "Osteopontin–Stimulated Vascular Smooth Muscle Cell Migration Is Mediated by $\beta_3$ Integrin", *Experimental Cell Research*, vol. 214, 459–464 (1994).

\* cited by examiner

PYRIMIDINE COMPOUNDS AND DERIVATIVES THEREOF

This application is a divisional of U.S. Ser. No. 08/713,555, filed Aug. 27, 1996, now allowed as U.S. Pat. No. 6,028,223, which claims priority under 35 USC §119(e) of U.S. provisional application Serial No. 60/003,277 filed Aug. 30, 1995.

FIELD OF THE INVENTION

The present invention relates to pharmaceutical agents (compounds) which are useful as $\alpha_v\beta_3$ integrin antagonists and as such are useful in pharmaceutical compositions and in methods for treating conditions mediated by $\alpha_v\beta_3$ by inhibiting or antagonizing $\alpha_v\beta_3$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different a subunits have been identified and six different $\beta$ subunits have been identified. The various a subunits can combine with various $\beta$ subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis and smooth muscle cell migration (e.g. restenosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy (Adonis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic targets for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis. The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The present invention relates to a class of compounds represented by the Formula I

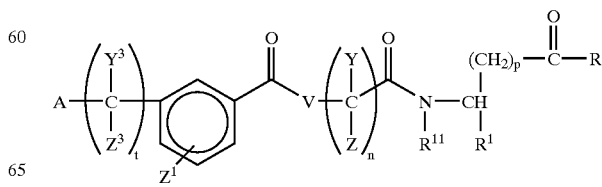

or a pharmaceutically acceptable salt thereof, wherein
A is

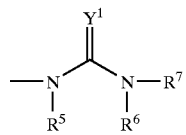

wherein $Y^1$ is selected from the group consisting of $N-R^2$, O, and S;

$R^2$ is selected from the group consisting of H; alkyl; aryl; hydroxy; alkoxy; cyano; nitro; amino; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl;

or $R^2$ taken together with $R^7$ forms a 5 membered heteroaromatic ring optionally substituted with one or more substituent selected from lower alkyl, phenyl and hydroxy;

or $R^2$ taken together with $R^7$ forms a 5 membered heteroaromatic ring fused with a phenyl group;

$R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; $-SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

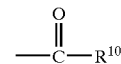

wherein $R^{10}$ is defined above;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl;

or

A is

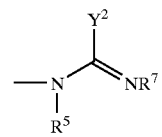

wherein $Y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; $-S-R^9$ and $-O-R^9$ wherein $R^9$ is selected from the group consisting of H; alkyl; aralkyl; aryl; alkenyl; and alkynyl; or $R^9$ taken together with $R^7$ forms a 4–12 membered mononitrogen and monosulfur or monooxygen containing heterocyclic ring optionally substituted with lower alkyl, hydroxy, keto, phenyl, carboxyl or carboxyl ester, and fused phenyl; or $R^9$ taken together with $R^7$ is thiazole; oxazole; benzoxazole; or benzothiazole; and $R^5$ and $R^7$ are as defined above;

or $Y^2$ (when $Y^2$ is carbon) taken together with $R^7$ forms a 4–12 membered mononitrogen or dinitrogen containing ring optionally substituted with alkyl, aryl, keto or hydroxy;

or A is

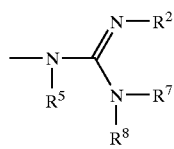

where $R^2$ and $R^7$ taken together form a 5–8 membered dinitrogen containing heterocycle optionally substituted with one or more substituent selected from the group consisting of lower alkyl, hydroxy, keto, phenyl, or carboxyl derivatives; and $R^8$ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; and $R^5$ is defined as above or A is

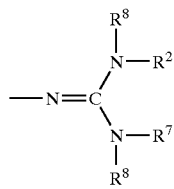

where $R^2$ and $R^7$ taken together form a 5–8 membered dinitrogen containing heterocycle optionally substituted with hydroxy, keto, phenyl, or alkyl; and $R^8$ are both selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl and acyloxymethoxycarbonyl;

$Z^1$ is one or more substituent selected from the group consisting of H; alkyl; hydroxy; alkoxy; aryloxy; halogen; haloalkyl; haloalkoxy; nitro; amino; alkylamino; acylamino; dialkylamino; cyano; alkylthio; alkylsulfonyl; carboxyl derivatives; trihaloacetamide; acetamide; aryl; fused aryl; cycloalkyl; thio; monocyclic heterocycles; fused monocyclic heterocycles; and A, wherein A is defined above;

V is selected from the group consisting of —N—($R^6$)— wherein $R^6$ is selected from the group consisting of H; lower alkyl; cycloalkyl; aralkyl; aryl; and monocyclic heterocycles; or $R^6$ taken together with Y, forms a 4–12 membered mononitrogen containing ring;

Y, $Y^3$, Z and $Z^3$ are independently selected from the group consisting of hydrogen; alkyl; aryl; and cycloalkyl; or Y and Z taken together form a cycloalkyl; or $Y^3$ and $Z^3$ taken together form a cycloalkyl;

n is an integer 1, 2, or 3;

t is an integer 0, 1, or 2;

p is an integer 0, 1, 2, or 3;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; sugars; steroids; polyalkylethers; alkylamido; alkyl N,N-dialkylamido; pivaloyloxymethyl; and in the case of the free acid, all pharmaceutically acceptable salts thereof;

$R^1$ is selected from the group consisting of hydrogen; alkyl; alkenyl; alkynyl; aryl; carboxyl derivatives; haloalkyl; cycloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;

alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

alkylcarbonyl, haloalkylcarbonyl, and arylcarbonyl;

aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, carboxyl derivatives, carboxyalkoxy; amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

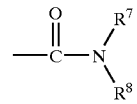

wherein $R^7$ and $R^8$ are as defined above and provided that taken together with the nitrogen, $R^7$ and $R^8$ comprise an amino acid;

and $R^{11}$ is selected from the group consisting of H, alkyl, aralkyl, alkenyl, alkynyl, haloalkyl or haloalkynyl or $R^{11}$ taken together with Y forms a 4–12 membered mononitrogen containing ring.

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formula I, described above.

A preferred embodiment of the present invention is a compound of the Formula II

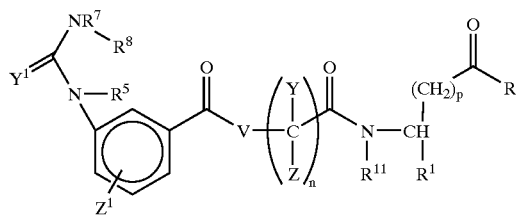

wherein $R^5$, $R^7$ and $R^8$ are independently selected from H, alkyl, aryl, carboxyalkyl, substituted aryl, substituted arylsulfonyl, and arylalkyl or $NR^7$ and $R^8$ taken together form a 4–12 membered mononitrogen containing ring optionally substituted and the other variables are as described in Formula I.

Another preferred embodiment of the present invention is a compound of the Formula III

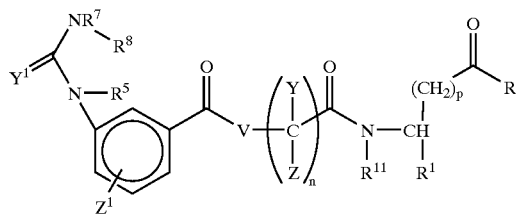

wherein $Y^1$ is $—NR^2$ and $R^2$ taken together with $R^7$ forms an optionally substituted 4–12 membered ring and the other variables are as defined above in Formula I.

Another preferred embodiment of the present invention is a compound of the Formula IV

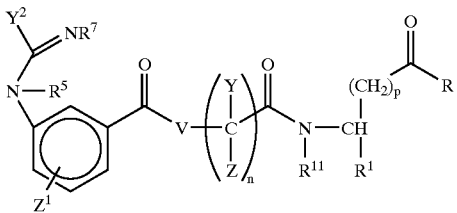

wherein $Y^2$ taken together with $R^7$ forms a 4–12 membered ring and the other variables are as defined above in Formula I.

Another preferred embodiment of the present invention is a compound of the Formula V

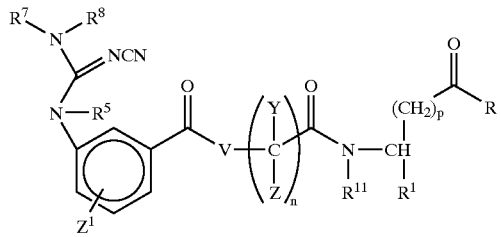

wherein the variables are as defined above in Formula I.

The invention further relates to pharmaceutical compositions containing therapeutically effective amounts of the compounds of Formulas I–V.

The invention also relates to a method of selectively inhibiting or antagonizing the $\alpha_v\beta_3$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, smooth muscle cell migration and restenosis by administering a therapeutically effective amount of a compound of the Formula I–V to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula ⊢—CN.

The terms "hydroxy" and "hydroxyl" as used herein are synonymous and are represented by a radical of the formula ⊢—OH.

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula —OR, wherein $R^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula $|—R^{22}—R^{21}$ wherein $R^{21}$ is aryl as defined above and $R^{22}$ is an alkylene as defined above. Examples of aralkyl groups include benzyl, pyridylmethyl, naphthylpropyl, phenethyl and the like.

As used herein the term "nitro" is represented by a radical of the formula $|—NO_2$.

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "carboxyl ester" refers to a radical of the formula —COOR$^{23}$ wherein $R^{23}$ is selected from the group consisting of H, alkyl, aralkyl or aryl as defined above.

As used herein the term "carboxyl derivative" refers to a radical of the formula

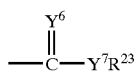

wherein $Y^6$ and $Y^7$ are independently selected from the group consisting of O, N or S and $R^{23}$ is selected from the group consisting of H, alkyl, aralkyl or aryl as defined above.

As used herein the term "amino" is represented by a radical of the formula —NH$_2$.

As used herein the term "alkylsulfonyl" or "alkylsulfone" refers to a radical of the formula

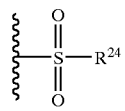

wherein $R^{24}$ is alkyl as defined above.

As used herein the term "alkylthio" refers to a radical of the formula —SR$^{24}$ wherein $R^{24}$ is alkyl as defined above.

As used herein the term "sulfonic acid" refers to a radical of the formula

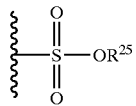

wherein $R^{25}$ is H, alkyl or aryl as defined above.

As used herein the term "sulfonamide" refers to a radical of the formula

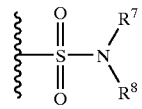

wherein $R^7$ and $R^8$ are as defined above.

As used herein the term "fused aryl" refers to an aromatic ring such as the aryl groups defined above fused to one or more phenyl rings. Embraced by the term "fused aryl" is the radical naphthyl.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

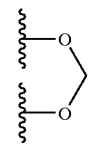

and the term "ethylenedioxy" refers to the radical

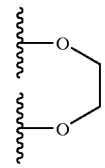

As used herein the term "4–12 membered dinitrogen containing heterocycle refers to a radical of the formula

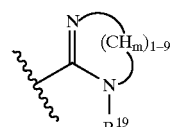

wherein a is 1 or 2 and $R^{19}$ is H, alkyl, aryl, or aralkyl and more preferably refers to 4–9 membered ring and includes rings such as imidazoline.

As used herein the term "5-membered optionally substituted heteroaromatic ring" includes for example a radical of the formula

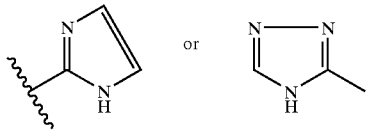

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

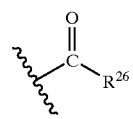

wherein $R^{26}$ is alkyl, alkenyl, alkynyl, aryl or aralkyl and optionally substituted thereon as defined above. Encompassed by such radical are the groups acetyl, benzoyl and the like.

As used herein the term "thio" refers to a radical of the formula

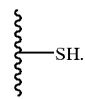

As used herein the term "sulfonyl" refers to a radical of the formula

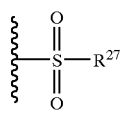

wherein R is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

wherein $R^{30}$ is alkyl, aralkyl or aryl as defined above.

As used herein the term "amido" refers to a radical of the formula

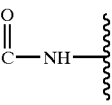

As used herein the term "alkylamino" refers to a radical of the formula —$NHR^{32}$ wherein $R^{32}$ is alkyl as defined above.

As used herein the term "dialkylamino" refers to a radical of the formula —$NR^{33}R^{34}$ wherein $R^{33}$ and $R^{34}$ are the same or different alkyl groups as defined above.

As used herein the term "trifluoromethyl" refers to a radical of the formula

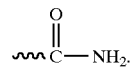

As used herein the term "trifluoroalkoxy" refers to a radical of the formula

wherein $R^{35}$ is a bond or an alkylene as defined above.

As used herein the term "alkylaminosulfonyl" refers to a radical of the formula

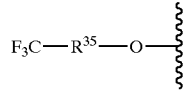

wherein $R^{36}$ is alkyl as defined above.

As used herein the term "alkylsulfonylamino" refers to a radical of the formula

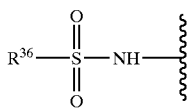

wherein $R^{36}$ is alkyl as defined above.

As used herein the term "trifluoromethylthio" refers to a radical of the formula

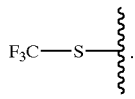

As used herein the term "trifluoromethylsulfonyl" refers to a radical of the formula

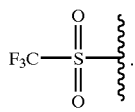

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

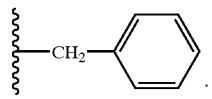

As used herein the term "phenethyl" refers to the radical

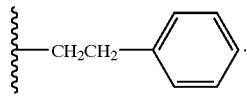

As used herein the term "4–12 membered mono-nitrogen containing monosulfur or monooxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

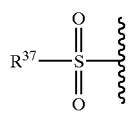

wherein $R^{37}$ is aryl as defined above.

As used herein the terms "alkylsulfoxide" or "arylsulfoxide" refer to radicals of the formula

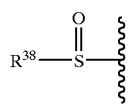

wherein $R^{38}$ is, respectively, alkyl or aryl as defined above.

As used herein the term "phosphonic acid derivative" refers to a radical of the formula

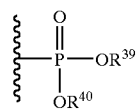

wherein $R^{39}$ and $R^{40}$ are the same or different H, alkyl, aryl or aralkyl.

As used herein the term "phosphinic acid derivatives" refers to a radical of the formula

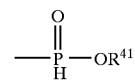

wherein $R^{41}$ is H, alkyl, aryl or aralkyl as defined above.

As used herein the term "arylthio" refers to a radical of the formula

wherein $R^{42}$ is aryl as defined above.

As used herein the term "monocyclic heterocycle thio" refers to a radical of the formula

wherein $R^{43}$ is a monocyclic heterocycle radical as defined above.

As used herein the terms "monocyclic heterocycle sulfoxide" and "monocyclic heterocycle sulfone" refer, respectively, to radicals of the formula

wherein $R^{43}$ is a monocyclic heterocycle radical as defined above.

As used herein the term "alkylcarbonyl" refers to a radical of the formula

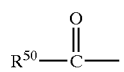

wherein $R^{50}$ is alkyl as defined above.

As used herein the term "arylcarbonyl" refers to a radical of the formula

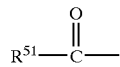

wherein $R^{51}$ is aryl as defined above.

As used herein the term "alkoxycarbonyl" refers to a radical of the formula

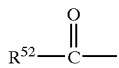

wherein $R^{52}$ is alkoxy as defined above.

As used herein the term "aryloxycarbonyl" refers to a radical of the formula

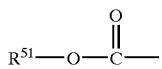

wherein $R^{51}$ is aryl as defined above.

As used herein the term "haloalkylcarbonyl" refers to a radical of the formula

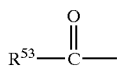

wherein $R^{53}$ is haloalkyl as defined above.

As used herein the term "haloalkoxycarbonyl" refers to a radical of the formula

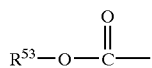

wherein $R^{53}$ is haloalkyl as defined above.

As used herein the term "alkylthiocarbonyl" refers to a radical of the formula

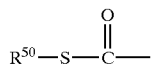

wherein $R^{50}$ is alkyl as defined above.

As used herein the term "arylthiocarbonyl" refers to a radical of the formula

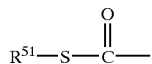

wherein $R^{51}$ is aryl as defined above.

As used herein the term "acyloxymethoxycarbonyl" refers to a radical of the formula

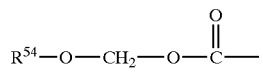

wherein $R^{54}$ is acyl as defined above.

As used herein the term "arylamino" refers to a radical of the formula $R^{51}$—NH— wherein $R^{51}$ is aryl as defined above.

As used herein the term "polyalkylether" refers to commonly used glycols such as triethyleneglycol, tetraethylene glycol, polyethylene glycol and the like.

As used herein the term "alkylamido" refers to a radical of the formula

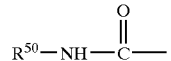

wherein $R^{50}$ is alkyl as defined above.

As used herein the term "N,N-dialkylamido" refers to a radical of the formula

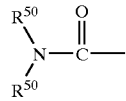

wherein $R^{50}$ is the same or different alkyl group as defined above.

As used herein the term "pivaloyloxymethyl" refers to a radical of the formula

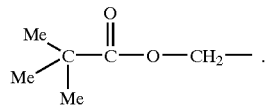

As used herein the term "acyloxy" refers to a radical of the formula $R^{55}$—O— wherein $R^{55}$ is acyl as defined above.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:
$^1$H-NMR=proton nuclear magnetic resonance
AcOH=acetic acid
$BH_3$-THF=borane-tetrahydrofuran complex
Bn=benzyl
BOC=tert-butoxycarbonyl
ButLi=butyl lithium
Cat.=catalytic amount
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DCC=1,3-dicyclohexylcarbodiimide
DIBAL=diisobutylaluminum hydride
DIEA=diisopropylethylamine
DMA=N,N-dimethylacetamide
DMAP=4-(N,N-dimethylamino)pyridine
DMF=N,N-dimethylformamide
DSC=disuccinyl carbonate
EDCl=1-(3-dimethylaminopropyl)-3-ethylcarbodiimide hydrochloride
Et=ethyl
$Et_2O$=diethyl ether
$Et_3N$=triethylamine EtOAc=ethyl acetate
EtOH=ethanol
FAB MS=fast atom bombardment mass spectroscopy
g=gram(s)
GIHA=meta-guanidinohippuric acid
GIHA HCl=meta-guanidinohippuric acid hydrochloride
HPLC=high performance liquid chromatography
IBCF=isobutylchloroformate
i-Pr=iso propyl
i-Prop=iso propyl
$K_2CO_3$=potassium carbonate
KOH=potassium hydroxide
KSCN=potassium thiocyanate
LiOH=lithium hydroxide
MCPBA=m-chloroperoxybenzoic acid or m-chloroperbenzoic acid
Me=methyl
MeOH=methanol
MesCl=methanesulfonylchloride
mg=milligram
$MgSO_4$=magnesium sulfate
ml=milliliter
mL=milliliter
MS=mass spectroscopy
$N_2$=nitrogen
$NaCNBH_3$=sodium cyanoborohydride
NaH—sodium hydride
$NaHCO_3$=sodium bicarbonate
NaOH=sodium hydroxide
$Na_2PO_4$=sodium phosphate
$Na_2SO_4$=sodium sulfate
$NEt_3$=triethylamine
$NH_4HCO_3$=ammonium bicarbonate
$NH_4^+HCO_2$=ammonium formate
NMM=N-methylmorpholine
NMR=nuclear magnetic resonance
RPHPLC=reverse phase high performance liquid chromatography
RT=room temperature
Pd/C=palladium on carbon
Ph=phenyl
Pt/C=platinum on carbon
t-BOC=tert-butoxycarbonyl
TFA=trifluoroacetic acid
THF=tetrahydrofuran
TMEDA=trimethylethylenediamine
TMS=trimethylsilyl
Δ=heating the reaction mixture The compounds as shown in Formulas I–V can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available, atom on the ring.

The term "pharmaceutically acceptable salt" refers to a salt prepared by contacting a compound of Formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts may be prepared by conventional means. (See Berge et al., *J Pharm. Sci.*, 66(1), 1–19 (1977) for additional examples of pharmaceutically acceptable salts.)

For the selective inhibition or antagonism of $\alpha_v\beta_3$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ cell surface receptor which method comprises administering a therapeutically effective amount of a compound selected from the class of compounds depicted in Formulas I–V, wherein one or more compounds of the Formulas I–V is administered in association with one or more non-toxic, pharmaceutically acceptable carriers and/or diluents and/or adjuvants (collectively referred to herein as "carrier" materials) and if desired other active ingredients. More specifically, the present invention provides a method for inhibition of the $\alpha_v\beta_3$ cell surface receptor. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions.

The active ingredient administered by injection is formulated as a composition wherein, for example, saline, dextrose or water may be used as a suitable carrier. A suitable daily dose would typically be about 0.01 to 10 mg/kg body weight injected per day in multiple doses depending on the factors listed above.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in Schemes I–XXI. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the compounds of the present invention.

Unless otherwise indicated all starting materials and equipment employed were commercially available.

SCHEME I

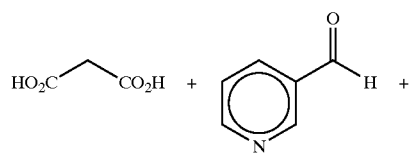

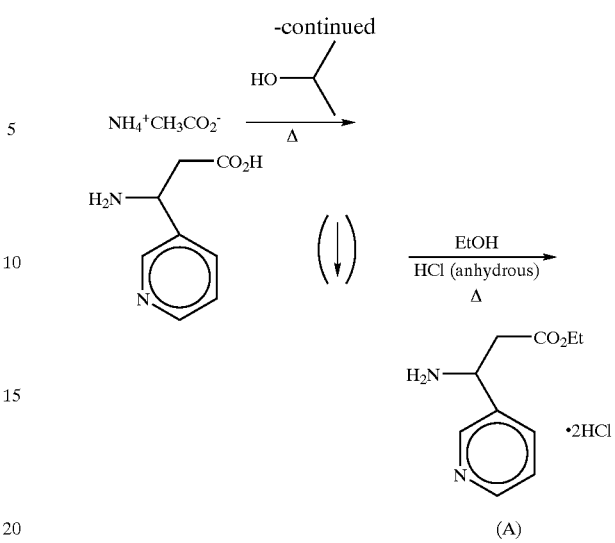

(A)

Scheme I describes a synthesis of a pyridyl β-aminoacid which can be used to synthesize compounds of the present invention wherein $R^1$ is pyridyl. The reaction can be modified using conventional methodology to prepare other aromatic, alkyl or heterocyclic substituted β-amino acids by substitution of the pyridyl carboxaldehyde with any other appropriate aldehyde. Briefly, in Scheme I to pyridinecarboxaldehyde in isopropanol is added ammonium acetate followed by malonic acid. The reaction mixture is stirred at reflux, the resulting precipitate filtered and washed with hot isopropanol and dried to yield 3-amino-3-(3-pyridyl)propionic acid. The ethyl ester is synthesized by heating this acid in excess ethanol in the presence of excess HCl gas.

Additionally, β-amino acids which are useful in the present invention are accessible through modified Knoevenagel reactions (Secor, H. V.; Edwards, W. B. J. *J. Org. Chem.* 1979, 44, 3136–40; Bellasoued, M.; Arous-Chtar, R.; Gaudemar, M. J.; *J. Organometal. Chem.* 1982, 231, 185–9), through Reformatski reaction with Schiff bases (Furukawa, M.; Okawara, T.; Noguchi, Y.; Terawaki, Y. *Chem. Pharm. Bull.* 1978, 26, 260), Michael addition into an acrylic derivative (Davies, S. G.; Ichihara, O. *Tetrahedron:Asymmetry* 1991, 2, 183–6; Furukawa, M.; Okawara, T R.; Terawaki, Y. *Chem. Pharm. Bull.*, 1977, 25, 1319–25). More recent methods include the use of organometallic reagents in Pd or Zn mediated couplings (Konopelski, J.; Chu, K. S.; Negrete, G. R. *J. Org. Chem.* 1991, 56, 1355; Mokhallalati, N. K.; Wu, M-J.; Prigden, L. N. *Tetrahedron Lett.* 1993, 34, 47–50) to complement more traditional reactions such as reductive amination of β-ketoesters.

The racemic beta-alkyl beta amino esters can also conveniently be prepared from the corresponding beta lactam by treatment with anhydrous HCl gas in ethanol. The beta lactams were prepared from the corresponding alkene and chlorosulfonyl isocyanate (Szabo, W. A. *Aldrichimica Acta*, 1977, 23 and references cited therein). The latter method is useful for the preparation of α and β-substituted β-aminoacids. (Manhas, M. S.; Wagle, D. R.; Chong, J.; Bose, A. K. *Heterocycles*, 1988, 27, 1755.) Another route to α-substituted β-aminoacids is the Raney Nickel reduction of cyanoacetic esters at temperatures ranging between 20 and 80° C. and at 20 to 100 atm pressure (Testa, E.; Fontanella, L.; Fava, F. *Fermaco Ed. Sci.*, 1958, 13, 152; Testa, E.; Fontanella, L. *Annalen* 1959, 625, 95). Also, a number of procedures are available for the preparation of β-aminoacids by reduction of hydrazones of keto-acids (Gootijes, J.; Nomte, W. Th. *Rec. Trav. Chem.* 1953, 72, 721), oximes (Anziegin, A.; Gulewivich, W. *Z. Physiol. Chem.*, 1926, 158, 32) and nitropropionic acids. Purification of final compounds is usually by reverse phase high performance liquid chromatography (RP HPLC) [High Performance Liquid Chromatography Protein and Peptide Chemistry, F. Lottspeich, A. Henscher, K. P. Hupa, (eds.) Walter DeGruyter, New York, 1981] or crystallization.

SCHEME II

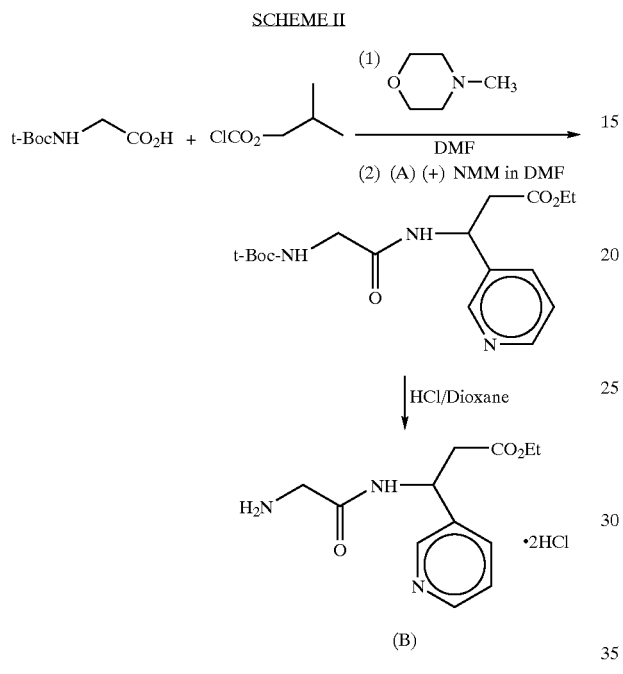

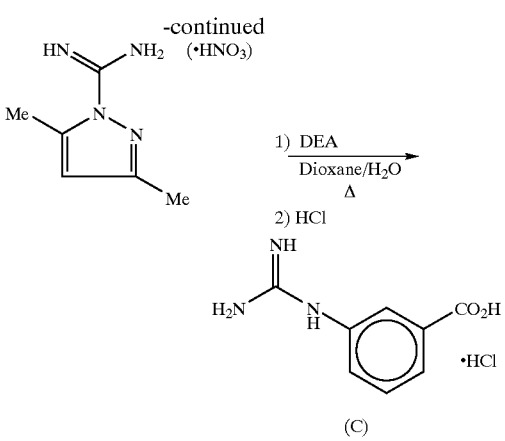

Scheme III is illustrative of methodology useful for preparing the guanidinobenzoic acid portion of the present invention which can be used for coupling to the gly-β-amino acid. This can also be accomplished using other appropriate guanidating reagents known to those skilled in the art for example using pyrazolecarboxamidine.HCl (Aldrich). The methodology of Scheme III can be modified using conventional techniques and methods to prepare alternate compounds useful for coupling to the β-amino acids.

Briefly, in Scheme III, to 3,5-dimethylpyrazole-1-carboxamidine nitrate in dioxane, water and DIEA, is added 3-aminobenzoic acid. The mixture is stirred at reflux, the precipitate filtered, washed and dried. The precipitate is then further slurried in water, acidified with HCl and concentrated. The solvent is removed and the residue slurried in ether and dried to yield 3-guanidinobenzoic acid hydrochloride (C).

Scheme II is illustrative of methodology useful for coupling an α-amino acid to the β-amino acid compounds prepared in Scheme I. The compounds thus prepared are useful for coupling to substituted benzoic acid compounds to prepare the desired compounds of the present invention. Such methodology can be modified using conventional methodology to couple other aminoalkyl acids to the β-amino esters prepared in Scheme I.

Briefly, in Scheme II, to a solution of t-Boc-glycine in DMF is added N-methylmorpholine followed by isobutylchloroformate. In a separate flask, the substituted β-amino ester in DMF is mixed with N-methylmorpholine. The two mixtures are combined and stirred at room temperature to yield

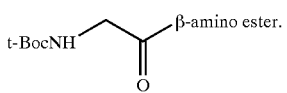

The resulting product is deprotected using HCl/Dioxane to give (B).

SCHEME III

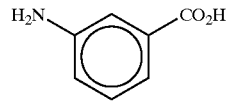

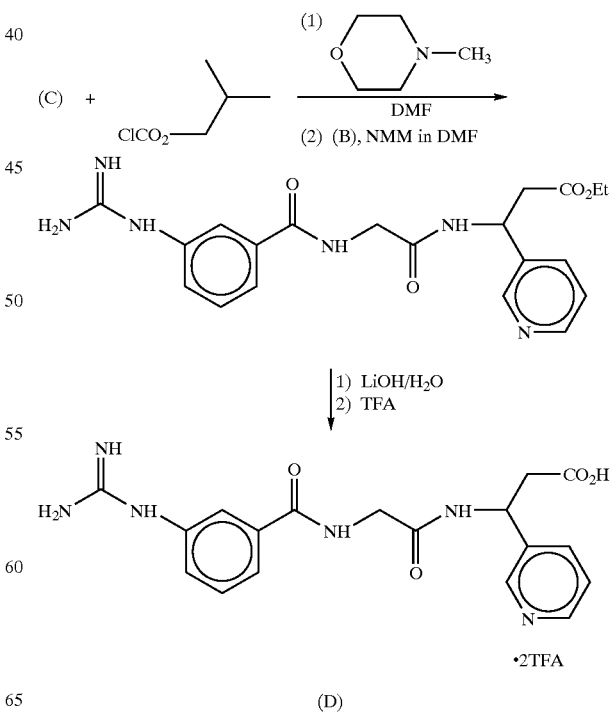

Scheme IV illustrates methodology useful for coupling the guanidinobenzoic acid (C) to the β-amino ester (B) portion of the desired compounds of the present invention. Such methodology can be modified using conventional methods known to those having ordinary skill in the art.

Briefly, in Scheme IV to the 3-guanidinobenzoic acid (C) (prepared in Scheme III) in DMF and N-methylmorpholine was added isobutylchloroformate. The reaction was stirred and a slurry of the β-amino ester compound (B) (prepared in Scheme II) in DMF and N-methylmorpholine was added portionwise. The reaction was stirred, the precipitate filtered and washed with DMF. The DMF was removed. The resulting ester is dissolved in water, washed with ether and LiOH is added to the aqueous layer and stirred for approximately 1 hour. The solution is treated with trifluoroacetic acid to pH=5 and the product purified by RPHPLC to yield the desired compounds (D).

SCHEME V

Step A

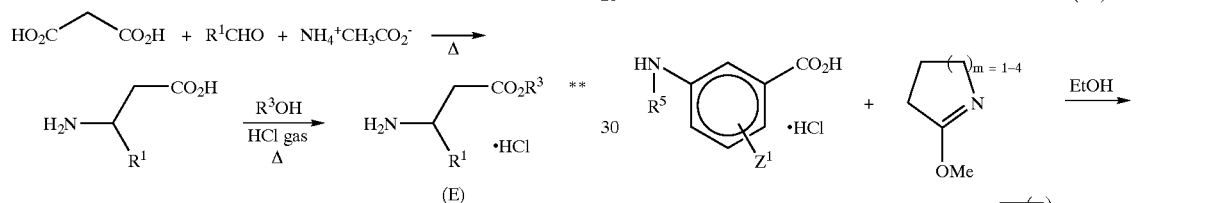

Step B

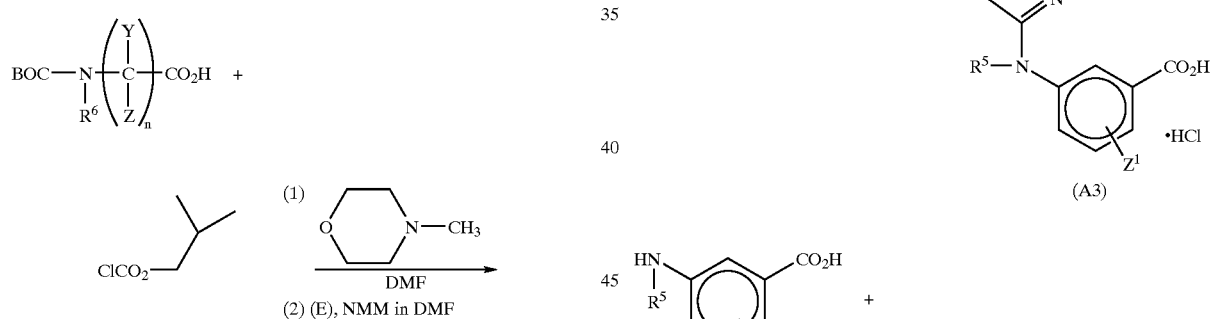

Step C

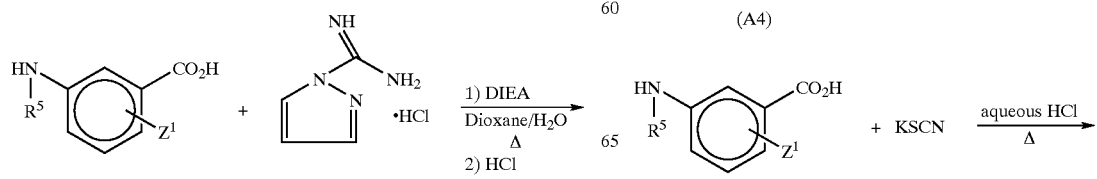

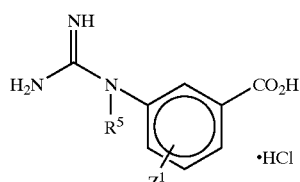

(A1)

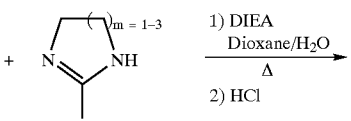

(A2)

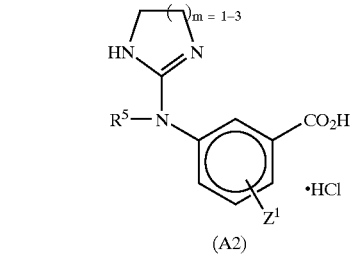

(A3)

(A4)

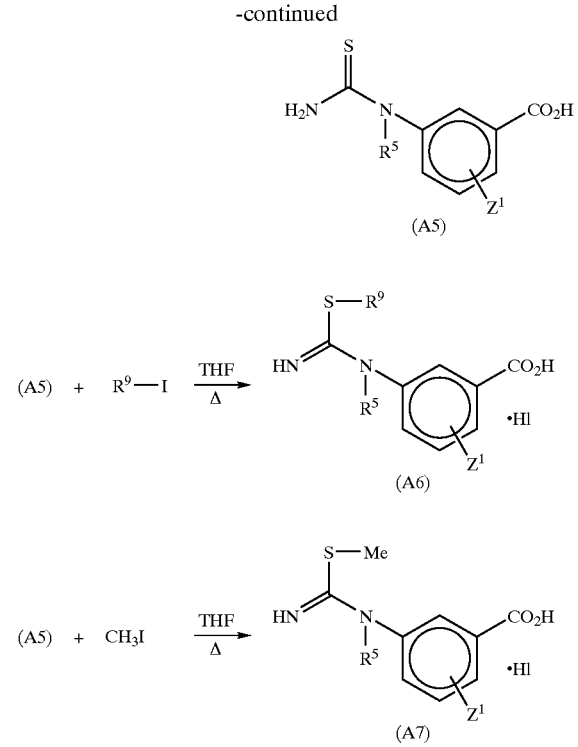
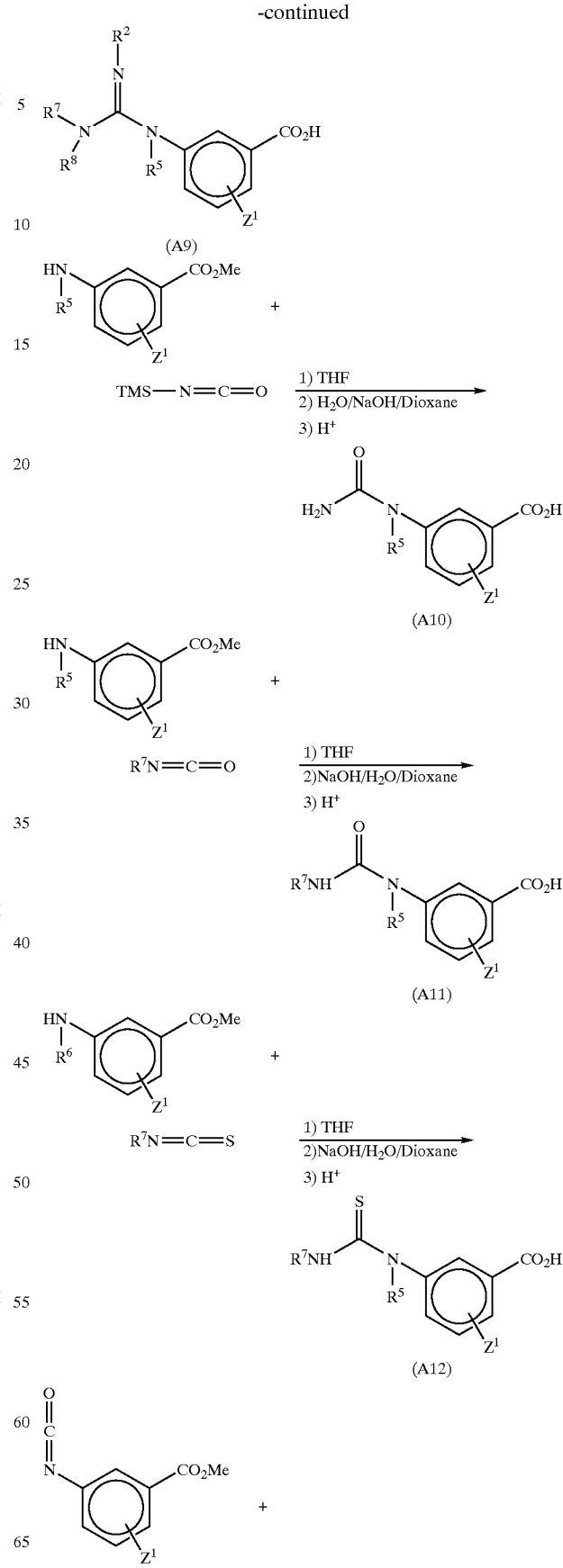

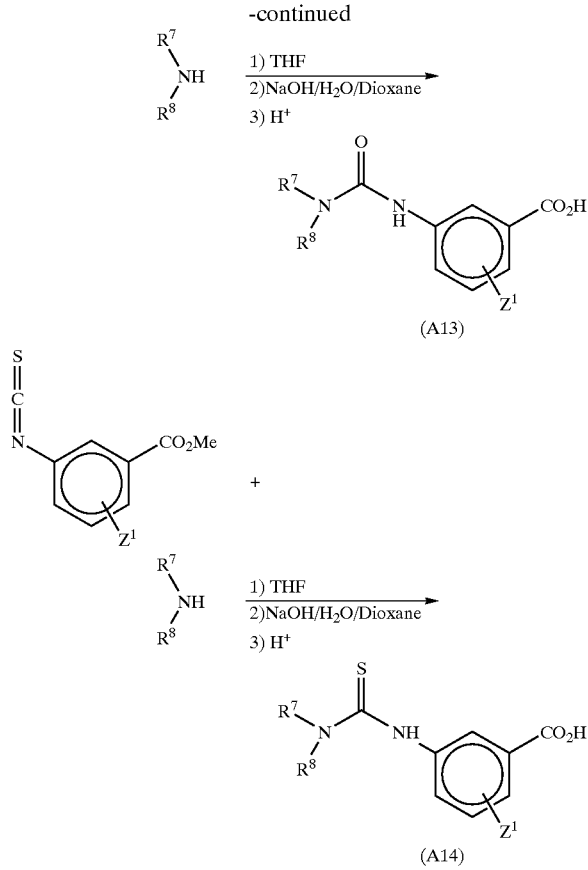

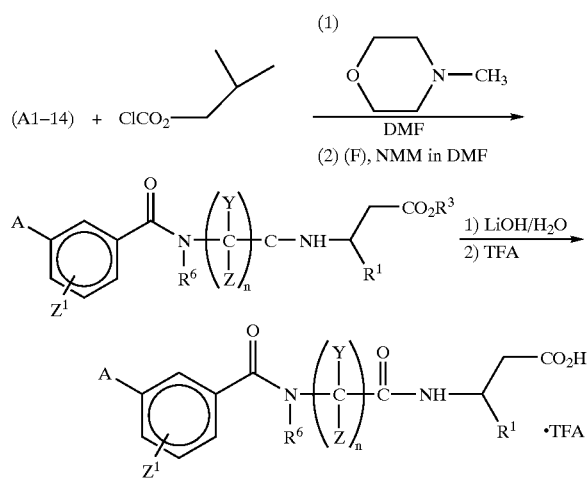

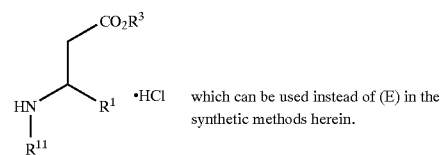

Scheme V is illustrative of methodology useful for preparing various compounds of the present invention. Such methodology is more specifically defined in the following examples and in Schemes I–IV. Such methodology can be modified by one skilled in the art, substituting known reagents and conditions from conventional methodology to produce the desired compounds.

Specifically, in Scheme V, Step C:

In the synthesis of intermediate benzoic acids (A1) through (A14), the starting amino benzoic acids

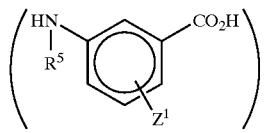

are either commercially available or can be converted to such amino benzoic acids via reduction of the corresponding nitro benzoic acid, which can be obtained commercially or syntheized by nitration of the appropriate benzoic acid, followed by reduction to the desired amino benzoic acid. These are all when $R^5$ is H. If $R^5$ is other than H, alkylation of the amino functionality can be achieved by conventional methodology.

Furthermore, synthesis of intermediate (A2) can also be accomplished as disclosed generally in U.S. Pat. No. 3,202,660, starting with the appropriate amino benzoic acid.

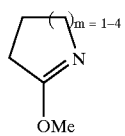

used in the synthesis of intermediates (A3), can be synthesized from

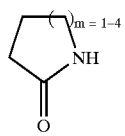

and $(Me)_3OBF_4$ in dichloromethane.

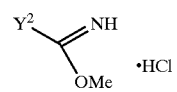

used in the synthesis of intermediate (A4), can be synthesized from $Y^2$—CN and MeOH (1 equivalent) and HCl gas (1 equivalent) in heptane.

All other reagents in Scheme V are either commercially available or readily synthesized by methodologies known by those skilled in the art.

Coupling of the intermediates from Scheme V, Step C [(A1) through (A14)] with the intermediate (7) (from Scheme V Step B) can be accomplished using other coupling reagents known to those skilled in the art in addition to the mixed anhydride method described in Scheme V Step D, to give the final desired products.

SCHEME VA

Alternate synthesis of aldehydes

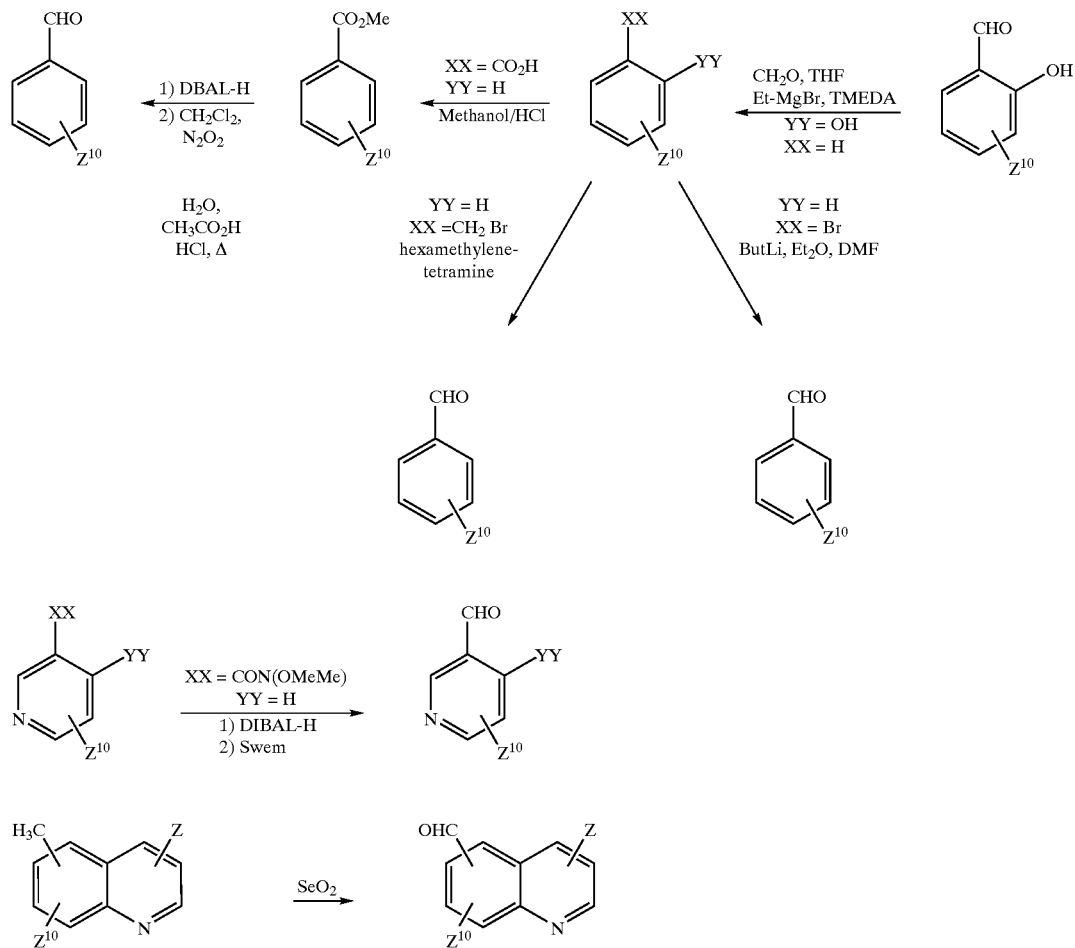

$Z^{10}$ is defined the same as $Z^1$

Scheme VA is illustrative of methodology useful for the preparation of aldehydes ($R^1$) which are not commercially available, and are used in the preparation of β-amino acids as in Scheme V, Step A. Such β-amino acids are then further used to synthesize the compounds of the present invention as further exemplified in Scheme V, Steps A through D.

Other such methodologies known to those skilled in the art are available and can also be used to synthesize aldehydes useful in preparing compounds of the present invention.

SCHEME VI (A)

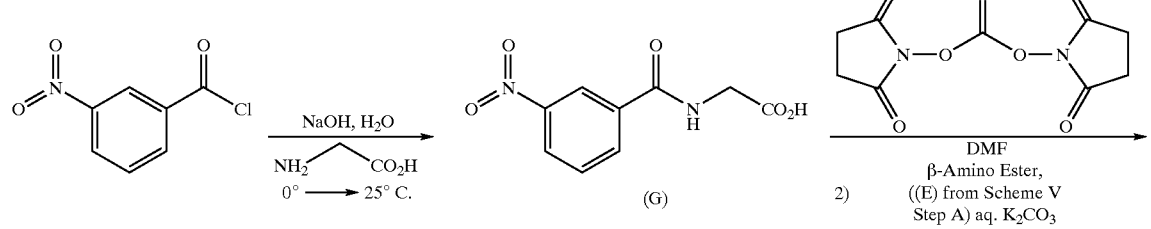

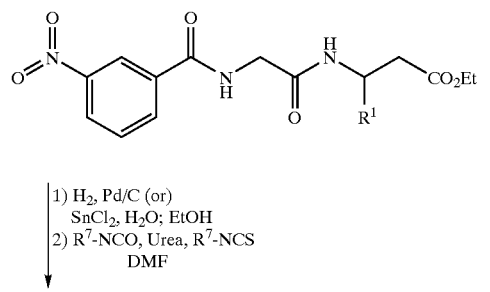
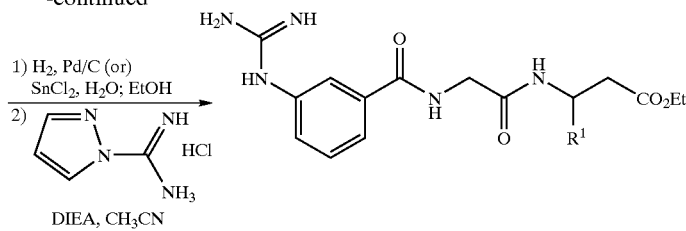
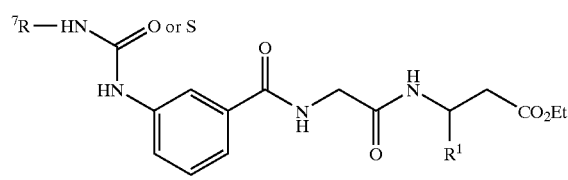
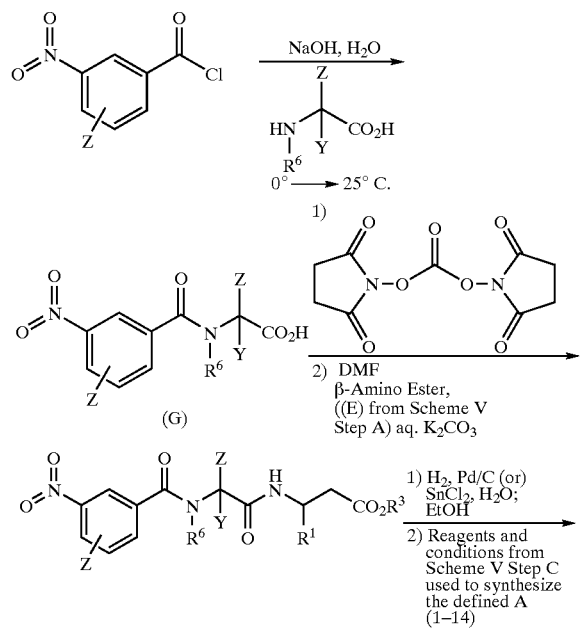
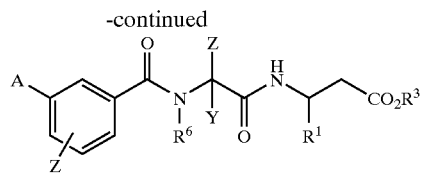

Scheme VI(A) represents an alternative method of synthesis of the compounds of the Formula I. All reagents are either commercially available or are made via methods known to those skilled in the art.

The synthesis of β-amino esters is as described for Compound (B) in Scheme V, Step A.

Alternative methods of coupling, guanidation or formation of ureas and thioureas can be used and are readily known to those skilled in the art.

Scheme VI(B) represents another alternative synthesis of the compounds of the present invention. All reagents are either commercially available or are made via standard and known methodologies.

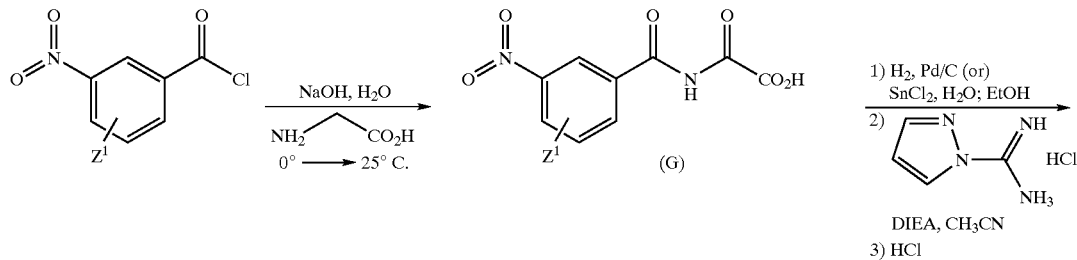

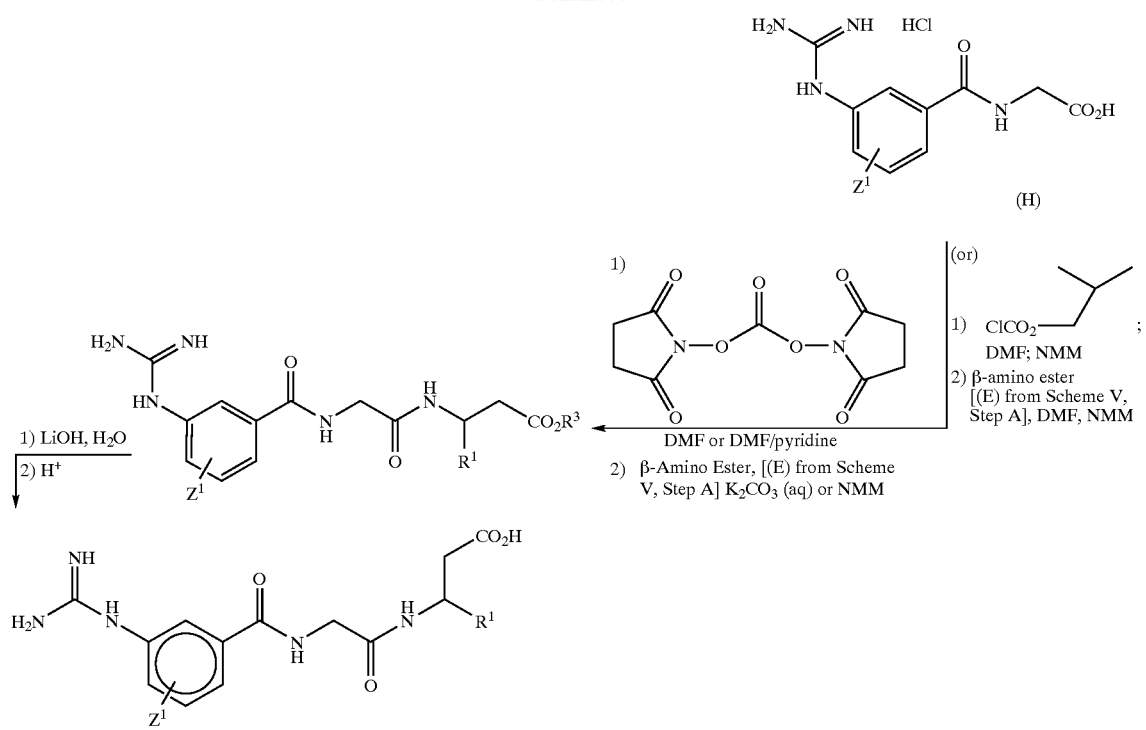
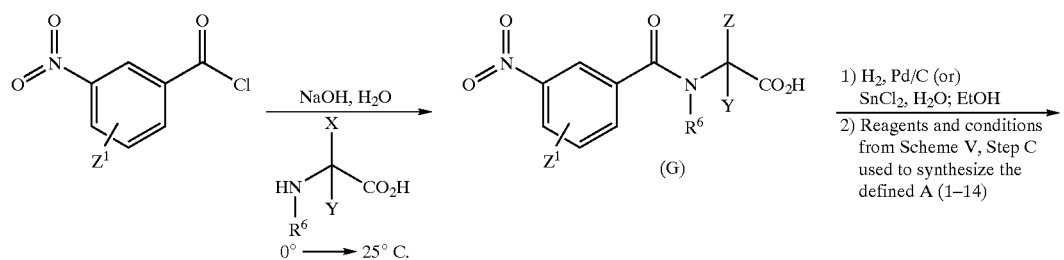
SCHEME VII (B)
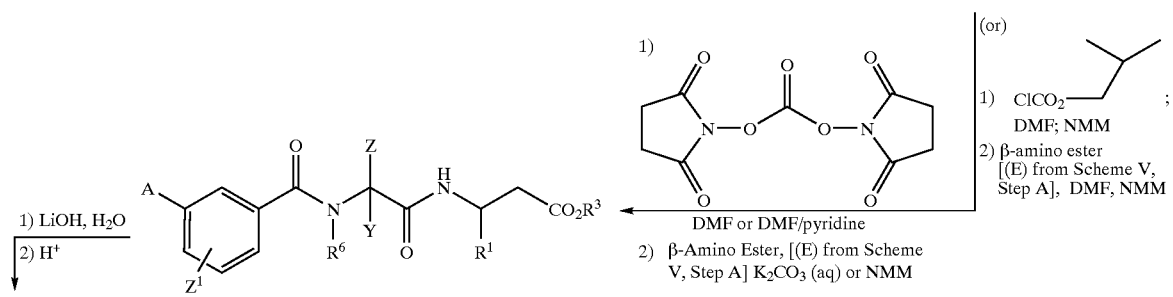

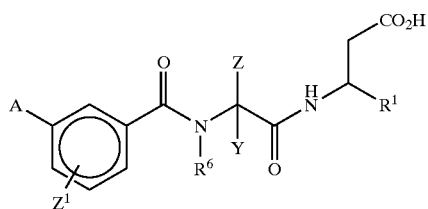

-continued

Schemes VII(A) and (B) are similar to Schemes VI(A) and (B) and provide additional methods of synthesis of compounds of the present invention. (Scheme VIIB being a more general scheme than Scheme VIIA.) As in Scheme VI, reagents and conditions are not restricted to those defined in these schemes but may be substituted for with alternative reagents known to those skilled in the art.

Scheme VIII is illustrative of the synthesis used to form group A in the general Formula I where A is an aminothiazoline or aminothiazine. All starting materials and reagents are commercially available or are defined elsewhere in the enclosed Schemes and Examples. Alternative methods of coupling or alternative reagents and conditions may be employed as are known to those skilled in the art.

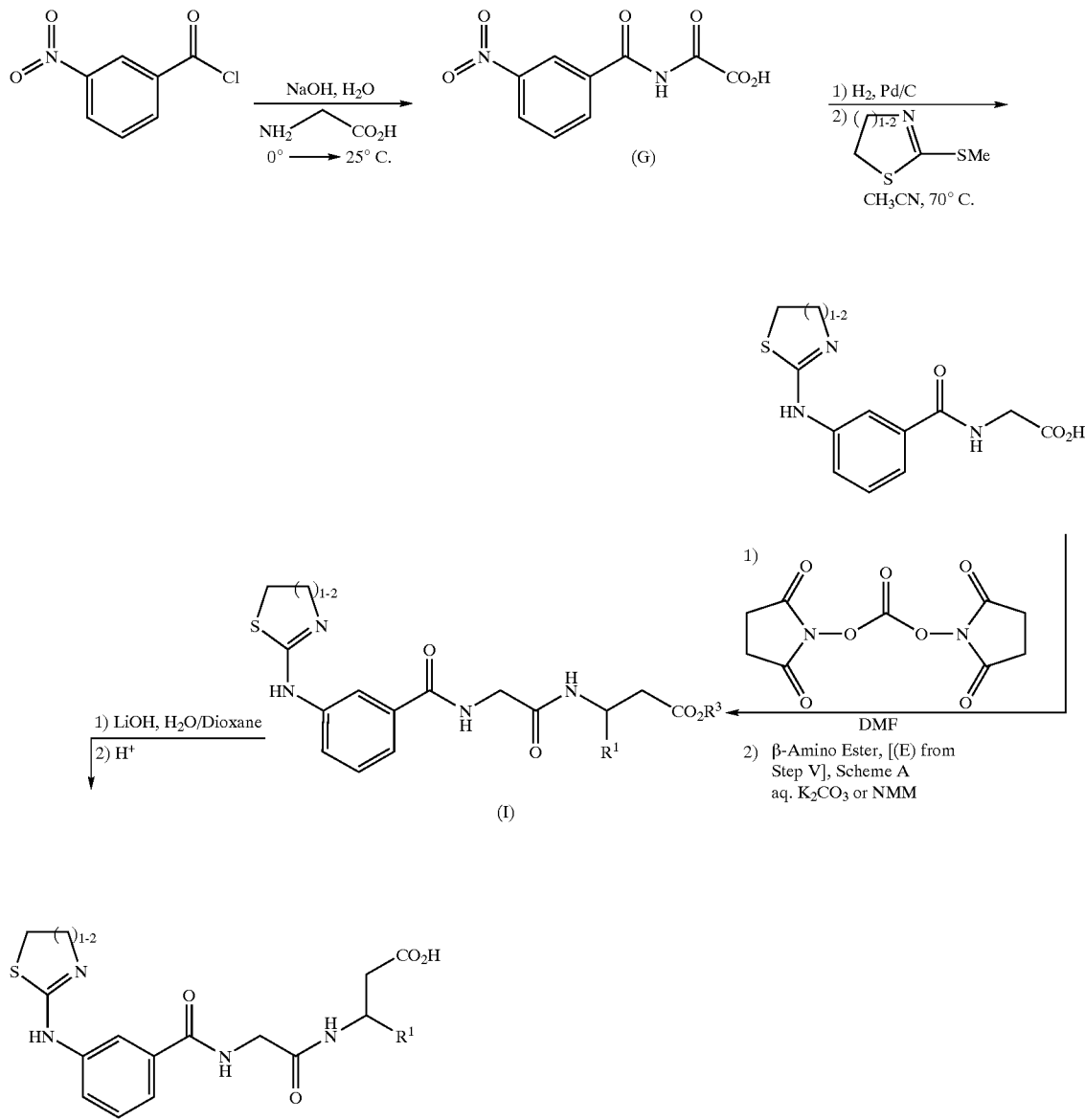

SCHEME IX

Cyanoguanidines

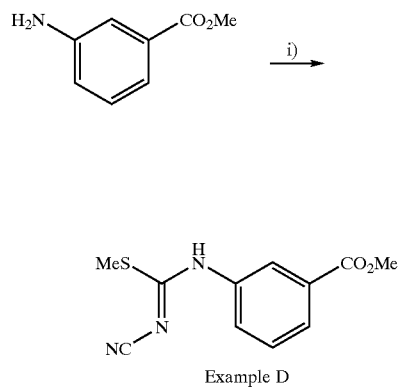

Example D

R⁷ = Bn, Example E
R⁷ = Me, Example F
R⁷ = H, Example G
R⁷ = Et, Example H

R⁷ = Bn, Example I
R⁷ = Me, Example J
R⁷ = H, Example K
R⁷ = Et, Example L

R⁷ = Bn, R¹ = Ph, R = Bn, Example 132
R⁷ = Me, R¹ = Ph, R = Bn, Example 133
R⁷ = H, R¹ = Ph, R = Bn, Example 134
R⁷ = Et, R¹ = Ph, R = Et, Example 135
R⁷ = Me, R¹ = Acetylene, R = Et, Example 140

R⁷ = Bn, R¹ = Ph, Example 136
R⁷ = Me, R¹ = Ph, Example 137
R⁷ = H, R¹ = Ph, Example 138
R⁷ = Et, R¹ = Ph, Example 139
R⁷ = Me, R¹ = Acetylene, Example 141 i) Pyridine, Dimethyl N-cyanodithioiminocarbonate, 70° C. ii) R⁷NH₂, EtOH, Reflux. iii) THF, MeOH, H₂O, NaOH. iv) CH₂Cl₂, DMAP, NEt₃, EDCL. v) 1) THF, MeOH, H₂O, NaOH 2) H⁺.

SCHEME X

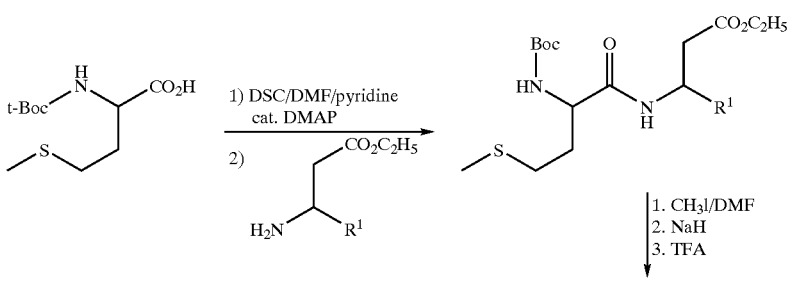

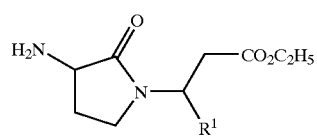

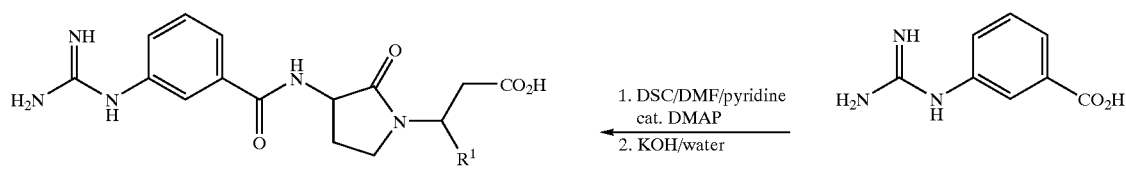

SCHEME XI

Example 147 (4-Cl)
Example 152 (6-Cl)

Example 148 (4-Cl)
Example 153 (6-Cl)

Example 149 (4-Cl)
Example 154 (6-Cl)

Example 150 (4-Cl)
Example 155 (6-Cl)

i) N,N¹-Bis-Boc-thiourea, DMF, NEt₃, HgCl₂, 0°, 15 mins.
ii) MeOH, THF, H₂O, KOH.
iii) CH₂Cl₂, TFA, 0°, 90 mins.

Schemes IX, X and XI are further examples of synthesis of particular compounds of the present invention. All starting materials and reagents are commercially available or are disclosed in the present specification. Alternative methods, reagents and conditions can be employed by those skilled in the art.

SCHEME XII

For compounds wherein

1) $R^1 = CO_2H$
   (E) is the commercially available

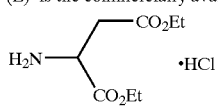
   •HCl

2) $R^1 = \overset{O}{\underset{}{C}} - N\overset{R_7}{\underset{R_8}{}}$

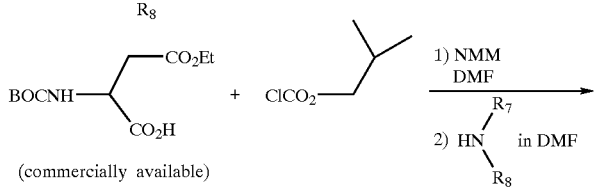

(commercially available)

-continued

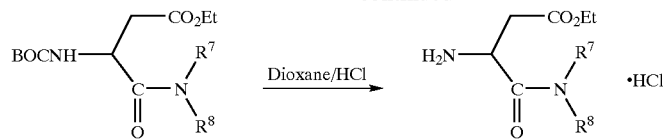

((E) from scheme V, Step A

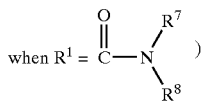

when $R^1 = \overset{O}{\underset{}{\overset{\|}{C}}}-N\overset{R^7}{\underset{R^8}{<}}$ )

wherein $HN\overset{R^7}{\underset{R^8}{<}}$ denotes an amino acid, the amino acid being protected with the appropriate protecting groups.

Additional methodologies for further $R^1$ groups are as follows:

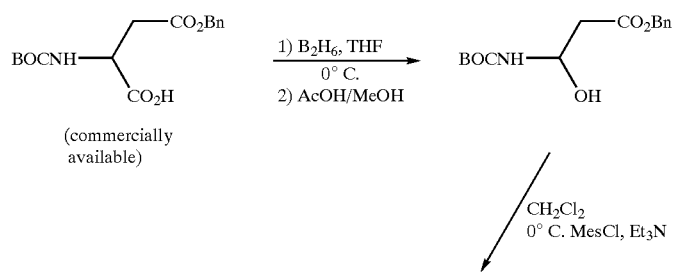

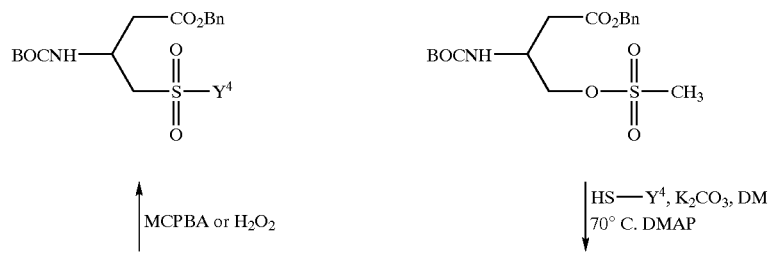

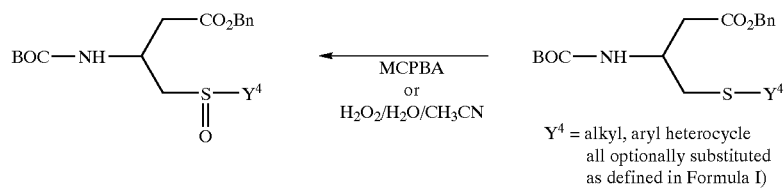

$Y^4$ = alkyl, aryl heterocycle all optionally substituted as defined in Formula I)

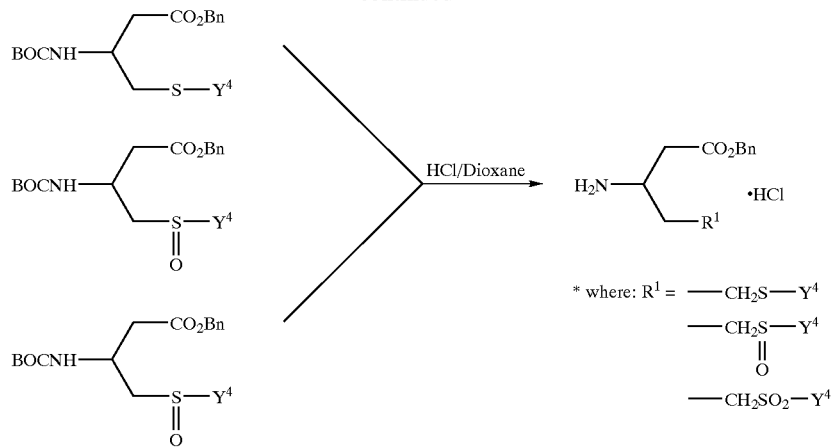
In a similar manner, compounds of the present invention wherein $R^1$ is substituted alkyl can be synthesized in the following manner:
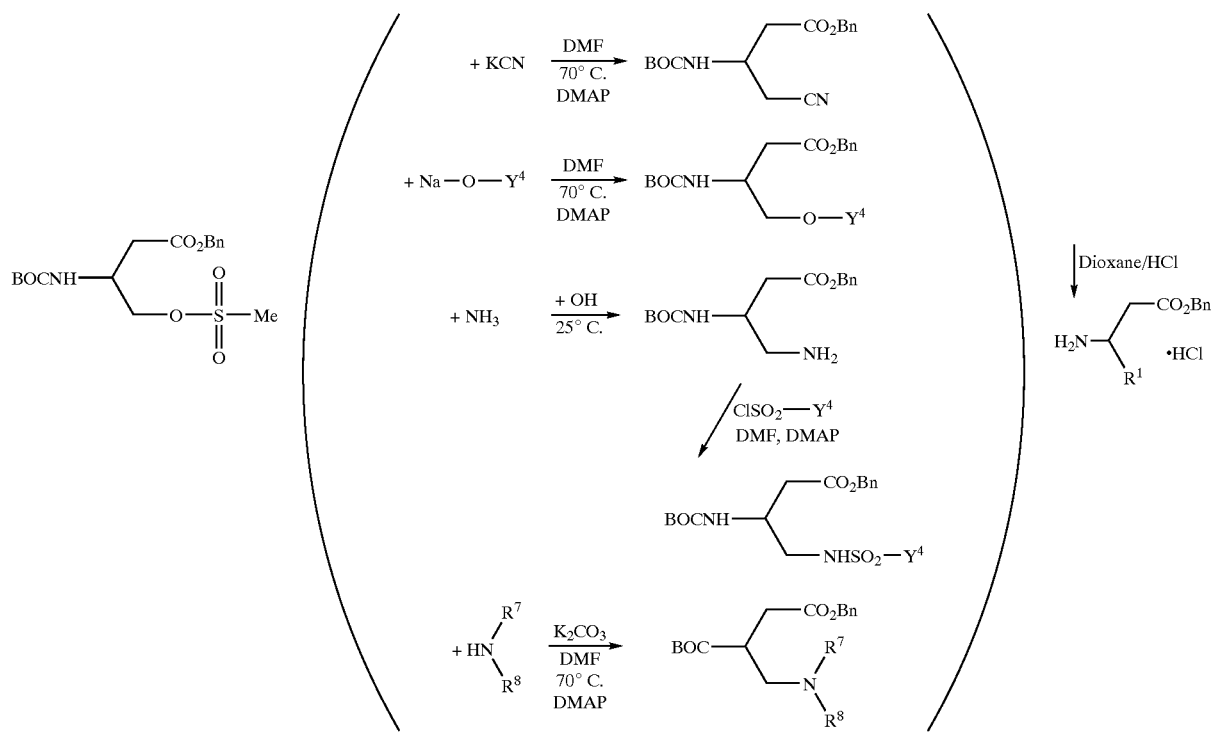
* These can all be further used as an intermediate such as (E) in the various Schemes used to exemplify the method of synthesis of the compounds of the present invention.

SCHEME XIIA

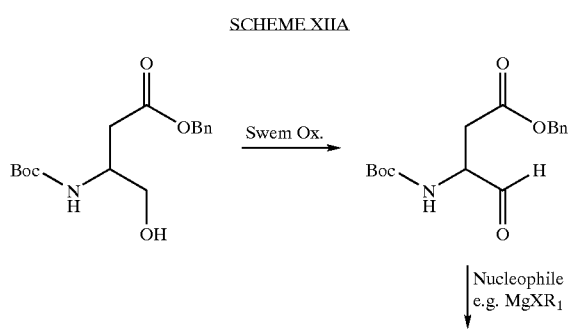

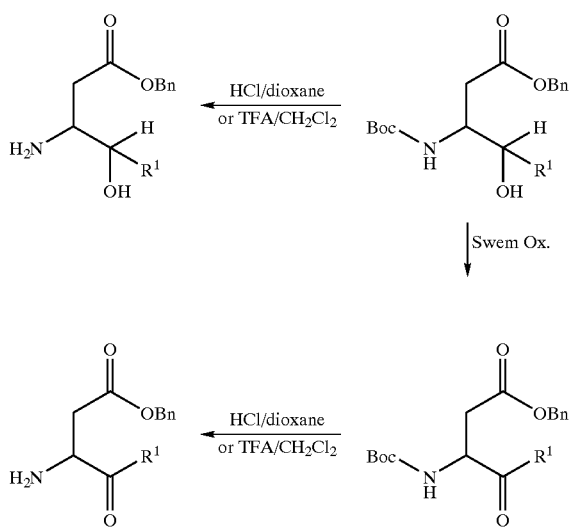

Scheme XII A outlines the synthesis of protected aspartyl aldehyde from aspartyl alcohol prepared in Scheme XII using Swern oxidation procedures and elaboration of the aldehyde by reaction with a nucleophile, e.g., either a commercially available Grignard Reagent or a Grignard Reagent prepared by standard procedures, to afford the C-4, $R_1$-substituted aspartyl alcohol derivative. The primary amine product may be prepared by removing the BOC group by employing standard acidic conditions to provide the intermediate β-amino acids (e.g. Scheme I). The BOC protected C-4 substituted alcohol may be converted to the keto-derivative by a second Swern oxidation followed by BOC removal to give the desired intermediate amine (e.g. Scheme I).

SCHEME XIII

To synthesize compounds wherein

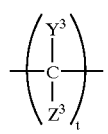 where t = 1 and $Y^3$ and $Z^3$ are both hydrogen:

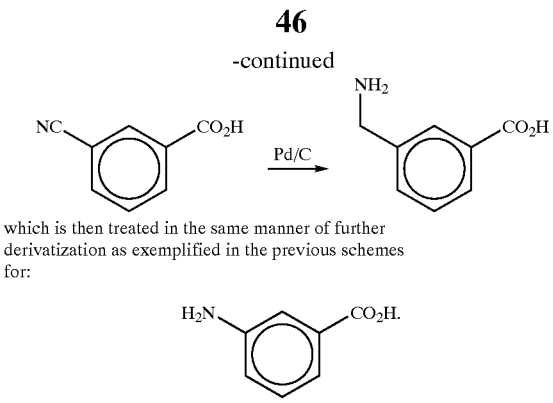

which is then treated in the same manner of further derivatization as exemplified in the previous schemes for:

SCHEME XIV

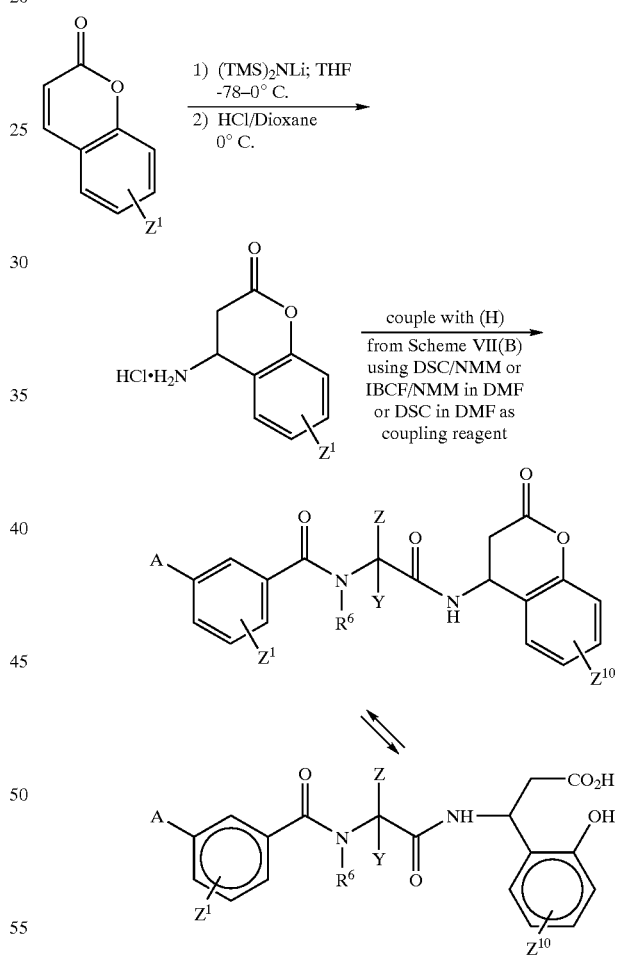

$Z^{10}$ is defined as in $Z^1$

Scheme XIV represents the synthesis of aminohydrocoumarins (see J. Rico, *Tett. Let.*, 1994, 35, 6599–6602) which are readily opened to form $R^1$ being an orthohydroxyphenyl moiety, further substituted by $Z^1$.

SCHEME XIV A

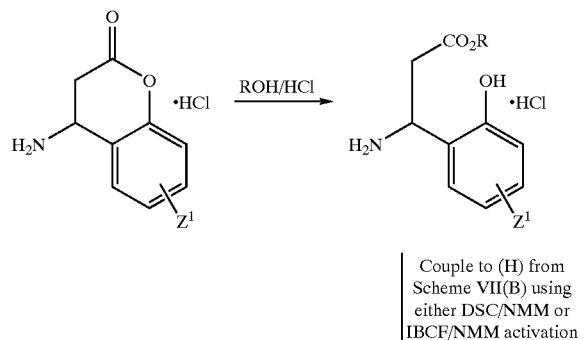

SCHEME XIV B

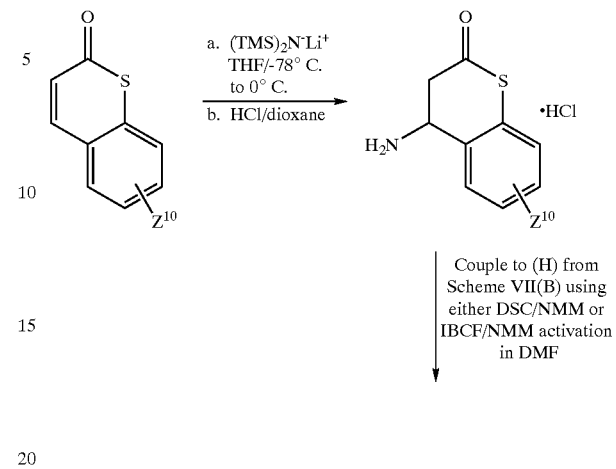

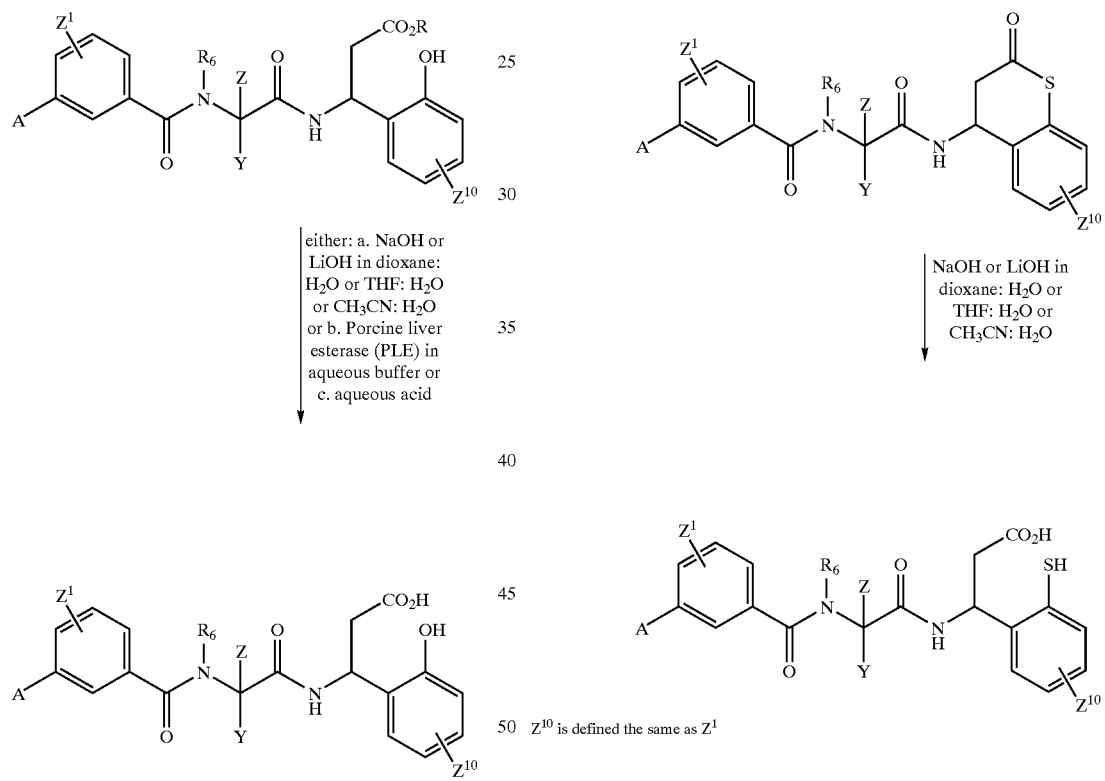

$Z^{10}$ is the same as defined in $Z^1$ $Z^{10}$ is defined the same as $Z^1$

Scheme XIV A represents the synthesis of aminohydrocoumarin esters from the aminohydrocoumarins of Scheme XIV and subsequent coupling with intermediates (H) from Scheme VII(B) using either activation of (H) by DSC/NMM/DMF or IBCF/NMM/DMF followed by aminohydrocoumarin ester hydrochloride salt/NMM. Subsequent hydrolysis using standard conditions resulted in formation of the carboxylic acid derivative.

Scheme XIV B represents the synthesis of 4-aminohydrothiocoumarin from thiocoumarins. Thiocoumarins are readily prepared according to J. A. Panetta and H. Rapoport, *J. Org. Chem.*, 1982, 41, 2626–2628 and references cited therein and may be converted to the 4-aminohydrothiocoumarin derivative according to the general procedure of Scheme XIV. Coupling of the aminohydrothiocoumarin to intermediate (H) from Scheme VII(B) can be achieved using methodology similar to Scheme XIV and XIV A. Hydrolysis to give the carboxylate-thiol product is readily achieved using a base (e.g. LiOH or NaOH) in an aqueous organic solvent.

SCHEME XVI
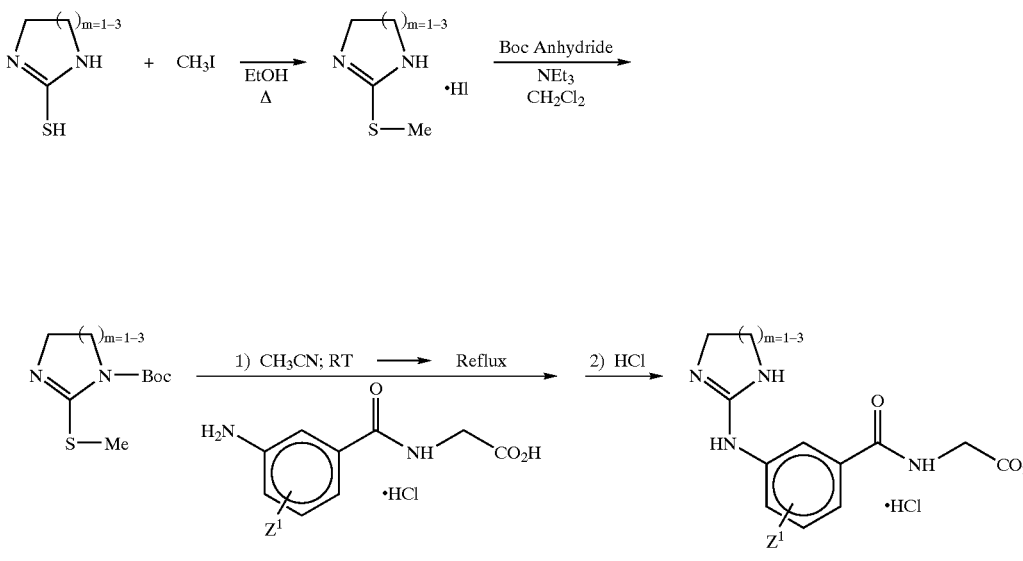
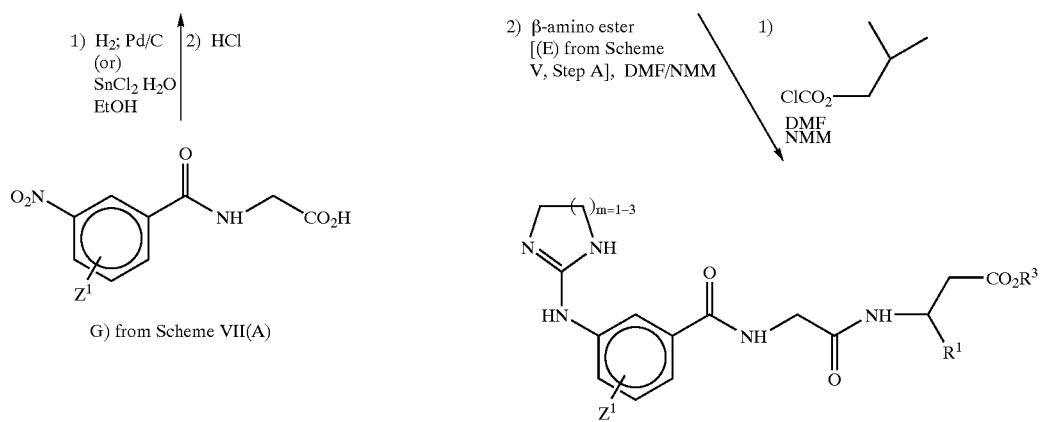
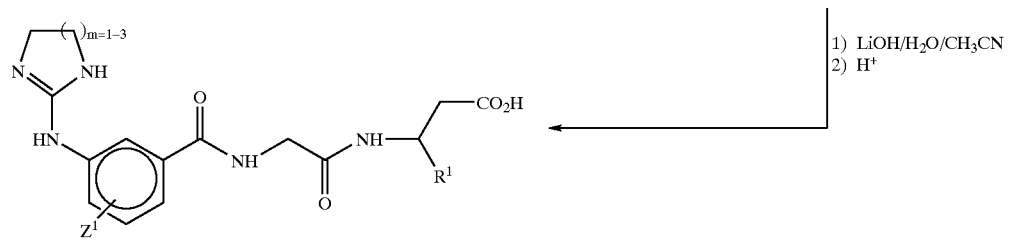
Scheme XVI represents an alternate synthesis of the compounds of the present invention wherein A is represented by cyclic guanidines. Alternate reagents and materials known to those skilled in the art can be substituted appropriately as readily recognized by one skilled in the art to produce the desired compounds.

SCHEME XVII

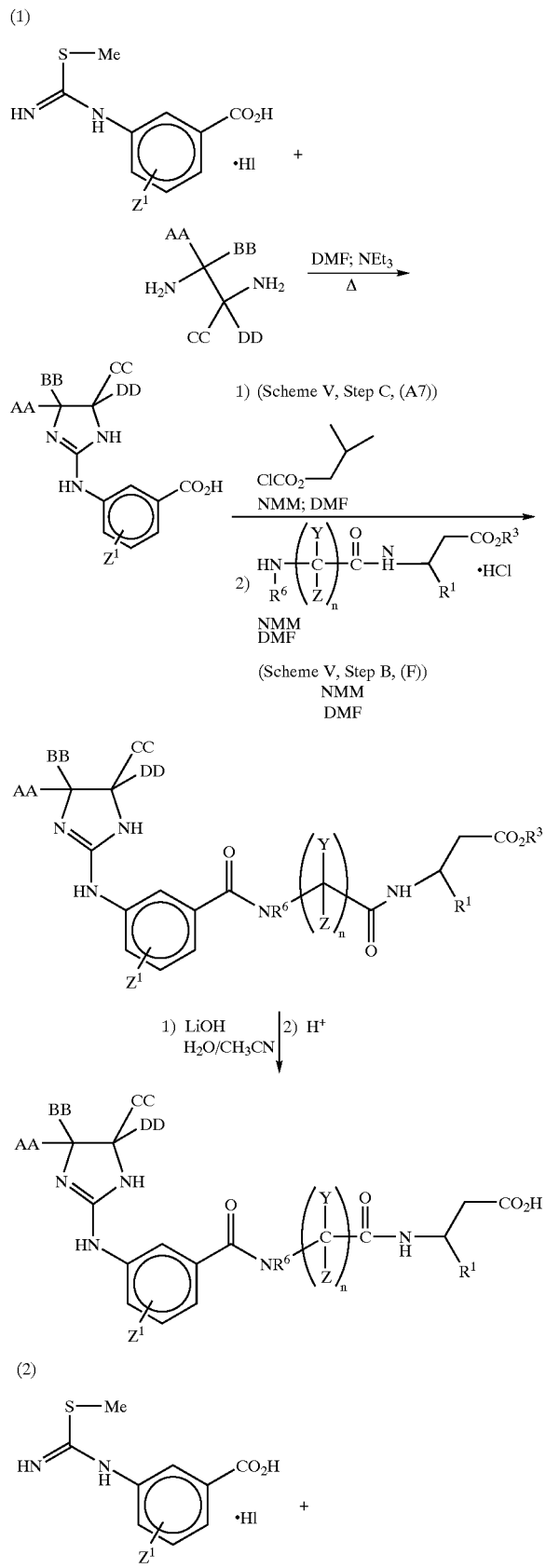

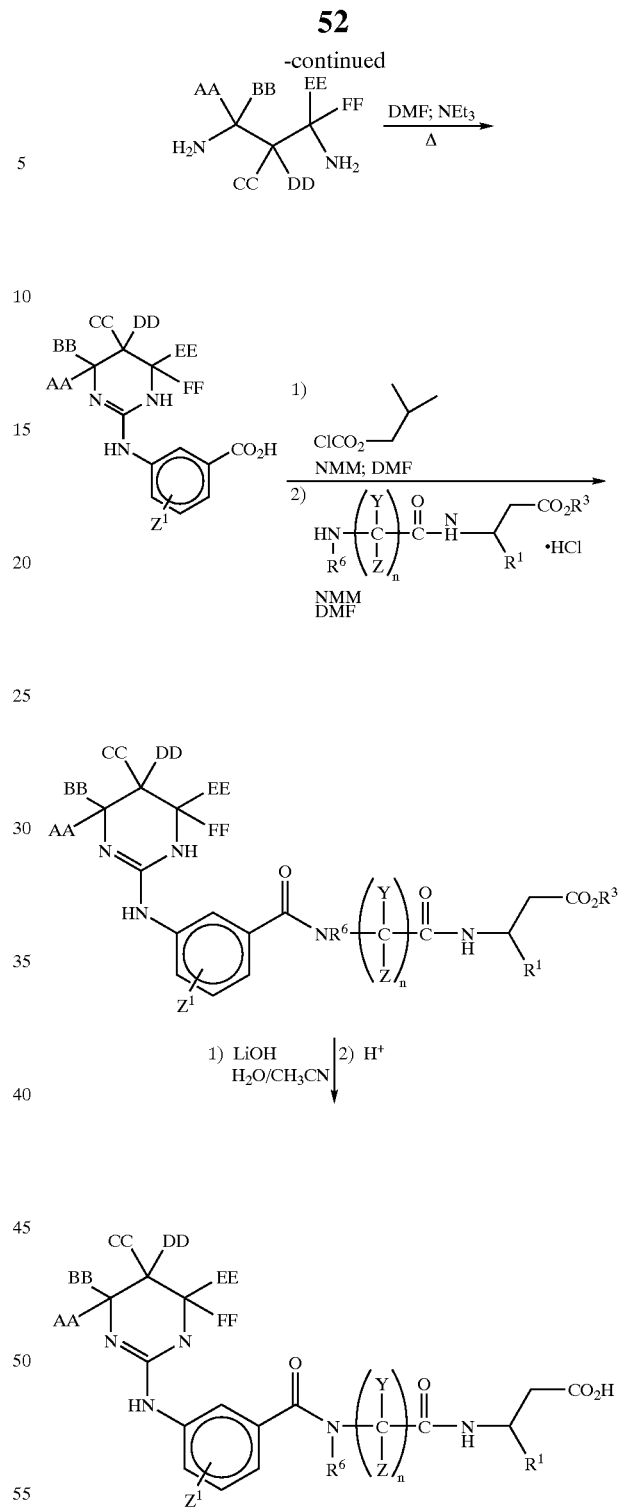

Scheme XVII depicts methods of synthesis wherein A is represented by a 5 or 6 membered cyclic guanidine.

AA through FF can be hydrogen or the additional substituents as defined above where A is a dinitrogen heterocycle, provided the appropriate substituted diamine is either commercially available or can be readily synthesized by one skilled in the art.

SCHEME XVIII
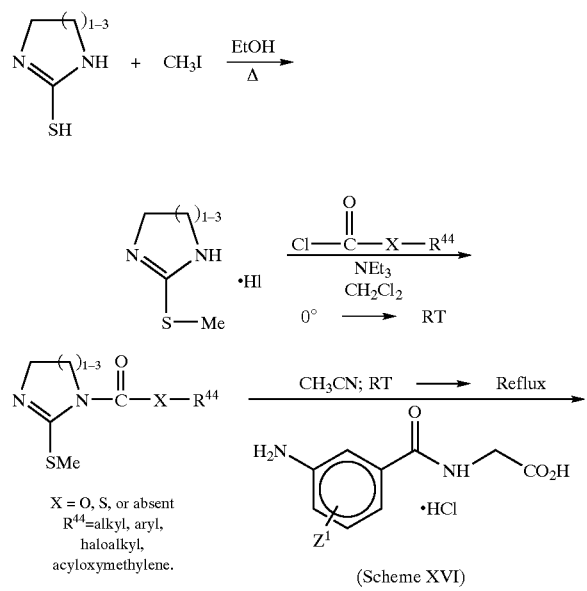
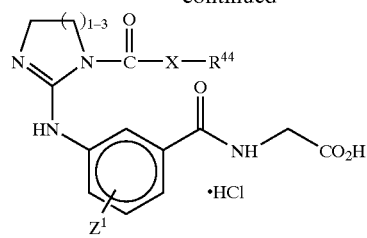
SCHEME XIX
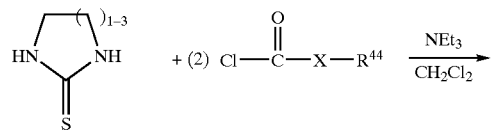
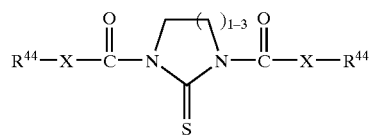
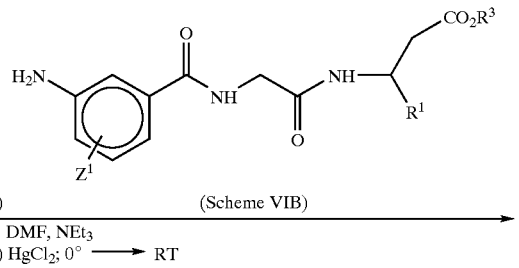
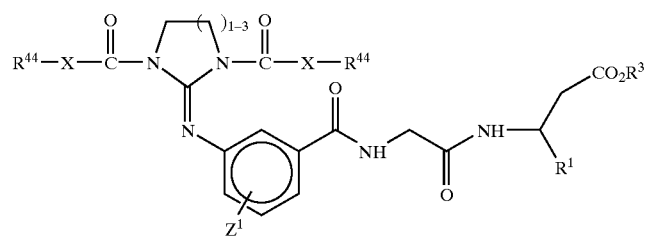

SCHEME XX

A.

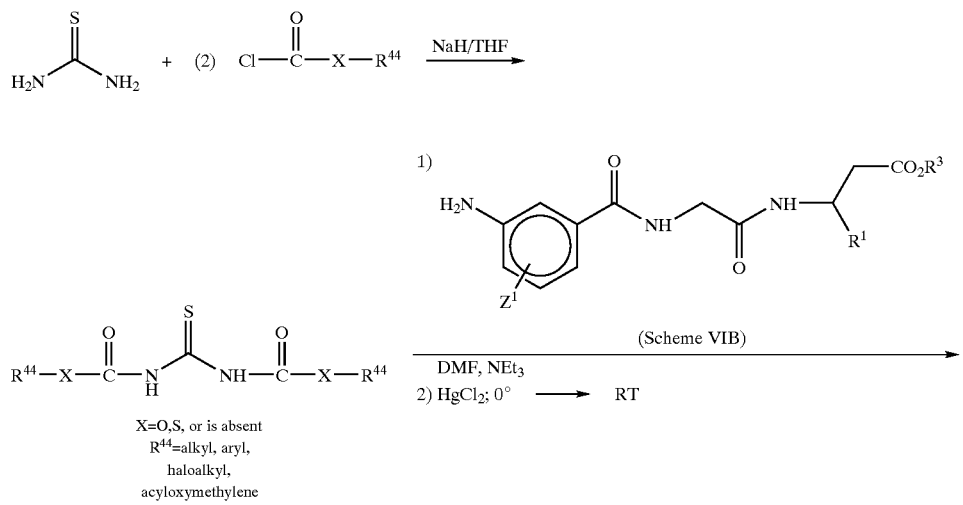

B.

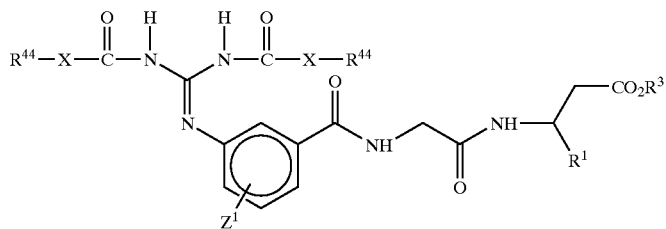

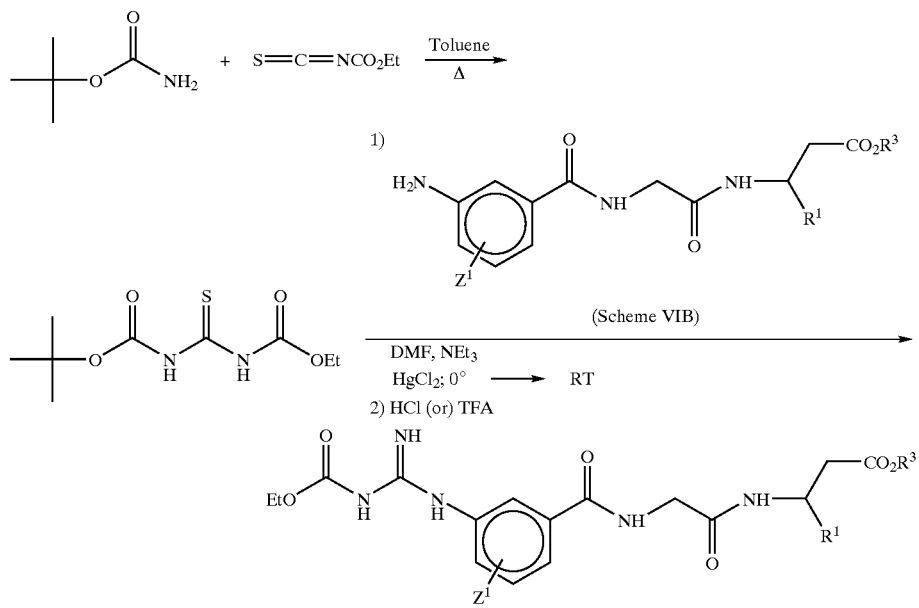

Schemes XVIII–XX represent synthesis of potential prodrugs where either one or two of the guanidine nitrogens are derivatized with a potentially labile functionality. These methods are intended to be merely illustrative of methodology for preparing the compounds of the present invention, and not limiting thereof in either scope or spirit. Other methodologies, reagents and conditions known to those skilled in the art may be employed to synthesize the compounds of the present invention.

SCHEME XXI

A.

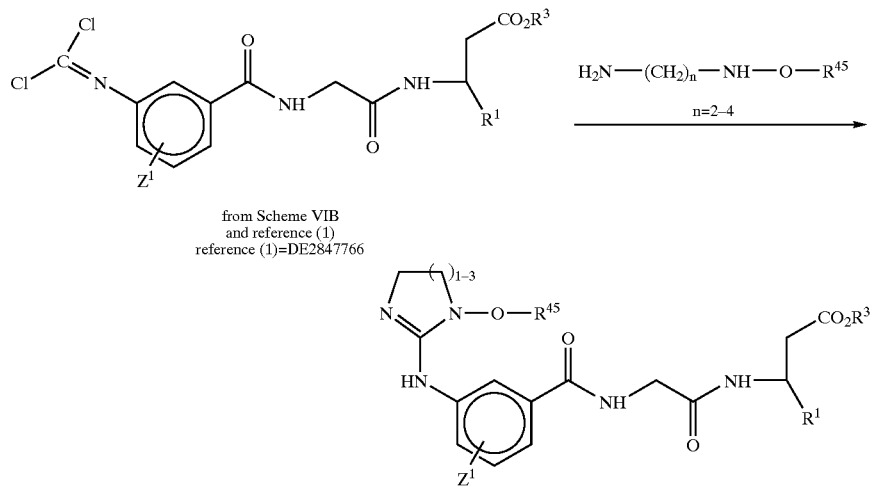

from Scheme VIB
and reference (1)
reference (1)=DE2847766

$R^{45}$ is H, alkyl, aryl or aralkyl

B.

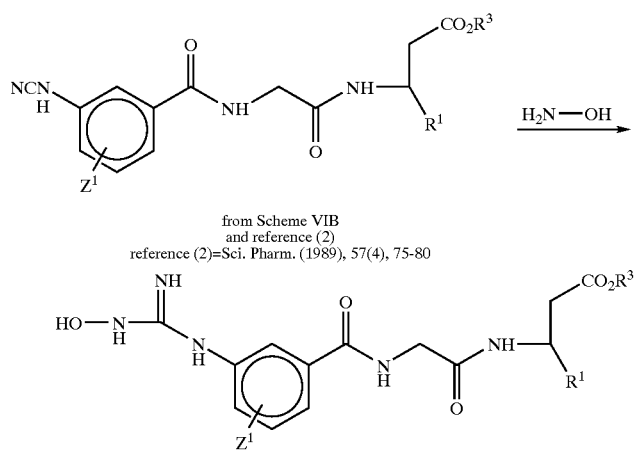

from Scheme VIB
and reference (2)
reference (2)=Sci. Pharm. (1989), 57(4), 75-80

Scheme XXI further illustrates examples of potential pro-drugs or active entities of compounds of the present invention.

In particular, Scheme XXI illustrates the synthesis of N-hydroxy or N-alkoxy analogues of cyclic and acyclic guanidine compounds.

The cited references provide synthetic details of the appropriate derivatization of the anilines exemplified in Scheme VIB.

EXAMPLE A
Preparation of benzyl-3-N-t-Boc-amino-4-hydroxy-(3S)-butyrate

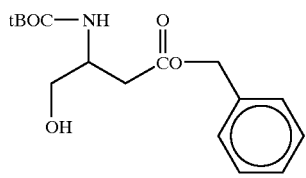

N-t-Boc-L-aspartic acid, β-benzyl ester (75 g, 20 mmol) was dissolved in THF (30 ml) and added dropwise over a period of 30 minutes to $BH_3$-THP (400 ml, 40 mmol) at 0° C. under a $N_2$ atmosphere. After the solution was stirred for 2.5 hours at 0° C., the reaction was quenched with 10% acetic acid in MeOH (50 ml), and the solvent was evaporated. The residue was dissolved in ether (200 ml) and washed with 1N HCl, saturated $K_2CO_3$, water and dried over $MgSO_4$. The product was isolated by removal of the solvent in vacuo (mp 56–57° C. from isopropyl ether/hexane). $^1$H-NMR ($d_6$-DMSO) δ 1.4 (s, 9H), 2.68 (d, 2H, J=6 Hz), 3.82 (d, 2H, J=5 Hz), 4.01 (m, 1H), 5.16 (s, 2H), 5.21 (bs, 1H), 7.37 (bs, 5H).

EXAMPLE B
Preparation of benzyl-3-amino-4-(anthranilate)-(3S)-butyrate

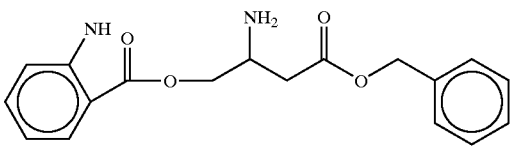

Benzyl-3-N-t-Boc-amino-4-hydroxy-(3S)-butyrate from Example A (10 g, 32 mmol) was dissolved in dimethylformamide (50 ml) followed by triethylamine (4.4 g, 46 mmol).

Isatoic anhydride (5.0 g, 3 mmol) was added and the solution was stirred for 24 hours at 25° C. After the reaction (monitored by RPHPLC) was complete, water was added and the product extracted with ethyl acetate (100 mL) and dried over Na$_2$SO$_4$. Upon evaporation of solvent 12 g of a yellow oil was obtained. To this oil, was added dioxane (20 mL) followed by 4N HCl in dioxane (20 mL). The reaction was left to proceed for 4 hours, ether was added and an oily mass separated from the solution. Ether was again added to the oily mass and decanted. This procedure was repeated two times. Ether was added to the semi solid and stirred vigorously for 16 hours. A white solid was obtained having MS and NMR consistent with the proposed structure.

EXAMPLE BB

Preparation of 3-nitrobenzoyl glycine

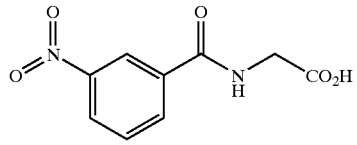

Glycine (20 g, 266 mmol) was added to water (200 mL), followed by potassium hydroxide (20 g, 357 mmol) and cooled to 0° C. in an ice bath. To this solution was added 3-nitrobenzoyl chloride (20 g, 108 mmol) in acetonitrile (20 mL) drop-wise over a 10 minute period. After the reaction was complete (3–4 hours) concentrated hydrochloric acid was added until pH=2 followed by saturated aqueous NaCl (75 mL). The product was filtered, washed with water and air dried (22 g, 90% yield). $^1$H-NMR (d$_6$-DMSO) δ, 3.92 (d, 2H, J=6.1), 7.9 (t, 1H, J=7.9), 8.3 (t, 1H, J=5.6), 8.35 (m, 2H), 8.69 (s, 1H), 9.25 (t, 1H, J=7.2 Hz). MS (FAB) m/e 231.0 (M+Li+).

Elemental Analysis; C$_9$H$_8$N$_2$O$_5$; Calc'd.: C, 45.89; H, 4.25; N, 9.92; Found: C, 45.97; H, 4.44; N, 10.11.

EXAMPLE C

Preparation of N-[2-[[(3-nitrophenyl)carbonyl] amino]-1-oxoethyl]-β-alanine, ethyl ester

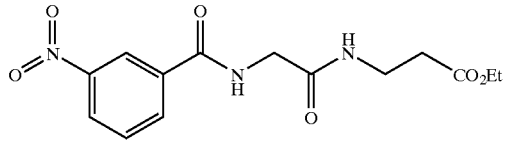

N,N'-Disuccinimidyl carbonate (14 g, 5.5 mmol) was added to 3-nitrobenzoyl glycine (10 g, 4.5 ml) of Example BB in dry dimethylformamide (30 mL) followed by N,N-dimethylaminopyridine (200 mg). After a period of 1 hour beta-alanine ethyl ester hydrochloride (7 g, 4.6 mmol) in 20% aqueous potassium carbonate (50 mL) was added in one portion. After complete reaction the product was collected by filtration (14 g, 97% yield). $^1$H-NMR (d$_6$-DMSO) δ, 1.18 (t, 3H, J=7.2 Hz), 2.46 (t, 2H, J=7.0), 3.34 (q, 2H, J$_1$=6.7 Hz, J$_2$=12.6 Hz), 3.87 (d, 2H, J=5.9 Hz), 4.05 (q, 2H, J$_1$=7.4 Hz, J$_2$=14.2 Hz), 7.8 (t, 1H, J=8.0 Hz), 8.1 (t, 1H, J=5.6 Hz), 8.35 (m, 2H), 8.71 (s, 1H), 9.22 (bs, 1H).

MS (FAB) m/e 324.2 (M+H+).

| Elemental Analysis | | | | |
|---|---|---|---|---|
| C$_{14}$H$_{17}$N$_3$O$_6$ H$_2$O | Calc'd.: | C, 49.26 | H, 4.99 | N, 12.32 |
| | Found: | C, 49.42 | H, 5.01 | N, 12.21 |

EXAMPLE D

Preparation of methyl 3-[[(cyanoimino)(methylthio) methyl]amino]benzoate

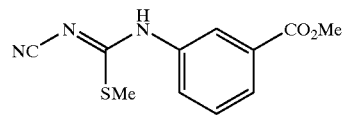

A stirred mixture of 3-aminomethylbenzoate (6.04 g, 40 mM) and dimethyl N-cyanodithioiminocarbonate (11.96 g, 80 mM) in pyridine (70 ml) was heated at reflux under a nitrogen atmosphere for 2.5 hours. The reaction mixture was cooled to room temperature. On standing overnight at room temperature the title compound crystallized from the reaction mixture affording 6.2 g (two crops). The title compound was used without further purification in the proceeding examples.

NMR was consistent with the proposed structure.

EXAMPLE E

Preparation of methyl 3-[[(cyanoimino) [(phenylmethyl)amino]methyl]amino]benzoate

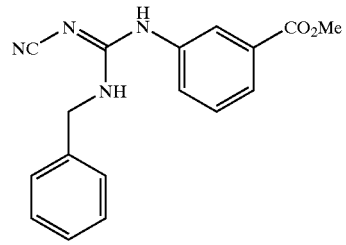

A stirred mixture of the compound from Example D (1.0 g) and benzylamine (440 mg) in ethanol (15 ml) was heated at reflux under a nitrogen atmosphere for 3 hours. The reaction mixture was cooled to room a temperature. On standing overnight at room temperature a white solid was obtained and isolated by filtration (720 mg). The crude filtrate was further purified by chromatography on silica (eluant; ethyl acetate/hexane, 1:1) to afford the title compound (550 mg) as a white solid.

NMR was consistent with the proposed structure.

EXAMPLE F

Preparation of methyl 3-[[(cyanoimino)(methylamino)methyl]amino]benzoate

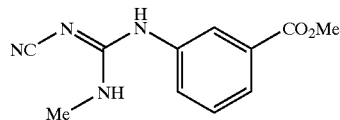

The title compound was prepared as described in Example E, replacing benzylamine with an equivalent amount of methylamine. The title compound was obtained as a white solid (55% yield).

NMR was consistent with the proposed structure.

EXAMPLE G

Preparation of methyl 3-[[amino(cyanoimino)methyl]amino]benzoate

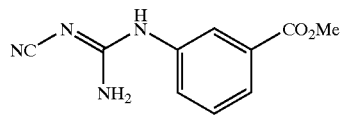

A mixture of the compound from Example D (1.0 g) and ammonium hydroxide (2 ml) in ethanol (20 ml) was heated at 70° in a sealed tube for 3.5 hours. The reaction mixture was cooled to room temperature and reduced to half its volume. After standing overnight at room temperature a white solid was obtained, which was isolated by filtration and washed with methanol. This afforded the title compound (389 mg) as a white solid.

NMR was consistent with the proposed structure.

EXAMPLE H

Preparation of methyl 3-[[(cyanoimino)(ethylamino)methyl]amino]benzoate

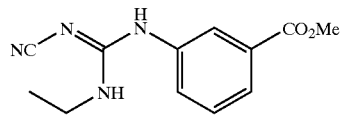

The reaction was carried out as described in Example G except ammonium hydroxide was replaced with an equivalent amount of ethyl amine. This afforded the title compound (78%) as a white solid.

NMR was consistent with the proposed structure.

EXAMPLE I

Preparation of 3-[[(cyanoimino)(phenylmethyl)amino]methyl]amino]benzoic acid

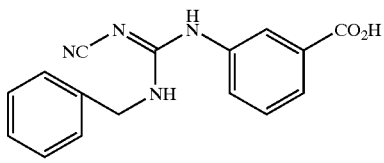

To a stirred solution of the compound from Example E (250 mg) in THF (2 ml) and MeOH (2 ml), 1N-NaOH (2 ml) was added. The reaction mixture was stirred at room temperature for 2 hours and concentrated in vacuo to afford a white solid. The residue was acidified by suspension in water followed by addition of 1N-HCl. The resultant solid was filtered, washed with diethyl ether and dried to afford the title compound (140 mg) which was used in subsequent examples without further purification.

NMR was consistent with the proposed structure.

EXAMPLE J

Preparation of 3-[[(cyanoimino)(methylamino)methyl]amino]benzoic acid

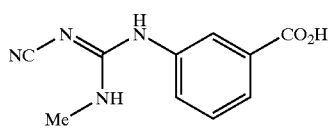

The title compound was prepared as described in Example I except the compound of Example E was replaced with an equivalent amount of the compound of Example F. This afforded the title compound (87%) as a white solid.

NMR was consistent with the proposed structure.

EXAMPLE K

Preparation of 3-[[amino(cyanoimino)methyl]amino]benzoic acid

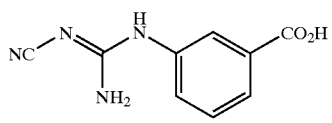

The title compound was prepared as described in Example I except that the compound of Example E was replaced with an equivalent amount of the compound of Example G. This afforded the title compound (92%) as a white solid.

NMR was consistent with the proposed structure.

EXAMPLE L

Preparation of 3-[[(cyanoimino)(ethylamino)methyl]amino]benzoic acid

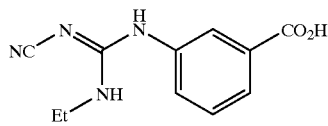

The title compound was prepared as described in Example I except that the compound of Example E was replaced with an equivalent amount of the compound of Example H. This afforded the title-compound (81%) as a white solid.

NMR was consistent with the proposed structure.

EXAMPLE M

Preparation of m-guanidinohippuric acid HCl

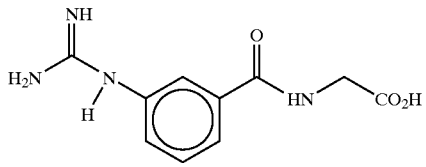

Step A

A solution of glycine (200 g) and KOH (200 g) in water (1000 ml) at 0° C. was treated dropwise with a solution of m-nitrobenzoyl chloride (100 g) in acetonitrile (100 ml). The reaction was allowed to wars to room temperature and was stirred for 4 hours. 12N aqueous HCl was added until pH<2. The reaction was allowed to stand overnight at room temperature. The resulting solid was filtered and washed with water (2×250 ml) and dried in vacuo at 60° C. 100 g of m-nitrohippuric acid was isolated. MS, $^1$H-NMR and CHN analysis were consistent with the desired product.

Step B

A suspension of m-nitrohippuric acid (50 g) and 5% Pd/C (5 g) in methanol (200 ml) was subjected to 50 psi of $H_2$. After 2 hours, the reaction was filtered. The resulting gray solid was washed with 2% aqueous HCl (2×250 ml). The yellowish solution was lyophilized to give m-aminohippuric acid HCl (30 g).

Step C

A mixture of m-aminohippuric acid HCl (10 g), NMM (12 ml) and 1H-pyrazole-1-carboxamidine HCl (8.3 g) in dioxane (80 ml) and water (20 ml) was refluxed for 6 hours. The heat was removed and the reaction cooled to room temperature. Saturated aqueous NaCl (10 ml) was added and the reaction mixture was filtered. The resulting solid was washed with dioxane (20 ml) followed by acetone (20 ml). The salmon color solid was dissolved in 1:1 $CH_3CN:H_2O$ and treated with 20% aqueous HCl (pH<3). The lyophilized solid, m-guanidinohippuric acid HCl (10 g), had MS, $^1$H-NMR and CHN analysis that were consistent with the desired product.

EXAMPLE N

Preparation of methyl 3-[[(cyanoimino)[(2-pyridinylmethyl)amino]methyl]amino]benzoate

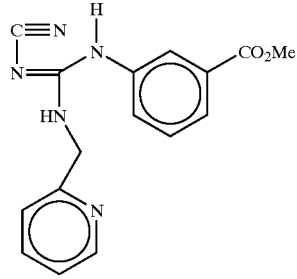

The title compound was prepared following the procedure described in Example E, replacing benzyl amine with an equivalent amount of 2-(aminomethyl)pyridine. The title compound was obtained as a white solid (75% yield).

NMR was consistent with proposed structure.

EXAMPLE O

Preparation of 3-[[(cyanoimino)[(2-pyridinylmethyl)amino]methyl]amino]benzoic acid

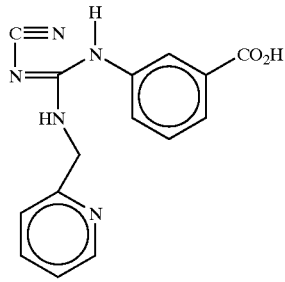

The title compound was prepared following the procedure described in Example I except that the compound of Example E was replaced with an equivalent amount of the compound of Example N. This afforded the title compound as a white solid (70% yield).

NMR was consistent with the proposed structure.

EXAMPLE P

Preparation of methyl 3-[[(cyanoimino)[(3-pyridinylmethyl)amino]methyl]amino]benzoate

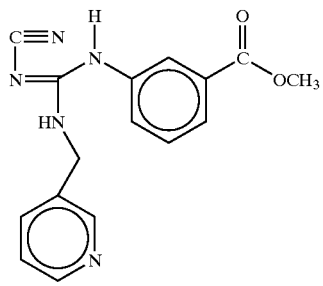

The title compound was prepared following the procedure described in Example E, replacing benzyl amine with an equivalent amount of 3-(aminomethyl)pyridine. The title compound was obtained as a white solid (70% yield).

NMR was consistent with the proposed structure.

EXAMPLE Q

Preparation of 3-[[(cyanoimino)[(3-pyridinylmethyl)amino]methyl]amino]benzoic acid

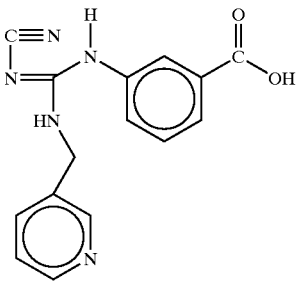

The title compound was prepared following the procedure described in Example I except that the compound of Example E was replaced with an equivalent amount of the compound of Example P. This afforded the title compound as a white solid (65% yield).

NMR was consistent with the proposed structure.

EXAMPLE R

Preparation of

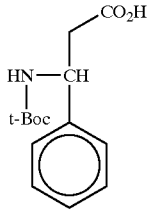

To a stirred solution of DL-3-amino-3-phenyl propionic acid (16.5 g, 0.1 M), dioxane (160 ml), water (40 ml), and triethylamine (25 ml) were added di-tert-butyl dicarbonate (18.6 g, 0.1 mole). The reaction mixture was stirred at room temperature for 16 hours. The reaction mixture was concentrated in vacuo to afford an oily gum which was dissolved in ethyl acetate. The resulting solution was washed with water, saturated NaCl and water. The organic layer was separated, dried ($Na_2SO_4$) and evaporated to afford the crude product (8.9 g), which was taken up in the next step (Example S) without further purification.

NMR was consistent with the proposed structure.

EXAMPLE S

Preparation of

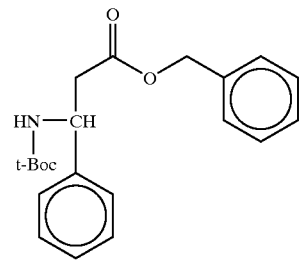

To a stirred solution of the compound from Example R (8.3 g, 30 mmole) in DMF (50 ml), $K_2CO_3$ (10 g) and benzyl bromide (5.7 g, 30 mmole) were added. The reaction mixture was stirred under a nitrogen atmosphere at room temperature for 16 hours. The reaction mixture was diluted with water (400 ml) and extracted with ethyl acetate. The organic layer was separated and washed with water, 5% $NaHCO_3$, water, dried ($Na_2SO_4$) and concentrated in vacuo to yield the crude ester (8.5 g). The title compound was used in the next step (Example T) without further purification.

NMR was consistent with the proposed structure.

EXAMPLE T

Preparation of

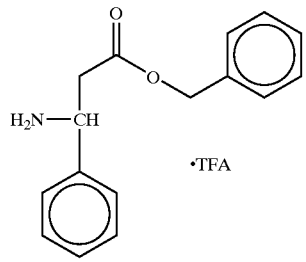

To a stirred solution of the compound from Example S (2.0 g) in methylene chloride (20 ml), trifluoroacetic acid (20 ml) was added and the reaction mixture was stirred at room temperature for 16 hours. The reaction mixture was concentrated in vacuo to afford 2.05 g of crude product, which was taken up in the next step (Example U) without further purification.

NMR was consistent with the proposed structure.

EXAMPLE U

Preparation of

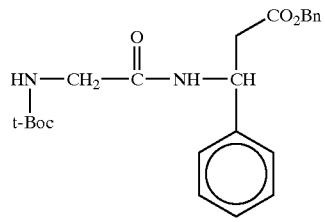

A stirred solution of N-t-Boc-Glycine (876 mg, 5 mmole), methylene chloride (20 ml), N-methylmorpholine (1.01 g) at 0° C., IBCF (690 mg) was added and the reaction mixture was stirred at 0° C. for 15 minutes. The product of Example T (1.845 g) was added to the reaction mixture at 0° C. The reaction mixture was warmed to room temperature and was stirred for a further 6 hours. The mixture was washed with water, followed by saturated sodium bicarbonate solution and water, dried ($Na_2SO_4$), and concentrated in vacuo to afford crude product (2.2 g). The crude product was purified through a flash column using 92.5:7:0.5/ $CHCl_3$:ethanol:$NH_4H$ as eluent to give the title compound (1.82 g) as an oil.

NMR spectrum was consistent with the proposed structure.

EXAMPLE V

Preparation of

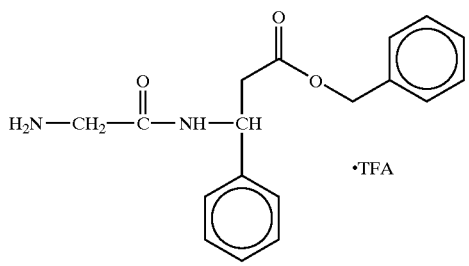

To a stirred solution of the product of Example U (1.8 g) and methylene chloride (20 ml) was added trifluoroacetic acid (12 ml), and the reaction mixture was stirred at room temperature for 16 hours. The mixture was concentrated in vacuo to afford crude product (1.7 g) as an oily gum, which was used in the next step (Example 132, Example 133, Example 134) without further purification.

NMR was consistent with the proposed structure.

EXAMPLE 1

Preparation of (±)ethyl β-[[2-[[[3-[(aminoiminomethyl)amino]phenyl]carbonyl]amino] acetyl]amino]pyridine-3-propanoate, bis (trifluoroacetate)salt

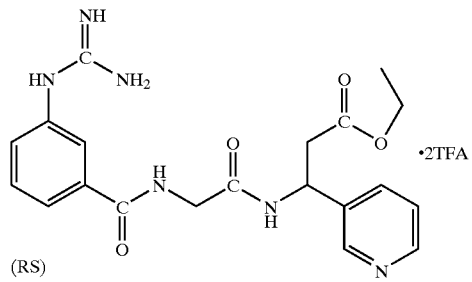

Step A

To 3-pyridine carboxaldehyde (300 ml) in 2-propanol (3 liters) was added ammonium acetate (297 g) followed by malonic acid (398 g). The reaction mixture was stirred at reflux for 5 hours. The precipitate was filtered while hot and washed with hot isopropanol (2 liters). The resulting white solid was then dried to yield DL-3-amino-3-(3-pyridyl) propionic acid (220 g) as a white solid.

NMR and MS were consistent with the desired product.

Step B

DL-3-amino-3-(3-pyridyl)propionic acid (220 g) from Step A was slurried in absolute EtOH (3.6 liters). HCl gas (one lecture bottle—½ lb) was bubbled into the reaction while stirring over 40 minutes (slow exotherm to 61° C.). The slurry was then heated at reflux for 4 hours (a solution forms after 1 to 1.5 hours). The reaction mixture was cooled to 5° C. in an ice bath. After stirring at 5° C. for 1.5 hours, the resulting white precipitate was filtered and washed thoroughly with ether. After drying under vacuum at 50° C., the yield of ethyl DL-3-amino-3-(3-pyridyl)propionate dihydrochloride was 331.3 g as a white solid.

NMR and MS were consistent with the desired product.

Step C

To ethyl DL-3-amino-3-(3-pyridyl)propionate dihydrochloride (220.6 g, 0.83 mole) from Step B in anhydrous THF (2 liters) and triethylamine (167.2 g, 1.65 moles), N-t-BOC-glycine N-hydroxysuccinimide ester (225 g, 0.826 moles) (Sigma) was added in several portions at 5–10° C. (no exotherm). The reaction mixture was stirred overnight at room temperature. The resulting precipitate was filtered and washed with THF. The solvent from the filtrate was then removed under vacuum. The residue was taken up in ethyl acetate (2.3 liters). The ethyl acetate layer was washed with saturated sodium bicarbonate (2×900 ml) and $H_2O$ (3×900 ml), dried over $MgSO_4$ and removed under vacuum. The residue was slurried overnight in 10% ethyl acetate/hexane (2.5 liters). The precipitate was filtered, washed with 10% ethyl acetate/hexane (1 liter), then hexane, then dried to yield ethyl β-[(2-[[2-[[(1,1-dimethylethoxy)carbonyl] amino]acetyl]amino]pyridine-3-propanoate (233 g) as a white solid.

NMR and MS were consistent with the desired structure.

Step D

Ethyl β-[[2-[[(1,1-dimethylethoxy)carbonyl]amino] acetyl]amino]pyridine-3-propanoate (from Step C) (232 g, 0.66 mole) was dissolved in warm dioxane (1 liter). After cooling to room temperature, 4M HCl in dioxane (1.6 liters) (Aldrich) was slowly added. A white precipitate formed after several minutes and then turned to a thick goo. After 2 hours, the solvent was decanted off. The goo was slurried in ether and the ether decanted off until a white solid resulted. This was dried under vacuum to yield ethyl β-[(2-aminoacetyl) amino]pyridine-3-propanoate, bis hydrochloride salt (224.2 g) as a white hygroscopic solid.

NMR and MS were consistent with the desired structure.

Step E

To 3,5-dimethylpyrazole-1-carboxamidine nitrate (6 g, 0.03 mole) (Aldrich) and diisopropylamine (3.8 g, 0.03 mole) in dioxane (20 ml) and $H_2O$ (10 ml) was added 3-aminobenzoic acid (2.7 g, 0.02 mole). The reaction was stirred at reflux for 2.5 hours then overnight at room temperature. The resulting precipitate was filtered, washed with dioxane/$H_2O$ and dried. The precipitate was then slurried in $H_2O$ and acidified with concentrated HCl until a solution formed. The solvent was removed under vacuum and the residue was slurried twice in ether (ether decanted off). The product was dried under vacuum to yield 3-quanidinobenzoic acid hydrochloride (1.77 g) as a white solid. MS and NMR were consistent with the desired structure.

Step F

To the product from Step B (0.49 g, 0.0023 mole) and N-methylmorpholine (0.23 g, 0.0023 mole) in anhydrous DMF (8 ml) was added isobutylchloroformate (0.31 g, 0.0023 mole) at ice bath temperature. After stirring for 5 minutes at ice bath temperature, a slurry of the product from Step D (0.73 g, 0.0023 mole) and N-methylmorpholine (0.46 g, 0.0045 mole) in anhydrous DMF (8 ml) was added in one portion. The reaction mixture was stirred overnight at room temperature. The solvent was removed under vacuum on a 78° C. water bath and the product was isolated by RPHPLC to yield (±)ethyl β-[[2-[[[3-[(aminoiminomethyl)amino]phenyl]carbonyl]amino]acetyl]amino]pyridine-3-propanoate, bis(trifluoroacetate)salt (800 mg) as a hygroscopic white solid. MS and NMR were consistent with the desired structure.

EXAMPLE 2

Preparation of (±)β-[[2-[[[3-[(aminoiminomethyl)amino]phenyl]carbonyl]amino]acetyl]amino]pyridine-3-propanoic acid, bis(trifluoroacetate)salt

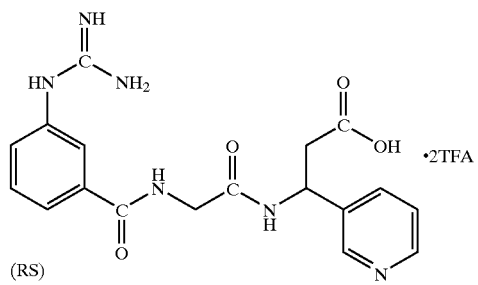

(RS)

To the product from Example 1 (700 mg, 0.001 mole), in $H_2O$ (20 ml) was added LiOH (160 mg, 0.0038 mole). The reaction mixture was stirred for 1 hour at room temperature. After lowering the pH to ≈5 with TFA, the product was isolated by RPHPLC to yield (±)β-[[2-[[[3-[(aminoiminomethyl)amino]phenyl]carbonyl]amino]acetyl]amino]pyridine-3-propanoic acid, bis(trifluoroacetate)salt (640 mg) as a white solid. MS and NMR were consistent with the desired structure.

EXAMPLE 3

Preparation of (±)ethyl β-[[2-[[[3-[(aminoiminomethyl)amino]phenyl]carbonyl]amino]acetyl]amino]benzenepropanoate, trifluoroacetate salt

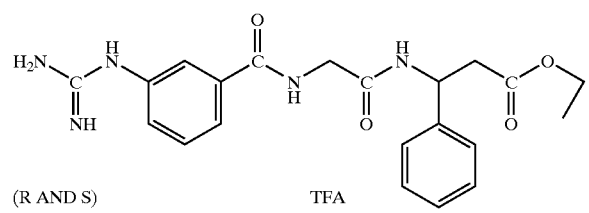

(R AND S)  TFA

The above compound was prepared according to the methodology of Example 1, substituting an equivalent amount of benzaldehyde for 3-pyridinecarboxaldehyde in Step A.

NMR and MS were consistent with the desired structure.

EXAMPLE 4

Preparation of (±)β-[[2-[[[3-[(aminoiminomethyl)amino]phenyl]carbonyl]amino]acetyl]amino]benzene-propanoic acid, trifluoroacetate salt

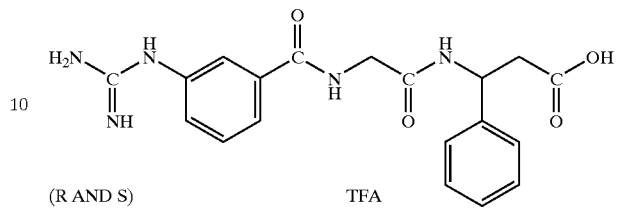

(R AND S)  TFA

To the product of Example 3 (0.37 g, 0.0007 mole) in $H_2O$ (10 ml) was added LiOH (80 mg, 0.002 mole). The reaction mixture was stirred at room temperature for 1 hour. The pH was lowered to ≈3 with TFA and the product was isolated by RPHPLC to yield β-[[2-[[[3-[(aminoiminomethyl)amino]phenyl]carbonyl]amino]acetyl]amino]benzenepropanoic acid, trifluoroacetate salt (280 mg) as a white solid. MS and NMR were consistent with the desired structure.

EXAMPLE 5

Preparation of (±)ethyl β-[[2-[[[3-[(aminoiminomethyl)amino]phenyl]carbonyl]amino]acetyl]amino]-1,3-benzodioxole-5-propanoate, trifluoroacetate salt

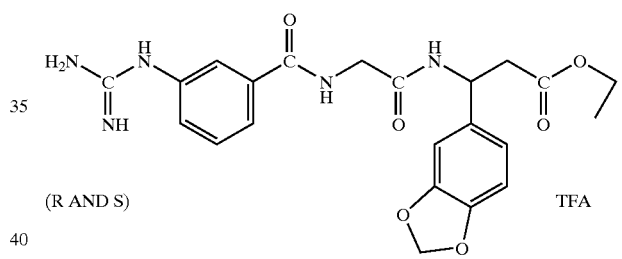

(R AND S)  TFA

The above compound was prepared according to the methodology of Example 1, substituting the equivalent amount of piperonal (Aldrich) for 3-pyridinecarboxaldehyde in Step A.

MS and NMR were consistent with the desired structure.

EXAMPLE 6

Preparation of (±)β-[[2-[[[3-[(aminoiminomethyl)amino]phenyl]carbonyl]amino]acetyl]amino]-1,3-benzodioxole-5-propanoic acid, trifluoroacetate salt

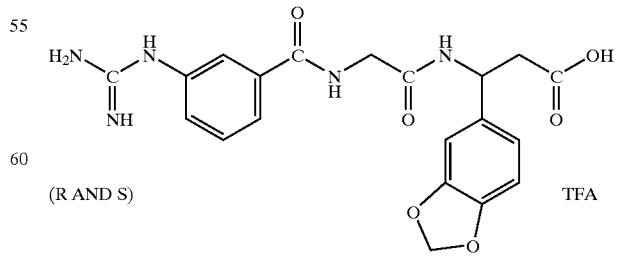

(R AND S)  TFA

To the product of Example 5 (0.35 g, 0.0006 mole) in $H_2O$ (40 ml) and $CH_3CN$ (5 ml) was added LiOH (70 mg, 0.0017 mole). The reaction mixture was stirred at room temperature for 1 hour. The pH was lowered to ≈4.5 with TFA and the product was isolated by RPHPLC to yield (±)β-[[2-[[[3-[(aminoiminomethyl)amino]phenyl]carbonyl]amino]acetyl]amino]-1,3-benzodioxole-5-propanoic acid, trifluoroacetate salt (280 mg) as a white solid. MS and NMR were consistent with the desired structure.

EXAMPLE 7

Preparation of (±)ethyl β-[[2-[[[3-[(aminoiminomethyl)amino]naphthalen-1-yl]carbonyl]amino]acetyl]amino]pyridine-3-propanoate, bis(trifluoroacetate)salt

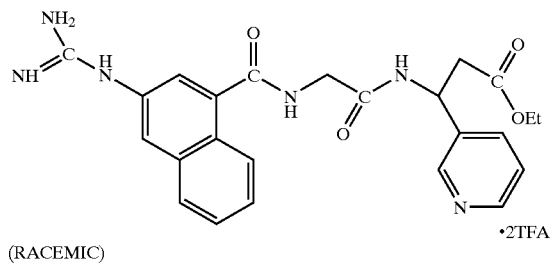

(RACEMIC)

Step A

To methyl 3-nitro-1-naphthoate (2.5 g, 0.011 mole) (Aldrich) in MeOH/H₂O (40 ml) (1:1) was added LiOH (1.8 g, 4 equivalents). The solution was stirred overnight at room temperature. The solvent was removed under a stream of N₂. The residue was dissolved in H₂O and the solution acidified with concentrated HCl. The resulting precipitate was filtered, washed with H₂O and dried to yield 3-nitro-1-naphthoic acid (2.18 g) as a white solid.

Step B

3-Nitro-1-naphthoic acid (1.77 g, 0.008 mole) was dissolved in a minimum of warm MeOH. 10% Pd/C (300 mg) was added and the reaction shaken on a Parr shaker under 50 psi H₂ for 5 hours. The catalyst was filtered through celite and the solvent was removed under vacuum. The residue was dried to yield 3-amino-1-naphthoic acid (1.43 g) as a pink colored solid.

Step C

To 3,5-dimethylpyrazole-1-carboxamidine nitrate (1.6 g, 0.008 mole) (Aldrich) and diisopropylethylamine (1.02 g, 0.008 mole) in dioxane (5 ml) and H₂O (2.5 ml) was added 3-amino-1-naphthoic acid (1 g, 0.0053 mole). The reaction mixture was stirred at reflux overnight. The reaction was cooled to room temperature and the precipitate was filtered, washed with dioxane/H₂O then dried. The precipitate was then slurried in H₂O and acidified with concentrated HCl. The solvent was removed under vacuum on a 70° C. water bath. The residue was slurried in ether 3× (ether decanted off), then dried under vacuum to yield 3-guanidino-1-naphthoic acid hydrochloride (460 mg) as a white solid.

Step D

To 3-guanidino-1-naphthoic acid hydrochloride (400 mg, 0.0015 mole) and N-methylmorpholine (150 mg) in anhydrous DMF (8 ml) was added isobutylchloroformate (210 mg) at ice bath temperature. After stirring at ice bath temperature for 5 minutes, a slurry of the product from Example 1, Step D (490 mg, 0.0015 mole), N-methylmorpholine (300 mg) and anhydrous DMF (6 ml) was added in one portion. The reaction mixture was stirred overnight at room temperature. The solvent was removed under vacuum on a 78° C. water bath. The product was isolated by RPHPLC to yield (±)ethyl β-[[2-[[[1-[(aminoiminomethyl)amino]naphthalen-3-yl]carbonyl]amino]acetyl]amino]pyridine-3-propanoate, bis(trifluoroacetate)salt (410 mg) as a white solid.

NMR and MS were consistent with the desired structure.

EXAMPLE 8

Preparation of (±)β-[[2-[[[3-[(aminoiminomethyl)amino]naphthalen-1-yl]carbonyl]amino]acetyl]amino]pyridine-3-propanoic acid, bis(trifluoroacetate)salt

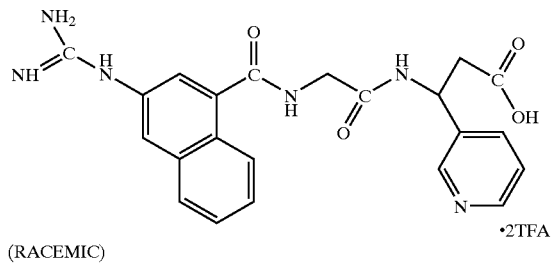

(RACEMIC)

To the product of Example 7, Step D (280 mg, 0.0004 mole) in H₂O (15 ml) and CH₃CN (2 ml) was added (70 mg, 0.0016 mole) LiOH. The reaction mixture was stirred at room temperature for 1 hour. The pH was lowered to 5 with TFA and the product was isolated by RPHPLC to yield (±)β-[[2-[[[1-[(aminoiminomethyl)amino]naphthalen-3-yl]carbonyl]amino]acetyl]amino]pyridine-3-propanoic acid, bis(trifluoroacetate)salt (240 mg) as a hygroscopic white solid. MS and NMR were consistent with the desired structure.

EXAMPLE 9

Preparation of (±)ethyl β-[[2-[[[3-[(4,5-dihydro-1H-imidazol-2-yl)amino]phenyl]carbonyl]amino]acetyl]amino]pyridine-3-propanoate, bis(trifluoroacetate) salt

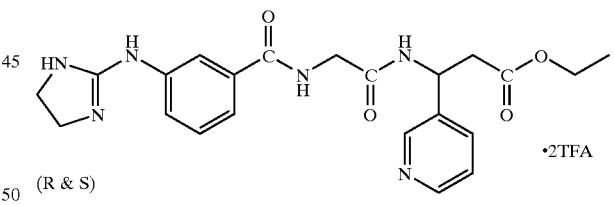

(R & S)

Step A

To 2-methylthio-2-imidazoline hydroiodide (14.6 g, 0.06 mole) (Aldrich) and diisopropylethylamine (7.6 g, 0.06 mole) in dioxane (40 ml) and H₂O (20 ml) was added 3-aminobenzoic acid (5.4 g, 0.04 mole). The reaction was stirred overnight at reflux. The solution was cooled in an ice bath and the resulting precipitate was filtered and washed with dioxane. The crude product was purified by RPHPLC to yield 3-(2-aminoimidazoline)benzoic acid (800 mg).

Step B

To the product from Step A (400 mg, 0.00125 mole) and N-methylmorpholine (130 mg, 0.00125 mole) in anhydrous DMF (8 ml) was added isobutylchloroformate (170 mg, 0.00125 mole). After stirring at ice bath temperature for 5 minutes, the product from Example 1, Step D (410 mg, 0.00125 mole) and N-methylmorpholine (250 mg, 0.0025 mole) in anhydrous DMF (6 ml) was added in one portion. The reaction mixture was stirred overnight at room temperature. The solvent was removed under vacuum on a 79° C. water bath and the product was isolated by RPHPLC to yield (±)ethyl β-[[2-[[[3-[(4,5-dihydro-1H-imidazol-2-yl)amino]phenyl]carbonyl]amino]acetyl]amino]pyridine-3-propanoate, bis(trifluoroacetate)salt (600 mg) as a hygroscopic white solid. MS and NMR were consistent with the desired structure.

EXAMPLE 10

Preparation of (±)β-[[2-[[[3-[(4,5-dihydro-1H-imidazol-2-yl)amino]phenyl]carbonyl]amino]acetyl]amino]pyridine-3-propanoic acid, bis(trifluoroacetate)salt

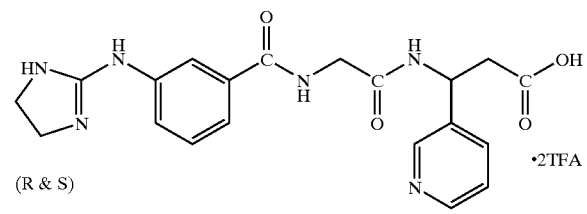

(R & S)

To the product of Example 9, Step B (450 mg, 0.00068 mole) in H$_2$O (20 ml) was added LiOH (110 mg, 0.0027 mole). The reaction mixture was stirred at room temperature for 1 hour. The pH was lowered to 5 with TFA and the product was isolated by RPHPLC to yield (±)β-[[2-[[[3-[(4,5-dihydro-1H-imidazol-2-yl)amino]phenyl]carbonyl]amino]acetyl]amino]-pyridine-3-propanoic acid, bis(trifluoroacetate)salt (250 mg) as a hygroscopic white solid. MS and NMR were consistent with the desired structure.

EXAMPLE 11

Preparation of (±)ethyl β-[[2-[[[3-[(3,4,5,6-tetrahydro-2H-azepin-7-yl)amino]phenyl]carbonyl]amino]acetyl]amino]pyridine-3-propanoate, bis(trifluoroacetate)salt

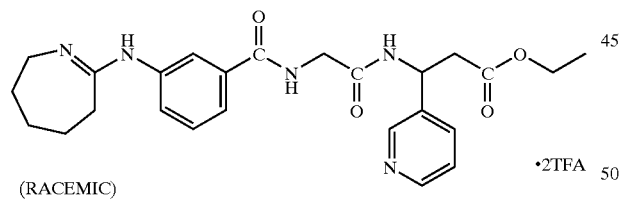

(RACEMIC)

Step A

To 1-aza-2-methoxy-1-cycloheptene (3.67 g, 0.0288 mole) (Aldrich) in absolute ethanol (20 ml) was added 3-aminobenzoic acid hydrochloride (5 g, 0.0288 mole). A solution quickly formed. The reaction mixture was stirred overnight at room temperature. The resulting precipitate was filtered, washed with ether and dried under vacuum to yield 3-(1-aza-2-amino-1-cycloheptene)benzoic acid (4.9 g).

Step B

To the product from Step A (0.5 g, 0.0019 mole) and N-methylmorpholine (0.19 g, 0.0019 mole) in anhydrous DMF (8 ml) was added isobutylchloroformate (0.25 g, 0.0019 mole) at ice bath temperature. After stirring at ice bath temperature for 5 minutes, a slurry of the product from Example 1, Step D (0.6 g, 0.0019 mole) and N-methylmorpholine (0.38 g, 0.0037 mole) in anhydrous DMF (7 ml) was added in one portion. The reaction mixture was stirred overnight at room temperature. The solvent was removed under vacuum on a 78° C. water bath and the product was isolated by RPHPLC to yield the title compound (490 mg). NMR and MS were consistent with the desired structure.

EXAMPLE 12

Preparation of (±)β-[[2-[[[3-[(3,4,5,6-tetrahydro-2H-azepin-7-yl)amino]phenyl]carbonyl]amino]acetyl]amino]pyridine-3-propanoic acid, bis(trifluoroacetate)salt

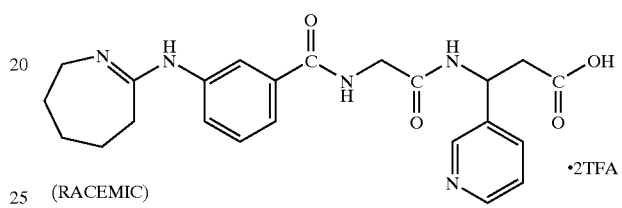

(RACEMIC)

To the product of Example 11, Step B (400 mg, 0.00058 mole) in H$_2$O (20 ml) was added LiOH (80 mg, 0.0019 mole). The reaction mixture was stirred at room temperature for 1 hour. The pH was lowered to 4.5 with TFA and the product was isolated by RPHPLC to yield 320 mg of (±)β-[[2-[[[3-[(3,4,5,6-tetrahydro-2H-azepin-7-yl)amino]phenyl]carbonyl]amino]acetyl]amino]pyridine-3-propanoic acid, bis(trifluoroacetate)salt as a white solid. MS and NMR are consistent with the desired structure.

EXAMPLE 13

Preparation of (±)ethyl β-[[2-[[[3-[(3,4,5,6-tetrahydro-2H-azepin-7-yl)amino]phenyl]carbonyl]amino]acetyl]amino]-1,3-benzodioxole-5-propanoate, TFA salt

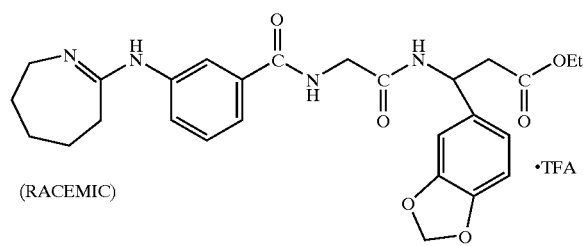

(RACEMIC)

The above compound was prepared according to the methodology of Example 11, substituting the equivalent amount of piperonal (Aldrich) for 3-pyridinecarboxaldehyde in Example 1, Step A, in Example 11, Step B.

MS and NMR were consistent with the desired structure.

EXAMPLE 14

Preparation of (±)β-[[2-[[[3-[(3,4,5,6-tetrahydro-2H-azepin-7-yl)amino]phenyl]carbonyl]amino]acetyl]amino]-1,3-benzodioxole-5-propanoic acid, TFA salt

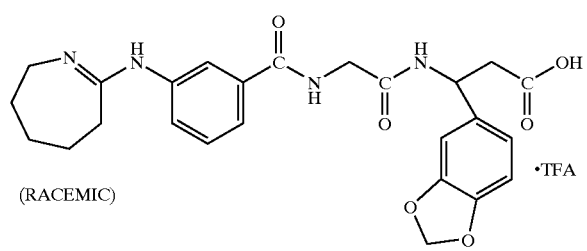

(RACEMIC)

To the product of Example 13 (0.46 g, 0.00091 mole) in H$_2$O (10 ml) and dioxane (7.5 ml) was added LiOH (80 mg, 0.0018 mole). The reaction was stirred at room temperature for 2 hours. The pH was lowered to 5 with TFA and the product was isolated by RPHPLC to yield (±)β-[[2-[[[3-[(3,4,5,6-tetrahydro-2H-azepin-7-yl)amino]phenyl]carbonyl]amino]acetyl]amino]-1,3-benzodioxole-5-propanoic acid (440 mg) as a white solid. MS and NMR were consistent with the desired structure.

EXAMPLE 15

Preparation of (±)β-[[2-[[[3-[(3,4,5,6-tetrahydro-2H-azepin-7-yl)amino]phenyl]carbonyl]amino]acetyl]amino]benzenepropanoic acid, trifluoroacetate salt

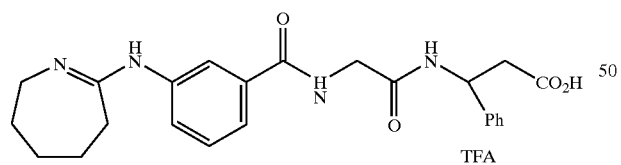

The above compound was prepared according to the methodology of Example 12, substituting the equivalent amount of benzaldehyde for 3-pyridinecarboxaldehyde in Example 1, Step A, and further used in Example 1, Step D as described in Example 11, Step B.

MS and NMR were consistent with the desired structure.

EXAMPLE 16

Preparation of (±)ethyl β-[[2-[[[3-[(3,4-dihydro-2H-pyrrol-5-yl)amino]phenyl]carbonyl]amino]acetyl]amino]pyridine-3-propanoate, bis(trifluoroacetate) salt

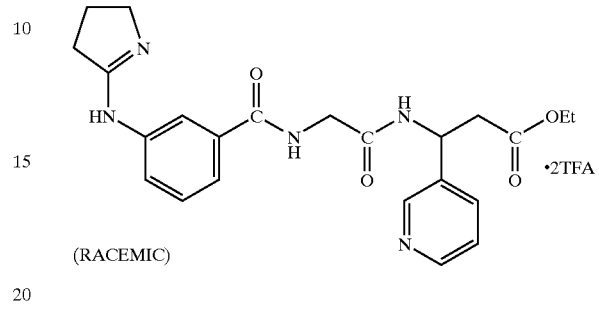

(RACEMIC)

The above compound was prepared according to the methodology of Example 11, substituting 1-aza-2-methoxy-1-cyclopentene* for 1-aza-2-methoxy-1-cycloheptene in Step A. MS and NMR were consistent with the desired structure.

* 1-aza-2-methoxy-1-cyclopentene was made as follows: To 2-pyrrolidinone (2.7 g, 0.033 mole) in CH$_2$Cl$_2$ (100 ml) was added trimethyloxonium tetrafluoroborate (10 g) (Aldrich). The reaction was stirred at room temperature for 2 days. Saturated NaHCO$_3$ was added and after shaking in a separatory funnel, the CH$_2$Cl$_2$ was separated and distilled off. 1 g of desired product was isolated by further distillation at atmospheric pressure collecting the portion boiling at ≈120° C.

EXAMPLE 17

Preparation of β-[[2-[[[3-[(3,4-dihydro-2H-pyrrol-5-yl)amino]phenyl]carbonyl]amino]acetyl]amino]pyridine-3-propanoic acid, bis(trifluoroacetate)salt

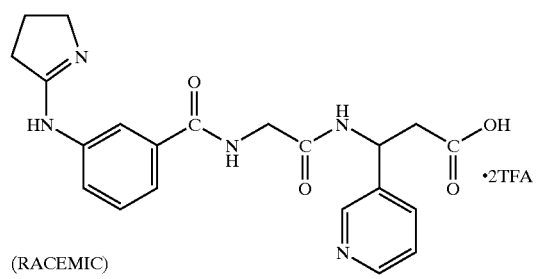

(RACEMIC)

To the product of Example 16 (380 mg, 0.00057 mole) in H$_2$O (15 ml) was added LiOH (100 mg, 0.002 mole). The reaction was stirred at room temperature for 2 hours. The pH was lowered to 5 with TFA and the product was isolated by RPHPLC to yield β-[[2-[[[3-[(3,4-dihydro-2H-pyrrol-5-yl)amino]phenyl]carbonyl]amino]acetyl]amino]pyridine-3-propanoic acid, bis(trifluoroacetate)salt (150 mg) as a white solid. MS and NMR were consistent with the desired structure.

EXAMPLE 18

Preparation of (±)ethyl β-[[1-[[[3-[(aminoiminomethyl)amino]phenyl]carbonyl]amino)-1-cyclopropyl]carbonyl]amino]pyridine-3-propanoate, bis(trifluoroacetate)salt

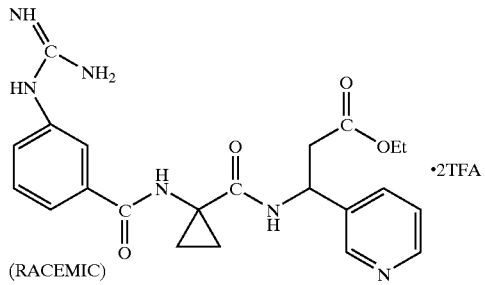
(RACEMIC)

The above compound was prepared according to the methodology of Example 1, substituting an equivalent amount of 1-(N-t-Boc-amino)cyclopropane-N-hydroxysuccinimide carboxylate (Sigma) for N-t-BOC-glycine N-hydroxysuccinimide ester in Example 1, Step C. MS and NMR were consistent with the desired structure.

EXAMPLE 19

Preparation of β-[[1-[[[3-[(aminoiminomethyl)amino]phenyl]carbonyl]amino]cycloprop-1-yl]carbonyl]amino]pyridine-3-propanoic acid, bis(trifluoroacetate)salt

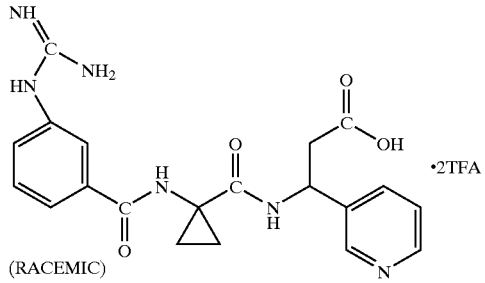
(RACEMIC)

To the product of Example 18 (220 mg, 0.00033 mole) in H$_2$O (15 ml) was added LiOH (60 mg, 0.0013 mole). The reaction was stirred at room temperature for 1.5 hours. The pH was lowered to 3 with TFA and the product was isolated by RPHPLC to yield β-[[1-[[[3-[(aminoiminomethyl)amino]phenyl]carbonyl]amino]cycloprop-1-yl]carbonyl]amino]pyridine-3-propanoic acid, bis(trifluoroacetate)salt (170 mg) as a white solid. MS and NMR were consistent with the desired structure.

EXAMPLE 20

Preparation of (±)ethyl β-[[2-[[[4-chloro-3-[(3,4,5,6-tetrahydro-2H-azepin-7-yl)amino]phenyl]carbonyl]amino]acetyl]amino]pyridine-3-propanoate, bis TFA salt

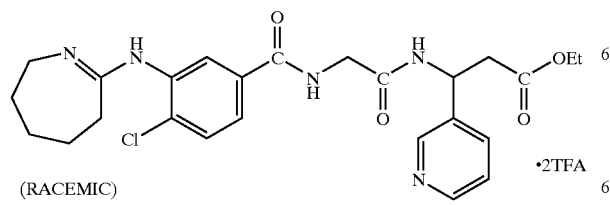
(RACEMIC)

The above compound was prepared according to the methodology of Example 11, substituting an equivalent amount of 3-amino-4-chloro-benzoic acid hydrochloride (Aldrich) for 3-amino-benzoic acid hydrochloride in Example 11, Step A. MS and NMR were consistent with the desired structure.

EXAMPLE 21

Preparation of (±)β-[[2-[[[4-chloro-3-[(3,4,5,6-tetrahydro-2H-azepin-7-yl)amino]phenyl]carbonyl]amino]acetyl]amino]pyridine-3-propanoic acid, bis TFA Salt

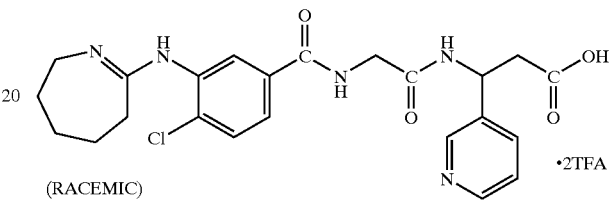
(RACEMIC)

To the product of Example 20 (150 mg, 0.0002 mole) in H$_2$O (15 ml) was added LiOH (40 mg, 0.0008 mole). The reaction was stirred at room temperature for 1 hour. The pH was lowered to 3 with TFA and the product was isolated by RPHPLC to yield (±)β-[[2-[[[4-chloro-3-[(3,4,5,6-tetrahydro-2H-azepin-7-yl)amino]phenyl]carbonyl]amino]acetyl]amino]pyridine-3-propanoic acid (100 mg) as a white solid. MS and NMR were consistent with the desired structure.

EXAMPLE 22

Preparation of (±)β-[[2-[[[3,5-bis[(3,4,5,6-tetrahydro-2H-azepin-7-yl)amino]phenyl]carbonyl]amino]acetyl]amino]pyridine-3-propanoic acid, tris(trifluoroacetate)salt

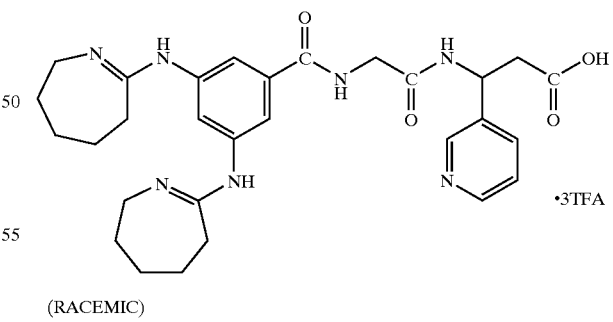
(RACEMIC)

The above compound was prepared according to the methodology of Example 12, substituting an equivalent amount of 3,5-diaminobenzoic acid dihydrochloride (0.3 equivalents) (Fluka) for 3-aminobenzoic acid hydrochloride in Example 11, Step A. MS and NMR were consistent with the desired structure.

EXAMPLE 23

Preparation of (±)ethyl β-[[2-[[[3-[[imino[(phenylmethyl)amino]methyl]amino]phenyl]carbonyl]amino]acetyl]amino]pyridine-3-propanoate, bis(trifluoroacetate)salt

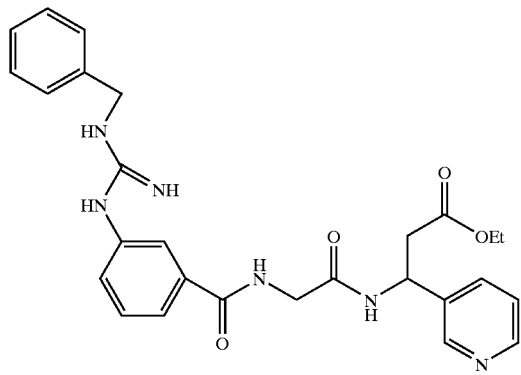

Step A 1-(3-Carboxyphenyl)-2-thiourea (5 g, 0.025 mole) (Trans World Chemicals) in THF (75 ml) and CH₃I (3.62 g, 0.025 mole) were stirred at reflux for 2 hours. The solvent was removed under vacuum and the residue was slurried in ether (3×), (the ether decanted off each time) to yield, after drying under vacuum, N-(3-carboxyphenyl)-S-methylisothiouronium hydroiodide (7.8 g) as a yellow solid.

Step B

To the product of Step A (1.5 g, 0.0044 mole) and diisopropylethylamine (0.57 g, 0.0044 mole) in H₂O (5 ml) and dioxane (5 ml) was added benzylamine (0.48 g, 0.0044 mole). The reaction mixture was heated at reflux for 6 hours. The reaction was cooled to room temperature and a precipitate formed. Dioxane (6 ml) was added and the slurry was stirred overnight at room temperature. The precipitate was filtered, washed with dioxane/H₂O, dried, slurried in 20, and acidified with concentrated HCl. The solvent was removed under vacuum and the residue was slurried in ether (3×; ether decanted off each time). After drying, 1-(3-carboxyphenyl)-2-benzylguanidine hydrochloride (800 mg) was isolated as a white solid. MS and NMR were consistent with the desired structure.

Step C

The title compound was prepared according to Example 1, Step F, substituting an equivalent amount of the product from Step B above for the product from Example 1, Step E in Step F. MS and NMR were consistent with the desired structure.

EXAMPLE 24

Preparation of (±)β-[[2-[[[3-[[imino[(phenylmethyl)amino]methyl]amino]phenyl]carbonyl]amino]acetyl]amino]pyridine-3-propanoic acid, bis(trifluoroacetate)salt

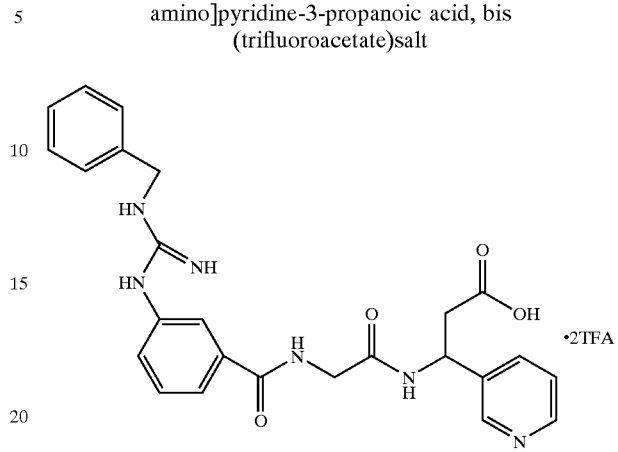

To the product of Example 23, Step C (330 mg, 0.00045 mole) in H₂O (20 ml) was added LiOH (80 mg). The reaction was stirred at room temperature for 1 hour. The pH was lowered to 3 with TFA and the product was isolated by RPHPLC to yield (±)β-[[2-[[[3-[[imino[(phenylmethyl)amino]methyl]amino]phenyl]carbonyl]amino]acetyl]amino]pyridine-3-propanoic acid, bis(trifluoroacetate)salt (330 mg) as a white solid. MS and NMR were consistent with the desired structure.

EXAMPLE 25

Preparation of (±)ethyl β-[[2-[[[3-[(iminophenylmethyl)amino]phenyl]carbonyl]amino]acetyl]amino]pyridine-3-propanoate, bis(trifluoroacetate)salt

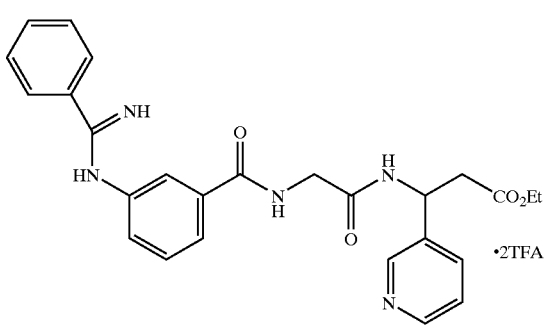

Step A

To ethyl benzimidate hydrochloride (3 g, 0.016 mole) (Fluka) and (2.1 g, 0.016 mole) diisopropylethylamine in H₂O (15 ml) and dioxane (15 ml) was added 3-aminobenzoic acid (2.22 g, 0.016 mole) (Aldrich). The reaction mixture was stirred at room temperature for 4 days. The resulting precipitate was filtered, washed with dioxane/H₂O and dried. The precipitate was slurried in H₂O and acidified with concentrated HCl. The solvent was removed under vacuum and the residue was slurried in ether. The ether was decanted off and the residue dried under vacuum to yield N-(3-carboxyphenyl)benzamidine hydrochloride (700 mg) as a white solid. MS and NMR were consistent with the desired structure.

Step B

The title compound was prepared according to the methodology of Example 1, Step P, substituting an equivalent amount of the product from Step A above for the product from Example 1, Step E in Step F. MS and NMR were consistent with the desired structure.

EXAMPLE 26

Preparation of (±)β-[[2-[[[3-[(iminophenylmethyl)amino]phenyl]carbonyl]amino]acetyl]amino]pyridine-3-propanoic acid, bis(trifluoroacetate)salt

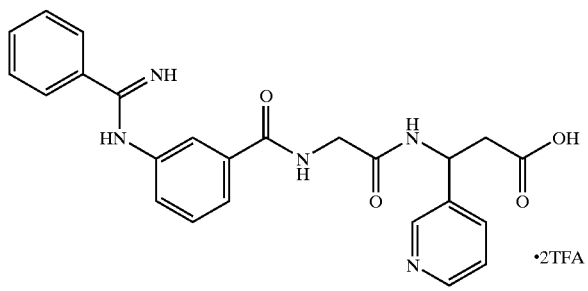

To the product of Example 25, Step B (240 mg, 0.0034 mole) in H₂O (20 ml) was added LiOH (50 mg). The reaction mixture was stirred at room temperature for 35 minutes. The pH was lowered to 3 with TFA and the product was isolated by RPHPLC to yield (±)β-[[2-[[[3-[(iminophenylmethyl)amino]phenyl]carbonyl]amino]acetyl]amino]pyridine-3-propanoic acid, bis(trifluoroacetate) salt (120 mg) as a white solid. MS and NMR were consistent with the desired structure.

EXAMPLE 27

Preparation of β-[[2-[[[3-[(aminoiminomethyl)amino]phenyl]carbonyl]amino]acetyl]amino]-3,5-dichlorobenzenepropanoic acid, trifluoroacetate salt

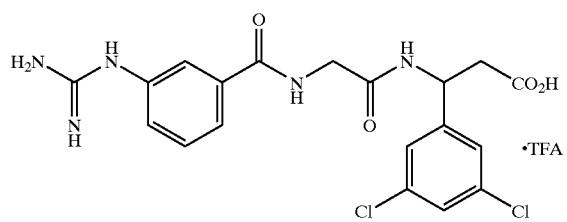

The above compound was prepared according to the method of Example 2 substituting an equivalent amount of 3,5-dichlorobenzaldehyde (Aldrich) for 3-pyridinecarboxaldehyde in Example 1, Step A.

EXAMPLE 30

Preparation of βS-[[2-[[[3-[(3,4,5,6-tetrahydro-2H-azepin-7-yl)amino]phenyl]carbonyl]amino]acetyl]amino]-4-pentynoic acid, trifluoroacetate salt

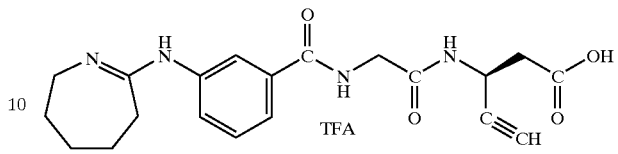

The above compound was prepared according to the method of Example 12, substituting an equivalent amount of ethyl 3-S-amino-4-pentynoate hydrochloride (J. Med. Chem. 1995, 38, 3378–2394) for ethyl DL-3-amino-3-(3-pyridyl)propionate dihydrochloride in Example 1, Step C and further used in Example 1, Step D as described in Example 11, Step B.

EXAMPLE 134

Preparation of βS-[[2-[[[3-[[imino(1-pyrrolidinyl)methyl]amino]phenyl]carbonyl]amino]acetyl]amino]-4-pentynoic acid, trifluoroacetate salt

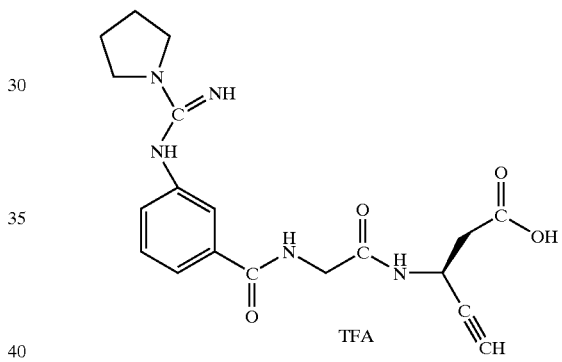

The above compound was prepared according to methodology of Example 24, substituting an equivalent amount of pyrrolidine for benzylamine in Example 23, Step B and an equivalent amount of ethyl 3-S-amino-4-pentynoate hydrochloride for ethyl DL-3-amino-3-(3-pyridyl)propionate dihydrochloride in Example 1, Step C and further used in Example 1, Step D as described in Example 23, Step C.

EXAMPLE 35

Preparation of βS-[[2-[[[3-[(aminoiminomethyl)amino]-2,5,6-trifluorophenyl]carbonyl]amino]acetyl]amino]-4-pentynoic acid, trifluoroacetate salt

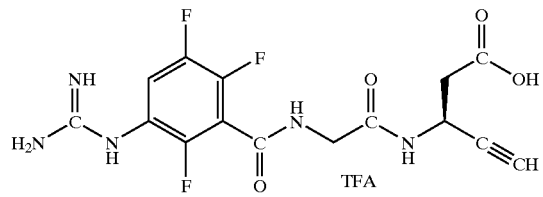

The above compound was prepared according to the methodology of Example 2, substituting an equivalent amount of ethyl 3-S-amino-4-pentynoate hydrochloride for ethyl DL-3-amino-3-(3-pyridyl)propionate dihydrochloride in Example 1, Step C and substituting an equivalent amount of 3-amino-2,5,6-trifluorobenzoic acid for 3-aminobenzoic acid in Example 1, Step E.

EXAMPLE 36

Preparation of (±)β-[[2-[[[3-[(aminoiminomethyl)amino]phenyl]carbonyl]amino]acetyl]amino]-3,5-bis(trifluoromethyl)benzenepropanoic acid, trifluoroacetate salt

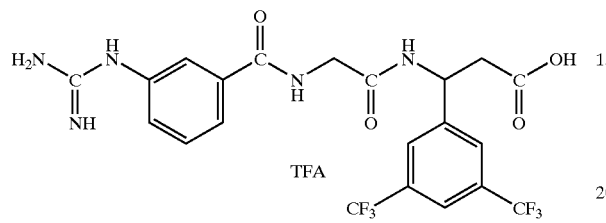

Step A
Preparation of ethyl(±)β-[[2-[[[3-[(aminoiminomethyl)amino]phenyl]carbonyl]amino]acetyl]amino]-3,5-bis(trifluoromethyl)benzenepropanoate.

The above compound was prepared according to the methodology of Example 1, substituting the equivalent amount of 3,5-bis-trifluoromethylbenzaldehyde (Aldrich) for 3-pyridinecarboxaldehyde in Step A.

NMR and mass spectrometry were consistent with the desired structure.

Step B
To 260 mg (0.00039 mole) of the product of Step A above in H$_2$O (25 ml) and CH$_3$CN (10 ml) was added LiOH (41 mg, 0.00098 mole). The reaction was stirred at room temperature for 1 hour. The pH was lowered to 3 with TFA and the product was isolated by reverse phase prep HPLC to yield (after lyophilization) 210 mg of the title compound as a white solid.

NMR and mass spectrometry were consistent with the desired structure.

EXAMPLE 37

Preparation of (±)β-[[2-[[[3-[(aminoiminomethyl)amino]phenyl]carbonyl]amino]acetyl]amino][1,1'-biphenyl]-4-propanoic acid, trifluoroacetate salt

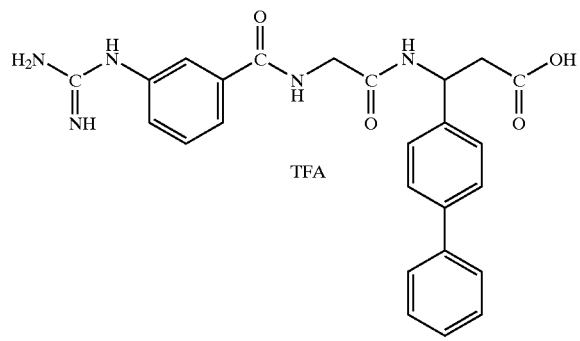

The above compound was prepared according to the methodology of Example 2, substituting an equivalent amount of 4-biphenylcarboxaldehyde for 3-pyridinecarboxaldehyde in Example 1, Step A.

EXAMPLE 38

Preparation of (±)ethyl β-[[2-[[[3-[(aminoiminomethyl)amino]-5-(trifluoromethyl)phenyl]carbonyl]amino]acetyl]amino]-3,5-bis(trifluoromethyl)benzenepropanoate, trifluoroacetate salt

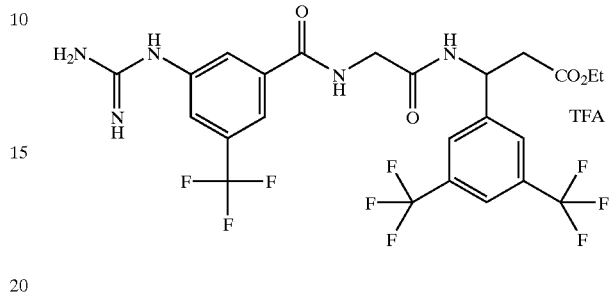

The above compound was prepared according to the methodology of Example 1, substituting the equivalent amount of 3,5-bis-trifluoromethylbenzaldehyde (Aldrich) for 3-pyridinecarboxaldehyde in Step A and substituting the equivalent amount of 3-amino-5-trifluoromethylbenzoic acid [which was synthesized by reduction of 3-nitro-5-trifluoromethylbenzoic acid (Lancaster) in ethanol with 10% Pd/C under 50 psi H$_2$O for 4 hours] for 3-aminobenzoic acid in Step E and stirring the resulting reaction mixture from Step E at reflux overnight instead of 2.5 hours.

NMR and mass spectrometry were consistent with the desired structure.

EXAMPLE 39

Preparation of (±)β-[[(2-[[[3-[(aminoiminomethyl)amino]-5-(trifluoromethyl)phenyl]carbonyl]amino]acetyl]amino]-3,5-bis(trifluoromethyl)benzenepropanoic acid, trifluoroacetate salt

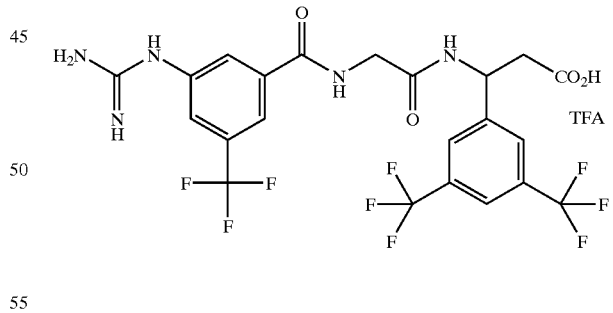

To 600 mg (0.00082 mole) of the product of Example 38 in 12 ml of H$_2$O and 12 ml of CH$_3$CN was added 140 mg (0.0033 mole) of LiOH. The reaction was stirred at room temperature for 1.5 hours. The pH was lowered to 2.5 with TFA and the product isolated by reverse phase prep HPLC to yield (after lyophilization) 520 mg of (±)β-[[2-[[[3-[(aminoiminomethyl)amino)-5-(trifluoromethyl)phenyl]carbonyl]amino]acetyl]amino]-3,5-bis(trifluoromethyl)benzenepropanoic acid, trifluoroacetate salt as a white solid.

NMR and mass spectrometry were consistent with the desired structure.

EXAMPLE 40

Preparation of 3S-[[2-[[[3-(aminocarbonylamino)phenyl]carbonyl]amino]acetyl]amino]-4-pentynoic acid

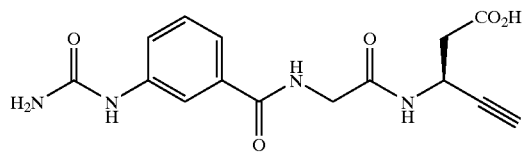

Step A
Ethyl 3S-amino-4-pentynoate hydrochloride was prepared using the method in J. Med. Chem. 1995, 38, 3378–94.

Step B
2 g m-aminohippuric acid in 5% aqueous HCl (25 ml) was treated with urea (2 g) and the solution was refluxed for 4 hours. m-N-carbamoylaminohippuric acid was purified by HPLC (RP-CH$_3$CN/H$_2$O) and lyophilized to give 1.2 g of white solid. The MS was consistent with the desired product.

Step C
A suspension of m-ureahippuric acid (1.2 g) in DMF (5 ml) and pyridine (5 ml) was treated with DSC (1.5 g). A catalytic amount of DMAP was added and the reaction mixture was stirred for 3 hours. A solution of 3S-aminopentynoic acid, hydrochloride (0.8 g) and K$_2$CO$_3$ (0.7 g) in saturated aqueous NaHCO$_3$ (5 ml) was added to the reaction mixture. The resulting mixture was stirred overnight at room temperature. The reaction was diluted to 45 ml with 1:1 CH$_3$CN:H$_2$O and acidified with of trifluoracetic acid (5 ml). The ester was purified by HPLC (RP-CH$_3$CN/H$_2$O) and a white solid (125 mg) was recovered after lyophilization. This material was then treated with 1:1 CH$_3$CN:H$_2$O (20 ml) and made basic (pH>12) with LiOH. After complete reaction, the product was purified by HPLC (RP-CH$_3$CN/H$_2$O) and the desired product (60 mg) was obtained. MS, $^1$H-NMR and CHN analysis were consistent with the desired product.

EXAMPLE 41

Preparation of (±)β-[[2-[[[3-[(aminoiminomethyl)amino]phenyl]carbonyl]amino]acetyl]amino] naphthalene-1-propanoic acid, trifluoroacetate salt

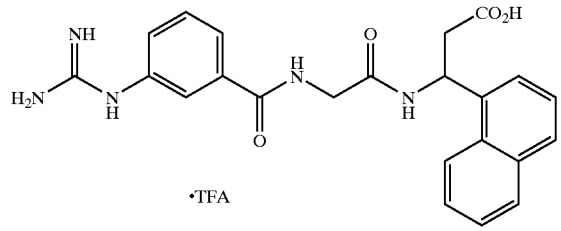

Step A
A mixture of freshly distilled 1-napthalenecarboxaldehyde (8.6 g), ammonium acetate (10.6 g) and malonic acid (5.7 g) in isopropyl alcohol (50 ml) was refluxed for 4 hours. The reaction was filtered while hot and washed with hot isopropyl alcohol (2×50 ml), washed with H$_2$O (125 ml) and isopropanol (100 ml) and dried in vacuo at 40° C. 4.6 g of βS-aminonaphthalene-1-propanoic acid as a white solid was isolated. MS and $^1$H-NMR were consistent with the desired product.

Step B
A suspension of the product of Step A (4.6 g) in methanol (100 ml) was treated with 4N HCl/dioxane (10 ml). The reaction was stirred overnight and the excess solvent was removed under reduced pressure. The oil was dissolved into 1:1 CH$_3$CN:H$_2$O and purified by HPLC (RP-CH$_3$CN/H$_2$O). Methyl βS-aminonaphthalene-1-propanoate (4.6 g) as a white solid was obtained. MS and $^1$H-NMR were consistent with the desired product.

Step C
A suspension of m-guanidinohippuric acid HCl (1.4 g) in DMF (5 ml) and pyridine (5 ml) was treated with DSC (3 g) and a catalytic amount of DMAP. The reaction was stirred overnight at room temperature. The resulting solution was treated with a solution of the product of Step B (1.7 g) and NMM (0.6 ml) in DMF (2.5 ml) and pyridine (2.5 ml). The mixture was stirred overnight at room temperature. The reaction was then treated with TFA and diluted to 50 ml with 1:1 CH$_3$CN:H$_2$O. The solution was purified by HPLC (RP-CH$_3$CN/H$_2$O) and (±)methyl βS-[[2-[[[3-[(aminoiminomethyl)amino]phenyl]carbonyl]amino]acetyl]amino]naphthalene-1-propanoate (1.3 g) as a white solid was obtained after lyophilization. MS and $^1$H-NMR were consistent with the desired product.

Step D
A solution of the product of Step C (0.5 g) in 1:1 CH$_3$CN:H$_2$O (15 ml) was treated with LiOH until pH>12. The reaction was monitored by HPLC (RP-CH$_3$CN/H$_2$O) and when hydrolysis was complete, the desired material was purified by HPLC (RP-CH$_3$CN/H$_2$O). A white solid (0.3 g) was recovered after lyophilization. MS, $^1$H-NMR and CHN were consistent with the desired product.

EXAMPLE 42

Preparation of (±)3-[[[3-[(aminoiminomethyl)amino]phenyl]carbonyl]amino]-2-oxopyrrolidine-1-propanoic acid, trifluoroacetate salt

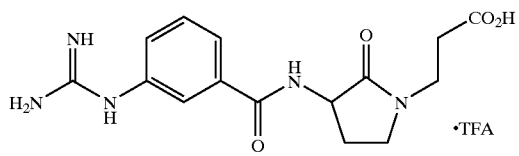

Step A
A solution of N-(tert-butoxycarbonyl)-L-methionine (6.2 g) in DMF (25 ml) and pyridine (25 ml) was treated with DSC (9.6 g) and a catalytic amount of DMAP. After 4 hours, a solution of β-alanine ethyl ester HCl (3.8 g) and K$_2$CO$_3$ (3.5 g) in saturated aqueous NaHCO$_3$ (25 ml) was added. The reaction mixture was stirred overnight at room temperature. The excess solvent was removed under reduced pressure and purified by HPLC (RP-CH$_3$CN/H$_2$O). N-[2-[[(1,1-dimethylethoxy)carbonyl]amino]-4-(methylthio)-1-oxobutyl]-β-alanine, ethyl ester (7.0 g) as a colorless oil was obtained. The oil was confirmed as the desired product by MS and used without further purification.

Step B
6.5 g of the oil from Step A was dissolved in DMF (25 ml) and treated with CH$_3$I (5.0 ml). After approximately 1 hour, NaH (0.50 g) was added, followed by further addition of NaH (0.50 g). The reaction was treated with H$_2$O (25 ml) and EtOAc (200 ml). The organic layer was washed with additional H$_2$ (3×25 ml), saturated aqueous NaCl (1×25 ml) and dried over NaSO$_4$. The excess solvent was removed under reduced pressure to give 4 g of

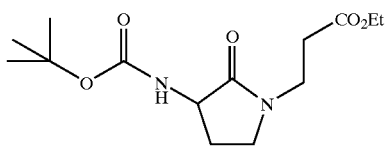

as a tan semi-solid. MS was consistent with the structure and the product was used without further purification.

Step C

A solution of the product of Step B (4 g) in ethanol (50 ml) was treated with 4N HCl/dioxane (20 ml). The excess solvent was removed under reduced pressure. The crude solid was purified by HPLC (RP-CH$_2$CN/H$_2$O). 20% aqueous HCl (10 ml) was added and 1 g of ethyl 3-amino-2-oxopyrrolidine-1-propanoate was obtained as a white solid after lyophilization. MS was consistent with the desired product.

Step D

A solution of m-guanidinobenzoic acid HCl (0.7 g) in DMF (3 ml) and pyridine (3 ml) was treated with DSC (0.8 g) and a catalytic amount of DMAP. After 3 hours a solution of the product of Step C (0.7 g) in H$_2$O (3 ml) with an equal molar amount of K$_2$CO$_3$ was added. The reaction was stirred overnight at room temperature. The desired ester was isolated by HPLC (RP-CH$_3$CN/H$_2$O). The white solid (100 mg) was treated with H$_2$O (10 ml) and made basic with LiOH (pH>12). After 2 hours, the desired product was isolated by HPLC (RP-CH$_3$CN/H$_2$O) and lyophilized. 75 mg of (±)3-[[[3-[(aminoiminomethyl)amino]phenyl]carbonyl]amino)-2-oxopyrrolidine-1-propanoic acid, trifluoroacetate salt as a white solid was obtained. MS, $^1$H-NMR and CHN analysis were consistent with the desired product.

EXAMPLE 43

Preparation of 3R-[[2-[[[(3-[(aminoiminomethyl)amino]phenyl]carbonyl]amino]acetyl]amino]-4-pentynoic acid, hydrochloride salt

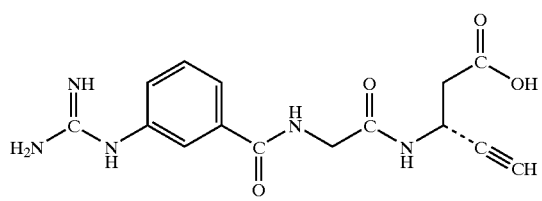

Step A

Ethyl 3-(N-(tert-butoxycarbonyl)amino)pent-4-ynoic ester (3 g) (J. Med. Chem., 1995, 38, 3378–94] in CH$_2$Cl$_2$ (60 ml) at 0° C. was treated with TFA (30 ml). The reaction was stirred for 3 hours. The excess solvent was removed under reduced pressure and a yellow oil (3.3 g) was obtained. The oil was confirmed as the desired product by MS.

Step B

A solution of m-guanidinohippuric acid HCl (3.3 g) in DMF (12 ml) and pyridine (12 ml) was treated with DSC (6.1 g) and a catalytic amount of DMAP. After 3 hours, a solution of crude product (3.3 g) from Step A in saturated aqueous NaHCO$_3$ (12 ml) was added. The reaction was stirred overnight at room temperature. The excess solvent was removed under reduced pressure. The resulting solid was treated with TFA and 1:1 CH$_3$CN:H$_2$O. The product was isolated by HPLC (RP-CH$_3$CN/H$_2$O) to yield ethyl 3R-[[2-[[[3-[(aminoiminomethyl)amino]phenyl]carbonyl]amino] acetyl]amino]propynoate trifluoroacetate salt (3 g) as a white solid. MS and $^1$H-NMR were consistent with the desired product.

Step C

The product of Step B (3 g) was dissolved in 1:1 CH$_3$CN:H$_2$O (50 ml) and treated with LiOH (pH>12). After 4 hours the reaction was acidified with TFA and the TFA salt of the desired product was isolated by HPLC (RP-CH$_3$CN/H$_2$O). The lyophilized solid (2.5 g) was slurried with 1:3 CH$_3$CN:H$_2$O (100 ml) and ion exchange resin, AG 2-X8 chloride form (BioRad) (50 g). The mixture was filtered and treated with 20% HCl (5 ml). The clear solution was lyophilized and the resin exchange process was repeated. The desired product (2.2 g) was obtained. MS, $^1$H-NMR and CHNCl were consistent with the desired product.

EXAMPLE 44

Preparation of 3S-[[2-[[[3-[[[(phenylmethyl)amino]carbonyl]amino]phenyl]carbonyl]amino]acetyl]amino]-4-pentynoic acid

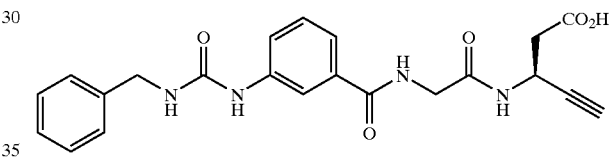

Step A m-Aminohippuric acid HCl (20 g) in CH$_3$CN (100 ml) was treated with benzyl isocyanate (16 ml). The reaction was treated with 5% aqueous HCl (400 ml), filtered and washed with H$_2$O (50 ml) to give 21 g of m-(benzylurea) hippuric acid. The MS and $^1$H-NMR were consistent with the desired product. No further purification was done.

Step B

Ethyl 3S-[[2-[[[3-[[[(phenylmethyl)amino]carbonyl]amino]phenyl]carbonyl]amino]acetyl]amino]-4-pentynoate was prepared using the method in Example 40 substituting an equal molar amount of m-(benzylurea)hippuric acid for m-ureahippuric acid. The desired ester was purified by HPLC (RP-CH$_3$CN/H$_2$O) to give 1.2 g as a white solid. The MS and $^1$H-NMR were consistent with the desired ester.

Step C

A solution of ethyl 3S-[[2-[[[3-[[[(phenylmethyl)amino] carbonyl]amino]phenyl]carbonyl]amino]acetyl]amino]-4-pentynoate (1.0 g) in 1:1 CH$_3$CN:H$_2$O (20 ml) was treated with KOH (pH>12). After 4 hours the reaction was acidified with TFA and purified twice by HPLC (RP-CH$_3$CN/H$_2$O). A white solid (300 mg) was obtained. MS, $^1$H-NMR and CHN were consistent with the desired product.

EXAMPLE 45

Preparation of 3S-[[2-[[[3-[(aminoiminomethyl)amino]phenyl]carbonyl]amino]acetyl]amino]-4-pentynoic acid, hydrochloride salt

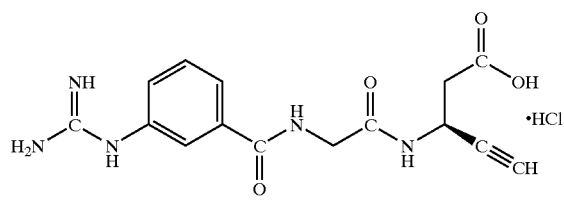

The product of Example 58 (6 g) was dissolved in 1:1 CH₃CN:H₂O (75 ml) and treated with KOH. The pH was maintained greater than 12 by addition of KOH. After 4 hours the reaction was acidified with TFA and purified by HPLC (RP-CH₃CN/H₂O). The TFA salt (4.2 g) was obtained after the appropriate fractions were lyophilized. The solid was slurried in 1:1 CH₃CN:H₂O (100 ml) and treated with ion exchange resin AG 2-X8 chloride form (BioRad) (50 g). The mixture was filtered and treated with 20% HCl (5 ml). After lyophilization the resin exchange was repeated. The desired product as the HCl salt (3.5 g) was obtained. MS, ¹H-NMR and CHNCl were consistent with the desired product.

EXAMPLE 46

Preparation of β-[[2-[[[3-(aminocarbonylamino)phenyl]carbonyl]amino]acetyl]amino]pyridine-3-propanoic acid, hydrochloride salt

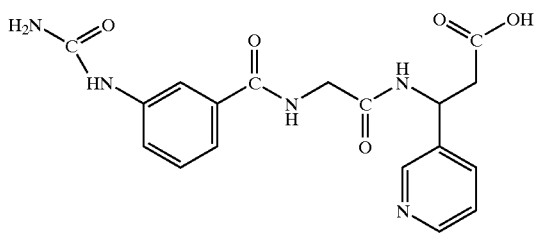

Urea (4 g) and ethyl β-[[2-[[(3-aminophenyl)carbonyl]amino]acetyl]amino]pyridine-3-propanoate trifluoroacetate salt (4 g) were dissolved in 20% aqueous HCl (50 ml) and refluxed for 6 hours. The reaction was made basic with KOH (pH>12). After 4 hours the reaction was acidified with TFA and purified by HPLC (RP-CH₃CN/H₂O). The white solid was dissolved in 1:1 CH₃CN:H₂O (100 ml) and subjected to the resin exchange described in Example 43, Step C. Lyophilization gave the desired product (3.2 g). MS, ¹H-NMR and CHNCl were consistent with the desired product.

EXAMPLE 47

Preparation of (±)β-[[2-[[[3-[[[(phenylmethyl)amino]carbonyl]amino]phenyl]carbonyl]amino]acetyl]amino]pyridine-3-propanoic acid, hydrochloride salt

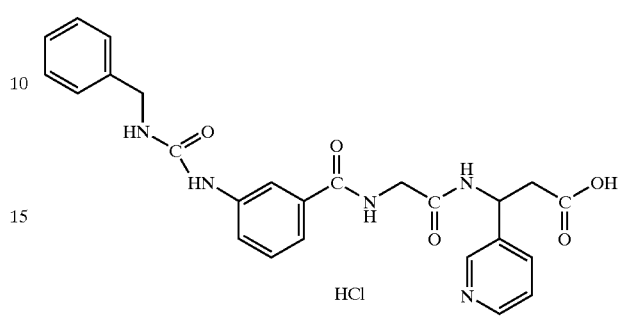

The product of Example 48 (5 g) was dissolved in 1:1 CH₃CN:H₂O (75 ml) and treated with KOH. The pH was maintained greater than 12 by addition of KOH. After 4 hours the reaction was acidified with TFA and purified by HPLC (RP-CH₃CN/H₂O). The TFA salt (4.5 g) was obtained after lyophilization. The solid was slurried in 1:1 CH₃CN:H₂O (100 ml) and ion exchange resin, AG 2-X8 chloride form (BioRad) (50 g). The mixture was filtered and treated with 20% HCl (5 ml). After lyophilization the resin exchange process was repeated. The desired product (4.1 g) was obtained as a white solid. MS, ¹H-NMR and CHNCl were consistent with the desired product.

EXAMPLE 48

Preparation of (±)ethyl β-[[2-[[[3-[[[(phenylmethyl)amino]carbonyl]amino]phenyl]carbonyl]amino]acetyl]amino]pyridine-3-propanoate, hydrochloride salt

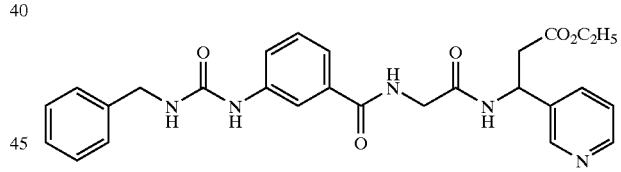

Step A

A solution of m-nitrohippuric acid (5.6 g) in DMF (25 ml) was treated with DSC (9.6 g) and a catalytic amount of DMAP. After 5 hours, a solution of ethyl 3-amino-3-(3-pyridyl)propanoate 2HCl (8 g) and K₂CO₃ (2 g) in saturated aqueous NaHCO₃ (25 ml) was added. The reaction mixture was stirred overnight at room temperature. H₂O (25 ml) was added and the mixture was filtered. The resulting solid was washed with H₂O (25 ml), slurried with CH₃CN (25 ml) and filtered. Ethyl β-[[2-[[(3-nitrophenyl)carbonyl]amino]acetyl]amino]pyridine-3-propanoate (6.5 g) was obtained as a white solid. MS was consistent with the desired product.

Step B

A suspension of the product of Step A (6.5 g) and 5% Pd/C (0.6 g) in H₂O (50 ml) and ethanol (50 ml) was subjected to 50 psi H₂ for 3 hours. The mixture was filtered through a celite pad and the excess solvent was removed under reduced pressure. The resulting oil was treated with CH₂Cl and the solvent was again removed under reduced pressure. Ethyl β-[[2-[[(3-aminophenyl)carbonyl]amino]acetyl]

amino]pyridine-3-propanoate (5.8 g) was recovered as a tan foam. MS and ¹H-NMR were consistent with the desired product.

Step C

A solution of the product of Step B (1.9 g) in CH₃CN (5 ml) was treated with benzyl isocyanate (0.8 ml). After 1 hour benzyl isocyanate (0.1 ml) was added to complete the reaction. After 0.25 hour the reaction was treated with H₂O (50 ml). The resulting viscous oil was dissolved in CH₃CN and was acidified with TFA. The solution was purified by HPLC (RP-CH₃CN/H₂O) and lyophilized. The white solid was repurified by HPLC (RP-CH₃CN/H₂O) and treated with 20% HCl (5 ml). The desired product (1.3 g) was obtained as a white solid. MS, ¹H-NMR and CHNCl were consistent with the desired product.

EXAMPLE 51

Preparation of (±)ethyl β-[[2-[[[3-[(aminoiminomethyl)amino]phenyl]carbonyl]amino]acetyl]amino]furan-3-propanoate, trifluoroacetate salt

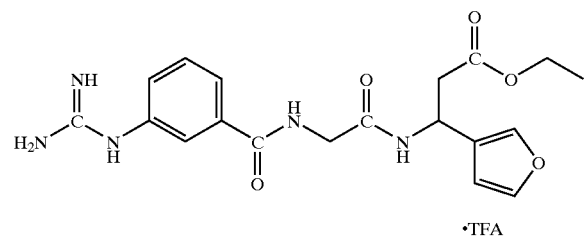

Step A

A suspension of 3-furancarboxaldehyde (8.6 ml), malonic acid monoethyl ester (15.8 g) and ammonium acetate (9.6 g) in isopropyl alcohol (200 ml) was heated to reflux under nitrogen. After 5 hours, the excess solvent was removed under reduced pressure and the semi-solid was treated with H₂O (250 ml) and acidified to pH 2 using 12N HCl. The aqueous layer was washed with CH₂Cl₂ (2×100 ml). The aqueous layer was neutralized to pH>9 with K₂CO₃. The product was extracted with CH₂Cl₂ (2×100 ml). The organic layer was dried over Na₂SO₄ and the excess solvent was removed under reduced pressure to give ethyl β-aminofuran-3-propanoate (5 g) as a golden oil. The MS and ¹H-NMR were consistent with the desired product.

Step B

A solution of m-guanidinohippuric acid HCl (1.4 g) in DMF (5 ml) and pyridine (5 ml) was treated with DSC (1.9 g) and a catalytic amount of DMAP. After 5 hours, to a solution of the product of Step A (1.2 g) in CH₃CN (1 ml) was added saturated aqueous NaHCO₃ (1 ml). The mixture was stirred overnight at room temperature and purified by HPLC (RP-CH₃CN/H₂O). The lyophilized solid (1.2 g) had MS, ¹H-NMR and CHN analysis that were consistent with the desired product.

EXAMPLE 52

Preparation of (±)β-[[2-[[[3-[(aminoiminomethyl)amino]phenyl]carbonyl]amino]acetyl]amino]furan-3-propanoic acid, trifluoroacetate salt

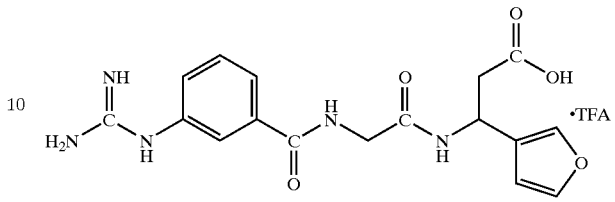

The product of Example 51 (0.6 g) was dissolved in 1:1 CH₃CN:H₂O (15 ml) and was treated with NaOH (pH>12). After 4 hours the reaction was acidified with TFA and purified by HPLC (RP-CH₃CN/H₂O). The lyophilized solid (0.3 g) had MS, ¹H-NMR and CHN analysis that were consistent with the desired product.

EXAMPLE 53

Preparation of 3-[[2-[[[3-[(aminoiminomethyl)amino]phenyl]carbonyl]amino]acetyl]amino]pentanedioic acid, trifluoroacetate salt

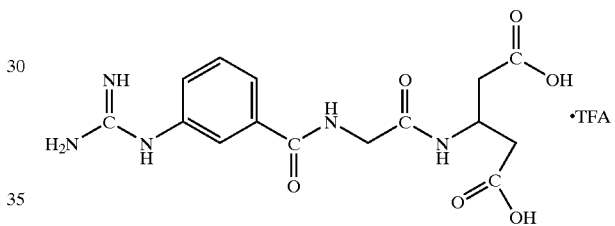

Step A

Dimethyl 3-ketoglutarate (13 g) in methanol (50 ml) was treated with ammonium formate (5 g) and NaCNBH₃ (2 g). 10 ml of H₂O was added and the excess solvent removed under reduced pressure. The semi-solid was dissolved in 5% aqueous HCl (250 ml), and washed with CH₂Cl₂ (2×50 ml). The aqueous layer was made basic (pH>9) with K₂CO₃ and the product was extracted using CH₂Cl₂ (2×75 ml). The organic layers were combined and dried with Na₂SO₄. The excess solvent was removed to give 2.5 g of the dimethyl (±)3-aminoglutarate. This was dissolved in methanol (50 ml) and treated with 4N HCl/Dioxane (10 ml). The excess solvent was removed under reduced pressure to give a 2.7 g of dimethyl (±)3-aminoglutarate hydrochloride. MS and ¹H-NMR were consistent with the desired product.

Step B

A solution of m-guanidinohippuric acid HCl (1.5 g) in DMF (4.5 ml) and pyridine (4.5 ml) was treated with DSC (1.8 g) and a catalytic amount of DMAP. After 2 hours, a solution of dimethyl 3-aminoglutarate HCl (1.1 g) and NMM (350 μl) in H₂O (3 ml) was added to the reaction. The reaction was stirred overnight at room temperature and the product was isolated by HPLC. 1.5 g of 3-[[2-[[[3-[(aminoiminomethyl)amino]phenyl]carbonyl]amino]acetyl]amino]pentanedioic acid, bismethyl ester was obtained as a white solid. MS and ¹H-NMR were consistent with the desired product.

Step C

The product of Step B (750 mg) was dissolved in 1:1 CH₃CN:H₂O (40 ml) and treated with KOH (pH>12). After 4 hours, the reaction was acidified with TFA and purified by HPLC (RP-CH₃CN/H₂O). The lyophilized solid (400 mg) had MS, ¹H-NMR and CHN analysis that were consistent with the desired product.

EXAMPLE 54

Preparation of (±)hydrogen methyl 3-[[2-[[[3-[(aminoiminomethyl)amino]phenyl]carbonyl]amino]acetyl]amino]pentanedioate, trifluoroacetate salt

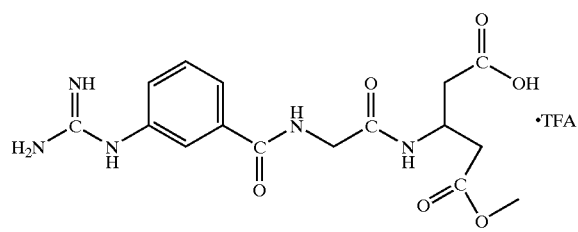

Step A

A solution of m-guanidinohippuric acid HCl (1.5 g) in DMF (4.5 ml) and pyridine (4.5 ml) was treated with DSC (1.8 g) and a catalytic amount of DMAP. After 2 hours, a solution of dimethyl 3-aminoglutarate HCl (1.1 g) and NMM (350 µl) in H₂O (3 ml) was added to the reaction. The reaction was stirred overnight at room temperature and the product was isolated by HPLC. 3-[[2-[[[3-[(aminoiminomethyl)amino]phenyl]carbonyl]amino]acetyl]amino]pentanedioic acid, bis methyl ester (1.5 g) as a white solid was obtained. MS and ¹H-NMR were consistent with the desired product.

Step B 750 mg of the product of Step A was dissolved in Na₂PO₄ buffer (50 ml, 50 mM, pH 8.5) and treated with porcine esterase (200 µl). The pH was adjusted using LiOH. After 48 hours, the solution was acidified with 30 TFA and purified by HPLC (RP-CH₃CN/H₂O). The lyophilized solid (175 mg) had MS, ¹H-NMR and CHN analysis consistent with the desired product.

EXAMPLE 55

Preparation of (±)β-[[2-[[[3-[(aminoiminomethyl)amino]phenyl]carbonyl]amino]acetyl]amino]furan-2-propanoic acid, trifluoroacetate salt

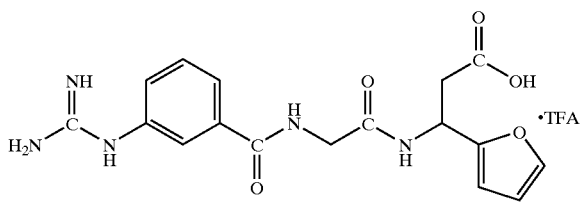

Step A

A suspension of 2-furancarboxaldehyde (4.8 g), ammonium acetate (9.6 g) and malonic acid monoethyl ester (6.6 g) in isopropanol (50 ml) was refluxed for 6 hours. The excess solvent was removed under reduced pressure and the resulting oil was treated with ethyl acetate (100 ml) and 5% aqueous HCl (400 ml). The aqueous layer was then washed with ethyl acetate (100 ml). The aqueous layer was made basic with K₂CO₃ (pH 9). The product was extracted with CH₂Cl₂ (2×100 ml). The organic layers were combined and dried with Na₂SO₄ and the excess solvent was removed.

Ethyl β-aminofuran-2-propanoate (2.5 g) as a dark oil was recovered. MS and ¹H-NMR were consistent with the desired product. The dark oil was treated as described in Example 53, Step A to give 2.7 g of ethyl β-aminofuran-2-propanoate hydrochloride.

Step B

A solution of m-guanidinohippuric acid HCl (272 mg) in DMF (1 ml) and pyridine (1 ml) was treated with DSC (450 mg) and a catalytic amount of DMAP. After 2 hours, a solution of the product of Step A (221 mg), NMM (111 µl) in H₂O (1 ml) and CH₃CN (1 ml) was added. The reaction was stirred overnight at room temperature. (±)Ethyl β-[[2-[[[3-[(aminoiminomethyl)amino]phenyl)carbonyl]amino]acetyl]amino]furan-2-propanoate was purified by HPLC (RP-CH₃CN/H₂O) and lyophilized to give a white solid (200 mg). MS was consistent with the desired product.

Step C

The product of Step B (200 mg) was dissolved in 1:1 CH₃CN:H₂O (20 ml) and treated with LiOH (pH>12). After 4 hours, the reaction was acidified with TFA and purified by HPLC (RP-CH₃CN/H₂O). The lyophilized solid (175 mg) had MS, ¹H-NMR and CHN analysis that were consistent with the desired product.

EXAMPLE 56

Preparation of (±)β-[[2-[[[3-[(aminoiminomethyl)amino]phenyl]carbonyl]amino]acetyl]amino]naphthalene-2-propanoic acid, trifluoroacetate salt

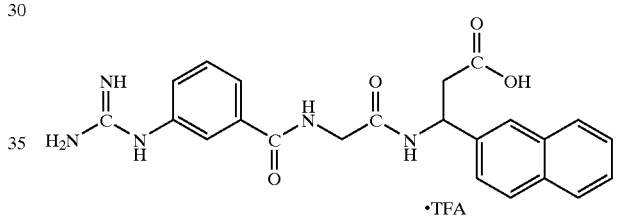

Step A

A suspension of 2-naphthaldehyde (7.8 g) and ammonium acetate (9.6 g) in isopropyl alcohol (50 ml) was heated for 1 hour at reflux. Malonic acid (5.2 g) was added and reflux was continued for 3 hours. The reaction was filtered while hot and the solid washed with hot isopropyl alcohol (50 ml) followed by CH₃CN (100 ml). The white solid was dried overnight in vacuo and β-aminonaphthalene-2-propanoic acid (9 g) was recovered. MS and ¹H-NMR were consistent with the structure.

Step B

A suspension of the product of Step A (2.5 g) in methanol (100 ml) was treated with 4N HCl/dioxane (10 ml). The resulting solution was stirred overnight. The excess solvent was removed under reduced pressure and the semi solid was purified by HPLC (RP-CH₃CN/H₂O). The solid was dissolved in CH₃CN/H₂O, treated with 20% aqueous HCl (5 ml) and lyophilized to give methyl β-aminonaphthalene-2-propanoate hydrochloride (1.1 g). MS and ¹H-NMR were consistent with the structure.

Step C

A solution of m-guanidinohippuric acid (0.7 g) in DMF (4 ml) and pyridine (4 ml) was treated with DSC (1.1 g) and a catalytic amount of DMAP. After 4 hours, a solution of the product of Step B (0.9 g), NMM (0.4 ml) in DMF (2 ml), pyridine (2 ml) and H₂O (1 ml) were added. The reaction was stirred overnight at room temperature and acidified with TFA. The desired product was isolated by HPLC (RP- CH$_3$CN/H$_2$O). The lyophilized solid (0.7 g) had MS, $^1$H-NMR and CHN analysis that were consistent with the desired product.

Step D

The product of Step C (200 mg) was dissolved in 1:1 CH$_3$CN:H$_2$O (20 ml) and treated with KOH (pH>12). After 4 hours, the reaction was acidified with TFA and purified by HPLC (RP-CH$_3$CN/H$_2$O). The lyophilized solid (175 mg) had MS, $^1$H-NMR and CHN analysis that were consistent with the desired product.

EXAMPLE 57

Preparation of (±)methyl β-[[2-[[[3-[(aminoiminomethyl)amino]phenyl]carbonyl]amino]acetyl]amino]thiophene-3-propanoate, trifluoroacetate salt

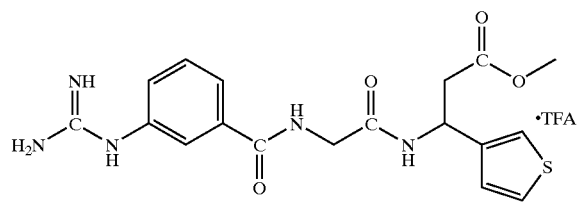

Step A

A solution of 3-thiophenecarboxaldehyde (11.2 g) in isopropanol (100 ml) was treated with ammonium acetate (20 g). The resulting mixture was heated and malonic acid (10.4 g) was added. The reaction was refluxed for 4 hours and filtered while hot. The solid was washed with hot isopropanol (2×50 ml) and dried in vacuo overnight at 40° C. 8 g of β-aminothiophene-3-propanoic acid was recovered. MS and $^1$H-NMR were consistent with the desired product.

Step B

A suspension of the product of Step A (5 g) in methanol (100 ml) was treated with 4N HCl/dioxane (10 ml). The reaction was stirred overnight. The excess solvent was removed under reduced pressure. Methyl β-aminothiophene-3-propanoate hydrochloride (7.8 g) was isolated as a yellow foam. MS and $^1$H-NMR were consistent with the desired product.

Step C

A solution of m-guanidinohippuric acid HCl (2.7 g) in DMF (10 ml) and pyridine (10 ml) was treated with DSC (4.5 g) and a catalytic amount of DMAP. After 4 hours, a solution of the product of Step B (2.2 g) and NMM (1.3 ml) in DMF (5 ml) was added and the reaction was stirred overnight at room temperature. The reaction mixture was treated with 1:1 CH$_3$CN:H$_2$O (50 ml) and acidified with TFA. The desired compound was isolated by HPLC (RP-CH$_3$CN/H$_2$O). The lyophilized solid (2.2 g) had MS, $^1$H-NMR and CHN analysis that were consistent with the desired product.

EXAMPLE 58

Preparation of ethyl 3S-[[2-[[[3-[(aminoiminomethyl)amino]phenyl)carbonyl]amino]acetyl]amino]-4-pentynoate, trifluoroacetate salt

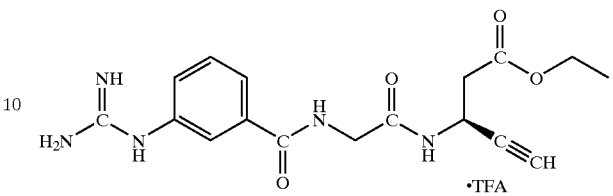

A solution of m-guanidinohippuric acid HCl (2.7 g) in DMF (10 ml) and pyridine (10 ml) was treated with DSC (4.5 g) and a catalytic amount of DMAP. After 4 hours, a solution of ethyl 3S-amino-4-pentynoic acid, hydrochloride (1.8 g) and NMM (1.1 ml) in DMF (5 ml) was added and the reaction was stirred overnight at room temperature. The reaction mixture was treated with 1:1 CH$_3$CN:H$_2$O (50 ml) and acidified with TFA. The desired compound was isolated by HPLC (RP-CH$_3$CN/H$_2$O). The lyophilized solid (2.6 g) had MS, $^1$H-NMR and CHN analysis that were consistent with the desired product.

EXAMPLE 59

Preparation of (±)β-[[2-[[[3-[(aminoiminomethyl)amino]phenyl]carbonyl]amino]acetyl]amino]thiophene-3-propanoic acid, trifluoroacetate salt

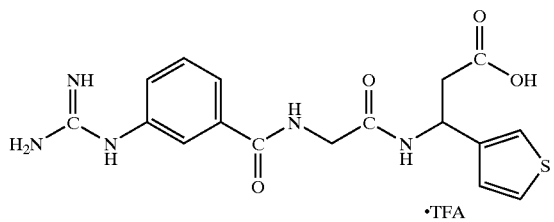

The product of Example 57 (750 mg) was dissolved in 1:1 CH$_3$CN:H$_2$O (20 ml) and treated with KOH (pH>12). After 4 hours, the reaction was acidified with TFA and purified by HPLC (RP-CH$_3$CN/H$_2$O). The lyophilized solid (500 mg) had MS, $^1$H-NMR and CHN analysis that were consistent with the desired product.

EXAMPLE 60

Preparation of (±)2-[3-[[2-[[[3-[(aminoiminomethyl)amino]phenyl]carbonyl]amino]acetyl]amino]-4-carboxybutyl]sulfonyl]benzoic acid, trifluoroacetate

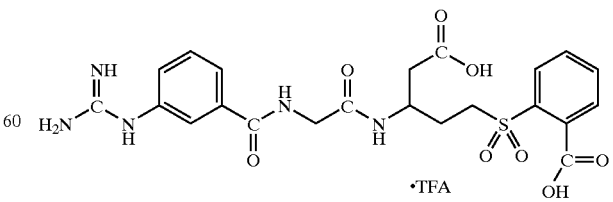

Step A

A solution of 2-[(3-amino-4-carboxybutyl)thio]benzoic acid (1 g) (prepared according to U.S. Pat. No. 5,409,939) in methanol (50 ml) was treated with 4N HCl/dioxane (10 ml) overnight. The excess solvent was removed under reduced pressure to give the desired product (0.9 g). MS of the white solid, methyl 2-[(3-amino-4-(methoxycarbonyl)butyl]thio]benzoate was consistent with the proposed structure.

Step B

A solution of m-guanidinohippuric acid HCl (0.8 g) in DMF (3 ml) and pyridine (3 ml) was treated with DSC (1.2 g) and a catalytic amount of DMAP. After 2 hours, a solution of the product of Step A (1 g), NMM (0.3 ml) in DMF (3 ml) was added. The reaction was stirred overnight at room temperature. KOH was added until pH greater than 12. After 4 hours, the reaction was acidified and purified by HPLC (RP-CH$_3$CN/H$_2$O). The lyophilized solid, (±)2-[3-[[2-[[[3-[(aminoiminomethyl)amino]phenyl)carbonyl]amino]acetyl]amino]-4-carboxybutyl]thio]benzoic acid, trifluoroacetate salt (750 mg) had MS, $^1$H-NMR and CHN analysis that were consistent with the desired product.

Step C

A solution of the product of Step B (320 mg) in 1:1 CH$_3$CN:H$_2$O (50 ml) was treated with m-chloroperoxybenzoic acid (340 mg). The reaction was stirred overnight at room temperature and purified by HPLC (RP-CH$_3$CN/H$_2$O). The lyophilized solid (300 mg) had MS, $^1$H-NMR and CHN analysis that were consistent with the desired product.

EXAMPLE 61

Preparation of (±)β-[[2-[[[3-[(aminoiminomethyl) amino]phenyl]carbonyl]amino]acetyl]amino] thiophene-2-propanoic acid, trifluoroacetate salt

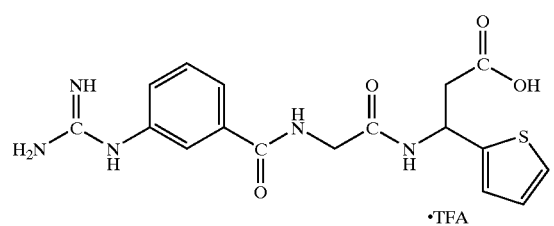

Step A

A solution of 3-amino-3-(2-thienyl)propanoic acid (0.5 g) (prepared substituting a molar equivalent amount of 2-thiophene-carboxaldehyde in Example 57, Step A) in methanol (50 ml) was treated with 4N HCl/dioxane (10 ml). After 6 hours the excess solvent was removed under reduced pressure to give a waxy solid. Treatment with Et$_2$O/CH$_3$CN produced methyl β-aminothiophene-2-propanoate (370 mg) as a white powder. MS and $^1$H-NMR were consistent with the desired product.

Step B

A solution of m-guanidinohippuric acid HCl (0.4 g) in DMF (1.5 ml) and pyridine (1.5 ml) was treated with DSC (0.6 g) and a catalytic amount of DMAP. After 3 hours, a solution of the product of Step A (0.3 g) and NMM (220 μl) in DMF (1.5 ml) was added. The reaction was stirred overnight at room temperature. The ester was isolated by HPLC (RP-CH$_3$CN/H$_2$O) and lyophilized. The resulting white solid was treated with KOH (pH>12) in 1:4 CH$_3$CN:H$_2$O. After 4 hours, the reaction was acidified by TFA and purified by HPLC (RP-CH$_3$CN/H$_2$O). The lyophilized solid (300 mg) had MS, $^1$H-NMR and CHN analysis that were consistent with the desired product.

EXAMPLE 62

Preparation of (±)methyl 2-[[3-[2-[[[3-[(aminoiminomethyl)amino]phenyl]carbonyl]amino] acetyl]amino]-4-carboxybutyl]thio]benzoate, trifluoroacetate salt

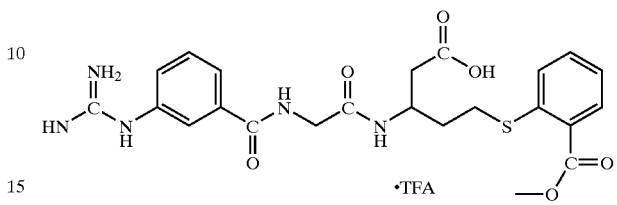

A solution of m-guanidinohippuric acid HCl (0.8 g) in DMF (3 ml) and pyridine (3 ml) was treated with DSC 119: (1.2 g) and a catalytic amount of DMAP. After 2 hours, a solution of methyl 2-[[3-amino-4-(methoxycarbonyl)butyl] thio]benzoate (1 g) [prepared according to U.S. Pat. No. 5,409,939], NMM (0.3 ml) in DMF (3 ml) was added. The reaction was stirred overnight at room temperature. KOH was added until the pH was greater than 12. After 2 hours, the reaction was acidified and purified by HPLC (RP-CH$_3$CN/H$_2$O). The lyophilized solid, (250 mg) had MS, $^1$H-NMR and CHN analysis that were consistent with the desired product.

EXAMPLE 63

Preparation of (±)methyl 3-[[2-[[[3-[(aminoiminomethyl)amino]phenyl]carbonyl]amino] acetyl]amino]-5-[(4-methylphenyl)thio]pentanoate, trifluoroacetate salt

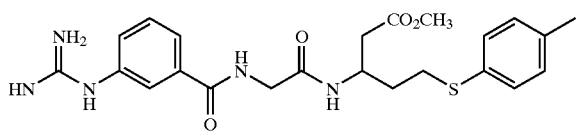

Step A

A solution of 3-amino-5-[(4-methylphenyl)thio]pentanoic acid (1.0 g) [prepared according to U.S. Pat. No. 5,409,939] in methanol (50 ml) was treated with 4N HCl/dioxane (10 ml). The reaction was stirred overnight at room temperature. The excess solvent was removed under reduced pressure. Methyl 3-amino-5-[(4-methylphenyl)thio]pentanoate (1.1 g) as a white solid was obtained. MS and $^1$H-NMR were consistent with the desired product.

Step B

A solution of m-guanidinohippuric acid HCl (0.6 g) in DMF (2 ml) and pyridine (2 ml) was treated with DSC (0.7 g) and a catalytic amount of DMAP. After 1 hour, a solution of the product of Step A (0.6 g) in saturated aqueous NaHCO$_3$ (1.5 ml) and acetonitrile (1.5 ml) was added. The reaction was stirred for 2 hours at room temperature. The reaction was acidified with TFA and the title compound (0.6 g) was isolated by HPLC as a white solid. MS and $^1$H-NMR were consistent with the desired product.

EXAMPLE 64

Preparation of (±)methyl 3-[[2-[[[3-[(aminoiminomethyl)amino]phenyl]carbonyl]amino]acetyl]amino]-4-[[(4-methylphenyl)sulfonyl]amino]butanoate, trifluoroacetate salt

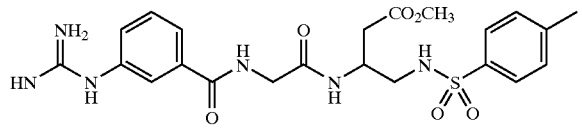

Step A

A mixture of aminoacetaldehyde dimethyl acetal (15.8 g), p-toluenesulfonylchloride (19.1 g) and Et$_3$N (10.1 g) in CH$_2$Cl$_2$ (200 ml) was stirred for 2 hours. The reaction was treated with 5% aqueous HCl (50 ml) and Et$_2$O (200 ml). The layers were separated and the organic layer was washed with 5% aqueous HCl (50 ml), H$_2$O (50 ml) and dried over Na$_2$SO$_4$. The excess solvent was removed under reduced pressure to give 30 g of the desired acetal;

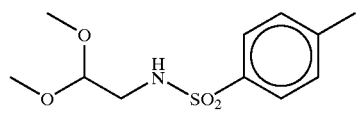

confirmed by MS and $^1$H-NMR.

Step B

A mixture of the acetal from Step A (10 g), CH$_3$CN (70 ml) and aqueous HCl (15 ml) was heated to 50° C. for 10 minutes. Diethylether was added and the desired aldehyde was extracted. The aldehyde was then used without further purification. The desired aldehyde

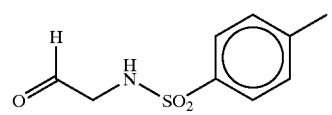

was verified by MS.

Step C

A mixture of ethyldiazoacetate (2.3 g), SnCl$_3$ (2.5 g) in CH$_2$Cl$_2$ (75 ml) was treated with the aldehyde from Step B (5 g). After 2 hours, aqueous HCl and Et$_2$O were added. The organic layer was separated and dried with MgSO$_4$. The solvent was removed under reduced pressure to yield 5 g of crude β-keto ester

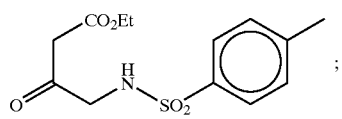

confirmed by MS and $^1$H-NMR and used without further purification.

Step D

The β-keto ester from Step C (12 g), methanol (100 ml), H$_4$N$^+$HCO$_2^-$ (30 g) and NaCNBH$_3$ (1.3 g) was stirred. After 24 hours, the excess solvent was removed under reduced pressure. The resulting semi-solid was treated with CH$_2$Cl$_2$ and the desired product was extracted using aqueous HCl. Removal of the solvent gave 6 g of crude β-amino ester

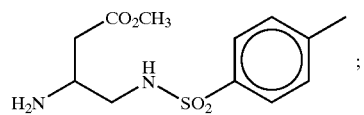

confirmed by MS and $^1$H-NMR.

Step E

A solution of m-guanidinohippuric acid HCl (337 mg) in DMF (1 ml) and pyridine (1 ml) was treated with DSC (0.4 g) and a catalytic amount of DMAP. After 2 hours, a solution of the product of Step D (322 mg) and NMM (220 μl) in DMF (1 ml) was added. The reaction was stirred overnight at room temperature. The reaction was acidified with TFA and the title compound (250 mg) was isolated by HPLC (RP-CH$_3$CN/H$_2$O) as a white solid. MS, CHN and $^1$H-NMR were consistent with the desired product.

EXAMPLE 65

Preparation of 3-[[2-[[[3-[(aminoiminomethyl)amino]phenyl]carbonyl]amino]acetyl]amino]-4-[[(4-methylphenyl)sulfonyl]amino]butanoic acid, trifluoroacetate salt

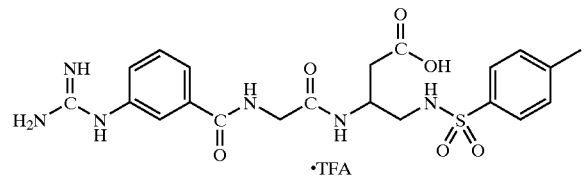

A solution of the product of Example 64 (180 mg) in 1:1 CH$_3$CN:H$_2$O (4 ml) was treated with LiOH (100 mg). After 2 hours, the reaction was acidified with TFA and purified by HPLC (RP-CH$_3$CN/H$_2$O). The title compound (100 mg) was isolated as a white solid. MS, $^1$H-NMR and CHN analysis were consistent with the desired product.

EXAMPLE 66

Preparation of (±)3-[[2-[[[3-[(aminoiminomethyl)amino]phenyl]carbonyl]amino]acetyl]amino]-5-[(4-methylphenyl)thio]pentanoic acid, trifluoroacetate salt

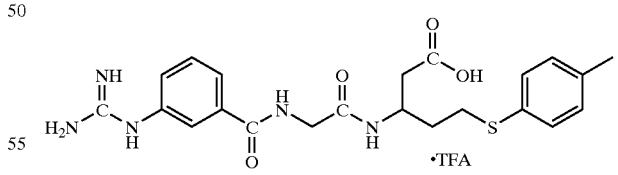

A solution of 180 mg of the product from Example 63 in 1:1 CH$_3$CN:H$_2$O (4 ml) was treated with LiOH (100 mg). After 2 hours, the reaction was acidified with TFA and purified by HPLC (RP-CH$_3$CN/H$_2$O). 3-[[2-[[[3-[(aminoiminomethyl)amino]phenyl]carbonyl]amino]acetyl]amino]-5-[(4-methylphenyl)thio]pentanoic acid, trifluoroacetate salt (100 mg) was isolated as a white solid. MS, $^1$H-NMR and CHN analysis were consistent with the desired product.

EXAMPLE 67

Preparation of (±)3-[[2-[[[3-[(aminoiminomethyl)amino]phenyl]carbonyl]amino]acetyl]amino]-5-[(4-methylphenyl)sulfonyl]pentanoic acid, trifluoroacetate salt

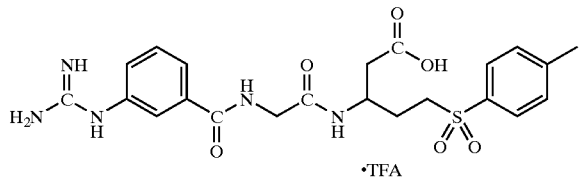

A solution of the product from Example 63 (200 mg) in 1:1 CH₃CN:H₂O (4 ml) was treated with of m-chloroperoxybenzoic acid (460 mg). The reaction was stirred overnight at room temperature. The reaction was treated with LiOH (200 mg). After 2 hours, the reaction was acidified with TFA and purified by HPLC (RP-CH₃CN/H₂O). 3-[[2-[[[3-[(aminoiminomethyl)amino]-phenyl]carbonyl]amino]acetyl]amino]-5-[(4-methylphenyl)sulfonyl]pentanoic acid, trifluoroacetate salt (180 mg) was isolated as a white solid. MS, ¹H-NMR and CHN analysis were consistent with the desired product.

EXAMPLE 68

Preparation of 3S-[[2-[[[3-[(aminoiminomethyl)amino]phenyl]carbonyl]amino]acetyl]amino]-4-(phenylthio)butanoic acid, trifluoroacetate salt

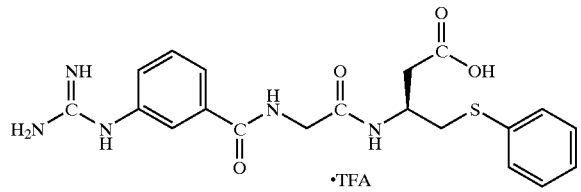

Step A

A suspension of phenylmethyl 3S-[[(1,1-dimethylethoxy)carbonyl]amino]-4-[(methylsulfonyl)oxy]butanoate (3.9 g) [prepared according to U.S. Pat. No. 5,409,939], thiophenol (1.1 ml) and K₂CO₃ (1.4 g) in DMF (20 ml) was stirred at room temperature overnight. The reaction was treated with ethyl acetate and the organic Ii layer was washed with H₂O (2×25 ml) and saturated NaCl (25 ml). The organic layer was dried with Na₂SO₄ and the excess solvent removed under reduced pressure to give a golden oil (4.5 g). The oil was dissolved in CH₂Cl₂ (100 ml) and treated with TFA (20 ml). After 4 hours the excess solvent was removed under reduced pressure and the product was purified by HPLC (RP-CH₃CN/H₂O). Phenylmethyl 3S-amino-4-(phenylthio)butanoate TFA salt (1.2 g) was isolated as a white solid. MS and ¹H-NMR were consistent with the desired product.

Step B

A solution of m-guanidinohippuric acid HCl (273 mg) and NMM (110 µl) in DMF (1 ml) was treated with pivaoyl chloride (120 µl). After 30 minutes, a solution of the product from Step A (208 mg), NMM (110 µl) and a catalytic amount of DMAP in DMF (1 ml) was added. After 4 hours, phenylmethyl 3S-[[2-[[[3-[(aminoiminomethyl)amino]phenyl]carbonyl]amino]acetyl]amino]-4-(phenylthio)butanoate (200 mg) was isolated by HPLC (RP-CH₃CN/H₂O) as a white solid. MS and ¹H-NMR were consistent with the desired product.

Step C

A solution of 200 mg of the product of Step B in 1:1 CH₃CN:H₂O (4 ml) was treated with KOH (pH>12). After 2 hours, the reaction was acidified with TFA and the product was isolated by HPLC (RP-CH₃CN/H₂O). 3S-[[2-[[[3-[(aminoiminomethyl)amino]phenyl]carbonyl]amino]acetyl]amino]-4-(phenylthio)butanoic acid, trifluoroacetate salt (100 mL) was isolated as a white solid. MS, ¹H-NMR and CHN analysis were consistent with the desired product.

EXAMPLE 69

Preparation of 3S-[[2-[[[3-[(aminoiminomethyl)amino]phenyl]carbonyl]amino]acetyl]amino]-4-pentynoic acid, trifluoroacetate salt

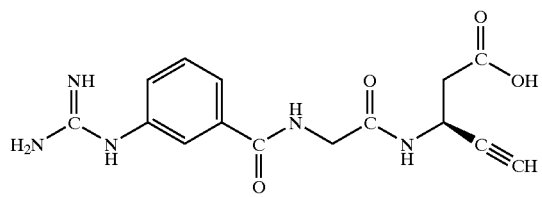

Step A

A solution of M-guanidinohippuric acid HCl (2.7 g) in DMF (10 ml) was treated with pivaoyl chloride (1.3 ml). After 30 minutes, a solution of 3S-amino-4-pentynoic acid, monohydrochloride (1.8 g), NMM 1(1.5 ml) and a catalytic amount of DMAP in DMF (10 ml) was added. The reaction was stirred overnight at room temperature. Ethyl 3S-[[2-[[[3-[(aminoiminomethyl)amino]phenyl]carbonyl]amino]acetyl]amino-4-pentynoate, TFA salt (1.5 g) was isolated by HPLC (RP-CH₃CN/H₂O) as a white solid. MS was consistent with the desired product.

Step B

A solution of the product of Step A (1.5 g) in 1:1 H₂O/CH₃CN (75 ml) was treated with LiOH (pH>12). After 2 hours, the reaction was acidified with TFA and the product was purified by HPLC (RP-CH₃CN/H₂O). The title compound as a lyophilized solid (1.2 g), had MS, ¹H-NMR and CHN analysis that were consistent with the desired product.

EXAMPLE 70

Preparation of 3R-[[2-[[[3-[(aminoiminomethyl)amino]phenyl]carbonyl]amino]acetyl]amino]-4-pentynoic acid, trifluoroacetate salt

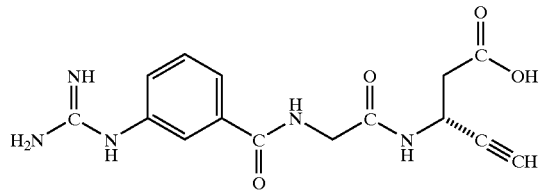

Step A

A suspension of m-guanidinohippuric acid HCl (0.8 g) and NM (0.3 ml) in DMF (2.5 ml) was treated with pivaoyl chloride (0.4 ml). After 30 minutes, a solution of ethyl 3R-amino-4-pentynoate (0.4 g), NMM (0.3 ml) and a catalytic amount of DMAP in DMF (2.5 ml) was added. The reaction was stirred overnight at room temperature. Ethyl 3R-[(2-[[[3-[(aminoiminomethyl)amino]phenyl]carbonyl] amino]acetyl]amino]-4-pentynoic acid trifluoroacetate salt (0.5 g) was isolated by HPLC (RP-CH$_3$CN/H$_2$O) as a white solid. MS was consistent with the desired product.

Step B

A solution of the product of Step A (0.5 g) in 1:1 CH$_3$CN/H$_2$O (75 ml) was treated with LiOH (pH>12). After 2 hours, the reaction was acidified with TFA and the product was purified by HPLC (RP-CH$_3$CN/H$_2$O). The title compound as a lyophilized solid (250 mg), had MS, $^1$H-NMR and CHN analysis that were consistent with the desired product.

EXAMPLE 71

Preparation of 2-[[2S-[[2-[[[3-[(aminoiminomethyl) amino]phenyl]carbonyl]amino]acetyl]amino]-2-(carboxymethyl)ethyl]sulfonyl]benzoic acid, TFA salt

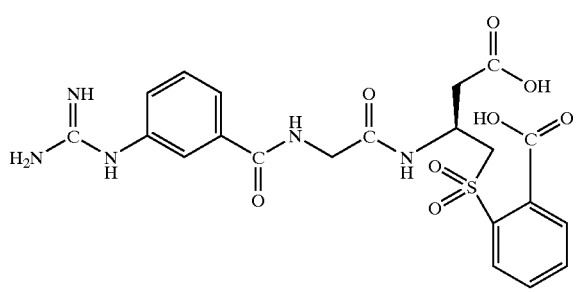

A solution of Example 72 (120 mg) in methanol (10 ml) was treated with m-chlorobenzoic acid (100 mg). The reaction was stirred overnight at room temperature. The product was purified by HPLC (RP-CH$_3$CN/H$_2$O). The title compound (100 mg) was isolated as a white solid. MS, $^1$H-NMR and CHNS analysis were consistent with the desired product.

EXAMPLE 72

Preparation of 2-[[2S-[[2-[[[3-[(aminoiminomethyl) amino]phenyl]carbonyl]amino]acetyl]amino]-2-(carboxymethyl)ethyl]thio]benzoic acid, trifluoroacetate salt

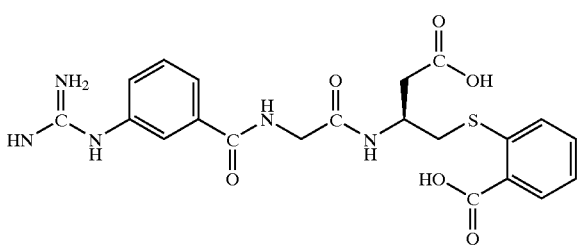

Step A

A solution of Example A (6.2 g) in CH$_2$Cl$_2$ (40 ml) at 0° C. was treated with triethylamine (4.25 ml) and mesyl chloride (2.3 ml). After 3 hours, phenylmethyl 3S-[[(1,1-dimethylethoxy)carbonyl]amino]-4-[(methylsulfonyl)oxy] butanoate was isolated by extraction using ethyl acetate/diethyl ether. The organic layer was dried using Na$_2$SO$_4$ and the excess solvent was removed to give phenylmethyl 3S-[[(1,1-dimethylethoxy)carbonyl]amino]-4-[(methylsulfonyl)oxy]-butanoate (8.8 g). A suspension of the resulting product, K$_2$CO$_3$ (3.0 g), and catalytic amounts of 18-crown-6, DMAP and tetrabutylammonium hydrogen sulfate in DMF (10 ml) was treated with methyl thiosalicylate (3.8 ml). After 2 hours the product was extracted with ethyl acetate. The organic layer was dried with Na$_2$SO$_4$ and the excess solvent was removed under reduced pressure. The resulting oil (10.2 g) was dissolved in CH$_2$Cl$_2$ (50 ml) and treated with TFA (20 ml). The reaction was stirred overnight at room temperature. The excess solvent was removed under reduced pressure and the oil was dissolved in 1:1 CH$_3$CN:H$_2$O and made basic using NaOH (pH>12). After 2 hours, the reaction was acidified using TFA and the product was isolated using HPLC (RP-CH$_3$CN/H$_2$O). 20% HCl (2 ml) was added and the product was lyophilized. A yellow solid (0.9 g) was obtained. MS was consistent with 2-[(2-amino-3-carboxypropyl)thio]benzoic acid HCl salt.

Step B

A solution of 3-aminobenzoic acid (41.1 g) in dioxane (300 ml) was treated with 3,5-dimethyl(pyrazole-1-carboxamidine) HNO$_3$ (100 g), DIEA (90 ml) and H$_2$O (100 ml). The reaction was refluxed for 3 hours and stirred overnight at room temperature. The solid was filtered and washed with dioxane (150 ml) and 1:1 dioxane:H$_2$O (250 ml). The solid was then suspended in diethyl ether (400 ml) and CH$_3$CN (100 ml) and treated with 4N HCl/dioxane (100 ml) and 20% HCl (1 ml). After 48 hours, the reaction was filtered and dried to give 3-[(aminoiminomethyl)amino] benzoic acid (34.1 g) as a lavender solid. MS was consistent with the desired product.

Step C

A solution of 2-[(2S-amino-4-carboxybutyl)thio]benzoic acid (0.9 g) and DIEA (1.5 ml) in DMF (5 ml) was treated with N-[1,1-dimethylethoxy)carbonyl]glycine, 2,5-dioxopyrrolidin-1-yl ester (1.1 g) and a catalytic amount of DMAP. After 1 hour, methanol (5 ml) and 4N HCl/dioxane (10 ml) were added. After 18 hours, methyl 2-[[2S-[(2-aminoacetyl]amino]-3-(methoxycarbonyl)-propyl]benzoate was isolated by HPLC (RP-CH$_3$CN/H$_2$O). The desired product (1.0 g) was obtained as a white solid. MS was consistent with the desired product.

Step D

A solution of the product of Step C (200 mg) and NMM (130 μl) in DMF (1 ml) was treated with of IBCF (152 μl). After 2 minutes, the reaction was treated with a solution of the product of Step B (330 mg), NMM (260 μl) and a catalytic amount of DMAP in DMF (1 ml). After 2 hours, the reaction was treated with H$_2$O and made basic using NaOH (pH>12). After 4 hours, the reaction was acidified with TFA and the product was isolated by HPLC (RP-CH$_3$CN/H$_2$O). The title compound (200 mg) was obtained as a white solid. MS, $^1$H-NMR and CHNS analysis were consistent with the desired product.

EXAMPLE 79

Preparation of (±)ethyl β-[[2-[[[3-[(aminoiminomethyl)amino]phenyl]carbonyl] methylamino]acetyl]amino]pyridine-3-propanoate, bis(trifluoroacetate)salt

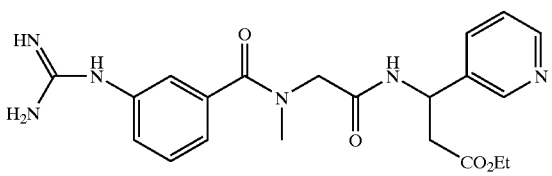

Step A

To a 200 mL flask equipped with a teflon coated stir bar was added N-t-Boc-sarcosine (3.80 g, 0.019 mole) and dry DMF (70 mL). To this was added N-methyl morpholine, (NMM), (2.1 mL, 1.92 g, 0.019 mole) and the resulting mixture was cooled to 0° C. (salt—ice water bath). After several minutes isobutyl-chloroformate, (IBCF), (95%, 2.74 g, 2.6 mL, 0.019 mole) was added. After about five minutes a solution of ethyl 3-amino-3-pyrid-3-yl propionate dihydrochloride salt (5.0 g, 0.019 mole) and NMM (3.84 g, 0.038 mole) in DMF (40 mL) was added and the resulting mixture allowed to react overnight at 0–5° C. The volatiles were removed on a rotary evaporator (60° C.) and a semi-solid was obtained. This was taken up in ethyl acetate and dilute hydrochloric acid, pH 2. To the aqueous layer was added EtOAc (200 mL) and the pH of the aqueous layer was brought to about 7 by the addition of solid sodium bicarbonate. The pH was adjusted to 8 by the addition of dilute aqueous NaOH. The layers were separated and the aqueous layer washed with EtOAc. The combined organic layers were dried ($Na_2SO_4$) and volatiles removed to give a thick oil whose MS was consistent with the desired product.

Step B

The product from Step A was dissolved in dioxane (20 mL) and transferred to a round-bottom flask equipped with a teflon-covered stir bar and connected to a mineral oil bubbler. To this was added 4 N HCl in dioxane (about 30 mL). After about one hour a vacuum was applied to remove excess HCl gas and the reaction mixture was concentrated on a rotovap. Excess HCl was chased with a second evaporation from dioxane to obtain a white foam. The MS and NMR were consistent with the desired product as a dihydrochloride salt.

Step C

The title compound was obtained by coupling 3-guanidinobenzoic acid with the product of Step B using substantially the same conditions and procedure as employed in Step A. Thus, to 3-guanidinobenzoic acid hydrochloride (1.5 g, 7.0 mmole, Aldrich) dissolved in DMF (70 mL) was added an equivalent of NMM (0.77 mL, 7.0 mole) and the mixture cooled to 0° C. To this was added one equivalent of IBCF (0.91 mL, 7 mmole) and after several minutes a solution of 1.1 equivalent of the sarcosine pyridyl amino acid ester prepared in Step B (2.4 g of di HCl salt) and NMM (0.78 mL) in DMF (about 50 mL) was added and the reaction mixture allowed to warm to room temperature overnight. Volatiles were removed and the product isolated by preparative reverse phase high performance liquid chromatography (RPHPLC) using a gradient of 99:1 water, 0.05% TFA: acetonitrile, 0.05% TFA to 45:55 over 60 minutes at 80 mL/min flow rate. The desired product fractions were combined and lyophilized to give the title compound (0.96 g) as a fluffy solid whose NMR and MS were consistent with the desired product.

EXAMPLE 80

Preparation of (±)β-[[2-[[[3-[(aminoiminomethyl) amino]phenyl]carbonyl]methylamino]acetyl]amino] pyridine-3-propanoic acid, bis(trifluoroacetate)salt

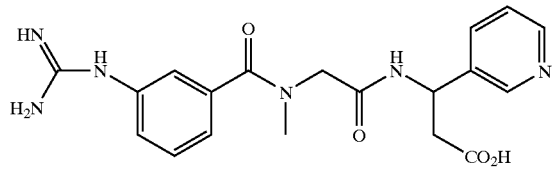

The product obtained in Example 79 (0.33 g) was dissolved in water (20 mL) and the pH adjusted to 11 by the addition of dilute aqueous LiOH. After about one hour the ester was substantially hydrolyzed as indicated by analytical C-18 HPLC. The desired product (±)β-[[2-[[[3-[(aminoiminomethyl)amino]phenyl]carbonyl]methylamino]acetyl]amino]pyridine-3-propanoic acid, bis(trifluoroacetate)salt was isolated by preparative C-18 HPLC using substantially the same conditions outlined in Example 79, Step C, and lyophilized (0.19 g). Proton NMR, FAB MS, and elemental analysis (CHN) were consistent with the desired product.

EXAMPLE 81

Preparation of ethyl β-[[2-[[[3-[(aminoiminomethyl) amino]phenyl]carbonyl]amino]-1-oxopropyl]amino] pyridine-3-propanoate, bis(trifluoroacetate)salt

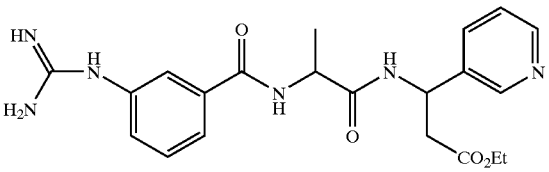

Step A

R,S-N-t-Boc alanine (2.0 g, 0.0106 mole) was coupled to ethyl 3-amino-3-pyridyl-propionate dihydrochloride (3.2g). Using the procedure of Example 79, Step A. The product obtained (3.42 g, 88% isolated yield) had MS and NMR consistent with the desired N-Boc product.

Step B

The Boc protecting group was removed from the product of Step A using the procedure of Example 79, Step B to obtain the dihydrochloride salt (3.5 g) as a white solid whose MS and NMR spectrum were consistent with the desired amino acid ester.

Step C

Preparation of ethyl β-[[2-[[[3-[(aminoiminomethyl) amino]phenyl]carbonyl]amino]-1-oxopropyl]amino] pyridine-3-propanoate, bis(trifluoroacetate)salt . The amino acid ester (1.6 g) obtained in Step B was coupled to 3-guanidinobenzoic acid (0.75 g, 3.5 mole) using the conditions of Example 79, Step C to obtain the title compound (1.8 g 2.7 mmole , 79% isolated yield) bis trifluoroacetate salt as a white solid after lyophilization. MS and proton NMR were consistent with the desired product.

EXAMPLE 82

Preparation of β-[[2-[[[3-[(aminoiminomethyl) amino]phenyl]carbonyl]amino]-1-oxopropyl]amino] pyridine-3-propanoic acid, bis(trifluoroacetate)salt

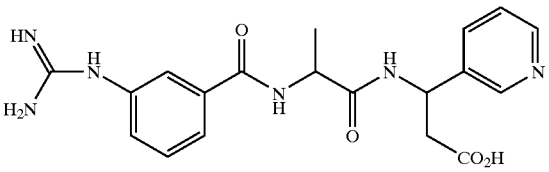

The product of Example 81 (0.5 g) was hydrolyzed to the acid using the procedure of Example 80. The desired product as the di-TFA salt was isolated by preparative C-18 HPLC using substantially the same conditions outlined in Example 79, Step C, and lyophilized (0.45 g). Proton NMR and FAB MS were consistent with desired product.

EXAMPLE 83

Preparation of (±)β-[[2-[[[3-[(aminoiminomethyl) amino]-4-methylphenyl]carbonyl]amino]acetyl] amino]pyridine-3-propanoic acid, bis(trifluoroacetate)salt

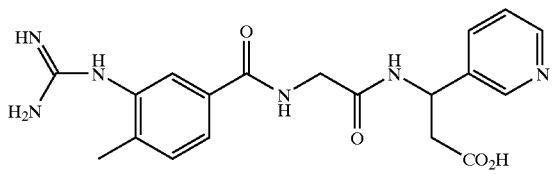

Step A

N-t-Boc glycine was coupled to 3-amino-3-(3-pyridyl) propionic acid dihydrochloride (5.0 g, 0.019 mole) using the procedure of Example 79, Step A to obtain, after work-up, a yellow oil (6.0 g, 90%) whose MS was consistent with the desired compound.

Step B

The Boc protecting group was removed by dissolving the product of Step A (5.9 g) in dioxane (about 20 mL) and TFA and the reaction was allowed to proceed for several minutes until the evolution of gas ceased. The volatiles were removed on a rotavap to obtain a brown oil. MS and NMR were consistent with the desired product.

Step C

The amino-ester prepared in Step B was coupled to 4-methyl-3-nitrobenzoic acid using the procedure of Example 79, Step C to obtain an oil that was purified by preparative RPHPLC (C-18) to obtain the desired coupled product (1.76 g) as an amorphous solid whose NMR and MS were consistent with the desired product.

Step D

The nitro group present in the product from Step C was reduced to the aniline using the following procedure. The product from Step C (1.75 g) was transferred to a 6 oz. Fischer-Porter pressure bottle equipped with a pressure gauge and inlet and outlet valves. The starting compound was dissolved in glacial acetic acid, 3% Pd on carbon catalyst (about 1 g) was added and the vessel sealed. After three vacuum-nitrogen cycles the vessel was pressurized with hydrogen (55 psig) and the reaction was allowed to proceed overnight at room temperature. The catalyst was removed by filtering through celite and the colorless solution concentrated to give a yellow, viscous oil (2.0 g) whose MS was consistent with the desired aniline.

Step E

The aniline (1.0 g, 2.12 mmole) from Step D was guanylated using the following procedure. The aniline was dissolved in acetonitrile (about 50 mL) and 1H-pyrazole-1-carboxamidine hydrochloride (0.342 g, 2.3 mmole) added in water along with triethylamine (0.64 g, 0.92 mL, 6.4 mmole) and the solution brought to reflux. After heating overnight the volatiles were removed on the rotovap and the semi-solid obtained purified by preparative RPHPLC to obtain the desired guanidated product (0.3 g after lyophilization) whose NMR and MS were consistent with the desired structure.

Step F

The guanidino-ester obtained in Step E was hydrolyzed to the acid by dissolving the ester (0.3 g) in water (20 mL) and the pH brought to 11 by the addition of dilute LiOH. After about an hour complete conversion to the acid was observed by analytical RPHPLC and the title compound, purified by preparative HPLC and lyophilized to obtain the di-TFA salt as a white powder (0.19 g) whose NMR and MS were consistent with the desired product.

EXAMPLE 84

Preparation of β-[[2-[[(3-amino-4-methylphenyl) carbonyl]amino]acetyl]amino]pyridine-3-propanoic acid, bis(trifluoroacetate)salt

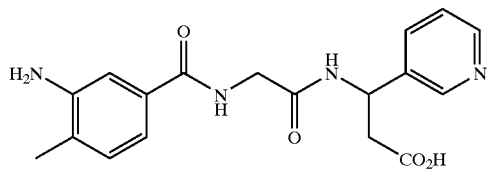

The aniline-ester obtained in Example 83, Step D was hydrolyzed to the acid using conditions similar and purification scheme similar to Example 83, Step F to obtain the desired aniline-acid, β-[[2-[[(3-amino-4-methylphenyl) carbonyl]amino]acetyl]amino]pyridine-3-propanoic acid, as the di-trifluoroacetate salt whose NMR and MS were consistent with the desired product.

EXAMPLE 85

Preparation of (±)β-[[2-[[[3-[[(aminoiminomethyl) amino]methyl]phenyl]carbonyl]amino]acetyl]amino] pyridine-3-propanoic acid, bis(trifluoroacetate)salt

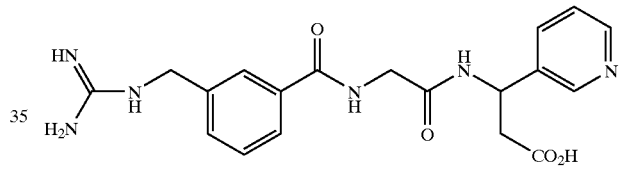

Step A

3-Cyanobenzoic acid (7.0 g, 0.0476 mole) was added to a round-bottom flask (200 mL) and dissolved in DMF:pyridine (50 mL). To this solution was added disuccinylcarbonate (DSC, 14.6 g, 0.0571 mole) and a catalytic amount of DMAP. Upon cessation of gas evolution, glycine t-butyl ester (9.6 g, 0.057 mole) was added and allowed to react overnight. Triethylamine (10 mL) was added and stirred for several minutes. Volatiles were removed on a rotovap and worked up by dissolving the crude reaction mixture in water and ethyl acetate. The aqueous layer was made acidic by addition of dilute hydrochloric acid, the layers separated, and the water layer discarded. The organic layer was washed with saturated aqueous sodium bicarbonate, dried ($Na_2SO_4$), and concentrated to obtain a product (11.1 g) whose MS was consistent with the desired, coupled product.

Step B

The cyano-t-butyl ester obtained in Step A was reduced to the corresponding benzylamine compound in similar fashion to Example 82, Step D. Thus, cyano-t-butyl ester (10.0 g, 0.0681 mole) was dissolved in acetic acid (about 70 mL) with heating and cooled. Catalyst was added (0.5 g 3% Pd on carbon) and the reaction transferred to a 6 oz Fischer-Porter bottle and pressurized with hydrogen (55 psig). Hydrogen was continually added until hydrogen uptake ceased. The catalyst was removed by filtration through celite and the solvent was removed by evaporation to obtain crude benzyl amino t-butyl ester whose MS was consistent with the desired compound.

Step C

The Boc group was removed from the product of Step B in a fashion similar to Example 83, Step B to obtain the benzyl amino acid whose MS was consistent with the desired product.

Step D

The amino acid (9.0 g, 0.03 mole) obtained in Step C was dissolved in acetonitrile:water (about 1:1) and excess triethylamine added. After several minutes volatiles were removed and crude triethylamine salt obtained. This was re-dissolved in acetonitrile:water (200 mL) and 1H-pyrazine-1-carboxamidine hydrochloride (4.3 g, 0.03 mole) was added and the reaction mixture brought to reflux. After allowing the reaction to reflux overnight the reaction was concentrated to a semisolid. This was dissolved in water (20 mL) and the pH was adjusted to about 7 by addition of solid sodium bicarbonate. A precipitate formed and was removed by filtration. The MS and NMR were consistent with the zwitter-ion. This product was converted to the hydrochloride salt by treating the zwitter-ion with water and adding hydrochloric acid until the pH was about 2. This was lyophilized to obtain the hydrochloride salt.

Step E

The guanidino-acid was obtained by hydrolyzing the product obtained in Step D (0.47 g) using the procedure of Example 83, Step F. Upon lyophilization a solid is obtained (0.41 g) as the di-TFA salt whose NMR and MS were consistent with the desired product.

Step F

The guanidino-acid prepared in Step E was coupled to 3-amino-3-(3-pyridyl)propionic acid using the procedure of Step A. Preparative RPHPLC was employed to obtain a solid (1.66 g) whose NMR and MS were consistent with the desired product.

EXAMPLE 86

Preparation of 3S-[[2-[[[3-[(aminoiminomethyl)amino]phenyl]carbonyl]amino]acetyl]amino]-4-hydroxybutanoic acid

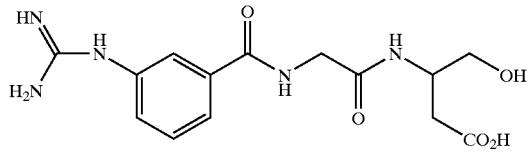

Step A
Preparation of 3-N-t-Boc-amino-4-hydroxy-butyric acid benzyl ester.

N-t-Boc aspartic acid, alpha-benzyl ester (10.0 mmol) was dissolved in THF (10 mL) and added dropwise over a period of 30 minutes to a 0° C. solution of $BH_3$-THF h(20 mL, 20.0 mmol), under $N_2$. After the mixture was stirred for an additional 1–2 hours at 0° C., the reaction was quenched with a solution of 10% AcOH in NeOH (10 mL), and the solvent evaporated. The residue was dissolved in EtOAc and extracted with 1N HCl, $H_2O$, and 1 M $NH_4HCO_3$. After being dried over $MgSO_4$, the product was recovered by removal of the solvent in vacuo. MS was consistent with the desired product.

Step B
Preparation of N-t-Boc-3-amino-2,3-dihydro-5-oxo-3S-furan.

The 3-N-t-Boc-amino-4-hydroxy-butyric acid benzyl ester (20 g, 64 mmol) was stirred in dichloromethane (200 mL) at 25° C. for 16 hours in the presence of a catalytic amount of camphor sulfonic acid. The solvent was removed in vacuo. The crude material was purified by flash chromatography on a bed of silica gel (22 cm×6 cm of Merck 60 Silicagel) eluted with a gradient of hexane/ethyl acetate (90/10 to 70/30; 200 mL/min flow rate). The pure N-t-Boc-3-aminolactone was isolated as a white solid (5.4 g) whose MS was consistent with the desired compound.

Step C
Preparation of 3-amino-2,3-dihydro-5-oxo-3S-furan hydrochloride.

The 3-N-t-Boc amino lactone (5.0 g, 25 mmol) isolated in Step B was dissolved in 4N HCl dioxane (20 mL). After stirring 45 minutes at 25° C., 4N HCl dioxane solution (10 mL) was added and after 1 hour at 25° C., the excess HCl was removed in vacuo. The resulting solution deposited crystals upon standing. The white crystalline material was filtered and dried (2.9 g); $^1$H NMR (DMSO-$d_6$) δ 2.55 (dd, 1H, J1=18.3 Hz, J2=2.5 Hz), 3.0 (dd, 1H, J1=8.5 Hz, J2=18.3 Hz), 4.1 (m, 1H), 4.35 (dd, 1H, J1=10.5 Hz, J2=2.7 Hz), 4.5 (dd, 1H, J1=10.5 Hz, J2=6.5 Hz), MS (FAB) 102.1(M+H+).

Step D
3-amino-2,3-dihydro-5-oxo-3S-furan hydrochloride was coupled to meta-guanidino-hippuric acid hydrochloride (GIHA) using the following procedure. To GIHA (1.6 g, 5.9 mmole) in DMF (about 30 mLs) was added an equivalent of NMM (0.59 g, 0.64 mL, 5.82 mmole) and the mixture allowed to stir for several minutes until a precipitate formed. The mixture was cooled to 0° C. and an equivalent of DSC (1.49 g, 5.82 mmole) and a catalytic amount of DMAP were added and the reaction allowed to proceed for at least 0.5 hour. Upon substantially complete activation 3-amino-5-oxo-3S-furan hydrochloride (0.8 g, 5.82 mmole) was added to the reaction mixture followed by an equivalent of NMM (0.59 g, 0.64 mL, 5.82 mmole) and the reaction allowed to proceed to completion (1–16 hours). The volatiles were removed (vacuum rotary evaporation at 60° C.) and the residue dissolved in a minimum amount of water:acetonitrile (using the minimum amount of acetonitrile to effect solution). The solution was brought to pH of about 3 by addition of neat TFA and isolation of desired coupled product was achieved by preparative RPHPLC to obtain the mono TFA salt as a hygroscopic solid after lyophilization (0.54 g).

Step E
The title compound was obtained by dissolving the product from Step D (0.54 g) in water (20 mL). The pH of the solution was brought to about 11 by addition of dilute aqueous NaOH. Upon completion of the reaction, as determined by analytical RPHPLC, the solution (final pH about 8) was lyophilized. The product's identity was confirmed by proton NMR and MS.

EXAMPLE 87

Preparation of (±)sodium β-[[2-[[[3-[(aminoiminomethyl)amino]phenyl]carbonyl]amino]acetyl]amino]-2-hydroxybenzenepropanoate, sodium salt, trifluoroacetate salt

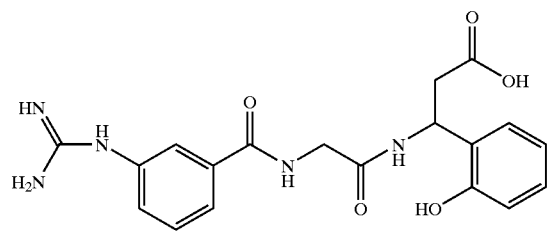

3-Amino-hydrocoumarin hydrochloride (2.0 g, 0.010 mole), prepared according to J. Rico, *Tett. Let.*, 1994, 35, 6599–6602, was coupled to GIHA (1.50 g, 0.0041 mole) using substantially the procedure of Example 86, Step D. Purification by preparative RPHPLC gave the desired product as a mixture of coumarin and hydroxy-acid TFA salts as a light yellow powder after lyophilization (1.50 g). Essentially complete conversion to the desired phenol-acid was obtained by dissolving the purified mixture in water, adjusting the pH to 7–8 with dilute aqueous NaOH, and lyophilizing. MS and proton NMM were consistent with the phenol-acid (carboxylate) form of the molecule (as the trifluoroacetate, sodium salt).

EXAMPLE 88

Preparation of (±)β-[[2-[[[3-[(aminoiminomethyl)amino]phenyl]carbonyl]amino]acetyl]amino]-2-hydroxy-5-methylbenzenepropanoic acid, trifluoroacetate salt

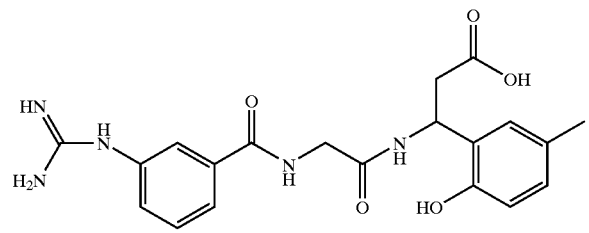

3-Amino-6-methylhydrocoumarin, prepared according to the reference cited in Example 87, was coupled to GIHA using amounts, conditions, and purification similar to Example 87 to obtain a tan solid (0.76 g) whose NMR and MS were consistent with the desired product (as the TFA, sodium salt).

EXAMPLE 89

Preparation of (±)3-[[2-[[[3-[(aminoiminomethyl)amino]phenyl]carbonyl]amino]acetyl]amino]-4-[(2-hydroxyethyl)amino]-4-oxobutanoic acid, trifluoroacetate salt

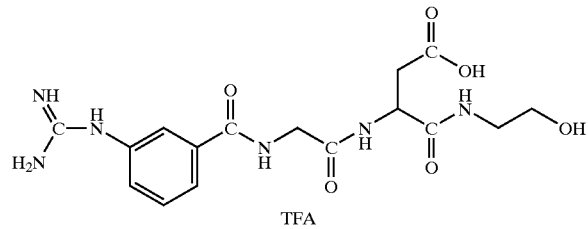

Step A

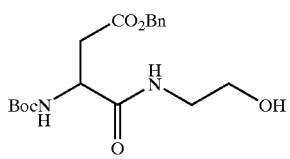

N-t-Boc aspartic acid, alpha-benzyl ester (7.7 mmol, 2.50 g) was dissolved in DMF: pyridine (1:1, 70 mL) and DSC (8.5 mmol, 2.2 g) was added together with a catalytic amount of DMAP. After cessation of gas evolution (about 1 hour), ethanol amine (0.52 g, 8.3 mmol) in pyridine (20 mL) was added and allowed to react at room temperature overnight. Volatiles were removed to obtain a golden oil. The resulting product was partitioned between EtOAc and aqueous HCl. The organic layer was washed with saturated aqueous sodium bicarbonate solution, water, dried (anhydrous sodium sulfate) and volatiles removed to obtain a golden oil (2.64 g) whose proton NMR and mass spectra correspond to the desired protected amide.

Step B

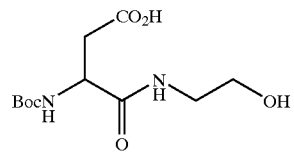

The crude product from Step A (2.3 g) was de-benzylated using standard procedures. Thus, the product from Step A was taken up in acetic acid (about 70 mL) transferred to a Fischer-Porter pressure bottle and 3% palladium on carbon (1 g) and hydrogen added (54 psig). The reaction was vigorously stirred and hydrogen replenished as needed. After no further hydrogen uptake (about 1 hour) the catalyst was removed by filtration through a celite pad and volatiles removed to obtain a colorless oil (1.73 g). Proton NMR and MS were consistent with the desired de-benzylated product.

Step C

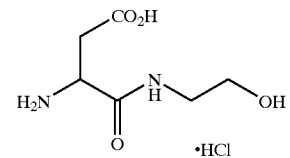

The crude product obtained in Step B was dissolved in dioxane (20 mL) and to this was added 4N HCl in dioxane (40 mL) with vigorous stirring. The reaction was allowed to proceed until gas evolution ceased (about 15 minutes). The volatiles were removed and a golden oil was obtained which was triturated with diethyl ether. Proton NMR and mass spectra were consistent with the desired N-deprotected, amino acid product.

Step D

The product of Step C (1.0 gm, 4.7 mmol) was coupled to GIHA (1.5 g, 4.11 mmol) using a procedure similar to that of Example 86, Step D. The crude coupling reaction was concentrated to a thick oil and reconstituted in water:acetonitrile, and purified by preparative RPHPLC to obtain the desired (±)3-[[2-[[[3-[(aminoiminomethyl)amino]phenyl]carbonyl]amino]acetyl]amino]-4-[(2-hydroxyethyl)amino]-4-oxobutanoic acid, trifluoroacetate salt (0.44 g after lyophilization). Proton NMR and mass spectra were consistent with the desired product.

EXAMPLE 94

Preparation of 2S-[[2-[[[3-[[aminoiminomethyl]
amino]phenyl]carbonyl]amino]acetyl]amino]-3-
carboxypropyl 2-aminobenzoate, bis
(trifluoroacetate)salt, monohydrate

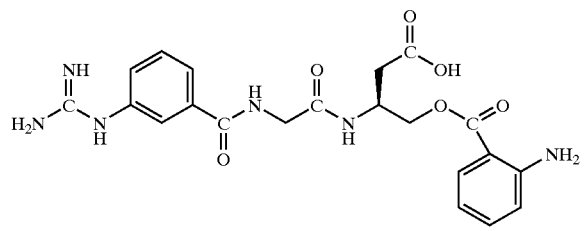

Step A
Preparation of Benzyl-3-N-tBoc-amino-4-hydroxy-(3S)-butyrate

N-tBoc-L-aspartic acid, β-benzyl ester (Sigma) (75 g, 20 mmol) was dissolved in THF (30 ml) and added dropwise over a period of 30 minutes to BH$_3$-THF (400 ml, 40 mmol) at 0° C. under a N$_2$ atmosphere; After the solution was stirred for 2.5 hours at 0° C., the reaction was quenched with 50 ml solution of 10% acetic acid in MeOH, and the solvent was evaporated. The residue was dissolved in ether (200 ml) and washed with 1N HCl, saturated K$_2$CO$_3$, water and dried over MgSO$_4$. The product was isolated by removal of the solvent in vacuo (mp 56–57° C. from isopropyl ether/hexane). $^1$H-NMR (d$_6$-DMSO) δ 1.4 (s, 9H), 2.68 (d, 2H, J=6 Hz), 3.82 (d, 2H, J=5 Hz), 4.01 (m, 1H), 5.16 (s, 2H), 5.21 (bs, 1H), 7.37 (bs, 5H).

Step B
Preparation of benzyl-3-amino-4-(anthranilate)-(3S)-butyrate

Benzyl-3-H-tBoc-amino-4-hydroxy-(3S)-butyrate (10 g, 32 mmol) was dissolved in 50 ml of dimethylformamide followed by triethylamine (4.4 g, 46 mmol). Isatoic anhydride (5.0 g, 3 mmol) was added and the solution was stirred for 24 hours at 25° C. After the reaction (monitored by reverse phase HPLC) was complete, water was added and the product extracted with ethyl acetate (100 mL) and dried over Na$_2$SO$_4$. Solvent evaporation resulted in 12 g of a yellow oil. To this oil, dioxane (20 mL) was added followed by 4N HCl in dioxane (20 mL). The reaction was left to proceed for 4 hours, ether was added and an oily mass separated from the solution. Ether was again added to the oily mass and decanted. This procedure was repeated two times. Ether was added to the semi solid and stirred vigorously for 16 hours. A white solid was collected having MS and $^1$H-NMR consistent with the proposed structure.

Step C
N,N'-Disuccinimidylcarbonate (DSC) (1.4 g, 0.5 mmol) was added to GIHA (1.0 g, 0.5 mmol) in dry dimethylformamide (20 mL) followed by dimethylaminopyridine (100 mg). After a period of 1 hour benzyl-3-amino-4-anthranilate-(3S)-butyrate (0.7 g, 0.5 mmol) in DMF/NMM (1:1) (5.0 mL) was added in one portion. The product was purified by reverse phase chromatography (water/acetonitrile) to result in a white solid (1.0 g). MS, and $^1$H-NMR were consistent with proposed structure.

Step D
The benzyl ester from Step C was hydrogenated using H$_2$ gas and catalytic Pd/C (500 mg, 5%) for 4 hours. After complete reaction the product was purified by reverse phase chromatography (water/acetonitrile) to result in a white solid (1.0 g). MS and $^1$H-NMR were consistent with the proposed structure.

EXAMPLE 95

Preparation of β-[[(2-[[[3-[(aminoiminomethyl)
amino]phenyl]carbonyl]amino]acetyl]amino]-1,4-
benzodioxin-6-propanoic acid, trifluoroacetate salt

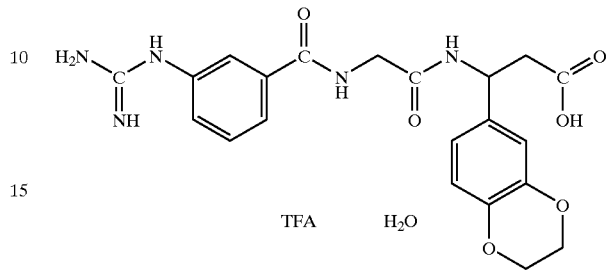

Step A

To 1,4-benzodioxan-6-carboxaldehyde (Aldrich) (10 g) in isopropanol (205 mL) was added ammonium acetate (12.5 g) followed by malonic acid (6.0 g). The reaction mixture was stirred at reflux for 5 hours. The reaction mixture was filtered hot and washed with hot isopropanol (100 mL). The resulting white solid was dried to give DL-3-amino-3-(1,4-benzodioxane)propionic acid (6.3 g) as a white solid. MS, and $^1$H-NMR were consistent with the proposed structure.

Step B

DL-3-amino-3-(1,4-benzodioxane)propionic acid (6 g) from Step A was slurried in absolute EtOH (250 mL) and acetyl chloride (20 mL). The slurry was then heated at reflux for 4 hours. The reaction mixture was cooled to 25° C. and the solvent evaporated under reduced pressure to give a solid which was washed with ethyl ether (50 mL) to give DL-ethyl-3-amino-3-(1,4-benzodioxane)propionate (6.5 g) as a white solid. MS and $^1$H-NMR were consistent with proposed structure.

Step C

N,N'-Disuccinimidyl carbonate (DSC) (1.4 g, 0.5 mmol) was added to GIHA (1.0 g, 0.5 mmol) in dry dimethylformamide (20 mL) followed by dimethylaminopyridine (100 mg). After a period of 1 hour the product from Step B (0.7 g, 0.5 mmol) in DMF/NMM (1:1) (5.0 mL) was added in one portion. After complete reaction the product was purified by reverse phase chromatography (water/acetonitrile) to result in a white solid (1.1 g). MS and $^1$H-NMR were consistent with the proposed structure.

Step D

DL-ethyl-3-amino-3-(1,4-benzodioxane)propionate adduct (the product from Step C) (500 mg) was dissolved in water/acetonitrile (1:1), followed by the addition of lithium hydroxide (100 mg). The reaction mixture was stirred at 25° C., and monitored by HPLC. After complete hydrolysis (1–2 hours) trifluoroacetic acid was added until pH=2. The product was purified by reverse phase chromatography (water/acetonitrile) to result in 255 mg of a white solid. MS and $^1$H-NMR were consistent with the proposed structure.

EXAMPLE 96

Preparation of N-[2-[[[3-[(aminoiminomethyl)amino]phenyl]carbonyl]amino]acetyl]-β-alanine, ethyl ester

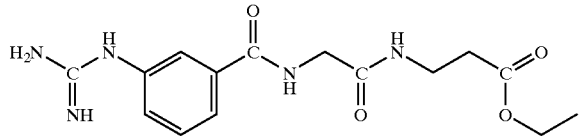

N,N'-Disuccinimidyl carbonate (DSC) (1.4 g, 0.5 mmol) was added to GIHA (1.0 g, 0.5 mmol) in dry dimethylformamide (20 mL) followed by dimethylaminopyridine (100 mg). After a period of 1 hour beta-alanine ethyl ester hydrochloride (0.7 g, 0.5 mmol) in DMF/NMM (1:1) (5.0 mL) was added in one portion. The product was purified by reverse phase chromatography (water/acetonitrile) to result in 1.1 mg of a white solid. MS and ¹H-NMR were consistent with proposed structure.

EXAMPLE 97

Preparation of N-[2-[[[3-[(aminoiminomethyl)amino]phenyl]carbonyl]amino]acetyl]-β-alanine

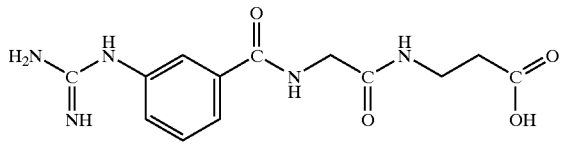

The compound of Example 96 (500 mg) was dissolved in water/acetonitrile (1:1) followed by the addition of lithium hydroxide (200 mg). The reaction mixture was stirred at 25° C., and monitored by HPLC. After complete hydrolysis (1–2 hours) triflouroacetic acid was added until pH=2. The product was purified by reverse phase chromatography (water/acetonitrile) to result in 375 mg of a white solid. MS and ¹H-NMR were consistent with the proposed structure.

EXAMPLE 98

Preparation of (±)ethyl β-[[2-[[[3-[(aminoiminomethyl)amino]phenyl]carbonyl]amino]acetyl]amino]-quinoline-3-propanoate, bis(trifluoroacetate)salt

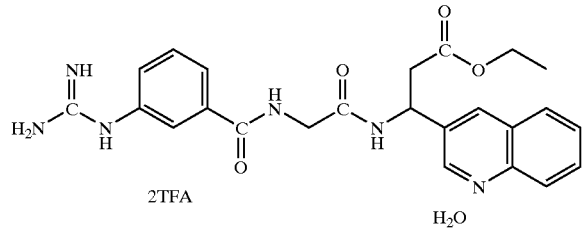

Step A

To 3-quinolinecarboxaldehyde (Aldrich) (10 g) in isopropanol (205 mL) was added ammonium acetate (12.5 g) followed by malonic acid (6 g). The reaction mixture was stirred at reflux for 5 hours. The reaction mixture was filtered hot and washed with hot isopropanol (100 mL). The resulting white solid was dried to give DL-3-amino-3-(3-quinoline)propionic acid (6.3 g) as a white solid. MS and ¹H-NMR were consistent with the proposed structure.

Step B

DL-3-amino-3-(3-quinoline)propionic acid (6 g) from Step A was slurried in absolute EtOH (250 mL) and acetyl chloride (20 mL). The slurry was then heated at reflux for 4 hours. The reaction mixture was cooled to 25° C. and the solvent evaporated under reduced pressure to give a solid which was washed with ethyl ether (50 mL) to give DL-ethyl-3-amino-3-(3-quinoline)propionate (6.5 g) as a white solid. MS and ¹H-NMR were consistent with the proposed structure.

Step C

To N,N'-disuccinimidyl carbonate (DSC) (1.4 g, 0.5 mmol) was added GIHA (1.0 g, 0.5 mmol) in dry dimethylformamide (20 mL) followed by dimethylaminopyridine (100 mg). After a period of 1 hour ethyl DL-3-amino-3-(3-quinoline)propionate (1.2 g, 0.5 mmol) in DMF/NMM (1:1) (5.0 mL) was added in one portion. The product was purified by reverse phase chromatography (water/acetonitrile) to result in a white solid (1.2 g). MS and ¹H-NMR were consistent with the proposed structure.

EXAMPLE 99

Preparation of β-[[2-[[[3-[(aminoiminomethyl)amino]phenyl]carbonyl]amino]acetyl]amino]quinoline-3-propanoic acid, bis(trifluoroacetate)salt

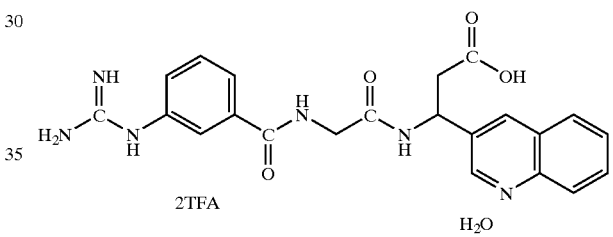

The compound from Example 98 (600 mg) was dissolved in water/acetonitrile (1:1), followed by the addition of lithium hydroxide (100 mg). The reaction mixture was stirred at 25° C. and monitored by HPLC. After complete hydrolysis (1–2 hours) triflouroacetic acid was added until pH=2. The product was purified by reverse phase chromatography (water/acetonitrile) to result in 470 mg of a white solid. MS and ¹H-NMR were consistent with the proposed structure.

EXAMPLE 100

Preparation of ethyl β-[[2-[[[3-[(4,5-dihydrothiazol-2-yl)amino]phenyl]carbonyl]amino]acetyl]amino]pyridine-3-propanoate, trifluoroacetate salt

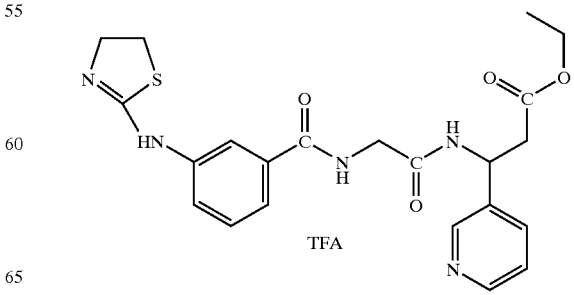

Step A

Preparation of 3-Nitrobenzoyl Glycine:

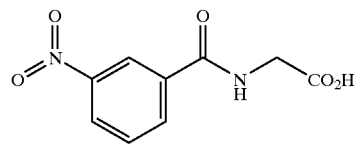

Glycine (20 g, 266 mmol) was added to water (200 mL), followed by potassium hydroxide (20 g, 357 mmol) and cooled to 0° C. in an ice bath. To this solution 3-nitrobenzoyl chloride (Aldrich) (20 g, 108 mmol) was added in a solution in acetonitrile (20 mL) drop-wise over a 10 minute period. After complete reaction (3–4 hours) concentrated hydrochloric acid was added until pH=1 followed by saturated aqueous NaCl (75 mL). The product was filtered, washed with water and air dried (22 g, 90% yield). $^1$H-NMR ($d_6$-DMSO) δ, 3.92 (d, 2H, J=6.1), 7.9 (t, 1H, J=7.9), 8.3 (t, 1H, J=5.6), 8.35 (m, 2H), 8.69 (s, 1H), 9.25 (t, 1H, J=7.2 Hz). MS (FAB) m/e 231.0 (M+Li+).

Elemental Analysis for $C_9H_8N_2O_5$; Calc'd: C, 45.89; H, 4.25; N, 9.92; Found: C, 45.97; H, 4.44; N, 10.11.

Step B 3-nitrobenzoyl glycine, prepared in Step A above (4 g) was dissolved in ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo.

Step C

Acetonitrile (5 mL) was added to the crude aniline from Step B followed by 2-(methylthio)-2-thiazoline (7 g) and heated to reflux for 6 hours. The solvent was removed under reduced pressure to give a solid. Diethyl ether was added and the solid was filtered to give a tan colored solid (4.6 g).

Step D

N,N'-Disuccinimidyl carbonate (DSC) (1.4 g, 0.5 mmol) was added to 2-(methylthio)-2-thiazoline (1.0 g, 0.5 mmol) in dry dimethylformamide (20 mL) followed by dimethylaminopyridine (100 mg). After a period of 1 hour ethyl DL-3-amino-3-(3-pyridyl)propionate (1.2 g, 0.5 mmol) in DMF/NMM (1:1) (5.0 mL) was added in one portion. The product was purified by reverse phase chromatography (water/acetonitrile) to result in a white solid (520 g). MS and $^1$H-NMR were consistent with the proposed structure.

EXAMPLE 101

Preparation of β-[[2-[[[3-[(4,5-dihydrothiazol-2-yl)amino]phenyl]carbonyl]amino]acetyl]amino]pyridine-3-propanoic acid, trifluoroacetate salt

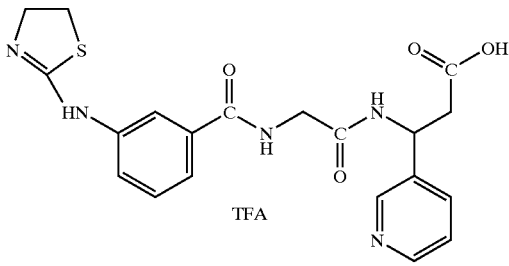

The compound of Example 100 (600 mg) was dissolved in water/acetonitrile (1:1) followed by the addition of lithium hydroxide (100 mg). The reaction was allowed to stir at 25° C., and monitored by HPLC. After complete hydrolysis (1–2 hours) triflouroacetic acid was added until pH=2. The product was purified by reverse phase chromatography (water/acetonitrile) to result in 470 mg of a white solid. MS and $^1$H-NMR were consistent with the proposed structure.

EXAMPLE 102

Preparation of N-[2-[[[3-[[[(phenylmethyl)amino]carbonyl]amino]phenyl]carbonyl]amino]acetyl]-β-alanine, ethyl ester

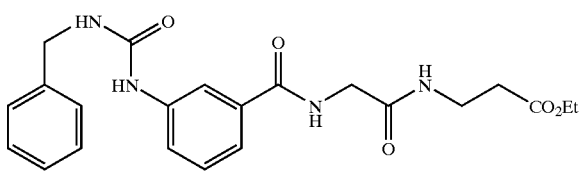

Ethyl (3-nitrobenzoylglycyl)-3-amido propionate (2 g, 0.62 mmol) (Example 100, Step A) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 mL) was added to the crude aniline followed by benzyl isocyanate (700 mg, 0.75 mmol). The solution turned to a solid. Diethyl ether was added and the solid was filtered to give the benzyl urea as a salmon colored solid (2.6 g, 99% yield). The product (1 g portion) was purified by reverse phase chromatography (water/acetonitrile) to result in a white solid: $H_2$ NMR ($d_6$-DMSO) δ, 1.17 (t, 3H, J=7.3 Hz), 2.48 (t, 2H, J=7.1 Hz), 3.45 (q, 2H, $J_1$=6.8 Hz, $J_2$=13.2 Hz), 3.80 (d, 2H, J=6.9 Hz), 4.06 (q, 2H, $J_1$=7.5 Hz, $J_2$=13.4 Hz), 4.31 (d, 2H, J=7.5 Hz), 7.2–7.4 (m, 5H), 7.8 (t, 1H, J=8.0 Hz), 7.85 (bs, 1H), 8.1 (t, 1H, J=5.6 Hz), 8.35 (m, 2H), 8.71 (s, 1H), 8.78 (bs, 1H), 9.22 (bs, 1H). MS (FAB) m/e 427.3 (M+H+).

| Elemental Analysis | | | |
|---|---|---|---|
| $C_{22}H_{26}N_4O_5$ 1.5$H_2O$ | Calc'd.: C, 58.28 | H, 5.74 | N, 12.36 |
| | Found: C, 58.48 | H, 5.57 | N, 12.25 |

EXAMPLE 103

Preparation of 3-[[2-[[[3-[[[(phenylmethyl)amino]carbonyl]amino]phenyl]carbonyl]amino]acetyl]amino]propanoic acid

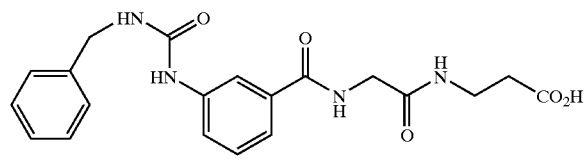

The compound of Example 102 (400 mg, 0.094 mmol) was dissolved in water/acetonitrile (1:1), followed by addition of lithium hydroxide (100 mg, 0.4 mmol). The reaction was stirred at 25° C., and monitored by HPLC. After complete hydrolysis (1–2 hours) trifluoroacetic acid was added until pH=2. The product was purified by reverse phase chromatography (water/acetonitrile) to result in 265 mg of a white solid: $^1H$ NMR ($d_6$-DMSO) δ, 2.48 (t, 2H, J=7.1 Hz), 3.45 (q, 2H, $J_1$=6.8 Hz, $J_2$=13.2 Hz), 3.80 (d, 2H, J=6.9 Hz), 4.31 (d, 2H, J=7.5 Hz), 7.2–7.4 (m, 5H), 7.8 (t, 1H, J=8.0 Hz), 7.85 (bs, 1H), 8.1 (t, 1H, J=5.6 Hz), 8.35 (m, 2H), 8.71 (s, 1H), 8.78 (bs, 1H), 9.22 (bs, 1H). MS (FAB) m/e 405.6 (M+Li+).

| Elemental Analysis | | | |
|---|---|---|---|
| $C_{20}H_{22}N_4O_5$ 0.5$H_2O$ | Calc'd.: C, 59.00 | H, 5.39 | N, 13.75 |
| | Found: C, 59.29 | H, 5.11 | N, 13.63 |

EXAMPLE 104

Preparation of ethyl β-[[2-[[[3-nitrophenyl)carbonyl]amino]acetyl]amino]pyridine-3-propanoate

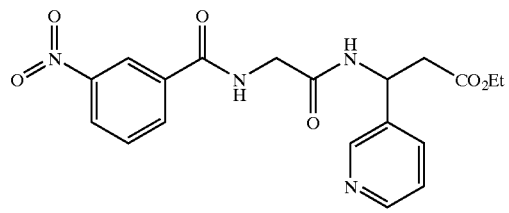

The same procedure used in the preparation of Example C was followed substituting an equivalent amount of DL-ethyl 3-amino-3-pyridyl propionate for ethyl beta-alanine hydrochloride. N,N'-Disuccinimidyl carbonate (14 g, 5.5 mmol) was added to 3-nitro-benzoyl glycine (10 g, 4.5 mmol) in dry dimethylformamide (30 mL) followed by dimethylaminopyridine (200 mg). After a period of 1 hour DL-ethyl 3-amino-3-(3-pyridyl)propionate dihydrochloride (13 g, 4.6 mmol) in 20% aqueous potassium carbonate (50 mL) was added in one portion. After complete reaction the product was collected by filtration (11.5 g, 80% yield). MS and $^1$H-NMR were consistent with the proposed structure.

EXAMPLE 105

Preparation of ethyl β-[[2-[[[3-[[[(phenylmethyl)amino]carbonyl]amino]phenyl]carbonyl]amino]acetyl]amino]pyridine-3-propanoate, trifluoroacetate salt

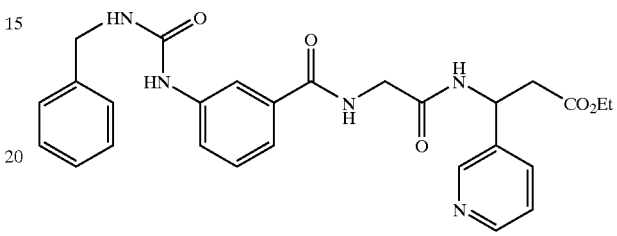

DL-Ethyl(3-nitrobenzoyl glycyl)-3-amido-3-pyridyl propionate (2 g, 0.62 mmol) of Example 104 was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 mL) was added to the crude aniline followed by benzyl isocyanate (700 mg, 0.75 mmol). The solution turned to a solid. Diethyl ether was added and the product was filtered. The product was purified by reverse phase chromatography (water/acetonitrile) to result in a white solid (1.5 g). MS and NMR were consistent with the proposed structure.

EXAMPLE 106

Preparation of (±)β-[[2-[[[3-[[[(phenylmethyl)amino]carbonyl]amino phenyl]carbonyl]amino]acetyl]-amino]pyridine-3-propanoic acid

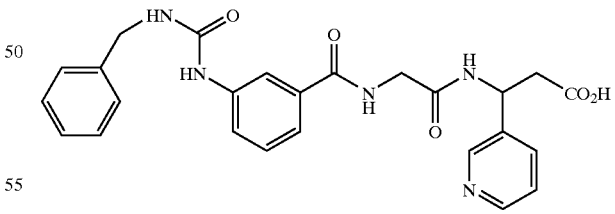

The compound of Example 105 (400 mg, 0.094 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) to result in a white solid (200 mg). MS and $^1$H-NMR were consistent with the proposed structure.

EXAMPLE 107

Preparation of ethyl β-[[2-[[[3-[[(phenylamino]carbonyl]amino]phenyl]carbonyl]amino]acetyl]amino]-pyridine-3-propanoate

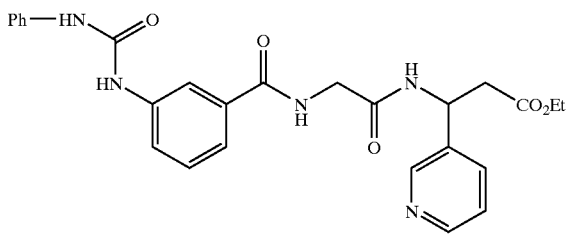

DL-ethyl(3-nitrobenzoylglycyl)-3-amido-3-(3-pyridyl)propionate (2 g, 0.64 mmol) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 ml) was added to the crude aniline followed by phenyl isocyanate (600 mg, 0.75 mmol). The solution turned to a solid. Diethyl ether was added and the product was filtered. The product was purified by reverse phase chromatography (water/acetonitrile) to result in a white solid (1.1 g). MS and $^1$H-NMR were consistent with the proposed structure.

EXAMPLE 108

Preparation of β-[[2-[[[3-[[(phenylamino]carbonyl]amino]phenyl]carbonyl]amino]acetyl]amino]pyridine-3-propanoic acid, trifluoroacetate salt

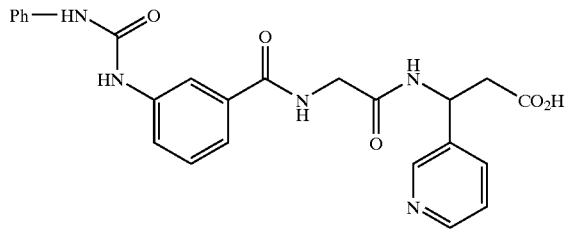

The compound of Example 107 (500 mg, 0.095 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) to result in a white solid (350 mg). MS and $^1$H-NMR were consistent with proposed structure.

EXAMPLE 109

Preparation of ethyl β-[[2-[[[3-(aminocarbonylamino]phenyl]carbonyl]amino]acetyl amino]pyridine-3-propanoate, trifluoroacetate salt

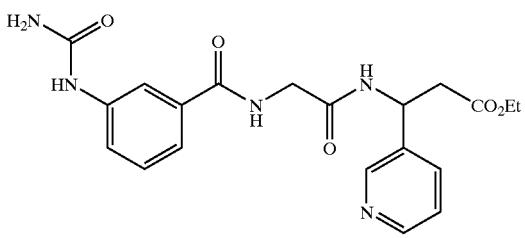

DL-ethyl(3-nitrobenzoylglycyl)-3-amido-3-(3-pyridyl)propionate (2 g, 0.62 mmol) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Hydrochloric acid (20%, 75 mL) was added to the crude aniline followed by urea (2 g). The solution was heated to reflux for 15 hours. After complete reaction (15 hours), the product was purified by reverse phase chromatography (water/acetonitrile) and lyophilized to result in a white solid (1.2 g). MS and $^1$H-NMR were consistent with the proposed structure.

EXAMPLE 110

Preparation of β-[[2-[[[3-(aminocarbonylamino)phenyl]carbonyl]amino]acetyl]amino]pyridine-3-propanoic acid, trifluoroacetate salt

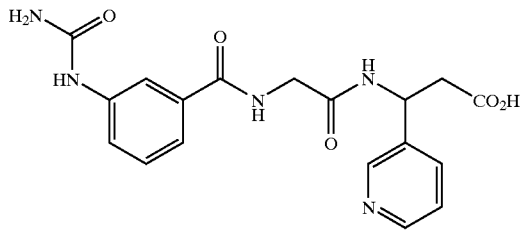

The compound of Example 109 (500 mg, 0.095 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in a white solid (350 mg). MS and $^1$H-NMR were consistent with the proposed structure.

EXAMPLE 111

Preparation of ethyl β-[[2-[[[3-[[[[(4-methylphenyl)sulfonyl]amino]carbonyl]amino]phenyl]carbonyl]amino]acetyl]amino]pyridine-3-propanoate, trifluoroacetate salt

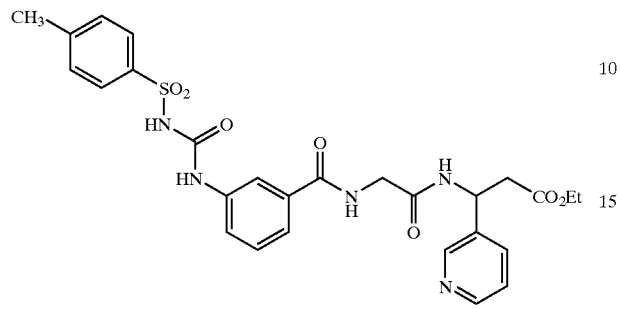

DL-ethyl(3-nitrobenzoylglycyl)-3-amido-3-(3-pyridyl)propionate (2 g, 0.64 mmol) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 mL) was added to the crude aniline followed by p-toluensulfonyl isocyanate (600 mg, 0.75 mmol). The solution turned to a solid. Diethyl ether was added and the product was filtered. The product was purified by reverse phase chromatography (water/acetonitrile) and lyophilized to result in a white solid (1.1 g). MS and $^1$H-NMR were consistent with the proposed structure.

EXAMPLE 112

Preparation of β-[[2-[[[3-[[[[(4-methylphenyl)sulfonyl]amino]carbonyl]amino]phenyl]carbonyl]amino]acetyl]amino]pyridine-3-propanoic acid, trifluoroacetate salt

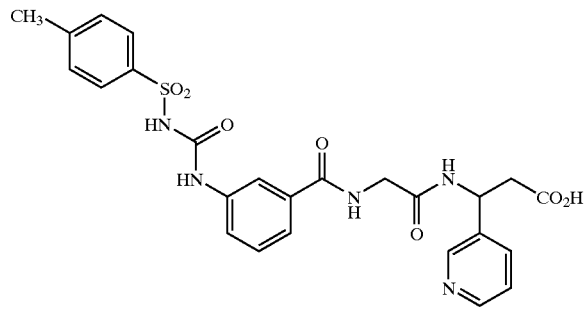

The compound of Example 111 (500 mg, 0.095 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in a white solid (350 mg). MS and $^1$H-NMR were consistent with the proposed structure.

EXAMPLE 113

Preparation of ethyl β-[[2-[[[3-[(aminothioxomethyl)amino]phenyl]carbonyl]amino]acetyl]amino]pyridine-3-propanoate, trifluoroacetate salt

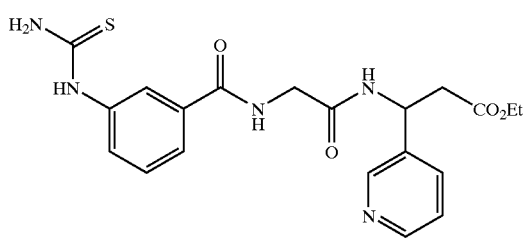

DL-ethyl(3-nitrobenzoylglycyl)-3-amido-3-(3-pyridyl)propionate (2 g, 0.64 mmol) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 mL) was added to the crude aniline followed by benzoyl isothiocyanate (600 mg, 0.75 mmol). After complete reaction the solvent was removed under reduced pressure. To the resulting oil was added methanol (50 mL) followed by $K_2CO_3$ (2 g) and the reaction was left to stir until the hydrolysis was complete. The product was purified by reverse phase chromatography (water/acetonitrile) and lyophilized to result in a white solid (980 mg). MS and $^1$H-NMR were consistent with the proposed structure.

EXAMPLE 114

Preparation of β-[[2-[[[3-[(aminothioxomethyl)amino]phenyl]carbonyl]amino]acetyl]amino]pyridine-3-propanoic acid, trifluoroacetate salt

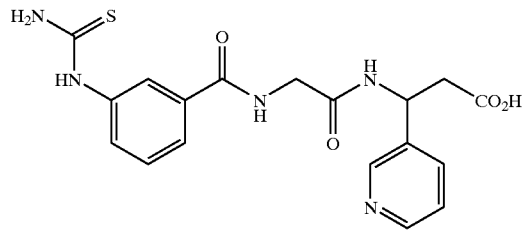

The compound of Example 113 (500 mg, 0.095 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in a white solid (350 mg). MS and $^1$H-NMR were consistent with the proposed structure.

EXAMPLE 115

Preparation of DL-ethyl(3-nitrobenzoylglycyl)-3-amidophenyl propionate

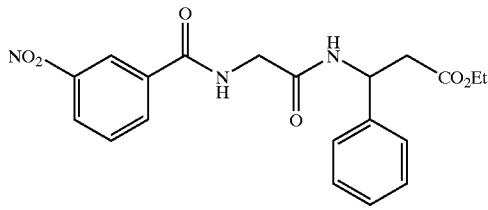

N,N'-disuccinimidyl carbonate (14 g, 5.5 mmol) was added to 3-nitro-benzoyl glycine (10 g, 4.5 mmol) in dry dimethylformamide (30 mL) followed by dimethylaminopyridine (200 mg). After a period of 1 hour DL-ethyl-3-amino-3-phenylpropionate hydrochloride (12 g, 4.6 mmol) in 20% aqueous potassium carbonate (50 mL) was added in one portion. After complete reaction the product was collected by filtration (12 g, 87% yield). MS and $^1$H-NMR were consistent with the proposed structure.

EXAMPLE 116

Preparation of ethyl β-[[2-[[[3-[(aminothioxomethyl)amino]phenyl]carbonyl]amino]acetyl]amino]benzenepropanoate

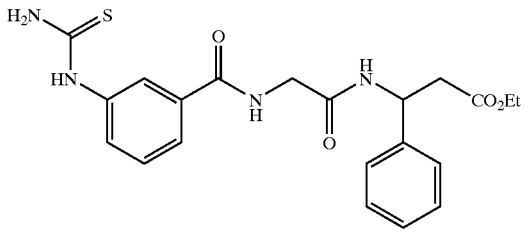

The compound of Example 115 (2 g, 0.64 mmol) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 mL) was added to the crude aniline followed by benzoyl isothiocyanate (600 mg, 0.75 mmol). After complete reaction the solvent was removed under reduced pressure. To this oil, methanol (50 mL) was added followed by K$_2$CO$_3$ (2 g) and the reaction was left to stir until the hydrolysis was complete. The product was purified by reverse phase chromatography (water/acetonitrile) and lyophilized to result in a white solid (980 mg). MS and NMR were consistent with the proposed structure.

EXAMPLE 117

Preparation of β-[[2-[[[3-[(aminothioxomethyl)amino]phenyl]carbonyl]amino]acetyl]amino]benzenepropanoic acid

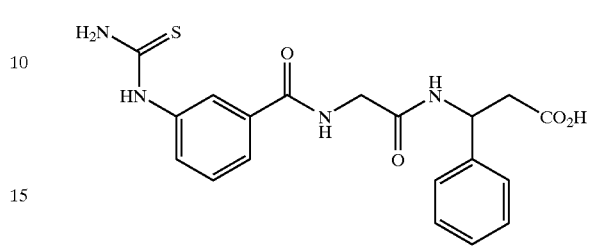

The product of Example 116 (500 mg, 0.095 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in a white solid (350 mg). MS and $^1$H-NMR were consistent with the proposed structure.

EXAMPLE 118

Preparation of ethyl β-[[2-[[[3-[[[(phenylmethyl)amino]carbonyl]amino]phenyl]carbonyl]amino]acetyl]amino]benzenepropanoate

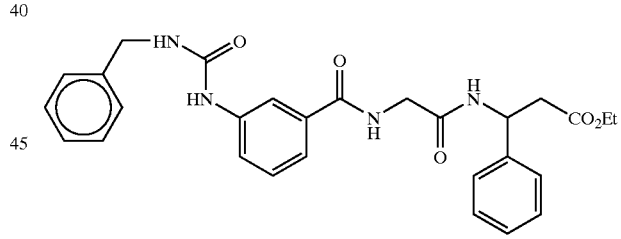

DL-ethyl(3-nitrobenzoylglycyl)-3-amido-3-phenyl propionate (2 g, 0.62 mmol) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 mL) was added to the crude aniline followed by benzyl isocyanate (700 mg, 0.75 mmol). The solution turned to a solid. Diethyl ether was added and the product filtered. The product was purified by reverse phase chromatography (water/acetonitrile) and lyophilized to result in a white solid (1.5 g). MS and $^1$H-NMR were consistent with the proposed structure.

EXAMPLE 119

Preparation of β-[[2-[[[3-[[[(phenylmethyl)amino]carbonyl]amino]phenyl]carbonyl]amino]acetyl]amino]benzenepropanoic acid

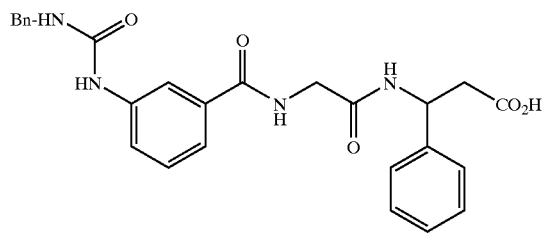

The product of Example 118 (400 mg, 0.094 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in a white solid (200 mg). MS and $^1$H-NMR were consistent with the proposed structure.

EXAMPLE 120

Preparation of β-[[2-[[[3-nitrophenyl)carbonyl]amino]acetyl]amino]-1,3-benzodioxole-5-propanoate

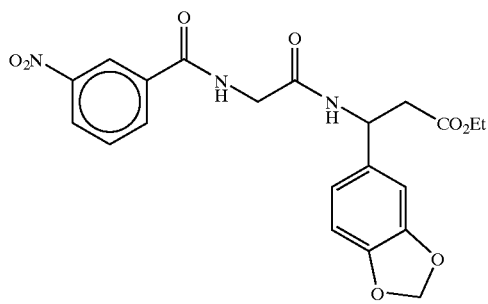

N,N'-disuccinimidyl carbonate (14 g, 5.5 mmol) was added to 3-nitro-benzoyl glycine (10 g, 4.5 mmol) in dry dimethylformamide (30 mL) followed by dimethylaminopyridine (200 mg). After a period of 1 hour ethyl DL-3-amino-3-piperinalpropionate hydrochloride (7 g, 4.6 mmol) in 20% aqueous potassium carbonate (50 mL) was added in one portion. After complete reaction the product was collected by filtration (14 g, 97% yield). MS and $^1$H-NMR were consistent with the proposed structure.

EXAMPLE 121

Preparation of ethyl β-[[2-[[[3-[[[(phenylmethyl)amino]carbonyl]amino]phenyl]carbonyl]amino]acetyl]amino]-1,3-benzodioxole-5-propanoate

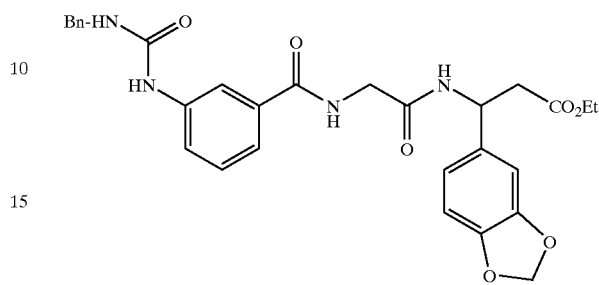

The compound of Example 120 (2 g, 0.62 mmol) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 mL) was added to the crude aniline followed by benzyl isocyanate (700 mg, 0.75 mmol). The solution turned to a solid. Diethyl ether was added and the product filtered. The product was purified by reverse phase chromatography (water/acetonitrile) and lyophilized to result in a white solid (1.5 g). MS and $^1$H-NMR were consistent with the proposed structure.

EXAMPLE 122

Preparation of β-[[2-[[[3-[[[(phenylmethyl)amino]carbonyl]amino]phenyl]carbonyl]amino]acetyl]amino]-1,3-benzodioxole-5-propanoic acid

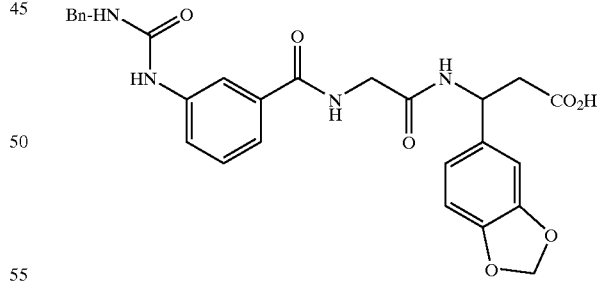

The compound of Example 121 (400 mg, 0.094 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in a white solid (200 mg). MS and $^1$H-NMR were consistent with the proposed structure.

EXAMPLE 123

Preparation of ethyl β-[[2-[[[3-3-[[(phenylamino)carbonyl]amino]phenyl]carbonyl]amino]acetyl]amino]-1,3-benzodioxole-5-propanoate

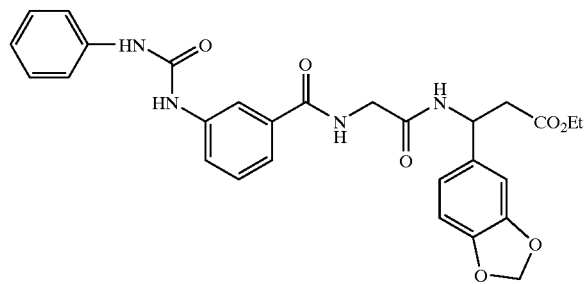

DL-ethyl(3-nitrobenzoylglycyl)-3-amido-3-piperidinal propionate (2 g, 0.62 mmol) was added to absolute ethanol (60 mL) in a Parr jar. Palladium on carbon 5% (500 mg) was added and the mixture was hydrogenated under 50 psi in a Parr apparatus for a period of 1.5 hours. After complete reaction the palladium catalyst was removed by filtration through a plug of celite. The solvent was removed under reduced pressure and the sample dried in vacuo. Acetonitrile (5 mL) was added to the crude aniline followed by phenyl isocyanate (700 mg, 0.75 mmol). The solution turned to a solid. Diethyl ether was added and the product filtered. The product was purified by reverse phase chromatography (water/acetonitrile) and lyophilized to result in a white solid (1.5 g). MS and $^1$H-NMR were consistent with the proposed structure.

EXAMPLE 124

Preparation of β-[[2-[[[3-3-[[(phenylamino]carbonyl]amino]phenyl]carbonyl]amino]acetyl]amino]-1,3-benzodioxole-5-propanoic acid

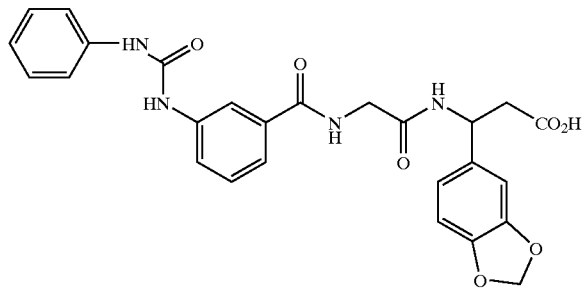

The product of Example 123 (400 mg, 0.094 mmol) was dissolved in water/acetonitrile (1:1), followed by the addition of lithium hydroxide (100 mg, 0.4 mmol). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in a white solid (200 mg). MS and NMR were consistent with the proposed structure.

EXAMPLE 126

Preparation of β-[[2-[[[3-[[[[(4-(aminosulfonyl)phenylmethyl]amino]carbonyl]amino]phenyl]carbonyl]amino]acetyl]amino]pyridine-3-propanoic acid, trifluoroacetate salt

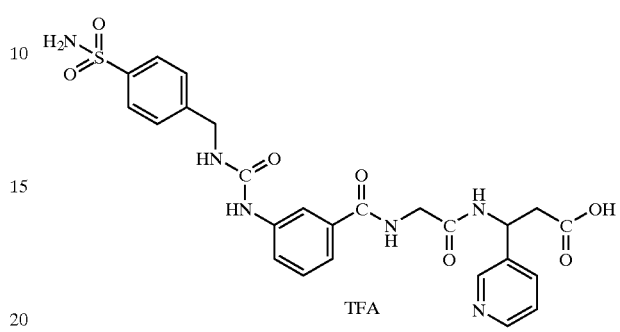

Step A

To 4-(aminomethyl)-benzenesulfonamide hydrochloride hydrate (Aldrich) (6 g) in acetonitrile was added 3-ethoxycarbonyl phenylisocyanate (Lancaster) (5 g) and triethylamine (5 ml). The reaction was stirred for 1 hour. The solvent was removed under reduced pressure to give a solid mass. Water was added and the solid filtered (10.2 g). MS and $^1$H-NMR were consistent with the proposed structure.

Step B

The compound from Step A (10 g) was dissolved in water/acetonitrile (1:1), followed by the addition of lithium hydroxide (4 g). The reaction mixture was stirred at 25° C., and monitored by HPLC. After complete hydrolysis (4–6 hours) 10% aqueous HCl was added until pH=2. The product was purified by filtration to give a white solid (7 g). MS and $^1$H-NMR were consistent with the proposed structure.

Step C

N,N'-Disuccinimidyl carbonate (DSC) (1.4 g, 0.5 mmol) was added to the carboxylic acid-urea of 4-(aminomethyl) benzenesulfonamide and 3-ethoxycarbonyl phenylisocyanate (1 g, 0.5 mmol) [See Scheme V(A13)] in dry dimethylformamide (20 mL) followed by dimethylaminopyridine (100 mg). After a period of 1 hour the compound from Example 1, Step C was added (2.2 g, 0.5 mmol) in DMF/NMM (1:1) (5.0 mL) in one portion. After complete reaction the product was purified by reverse phase chromatography (water/acetonitrile) and lyophilized to result in a white solid (1.2 g). MS and $^1$H-NMR were consistent with the proposed structure.

Step D

The compound from Step C (600 mg) was dissolved in water/acetonitrile (1:1), followed by the addition of lithium hydroxide (100 mg). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in 500 mg of a white solid. MS and $^1$H-NMR were consistent with the proposed structure.

EXAMPLE 127

Preparation of β-[[2-[[[3-[[[3-pyridinylmethyl)
amino]carbonyl]amino]phenyl]carbonyl]amino]
acetyl]amino]pyridine-3-propanoic acid, bis
trifluoroacetate salt

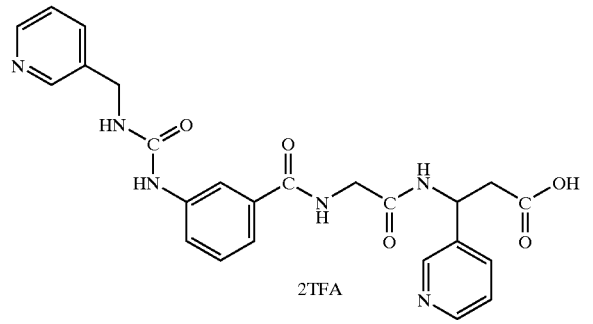

2TFA

Step A

To 3-pyridinemethylamine (Aldrich) (6 g) in acetonitrile was added 3-ethoxycarbonyl phenylisocyanate (Lancaster) (5 g) and triethylamine (5 ml). The reaction was stirred for 1 hour. The solvent was removed under reduced pressure to give a solid mass. Water was added and the solid filtered (12 g). MS and $^1$H-NMR were consistent with the proposed structure.

Step B

The compound from Step A (10 g) was dissolved in water/acetonitrile (1:1), followed by the addition of lithium hydroxide (4 g). The reaction mixture was stirred at 25° C., and monitored by HPLC. After complete hydrolysis (4–6 hours) 10% aqueous HCl was added until pH=2. The product was purified by filtration to give a white solid (5.6 g). MS and $^1$H-NMR were consistent with the proposed structure.

Step C

N,N'-Disuccinimidyl carbonate (DSC) (1.4 g, 0.5 mmol) was added to the carboxylic acid-urea of 3-pyridine methylamine (Aldrich) and 3-ethoxycarbonyl phenylisocyanate (1 g, 0.5 mmol) [See Scheme V(A13)] in dry dimethylformamide (20 mL) followed by dimethylaminopyridine (100 mg). After a period of 1 hour the compound from Example 1, Step C was added (2.2 g, 0.5 mmol) in DMF/NMM (1:1) (5.0 mL) in one portion. After complete reaction the product was purified by reverse phase chromatography (water/acetonitrile) and lyophilized to result in a white solid (1.1 g). MS and $^1$H-NMR were consistent with the proposed structure.

Step D

The compound from Step C (500 mg) was dissolved in water/acetonitrile (1:1), followed by the addition of En lithium hydroxide (100 mg). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in 430 mg of a white solid. MS and $^1$H-NMR were consistent with the proposed structure.

EXAMPLE 129

Preparation of β-[[2-[[[3-[[[(2-carboxyethyl)amino]
carbonyl]amino phenyl]carbonyl]amino]acetyl]
amino]pyridine-3-propanoic acid, trifluoroacetate
salt

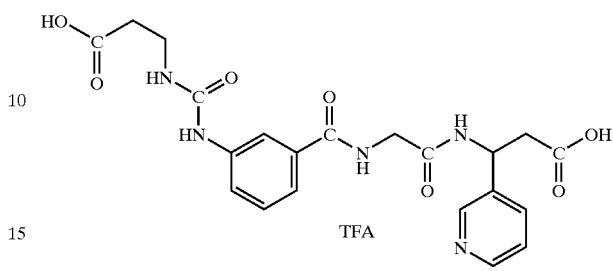

TFA

The compound of Example 104 (1.5 g) was dissolved in ethanol (60 mL) in a Parr jar. Palladium on carbon 5% (500 mg) was added and the mixture was hydrogenated under 50 psi in a Parr apparatus for a period of 1.5 hours. The palladium catalyst was removed by filtration through a plug of celite. The solvent was removed under reduced pressure and the sample dried in vacuo.

Step B

Acetonitrile (5 mL) was added to the crude aniline from Step A followed by ethyl isocyanatopropionate (Aldrich) (800 mg) and stirred for 1 hour. The solvent was removed under reduced pressure to give a solid. Diethyl ether was added and the solid was filtered to give a tan colored solid. The product was purified by reverse phase chromatography (water/acetonitrile) and lyophilized to result in 500 mg of a white solid. MS and $^1$H-NMR were consistent with the proposed structure.

Step C

The compound from Step B (500 mg) was dissolved in water/acetonitrile (1:1), followed by the addition of lithium hydroxide (100 mg). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in 220 mg of a white solid. MS and $^1$H-NMR were consistent with the proposed structure.

EXAMPLE 130

Preparation of β-[[2-[[[3-[[[(2-phenylethyl)amino]
carbonyl]amino]phenyl]carbonyl]amino]acetyl]
amino]pyridine-3-propanoic acid, trifluoroacetate
salt

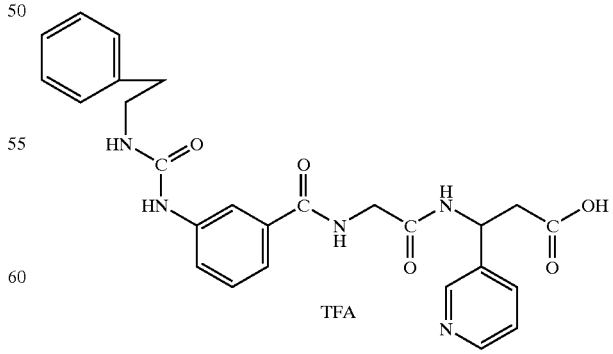

TFA

To phenylethylamine hydrochloride (Aldrich) (6 g) in acetonitrile was added 3-ethoxycarbonyl phenylisocyanate (Lancaster) (5 g) and triethylamine (5 ml). The reaction was stirred for 1 hour. The solvent was removed under reduced pressure to give a solid mass. Water was added and the solid filtered (11 g). MS and $^1$H-NMR were consistent with the proposed structure.

Step B

The compound from Step A (10 g) was dissolved in water/acetonitrile (1:1), followed by the addition of lithium hydroxide (4 g). The reaction mixture was stirred at 25° C., and monitored by HPLC. After complete hydrolysis (4–6 hours) 10% aqueous HCl was added until pH=2. The product was purified by filtration to give a white solid (5.6 g). MS and $^1$H-NMR were consistent with the proposed structure.

Step C

N,N'-Disuccinimidyl carbonate (DSC) (1.4 g, 0.5 mmol) was added to the carboxylic acid-urea of phenylethylamine and 3-ethoxycarbonyl phenylisocyanate (1 g, 0.5 mmol) (See Scheme V(A13)] in dry dimethylformamide (20 mL) followed by dimethylaminopyridine (100 mg). After a period of 1 hour the compound from Example 1, Step C was added (2.2 g, 0.5 mmol) in DMF/NMM (1:1) (5.0 mL) in one portion. After complete reaction the product was purified by reverse phase chromatography (water/acetonitrile) and lyophilized to result in a white solid (1.0 g). MS and $^1$H-NMR were consistent with the proposed structure.

Step D

The compound from Step C (800 mg) was dissolved in water/acetonitrile (1:1), followed by the addition of lithium hydroxide (100 mg). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in 633 mg of a white solid. MS and $^1$H-NMR were consistent with the proposed structure.

EXAMPLE 131

Preparation of β-[[2-[[[3-[[[(1-naphthalenylmethyl)amino]carbonyl]amino]phenyl]carbonyl]amino]acetyl]amino]pyridine-3-propanoic acid, trifluoroacetate salt

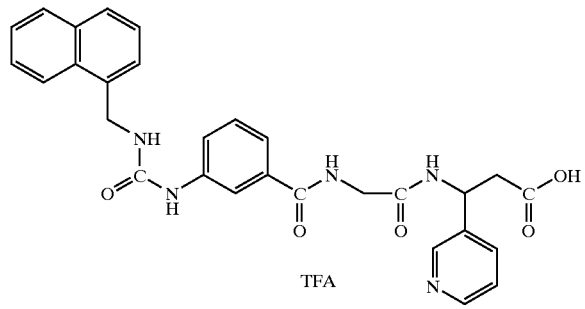

Step A

To 1-naphthalene methylamine (Aldrich) (5 g) in acetonitrile was added 3-ethoxycarbonyl phenylisocyanate (Lancaster) (5 g) and triethylamine (5 ml). The reaction was stirred for 1 hour. The solvent was removed under reduced pressure to give a solid mass. Water was added and the solid filtered (9 g). MS and $^1$H-NMR were consistent with the proposed structure.

Step B

The compound from Step A (8 g) was dissolved in water/acetonitrile (1:1), followed by the addition of lithium hydroxide (3 g). The reaction mixture was stirred at 25° C., and monitored by HPLC. After complete hydrolysis (4–6 hours) 10% aqueous HCl was added until pH=2. The product was purified by filtration to give a white solid (5.6 g). MS and $^1$H-NMR were consistent with the proposed structure.

Step C

N,N'-Disuccinimidyl carbonate (DSC) (1.4 g, 0.5 mmol) was added to the carboxylic acid-urea of 1-naphthalene methylamine and 3-ethoxycarbonyl phenylisocyanate (1 g, 0.5 mmol) [See Scheme V(A13)] in dry dimethylformamide (20 mL) followed by dimethylaminopyridine (100 mg). After a period of 1 hour the compound from Example 1, Step C was added (2.2 g, 0.5 mmol) in DMF/NMM (1:1) (5.0 mL) in one portion. After complete reaction the product was purified by reverse phase chromatography (water/acetonitrile) and lyophilized to result in a white solid (1.0 g). MS and $^1$H-NMR were consistent with the proposed structure.

Step D

The compound from Step C (600 mg) was dissolved in water/acetonitrile (1:1), followed by the addition of lithium hydroxide (100 mg). The reaction mixture was stirred at 25° C., and monitored by HPLC. After complete hydrolysis (1–2 hours) trifluoroacetic acid was added until pH=2. The product was purified by reverse phase chromatography (water/acetonitrile) and lyophilized to result in 410 mg of a white solid. MS and $^1$H-NMR were consistent with the proposed structure.

EXAMPLE 132

Preparation of phenylmethyl β-[[2-[[[3-[[(cyanoimino)phenylmethylamino)methyl]amino]phenyl]carbonyl]amino]acetyl]amino]benzenepropanoate

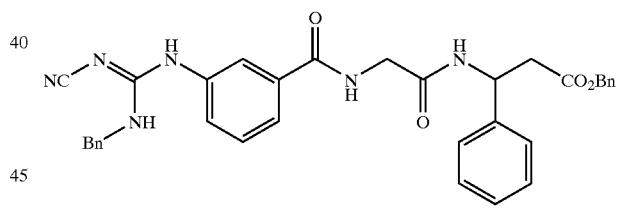

To a stirred solution of the product of Example I (140 mg, 0.52 mM), in methylene chloride (25 ml) at 0°, triethylamine, (0.5 ml), DMAP (10 mg), EDCl (95 mg) and the compound from Example V (215 mg, 0.52 mM) were added. The reaction mixture was stirred at 0° C. for 15 minutes, allowed to attain room temperature and then stirred for another 16 hours. The reaction mixture was concentrated in vacuo to afford an oily gum which was dissolved in ethyl acetate. The resulting solution was washed with water, saturated aqueous NaHCO$_3$ and water. The organic layer was separated, dried (Na$_2$SO$_4$) and evaporated to afford the crude product. The crude product was further purified by chromatography on silica (eluant: ethyl acetate) and excess solvent removed to afford the title compound (88 mg) as a clear oil.

NMR and MS were consistent with the proposed structure.

EXAMPLE 133

Preparation of phenylmethyl β-[[2-[[[3-[[[(cyanoimino)methylamino)methyl]amino]phenyl]carbonyl]amino]acetyl]amino]benzenepropanoate

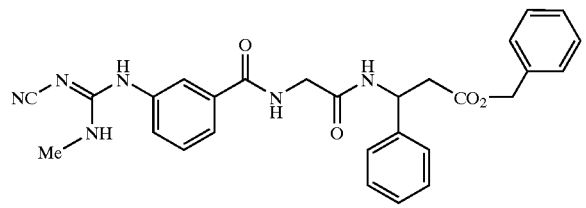

To a stirred solution of the product of Example J (90 mg, 0.41 mM), in methylene chloride (25 ml) at 0°, triethylamine, (0.5 ml), DMAP (10 mg), EDCl (95 mg) and the compound from Example V (215 mg, 0.52 mM) were added. The reaction mixture was stirred at 0° C. for 15 minutes, allowed to attain room temperature and then stirred for another 16 hours. The reaction mixture was concentrated in vacuo to afford an oily gum which was dissolved in ethyl acetate. The resulting solution was washed with water, saturated $NaHCO_3$ and finally water again. The organic layer was separated, dried ($Na_2SO_4$) and evaporated to afford the crude product. The crude product was further purified by chromatography on silica (eluant: ethyl acetate) and excess solvent removed to afford the title compound (80 mg) as a clear oil.

NMR was consistent with the proposed structure.

EXAMPLE 134

Preparation of phenylmethyl β-[[2-[[[3-[[[(cyanoimino)(amino)methyl]amino]phenyl]carbonyl]amino]acetyl]amino]benzenepropanoate

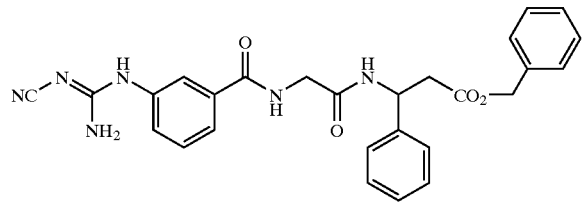

To a stirred solution of the product of Example K (212 mg, 1.0 mM), in methylene chloride (25 ml) at 0°, triethylamine, (0.5 ml), DMAP (10 mg), EDCl (95 mg) and the compound from Example V (215 mg, 0.52 mM) were added. The reaction mixture was stirred at 0° C. for 15 minutes, allowed to attain room temperature and then stirred for another 16 hours. The reaction mixture was concentrated in vacuo to afford an oily gum which was dissolved in ethyl acetate. The resulting solution was washed with water, saturated $NaHCO_3$ and again with water. The organic layer was separated, dried ($Na_2SO_4$) and evaporated to afford the crude product. The crude product was further purified by chromatography on silica (eluant:ethyl acetate) and excess solvent removed to afford the title compound (285 mg) as a clear oil.

NMR was consistent with the proposed structure.

EXAMPLE 135

Preparation of ethyl β-[[2-[[[3-[[(cyanoimino)(ethylamino)methyl]amino]phenyl]carbonyl]amino]acetyl]amino]benzenepropanoate

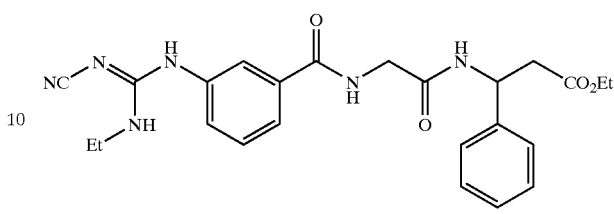

To a stirred solution of the product of Example L (464 mg, 2.0 mM), DL ethyl β-[(2-amino-1-oxoethyl)amino]phenyl-3-propanoate (728 mg, 2.0 mM) [prepared according to Example 1 (Step B, C and D) replacing DL-3-amino-3-(3-pyridyl)propionic acid with an equivalent amount of DL-3-amino-3-(3-phenyl)propionic acid], triethylamine (2.0 ml)and DMAP (20 mg) in methylene chloride (15 ml) at 0° C., EDCl (191 mg) was added. The reaction mixture was stirred at 0° C. for 15 minutes, allowed to attain room temperature and then stirred for another 16 hours. The reaction mixture was concentrated in vacuo to afford an oily gum which was dissolved in ethyl acetate. The resulting solution was washed with water, saturated $NaHCO_3$ and water. The organic layer was separated, dried ($Na_2SO_4$) and evaporated to afford the crude product. The crude product was further purified by reverse phase HPLC on a C18 column (eluant: 0.5% TFA-water/acetonitrile) to afford the title compound (280 mg) as a white solid.

Analysis for $C_{24}H_{28}N_6O_4$ 0.3 $H_2O$: Calcd: C, 61.34; H, 6.13; N, 17.88. Found: C, 61.17; H, 6.26; N, 17.85.

NMR was consistent with the proposed structure.

EXAMPLE 136

Preparation of β-[[2-[[[3-[[(cyanoimino)[(phenylmethyl)amino]methyl]amino]phenyl]carbonyl]amino]acetyl]amino]benzenepropanoic acid

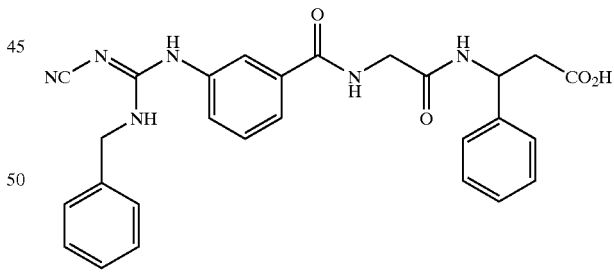

To a stirred solution of the compound from Example 132 (88 mg) in methanol (2 ml) and THF (2 ml), 1N sodium hydroxide (2 ml) was added. The reaction mixture was stirred at room temperature for 2 hours, evaporated and the residue dissolved in water. The resulting solution was adjusted to pH 4 with 1N hydrochloric acid and the resulting solid was isolated by filtration. The filtrate was further washed with water followed by diethyl ether.

This afforded the title compound (62 mg) as a white solid.

Analysis for $C_{27}H_{26}N_6O_4$ 0.5 $H_2O$ 0.25 $Et_2O$: Calcd: C, 63.93; H, 5.65; N, 15.97. Found: C, 63.96; H, 5.73; N, 15.81.

NMR was consistent with the proposed structure.

EXAMPLE 137

Preparation of β-[[2-[[[3-[[(cyanoimino)
(methylamino)methyl]amino]phenyl]carbonyl]
amino]acetyl]amino]benzenepropanoic acid

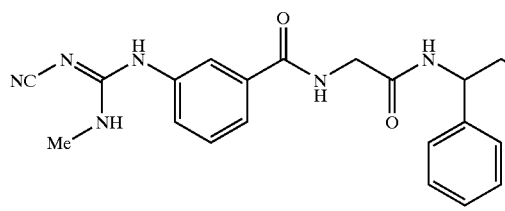

To a stirred solution of the compound from Example 133 (240 mg) in methanol (3 ml) and THF (3 ml), 1N sodium hydroxide (3 ml) was added. The reaction mixture was stirred at room temperature for 2 hours, evaporated and the residue dissolved in water. The resulting solution was adjusted to pH 4 with 1N hydrochloric acid and extracted with ethyl acetate/MeOH. The organic extracts were washed with water, dried ($Na_2SO_4$) and evaporated to afford a clear gum. The crude product was further purified by reverse phase HPLC on a C18 column (eluant: 0.5% TFA-water/acetonitrile) and lyophilized to afford the title compound (88 mg) as a white solid.

Analysis for $C_{21}H_{22}N_6O_4$ 0.55 TFA: Calcd: C, 54.71; H, 4.68; N, 17.32. Found: C, 54.92; H, 4.70; N, 16.93.

NMR was consistent with the proposed structure.

EXAMPLE 138

Preparation of β-[[2-[[[3-[[amino(cyanoimino)
methyl]amino]phenyl]carbonyl]amino]acetyl]amino]
benzenepropanoic acid

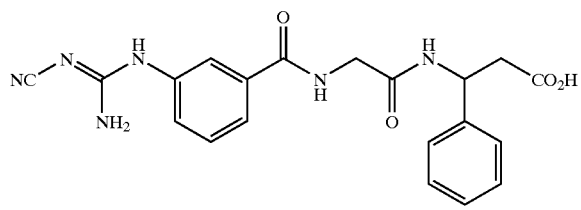

To a stirred solution of the compound from Example 134 (285 mg) in methanol (3 ml) and THF (3 ml), 1N sodium hydroxide (3 ml) was added. The reaction mixture was stirred at room temperature for 2 hours, evaporated and the residue dissolved in water. The resulting solution was adjusted to pH 4 with 1N hydrochloric acid and extracted with ethyl acetate/MeOH. The organic extracts were washed with water, dried ($Na_2SO_4$) and evaporated to afford an off white solid. The crude product was further purified by reverse phase HPLC on a C18 column (eluant: 0.5% TFA-water/acetonitrile) and lyophilized to afford the title compound (65 mg) as a white solid.

Analysis for $C_{20}H_{20}N_6O_4$ 1.25 $H_2O$, 0.3 MeOH: Calcd: C, 55.35; H, 5.42; N, 19.08. Found: C, 55.70; H, 5.01; N, 18.69.

NMR was consistent with the proposed structure.

EXAMPLE 139

Preparation of β-[[2-[[[3-[[(cyanoimino)
(ethylamino)methyl]amino]phenyl]carbonyl]amino]
acetyl]amino]benzenepropanoic acid

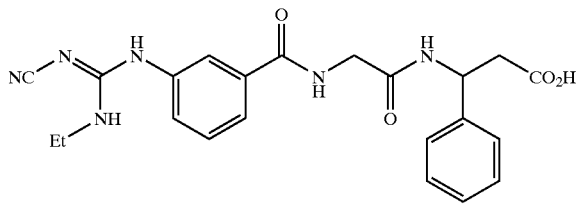

To a stirred solution of the compound from Example 135 (285 mg) in methanol (3 ml) and THF (3 ml) was added, 1N sodium hydroxide (3 ml). The reaction mixture was stirred at room temperature for 2 hours, evaporated and the residue dissolved in water. The resulting solution was adjusted to pH 4 with 1N hydrochloric acid and extracted with ethyl acetate/MeOH. The organic extracts were washed with water, dried ($Na_2SO_4$) and evaporated to afford an off white solid. The crude product was further purified by RPHPLC on a C18 column (eluant: 0.5% TFA-water/acetonitrile) and lyophilized to afford the title compound (180 mg) as a white solid.

Analysis for $C_{22}H_{24}N_6O_4$ 0.35 $H_2O$: Calcd: C, 59.68; H, 5.62; N, 18.98. Found: C, 59.80; H, 5.61; N, 18.59.

NMR was consistent with the proposed structure.

EXAMPLE 140

Preparation of ethyl 3S-[[2-[[[3-[[(cyanoimino)
(methylamino)methyl]amino]phenyl]carbonyl]
amino]acetyl]amino]-4-pentynoate

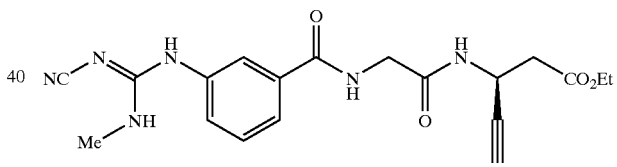

To a stirred solution of the product of Example J (436 mg, 2.0 mM), ethyl DL β-[(2-amino-1-oxoethyl)amino]-4-pentynoate (624 mg, 2.0 mM) [prepared according to Example 1 (Step B, C and D) replacing DL-3-amino-3-(3-pyridyl)propionic acid with an equivalent amount of ethyl-3S-amino-4-pentynoate (J. Med. Chem., 1995, 38, 3378)], triethylamine (2.0 ml) and DMAP (20 mg) in methylene chloride (20 ml) at 0° C., EDCl (382 mg, 2.0 mM) was added. The reaction mixture was stirred at 0° C. for 15 minutes, allowed to attain room temperature and then stirred for another 16 hours. The reaction mixture was concentrated in vacuo to afford an oily gum which was dissolved in ethyl acetate. The resulting solution was washed with water, saturated $NaHCO_3$ and water. The organic layer was separated, dried ($Na_2SO_4$) and evaporated to afford the crude product. The crude product was further purified by RPHPLC on a C18 column (eluant: 0.5% TFA-water/acetonitrile) and lyophilized to afford the title compound (280 mg) as a white solid.

NMR was consistent with the proposed structure.

Analysis for $C_{17}H_{18}N_6O_4$ 0.45 TFA: Calcd: C, 50.99; H, 4.41; N, 19.93. Found: C, 51.28; H, 4.70; N, 19.72.

EXAMPLE 141

Preparation of 3S-[[2-[[[3-[[(cyanoimino)(methylamino)methyl]amino]phenyl]carbonyl]amino]acetyl]amino]-4-pentynoic acid

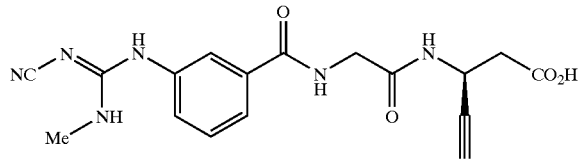

To a stirred solution of the compound from Example 140 (280 mg) in methanol (3 ml) and THF (3 ml), 1N sodium hydroxide (3 ml) was added. The reaction mixture was stirred at room temperature for 2 hours, evaporated and the residue dissolved in water. The resulting solution was adjusted to pH 4 with 1N hydrochloric acid and extracted with ethyl acetate/MeOH. The organic extracts were washed with water, dried ($Na_2SO_4$) and evaporated to afford an off white solid. The crude product was further purified by reverse phase HPLC on a C18 column (eluant: 0.5% TFA-water/acetonitrile) and lyophilized to afford the title compound (122 mg) as a white solid.

Analysis for $C_{17}H_{18}N_6O_4$ 0.45 TFA: Calcd: C, 50.99; H, 4.41; N, 19.93. Found: C, 51.28; H, 4.70; N, 19.72.

NMR was consistent with the proposed structure.

EXAMPLE 143

Preparation of ethyl β-[[2-[[[3-[[(cyanoimino)[2-pyridinylmethyl)amino]methyl]amino]phenyl]carbonyl]amino]acetyl]amino]benzenepropanoate, trifluoroacetate salt

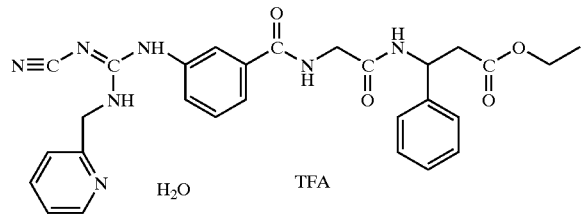

The title compound was synthesized following the procedure described in Example 135 except the compound of Example L was replaced with an equivalent amount of Example O. This afforded the title compound.

NMR was consistent with the proposed structure.

$C_{28}H_{29}N_7O_4$ 1$H_2O$: Calcd.: C, 54.63; H, 4.89; N, 14.86; Found: C, 54.28; H, 4.58; N, 14.63.

EXAMPLE 144

Preparation Of β-[[2-[[[3-[[(cyanoimino)[2-pyridinylmethyl)amino]methyl]amino]phenyl]carbonyl]amino]acetyl]amino]benzenepropanoic acid, bis(trifluoroacetate)salt

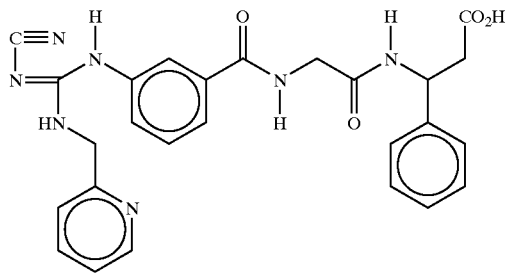

The title compound was prepared following the procedure described in Example 136 except the compound of Example 132 was replaced with an equivalent amount of the compound of Example 143. This afforded the title compound as a white solid.

NMR was consistent with the proposed structure.

$C_{26}H_{25}N_7O_4$ 2TFA, 1$H_2O$: Calcd.: C, 48.33; H, 3.92; N, 13.15; Found: C, 48.21; H, 3.59; N, 13.19.

EXAMPLE 145

Preparation of ethyl β-[[2-[[[3-[[(cyanoimino)[3-pyridinylmethyl)amino]methyl]amino]phenyl]carbonyl]amino]acetyl]amino]benzenepropanoate, trifluoroacetate salt

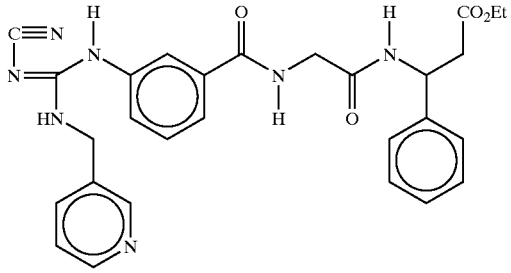

The title compound was prepared following the procedure described in Example 135 except the compound of Example L was replaced with an equivalent amount of the compound of Example Q. This afforded the title compound as a white solid.

NMR was consistent with the proposed structure.

$C_{28}H_{29}N_7O_4$ 1TFA, 1$H_2O$: Calcd.: C, 54.63; H, 4.89; N, 14.86; Found: C, 54.24; H, 4.85; N, 14.41.

EXAMPLE 146

Preparation of β-[[2-[[[3-[[(cyanoimino)[3-pyridinylmethyl)amino]methyl]amino]phenyl]carbonyl]amino]acetyl]amino]benzenepropanoic acid, bis(trifluoroacetate)salt

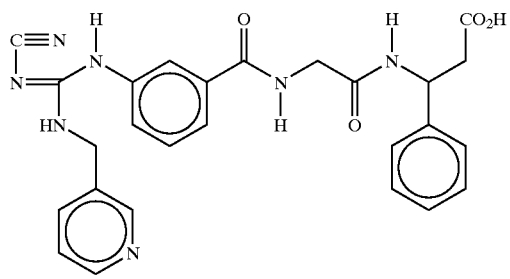

The title compound was prepared following the procedure described in Example 136 except the compound of Example 132 was replaced with an equivalent amount of the compound of Example 145, to yield the title compound as a white solid.

NMR was consistent with the proposed structure.

$C_{26}H_{25}N_7O_4$ 2TFA, 0.25$H_2O$: Calcd.: C, 49.22; H, 3.79; N, 13.39; Found: C, 49.50; H, 4.05; N, 13.64.

EXAMPLE 147

Preparation of ethyl β-[[2-[[[3-amino-4-chlorophenyl]carbonyl]amino]acetyl]amino]benzenepropanoate

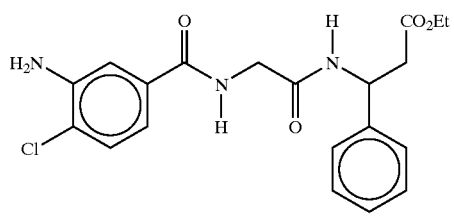

The title compound was prepared following the procedure described in Example 135 except the compound of Example L was replaced with an equivalent amount of 3-amino-4-chlorobenzoic acid to yield the title compound as brown solid (93.5% yield).

The NMR was consistent with the proposed structure.

EXAMPLE 148

Preparation of ethyl β-[[2-[[[4-chloro-3-[[[[(1,1-dimethylethoxy)carbonyl]amino]][(1,1-dimethylethoxy)carbonyl]imino]methyl]amino]phenyl]carbonyl]amino]acetyl]amino]benzenepropanoate

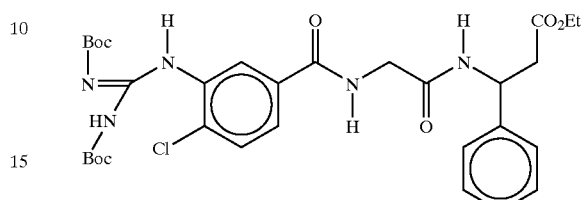

To a stirred solution of the product of Example 147 (400 mg, 1.13 mM), N,N'-bis-Boc-thiourea (311 mg, 1.13 m) [Edwin J. Iwanowicz et al., Synthetic Communications, 23(10)(1993) 1443–1445), DMF (6 ml), triethylamine (0.6 ml) was added $HgCl_2$ (360 mg) at 0–5° C. The mixture was stirred at 0–5° C. for 15 minutes and was allowed to warm to room temperature. The mixture was stirred at room temperature for 2 hours. The mixture was diluted with ethyl acetate (50 ml) and was filtered through celite under vacuum. The filtrate was concentrated in vacuo to afford an oily gum which was purified through flash silica column using 100% ethyl acetate as an eluent to afford the title compound (254 mg) as a white solid.

NMR was consistent with the proposed structure.

$C_{31}H_{40}N_5O_8$ 1.5 $H_2O$: Calcd.: C, 55.31; H, 6.44; N, 10.40; Found: C, 55.17; H, 6.50; N, 10.56.

EXAMPLE 149

Preparation of ethyl β-[[2-[[[3-[(aminoiminomethyl)amino]-4-chlorophenyl)carbonyl]amino]acetyl]amino]benzenepropanoate, trifluoroacetate salt

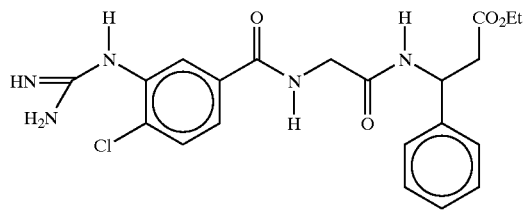

To a stirred solution of Example 148 (420 mg) in methylene chloride (5 ml) was added TFA (9 ml) at 0° C. The mixture was warmed to room temperature and stirred at room temperature for 1½ hours. The mixture was concentrated in vacuo to afford the crude product. The crude product was further purified by reverse phase HPLC on a C18 column (eluant: 0.5% TFA-$H_2O$/acetonitrile) and lyophilized to afford the title compound (68 mg) as a white solid.

$C_{21}H_{24}N_5O_4Cl$ 1.0 TFA 0.45 $H_2O$: Calcd.: C, 48.63; H, 4.60; N, 12.33; Found: C, 48.28; H, 4.16; N, 12.13.

EXAMPLE 150

Preparation of β-[[2-[[[3-[(aminoiminomethyl)amino]-4-chlorophenyl)carbonyl]amino]acetyl]amino]benzenepropanoic acid

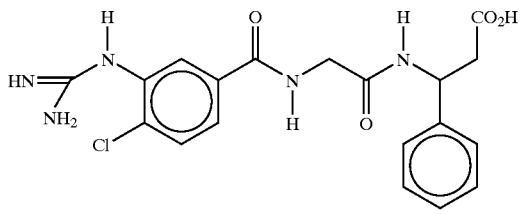

The title compound was prepared following the procedure described in Example 136 except the compound of Example 132 was replaced with an equivalent amount of the compound of Example 149 to yield the title compound as a white solid.

The NMR was consistent with the proposed structure.
$C_{19}H_{20}N_5O_4Cl$ 1.5 TFA: Calcd.: C, 44.87; H, 3.68; N, 11.89; Found: C, 44.54; H, 3.80; N, 11.43.

EXAMPLE 152

Preparation of methyl β-[[2-[[(5-amino-2-chlorophenyl)carbonyl]amino]acetyl]amino]benzenepropanoate

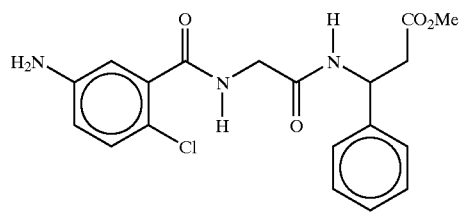

The title compound was prepared following the procedure described in Example 135 except the compound of Example L was replaced with an equivalent amount of 3-amino-6-chlorobenzoic acid to yield the title compound as pale brown solid.

The NMR was consistent with the proposed structure.

EXAMPLE 153

Preparation of methyl β-[[2-[[[2-chloro-5-[[[[(1,1-dimethylethoxy)carbonyl]amino][[1,1-dimethylethoxy)carbonyl]imino]methyl]amino]phenyl]carbonyl]amino]acetyl]amino]benzenepropanoate

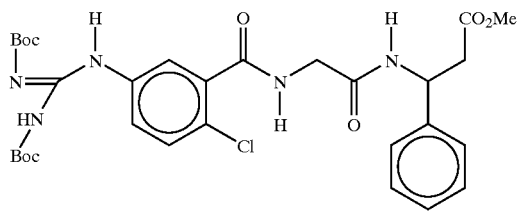

The title compound was prepared following the procedure described in Example 148 except the compound of Example 146 was replaced with an equivalent amount of the compound of Example 152 to yield the title compound as a white solid.

The NMR was consistent with the proposed structure.

EXAMPLE 154

Preparation of β-[[2-[[[2-chloro-5-[[[[(1,1-dimethylethoxy)carbonyl]amino][[(1,1-dimethylethoxy)carbonyl]imino]methyl]amino]phenyl]carbonyl]amino]acetyl]amino]benzenepropanoic acid

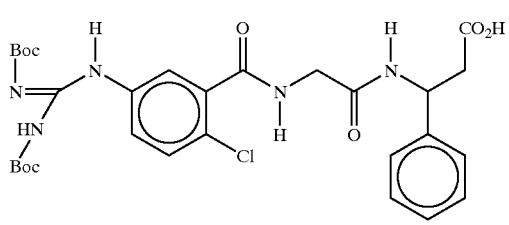

The title compound was prepared following the procedure described in Example 136 except the compound of Example 132 was replaced with an equivalent amount of the compound of Example 153 to yield the title compound as a white solid.

The NMR was consistent with the proposed structure.

EXAMPLE 155

Preparation of β-[[2-[[[5-[(aminoiminomethyl)amino]-2-chlorophenyl]carbonyl]amino]acetyl]amino]benzenepropanoic acid, trifluoroacete salt

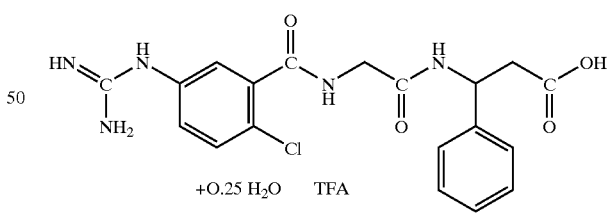

The title compound was prepared following the procedure described in Example 150 except the compound of Example 149 was replaced with an equivalent amount of the compound of Example 154 to yield the title compound as a white solid.

NMR was consistent with the proposed structure.
$C_{19}H_{20}N_5O_4Cl$ 1TFA, 0.25 $H_2O$: Calcd.: C, 47.02; H, 4.04; N, 13.06; Found: C, 47.17; H, 3.85; N, 12.72.

EXAMPLE 156
Using the procedures of the present disclosure and starting with the requisite reagents, the following compounds are prepared:
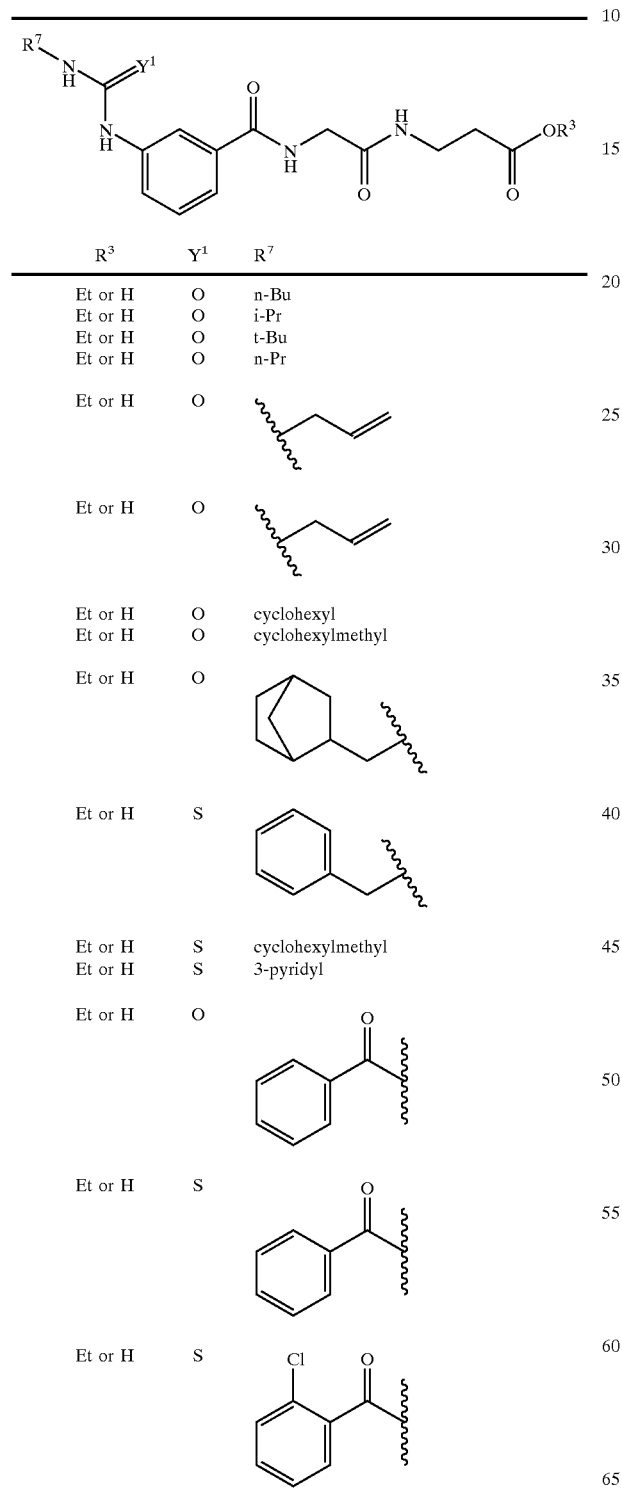
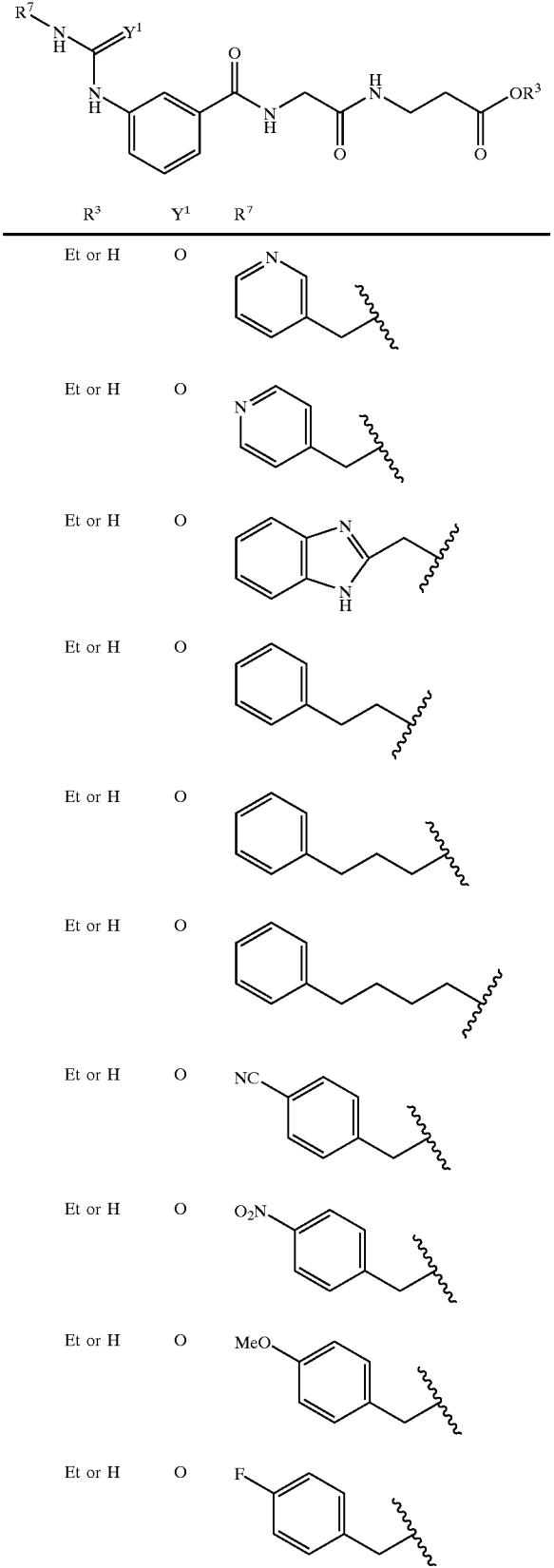

-continued

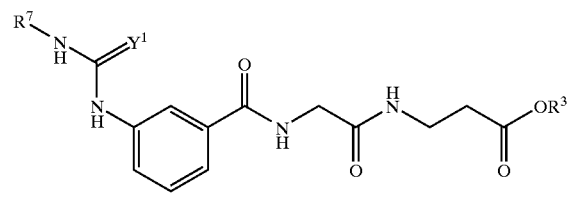

| R³ | Y¹ | R⁷ |
|---|---|---|
| Et or H | O | 4-Me-C₆H₄-CH₂- |
| Et or H | O | 4-CF₃-C₆H₄-CH₂- |
| Et or H | O | 4-H₂NO₂S-C₆H₄-CH₂- |
| Et or H | O | 4-MeO₂S-C₆H₄-CH₂- |
| Et or H | O | 4-H₂NC(O)-C₆H₄-CH₂- |
| Et or H | O | 4-H₂N-C₆H₄-CH₂- |
| Et or H | O | 4-AcHN-C₆H₄-CH₂- |
| Et or H | O | 4-MeO₂S-NH-C₆H₄-CH₂- |
| Et or H | O | 4-Cl-C₆H₄-CH₂- |
| Et or H | O | 4-Br-C₆H₄-CH₂- |

-continued

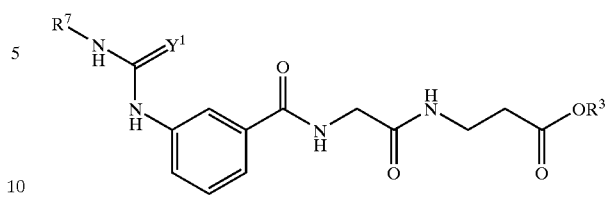

| R³ | Y¹ | R⁷ |
|---|---|---|
| Et or H | O | 4-I-C₆H₄-CH₂- |
| Et or H | O | 4-Me₂N-C₆H₄-CH₂- |
| Et or H | O | 4-F₃CO-C₆H₄-CH₂- |
| Et or H | O | 4-PhO-C₆H₄-CH₂- |
| Et or H | O | 4-F₃CS-C₆H₄-CH₂- |
| Et or H | O | 4-F₃CO₂S-C₆H₄-CH₂- |
| Et or H | O | C₆F₅-CH₂- |
| Et or H | O | 2,6-Cl₂-C₆H₃-CH₂- |
| Et or H | O | 2,6-(MeO)₂-C₆H₃-CH₂- |

-continued

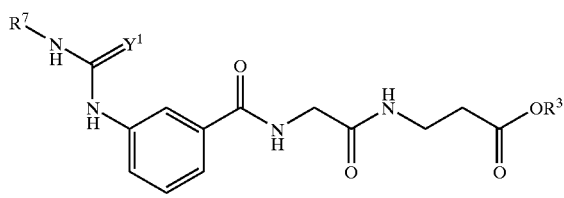

| $R^3$ | $Y^1$ | $R^7$ |
|---|---|---|
| Et or H | O | 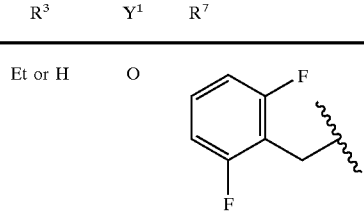 |
| Et or H | O | 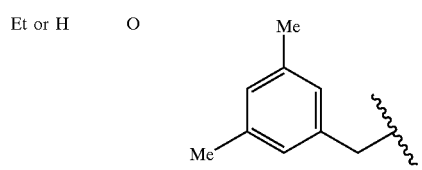 |
| Et or H | O | 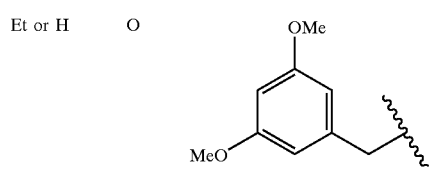 |
| Et or H | O | 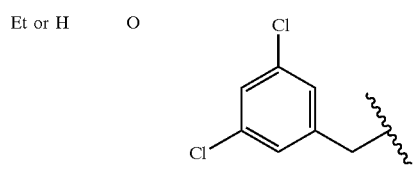 |
| Et or H | O | 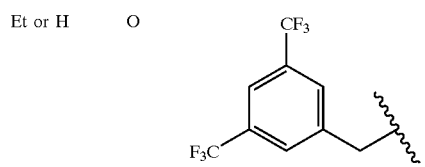 |
| Et or H | O | 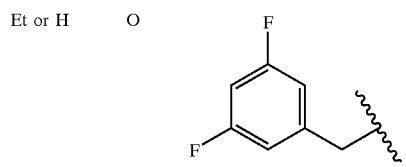 |
| Et or H | O | 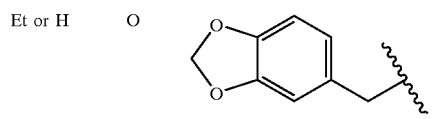 |

EXAMPLE AA

Preparation of

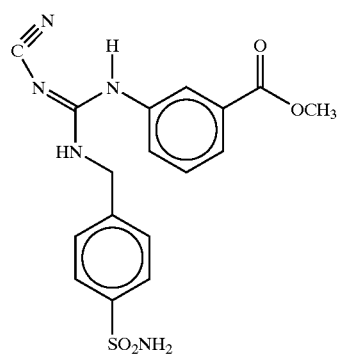

The above compound was prepared following the procedure described in Example E, replacing benzylamine with p-aminomethyl benzenesulfonamide. The above compound was obtained as a white solid.

NMR was consistent with the proposed structure.

EXAMPLE AB Preparation of

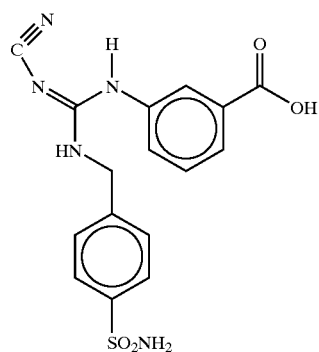

The above compound was prepared following the procedure described in Example I, replacing the compound of Example E with the compound of Example R. The above compound was obtained as a white solid.

NMR was consistent with the proposed structure.

EXAMPLE AC

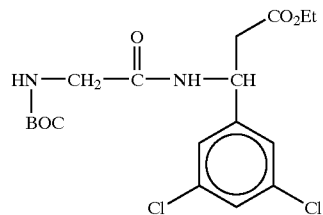

Preparation of

The above compound was prepared following the procedure described in Example 140, replacing the compound of Example J with N-t-Boc glycine and replacing DL ethyl β-[(2-amino-1-oxoethyl)amino]-4-pentynoate with ethyl-DL-3-amino-3-(3,5-dichlorophenyl)propionate. The above compound was obtained as an oily gum.

NMR was consistent with the proposed structure.

EXAMPLE AD

Preparation of

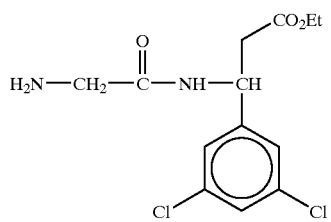

The above compound was prepared following the procedure described in Example 161, replacing the compound of Example 159 with that of Example AC. The above compound was obtained as an oily gum.

NMR was consistent with the proposed structure.

EXAMPLE 157

Preparation of ethyl 3S-[[2-[[[3-[[[[(4-(aminosulfonyl)phenylmethyl]amino](cyanoimino)methyl]amino]phenyl]carbonyl]amino]acetyl]amino-4-pentynoate

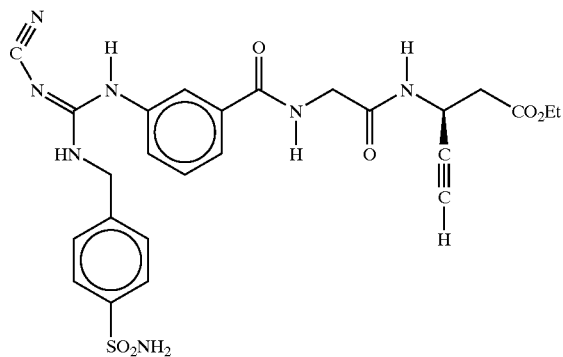

The title compound was prepared following the procedure described in Example 140, replacing the compound of Example J with that of Example AA. The above compound was obtained as an oily gum.

NMR was consistent with the proposed structure.

EXAMPLE 158

Preparation of 3S-[[2-[[[3-[[[[(4-(aminosulfonyl)phenylmethyl]amino](cyanoimino)methyl]amino]phenyl]carbonyl]amino]acetyl]amino]-4-pentynoic acid, trifluoroacetate salt, monohydrate

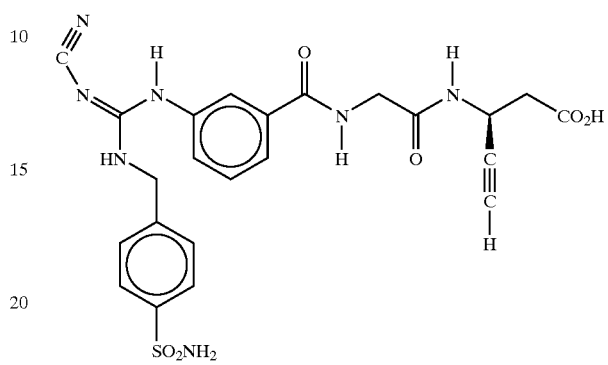

The above compound was prepared following the procedure described in Example 141, replacing the compound of Example 140 with that of Example 157. The crude product was purified by RPHPLC on a C18 column (eluant: 0.5% TFA-water/acetonitrile) and lyophilized to afford the title compound as a white solid.

NMR was consistent with the proposed structure.

Analysis for $C_{23}H_{23}N_7O_6S \cdot 1.25$ TFA; Calculated: C, 44.64; H, 3.86; N, 14.29. Found: C, 44.85; H, 4.00; N, 14.36.

EXAMPLE 159

Preparation of ethyl β-[[2-[[[3-[amino(cyanoimino)methyl]amino]phenyl]carbonyl]amino]acetyl]amino]-3,5-dichlorobenzenepropanoate

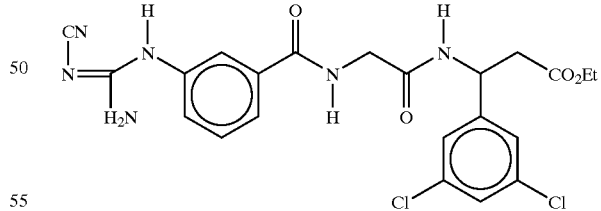

The title compound was prepared following the procedure described in Example 140, replacing the compound of Example J with that of Example K and replacing DL ethyl-β-[(2-amino-1-oxoethyl)amino]-3-4-pentynoate with compound of Example AD. The title compound was obtained as an oily gum.

NMR was consistent with the proposed structure.

EXAMPLE 160

Preparation of β-[[2-[[[3-[[amino(cyanoimino)methyl]amino]phenyl]carbonyl]amino]acetyl]amino]-3,5-dichlorobenzenepropanoic acid

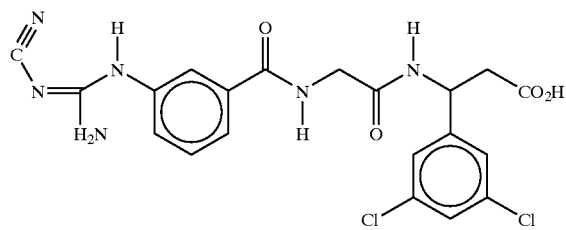

The title compound was prepared following the procedure described in Example 141, replacing the compound of Example 140 with that of Example 159. The crude product was purified by RHPLC on a C-18 column (eluant: 0.5% TFA/water/acetonitrile) and lyophilized to afford the title compound as a white solid.

NMR was consistent with the proposed structure.

EXAMPLE 161

Preparation of ethyl β-[2-[[[3-[[amino(aminocarbonyl)imino]methyl]amino]phenyl]carbonyl]amino]acetyl]amino]-3,5-dichlorobenzenepropanoate, trifluoroacetate salt

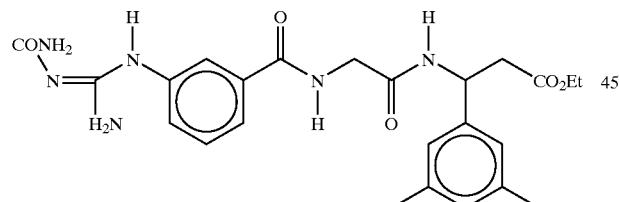

To a stirred solution of Example 159 (2.65 g) in methylene chloride (120 ml) was added trifluoroacetic acid (60 ml). The reaction mixture was stirred at 25° C. for 1 hour. The reaction mixture was concentrated in vacuo to afford crude product which upon crystallization from ether afforded the title compound (2.02 g) as a white solid.

NMR was consistent with the proposed structure.

Analysis for $C_{21}H_{22}N_5O_4Cl_3$ 1.05 TFA. Calculated: C, 43.31; H, 3.79; N, 10.98. Found: C, 43.18; H, 3.81; N, 10.64.

EXAMPLE 162

Preparation of β-[[(2-[[[3-[[amino(aminocarbonyl)imino]methyl]amino]phenyl]carbonyl]amino]acetyl]amino]-3,5-dichlorobenzenepropanoic acid, trifluoroacetate salt

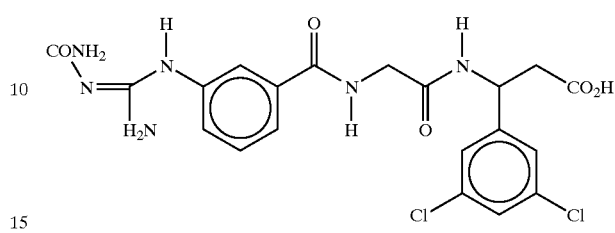

The title compound was prepared following the procedure described in Example 141, replacing the compound of Example 140 with the compound of Example 161. The title compound was obtained as a white solid.

NMR was consistent with the proposed structure.

Analysis for $C_{20}H_{20}N_6O_5Cl_2$ 1.25 TFA: Calculated: C, 42.37; H, 3.36; N, 13.18. Found: C, 42.48; H, 3.46; N, 12.96.

EXAMPLE AE

Preparation of

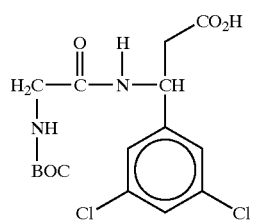

The title compound was prepared following the procedure described in Example 141 except that the compound of Example 140 was replaced with the compound of Example AC. The title compound was obtained as a white solid.

NMR was consistent with the proposed structure.

EXAMPLE AF

Preparation of

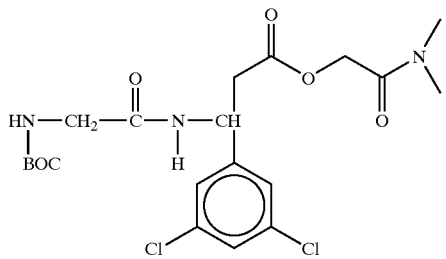

To a stirred solution of the compound of Example AE (954 mg, 33 mmol), DMF (10 ml), $K_2CO_3$ (1 g), NaI (129 mg) was added 363 mg of 2-chloro-N,N-dimethylacetamide (363 mg, 3 mmole) and the mixture was stirred at room temperature for 16 hours. The reaction mixture was concentrated in vacuo to afford an oily gum, which upon crystallization from diethylether yielded a white solid (AF) (610 mg).

NMR was consistent with the proposed structure.

EXAMPLE AG

Preparation of

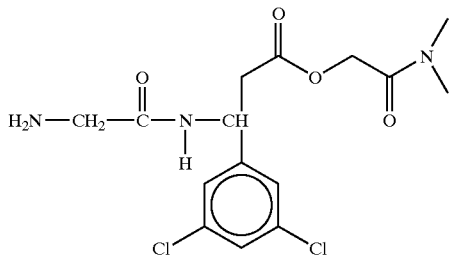

The title compound was prepared following the procedure described in Example 161, replacing the compound of Example 159 with the compound of Example AF. The title compound was obtained as an oily gum.

NMR was consistent with the proposed structure.

EXAMPLE 163

Preparation of [(dimethylamino)carbonyl]methyl β-[[2-[[[3-[(aminoiminomethyl)amino)phenyl]carbonyl]amino]acetyl]amino]-3,5-dichlorobenzenepropanoate

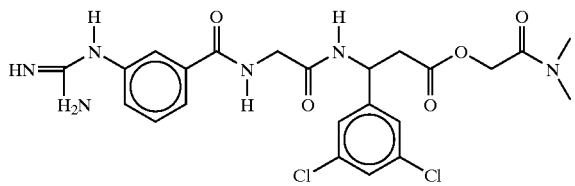

The title compound was prepared following the procedure described in Example 132, replacing the compound of Example I with m-guanidino benzoic acid and replacing the compound of Example V with the compound of Example AG. The title compound was obtained as a white solid.

NMR was consistent with the proposed structure.

Analysis for $C_{23}H_{26}N_6O_3Cl_2$ 1.3 TFA: Calculated: C, 44.85; H, 4.01; N, 12.28; Found: C, 44.51; H, 3.88; N, 12.38.

EXAMPLE AH

Preparation of

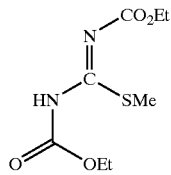

To a stirred solution of 2-methyl-2-thiopseudourea sulfate (11.1 g) in methylene chloride (150 ml) was added ethyl-chloroformate (8 ml) and saturated solution of sodium bicarbonate (150 ml). The reaction-mixture was stirred at room temperature for 18 hours. The reaction mixture was washed with water, dried over $Na_2SO_4$ and concentrated in vacuo to afford a crude oily gum, which upon purification by flash column chromatography afforded the above compound (9.8 g) as a white solid.

NMR was consistent with the proposed structure.

EXAMPLE 164

Preparation of

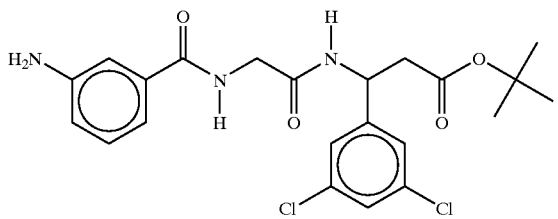

The title compound was prepared following the procedure described in Example 140, replacing the compound of Example J with 3-aminobenzoylglycine and replacing DL ethyl-β[(2-amino-1-oxoethyl)amino]-4-pentynoate with 3-amino-3-(3,5-dichlorophenyl)propionic acid tert-butyl ester. The title compound was obtained as an oily gum.

NMR was consistent with the proposed structure.

EXAMPLE 165

Preparation of 1,1-dimethylethyl 3,5-dichloro-β-[[2-[[[3-[[[(ethoxycarbonyl)amino][(ethoxycarbonyl)imino]methyl]amino]phenyl]carbonyl]amino]acetyl]amino]benzenepropanoate

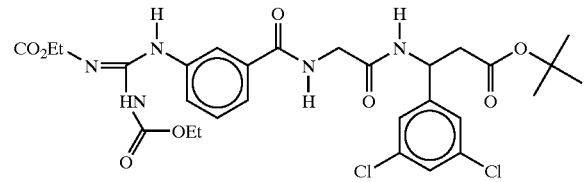

To a stirred solution of the compound of Example AH (250 mg) in DMF (2 ml), and triethylamine (150 mg) was added the compound of Example 164 (150 mg). The mixture was cooled to 0° C. and stirred at 0° C. for 5 minutes. The mixture was treated with $HgCl_2$ (50 mg), and stirred at room temperature for 1 hour. The mixture was concentrated in vacuo to afford an oily gum which upon further purification by flash column chromatography yielded an oily gum.

NMR was consistent with the proposed structure.

EXAMPLE 166

Preparation of 3,5-dichloro-β-[[2-[[[3-[[[(ethoxycarbonyl)amino][(ethoxycarbonyl)imino]methyl]amino]phenyl]carbonyl]amino]acetyl]amino]benzenepropanoic acid

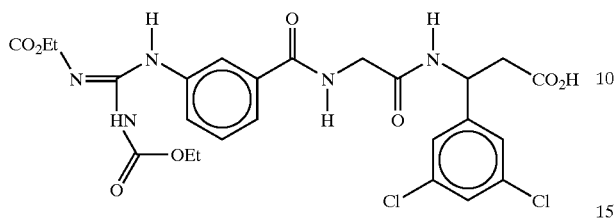

The title compound was prepared following the procedure described in Example 160, replacing the compound of Example 159 with the compound of Example 165. The title compound was obtained as a white solid.

NMR was consistent with the proposed structure.

Analysis for $C_{25}H_{27}N_5O_8Cl_2$ 0.5 $H_2O$, 0.25 TFA: Calculated: C, 48.31; H, 4.49; N, 11.05. Found: C, 48.55; H, 4.21; N, 10.84.

EXAMPLE AI

Preparation of

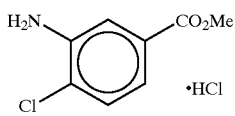

To a stirred suspension of 3-amino-4-chlorobenzoic acid (25.0 g, 157 mmol) in MeOH (300 ml) at 0° C., hydrogen chloride gas was added until the methanolic solution was saturated. The reaction mixture was stirred at 0–5° C. for 30 minutes, allowed to attain room temperature, and then stirred for a further 4 days. The reaction mixture was Li concentrated in vacuo and the resulting white solid triturated with diethyl ether to afford the above compound; 26.2 g as a white solid.

NMR was consistent with the proposed structure.

EXAMPLE AJ

Preparation of

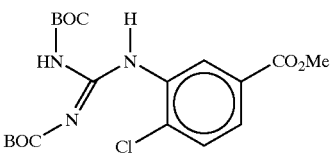

To a solution of bis-t-Boc-thiourea (24.8 g, 90 mmol) and methyl 3-amino-4-chlorobenzoate (20 g, 90 mmol) in dimethylformamide (120 ml) and triethylamine (45 ml) at 0° C., mercury (II) chloride (30.1 g, 111 mmol) was added. The reaction mixture was stirred for 15 minutes at 0° C., allowed to attain room temperature and stirred for a further 2 hours. The reaction mixture was diluted with ethyl acetate (600 ml) and the resulting slurry filtered under reduced pressure. The filtrate was concentrated, to afford an oily gum which was purified by chromatography on silica (eluent: ethyl acetate/heptane 20:80) to afford the above compound (8.6 g) as a white solid.

NMR was consistent with the proposed structure.

EXAMPLE AK

Preparation of

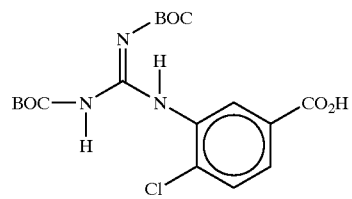

The product of Step AI was dissolved in MeOH (3 mL) and 1 M NaOH (14 mL) was added at room temperature. The reaction was stirred at room temperature for 2 hours. The reaction was concentrated in vacuo and the residue dissolved in water, washed with ether. The aqueous layer was acidified to pH=3 with 1N HCl. A white precipitate formed, was filtered and washed with water and ether and dried to give 1.2 g of white solid.

NMR was consistent with the proposed structure.

EXAMPLE AL

Preparation of

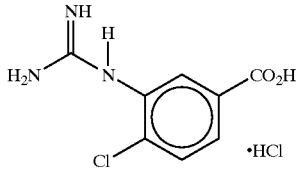

To a solution of the product of Step AJ (550 mg, 1.37 mmol) in $CH_2Cl_2$ (4 mL) was added TFA (1 mL) at 0° C. The ice bath was removed after the addition and the reaction was stirred at room temperature for 2 hours. The reaction was concentrated in vacuo to give a colorless oil. To this was added 4N HCl solution in dioxane (2 mL) and white precipitate formed. The solution was concentrated in vacuo to afford 280 mg of the desired product as a white solid.

NMR was consistent with the proposed structure.

EXAMPLE 167

Preparation of ethyl β-[[2-[[[3-[(aminoiminomethyl)amino]-4-chlorophenyl]carbonyl]amino]acetyl]amino]3,5-dichlorobenzenepropanoate

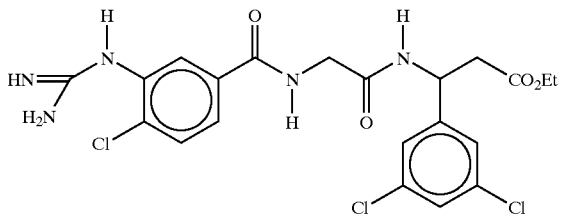

A solution of the compound of Example AL (500 mg) and 1-methylpiperidine (400 mg), in DMF (20 ml) was cooled to 0° C. and isobutyl chloroformate (274 mg) was added under a nitrogen atmosphere. The reaction mixture was allowed to stir for 5 minutes before adding a solution of the compound of Example AD (866 mg) in DMF (2 ml). The reaction mixture was allowed to warm slowly to room temperature and was stirred at room temperature for 16 hours. The solution was quenched with water and extracted with ethyl acetate. The organic extracts were washed with water, dried over $Na_2SO_4$ and concentrated in vacuo. The residue was purified by RPHPLC and lyophilized to yield the desired product as an oily gum (329 mg).

Analysis for $C_{21}H_{22}N_5O_4Cl_3$ 1 TFA, 0.5 $H_2O$: Calculated: C, 43.31; H, 3.79; N, 10.98; Found: C, 43.18; H, 3.81; N, 10.64.

EXAMPLE 168

Preparation of β-[[2-[[[3-[(aminoiminomethyl)amino]-4-chlorophenyl]carbonyl]amino]acetyl]amino]-3,5-dichlorobenzenepropanoic acid, trifluoroacetate salt

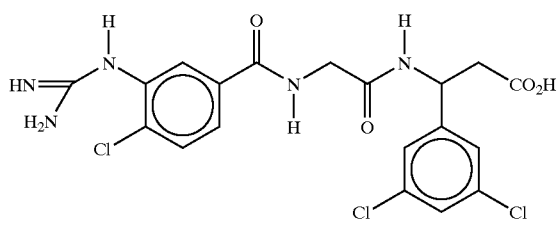

The title compound was prepared following the procedure described in Example 141, replacing the compound of Example 140 with that of Example 167. The title compound was obtained as a white solid. NMR was consistent with the proposed structure.

Analysis for $C_{19}H_{18}N_5O_4Cl_3$.1 TFA: Calculated: C, 41.98; H, 3.19; N, 11.66. Found: C, 42.14; H, 3.30; N, 11.18.

EXAMPLE 169

Preparation of

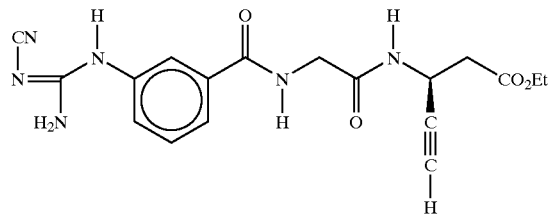

The title compound was prepared following the procedure described in Example 140, replacing the compound of Example J with that of Example K. The title compound was obtained as an oily gum.

NMR was consistent with the proposed structure.

Analysis for $C_{18}H_{20}N_6O_4$ 0.6 TFA: Calculated: C, 50.93; H, 4.59; N, 18.56. Found: C, 50.69; H, 4.71; N, 18.32.

EXAMPLE 170

Preparation of ethyl 3S-[[2-[[[3-[(amino[(aminocarbonyl)imino]methyl]amino]phenyl]carbonyl]amino]acetyl]amino]-4-pentynoate

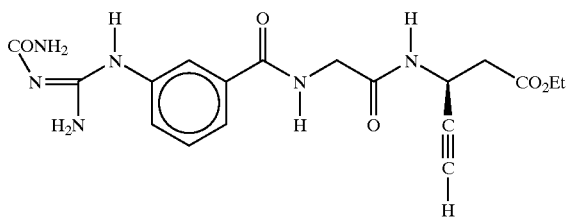

The title compound was prepared following the procedure described in Example 161, replacing the compound of Example 159 with that of Example 169. The title compound was obtained as an oily gum.

NMR was consistent with the proposed structure.

EXAMPLE 171

Preparation of 3S-[[2-[[[3-[[amino[(aminocarbonyl)imino]methyl]amino]phenyl]carbonyl]amino]acetyl]amino]-4-pentynoic acid, trifluoroacetate salt, hydrate

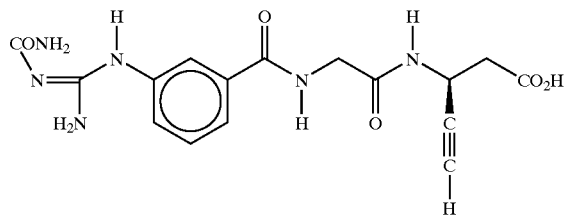

The title compound was prepared following the procedure described in Example 141, replacing the compound of Example 140 with the compound of Example 170. The title compound was obtained as a white solid.

NMR was consistent with the proposed structure.

EXAMPLE 172

Preparation of ethyl 3S-[[2-[[[3-[(aminoiminomethyl)amino]-4-chlorophenyl]carbonyl]amino]acetyl]amino]-4-pentynoate

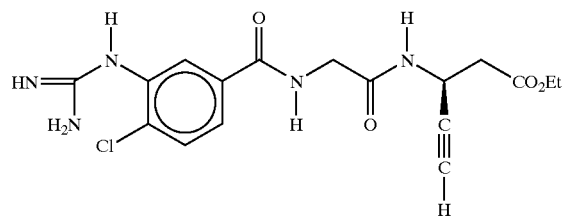

The title compound was prepared following the procedure described in Example 167, replacing the compound of Example AD with DL ethyl-β-[(2-amino-1-oxoethyl)amino]-4-pentynoate. The title compound was obtained as an oily gum.

NMR was consistent with the proposed structure.

EXAMPLE 173

Preparation of 3S-[[2-[[[3-[(aminoiminomethyl)amino]-4-chlorophenyl]carbonyl]amino]acetyl]amino]-4-pentynoic acid, trifluoroacetate salt

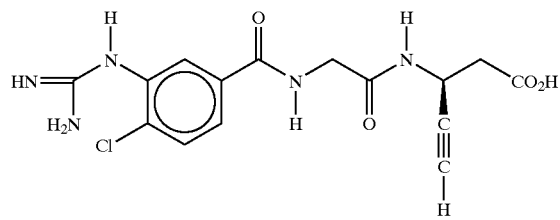

The title compound was prepared following the procedure described in Example 141, replacing the compound of Example 140 with the compound of Example 172. The title compound was obtained as a white solid.

NMR was consistent with the proposed structure.

Analysis for $C_{15}H_{16}N_5O_4Cl$, 1 TFA, 0.5 $H_2O$: Calculated: C, 41.77; H, 3.71; N, 14.33. Found: C, 41.84; H, 3.64; N, 13.94.

EXAMPLE 174

Preparation of (±)ethyl β-[[2-[[[3-[(aminoiminomethyl)amino]phenyl]carbonyl]amino]acetyl]amino]-3,4-dichlorobenzenepropanoate, trifluoroacetate salt

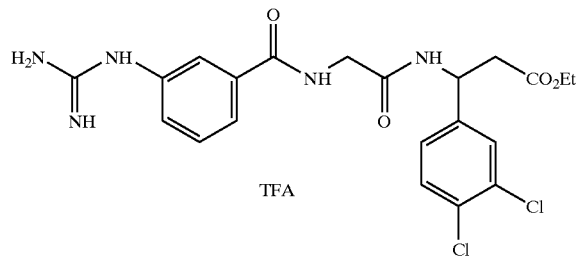

Step A

Ethyl-DL-3-amino-3-(3,4-dichlorophenyl)propionate hydrochloride was prepared according to Example 1, Steps A and B, substituting an equivalent amount of 3,4-dichlorobenzaldehyde (Aldrich) for 3-pyridinecarboxaldehyde in Example 1, Step A.

Step B

To m-guanidinohippuric acid hydrochloride (Example M) (400 mg, 0.0015 mole) and N-methylmorpholine (150 mg, 0.0015 mole) in anhydrous DMF (6 mL) was added, at ice bath temperature, isobutylchloroformate (200 mg, 0.0015 mole). After stirring for 5 minutes, a slurry of the product from Step A above (ethyl-DL-3-amino-3-(3,4-dichlorophenyl)propionate hydrochloride (440 mg, 0.0015 mole) and N-methylmorpholine (150 mg, 0.0015 mole) in anhydrous DMF (6 mL) was added in one portion at ice bath temperature. The reaction was stirred overnight at room temperature. The solvent was removed under vacuum on a 78° C. water bath and the product was isolated by RPHPLC to yield the title compound (520 mg) as a white solid.

MS and NMR were consistent with the desired structure.

EXAMPLE 175

Preparation of (±)β-[[2-[[[3-[(aminoiminomethyl)amino]phenyl]carbonyl]amino]acetyl]amino]-3,4-dichlorobenzenepropanoic acid, trifluoroacetate salt

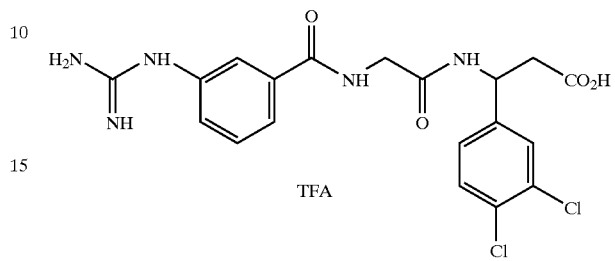

To the product from Example 174 (420 mg, 0.0007 mole) in $H_2O$ (8 mL) and $CH_3CN$ (8 mL) was added LiOH (118 mg, 0.003 mole). The reaction mixture was stirred at room temperature for 1.5 hours. The pH was lowered to ≈3 with TFA and the product was isolated by RPHPLC to yield the title compound (390 mg) (after lyophilization) as a white solid.

MS and NMR were consistent with the desired structure.

EXAMPLE 176

Preparation of (±)ethyl β-[[2-[[[3-[(aminoiminomethyl)amino]-5-(trifluoromethyl)carbonyl]amino]acetyl]amino]3,4-dichlorobenzenepropanoate, trifluoroacetate salt

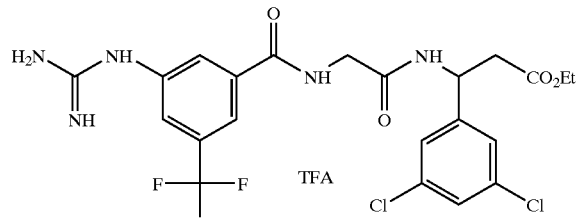

The above compound was prepared according to the methodology of Example 38, substituting the equivalent amount of 3,5-dichlorobenzaldehyde (Aldrich) for 3,5-bis-trifluoromethylbenzaldehyde.

MS and NMR were consistent with the desired structure.

EXAMPLE 177

Preparation of (±)β-[[2-[[[3-[(aminoiminomethyl)amino]-5-(trifluoromethyl)phenyl]carbonyl]amino]acetyl]amino]-3,5-dichlorobenzenepropanoic acid, trifluoroacetate salt

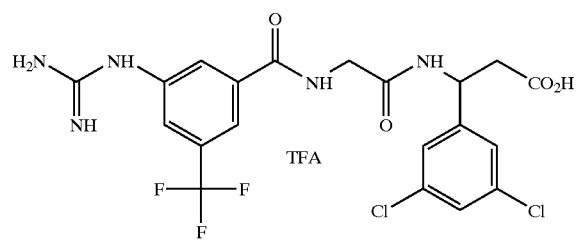

To the product from Example 176 (620 mg, 0.00094 mole) in H₂O (10 mL) and CH₃CN (10 mL) was added LiOH (157 mg, 0.0037 mole). The reaction mixture was stirred at room temperature for 2 hours. The pH was lowered to ≈3 with TFA and the product was isolated by RPHPLC to yield the title compound (560 mg after lyophilization) as a white solid.

MS and NMR were consistent with the desired structure.

EXAMPLE 178

Preparation of (±)ethyl β-[[2-[[[3-[(4,5-dihydro-1H-imidazol-2-yl)amino]phenyl]carbonyl]amino]acetyl]-amino]-3,5-bis(trifluoromethyl)benzenepropanoate, trifluoroacetate salt

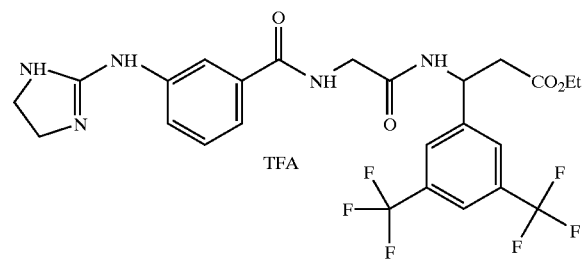

The above compound was prepared according to the methodology of Example 9, substituting the equivalent amount of 3,5-bis-trifluoromethylbenzaldehyde (Aldrich) for 3-pyridinecarboxaldehyde in Example 1, Step A from Example 9, Step B.

MS and NMR were consistent with the desired structure.

EXAMPLE 179

Preparation of (±)β-[[2-[[[3-[(4,5-dihydro-1H-imidazol-2-yl)amino]phenyl]carbonyl]amino]acetyl]-amino]-3,5-bis(trifluoromethyl)benzenepropanoic acid, trifluoroacetate salt

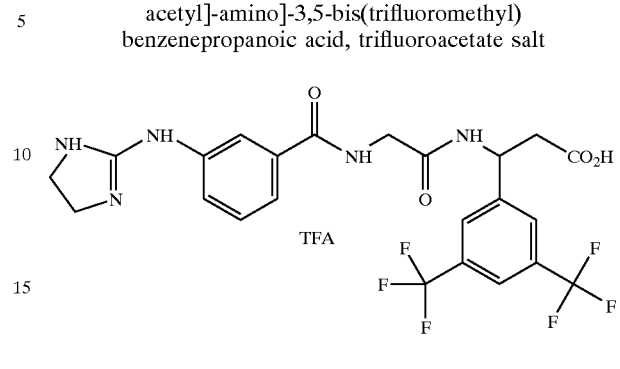

To the product from Example 178 (360 mg, 0.0005 mole) in H₂O (8 mL) and CH₃CN (8 mL) was added LiOH (88 mg, 0.0021 mole). The reaction was stirred at room temperature for 3 hours. The pH was lowered to ≈3 with TFA and the product was isolated by RPHPLC to yield the title compound (300 mg after lyophilization) as a white solid.

MS and NMR were consistent with the desired structure.

EXAMPLE 180

Preparation of (±)ethyl β-[[2-[[[3-[(aminoiminomethyl)amino]phenyl]carbonyl]amino]acetyl]amino]-2,5-dimethylbenzenepropanoate, trifluoroacetate salt

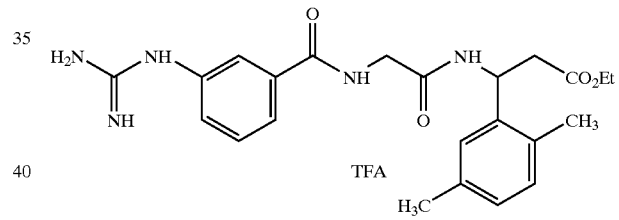

The above compound was prepared according to the methodology of Example 174, substituting an equivalent amount of 2,5-dimethylbenzaldehyde (Aldrich) for 3,4-dichlorobenzaldehyde in Example 174, Step A.

MS and NMR were consistent with the desired structure.

EXAMPLE 181

Preparation of (±)β-[[2-[[[3-[(aminoiminomethyl)amino]phenyl]carbonyl]amino]acetyl]amino]-2,5-dimethylbenzenepropanoic acid, trifluoroacetate salt

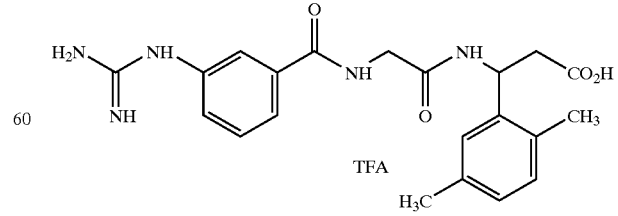

To the product from Example 180 (710 mg, 0.0013 mole) in H₂O (10 mL) and CH₃CN (10 mL) was added LiOH (215 mg, 0.005 mole). The reaction mixture was stirred at room temperature for 2.5 hours. The pH was lowered to ≈3 with TFA and the product was isolated by RPHPLC to yield the title compound (600 mg after lyophilization) as a white solid.

MS and NMR were consistent with the desired structure.

EXAMPLE 182

Preparation of (±)ethyl β-[[2-[[[3-[(aminoiminomethyl)amino]phenyl]carbonyl]amino]acetyl]amino]-3-chlorobenzenepropanoate, trifluoroacetate salt

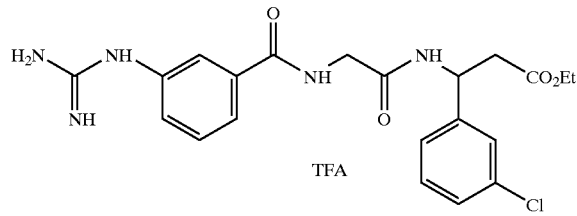

The above compound was prepared according to the methodology of Example 174, substituting an equivalent amount of 3-chlorobenzaldehyde (Aldrich) for 3,4-dichlorobenzaldehyde in Example 174, Step A.

MS and NMR were consistent with the desired structure.

EXAMPLE 183

Preparation of (±)β-[[2-[[[3-[(aminoiminomethyl)amino]phenyl]carbonyl]amino]acetyl]amino]-3-chlorobenzenepropanoic acid, trifluoroacetate salt

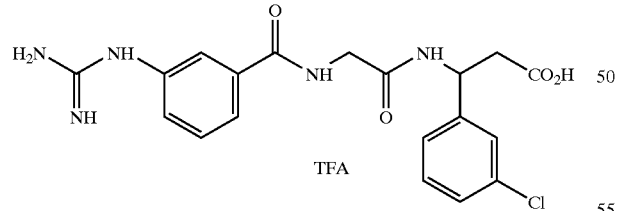

To the product from Example 182 (720 mg, 0.0013 mole) in H₂O (15 mL) and CH₃CN (10 mL) was added LiOH (880 mg, 0.02 mole). The reaction mixture was stirred at room temperature for 1 hour. The pH was lowered to ≈2 with TFA and the product was isolated by RPHPLC to yield the title compound (550 mg after lyophilization) as a white solid.

MS and NMR were consistent with the desired structure.

EXAMPLE 184

Preparation of (±)ethyl β-[[2-[[[3-[(aminoiminomethyl)amino]phenyl]carbonyl]amino]acetyl]amino]-3-bromobenzenepropanoate, trifluoroacetate salt

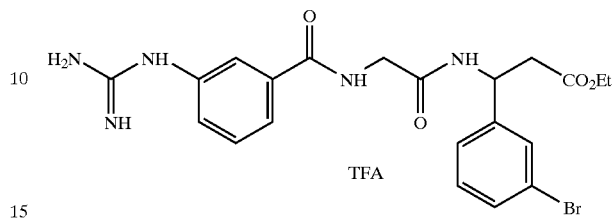

The above compound was prepared according to the methodology of Example 174, substituting an equivalent amount of 3-bromobenzaldehyde (Aldrich) for 3,4-dichlorobenzaldehyde in Example 174, Step A.

MS and NMR were consistent with the desired structure.

EXAMPLE 185

Preparation of (±)β-[[2-[[[3-[(aminoiminomethyl)amino]phenyl]carbonyl]amino]acetyl]amino]-3-bromobenzenepropanoic acid, trifluoroacetate salt

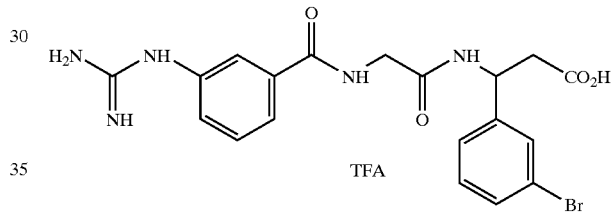

To the product from Example 184 (1.0 mg, 0.00165 mole) in go (15 mL) and CH₃CN (10 mL) was added LiOH (210 mg, 0.005 mole). The reaction mixture was stirred at room temperature for 1.5 hours. The pH was lowered to ≈2.5 with TFA and the product was isolated by RPHPLC to yield the title compound (460 mg after lyophilization) as a white solid.

MS and NMR were consistent with the desired structure.

EXAMPLE 186

Preparation of (±)ethyl β-[[2-[[[3-[(aminoiminomethyl)amino]phenyl]carbonyl]amino]acetyl]amino]-4-bromobenzenepropanoate, trifluoroacetate salt

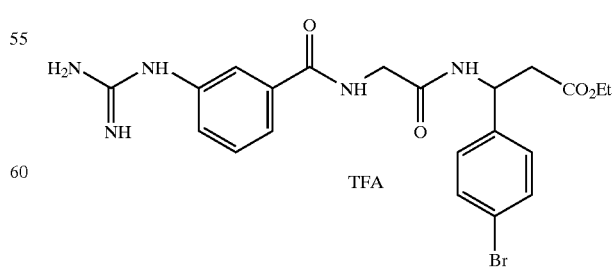

The above compound was prepared according to the methodology of Example 174, substituting an equivalent amount of 4-bromobenzaldehyde (Aldrich) for 3,4-dichlorobenzaldehyde in Example 174, Step A.

MS and NMR were consistent with the desired structure.

EXAMPLE 187

Preparation of (±)β-[[2-[[[3-[(aminoiminomethyl)amino]phenyl]carbonyl amino]acetyl]amino]-4-bromobenzenepropanoic acid, trifluoroacetate salt

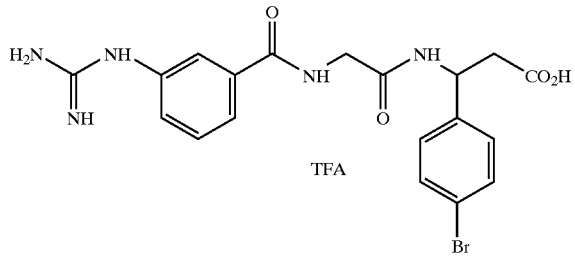

To the product from Example 186 (1.3 mg, 0.0023 mole) in H₂O (15 mL) and CH₃CN (15 mL) was added LiOH (290 mg, 0.0069 mole). The reaction mixture was stirred at room temperature for 1 hour. The pH was lowered to ≈2.5 with TFA and the product was isolated by RPHPLC to yield the title compound (1.1 g after lyophilization) as a white solid.

MS and NMR were consistent with the desired structure.

EXAMPLE 188

Preparation of (±)ethyl β-[[2-[[[3-[(3,4,5,6-tetrahydro-2H-azepin-7-yl)amino)phenyl]carbonyl]amino]acetyl]amino]-3,5-dichlorobenzenepropanoate, trifluoroacetate salt

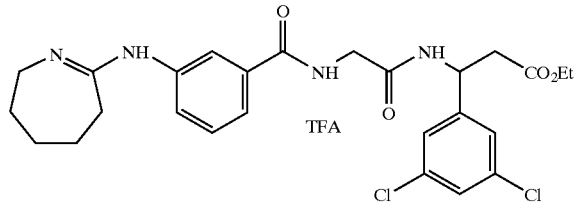

The above compound was prepared according to the methodology of Example 11, substituting an equivalent amount of 3,5-dichlorobenzaldehyde (Aldrich) for 3-pyridinecarboxaldehyde in Example 1, Step A from Example 11, Step B.

MS and NMR were consistent with the desired structure.

EXAMPLE 189

Preparation of (±)β-[[2-[[[3-[(3,4,5,6-tetrahydro-2H-azepin-7-yl)amino]phenyl]carbonyl]amino]acetyl]amino]-3,5-dichlorobenzenepropanoic acid, trifluoroacetate salt

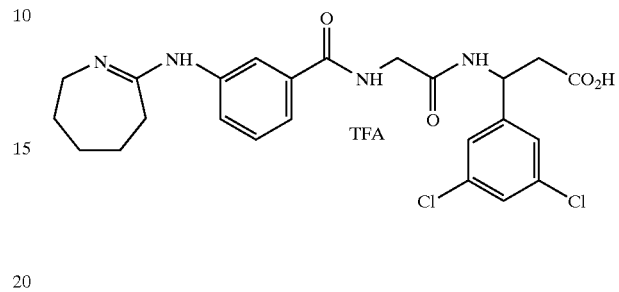

To the product from Example 188 (370 mg, 0.00057 mole) in H₂O (20 mL) and CH₃CN (15 mL) was added LiOH (192 mg, 0.0046 mole). The reaction mixture was stirred at room temperature for 3 hours. The pH was lowered to ≈2.5 with TFA and the product was isolated by RPHPLC to yield the title compound (280 mg after lyophilization) as a white solid.

MS and NMR were consistent with the desired structure.

EXAMPLE 190

Preparation of (±)ethyl β-[[2-[[[3-[(4,5-dihydro-1H-imidazol-2-yl)amino]phenyl]carbonyl]amino]acetyl]amino]-3,5-dichlorobenzenepropanoate, trifluoroacetate salt

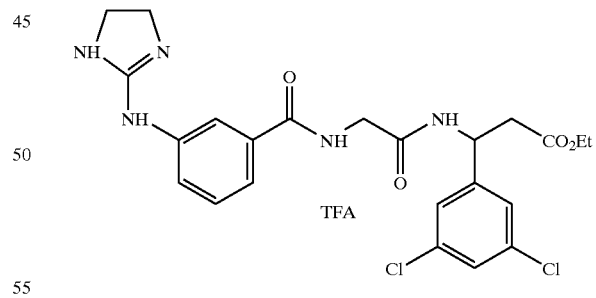

The above compound was prepared according to the methodology of Example 9, substituting an equivalent amount of 3,5-dichlorobenzaldehyde (Aldrich) for 3-pyridinecarboxaldehyde in Example 1, Step A from Example 9, Step B.

MS and NMR were consistent with the desired structure.

EXAMPLE 191

Preparation of (±)β-[[2-[[[3-[(4,5-dihydro-1H-imidazol-2-yl)amino]phenyl]carbonyl]amino]acetyl]amino]-3,5-dichlorobenzenepropanoic acid, trifluoroacetate salt

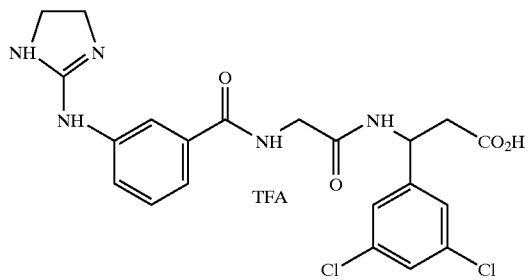

To the product from Example 190 (200 mg, 0.00032 mole) in $H_2O$ (10 mL) and $CH_3CN$ (10 mL) was added LiOH (54 mg, 0.0013 mole). The reaction mixture was stirred at room temperature for 1.5 hours. The pH was lowered to ≈2.5 with TFA and the product was isolated by RPHPLC to yield the title product (190 mg after lyophilization) as a white solid.

MS and NMR were consistent with the desired structure.

EXAMPLE 192

Preparation of (±)ethyl β-[[2-[[[3-[(aminoiminomethyl)amino]phenyl]carbonyl]amino]acetyl]amino]-3,5-dimethylbenzenepropanoate, trifluoroacetate salt

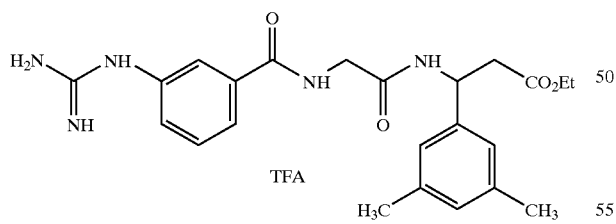

The above compound was prepared according to the methodology of Example 174, substituting an equivalent amount of 3,5-dimethylbenzaldehyde (Lancaster) for 3,4-dichlorobenzaldehyde in Example 174, Step A.

MS and NMR were consistent with the desired structure.

EXAMPLE 193

Preparation of (±)β-[[2-[[[3-[(aminoiminomethyl)amino]phenyl]carbonyl]amino]acetyl]amino]-3,5-dimethylbenzenepropanoic acid, trifluoroacetate salt

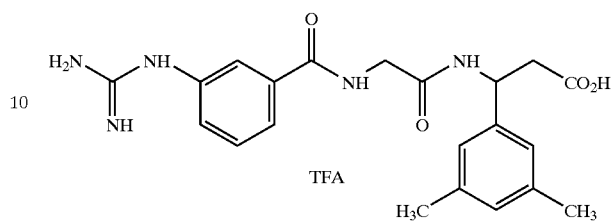

To the product from Example 192 (730 mg, 0.0013 mole) in $H_2O$ (10 mL) and $CH_3CN$ (10 mL) was added LiOH (221 mg, 0.005 mole). The reaction mixture was stirred at room temperature for 1 hour. The pH was lowered to ≈2.5 with TFA and the product was isolated by RPHPLC to yield the title compound (570 mg after lyophilization) as a white solid.

MS and NMR were consistent with the desired structure.

EXAMPLE 194

Preparation of (±)ethyl β-[[2-[[[3-[(aminoiminomethyl)amino]phenyl]carbonyl]amino]acetyl]amino]-3,5-dimethoxybenzenepropanoate, trifluoroacetate salt

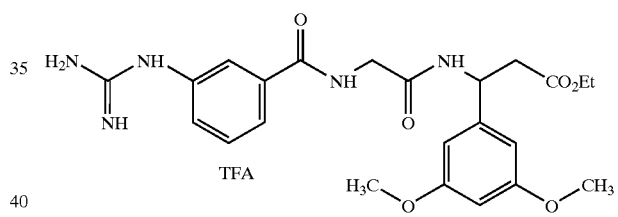

The above compound was prepared according to the methodology of Example 174, substituting an equivalent amount of 3,5-dimethoxybenzaldehyde (Aldrich) for 3,4-dichlorobenzaldehyde in Example 174, Step A.

MS and NMR were consistent with the desired structure.

EXAMPLE 195

Preparation of (±)β-[[2-[[[3-[(aminoiminomethyl)amino]phenyl]carbonyl]amino]acetyl]amino]-3,5-dimethoxybenzenepropanoic acid, trifluoroacetate salt

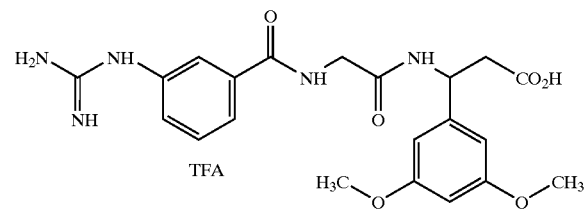

To the product from Example 194 (800 mg, 0.00014 mole) in $H_2O$ (20 mL) and $CH_3CN$ (8 mL) was added LiOH

EXAMPLE 196

Preparation of (±)(2,2-dimethyl-1-oxopropoxy) methyl β-[[2-[[[3-[(aminoiminomethyl)amino]phenyl]carbonyl]amino]acetyl]amino]-3,5-dichlorobenzenepropanoate, trifluoroacetate salt

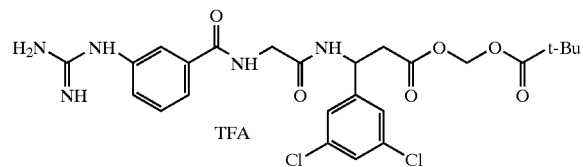

Step A

DL-3-amino-3-(3,5-dichlorophenyl)propionic acid was prepared according to the methodology of Example 1, Step A, substituting an equivalent amount of 3,5-dichlorobenzaldehyde (Aldrich) for 3-pyridine carboxaldehyde in Example 1, Step A. MS and NMR were consistent with the desired structure.

Step B

To the product from Step A (3.0 g, 0.0128 mole) in dioxane (25 mL) and E0 (13 mL) was added, at ice-bath temperature, NaOH (0.52 g, 0.013 mole) in $H_2O$ (13 mL). After stirring at ice-bath temperature for 10 minutes, BOC anhydride (3.0 g, 0.014 mole) was added at ice-bath temperature. The reaction mixture was then stirred for 2 hours at room temperature. After the dioxane was removed under vacuum, the aqueous solution was cooled in an ice-bath and the pH was lowered to 2.5 with $KHSO_4$ after overlaying with ethyl acetate. The ethyl acetate layer was separated and the aqueous layer extracted twice more with ethyl acetate. The combined ethyl acetate layers were washed with $H_2O$ (3×), dried over $MgSO_4$ and the solvent was removed under vacuum. The residue was slurried in 5% ethyl acetate/hexane overnight resulting in a white solid. This was filtered, washed with 10% ethyl acetate/hexane and dried to yield N-BOC-DL-3-amino-3-(3,5-dichlorophenyl)-propionic acid (2.9 g) as a white solid.

Step C

To the product from Step B (2.5 g, 0.0075 mole) in acetone (30 mL) and $H_2O$ (5 mL) was added KOH (87%) (0.5 g, 0.0075 mole). To this was added chloromethyl pivalate (1.3 g, 0.0084 mole) (Aldrich), followed by NaI (190 mg). The reaction mixture was stirred overnight at reflux. The solvent was removed under vacuum. The residue was taken up in ether. The ether was washed with saturated $NaHCO_3$ (2×), $H_2O$ (3×), dried over $MgSO_4$ and removed under vacuum to yield pivaloyloxymethyl N-BOC-DL-3-amino-3-(3,5-dichlorophenyl)propionate (2.92 g) as a white solid. MS and NMR were consistent with the desired structure.

Step D

To the product from Step C (2.92 g, 0.0065 mole) was added excess 4M HCl in dioxane (Aldrich). The reaction mixture was stirred at room temperature overnight. The solvent was removed under vacuum and the residue was slurried 2× with petroleum ether/isopropyl ether (50:50) and 1× with petroleum ether (the solvents are decanted off each time). The resulting solid was dried under vacuum to yield pivaloyloxymethyl DL-3-amino-3-(3,5-dichlorophenyl)propionate hydrochloride (2.0 g) as a white solid. MS and NMR were consistent with the desired structure.

Step E

The title compound was prepared according to the methodology of Example 174, Step B, substituting an equivalent amount of the product from Step D above for the product from Example 174, Step A in Example 174, Step B. The title compound was isolated as a white solid. MS and NMR were consistent with the desired structure.

EXAMPLE 197

Preparation of (±)ethyl 3,5-dichloro-β-[[2-[[[3-[(cyanoimino)(methylamino)methyl]amino]phenyl]carbonyl]amino]acetyl]amino]benzenepropanoate

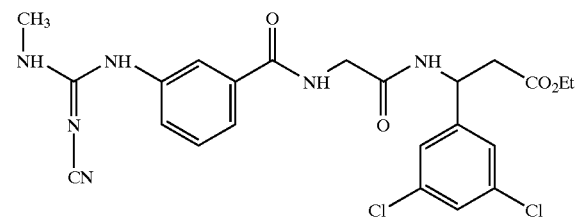

Step A

Ethyl β-[(2-aminoacetyl)amino](3,5-dichlorophenyl)-3-propanoate hydrochloride was prepared according to the methodology of Example 1, Steps A–D, substituting an equivalent amount of 3,5-dichlorobenzaldehyde for 3-pyridinecarboxaldehyde in Example 1, Step A. MS and NMR were consistent with the desired structure.

Step B

To the product from Step A above (1.1 g, 0.0031 mole), the product from Example J (680 mg, 0.0031 mole), DMAP (38 mg, 0.00031 mole), triethylamine (320 mg, 0.0031 mole) and methylene chloride (12 mL) was added, at ice-bath temperature, EDCl (600 mg, 0.0031 mole). The reaction mixture was stirred at ice-bath temperature for 15 minutes then at room temperature overnight. After removing the solvent under vacuum, the residue was taken up in ethyl acetate. The ethyl acetate was washed with saturated $NaHCO_3$ (1×), $H_2O$ (2×), dried over $MgSO_4$ then removed under vacuum. The resulting solid was slurried in ethyl acetate:isopropyl ether (1:3) for 1 hour. The resulting solid was filtered, washed with isopropyl ether and dried under vacuum to yield the title compound (1.35 g) as a white solid.

EXAMPLE 198

Preparation of (±)3,5-dichloro-β-[[2-[[[3-[[(cyanoimino)(methylamino)methyl]amino]phenyl]carbonyl]amino]acetyl]amino]benzenepropanoic acid

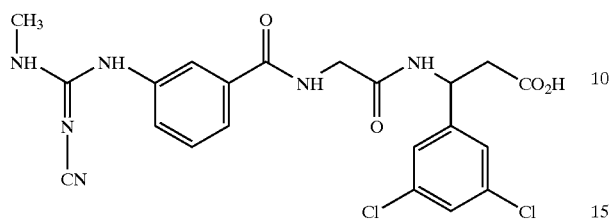

To the product from Example 197, Step B (1.18 g, 0.0023 mole) in H$_2$O (15 mL) and CH$_3$CN (15 mL) was added LiOH (240 mg, 0.0057 mole). The reaction mixture was stirred at room temperature for 3 hours. The pH was lowered to ≈3 with TFA and the product was isolated by RPHPLC to yield the title compound (1.02 g after lyophilization) as a white solid. MS and NMR were consistent with the desired structure.

EXAMPLE 199

Preparation of (±)ethyl 3,5-dichloro-β-[[2-[[[3-[(1,4,5,6-tetrahydropyrimidin-2-yl)amino]phenyl]carbonyl]amino]acetyl]amino]benzenepropanoate, trifluoroacetate salt

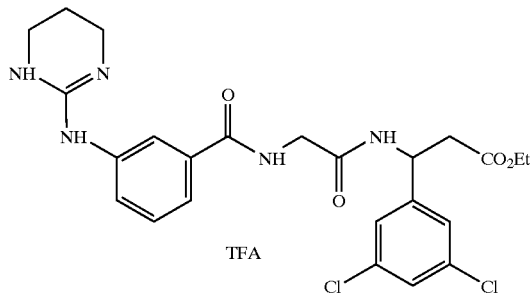

Step A

To the product from Example 23, Step A (10.1 g, 0.03 mole) in DMF (15 mL) was added 1,3-diaminopropane (2.3 g, 0.031 mole), triethylamine (3.9 g, 0.03 mole) and DMAP (420 mg). The reaction mixture was heated at 140–150° C. for 4.5 hours (thick precipitate). After cooling to room temperature, H$_2$O (30 mL) was added and, after stirring for 15 minutes, the precipitate was filtered and washed with H$_2$O. This precipitate was slurried in H$_2$O and made acidic with concentrated HCl. A solution formed. After lyophilizing off the solvent, the residue was slurried 2× with isopropyl ether (which was decanted off each time). After drying under vacuum, the yield of 3-(2-amino-1,4,5,6-tetrahydropyrimidine)benzoic acid hydrochloride was 4.0 g as a white solid. MS and NMR were consistent with the desired structure.

Step B

To the product from Step A above (884 mg, 0.0035 mole) and NMM (350 mg, 0.0035 mole) in anhydrous DMF (6 mL) was added, at ice-bath temperature, isobutylchloroformate (470 mg, 0.0035 mole). After stirring for 5 minutes, a slurry of the product from Example 197, Step A (1.07 g, 0.003 mole) and NMM (300 mg, 0.003 mole) in anhydrous DMF (6 mL) was added at ice-bath temperature. The solution was stirred overnight at room temperature. The solvent was removed under vacuum and the product was isolated by RPHPLC to yield the title compound (820 mg after lyophilization) as a white solid. MS and NMR were consistent with the desired structure.

EXAMPLE 200

Preparation of (±)3,5-dichloro-β-[[2-[[[3-[(1,4,5,6-tetrahydropyrimidin-2-yl)amino]phenyl]carbonyl]amino]acetyl]amino]benzenepropanoic acid, trifluoroacetate salt

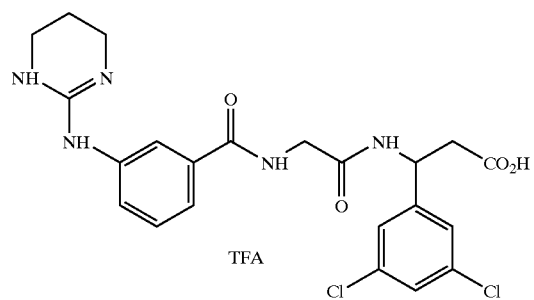

To the product from Example 199, Step B (780 mg, 0.0012 mole) in H$_2$O (10 mL) and CH$_3$CN (10 mL) was added LiOH (830 mg, 0.005 mole). The reaction mixture was stirred at room temperature for 1.5 hours. The pH was lowered to ≈2.5 with TFA and the product was isolated by RPHPLC to yield the title compound (560 mg after lyophilization) as a white solid. MS and NMR were consistent with the desired structure.

EXAMPLE 201

Preparation of (±)β-[[2-[[[3-[[[(aminocarbonyl)imino)methylamino)methyl]amino]phenyl]carbonyl]amino]acetyl]amino]-3,5-dichlorobenzenepropanoic acid

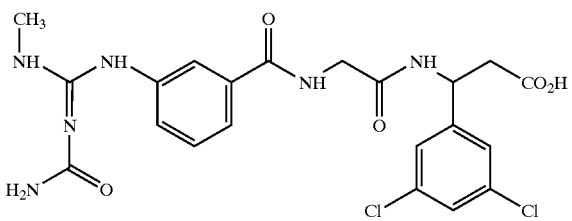

To the product from Example 198 (300 mg, 0.0006 mole) in CH$_3$CN (10 mL) and H$_2$O (25 mL) was added TFA (6 mL). The reaction mixture was stirred at room temperature for 2 weeks. The product was isolated by RPHPLC to yield the title compound (290 mg after lyophilization) as a white solid.

MS and NMR was consistent with the desired structure.

EXAMPLE 202

Preparation of (±)ethyl β-[[2-[[[3-[(3,4-dihydro-2H-pyrrol-5-yl)amino]phenyl]carbonyl]amino]acetyl]amino]-3,5-dichlorobenzenepropanoate, trifluoroacetate salt

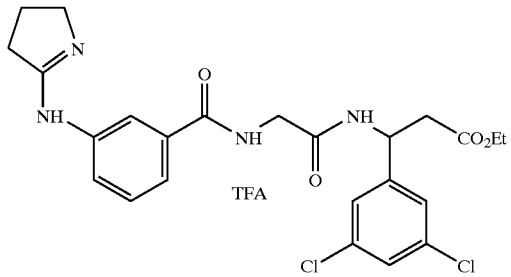

The above compound was prepared according to the methodology of Example 16, substituting an equivalent amount of 3,5-dichlorobenzaldehyde (Aldrich) for 3-pyridine carboxaldehyde in Example 1, Step A, which was used to synthesize the product from Example 1, Step D, used in Example 11, Step B. MS and NMR were consistent with the desired structure.

EXAMPLE 203

Preparation of (±)β-[[2-[[[3-[(3,4-dihydro-2H-pyrrol-5-yl)amino]phenyl]carbonyl]amino]acetyl]amino]-3,5-dichlorobenzenepropanoic acid, trifluoroacetate salt

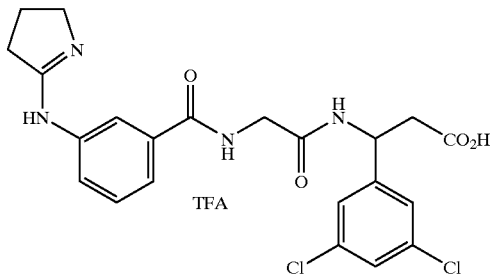

To the product from Example 202 (1.27 g, 0.002 mole) in $H_2O$ (15 mL) and $CH_3CN$ (15 mL) was added LiOH (345 mg, 0.0082 mole). The reaction mixture was stirred at room temperature for 1.5 hours. The pH was lowered to 2.7 with TFA and the product was isolated by RPHPLC to yield the title compound (80 mg after lyophilization) as a white solid. MS and NMR were consistent with the desired structure.

EXAMPLE 204

Preparation of (±)ethyl 3,5-dichloro-β-[[2-[[[3-[(2,3,4,5-tetrahydropyridin-6-yl)amino]phenyl]carbonyl]amino]acetyl]amino]benzenepropanoate, trifluoroacetate salt

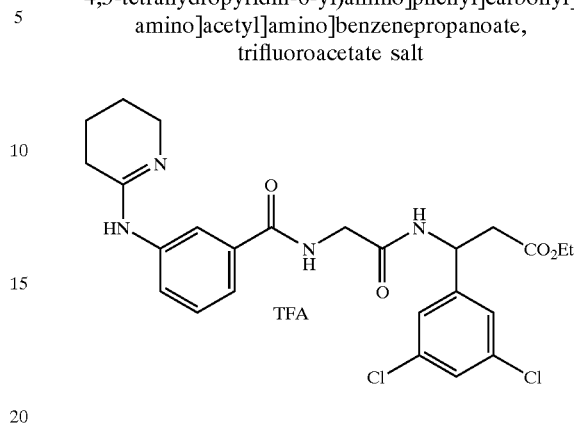

Step A

To o-methylvalerolactim (Oakwood) (6.9 g, 0.061 mole) in $CH_3CN$ (75 mL) was added 3-aminobenzoic acid, hydrochloride (Aldrich) (10 g, 0.0576 mole). After briefly heating to form a solution, the reaction mixture was stirred overnight at room temperature. The resulting precipitate was filtered, washed with $CH_3CN$ and dried under vacuum to yield 3-(1-aza-2-amino-1-cyclohexene)benzoic acid hydrochloride (12.2 g) as a white solid. MS and NMR were consistent with the desired structure.

Step B

The title compound was prepared according to the methodology of Example 199, substituting an equivalent amount of the product from Step A above, for the product from Example 199, Step A in Example 199, Step B.

MS and NMR were consistent with the desired structure.

EXAMPLE 205

Preparation of (±)3,5-dichloro-β-[[2-[[[3-[(2,3,4,5-tetrahydropyridin-6-yl)amino]phenyl]carbonyl]amino]acetyl]amino]benzenepropanoic acid, trifluoroacetate salt

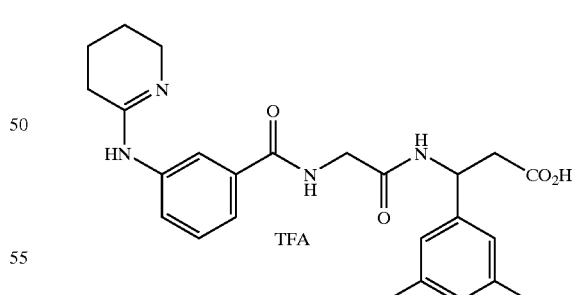

To the product from Example 204, Step B (890 mg, 0.0014 mole) in $H_2O$ (20 mL) and $CH_3CN$ (20 mL) was added LiOH (236 mg, 0.0056 mole). The reaction mixture was stirred at room temperature for 1 hour. The pH was lowered to ≈3 with TFA and the product was isolated by RPHPLC to yield the title compound (320 mg after lyophilization) as a white solid. MS and NMR were consistent with the desired structure.

EXAMPLE 206

Preparation of (±)β-[[2-[[[3-[(aminothioxomethyl)amino]phenyl]carbonyl]amino]acetyl]amino]-3,5-dichlorobenzenepropanoic acid

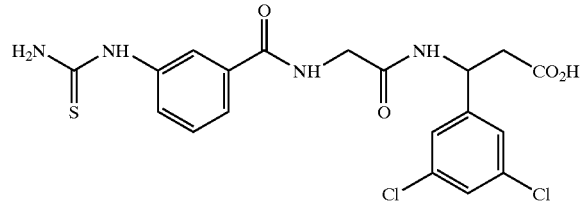

The above compound was prepared according to the methodology of Example 198, substituting an equivalent amount of 1-(3-carboxyphenyl)-2-thiourea (Transworld) for the product from Example J in Example 197, Step B. MS and NMR were consistent with the desired structure.

EXAMPLE 207

Preparation of (±)β-[[2-[[[3-[(aminoiminomethyl)amino]phenyl]carbonyl]amino]acetyl]amino]-3,4-dibromobenzenepropanoic acid, trifluoroacetate salt

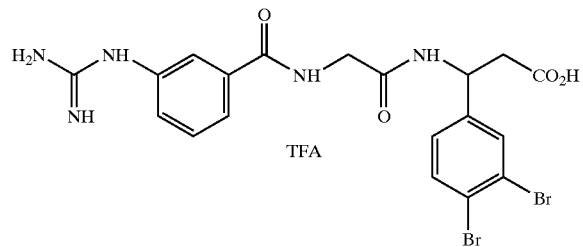

The above compound was prepared according to the methodology of Example 175, substituting an equivalent amount of 3,4-dibromobenzaldehyde (Lancaster) for 3,4-dichlorobenzaldehyde in Example 174, Step A. MS and NMR were consistent with the desired structure.

EXAMPLE 208

Preparation of (±)β-[[2-[[[3-[(aminoiminomethyl)amino]phenyl]carbonyl]amino]acetyl]amino]-3-fluoro-5-(trifluoromethyl)benzenepropanoic acid, trifluoroacetate salt

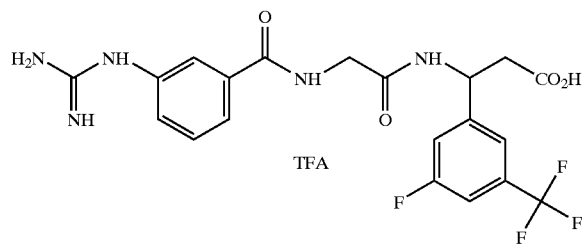

The above compound was prepared according to the methodology of Example 175, substituting an equivalent amount of 3-fluoro-5-trifluoromethylbenzaldehyde (Lancaster) for 3,4-dichlorobenzaldehyde in Example 174, Step A.

MS and NMR were consistent with the desired structure.

EXAMPLE 209

Preparation of (±)β-[[2-[[[3-[(aminoiminomethyl)amino]phenyl]carbonyl]amino]acetyl]amino]-3-bromo-5-fluorobenzenepropanoic acid, trifluoroacetate salt

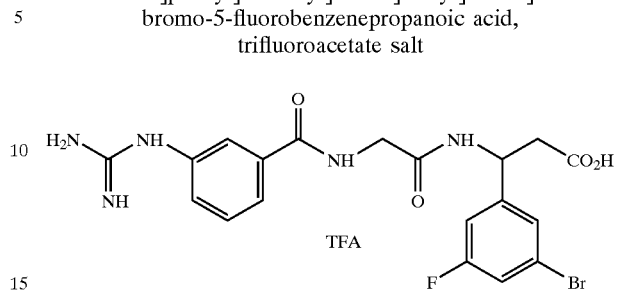

Step A

To 1-fluoro-3,5-dibromobenzene (Lancaster) (10 g, 0.0394 mole) in anhydrous ethyl ether (50 mL), in a flame dried flask under $N_2$ and at −78° C. was added 1.6 m butyl lithium in hexane (Aldrich) dropwise, keeping the temperature below −78° C. during the addition. After the addition was complete, the reaction was stirred at −78° C. for an additional 50 minutes. The reaction was slowly warmed to −30° C., then and hyrous DMF (3.6 g, 0.049 mole) was added dropwise and at such a rate as to keep the temperature below −20° C.

After the addition was complete, the temperature was slowly raised to 0° C. over an hour, then stirred overnight at room temperature. The reaction mixture was slowly poured into cold 10% aqueous HCl (80 mL). After stirring for 15 minutes, the ether layer was separated and the ether was washed with $H_2O$ (4×), dried over $MgSO_4$ and removed under vacuum to yield 3-bromo-5-fluorobenzaldehyde (8.16 g) as an amber liquid. MS and NMR were consistent with the desired product.

Step B

The title compound was prepared according to the methodology of Example 175, substituting an equivalent amount of 3-bromo-5-fluorobenzaldehyde (Step A above) for 3,4-dichlorobenzaldehyde in Example 174, Step A. MS and NMR were consistent with the desired structure.

EXAMPLE 210

Preparation of (±)β-[[2-[[[3-[(aminoiminomethyl)amino]phenyl]carbonyl]amino]acetyl]amino]-3,5-dibromobenzenepropanoic acid, trifluoroacetate salt

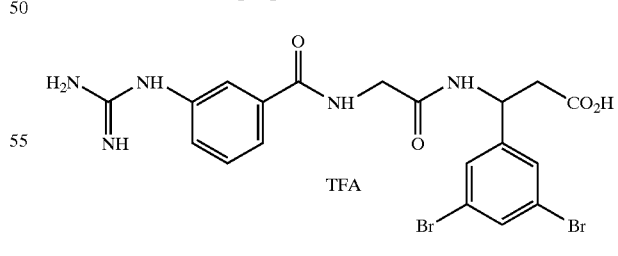

Step A

To 3,5-dibromobenzylbromide (Lancaster) (20 g, 0.061 mole) in $H_2O$ (27 mL) and glacial acetic acid (27 mL) was added hexamethylenetetramine (Aldrich). The reaction mixture was heated at reflux for 2 hours. Concentrated HCl (22 mL) was then added and the refluxing was continued for 30 minutes. After cooling to room temperature, the reaction mixture was poured into H₂O (230 mL) and stirred for 10 minutes. The resulting precipitate was filtered, washed with H₂) and dried to yield 3,5-dibromobenzaldehyde (11.45 g) as a white solid. MS and NMR were consistent with the desired structure.

Step B

The title compound was prepared according to the methodology of Example 175, substituting an equivalent amount of 3,5-dibromobenzaldehyde (Step A above) for 3,4-dichlorobenzaldehyde in Example 174, Step A. MS and NMR were consistent with the desired structure.

EXAMPLE 211

Preparation of (±)3,5-dibromo-β-[[2-[[[3-[(1,4,5,6-tetrahydropyrimidin-2-yl)amino]phenyl]carbonyl]amino]acetyl]amino]benzenepropanoic acid, trifluoroacetate salt

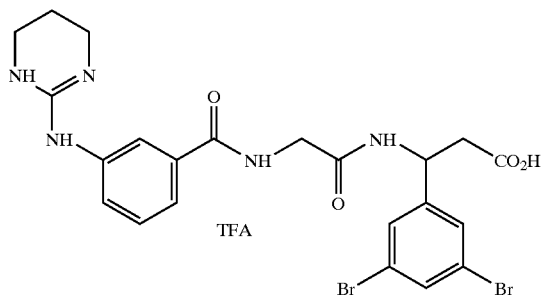

Step A

Ethyl-β-[(2-aminoacetyl)amino](3,5-dibromophenyl)-3-propanoate hydrochloride was prepared according to the methodology of Example 1, Steps A–D, substituting an equivalent amount of 3,5-dibromobenzaldehyde (Example 210, Step A) for 3-pyridinecarboxaldehyde in Example 1, Step A. MS and NMR were consistent with the desired structure.

Step B

The title compound was prepared according to the methodology of Example 200, substituting an equivalent amount of the product from Example 211, Step A (above) for the product from Example 197, Step A in Example 199, Step B. MS and NMR were consistent with the desired structure.

EXAMPLE 212

Preparation of (±)β-[[2-[[[3-[(aminoiminomethyl)amino]phenyl]carbonyl]amino]acetyl]amino]-3-bromo-5-methylbenzenepropanoic acid, trifluoroacetate salt

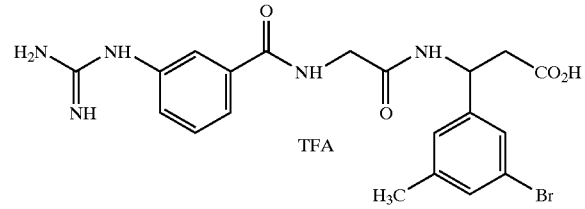

Step A

To 5-bromo-m-xylene (24.03 g, 0.13 mole) in benzene (125 mL) was added benzoylperoxide (3.04 g, 0.013 mole). The reaction mixture was heated to reflux in a 250 mL round bottom flask. N-bromosuccinimide (18.15 g, 0.10 mole) was added in portions over 15 minutes. After 2 hours, heating was discontinued and the reaction mixture was allowed to cool to room temperature. Precipitated solids were removed by filtration and the filtrate was concentrated. The residue was taken up in hexane and additional solids were removed by filtration. The filtrate was passed through a small pad of silica gel and the filtrate was concentrated. The resultant yellow oil was titurated with MeOH over ice to give 3-bromo-5-methylbenzyl bromide (7.34 g) as a white solid. MS and NMR were consistent with the desired structure.

Step B

To 3-bromo-5-methylbenzyl bromide (Step A above) (5.49 g, 20 mmole) in glacial acetic acid (9.0 mL) and H₂O (9 mL) was added hexamethylenetetramine (4.50 g, 32 mmole) and the reaction was stirred at reflux for 2 hours. Concentrated HCl (7.0 mL) was added and the mixture was refluxed an additional 15 minutes. After cooling to room temperature, the reaction mixture was diluted with H₂O (75 mL) and extracted with ether (150 mL). The ether layer was washed with H₂O (3×25 mL), 10% NaHCO₃ (2×50 mL) and dried over MgSO₄. The ether was removed under vacuum and the residue was chromatographed on silica gel eluting with hexane and 10% Et₂O/hexane to yield 3-bromo-5-methylbenzaldehyde (2.80 g) as a light yellow oil which solidified upon standing. MS and NMR were consistent with the desired structure.

Step C

The title compound was prepared according to the methodology of Example 175 substituting an equivalent amount of 3-bromo-5-methylbenzaldehyde (Step B above) for 3,4-dichlorobenzaldehyde in Example 174, Step A. MS and NMR were consistent with the desired structure.

EXAMPLE 213

Preparation of (±)β-[[2-[[[3-[(aminoiminomethyl)amino]-5-(trifluoromethyl)phenyl]carbonyl]amino]acetyl]amino]-3,5-dibromobenzenepropanoic acid, trifluoroacetate salt

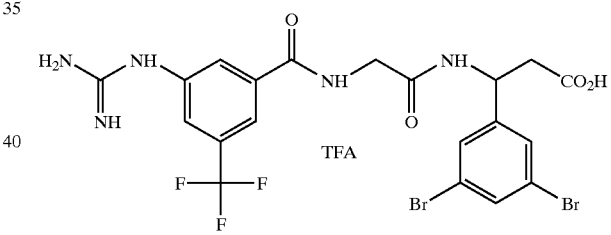

The above compound was prepared according to the methodology of Example 39, substituting the equivalent amount of 3,5-dibromobenzaldehyde (Example 210, Step A) for 3,5-bis-trifluoromethylbenzaldehyde in Example 38. MS and NMR were consistent with the desired structure.

EXAMPLE 214

Preparation of (±)β-[[2-[[[3-[(aminoiminomethyl)amino]phenyl]carbonyl]amino]acetyl]amino]-3-bromo-5-chlorobenzenepropanoic acid, trifluoroacetate salt

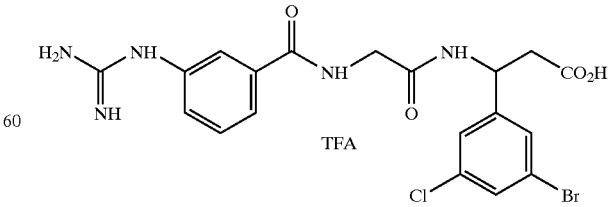

Step A

To 1-chloro-3,5-dibromobenzene (Esprit) (20 g, 0.074 In mole) in anhydrous ethyl ether (150 mL) in a flame dried flask under $N_2$ and at −78° C. was added 1.6 m butyl lithium in hexane dropwise, keeping the temperature below −78° C., then warmed to −30° C. Anhydrous DMF (6.8 g, 0.092 mole) was added dropwise, keeping the temperature below −20° C. After the addition was complete, the reaction was slowly warmed to 0° C., then stirred overnight at room temperature. The reaction mixture was poured slowly into chilled 10% aqueous HCl (160 mL). After stirring for 15 minutes, the ether was separated, washed with $H_2O$ (4×), dried over $MgSO_4$ and removed under vacuum to yield 3-bromo-5-chlorobenzaldehyde (13 g) as a white solid. MS and NMR were consistent with the desired structure.

Step B

The title compound was prepared according to the methodology of Example 175, substituting an equivalent amount of 3-bromo-5-chlorobenzaldehyde (Step A above) for 3,4-dichlorobenzaldehyde in Example 174, Step A. MS and NMR were consistent with the desired structure.

EXAMPLE 215

Preparation of (±)3-bromo-5-chloro-β-[[2-[[[3-[(1,4,5,6-tetrahydropyrimidin-2-yl)amino]phenyl]carbonyl]amino]acetyl]amino]-benzenepropanoic acid, trifluoroacetate salt

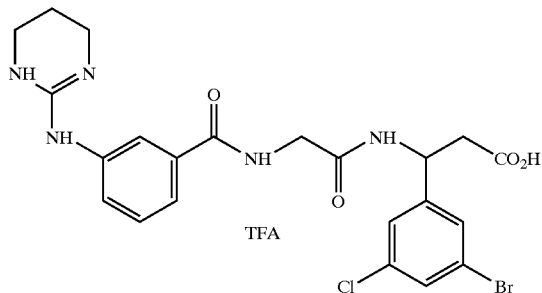

Step A

Ethyl β-[(2-aminoacetyl]amino](3-bromo-5-chlorophenyl)-3-propanoate hydrochloride was prepared according to the methodology of Example 1, Steps A–D, substituting an equivalent amount of 3-bromo-5-chlorobenzaldehyde (Example 214, Step A for 3-pyridinecarboxaldehyde in Example 1, Step A. MS and NMR were consistent with the desired structure.

Step B

The title compound was prepared according to the methodology of Example 200, substituting an equivalent amount of the product from Step A (above) for the product from Example 197, Step A in Example 199, Step B. MS and NMR were consistent with the desired structure.

EXAMPLE 216

Preparation of (±)β-[[2-[[[3-[(aminoiminomethyl)amino]-5-(trifluoromethyl)phenyl]carbonyl]amino]acetyl]amino]-3-bromo-5-chlorobenzenepropanoic acid, trifluoroacetate salt

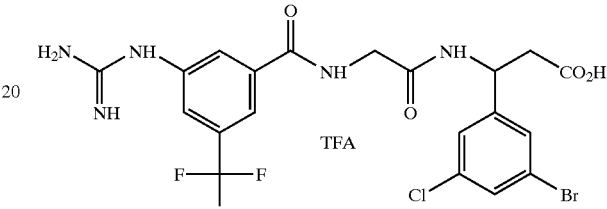

The above compound was prepared according to the methodology of Example 39, substituting an equivalent amount of 3-bromo-5-chlorobenzaldehyde (Example 214, Step A) for 3,5-bis-trifluoromethylbenzaldehyde in Example 38. MS and NMR were consistent with the desired structure.

EXAMPLE 217

Preparation of (±)[2-[2-[2-(2-hydroxyethoxy)ethoxy]ethoxy]ethyl]3,5-dichloro-β-[[2-[[[3-[(1,4,5,6-tetrahydropyrimidin-2-yl)amino]phenyl]carbonyl]amino]acetyl]amino]benzenepropanoate, trifluoroacetate salt

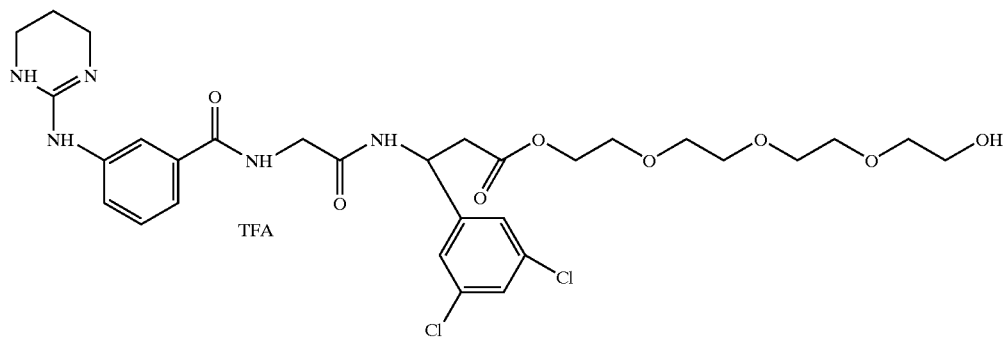

To the product of Example 200 (200 mg, 0.00033 mole) in DMA (1.5 mL) was added carbonyldiimidazole (67 mg, 0.00041 mole). The reaction was stirred at room temperature for 1 hour. Tetraethyleneglycol (214 mg, 0.0011 mole) was then added and the reaction mixture was stirred overnight at 60° C. The reaction was cooled to room temperature and the product was isolated by RPHPLC to yield the title compound (120 mg after lyophilization) as a hygroscopic white solid. MS and NMR were consistent with the desired structure.

EXAMPLE 218

Preparation of (±)[2-[2-[2-(2-hydroxyethoxy)ethoxy]ethoxy]ethyl]β-[[2-[[[3-[(aminoiminomethyl)amino]phenyl]carbonyl]amino]acetyl]amino]-3,5-dichlorobenzenepropanoate, trifluoroacetate salt

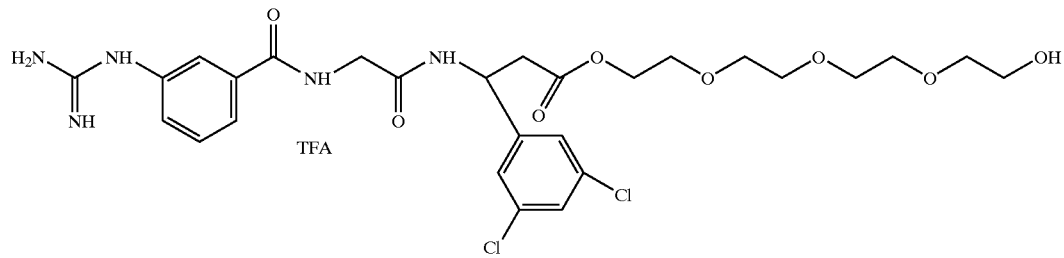

The above compound was prepared according to the methodology of Example 217, substituting an equivalent amount of the product of Example 27, for the product of Example 200. MS and NMR were consistent with the desired structure.

EXAMPLE 219

Preparation of (±)β-[[2-[[[3-[(aminoiminomethyl)amino]phenyl]carbonyl]amino]acetyl]amino]-3-bromo-5-iodobenzenepropanoic acid trifluoroacetate salt

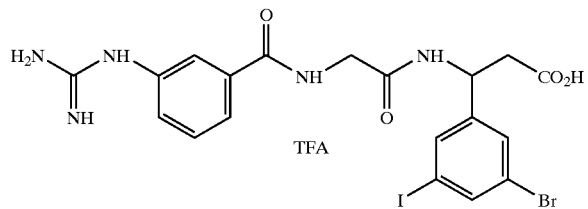

Step A

Methanol (40 mL) was added to a 250 mL round bottom flask followed by 60 mL of a solution saturated with anhydrous hydrochloric acid. 3-bromo-5-iodobenzoic acid (Aldrich) (5.02 g, 0.015 mole) was then added and the reaction mixture was stirred at room temperature for 6 hours. The reaction mixture was poured into chilled saturated NaHCO₃ solution (700 mL). The mixture was extracted 3× with methylene chloride (100 mL). The organic layers were combined, dried over MgSO₄ and concentrated under vacuum to yield methyl-5-bromo-3-iodobenzoate (5.08 g) as a pink solid. MP=55–57° C. MS and NMR were consistent with the desired structure.

Step B

To methyl 5-bromo-3-iodobenzoate (Step A above) (5.01 g, 0.015 mole) in anhydrous methylene chloride (100 mL) at −78° C., was added dropwise over two minutes, diisobutylaluminum hydride (5.50 mL, 0.03 mole). The mixture was stirred for 1 hour then allowed to warm to 0° C. The reaction solution was poured into 600 mL, chilled 3N HCl and extracted 3× with methylene chloride (150 mL). The organic layers were combined, dried over MgSO₄ and concentrated under vacuum to yield 5-bromo-3-iodobenzyl alcohol (4.54 g) as a white solid. MP=110–112° C. MS and NMR were consistent with the desired structure.

Step C

5-Bromo-3-iodobenzyl alcohol (3.01 g, 9.6 mmol) in a 50 mL round bottom flask was stirred magnetically and diluted with 15 mL anhydrous methylene chloride to give a turbid solution. The reaction flask was then stoppered and the septum stopper secured with wire.

Anhydrous=ethylene chloride (15 mL) was added to a separate 100 mL round bottom flask which was equipped with a cold finger. Nitrogen dioxide (1.72 g, 18.7 mmol) was condensed into the solution of methylene chloride at −20° C.

The benzyl alcohol solution was chilled to 0° C. and the nitrogen dioxide/methylene chloride solution was transferred via cannula into the reaction flask under a static nitrogen atmosphere. The reaction solution was stirred magnetically at 0° C. for 15 minutes after completion of the nitrogen dioxide solution transfer. The reaction solution was stirred at room temperature for 18 hours.

The reaction flask was vented in the hood and the excess nitrogen dioxide was expelled with a nitrogen stream. The reaction solution was then concentrated by rotary evaporation and resuspended in 30 mL ether. The ether solution was washed with 200 mL 10% sodium bicarbonate in a 500 mL separatory funnel. The resulting aqueous solution was extracted three times with 150 mL ether. The organic layers were combined, dried with sodium sulfate, filtered and concentrated in vacuo to afford 2.89 g of a yellow solid.

The product was isolated by flash chromatography to yield 5-bromo-3-iodobenzaldehyde as a white solid. MS and NMR were consistent with the desired structure.

Step D

The title compound was prepared according to the methodology of Example 175, substituting an equivalent amount of 5-bromo-3-iodobenzaldehyde (Step C, above) for 3,4-dichlorobenzaldehyde in Example 174, Step A. MS and NMR were consistent with the desired structure.

EXAMPLE 220

Preparation of (±)[2-[2-(2-hydroxyethoxy)ethoxy]ethoxy]ethyl]3,5-dichloro-β-[[2-[[[3-[(1,4,5,6-tetrahydropyrimidin-2-yl)amino]phenyl]carbonyl]amino]acetyl]amino]benzenepropanoate, trifluoroacetate salt

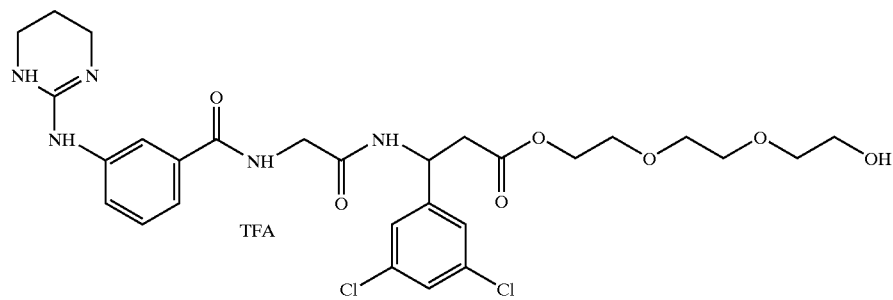

The above compound was prepared according to the methodology of Example 217, substituting an equivalent amount of triethyleneglycol for tetraethyleneglycol. MS and NMR were consistent with the desired structure.

EXAMPLE 222

Preparation of (±)β-[[2-[[[3-[(aminoiminomethyl)amino]phenyl]carbonyl]amino]acetyl]amino]-2-hydroxy-4-methoxybenzenepropanoic acid

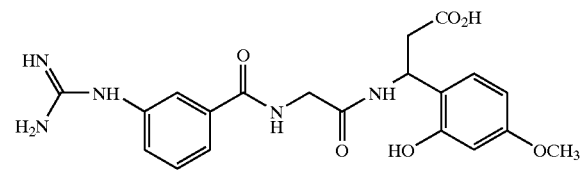

(RS)-4-amino-7-methoxy hydrocoumarin hydrochloride (1.26 g, 5.5 mmole), prepared from 7-methoxycoumarin (Aldrich) according to J. Rico, Tett. Let., 1994, 35, 6599–6602, was coupled to GIHA (1.50 g, 5.5 mmole) using substantially the procedure and proportions of Example 86, Step D. Purification by preparative RPHPLC gave the desired product as a mixture of hydrocoumarin (lactone) and phenoxy-acid TFA salts as a light yellow powder after lyophilization (1.25 gm). Essentially complete conversion to the desired phenol-acid can be obtained by dissolving the purified mixture in water, adjusting the pH to 7–8 with dilute aqueous NaOH until reaction is complete by HPLC, and lyophilizing (0.5 gm). MS and NMR were consistent with the desired phenol-carboxylic acid form of the molecule.

EXAMPLE 223

Preparation of (±)β-[[2-[[[3-[(aminoiminomethyl)amino]phenyl]carbonyl]amino]acetyl]amino]-5-hydroxy-4-methoxybenzofuran-6-propanoic acid, trifluoroacetate salt

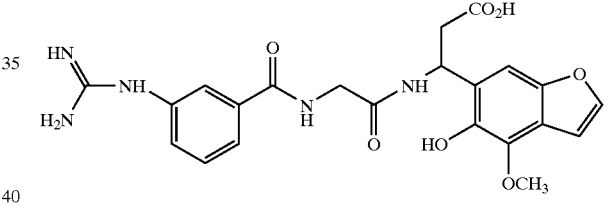

(RS)-4-amino-8-methoxy-hydropsoralen hydrochloride (2.2 gm, 8.1 mmole), prepared from 8-methoxypsoralen according to J. Rico, Tett. Let., 1994, 35, 6599–6602, was coupled to GIHA (2.0 g, 7.3 mmole) using substantially the procedure and proportions of Example 86, Step D. The product was isolated by preparative RPHPLC as the desired phenol-acid. NMR and MS were consistent with the desired structure.

EXAMPLE 224

Preparation of (±)β-[[2-[[[3-[(aminoiminomethyl)amino]phenyl]carbonyl]amino]acetyl]amino]-9H-fluorene-2-propanoic acid, trifluoroacetate salt

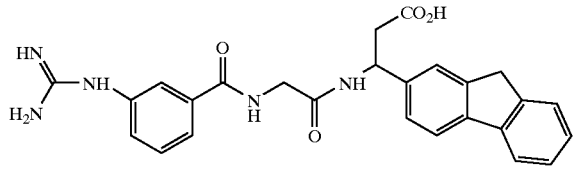

187

Step A (±)β-amino-9H-fluorene-2-propanoic acid

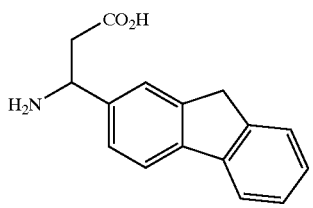

2-fluorene-carboxaldehyde (5.0 gm, 26 mmole, Aldrich) was combined with malonic acid (3.25 gm, 31 mmole), ammonium acetate (2.4 gm, 31 mmole), and isopropyl alcohol (70 mL) and refluxed overnight. After cooling the precipitated solid was collected by filtration and dried. NMR and MS were consistent with the proposed structure.

Step B

Ethyl(±)β-amino-9H-fluorene-2-propanoate

The product from Step A was taken up in absolute EtOH, dry HCl gas was added to saturation, and the mixture refluxed overnight. Volatiles were removed and the resulting semi-solid partitioned between ethyl acetate and water. The aqueous layer was made basic by addition of 2.5 N NaOH and extracted with EtOAc (2×200 mL). The organic layer was dried (anhydrous $NaSO_4$) and dry HCl gas added until precipitation ceased. Volatiles were removed until a semi-solid residue remained. This was triturated with diethyl ether to obtain a solid that was collected by filtration. NMR and MS were consistent with the proposed structure.

Step C

The title compound was prepared in the following manner. GIHA (0.41 gm, 1.5 mmole) was coupled to the product of Step B (0.42 gm, 1.5 mmole) above using substantially the procedure of Example 86, Step D. Preparative RPHPLC was used to isolate the ethyl ester of the title compound. This product (280 mg) was hydrolyzed to the acid by treating an aqueous dioxane solution (1:1) with excess LiOH, acidifying with TFA and purifying the product by RPHPLC. A white amorphous solid is obtained after lyophilization (250 mg). NMR and MS were consistent with the proposed structure.

EXAMPLE 225

Preparation of (±)β-[[2-[[[3-[(aminoiminomethyl)amino]phenyl]carbonyl]amino]acetyl]amino]-3,5-dichloro-2-hydroxybenzenepropanoic acid, trifluoroacetate salt, monohydrate

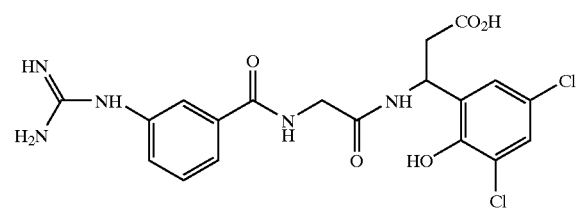

188

Step A

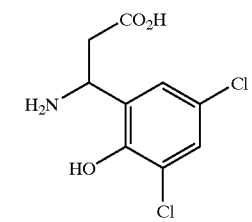

The above compound was prepared by reacting 3,5-dichlorosalicylaldehyde (10.0 gm, 52.4 mmole, Aldrich), malonic acid, and ammonium acetate in isopropyl alcohol using substantially the same procedure and proportions of Example 224, Step A. NMR and MS were consistent with the desired intermediate.

Step B

GIHA (1.0 gm, 3.7 mmole) and the product of Step A (1.1 gm, 4.4 mmole) were coupled using substantially the same procedure and proportions as Example 86, Step D. Desired product was isolated by C-18 RPHPLC and the appropriate fractions combined and lyophilized to give the title compound (0.42 gm). NMR and MS were consistent with the proposed structure.

EXAMPLE 226

Preparation of (±)β-[[2-[[[3-[(aminoiminomethyl)amino]phenyl]carbonyl]amino]acetyl]amino]-2-hydroxy-5-nitrobenzenepropanoic acid, trifluoroacetate salt

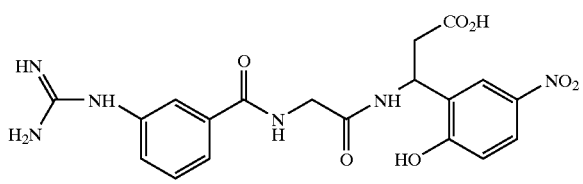

(RS)-4-amino-6-nitro-hydrocoumarin hydrochloride (1.1 g, 4.4 mmole) prepared from 6-nitrocoumarin (Aldrich) according to J. Rico, Tett. Let., 1994, 21, 6599–6602, was coupled to GIHA (1.0 g, 3.7 mmole) using substantially the procedure and proportions of Example 86, Step D. Purification by preparative RPHPLC gave the desired product as a mixture of hydrocoumarin (lactone) and phenoxy-acid TFA salts as a powder after lyophilization. Essentially complete conversion to the desired phenol-acid was obtained by dissolving the purified mixture in water, adjusting the pH to 7–8 with dilute aqueous NaOH until reaction is complete by HPLC, and lyophilizing. MS and NMR were consistent with the desired phenol-carboxylic acid form of the molecule.

EXAMPLE 227

Preparation of (±)β-[[2-[[[3-[(aminoiminomethyl)amino]phenyl]carbonyl]amino]acetyl]amino]-3,5-dibromo-2-hydroxybenzenepropanoic acid, trifluoroacetate salt, monohydrate

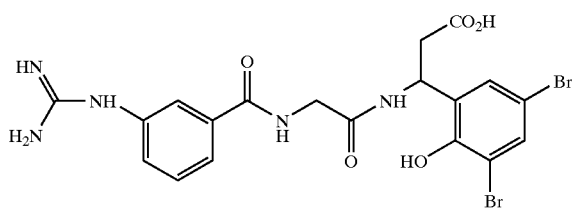

Step A

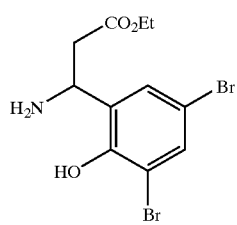

The above beta amino acid ester hydrochloride salt was prepared according to substantially the methodology of Example 1, Steps A and B substituting 3,5-dibromosalicylaldehyde (20.0 gm, 0.0715 mole, Aldrich) for 3-pyridine carboxaldehyde in Step A and keeping the proportions constant. NMR and MS were consistent with the proposed structure.

Step B

Ethyl(±)β-[[2-[[[3-[(aminoiminomethyl)amino]phenyl]carbonyl]amino]acetyl]amino]-3,5-dibromo-2-hydroxybenzenepropanoate, trifluoroacetate salt, monohydrate

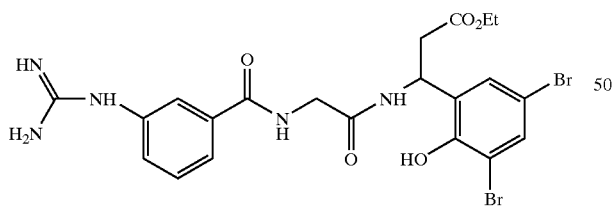

GHIA (1.0 gm, 3.7 mmole) and the product of Step A (1.78 gm, 4.4 mmole) were coupled using substantially the same procedure and proportions as Example 86, Step D. The desired product was isolated by C-18 RPHPLC and the appropriate fractions combined and lyophilized to give ethyl(±)β-[[2-[[[3-[(aminoiminomethyl)amino]phenyl]carbonyl]amino]acetyl]amino]-3,5-dibromo-2-hydroxybenzenepropanoate, trifluoroacetate salt, monohydrate (0.52 gm). NMR and MS were consistent with the proposed structure.

Step C

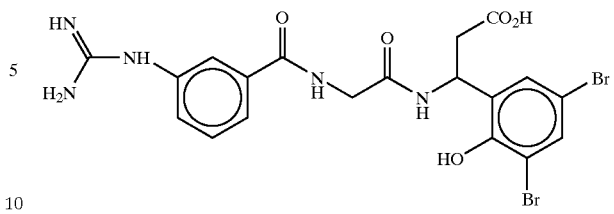

The product obtained in Step B was converted to the acid using substantially the procedure and conditions of Example 6, however, the hydrolysis solvent was dioxane:water. Preparative C-18 RPHPLC purification gave the TFA salt (300 mg). NMR and MS were consistent with the proposed structure.

EXAMPLE 228

Preparation of (±)β-[[2-[[[3-[(aminoiminomethyl)amino]phenyl]carbonyl]amino]acetyl]amino]-5-bromo-2-hydroxybenzenepropanoic acid, trifluoroacetate salt, monohydrate

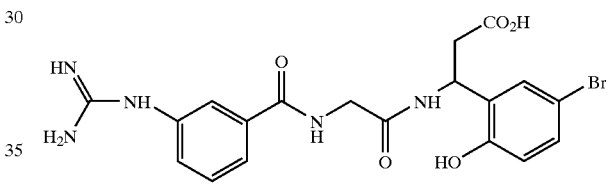

The title compound was prepared using substantially the procedure and proportions of Example 224, and substituting 5-bromosalicylaldehyde for 3,5-dichlorosalicylaldehyde to obtain the ethyl ester of the title compound. After ester hydrolysis the acid-phenol was obtained (0.3 gm after lyophilization). NMR and Ms were consistent with the proposed structure.

EXAMPLE 229

Preparation of (±)β-[[2-[[[3-[(aminoiminomethyl)amino]phenyl]carbonyl]amino]acetyl]amino]cyclohexanepropanoic acid, trifluoroacetate salt, monohydrate

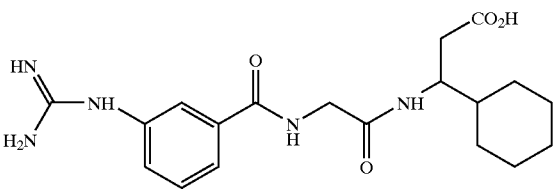

Step A

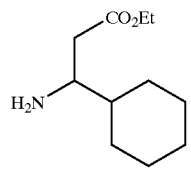

To a solution of ethyl (R,S)-3-amino-3-phenyl propionate hydrochloride (1.7 gm) dissolved in absolute EtOH (70 mL) was added 5% Pt on carbon and the reaction mixture transferred to a pressure bottle. After purging, the reaction vessel was pressurized with hydrogen (54 psig) and the reaction allowed to go to completion. Volatiles were removed and the product used without further purification. NMR and MS were consistent with the proposed structure.

Step B

Ethyl (R,S)3-amino-3-cyclohexylpropionate hydrochloride and GIHA were coupled using substantially the same procedure and proportions as Example 86, Step D. Ethyl(±) β-[[2-[[[3-[(aminoiminomethyl)amino]phenyl]carbonyl] amino]acetyl]amino]cyclohexane propanoic acid, trifluoroacetate salt, monohydrate was isolated using C-18 RPHPLC and lyophilized to give a white amorphous powder. Ethyl (±)β-[[2-[[[3-[(aminoiminomethyl)amino]phenyl]carbonyl] amino]acetyl]amino]cyclohexane propanoic acid, trifluoroacetate salt, monohydrate was hydrolyzed using the procedure of Example 224, Step C to give the title compound (0.5 gm). NMR and MS were consistent with the proposed structure.

EXAMPLE 230

Preparation of (±)ethyl β-[[2-[[[3-[(aminoiminomethyl)amino]phenyl]carbonyl]amino] acetyl]amino]-3,5-dichloro-2-hydroxybenzenepropanoate, trifluoroacetate salt, monohydrate

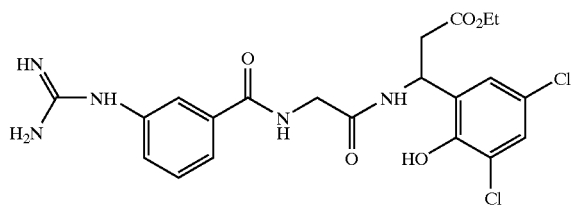

Step A

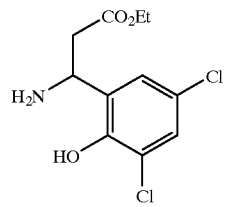

(RS)-4-Amino-6,8-dichlorocoumarin hydrochloride was prepared according to the procedure of Example 233, Steps A and B substituting 3,5-dichloro-salicylaldehyde for 3-bromo-5-chlorsalicylaldehyde in Example 233, Step A.

The above beta amino ethyl ester hydrochloride salt was prepared by dissolving the (RS)-4-amino-6,8-dichlorohydrocoumarin hydrochloride (8.0 g, 0.0207 mole) in absolute EtOH (30 ml) and adding 4 N HCl in dioxane (10 mL) and stirring the reaction mixture at room temperature for 2.5 hours. Excess HCl was removed by rotary evaporation (cold) and the reaction mixture was concentrated to a solid (50° C.). The solid was treated with EtOAc (25 mL) and Et$_2$O (10 mL) and stirred to give a white solid that was isolated by filtration (5.84 g). MS and NMR were consistent with the desired beta-amino acid ethyl ester as the hydrochloride salt.

Step B

To a solution of GIHA HCl (3.4 gm, 0.0124 mole) dissolved in dimethylacetamide (40 mL) was added N-methylmorpholine NMM, (1.36 mL, 0.0124 mole) and the solution cooled to 0–5° C. with gentle stirring. Isobutylchloroformate (1.61 mL, 0.0124 mole) was added and the reaction allowed to proceed for about 10 minutes. At this point a solution of the product of Step A (3.90 gm, 0.0124 mole) and NMM (1.36 mL) in DMA (20 mL) were added to the reaction mixture and the coupling allowed to proceed overnight. Volatiles were removed and the reaction mixture redissolved in acetonitrile:water and brought to pH of about 2 by the addition of TFA. The desired product was isolated by preparative C-18 RPHPLC and lyophilized to obtain the TFA salt (2.61 gm). NMR and MS were consistent with the structure of the title compound.

EXAMPLE 231

Preparation of (±)β-[[2-[[[3-[(aminoiminomethyl) amino]phenyl]carbonyl]amino]acetyl]amino]-5-chloro-2-hydroxybenzenepropanoic acid, trifluoroacetate salt, monohydrate

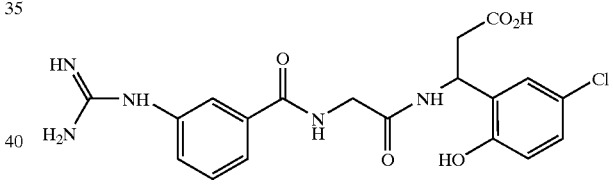

The above compound was prepared using substantially the procedure and proportions of Example 224 and substituting 5-chlorosalicylaldehyde for 3,5-dichlorosalicylaldehyde. After final ester hydrolysis the acid-phenol was obtained (0.3 gm after lyophilization). NMR and MS were consistent with the proposed structure.

EXAMPLE 232

Preparation of (±)3,5-dichloro-2-hydroxy-β-[[2-[[[3-[(3,4,5,6-tetrahydro-2H-azepin-7-yl)amino]phenyl] carbonyl]amino]acetyl]amino]benzenepropanoic acid, trifluoroacetate salt, monohydrate

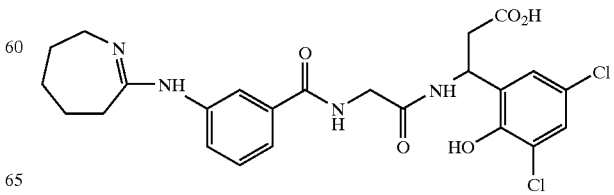

Step A

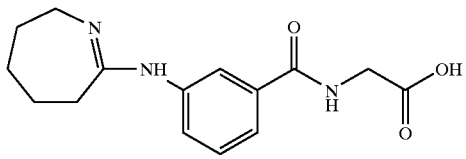

To m-aminohippuric acid (2.0 gm, 8.7 mmole) in acetonitrile (50 mL) was added 1-aza-2-methoxy-1-cycloheptane (1.2 gm, 9.5 mmole) (Aldrich). The reaction was allowed to proceed at room temperature over a weekend. Solvent was removed and the residue triturated with diethyl ether to give a solid (1.6 gm) that was substantially pure 3-(1-aza-2-amino-1-cycloheptane)hippuric acid by analytical RPHPLC, MS and NMR.

Step B

The product obtained in Step A, 3-(1-aza-2-amino-1-cycloheptane)-hippuric acid (1.0 gm, 3.2 mmole) was coupled to the compound prepared in Example 230, Step A (1.0 gm, 3.2 mmole), using substantially the conditions and procedure of Example 230, Step B and substituting 3-(1-aza-2-amino-1-cycloheptane)-hippuric acid for GIHA. Purification by C-18 RPHPLC gave the ethyl ester of the title compound (0.5 gm). NMR and MS were consistent with the proposed structure.

Step C

The product prepared in Step B (0.35 gm), was dissolved in dioxane-water (1:1, 30 mL) and the pH adjusted to about 11 by addition of LiOH (NaOH may be freely substituted for LiOH). Upon complete hydrolysis to the acid (determined by analytical RPHPLC) the reaction mixture was acidified to about pH 2–3 by addition of TFA and the desired compound was isolated by preparative scale C-18 RPHPLC. NMR and MS were consistent with the structure of the title compound.

EXAMPLE 233

Preparation of (±)β-[[2-[[[3-[(aminoiminomethyl)amino]phenyl]carbonyl]amino]acetyl]amino]-3-bromo-5-chloro-2-hydroxybezenepropanoic acid, trifluoroacetate salt, monohydrate

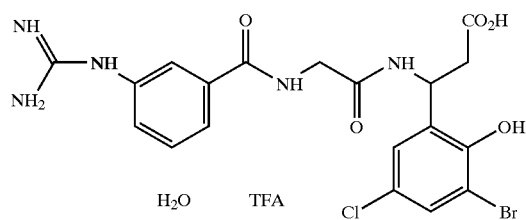

Step A

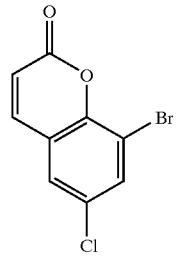

A solution of 3-bromo-5-chlorosalicylaldehyde (11.0 gm, 0.047 mole and triethylamine (5.6 mL) dissolved in acetic anhydride (14.0 mL) was heated to reflux for 4 hours. The reaction was allowed to cool to room temperature and volatiles were removed under vacuum. The resulting solid was partitioned between EtOAc and aqueous sodium bicarbonate and the layers separated. The aqueous layer was re-extracted with EtOAc and the organic layers combined, dried ($Na_2SO_4$) and volatiles removed under vacuum to obtain a solid (13.5 gm). NMR and MS were consistent with the proposed structure.

Step B

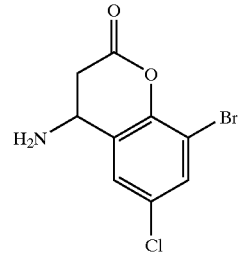

The product obtained in Step A (10.0 gm, 0.039 mole) was converted to (RS)-4-amino-6-chloro-8-bromohydrocoumarin hydrochloride (5.1 g, 18.5 mmole) according to J. Rico, Tett. Let., 1994, 3, 6599–6602 with the following modification: the addition product obtained by the addition of lithium bis-trimethylsilylamide to the coumarin of Step A was quenched by addition of one equivalent HOAc at 0° C. prior to workup.

Step C

The product of Step B (4.0 gm, 0.013 mole) was coupled to GHIA HCl (3.3 gm, 0.012 mole) using substantially the procedure of Example 230 but substituting the compound obtained in Step B for the compound of Example 30, Step A to give, after C-18 RPHPLC purification and hydrolysis of the appropriate fraction according to the procedure of Example 232, Step C, the desired compound (TFA salt) as a fluffy, white powder (4.8 g) after lyophilization. NMR and MS were consistent with the proposed structure.

EXAMPLE 234

Preparation of (±)5-amino-β-[[2-[[[3-[(aminoiminomethyl)amino]phenyl]carbonyl]amino]acetyl]amino]-2-hydroxybenzenepropanoic acid, bis(trifluoroacetate)salt, monohydrate

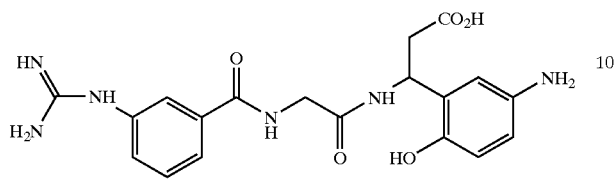

The product from Example 226 (0.5 gm) was dissolved in AcOH:H₂O (2:1, 60 mL) and 3% Pd on carbon added (0.5 gm, Aldrich). The reaction mixture was pressurized with hydrogen (20 psig) and allowed to react with vigorous stirring for 2 hours. Catalyst was removed by filtration and the mixture concentrated to a thick oil. The oil was dissolved in water and the desired compound isolated by C-18 RPHPLC. NMR and MS were consistent with the proposed structure.

EXAMPLE 235

Preparation of (±)β-[[2-[[[3-[(aminoiminomethyl)amino]phenyl]carbonyl]amino]acetyl]amino]-5-bromopyridine-3-propanoic acid, bis(trifluoroacetate)salt, monohydrate

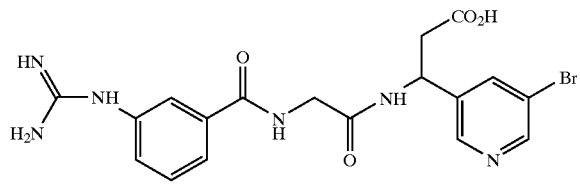

Step A

To a solution of 5-bromonicotinic acid (20.0 gm, 0.10 mole), O,N-dimethylhydroxylamine (9.8 gm, 0.1 mole) and 1-ethyl-3-(3-dimethylaminopropyl)carbodiimide hydrochloride salt in DMF (200 mL) was added 1-hydroxytriazole (200 mL of 0.5 M solution in DMF, 0.10 mole) and triethylamine (19.7 mL, 0.14 mole) and the reaction mixture stirred vigorously for 18 hours. Volatiles were removed under vacuum at 60° C. until a mush remained. The reaction mixture was partitioned between ethyl acetate (300 mL) and, saturated aqueous sodium bicarbonate, the layers separated and the aqueous layer re-extracted with EtOAc. The organic layers were combined dried (Na₂SO₄) and concentrated to a dark yellow oil (21.4 gm). NMR and MS were consistent with the proposed structure.

Step B

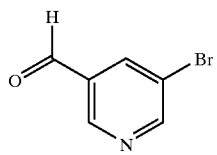

A solution of the product of Step A (12.9 gm, 0.053 mole) in THF (300 mL) was cooled to 0° C. and LAH in THF (53 mL of 1.0 M stock solution, Aldrich) was added via syringe. After 0.5 hour KHSO₄ (19.6 gm, 0.13 mole, in 100 mL water) was added. After several minutes dilute aqueous HCl (50 mL) was added and the organic layer separated, dried (Na₂SO₄) and volatiles removed to obtain a yellow oil that solidifies on standing. The solid was purified by sublimation to give the title compound as a white solid (7.8 gm). NMR and MS were consistent with the proposed structure.

Step C

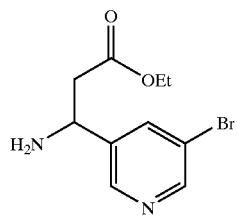

The above beta amino acid ester hydrochloride salt was prepared according to substantially the methodology of Example 1, Steps A and B substituting the compound of Step B (6.24 gm, 0.034 mole) for 3-pyridine carboxaldehyde in Step A and keeping the proportions constant. The product was isolated as the di-TFA salt by C-18 RPHPLC. NMR and MS were consistent with the proposed structure.

Step D

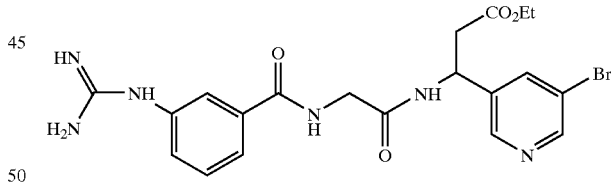

The product of Step C was coupled to GIHA HCl (0.5 gm, 1.8 mmole) using substantially the procedure of Example 230, Step B and substituting the product of Step C above (and correspondingly two equivalents of NMM) for the product of Example 230, Step A. The ethyl ester of the product was isolated as the di-TFA salt by C-18 RPHPLC. NMR and MS were consistent with the proposed structure.

Step E

Hydrolysis of the product of Step D (200 mg) to the corresponding acid was accomplished using substantially the procedure of Example 232, Step C. The product was isolated as the di-TFA salt by C-18 RPHPLC and lyophilized to give the title compound as a white solid (150 mg). NMR and MS were consistent with the proposed structure.

EXAMPLE 236

Preparation of (±)3-bromo-5-chloro-2-hydroxy-β-[[2-[[[3-[(1,4,5,6-tetrahydropyrimidin-2-yl)amino]phenyl]carbonyl]amino]acetyl]amino]benzenepropanoic acid, trifluoroacetate salt, monohydrate

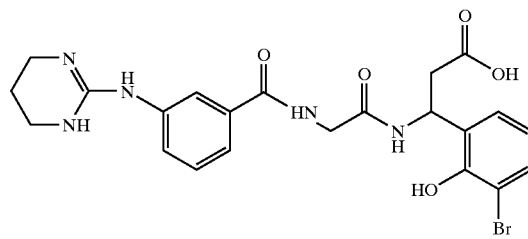

Step A

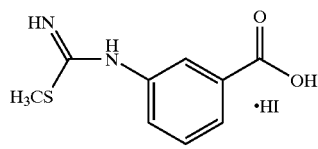

To a solution of 1-(3-carboxyphenyl)-2-thiourea (14.0 gm, 71.3 mmole) in EtOH (absolute, 140 mL) was added iodomethane (10.2 gm) and the solution refluxed for 2.5 hours. Volatiles were removed under vacuum at 60° C. to obtain a yellow oil. This was treated with t-butylmethylether and volatiles removed to give a yellow foam that became firm upon cooling. NMR and MS were consistent with the proposed structure.

Step B

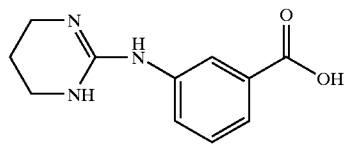

To the product from Step A (5.0 gm, 0.015 mole) dissolved in DMA (50 mL) was added a catalytic amount of DMAP and 1,3-diaminopropane (1.2 gm, 0.016 mole) and the solution heated to 100° C. for 48 hours. Volatiles were removed until a thick oil remained. This was treated sequentially with EtOAc, Et$_2$O and MeOH (50 mL) to obtain a solid that was isolated by filtration. This product was suspended in 4 N HCl in dioxane and stirred for several hours. The resulting solid was filtered, washed with Et$_2$O and dried (800 mg). NMR and MS were consistent with the proposed structure as the HCl salt.

Step C

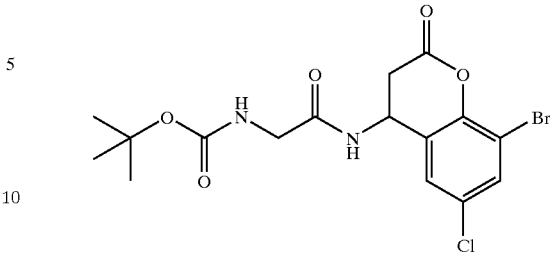

To a solution of (RS)-4-amino-6-chloro-8-bromohydrocoumarin hydrochloride (2.6 g) prepared in Example 233, Step B, dissolved in THF (50 mL) was added triethylamine (1.0 mL) and N-t-Boc-glycine-N-hydroxysuccinimide ester (2.0 gm, Sigma) and the reaction allowed to proceed to completion. Volatiles were removed and the residue partitioned between EtOAc and water. The organic layer was separated, washed with dilute aqueous HCl, saturated sodium bicarbonate and dried (Na$_2$SO$_4$) and concentrated to a dark foam (3.2 gm). This product was used in the next step without further purification.

Step D

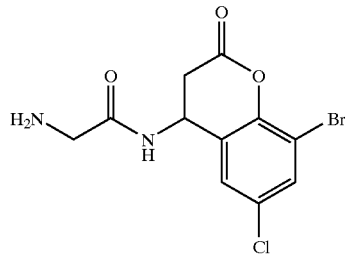

The BOC protecting group was removed by dissolving the reaction mixture obtained in Step C in dioxane (20 mL) and to the well stirred solution HCl (4 N in dioxane, Aldrich) was added. Upon cessation of gas evolution (about 0.5 hour) volatiles were removed to obtain a dark residue that was triturated with diethylether to obtain, upon filtration, a yellow solid (2.46 gm). NMR and MS were consistent with the proposed structure as the hydrochloride salt.

Step E

The product from Step D (1.4 gm) and the product from Step B (1.0 gm) were coupled using substantially the procedure of Example 230, Step B. Upon completion of the coupling reaction volatiles were removed from the crude reaction mixture. The reaction mixture was subsequently redissolved in dioxane:water and the pH adjusted to approximately 11 by addition of aqueous NaOH. The pH was maintained above 10 until complete hydrolysis was observed by analytical RPHPLC. At this point the pH was adjusted to 2–3 by addition of TFA and the desired product isolated by preparative C-13 RPHPLC (0.35 gm after lyophilization). NMR and MS were consistent with the proposed structure as the TFA salt.

EXAMPLE 237

Preparation of (±)3,5-dichloro-2-hydroxy-β-[[2-[[[3-[(1,4,5,6-tetrahydropyrimidin-2-yl)amino]phenyl]carbonyl]amino]acetyl]amino]benzenepropanoic acid, trifluoroacetate salt, monohydrate

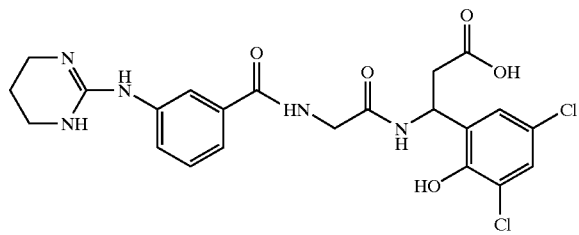

The above compound (350 mg) was prepared using essentially the conditions and procedures of Example 236 but substituting (RS)-4-amino-6,8-dichloro-hydrocoumarin hydrochloride prepared from the corresponding salicylaldehyde according to the procedure in Example 233, Steps A and B, for (RS)-4-amino-6-bromo-8-chlorohydrocoumarin hydrochloride in Step E. NMR and MS were consistent with the proposed structure as the TFA salt.

EXAMPLE 238

Preparation of (±)3,5-dichloro-β-[[2-[[[3-[(4,5-dihydro-1H-pyrrolidin-2-yl)amino]phenyl]carbonyl]amino]acetyl]amino]-2-hydroxybenzenepropanoic acid, trifluoroacetate salt, monohydrate

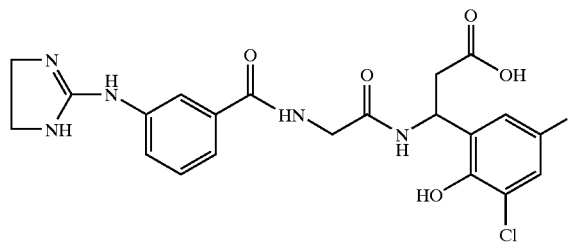

Step A

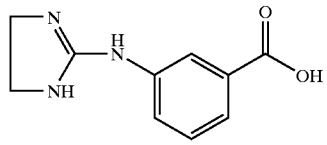

The above compound was prepared according to the procedure of Example 236, Steps a and B by substituting ethylene diamine (1,2-diaminoethane) for 1,3-diaminopropane in Step B.

Step B

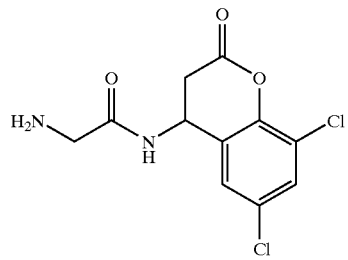

The desired end product (300 mg) was prepared by coupling the product of Step A with the hydrochloride salt of the above compound (prepared in Example 237) according to the coupling procedure of Example 237. NMR and MS were consistent with the proposed structure as the TFA salt.

EXAMPLE 239

Preparation of (±)3-bromo-5-chloro-β-[[2-[[[3-[(4,5-dihydro-1H-pyrrolidin-2-yl)amino]phenyl]carbonyl]amino]acetyl]amino]-2-hydroxybenzenepropanoic acid, trifluoroacetate salt, monohydrate

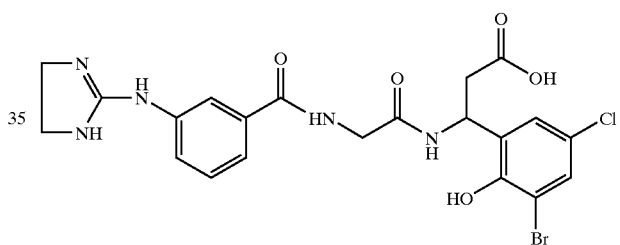

The above compound was prepared according to the procedure of Example 238 by substituting the product of Example 238, Step A for the product of Example 237, Step B. NMR and MS were consistent with the proposed structure as the TFA salt.

EXAMPLE 240

Preparation of 3,5-dichloro-β-[[2-[[[3-[[[(ethoxycarbonyl)amino]thioxomethyl]amino]phenyl]carbonyl]amino]acetyl]amino]benzenepropanoic acid

Step A

3-Amino-3-(3,5-dichlorophenyl)propionic acid, tert-butyl ester

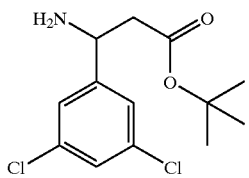

A mixture of 13.5 g of 1-bromo-3,5-dichlorobenzene (Aldrich, 13.5 g), tert-butyl acrylate (Aldrich, 11.1 mL), triethylamine (8.4 mL), Pd(OAc)$_2$ (0.12 g), tris-p-tolylphosphine (0.9 g) and acetonitrile (20 mL) was prepared in a steel bomb under nitrogen. The vessel was sealed and heated to 120° C. for 16 hours. Chloroform (40 mL) was added to the cooled reaction mixture and the mixture was extracted with ether and water. The organic phase was washed with water, dried over MgSO$_4$ and concentrated in vacuo. The residue was rapidly filtered through silica gel using 8% ethyl acetate in hexane as eluant, to provide 13 g of a thick liquid. A mixture of this product (12.6 g) tert-butanol (35 mL) and ammonia (40 mL) in a steel bomb was heated to 80° C. for 25 hours (pressure, at room temperature was 130 psi; at 80° C., 500 psi). After cooling and venting, the contents were concentrated in vacuo. The residue was extracted with ethyl acetate (100 mL) and cold, dilute hydrochloric acid (1N, 100 mL) added. The aqueous phase was basified with solid K$_2$CO$_3$ and extracted with ether and methylene chloride. The organic phase was dried over K$_2$CO$_3$ and concentrated in vacuo to give the above compound (11 g) as a thick, reddish brown liquid.

Step B

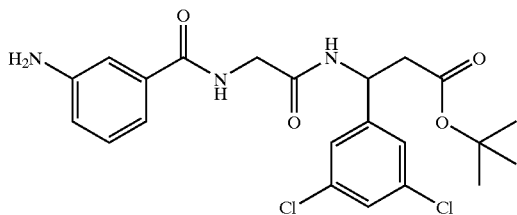

To a stirred solution of 3-nitrobenzoyl chloride (7 g, Aldrich) in CH$_2$Cl$_2$ at −78° C. was added glycine methyl ester hydrochloride (5 g, Aldrich) followed by triethylamine (20 mL). The mixture was allowed to warm to room temperature over 16 hours. The volatiles were removed and the residue was extracted with ethyl acetate and water. The organic phase was washed with water, dried over MgSO$_4$ and concentrated in vacuo. The residue was stirred in tetrahydrofuran (50 mL) and aqueous lithium hydroxide (50 mL, 1M) for 15 minutes. The volatiles were removed and the residue was treated with hydrochloric acid (50 mL, 3M) and extracted with ethyl acetate and water. The organic phase was washed with water, dried over MgSO$_4$ and concentrated in vacuo. To a stirred solution of the residue (2.24 g) in tetrahydrofuran (15 mL) at −78° C. was added in succession 4-methylmorpholine (1.1 mL, Aldrich) and isobutyl chloroformate (1.3 mL, Aldrich). After 30 minutes, 3-amino-3-(3,5-dichlorophenyl)propionic acid, tert-butyl ester (2.91 g, prepared in Step A) was added. The mixture was allowed to warm to room temperature over 2 hours. The volatiles were removed and the residue was extracted with ethyl acetate and water. The organic phase was washed with water, dried over MgSO$_4$ and concentrated in vacuo. A solution of the residue in tetrahydrofuran and ethanol (1:1, 30 mL) was shaken in a Parr hydrogenator with 3% Pd/C (0.5 g) under 5 psi hydrogen pressure for 5 hours. The mixture was filtered and the filtrate concentrated to provide the above compound as a thick gum. This sample was used without further purification.

Step C

A mixture of the compound of Step B (1.2 g) and ethoxycarbonyl isothiocyanate (Aldrich, 0.3 μL) in toluene (5 mL) was heated to reflux for 30 minutes. The mixture was concentrated and the residue chromatographed over silica gel to give the t-butyl ester of the title compound (0.78 g) as a white solid. A solution of the t-butyl ester (0.3 g) in trifluoroacetic acid (4 mL) was allowed to stand at 23° C. for 16 hours. The volatiles were removed and the residue purified by HPLC to give the title compound as a white solid.

C$_{22}$H$_{22}$N$_4$O$_6$S. 0.5H$_2$O; Calculated: C, 48.01; H, 4.21; N, 10.18; S, 5.83; Found: C, 47.61; H, 4.11; N, 9.94; S, 5.83.

EXAMPLE 241

Preparation of 3,5-dichloro-β-[[2-[[[3-[[[(ethoxycarbonyl)amino]iminomethyl]amino]phenyl]carbonyl]amino]acetyl]amino]benzenepropanoic acid, trifluoroacetate salt, monohydrate

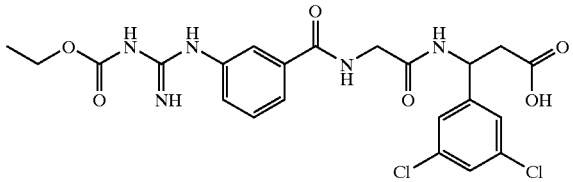

Step A

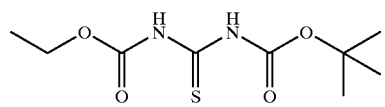

A mixture of tert-butyl carbamate (Lancaster, 5 g) and ethoxycarbonyl isothiocyanate (Aldrich, 5 mL) in toluene (15 mL) was heated to reflux for 2 hours. The solution was allowed to cool to room temperature over 16 hours. The precipitated solid was filtered and washed with hexane to give the above compound (5.5 g) as a white solid.

Step B

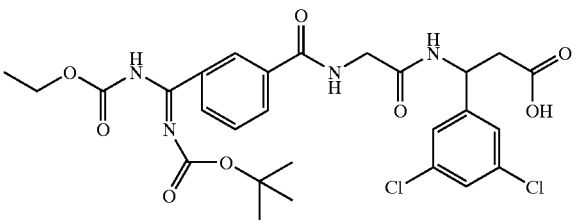

To a stirred solution of the compound produced in Example 240, Step B (1.3 g) and the product of Step A (0.7 g) in DMF (7 ml) at −15° C. was added, in succession, mercuric chloride (0.77 g) and triethylamine (0.8 mL). The mixture was allowed to warm to room temperature over 1 hour and continued stirring for 1 hour more. The mixture was diluted with ethyl acetate and filtered through celite. The filtrate was washed with water, dried over MgSO$_4$ and concentrated in vacuo. The residue was purified by chromatography to give the above compound as a white solid.

Step C

A solution of the product of Step B (0.5 g) in trifluoroacetic acid (10 mL) was allowed to stand at 23° C. for 2 hours. The volatiles were removed and the residue purified by HPLC to give the title compound as a white solid.

$C_{22}H_{23}N_5O_6Cl_2 \cdot 1.25\ CF_3COOH \cdot 0.5\ H_2O$; Calculated: C, 42.96; H, 3.86; N, 10.23; Cl, 10.35; Found: C, 43.21; H, 3.49; N, 10.20; Cl, 10.52.

EXAMPLE 242

Preparation of β-[[2-[[[3-[(aminoiminomethyl)amino]phenyl]carbonyl]amino]acetyl]amino][1,1'-biphenyl]-3-propanoic acid

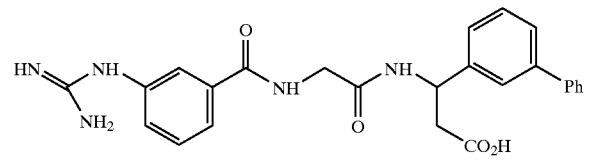

Step A

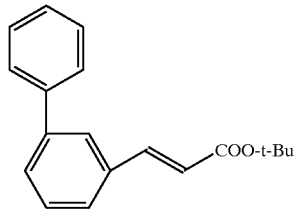

A mixture of 9.64 g (41.4 mmoles) of 3-bromobiphenyl, 5.8 ml (4.2 g, 41 mmoles) of triethylamine, 6.73 g (52.6 mmoles) of t-butyl acrylate, 624 mg (2.05 mmoles) of tri-p-tolylphosphine, and 83 mg of palladium acetate in 15 ml of dimethylformamide was stirred overnight at 110° in an oil bath. After cooling, the mixture was partitioned between ethyl acetate and water and the aqueous layer further extracted with ethyl acetate. The combined organic extracts were washed with brine, dried over sodium sulfate, filtered and concentrated. Chromatography of the residue over silica gel using mixtures of dichloromethane and hexane as eluents gave the above compound, 10.5 g, as a very pale yellow oil.

$^1$H NMR (CDCl$_3$) 7.77–7.36 (m, 9H), 7.69 (d, J=15 Hz, 1H), 6.47 (d, J=15 Hz, 1H), 1.58 (s, 9H).

Step B

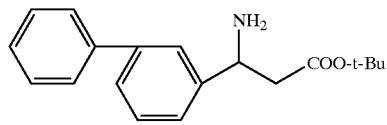

A mixture of 10.5 g (37.5 mmoles) of the product of Step A, 50 ml of liquid ammonia, 5.2 g of acetic acid, and 80 ml of t-butanol was heated at 100° C. for 18 hours. After cooling, the mixture was concentrated and partitioned between ethyl acetate and aqueous sodium bicarbonate. The aqueous layer was further extracted with ethyl acetate, the combined organic extracts washed with brine, dried over sodium sulfate, filtered, and evaporated. Chromatography of the residue over silica-gel using ethyl acetate and then 10% methanol—1% ammonium hydroxide-89% ethyl acetate as eluents gave the above compound, 4.75 g, as a colorless oil.

Analysis Calcd. for $C_{19}H_{23}NO_2 \cdot 1/8H_2O$ (MW 299.65): C, 76.16; H, 7.74; N, 4.67. Found: C, 76.29; H, 7.57; N, 4.66.

Step C 1,1-dimethylethyl β-[[2-[[[3-[(aminoiminomethyl)amino]phenyl]carbonyl]amino]acetyl]amino][1,1'-biphenyl]-3-propanoate

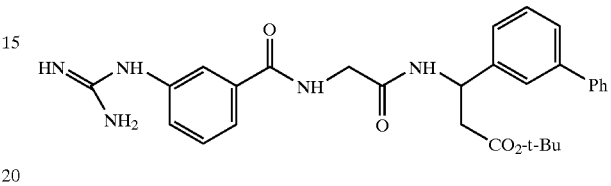

To a solution of 1.00 g (3.66 mmol) of the compound of Example M in 20 ml of dry dimethylformamide stirred in an ice bath under an argon atmosphere was added 467 μl (3.84 mmol) of N-methylpiperidine, producing a white solid. After stirring for 15 minutes, 500 μl (3.84 mmoles) of isobutyl chloroformate was added dropwise and stirred continuously for about 20 minutes, resulting in a homogeneous solution. A solution of 1.09 g (3.66 mmoles) of the product of Step B in 5 ml of dimethylformamide was added and the mixture stirred overnight at room temperature. The mixture was concentrated to give 2.88 g of an orange oil. Reverse phase preparative HPLC of 1.50 g of the crude mixture using a gradient of 90% to 50% aqueous trifluoroacetic acid—acetonitrile followed by evaporation of appropriate fractions gave the above compound, 800 mg, as a white solid.

$^1$H NMR (CDCl$_3$-DMSO) 8.93 (br s, 1H), 8.56 (t, 1H), 8.22 (d, 1H), 7.81–7.12 (m, 13H), 5.46 (dd, 1H), 4.12 (t, 2H), 2.88 (dd, 1H), 2.77 (dd, 1H), 1.31 (s, 9H).

Step D

A solution of 800 mg of the product of Step C in 10 ml of dichloromethane was added 10 ml of trifluoroacetic acid, and the mixture stirred overnight at room temperature. After concentration, reverse phase preparative HPLC using mixtures of aqueous trifluoroacetic acid-acetonitrile as eluent gave, after evaporation of appropriate fractions, the above compound (250 mg) as a pure white solid.

Analysis for $C_{25}H_{26}N_5O_4$ CFCOOH 1/2H$_2$O (MW 581.53): Calc'd.: C, 55.77; H, 4.33; N, 12.04. Found: C, 55.81; H, 4.57; N, 11.68.

EXAMPLE 243

Preparation of β-[[2-[[[3-[(aminoiminomethyl)amino]phenyl]carbonyl]amino]acetyl]amino][pyrimidine-5-propanoic acid, trifluoroacetate salt

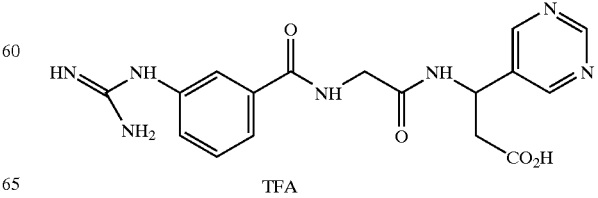

TFA

Step A

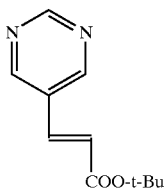

A mixture of 5.00 g (31.1 mmoles) of 5-bromopyrimidine, 3.14 g (31.1 mmoles) of triethylamine, 5.06 g (39.5 mmoles) of t-butyl acrylate, 475 mg of tri-o-tolylphosphine, and 63 mg of palladium acetate in 11 ml of acetonitrile was stirred at reflux under argon for 8 hours. After cooling, the mixture was partitioned between ethyl acetate and water. The aqueous layer was further extracted with ethyl acetate, the combined organic extracts washed with brine, dried over sodium sulfate, filtered, and evaporated. Chromatography of the residue over silica gel using a gradient of 30–50% ethyl acetate-hexane gave the above compound, 0.99 g, as a white crystalline solid.
$^1$H NMR (CDCl$_3$) 9.19 (s, 1H), 8.86 (s, 2H), 7.53 (d, J=15 Hz, 1H), 6.54 (d, J=15 Hz, 1H), 1.55 (s, 9H).

Step B

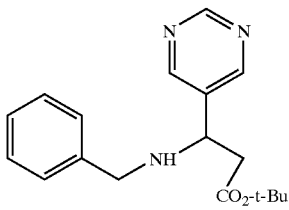

A solution of 1.28 g (6.21 mmoles) of the product of Step A in 12 ml of benzylamine was stirred in a 70–80° oil bath overnight. After cooling, the excess benzylamine was evaporated. Chromatography of the residue over silica gel using 50% ethyl acetate-hexane as eluent gave the above compound, 1.33 g, as a colorless oil.
$^1$H NMR (CDCl$_3$) 9.18 (s, 1H), 8.78 (s, 2H), 7.21 (m, 5H), 4.14 (t, 1H), 3.68 (d, 1H), 3.59 (d, 1H), 2.73 (dd, 1H), 2.57 (dd, 1H), 1.41 (s, 9H).

Step C

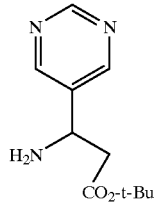

To a solution of 1.33 g (4.25 mmoles) of the product of Step B in 50 ml of 4:1 ethanol-cyclohexene was added 10% palladium on carbon. The mixture was stirred at reflux overnight under argon, 35 mg of pyridinium p-toluenesulfonate was added, and refluxing continued for another 8 hours. After cooling, the mixture was filtered through a filtering aid, and the filtrate concentrated. The residue was filtered through silica gel using 10% methanol-ethyl acetate as eluent to give the above compound (852 mg) as a waxy solid.
$^1$H NMR (CDCl$_3$) 9.26 (s, 1H), 8.78 (s, 2H), 4.46 (dd, 1H), 2.64 (t, 2H), 1.81 (br s, 1H), 1.43 (s, 9H).

Step D

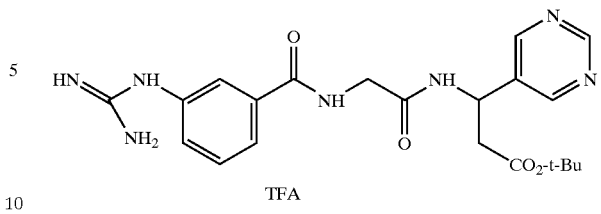

TFA

To a solution of 1.04 g (3.82 mmoles) of m-guanidinohippuric acid in 8 ml of dry dimethylformamide stirring in an ice bath under argon was added dropwise 398 mg (4.01 mmoles) of N-methylpiperidine, producing a white solid. The mixture was stirred for 10 minutes, and then 1.03 g (4.01 mmoles) of disuccinimidyl carbonate was added as a solid. After stirring for 1.5 hours, a clear, homogeneous solution was obtained, to which was added a solution of 852 mg (3.82 mmoles) of the product of Step C. After stirring overnight at room temperature, the mixture was evaporated to dryness. Reverse phase HPLC of the mixture using mixtures of aqueous trifluoroacetic acid-acetonitrile followed by evaporation of the appropriate fractions gave the above compound (230 mg) as a white solid.
$^1$H NMR (CDCl$_3$-DMSO) 10.58 (s, 1H), 9.09 (s, 1H), 8.76 (s, 2H), 8.57 (t, 1H), 8.49 (d, 1H), 7.79–7.11 (m, 4H), 5.36 (dd, 1H), 4.07 (t, 2H), 2.90 (dd, 1H), 2.79 (dd, 1H), 1.35 (s, 9H).

Step E 230 mg of the product of Step D was dissolved in 20 ml of 1:1 dichloromethane-trifluoroacetic acid, and the resulting mixture was stirred overnight at room temperature. After evaporation, reverse phase HPLC of the mixture using mixtures of aqueous trifluoroacetic acid-acetonitrile followed by evaporation of the appropriate fractions gave the above compound (183 mg) as a white solid.
Analysis for C$_{17}$N$_{19}$N$_7$O$_4$ CFCOOH 1/2H$_2$O (MW 508.41): Calc'd.: C, 44.89; H, 3.97. Found: C, 44.75; H, 4.16.

EXAMPLE 244

Preparation of β-[[2-[[[3-[(aminoiminomethyl)amino]phenyl]carbonyl]amino]acetyl]amino]-3-methylthiophene-2-propanoic acid, trifluoroacetate salt

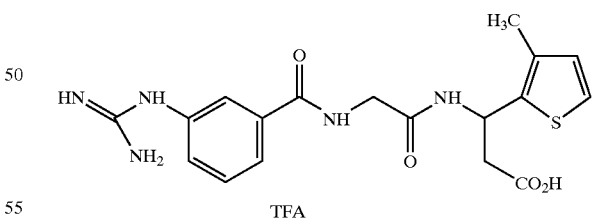

TFA

Step A

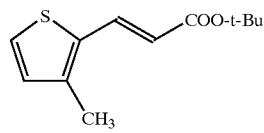

A mixture of 10.0 g (56.5 mmoles) of 2-bromo-3-methylthiophene, 10.5 ml (9.18 g, 71.8 mmoles) of t-butyl acrylate, 15.7 ml (11.4 g, 113 mmoles) of triethylamine, 857 mg of tri-o-tolylphosphine, and 113 mg of palladium acetate in 20 ml of acetonitrile was stirred at reflux under argon for 8 hours. After cooling, the mixture was partitioned between ethyl acetate and water, the aqueous layer was further extracted with ethyl acetate, the combined organic extracts dried over sodium sulfate, filtered, and evaporated to give the above compound (12.7 g) as a dark red oil.

¹H NMR (CDCl₃) 7.78 (d, J=15 Hz, 1H), 7.24 (d, J=6 Hz, 1H), 6.87 (d, J=6 Hz, 1H), 6.13 (d, J=15 Hz, 1H), 2.36 (s, 3H), 1.56 (s, 9H).

Step B

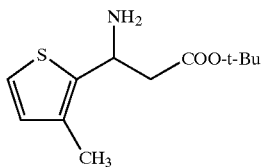

8.00 g (35.7 mmoles) of the product of Step A was reacted with ammonia by the method of Example 242, Step B. Chromatography of the crude product over silica gel using 50% ethyl acetate-hexane as eluent gave the above compound (1.78 g) as a reddish oil that crystallized on standing.

¹H NMR (CDCl₃) 7.11 (d, 1H), 6.78 (d, 1H), 4.72 (m, 1H), 2.58 (m, 2H), 2.23 (br s, 2H), 2.21 (s, 3H), 1.44 (s, 9H).

Step C 1,1-dimethylethyl β-[[2-[[[3-[(aminoiminomethyl)amino]phenyl]carbonyl]amino]acetyl]amino]-3-methylthiophene-2-propanoate

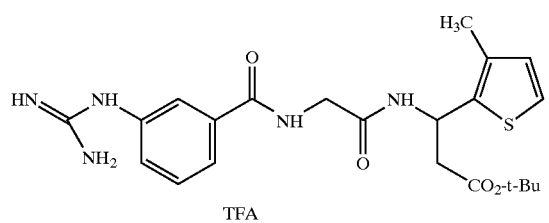

To a solution of 1.13 g (4.15 mmoles) of m-guanidinohippuric acid in 20 ml of dry dimethylformamide stirring in an ice bath under argon was added dropwise 530 μl (432 mg, 4.36 mmoles) of N-methylpiperidine, producing a white solid. To this mixture was added 1.12 g (4.36 mmoles) of disuccinimidyl carbonate as a solid, and the resulting mixture stirred for 30 minutes, producing a clear solution. A solution of 1.00 g (4.15 mmoles) of the product of Step B in 8 ml of dimethylformamide was added, the mixture stirred overnight at room temperature. Evaporation of the volatiles gave 3.8 g of residue. Reverse phase HPLC of 1.5 g of the mixture using mixtures of aqueous trifluoroacetic acid-acetonitrile followed by evaporation of the appropriate fractions gave the above compound (171 mg) as an off white solid which was identified by conversion to the acid as described in Step D.

Step D

A solution of 167 mg of the product of Step C in 15 ml of 1:1 dichloromethane-trifluoroacetic acid was stirred overnight at room temperature. Reverse phase HPLC of the residue using mixtures of aqueous trifluoroacetic acid-acetonitrile followed by evaporation of the appropriate fractions gave the above compound (103 mg) as a white solid.

Analysis for $C_{18}N_{21}N_5O_4S \cdot CF_3COOH$ (MW 517.48): Calc'd.: C, 46.42; H, 4.29; N, 13.53. Found: C, 46.88; H, 4.52; N, 13.24.

EXAMPLE 245

Preparation of (±)β-[[2-[[[3-[(aminoiminomethyl)amino]phenyl]carbonyl]amino]acetyl]amino]-3-(methylthio)benzenepropanoic acid, trifluoroacetate salt

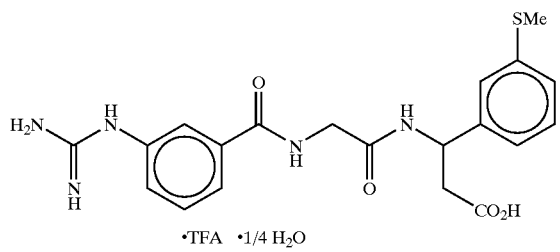

·TFA ·1/4 H₂O

Step A 1,1-dimethylethyl 3-[3-(methylthio)phenyl]-2E-propenoate

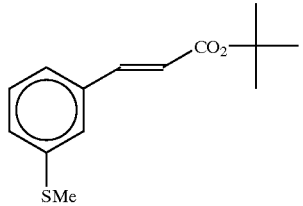

A solution of palladium acetate (110 mg, 0.00049 mole), 3-bromothioanisole (10 g, 0.05 mole), t-butylacrylate (7.7 g, 0.06 mole), tri-para-tolylphosphine (0.76 g, 0.0025 mole) and triethylamine (5.1 g, 0.05 mole) in 20 ml DMF was heated to 120° C. for 20 hours. The solid was removed by filtration and washed with CH₂Cl₂. The filtrate was concentrated to an oily solid. Ethyl acetate was added and the solid was removed by filtration. The filtrate was concentrated to an oil. The product was purified by silica gel chromatography. The structure was supported by NMR.

Analysis Calc'd for $C_{14}H_{18}O_2S$; (250.36): Calculated: C, 67.16; H, 7.25. Found: C, 67.33; H, 7.24.

Step B (±)1,1-dimethylethyl β-amino-3-(3-(methylthio)phenyl]propanoate, monohydrochloride

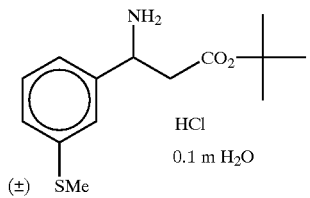

The product from Step A (10 g, 0.04 mole) was treated with t-BuOH saturated with ammonia and 1 ml acetic acid at 110° C. and 900 psi in a Parr shaker for 78 hours. The mixture was filtered and concentrated to a dark oil. The product was purified by silica gel chromatography. A solution of the free base in 100 ml EtOAc was treated with 7N HCl in dioxane. The precipitate was filtered, washed with EtOAc and dried. The structure was supported by NMR.

Analysis calculated for $C_{14}H_{22}NO_2SCl \cdot 0.1 H_2O$ 303.85+ 0.1 m H₂O): Calculated: C, 55.01; H, 7.32; N, 4.58. Found: C, 54.89; H, 7.36; N, 4.41.

Step C (±)1,1-dimethylethyl β-[[2-[[[3-[(aminoiminomethyl)amino]phenyl]carbonyl]amino]acetyl]amino]-3-(methylthio)phenylpropanoate, trifluoroacetate salt

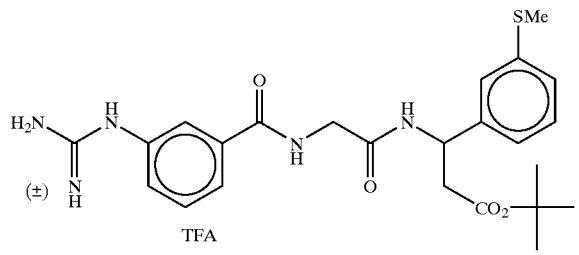

N-methylpiperidine (0.69 g, 0.007 mole) was added to the compound of Example M (0.91 g, 0.00334 mole) in 20 ml DMF at 0° C. A white solid precipitated. After 10 minutes IBCF (0.47 g, 0.00351 mole) was added. After 15 minutes (all in solution) a solution of the product from Step B (1.01 g, 0.00334 mole) in 6 ml DMF was added. The ice bath was removed and the solution was stirred at room temperature for 20 hours. The solution was concentrated to give an orange syrup. The product was purified by reverse phase HPLC. [$CH_3CN/H_2O$ (0.06% TFA)]. The structure was supported by NMR.

Analysis calculated for $C_{24}H_{31}N_5O_4S \cdot TFA \cdot 1/2\ H_2O$ (608.64): Calculated: C, 51.31; H, 5.47; N, 11.51; Found: C, 51.46; H, 5.67; N, 11.51.

Step D

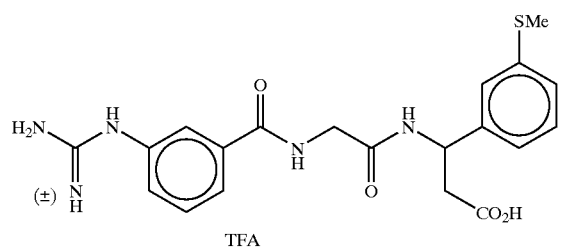

The product from Step C (0.50 g) in 10 ml $CH_2Cl_2$/TFA (1:1) was stirred for 24 hours at room temperature. After concentrating to a light yellow oil the product was purified by reverse phase HPLC ($CH_3CN/H_2O.0.06\%$ TFA). The structure was supported by NMR.

Analysis calculated for $C_{20}H_{23}N_5O_4S \cdot TFA \cdot 1/4\ H_2O$ (548.03): Calculated: C, 48.22; H, 4.51; N, 12.78. Found: C, 48.19; H, 4.66; N, 12.80.

EXAMPLE 246

Preparation of (±)β-[[2-[[[3-[(aminoiminomethyl)amino]phenyl]carbonyl]amino]acetyl]amino]-6-methylpyridine-2-propanoic acid, bis(trifluoroacetate)salt

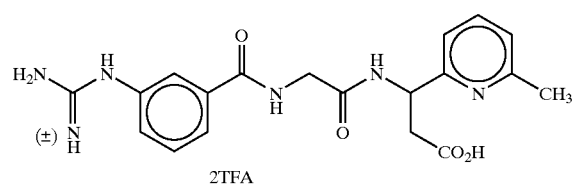

Step A 1,1-dimethylethyl 3-(6-methyl-2-pyridinyl)-2E-propanoate

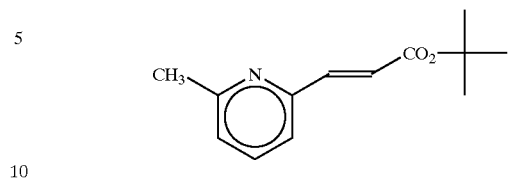

A solution of 6-methyl-2-pyridine carboxaldehyde (9.0 g, 0.074 mole) and (t-butylcarbonylmethylene)triphenylphosphorane (28.0 g, 0.074 mole) in 150 ml toluene was heated to 85–90° C. for 5 hours and stirred at room temperature for 20 hours. The white solid was removed by filtration and the filtrate was concentrated. Addition of 1:1 toluene/hexane (100 ml) precipitated more white solid which was removed by filtration. The filtrate was concentrated to an oil. The product was purified by silica gel chromatography. The structure was supported by NMR.

Analysis calc'd. for $C_{13}H_{17}NO_2$ (219.29): Calculated: C, 71.21; H, 7.81; N, 6.39. Found: C, 70.84; H, 7.81; N, 6.32.

Step B (±)1,1-dimethylethyl 6-methyl-β-[[(phenyloxycarbonyl)methyl]amino]-pyridine-2-propanoate

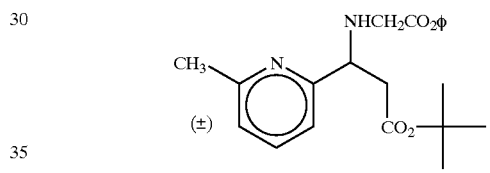

A solution of the product from Step A (5.0 g, 0.0228 mole) in benzylamine (48.9 g, 0.456 mole) was heated to 80° C. for 6 hours and then at 100° C. for 20 hours. The solution was heated at 115° C. for 3 hours and then concentrated to an oil. The product was purified by silica gel chromatography. The structure was supported by NMR.

Analysis calc'd. for $C_{20}H_{26}N_2O_2$ (326.44): Calculated: C, 73.59; H, 8.03; N, 8.58. Found: C, 73.12; H, 8.14; N, 8.41.

Step C (±)1,1-dimethylethyl β-amino-6-methylpyridine-2-propanoate

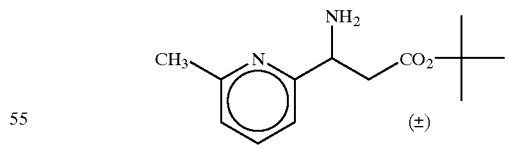

The product from Step B (5.7 g, 0.017 mole) in 3A-EtOH (100 ml) was treated with a catalytic amount of 4% Pd/C at 5 psi and room temperature for 48 hours. After filtration, the filtrate was concentrated to an oil. The product was purified by silica gel chromatography. The structure was supported by NMR.

Analysis calc'd. for $C_{13}H_{20}N_2O_2 \cdot 0.3$ m $H_2O$ (242.62): Calculated: C, 64.35; H, 8.60; N, 11.55. Found: C, 64.15; H, 8.38; N, 11.46.

Step D

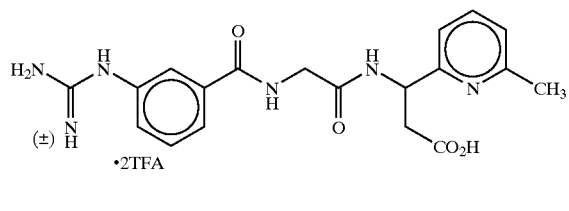

By following the reaction sequence described in Example 245, Steps C and D, and by the substitution of (±)1,1-dimethylethyl β-amino-6-methylpyridine-2-propanoate for (±)1,1-dimethylethyl β-amino-3-(methylthio)phenylpropanoate the title compound was prepared. The structure was supported by NMR.

Analysis calc'd. for $C_{23}H_{24}N_6O_8F_6$ (626.47): Calculated: C, 44.10; H, 3.86; N, 13.41. Found: C, 44.12; H, 3.70; N, 13.36.

EXAMPLE 247

Preparation of β-[[2-[[[3-[(aminoiminomethyl)amino]phenyl]carbonyl]amino]acetyl]amino]-3-(methylsulfonyl)benzenepropanoic acid, bis(trifluoroacetate)salt

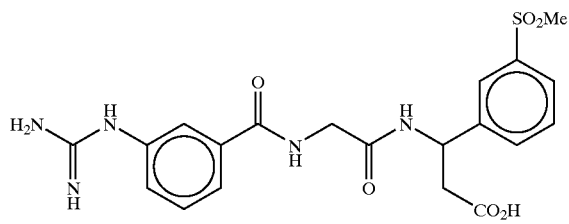

Step A

Methyl-3-bromophenylsulfone

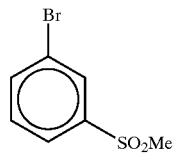

A solution of Oxone® (90.8 g, 0.15 mole) in 250 ml $H_2O$ was added to a stirring solution of 3-bromothioanisole (15 g, 0.0739 mole) in 250 mL MeOH and 200 ml acetone. The mixture was stirred at room temperature for 20 hours. The solution was concentrated to remove the MeOH and acetone. Water (400 ml) was added and the product extracted into EtOAc. The EtOAc was dried over $Na_2SO_4$, filtered and concentrated to give a solid. The structure was supported by NMR.

Step B

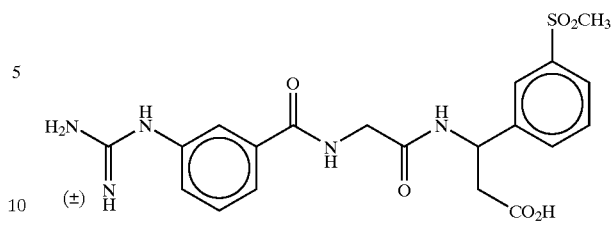

By following the reaction sequence described in Example 245, Steps A–D and by the substitution of methyl-3-bromophenyl sulfone for 3-bromothioanisole the title compound was prepared.

Analysis calc'd. for $C_{20}H_{23}N_5O_6S.2TFA$ (689.55): Calculated: C, 41.81; H, 3.65; N, 10.16; S, 4.65. Found: C, 41.91; H, 3.74; N, 10.45; S, 5.15.

EXAMPLE 249

Preparation of β-[[2-[[[3-[(aminoiminomethyl)amino]phenyl]carbonyl]amino]acetyl]amino]-3,5-diethoxybenzenepropanoic acid, trifluoroacetate salt

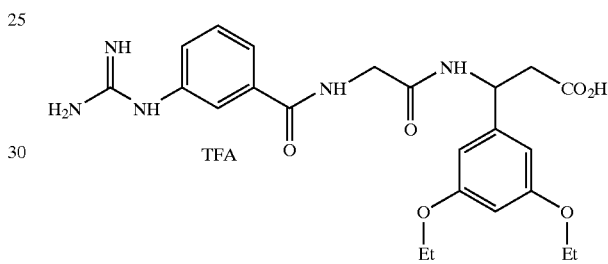

Step A

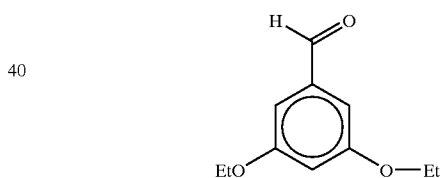

To 3,5-dihydroxybenzaldehyde (10 g) in DMF (100 mL) was added $K_2CO_3$ (20 g) and ethyliodide (20 g). The mixture was stirred for 3 days at 25° C. Water (250 mL) was added and the product extracted into ethyl acetate. The organic layer was separated, washed with water, brine and dried over $Na_2SO_4$ to give 3,5-diethoxyphenylcarboxaldehyde (12 g) as a dark oil. This material was used as is for the next step. MS and H-NMR were consistent with the proposed structure.

Step B

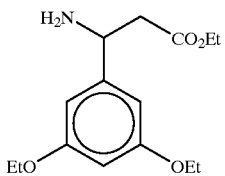

To 3,5-diethoxyphenylcarboxaldehyde (Step A) (10 g) in ethanol (70 mL) was added ammonium acetate (12.5 g) followed by ethyl hydrogen malonate (6.0 g). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid K$_2$CO$_3$. The resulting mixture was partitioned between methylene chloride (150 mL), separated and dried over Na$_2$SO$_4$. The solvent was evaporated to give DL ethyl-3-amino-3-(3,5-diethoxyphenyl)propionate as an oil. Ether (100 mL) was added, followed by HCl in dioxane (20 mL, 4N) and stirred vigorously for one hour. The HCl salt was collected by filtration (6.3 g). MS and H-NMR were consistent with the proposed structure.

Step C

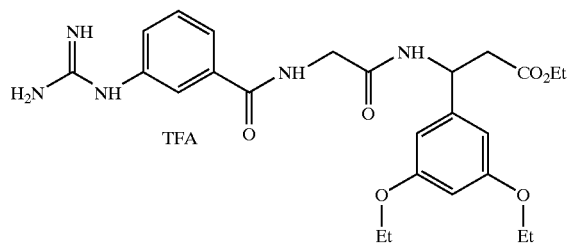

N,N'-Disuccinimidyl carbonate (DSC) (1.0 g, 0.4 mmol) was added to the compound of Example M (1.0 g, 0.4 mmol) in dry dimethylformamide (6 mL) followed by dimethylaminopyridine (100 mg). After a period of 20 minutes, DL ethyl-3-amino-3-(3,5-diethoxyphenyl)propionate hydrochloride (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step D

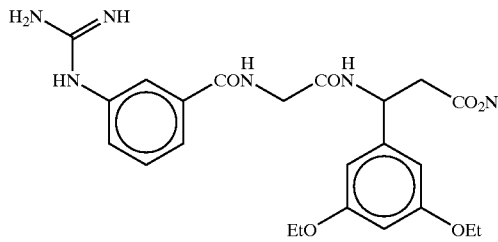

DL-ethyl 3-amino-3-(3,5-diethoxyphenyl)propionate adduct (500 mg) produced in Step C was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 250

Preparation of β-[[2-[[[3-[(aminoiminomethyl)amino]phenyl]carbonyl]amino]acetyl]amino]-4-bromothiophene-2-propanoic acid, trifluoroacetate salt

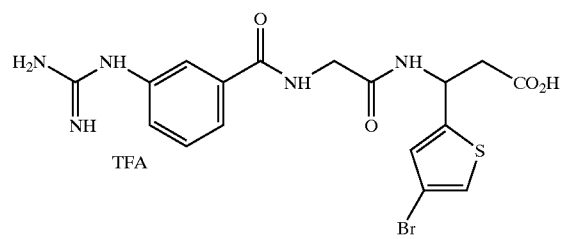

Step A

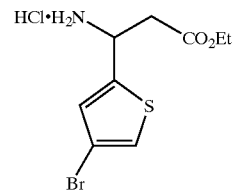

To 3-bromothiophene-5-carboxaldehyde (Aldrich) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid K$_2$CO$_3$. The resulting mixture was partitioned between methylene chloride (150 mL), separated and dried over Na$_2$SO$_4$. The solvent was evaporated to give DL ethyl-3-amino-3-(3-bromothiophene)propionate as an oil. Ether (100 mL) was added, followed by HCl in dioxane (20 mL, 4N) and stirred vigorously for one hour. The HCl salt was collected by filtration (6.3 g). MS and H-NMR were consistent with the proposed structure.

Step B

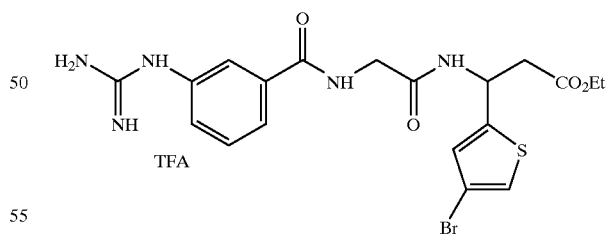

N,N'-Disuccinimidyl carbonate (DSC) (1.0 g, 0.4 mmol) was added to compound H in Scheme VII (1.0 g, 0.4 mmol) in dry dimethylformamide (6 mL) followed by dimethylaminopyridine (100 mg). After a period of 20 minutes DL ethyl-3-amino-3-(3-bromothiophene)propionate hydrochloride (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with proposed structure.

Step C

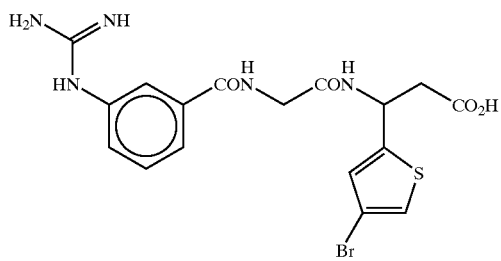

DL ethyl 3-amino-3-(3-bromothiophene)propionate adduct produced in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 251

Preparation of β-[[2-[[[3-[(aminoiminomethyl)amino]phenyl]carbonyl]amino]acetyl]amino]-5-chlorothiophene-2-propanoic acid, trifluoroacetate salt

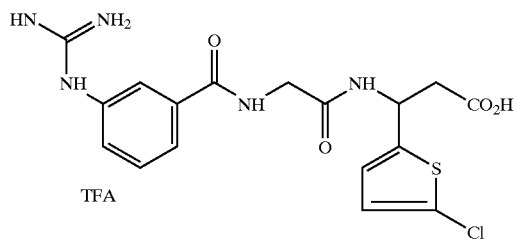

Step A

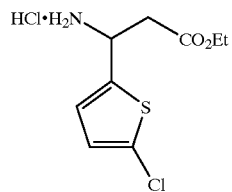

To 2-chlorothiophene-5-carboxaldehyde (Aldrich) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(2-chlorothiophene)propionate as an oil. Ether (100 mL) was added, followed by HCl in dioxane (20 mL, 4N) and stirred vigorouosly for one hour. The HCl salt was collected by filtration (6.3 g). MS and H-NMR were consistent with the proposed structure.

Step B

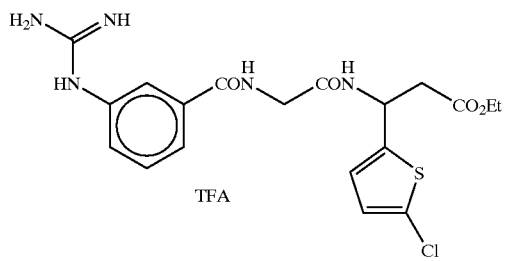

N,N'-Disuccinimidyl carbonate (DSC) (1.0 g, 0.4 mmol) was added to the compound of Example M (1.0 g, 0.4 mmol) in dry dimethylformamide (6 mL) followed by dimethylaminopyridine (100 mg). After a period of 20 minutes DL ethyl-3-amino-3-(2-chlorothiophene)propionate hydrochloride (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

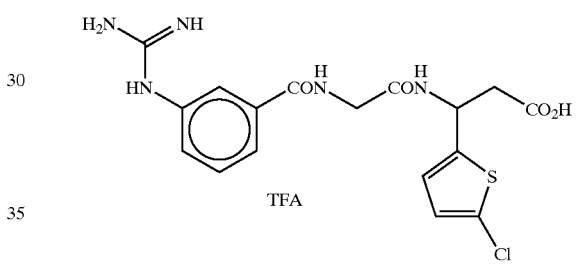

DL-ethyl 3-amino-3-(2-chlorothiophene)propionate adduct produced in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with proposed structure.

EXAMPLE 252

Preparation of β-[[2-[[[3-[(aminoiminomethyl)amino]phenyl]carbonyl]amino]acetyl]amino]-1H-pyrazole-3-propanoic acid, trifluoroacetate salt

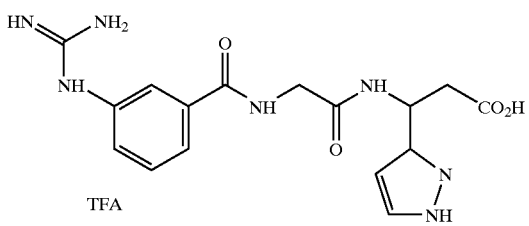

Step A

To 3-pyrazole carboxaldehyde (Maybridge) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(3-pyrazole)propionate as an oil. Ether (100 mL) was added, followed by HCl in dioxane (20 mL, 4N) and stirred vigorouosly for one hour. The HCl salt was collected by filtration (6.3 g). MS and H-NMR were consistent with the proposed structure.

Step B

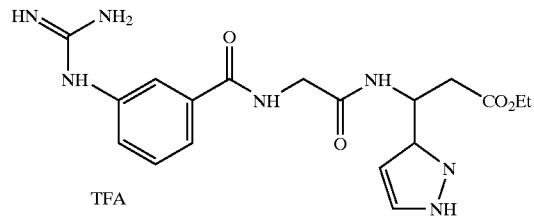

N,N'-Disuccinimidyl carbonate (DSC) (1.0 g, 0.4 mmol) was added to compound H in Scheme VII (1.0 g, 0.4 mmol) in dry dimethylformamide (6 mL) followed by dimethylaminopyridine (100 mg). After a period of 20 minutes DL ethyl-3-amino-3-(3-pyrazole)propionate hydrochloride (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

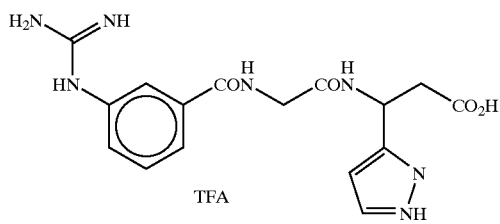

DL-ethyl 3-amino-3-(3-pyrazole)propionate adduct produced in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with proposed structure.

EXAMPLE 253

Preparation of β-[[2-[[[3-[(aminoiminomethyl)amino]phenyl]carbonyl]amino]acetyl]amino]-5-methylthiophene-2-propanoic acid, trifluoroacetate salt

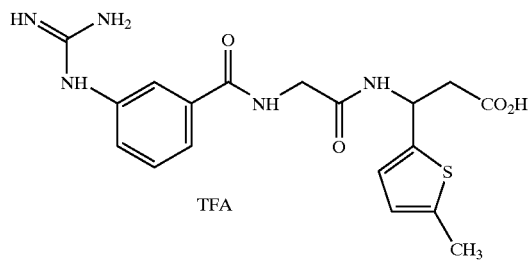

Step A

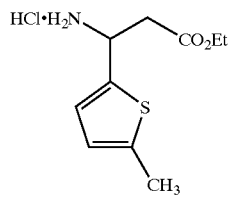

To 5-methythiophene-2-carboxaldehyde (Lancaster) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(5-methythiophene)propionate as an oil. Ether (100 mL) was added, followed by HCl in dioxane (20 mL, 4N) and stirred vigorouosly for one hour. The HCl salt was collected by filtration (6.3 g). MS and H-NMR were consistent with the proposed structure.

Step B

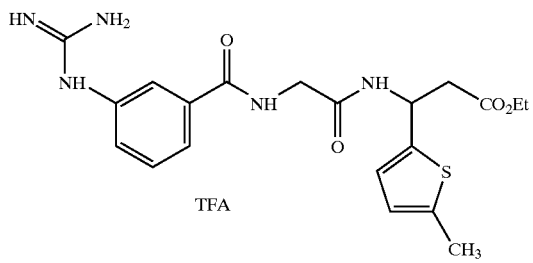

N,N'-Disuccinimidyl carbonate (DSC) (1.0 g, 0.4 mmol) was added to the compound of Example M (1.0 g, 0.4 mmol) in dry dimethylformamide (6 ml) followed by dimethylaminopyridine (100 mg). After a period of 20 minutes DL ethyl-3-amino-3-(5-methythiophene)propionate hydrochloride (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

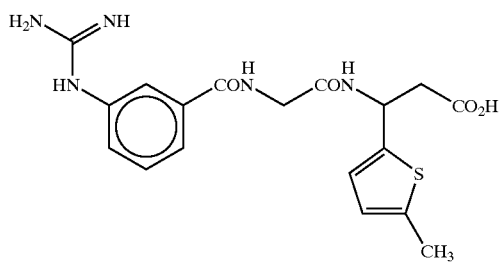

DL-ethyl 3-amino-3-(5-methythiophene)propionate adduct produced in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 254

Preparation of β-[[2-[[[3-[(aminoiminomethyl)amino]phenyl]carbonyl]amino]acetyl]amino]-2,3,5-trichlorobenzenepropanoic acid, trifluoroacetate salt

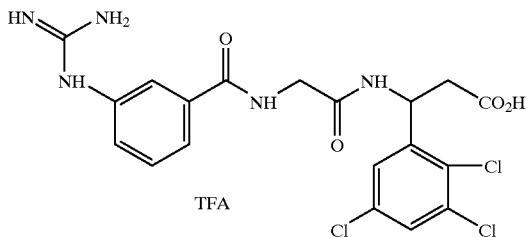

Step A

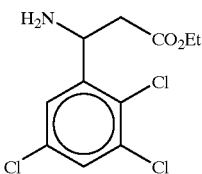

To 2,3,5-trichlorobenzaldehyde (Lancaster) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(2,3,5-trichlorophenyl)propionate as an oil (6.3 g). MS and H-NMR were consistent with the proposed structure.

Step B

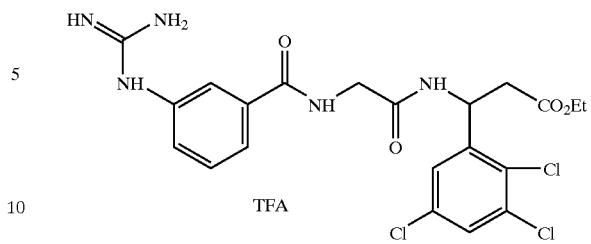

N,N'-Disuccinimidyl carbonate (DSC) (1.0 g, 0.4 mmol) was added to the compound of Example N (1.0 g, 0.4 mmol) in dry dimethylformamide (6 mL) followed by dimethylaminopyridine (100 mg). After a period of 20 minutes DL ethyl-3-amino-3-(2,3,5-trichlorophenyl)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

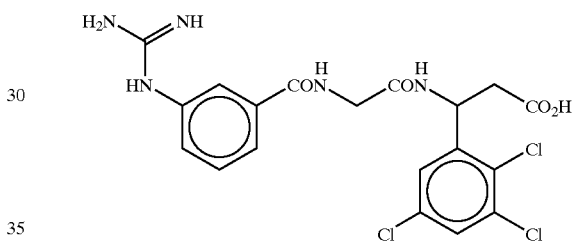

DL-ethyl 3-amino-3-(2,3,5-trichlorophenyl)propionate adduct produced in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 255

Preparation of β-[[2-[[[3-[(aminoiminomethyl)amino]phenyl]carbonyl]amino]acetyl]amino]-2(carboxymethoxy)benzenepropanoic acid, trifluoroacetate salt

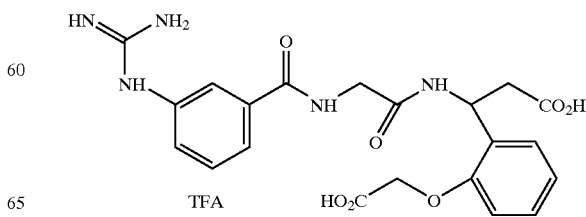

Step A

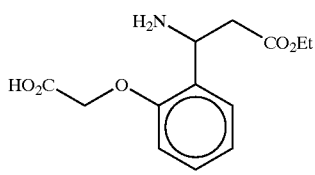

To 2-formyl phenoxyacetic acid (Fisher) (10 g) in ethanol (70 mL) was added ammonium acetate (2.5 equivalents) followed by ethyl hydrogen malonate (1.1 equivalents). The reaction mixture was stirred at reflux for 5 hours. The solution was filtered to give DL ethyl-3-amino-3-(2-formyl phenoxyacetic acid)propionate as a solid (6.3 g). MS and H-NMR were consistent with the proposed structure.

Step B

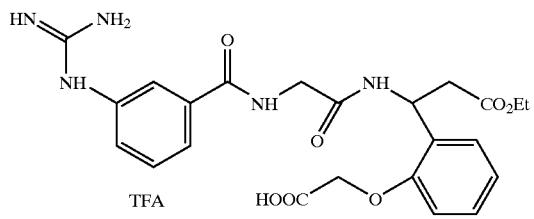

N,N'-Disuccinimidyl carbonate (DSC) (1.0 g, 0.4 mmol) was added to the compound of Example H (1.0 g, 0.4 mmol in dry dimethylformamide (6 mL) followed by dimethylaminopyridine (100 mg). After a period of 20 minutes DL ethyl-3-amino-3-(2-formyl phenoxyacetic acid)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

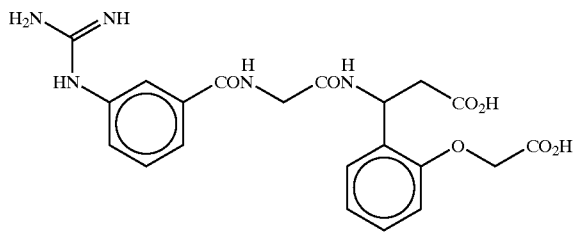

DL-ethyl 3-amino-3-(2-formyl phenoxyacetic acid) propionate adduct produced in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 256

Preparation of β-[[2-[[[3-[(aminoiminomethyl)amino]phenyl]carbonyl]amino]acetyl]amino]-4-methoxy-1,3-benzodioxole-6-propanoic acid, trifluoroacetate salt

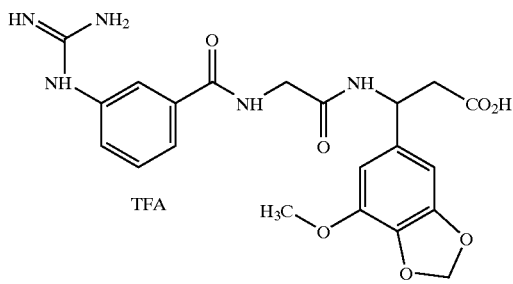

Step A

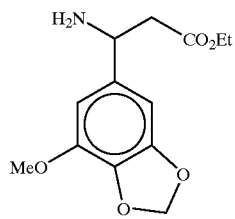

To 2-methoxy piperinal (Fisher) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(2-methoxy piperinal)propionate as an oil (6.3 g). MS and H-NMR were consistent with the proposed structure.

Step B

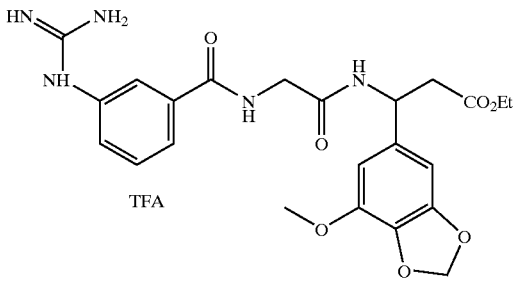

N,N'-Disuccinimidyl carbonate (DSC) (1.0 g, 0.4 mmol) was added to the compound of Example N (1.0 g, 0.4 mmol) in dry dimethylformamide (6 ml) followed by dimethylaminopyridine (100 mg). After a period of 20 minutes DL ethyl-3-amino-3-(2-methoxy piperinal)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

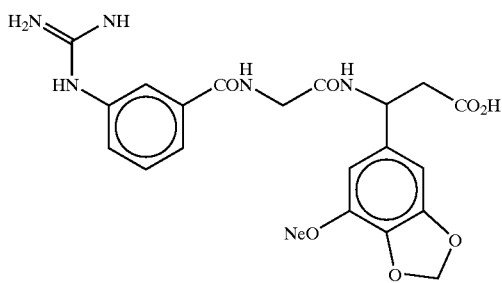

DL-ethyl 3-amino-3-(2-methoxy piperinal)propionate adduct prepared in Step B (500 mg) was dissolved in water/acetonitrile ((1:1)), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 257

Preparation of β-[[2-[[[3-[(aminoiminomethyl)amino]phenyl]carbonyl]amino]acetyl]amino]-5-bromo-2-methoxybenzenepropanoic acid, trifluoroacetate salt

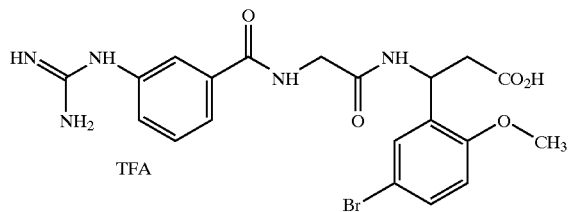

Step A

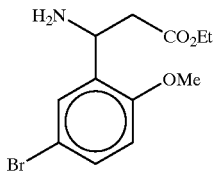

To 3-bromo-6-methoxybenzaldehyde (Aldrich) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(3-bromo-6-methoxyphenyl)propionate as an oil (6.3 g). MS and H-NMR were consistent with the proposed structure.

Step B

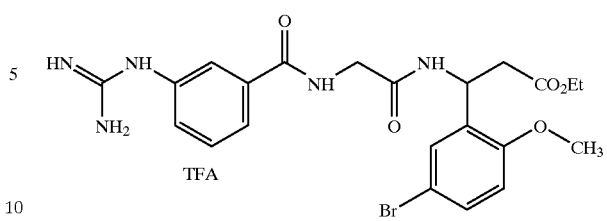

N,N'-Disuccinimidyl carbonate (DSC) (1.0 g, 0.4 mmol) was added to the compound of Example M (1.0 g, 0.4 mmol) in dry dimethylformamide (6 mL) followed by dimethylaminopyridine (100 mg). After a period of 20 minutes DL ethyl-3-amino-3-(3-bromo-6-methoxyphenyl)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

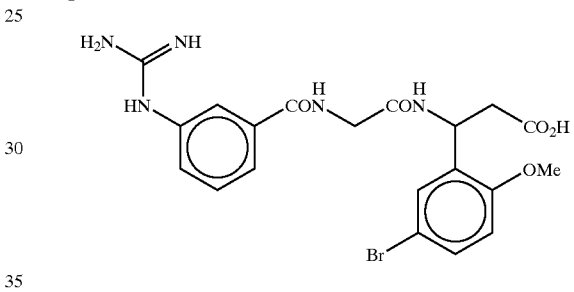

DL-ethyl 3-amino-3-(3-bromo-6-methoxyphenyl)propionate adduct prepared in Step B (500 mg) was dissolved in water/acetonitrile ((1:1)), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 258

Preparation of β-[[2-[[[3-[(aminoiminomethyl)amino]phenyl]carbonyl]amino]acetyl]amino]-6-chloro-1,3-benzodioxole-5-propanoic acid, trifluoroacetate salt

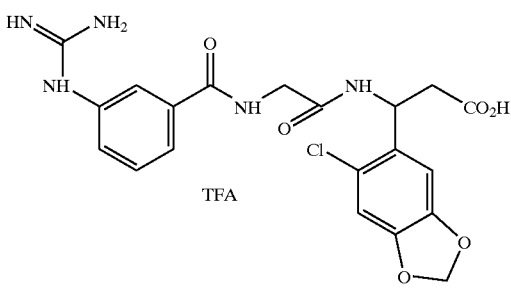

Step A

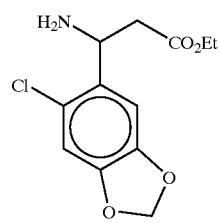

To 6-chloropiperinal (Lancaster) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(6-chloropiperinyl)propionate as an oil (6.3 g). MS and H-NMR were consistent with the proposed structure.

Step B

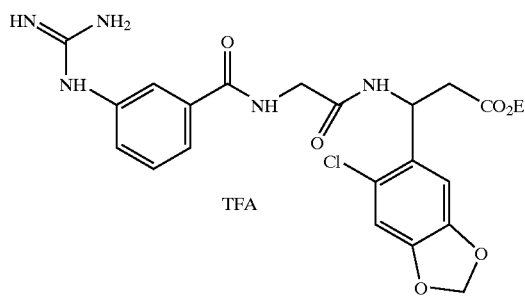

N,N'-Disuccinimidyl carbonate (DSC) (1.0 g, 0.4 mmol) was added to the compound of Example M (1.0 g, 0.4 mmol) in dry dimethylformamide (6 mL) followed by dimethylaminopyridine (100 mg). After a period of 20 minutes DL ethyl-3-amino-3-(3-chloropiperinyl)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

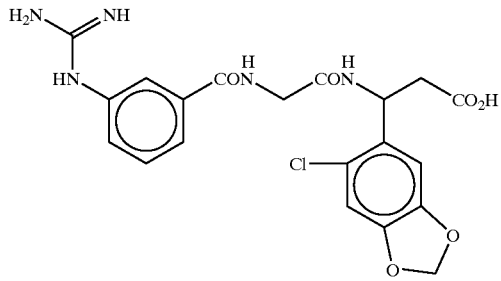

DL-ethyl 3-amino-3-(6-chloropiperinyl)propionate adduct prepared in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 259

Preparation of β-[[2-[[[3-[(aminoiminomethyl)amino]phenyl]carbonyl]amino]acetyl]amino] benzofuran-2-propanoic acid, trifluoroacetate salt

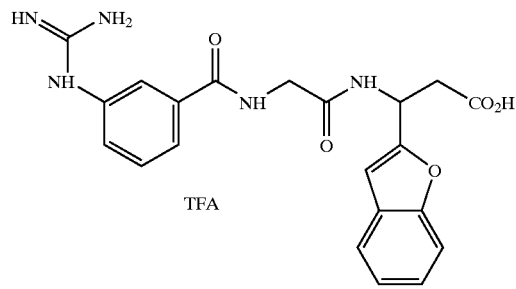

Step A

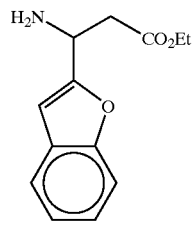

To 2-benzofuran carboxaldehyde (Lancaster) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(2-benzofuranyl)propionate as an oil (6.3 g). MS and H-NMR were consistent with the proposed structure.

Step B

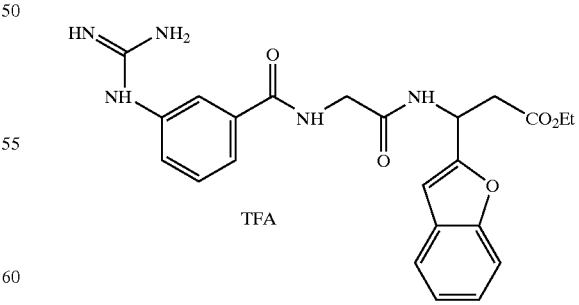

N,N'-Disuccinimidyl carbonate (DSC) (1.0 g, 0.4 mmol) was added to the compound of Example N (1.0 g, 0.4 mmol) in dry dimethylformamide (6 mL) followed by dimethylaminopyridine (100 mg). After a period of 20 minutes DL ethyl-3-amino-3-(2-benzofuranyl)propionate. (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

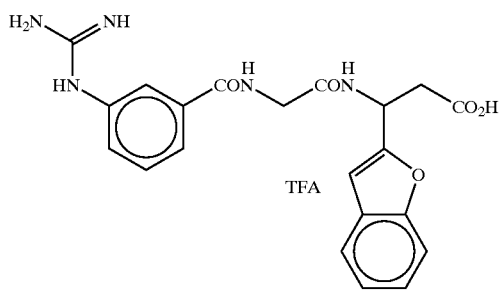

DL-ethyl 3-amino-3-(2-benzofuranyl)propionate adduct prepared in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 260

Preparation of β-[[2-[[[3-[(aminoiminomethyl) amino]phenyl]carbonyl]amino]acetyl]amino]-3-(carboxymethoxy)benzenepropanoic acid, trifluoroacetate salt

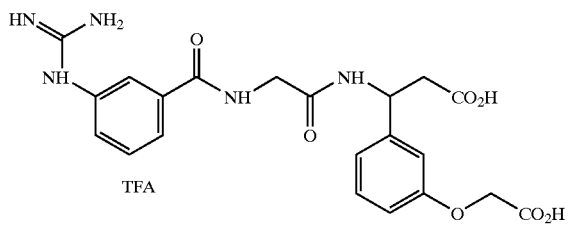

Step A

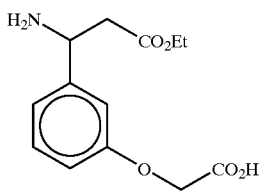

To 3-formyl phenoxyacetic acid (Fisher) (10 g) in ethanol (70 mL) was added ammonium acetate (2.5 equivalents) followed by ethyl hydrogen malonate (1.1 equivalents). The reaction mixture was stirred at reflux for 5 hours. The solution was filtered to give DL ethyl-3-amino-3-(3-formyl phenoxyacetic acid)propionate as an oil (6.3 g). MS and H-NMR were consistent with the proposed structure.

Step B

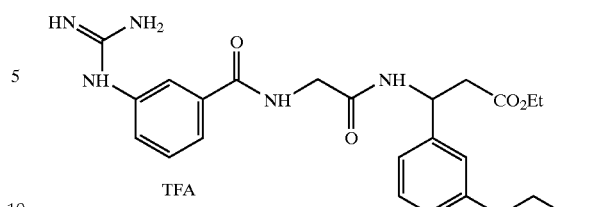

N,N'-Disuccinimidyl carbonate (DSC) (1.0 g, 0.4 mmol) was added to the compound of Example M (1.0 g, 0.4 mmol) in dry dimethylformamide (6 mL) followed by dimethylaminopyridine (100 mg). After a period of 20 minutes DL ethyl-3-amino-3-(3-formyl phenoxyacetic acid)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

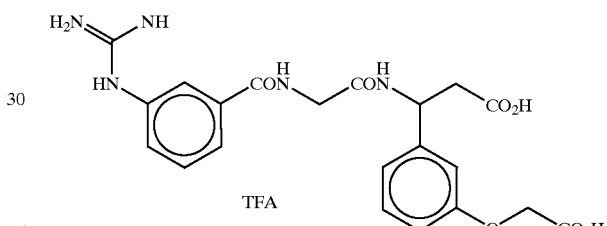

DL ethyl 3-amino-3-(3-formyl phenoxyacetic acid) propionate adduct prepared in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 261

Preparation of 3-[[2-[[[3-[(aminoiminomethyl) amino]phenyl]carbonyl]aminoacetyl]amino]-4,4,4-trifluorobutanoic acid, trifluoroacetate salt

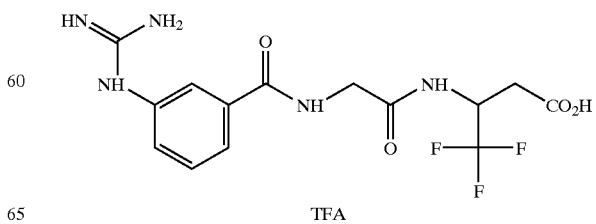

Step A

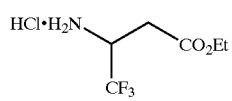

To 3-amino-4,4,4-trifluorobutyric acid (Lancaster) (2 g) in ethanol (70 mL) was added HCl in dioxane (20 mL, 4N) and stirred vigorously for 16 hours. The solvent was removed under reduced pressure. The HCl salt was collected as a solid (2.3 g). MS and H-NMR were consistent with the proposed structure.

Step B

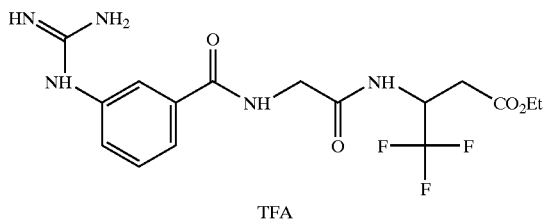

N,N'-Disuccinimidyl carbonate (DSC) (1.0 g, 0.4 mmol) was added to the compound of Example N (1.0 g, 0.4 mmol) in dry dimethylformamide (6 mL) followed by dimethylaminopyridine (100 mg). After a period of 20 minutes DL ethyl-3-amino-3-(4,4,4-trifluoro)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

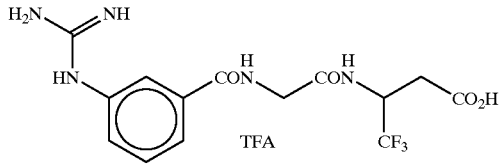

DL-ethyl 3-amino-3-(4,4,4-trifluoro)propionate adduct prepared in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 262

Preparation of (±)β-[[2-[[[3-[(aminoiminomethyl)amino]phenyl]carbonyl]amino]acetyl]amino]-3-bromo-4,5-dimethoxybenzenepropanoic acid, trifluoroacetate salt

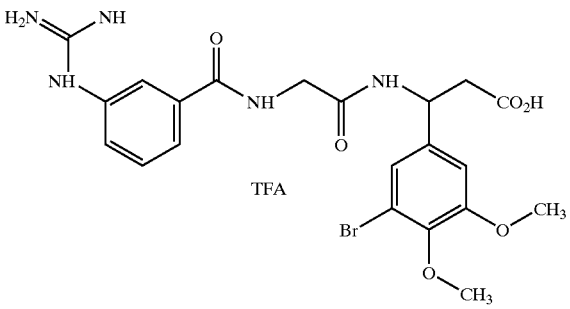

Step A

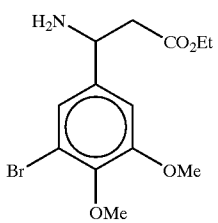

To 3-bromo-4,5-dimethoxy benzaldehyde (Aldrich) (10 g) in ethanol (70 mL) was added ammonium acetate (2.5 equivalents) followed by ethyl hydrogen malonate (1.1 equivalents). The reaction mixture was stirred at reflux for 5 hours. The solution was cooled, and ethanol removed under reduced pressure. Aqueous HCl (100 mL) was added and the mixture partitioned with ethyl acetate. The organic layer was discarded and the acid layer made basic with solid $K_2CO_3$. The resulting mixture was partitioned between methylene chloride (150 mL), separated and dried over $Na_2SO_4$. The solvent was evaporated to give DL ethyl-3-amino-3-(3-bromo-4,5-dimethoxyphenyl)propionate as an oil (6.3 g). MS and H-NMR were consistent with the proposed structure.

Step B

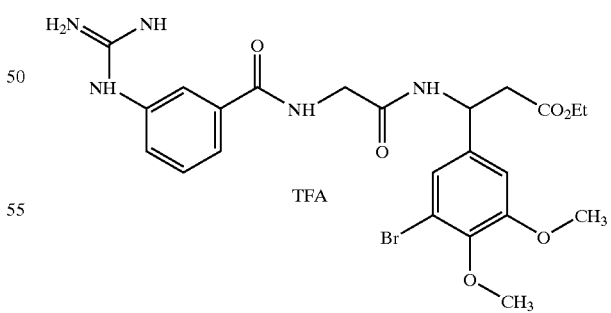

N,N'-Disuccinimidyl carbonate (DSC) (1.0 g, 0.4 mmol) was added to the compound of Example M (1.0 g, 0.4 mmol) in dry dimethylformamide (6 mL) followed by dimethylaminopyridine (100 mg). After a period of 20 minutes DL ethyl-3-amino-3-(2-bromo-4,5-dimethoxyphenyl)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.
Step C

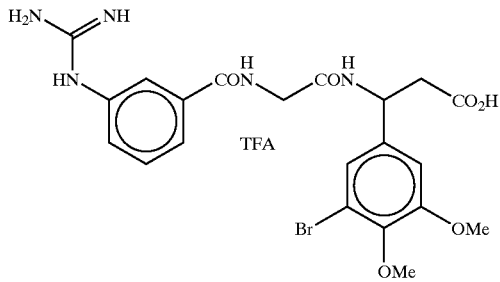

DL-ethyl 3-amino-3-(3-bromo-4,5-dimethoxyphenyl)propionate adduct prepared in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 263

Preparation of 3-[[2-[[[3-[(aminoiminomethyl)amino]phenyl]carbonyl]amino]acetyl]amino]-4-methylpentanoic acid, trifluoroacetate salt

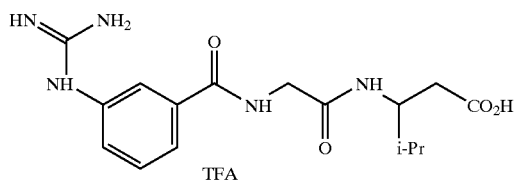

Step A

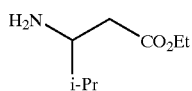

DL ethyl-3-amino-3-(isopropyl)propionate was prepared by the method of Example 53, Step A substituting isopropylacetoacetate (10 g) for dimethyl-3-ketoglutarate. MS and H-NMR were consistent with the proposed structure.
Step B

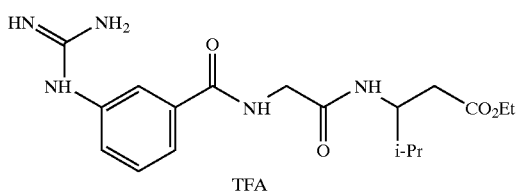

N,N'-Disuccinimidyl carbonate (DSC) (1.0 g, 0.4 mmol) was added to the compound of Example M (1.0 g, 0.4 mmol) in dry dimethylformamide (6 mL) followed by dimethylaminopyridine (100 mg). After a period of 20 minutes DL ethyl-3-amino-3-(isopropyl)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.
Step C

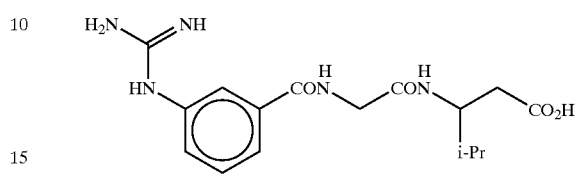

DL ethyl 3-amino-3-(isopropyl)propionate adduct prepared in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 264

Preparation of 3-[[2-[[[3-[(aminoiminomethyl)amino]phenyl]carbonyl]amino]acetyl]amino]pentanoic acid, trifluoroacetate salt

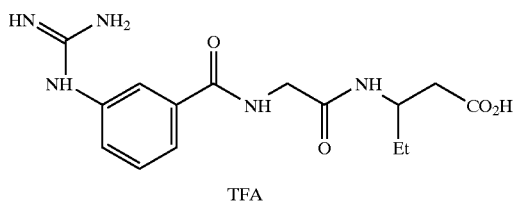

Step A

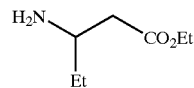

DL ethyl-3-amino-3-(3-ethyl)propionate was prepared by the method of Example 53. Step A, substituting ethylacetoacetate (10 g) for dimethyl-3-ketoglutarate. MS and H-NMR were consistent with the proposed structure.
Step B

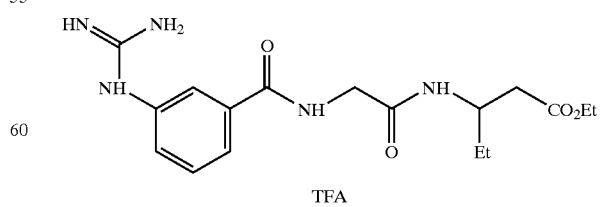

N,N'-Disuccinimidyl carbonate (DSC) (1.0 g, 0.4 mmol) was added to the compound of Example N (1.0 g, 0.4 mmol) in dry dimethylformamide (6 mL) followed by dimethylaminopyridine (100 mg). After a period of 20 minutes DL ethyl-3-amino-3-(ethyl)propionate (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

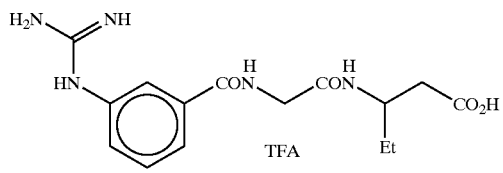

DL-ethyl 3-amino-3-(ethyl)propionate adduct prepared in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 265

Preparation of β-[[2-[[[3-[(aminoiminomethyl) amino]phenyl]carbonyl]amino]acetyl]amino]-5-bromo-3-chloro-2-hydroxybenzenepropanoic acid, trifluoroacetate salt

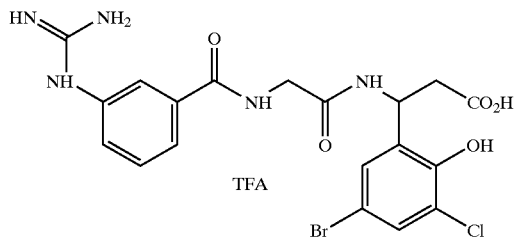

Step A

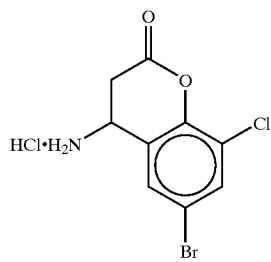

DL-3-bromo-5-chloro-2-hydroxy aminocoumarin hydrochloride was prepared according to Scheme XIV. The method of G. Casiraghi, et al. J. Chem. Soc. Perkin Trans 1 p.318, 1978, was employed for the preparation of the 4-bromo-2-chlorosalicylic aldehyde and 6-bromo-8-chlorocoumarin was prepared by the method of Vogel's The Textbook of Practical Organic Chemistry, fifth edition p. 1040. The amino coumarin was prepared by the method cited in Example 87 using 7-chloro-5-bromo coumarin (7 g). MS and H-NMR were consistent with the proposed structure.

Step B

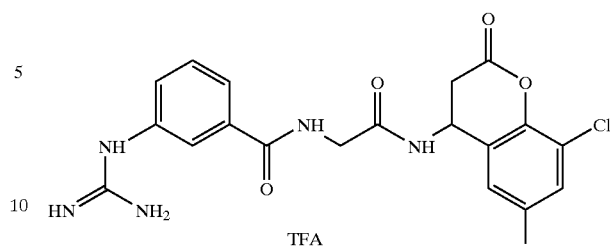

N,N'-Disuccinimidyl carbonate (DSC) (1.0 g, 0.4 mmol) was added to the compound of Example M (1.0 g, 0.4 mmol) in dry dimethylformamide (6 mL) followed by dimethylaminopyridine (100 mg). After a period of 20 minutes DL-3-bromo-5-chloro-2-hydroxy aminocoumarin hydrochloride (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step C

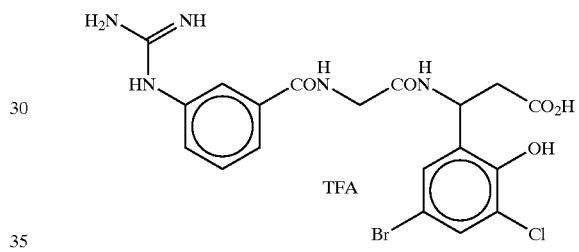

DL-3-bromo-5-chloro-2-hydroxy aminolactone adduct prepared in Step B (500 mg) dissolved in water/acetonitrile slowly opened to form a (2-hydroxy acid) resulting in 255 mg of the title compound as a white solid after purification by reverse phase chromatography and lyophylization as its TFA salt. MS and H-NMR were consistent with the proposed structure.

EXAMPLE 266

Preparation of β-[[2-[[[3-[[[(4-pyridinylmethyl) amino]carbonyl]amino]phenyl]carbonyl]amino] acetyl]amino]pyridine-3-propanoic acid, (bis) trifluoroacetate salt

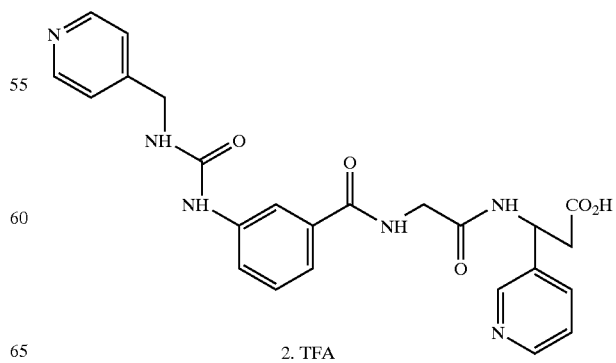

Step A

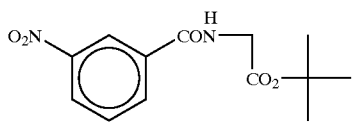

Glycine tert-butyl ester (20 g, 119 mmol) was added to water (200 mL) followed by potassium carbonate (20 g, 180 mmol) and cooled to 0° C. in an ice bath. To this solution 3-nitrobenzoyl chloride (20 g, 108 mmol) was added in acetonitrile (20 mL) drop-wise over a 10 minute period. After complete reaction (3–4 hours) concentrated hydrochloric acid was added until pH=3 followed by saturated aqueous NaCl (75 mL). The product was filtered, washed with water and air dried (22 g, 90% yield). MS and H-NMR were consistent with the proposed structure.

Step B

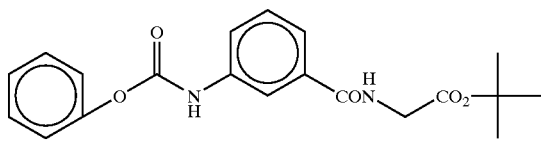

tert-Butyl(3-nitrobenzoyl) glycinate (1.0 g) was added to absolute ethanol (60 mL) in a Parr jar. Palladium on carbon 5% (1 mg) was added and the mixture was hydrogenolyzed under 50 psi in a Parr apparatus for a period of 2.5 hours. After complete reaction the palladium catalyst was removed by filtration through a plug of celite. The solvent was removed under reduced pressure and the sample dried in vacuo. Dimethylformamide (25 mL) was added to the crude aniline tert-butyl ester followed by triethylamine (1.5 equivalents) and cooled to 0° C. Phenyl chloroformate (6.5 g, 1.1 equivalents) was added and the reaction stirred for 2 hours. Water was added and the solid was filtered to give the phenyl carbamate tert-butyl ester as a white solid (12.5 g, 99% yield). MS and H-NMR were consistent with the proposed structure.

Step C

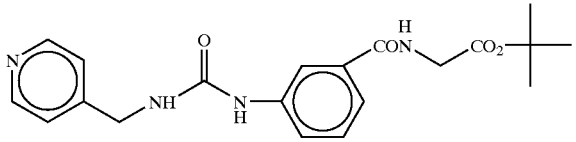

Dimethylformamide (25 mL) was added to the phenyl carbamate tert-butyl ester from Step B followed by 4-pyridylmethylamine (1.1 equivalents). The reaction was heated at 70° C. with stirring for 2 hours and stirred at 25° C. for 12 hours. Water was added, and the mixture partitioned between ethyl acetate, separated and washed with brine and dried over Na₂SO₄ to give an oil (6 g). MS and H-NMR were consistent with the proposed structure.

Step D

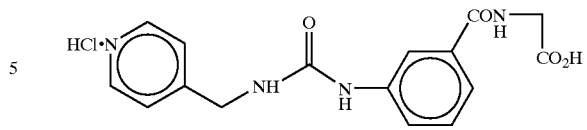

The compound from Step C (6 g) was dissolved in dioxane (25 mL). To this solution HCl in dioxane (20 mL, 4N) was added. The solution was stirred for 12 hours and the solvent was removed under reduced pressure followed by the addition of ether. The solid was filtered and dried in a vacuum oven for 12 hours.

Step E

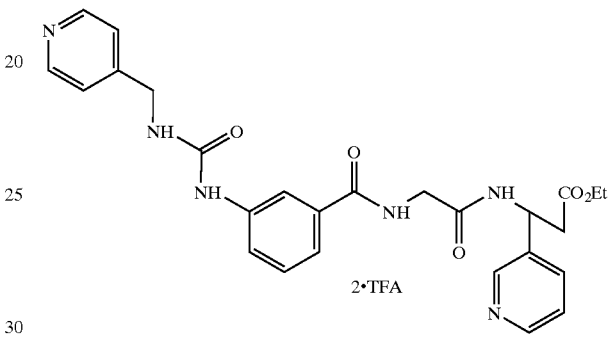

N,N'-disuccinimidyl carbonate (DSC) (1.0 g, 0.4 mmol) was added to the compound produced in Step D (1.0 g, 0.4 mmol) in dry dimethylformamide (6 mL) followed by addition of dimethylaminopyridine (100 mg). After a period of 20 minutes DL-ethyl 3-amino-3-pyridyl propionate hydrochloride (1.1 g, 0.5 mmol) was added followed by NMM (2.0 mL). After complete reaction (1–16 hours) the product was purified by reverse phase chromatography (water/acetonitrile) to result in a white solid (1.1 g). MS and H-NMR were consistent with the proposed structure.

Step F

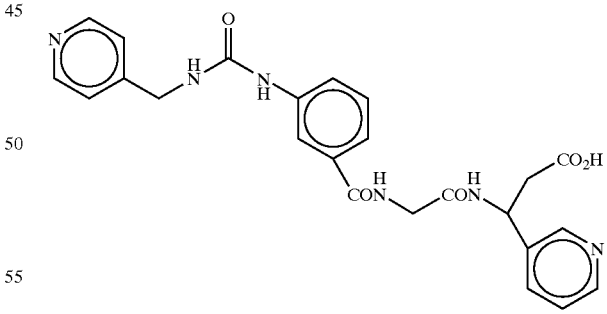

DL-ethyl 3-amino-3-pyridyl propionate adduct produced in Step E (500 mg) was dissolved in water/acetonitrile (1:1), followed by the addition of lithium hydroxide (100 mg). The reaction was allowed to stir at 25° C. and monitored by HPLC. After complete hydrolysis (1–2 hours) trifluoroacetic acid was added until pH=2. The product was purified by reverse phase chromatography (water/acetonitrile) to result in 255 mg of the title compound as a white solid. MS and H-NMR were consistent with the proposed structure.

EXAMPLE 267

Preparation of 3,5-dichloro-β-[[2-[[[3-[[[(4-pyridinylmethyl)amino]carbonyl]amino]phenyl]carbonyl]amino]acetyl]amino]benzenepropanoic acid, trifluoroacetate salt

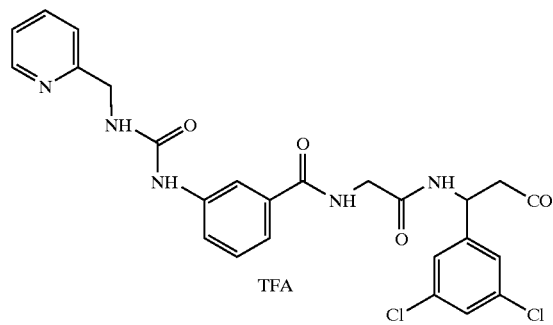

Step A

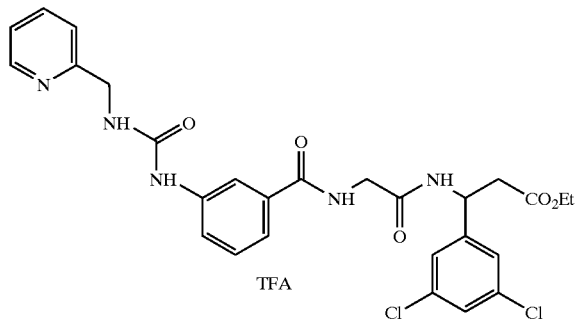

N,N'-disuccinimidyl carbonate (DSC) (1.0 g, 0.4 mmol) was added to the compound produced in Step B. Example 268 (1.0 g, 0.4 mmol) in dry dimethylformamide (6 mL) followed by addition of dimethylaminopyridine (100 mg). After a period of 20 minutes DL-ethyl 3-amino-3-(1,3-dichlorophenyl)propionate hydrochloride (1.1 g, 0.5 mmol) was added followed by NMM (2.0 mL). After complete reaction (1–16 hours) the product was purified by reverse phase chromatography (water/acetonitrile) to result in a white solid (1.0 g). MS and H-NMR were consistent with the proposed structure.

Step B

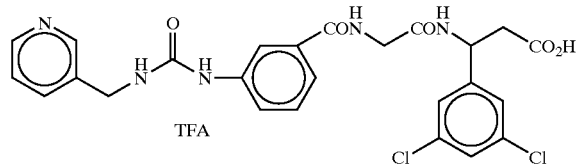

DL-ethyl 3-amino-3-(1,3-dichlorophenyl)propionate adduct produced in Step A (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 315 mg of the title compound as a white solid. MS and H-NMR were consistent with the proposed structure.

EXAMPLE 268

Preparation of β[[2-[[[3-[[[(2-pyridinylmethyl)amino]carbonyl]amino]phenyl]carbonyl]amino]acetyl]amino]pyridine-3-propanoic acid, (bis) trifluoroacetate salt

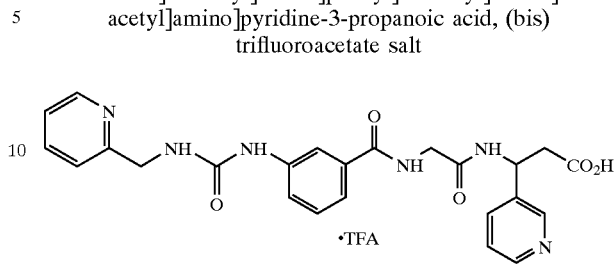

Step A

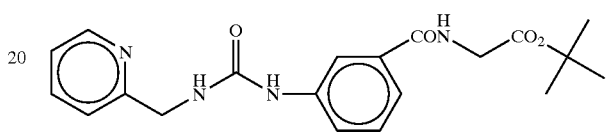

Dimethylformamide (25 mL) was added to the phenyl carbamate tert-butyl ester from Example 266, Step B, followed by 2-pyridylmethylamine (1.1 equivalents.) and the reaction was heated at 70° C. with stirring for 2 hours and stirred at 25° C. for 1–2 hours. Water was added and the mixture partioned between ethyl acetate, separated, washed with brine and dried over $Na_2SO_4$ to give an oil (6 g). MS and H-NMR were consistent with the proposed structure.

Step B

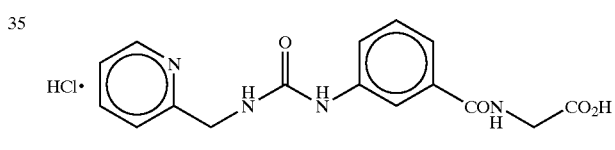

The compound produced in Step A (6 g) was disolved in dioxane (25 mL). To this solution HCl in dioxane (20 mL, 4N) was added. The solution was stirred for 1–2 hours. The solvent was removed under reduced pressure followed by addition of ether. The solid was filtered and dried in a vacuum oven for 12 hours.

Step C

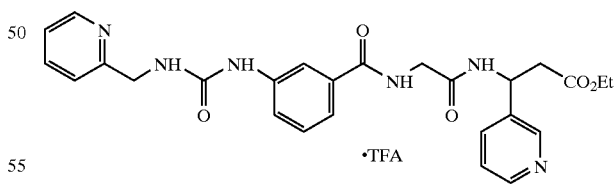

N,N'-Disuccinimidyl carbonate (DSC) (1.0 g, 0.4 mmol) was added to the compound produced in Step B (1.0 g, 0.4 mmol) in dry dimethylformamide (6 mL) followed by addition of dimethylaminopyridine (100 mg). After a period of 20 minutes DL-ethyl 3-amino-3-pyridyl propionate hydrochloride (1.1 g, 0.5=mmol) was added followed by NMM (2.0 mL). After complete reaction (1–16 hr) the product was purified by reverse phase chromatography (water/acetonitrile) to result in a white solid (1.1 g). MS and H-NMR were consistent with the proposed structure.

Step D

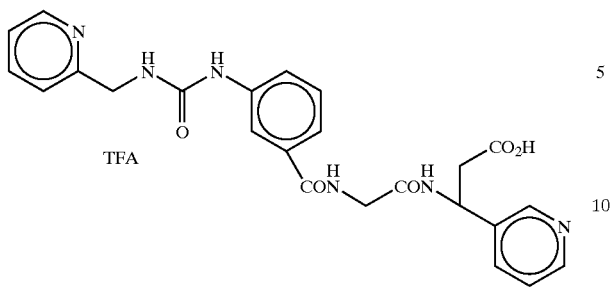

DL-ethyl 3-amino-3-pyridyl propionate adduct produced in Step C (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 550 mg of the title compound as a white solid. MS and H-NMR were consistent with the proposed structure.

EXAMPLE 269

Preparation of 3,5-dichloro-β-[[2-[[[3-[[[(phenylmethyl)amino]carbonyl]amino]phenyl]carbonyl]amino]acetyl]amino]benzenepropanoic acid, monohydrate

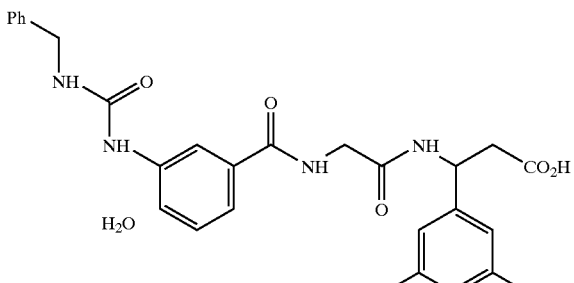

Step A

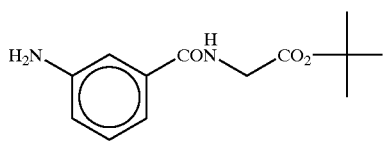

tert-butyl(3-nitrobenzoyl) glycinate (10 g) was added to absolute ethanol (60 mL) in a Parr jar. Palladium on carbon 5% (1 mg) was added and the mixture was hydrogenolyzed under 50 psi in a Parr apparatus for a period of 2.5 hours. After complete reaction the palladium catalyst was removed by filtration through a plug of celite. The solvent was removed under reduced pressure and the sample dried in vacuo.

Step B

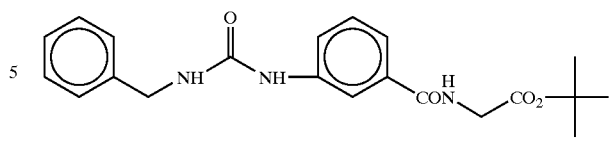

Acetonitrile (50 mL) was added to the crude aniline (10 g) produced in Step A followed by benzyl isocyanate (7.0 g). The solution was warmed to 70° C. for 2 hours, and the solvent removed. Diethyl ether was added and the solid was filtered to give the benzyl urea tert-butyl ester as a salmon colored solid (12.6 g).

Step C

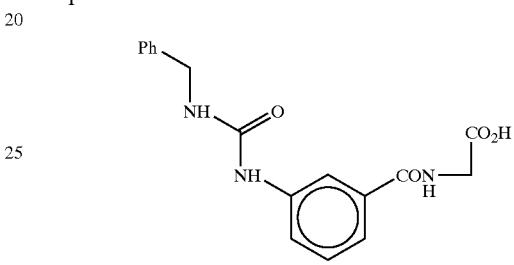

The compound produced in Step B (6 g) was disolved in dioxane (25 mL). To this solution HCl in dioxane (20 mL, 4N) was added. The solution was stirred for 12 hours and the solvent was removed under reduced pressure followed by addition of ether. The solid was filtered and dried in a vacumn oven for 12 hours.

Step D

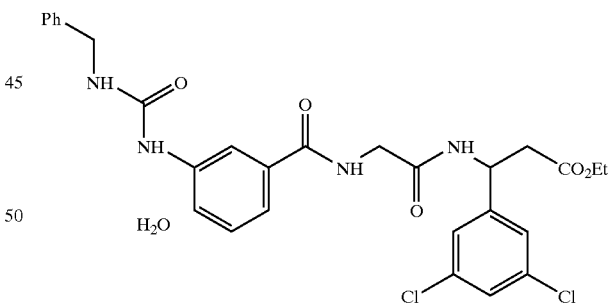

N,N'-disuccinimidyl carbonate (DSC) (1.0 g, 0.4 mmol) was added to compound produced in Step C (1.0 g, 0.4 mmol) in dry dimethylformamide (6 mL) followed by addition of dimethylaminopyridine (100 mg). After a period of 20 min DL-ethyl 3-amino-3-(1,3-dichlorophenyl) propionate hydrochloride (1.1 g, 0.5 mmol) was added followed by NMM (2.0 mL). After complete reaction (1–16 hours) the product was purified by reverse phase chromatography (water/acetonitrile) to result in a white solid (1.2 g). MS and H-NMR were consistent with the proposed structure.

Step E

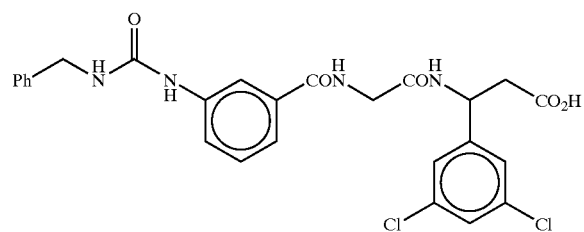

DL-ethyl 3-amino-3-(1,3-dichlorophenyl)propionate adduct produced in Step D (500 mg) was dissolved in water/acetonitrile (1:1)g followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 250 mg of the title compound as a white solid. MS and H-NMR was consistent with the proposed structure.

EXAMPLE 270

Preparation of 3-chloro-β-[[2-[[[3-[[[(phenylmethyl)amino]carbonyl]amino]phenyl]carbonyl]amino]acetyl]amino]benzenepropanoic acid, monohydrate

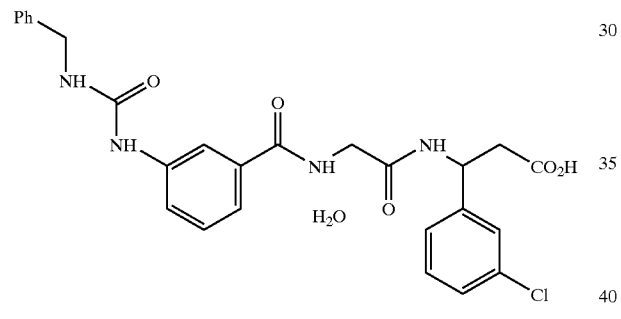

Step A

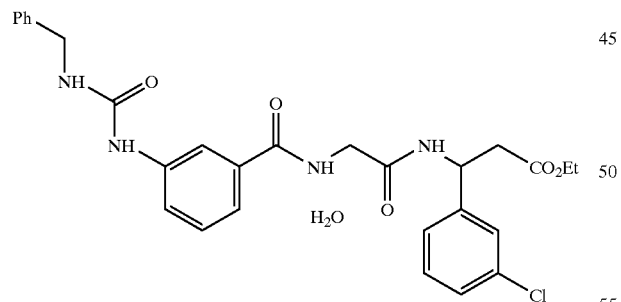

N,N'-disuccinimidyl carbonate (DSC) (1.0 g, 0.4 mmol) was added to the compound produce of Step C, Example 269 (1.0 g, 0.4 mmol) in dry dimethylformamide (6 mL) followed by addition of dimethylaminopyridine (100 mg). After a period of 20 minutes DL-ethyl 3-amino-3-(3-chlorophenyl)propionate hydrochloride (1.1 g, 0.5 mmol) was added followed by NMM (2.0 mL). After complete reaction (1–16 hours) the product was purified by reverse phase chromatography (water/acetonitrile) to result in a white solid (0.9 g). MS and H-NMR were consistent with the proposed structure.

Step B

DL-ethyl 3-amino-3-(3-chlorophenyl)propionate adduct produced in Step A (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 350 mg of the title compound as a white solid. MS and H-NMR were consistent with the proposed structure.

EXAMPLE 271

Preparation of β-[[2-[[[3-[[[(1-phenylethyl)amino]carbonyl]amino]phenyl]carbonyl]amino]acetyl]amino]pyridine-3-propanoic acid, trifluoroacetate salt

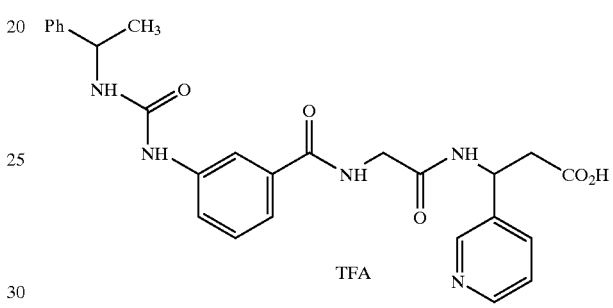

Step A

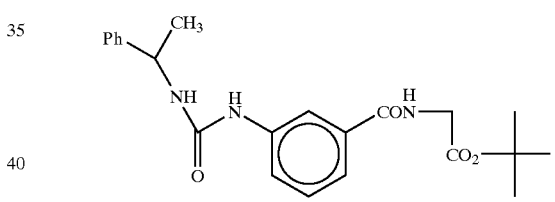

Dimethylformamide (25 mL) was added to the phenyl carbamate tert-butyl ester from Step B of Example 266 followed by α-methyl benzylamine (1.1 equivalents). The reaction was heated at 70° C. with stirring for 2 hours and stirred at 25° C. for 1–2 hours. Water was added, the mixture partitioned between ethyl acetate, separated, washed with brine and dried over $Na_2SO_4$, to give an oil (6 g). MS and H-NMR were consistent with the proposed structure.

Step B

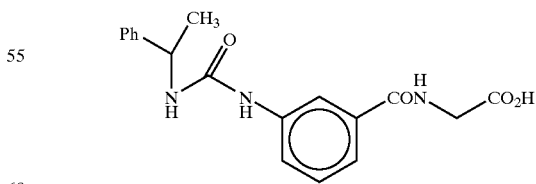

The compound produced in Step A (6 g) was dissolved in methylene chloride (50 mL). To this solution TFA (20 mL) was added. The solution was stirred for 12 hours. The solvent was removed under reduced pressure followed by addition of ether. The solid was filtered and dried in a vacuum oven for 1–2 hours.

Step C

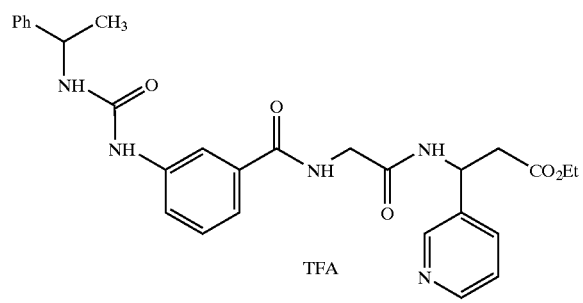

N,N'-disuccinimidyl carbonate (DSC) (1.0 g, 0.4 mmol) was added to the compound produced in Step B (1.0 g, 0.4 mmol) in dry dimethylformamide (6 mL) followed by addition of dimethylaminopyridine (100 mg). After a period of 20 minutes, DL-ethyl 3-amino-3-pyridylpropionate hydrochloride (1.1 g, 0.5 mmol) was added followed by NMM (2.0 mL). After complete reaction (1–16 hours) the product was purified by reverse phase chromatography (water/acetonitrile) to result in a white solid (1.0 g). MS and H-NMR were consistent with the proposed structure.

Step D

DL-ethyl 3-amino-3-pyridyl propionate adduct produced in Step C (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 150 mg of the title compound as a white solid. MS and H-NMR were consistent with the proposed structure.

EXAMPLE 272

Preparation of β-[[2-[[[3-[[[[(1H-benzimidazol-2-yl)methyl)amino]carbonyl]amino]phenyl]carbonyl]amino]acetyl]amino]-3,5-dichlorobenzenepropanoic acid, trifluoroacetate salt

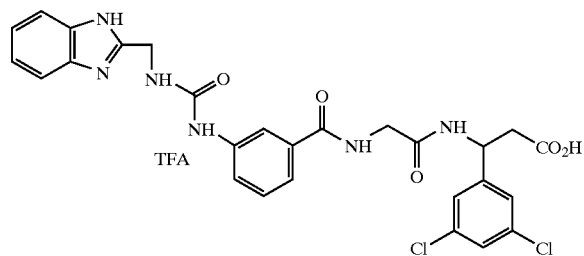

Step A

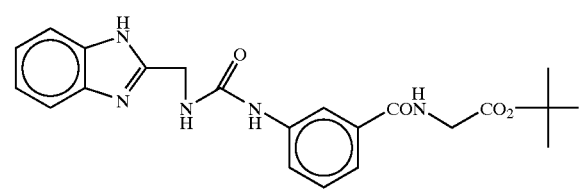

Dimethylformamide(25 mL) was added to the phenyl carbamate tert-butyl ester from Step B of Example 266, followed by addition of 2-aminomethyl benzimidazole (Aldrich) (1.1 equivalents). The reaction was heated to 70° C. with stirring for 2 hours and stirred at 25° C. for 1–2 hours. Water was added and the mixture partitioned between ethyl acetate, separated, washed with brine and dried over $Na_2SO_4$ to give an oil (6 g). MS and H-NMR was consistent with the proposed structure.

Step B

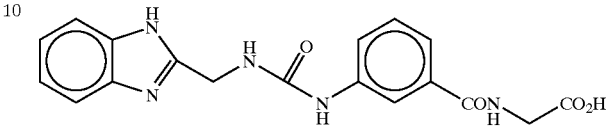

The compound produced in Step A (6 g) was dissolved in methylene chloride (50 mL). To this mixture TFA (20 mL) was added. The mixture was stirred for 1–2 hours. The solvent was removed under reduced pressure followed by addition of ether. The solid was filtered and dried in a vacuum oven for 1–2 hours.

Step C

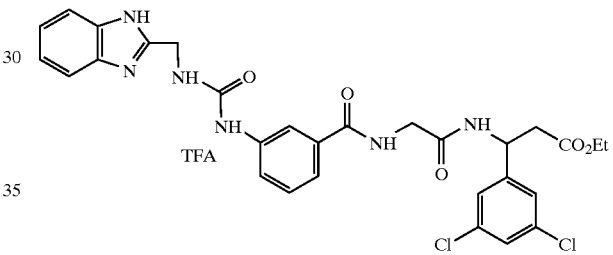

N,N'-disuccinimidyl carbonate (DSC) (1.0 g, 0.4 mmol) was added to the compound produced in Step B (1.0 g, 0.4 mmol) in dry dimethylformamide (6 mL) followed by addition of dimethylaminopyridine (100 mg). After a period of 20 minutes, DL-ethyl 3-amino-3-(1,3-dichlorophenyl) propionate hydrochloride (1.1 g, 0.5 mmol) was added followed by NMM (2.0 mL). After complete reaction (1–16 hours) the product was purified by reverse phase chromatography (water/acetonitrile) to result in a white solid (0.8 g). MS and HNMR were consistent with the proposed structure.

Step D

DL-ethyl 3-amino-3-(1,3-dichlorophenyl)propionate adduct produced in Step C (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 125 mg of the title compound as a white solid. MS and H-NMR were consistent with the proposed structure.

EXAMPLE 273

Preparation of β-[[2-[[[3-[[[[(3,5-dichlorophenyl)methyl]amino]carbonyl amino]phenyl]carbonyl]amino]acetyl]amino]pyridine-3-propanoic acid, trifluoroacetate salt

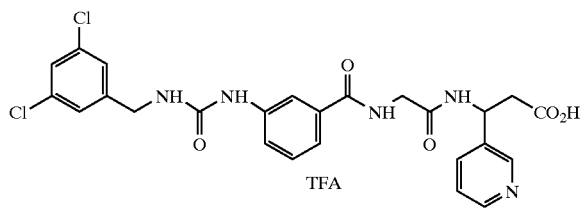

Step A

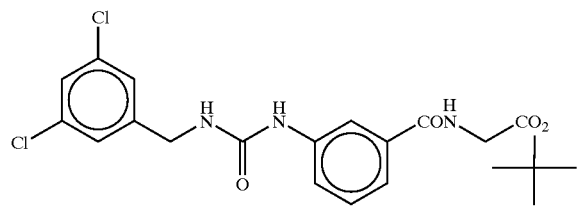

Dimethylformamide (25 mL) was added to the phenyl carbamate tert-butyl ester from Step B of Example 266, followed by addition of 3,5-dichlorobenzyl amine (Lancaster) (1.1 equivalents). The reaction was heated at 70° C. with stirring for 2 hours and stirred at 25° C. for 1–2 hours. Water was added and the mixture partitioned between ethyl acetate, separated, washed with brine and dried over $Na_2SO_4$, to give an oil (6 g). MS and H-NMR was consistent with the proposed structure.

Step B

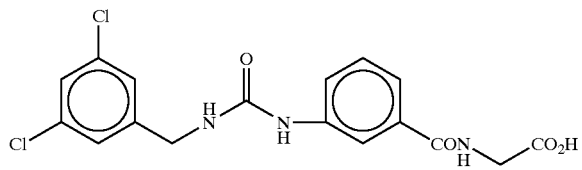

The compound produced in Step A (6 g) was dissolved in methylene chloride (50 mL). To this mixture TFA (20 mL, 4N) was added. The mixture was stirred for 1–2 hours. The solvent was removed under reduced pressure followed by addition of ether. The solid was filtered and dried in a vacuum oven for 1–2 hours.

Step C

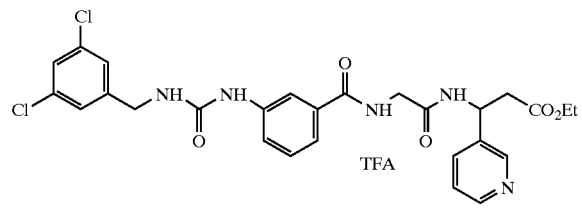

N,N'-disuccinimidyl carbonate (DSC) (1.0 g, 0.4 mmol) was added to the compound produced in Step 8 (1.0 g, 0.4 mmol) in dry dimethylformamide (6 mL) followed by addition of dimethylaminopyridine (100 mg). After a period of 20 minutes, DL-ethyl 3-amino-3-(pyridyl)propionate hydrochloride (1.1 g, 0.5 mmol) was added followed by NMM (2.0 mL). After complete reaction (1–16 hours) the product was purified by reverse phase chromatography (water/acetonitrile) to result in a white solid (0.8 g). MS and H-NMR was consistent with the proposed structure.

Step D

DL-ethyl 3-amino-3-(pyridyl)propionate adduct produced in Step C (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 125 mg of the title compound as a white solid. MS and H-NMR were consistent with the proposed structure.

EXAMPLE 274

Preparation of 3-[[2-[[[3-[[[[(3,5-dichlorophenyl)methyl]amino]carbonyl]amino]phenyl]carbonyl]amino]acetyl]amino]butanoic acid

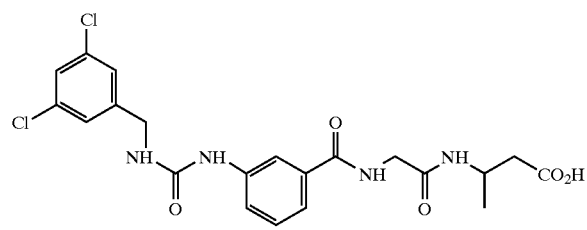

Step A

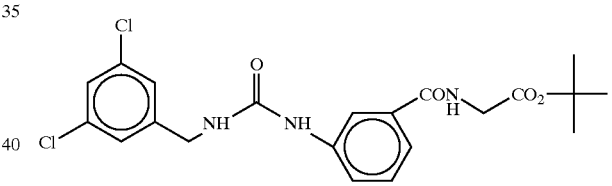

Dimethylformamide (25 mL) was added to the phenyl carbamate tert-butyl ester from Step B of Example 266, followed by addition of 3,5-dichlorobenzyl amine (Lancaster) (1.1 equivalents). The reaction was heated at 70° C. with stirring for 2 hours and stirred at 25° C. for 1 2 hours. Water was added and the mixture partitioned between ethyl acetate, separated, washed with brine and dried over $Na_2SO_4$ to give an oil (6 g). MS and H-NMR was consistent with proposed structure.

Step B

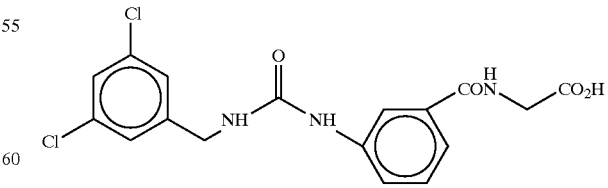

The compound produced in Step A (6 g) was dissolved in methylene chloride (50 mL). To this mixture TFA (20 mL) was added. The mixture was stirred for 1–2 hours. The solvent was removed under reduced pressure followed by addition of ether. The solid was filtered and dried in a vacuum oven for 1–2 hours. MS and H-NMR was consistent with the proposed structure.

Step C

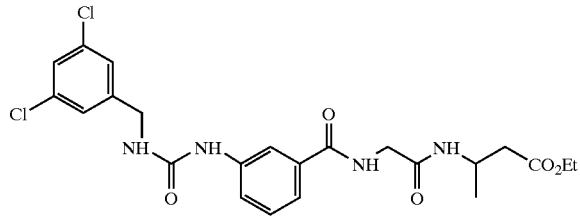

N,N'-disuccinimidyl carbonate (DSC) (1.0 g, 0.4 mmol) was added to the compound produced in Step B (1.0 g, 0.4 mmol) in dry dimethylformamide (6 mL) followed by addition of dimethylaminopyridine (100 mg). After a period of 20 minutes DL-ethyl 3-amino-3-(methyl)propionate (Aldrich) (1.1 g, 0.5 mmol) was added followed by addition of NMM (2.0 mL). After complete reaction (1–16 hours) the product was purified by reverse phase chromatography (water/acetonitrile) to result in a white solid (0.8 g). MS and H-NMR were consistent with the proposed structure.

Step D mL-ethyl 3-amino-3(methyl)propionate adduct produced in Step C (500 mg) was dissolved in water/acetonitrile (1:1), followed by addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 125 mg of the title compound as a white solid. MS and H-NMR were consistent with the proposed structure.

EXAMPLE 275

Preparation of β-[[2-[[[3-[(aminoiminomethyl)amino]phenyl]carbonyl]amino]acetyl]amino]-3,5-bis(1-methylethoxy)benzenepropanoic acid, trifluoroacetate salt

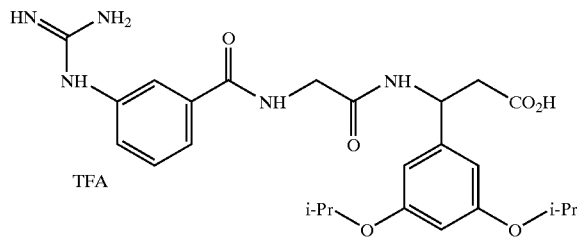

Step A

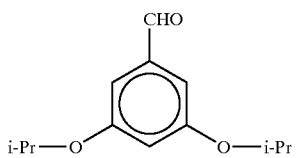

To 3,5-dihydroxybenzaldehyde (10 g) in acetone (100 mL) was added K$_2$CO$_3$ (20 g) and isopropyliodide (20 g). The mixture was heated at reflux and stirred for 2 days. Water (250 mL) was added and the product extracted into ethyl acetate. The organic layer was separated, washed with water, brine and dried over Na$_2$SO$_4$ to give 3,5-diisopropyloxyphenylcarboxaldehyde (12 g) as a dark oil. This material was used as is for the next step. MS and H-NMR were consistent with the proposed structure.

Step B

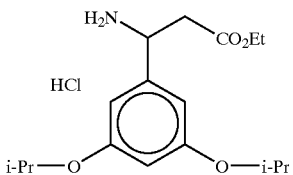

To 3,5-diisopropyloxyphenylcarboxaldehyde (Step A) (10 g) in ethanol (70 mL) was added ammonium acetate (12.5 g) followed by addition of ethyl hydrogen malonate (6.0 g). The reaction mixture was stirred at reflux for 5 hours. The mixture was cooled, and ethanol removed under reduced pressure. Aqueous HCl (100 mL) was added and the mixture partitioned with ethyl acetate. The organic layer was discarded and the acid layer made basic with solid K$_2$CO$_3$. The resulting mixture was partitioned between methylene chloride (150 mL), separated and dried over Na$_2$SO$_4$. The solvent was evaporated to give DL ethyl-3-amino-3-(3,5-diisopropylphenyl)propionate as an oil. Ether (100 mL) was added, followed by addition of HCl in dioxane (20 mL, 4N) and stirred vigorously for one hour. The HCl salt was collected by filtration (4.3 g). MS and H-NMR were consistent with the proposed structure.

Step C

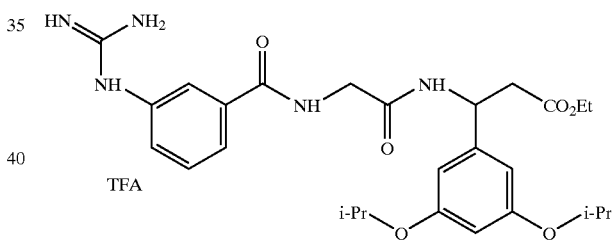

N,N'-disuccinimidyl carbonate (DSC) (1.0 g, 0.4 mmol) was added to the compound of Example M (1.0 g, 0.4 mmol) in dry dimethylformamide (6 mL) followed by addition of dimethylaminopyridine (100 mg). After a period of 20 minutes DL ethyl 3-amino-3-(3,5-diisopropyloxyphenyl)propionate hydrochloride (1.1 g, 0.5 mmol) was added followed by addition of NMM (2.0 mL). After complete reaction (1–16 hours) the product was purified by reverse phase chromatography (water/acetonitrile) to result in a white solid (0.8 g). MS and H-NMR were consistent with the proposed structure.

Step D

DL ethyl-3-amino-3-(3,5-diisopropyloxyphenyl)propionate adduct produced in Step C (500mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 625 mg of the title compound as a white solid. MS and H-NMR were consistent with the proposed structure.

EXAMPLE 276

Preparation of β-[[2-[[[3-[(aminoiminomethyl)amino]phenyl)carbonyl]amino]acetyl]amino]-3,5-dibromo-4-hydroxybenzenepropanoic acid, trifluoroacetate salt

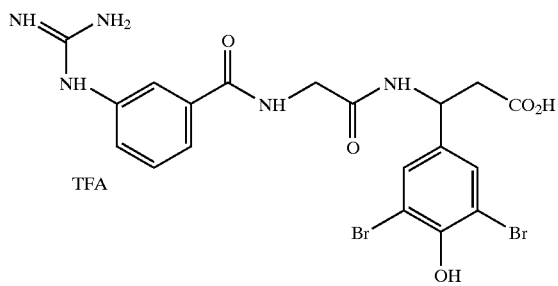

Step A

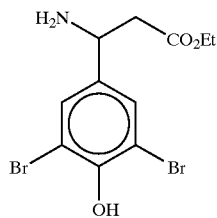

To 4-hydroxy-3,5-dibromobenzaldehyde (Aldrich) (10 g) in ethanol (70 mL) was added ammonium acetate (2.5 equivalents) followed by addition of ethyl hydrogen malonate (1.1 equivalents). The reaction mixture was stirred at reflux for 5 hours. The mixture was cooled, and ethanol removed under reduced pressure. Aqueous HCl (100 mL) was added and the mixture partitioned with ethyl acetate. The organic layer was discarded and the acid layer made basic with solid K₂CO₃. The resulting mixture was partitioned between methylene chloride (150 mL), separated and dried over Na₂SO₄. The solvent was evaporated to give DL ethyl-3-amino-3-(4-hydroxy-3,5-dibromophenyl)propionate as a solid and was collected by filtration (1.3 g). MS and H-NMR were consistent with the proposed structure.

Step B

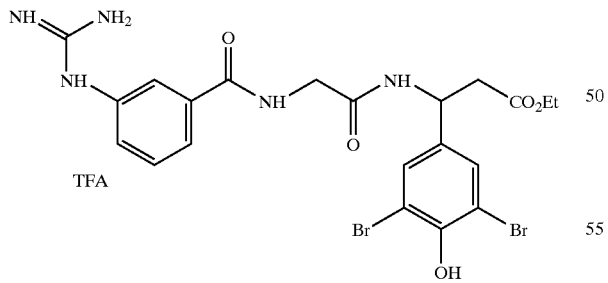

N,N'-disuccinimidyl carbonate (DSC) (1.0 g, 0.4 mmol) was added to the compound of Example X (1.0 g, 0.4 mmol) in dry dimethylformamide (6 mL) followed by addition of dimethylaminopyridine (100 mg). After a period of 20 minutes DL ethyl-3-amino-3-(4-hydroxy-3,5-dibromophenyl)propionate hydrochloride (1.1 g, 0.5 mmol) was added followed by addition of NMM (2.0 mL). After complete reaction (1–16 hours) the product was purified by reverse phase chromatography (water/acetonitrile) to result in a white solid (0.89 g). MS and H-NMR were consistent with the proposed structure.

Step C

DL ethyl-3-amino-3-(4-hydroxy-3,5-dibromophenyl)propionate adduct produced in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 425 mg of the title compound as a white solid. MS and H-NMR were consistent with the proposed structure.

EXAMPLE 277

Preparation of β-[[2-[[[3-[(aminoiminomethyl)amino]phenyl]carbonyl]amino]acetyl]amino]-3,5-dichloro-4-hydroxybenzenepropanoic acid, trifluoroacetate salt

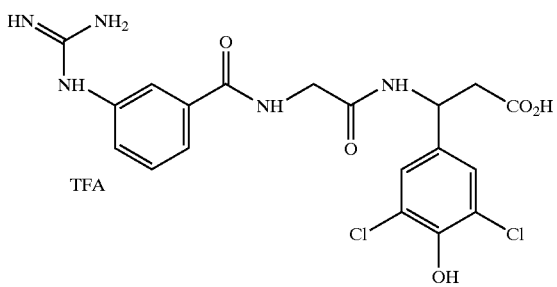

Step A

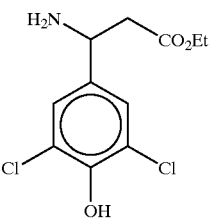

To 4-hydroxy-3,5-dichlorobenzaldehyde (Aldrich) (10 g) in ethanol (70 mL) was added ammonium acetate (2.5 equivalents) followed by addition of ethyl hydrogen malonate (1.1 equivalents). The reaction mixture was stirred at reflux for 5 hours. The mixture was cooled, and ethanol removed under reduced pressure. Aqueous HCl (100 mL) was added and the mixture partitioned with ethyl acetate. The organic layer was discarded and the acid layer made basic with solid K₂CO₃. The resulting mixture was partitioned between methylene chloride (150 mL), separated and dried over Na₂SO₄. The solvent was evaporated to give DL ethyl-3-amino-3-(4-hydroxy-3,5-dichlorophenyl)propionate as solid (2.5 g). MS and H-NMR were consistent with the proposed structure.

Step B

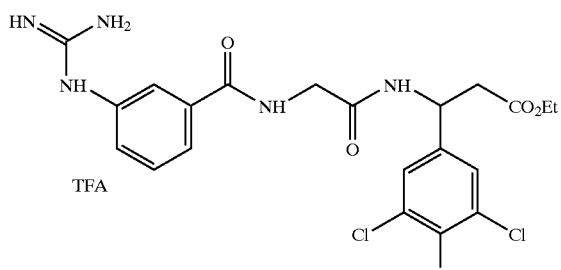

N,N'-disuccinimidyl carbonate (DSC) (1.0 g, 0.4 mmol) was added to the compound of Example M (1.0 g, 0.4 mmol) in dry dimethylformamide (6 mL) followed by addition of dimethylaminopyridine (100 mg). After a period of 20 minutes DL ethyl-amino-3-(4-hydroxy-3,5-dichlorophenyl) propionate hydrochloride (1.1 g, 0.5 mmol) was added followed by addition of NMM (2.0 mL). After complete reaction (1–16 hours) the product was purified by reverse phase chromatography (water/acetonitrile) to result in a white solid (0.9 g). MS and H-NMR were consistent with the proposed structure.

Step C

DL-ethyl-amino-3-(4-hydroxy-3,5-dichlorophenyl) propionate adduct prepared in Step B (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 325 mg of the title compound as a white solid. MS and R-NMR were consistent with the proposed structure.

EXAMPLE 278

Preparation of β-[[2-[[[3-[(5,6-dihydro-4H-thiazin-2-yl)amino]phenyl]carbonyl]amino]acetyl]amino]pyridine-3-propanoic acid, bis(trifluoroacetate)salt

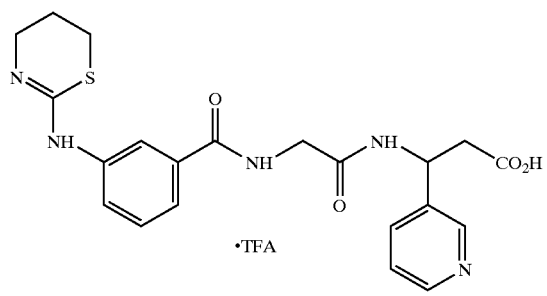

Step A

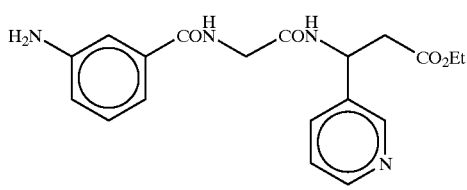

The compound prepared in Example 104 (2.0 g) was added to absolute ethanol (60 mL) in a Parr jar. Palladium on carbon 5% (500 mg) was added and the mixture was hydrogenolyzed under 50 psi in a Parr apparatus for a period of 2.5 hours. After complete reaction the palladium catalyst was removed by filtration through a plug of celite. The solvent was removed under reduced pressure and the sample dried in vacuo.

Step B

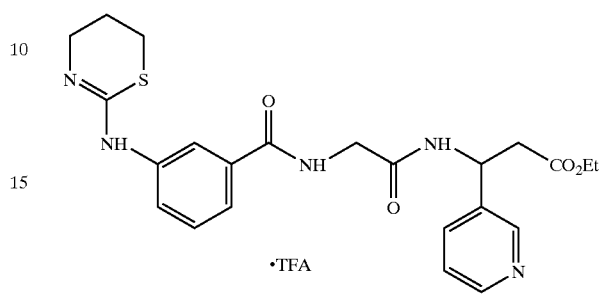

The compound prepared in Step A was added to acetonitrile (20 mL) followed by addition of 2-methyl thiodihydro-1,3-thiazine (2.0 g) (prepared according to J. Chem. Soc. Perkin Transaction, 1943, p.243–245] and heated for 4 hours. After complete reaction water was added and the product was purified by reverse phase chromatography (water/acetonitrile) to result in a white solid (1.3 g). MS and H-NMR were consistent with the proposed structure.

Step C

DL-ethyl 3-amino-3(pyridyl)propionate thiazine adduct prepared in Step B (700 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 520 mg of the title compound as a white solid. MS and H-NMR were consistent with the proposed structure.

EXAMPLE 279

Preparation of β-[[2-[[[5-[(aminoiminomethyl)amino]-2-hydroxyphenyl]carbonyl]amino]acetyl]amino]-3,5-dichlorobenzenepropanoic acid, trifluoroacetate salt

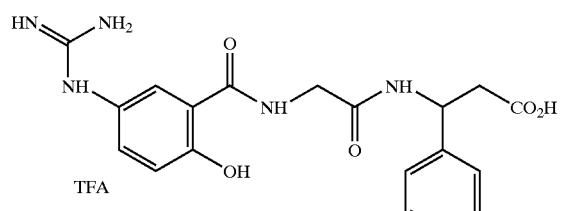

Step A

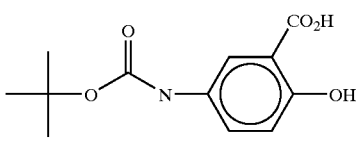

Amino salicylic acid (10 g), 2CO (10 g), and di-tert-butoxycarbonate (12 g) were placed in a flask containing water/acetonitrile (100 mL, (1:1)). The course of the reaction was monitored by RPHPLC. After complete reaction dilute aqueous HCl was added (pH=4), the product was separated from mixture, and filtered resulting in a tan-red solid (15 g). The compound was dried in an oven at 70° C. for 16 hours. MS and H-NMR were consistent with the proposed structure.

Step B

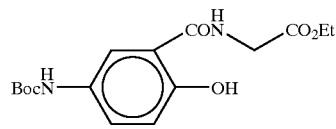

N,N'-disuccinimidyl carbonate (DSC) (2.0 g, 0.8 mmol) was added to the N-Boc compound produced in Step A (2.0 g, 0.4 mmol) in dry dimethylformamide (4 mL) followed by addition of dimethylaminopyridine (100 mg). After a period of 20 minutes, ethyl glycinate hydrochloride (2.1 g, 0.9 mmol) was added followed by addition of DIEA (2.0 mL). After complete reaction (2 hours) the product was extracted with ethyl acetate (100 mL) washed with aqueous HCl, brine and dried over Na$_2$SO$_4$ to give a dark oil (2.5 g). MS and H-NMR were consistent with the proposed structure.

Step C

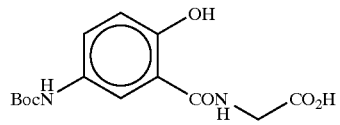

Ethyl glycinate N-Boc benzamide adduct produced in Step B (2 g) was dissolved in water/acetonitrile (1:1), followed by the addition of lithium hydroxide (200 mg). The reaction was allowed to stir at 25° C., and monitored by HPLC. After complete hydrolysis (1–2 hours) hydrochloric acid was added until pH=4. The product was extracted with ethyl acetate (100 mL) washed with aqueous HCl, brine and dried over Na$_2$SO$_4$ to give a dark oil. The oil was vigorously stirred with ether to result in a solid (1.9 g) after filtration and dried in a vacuum oven for 16 hours. MS and H-NMR were consistent with the proposed structure.

Step D

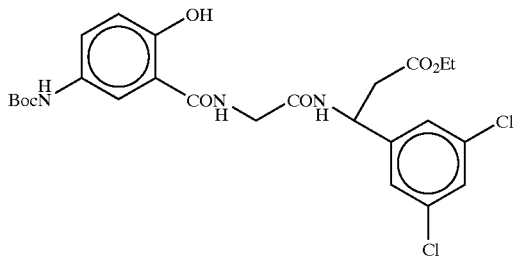

N,NO-disuccinimidyl carbonate (DSC) (1.0 g, 0.4 mmol) was added to the glycine compound produced in Step C (1.0 g, 0.4 mmol) in dry dimethylformamide (6 mL) followed by addition of dimethylaminopyridine (100 mg). After a period of 20 minutes DL ethyl-3-amino-3-(3,5-dichlorophenyl)propionate hydrochloride (1.1 g, 0.5 mmol) was added followed by addition of NMM (2.0 mL). After complete reaction (1–16 hours) the product was purified by reverse phase chromatography (water/acetonitrile) to result in a white solid (0.9 g). MS and H-NMR were consistent with the proposed structure.

Step E

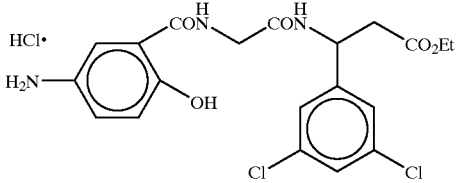

The compound produced in Step D (6 g) was dissolved in methylene chloride (50 m>). To this mixture HCl/dioxane (20 mL, 4N) was added. The mixture was stirred for 1–2 hours. The solvent was removed under reduced pressure followed by addition of ether. The solvent was removed again under reduced pressure. The solid was purified by reverse phase chromatography (water/acetonitrile) to result in a white solid (0.8 g). MS and H-NMR were consistent with the proposed structure.

Step F

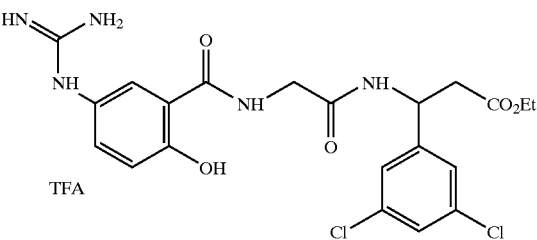

The aniline from step E was dissolved into acetonitrile (20 mL). To this mixture pyrazole carboxamidine hydrochloride (2 g) was added followed by addition of DIEA. The mixture was heated at reflux for 4 hours. After complete reaction (1–16 hours) the product was purified by reverse phase chromatography (water/acetonitrile) to result in a white solid (0.9 g). MS and H-NMR were consistent with the proposed structure.

Step G

DL-ethyl 3-amino-3-(3,5-dichlorophenyl)propionate adduct produced in Step F (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 125 mg of the title compound as a white solid. MS and H-NMR were consistent with the proposed structure.

EXAMPLE 280

Preparation of β-[[2-[[[3-[[[(phenoxyamino)carbonyl]amino]phenyl]carbonyl]amino]acetyl]amino]pyridine-3-propanoic acid, trifluoroacetate salt

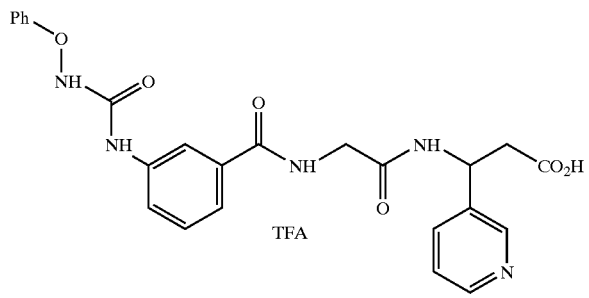

Step A

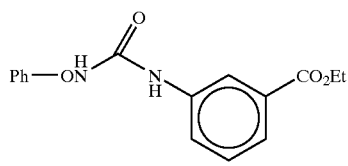

To O-phenyl hydroxyl amine hydrochloride (Fluka) (4 g) in acetonitrile was added 3-ethoxycarbonyl phenylisocyanate (Lancaster) (5 g) and NMM (1 equivalent). The reaction was stirred for 1 hour at 70° C. After complete reaction the solvent was removed under reduced pressure to give a solid mass. Water was added and a tan solid filtered (7.5 g). MS and H-NMR were consistent with the proposed structure.

Step B

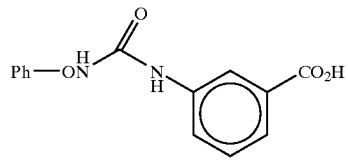

The compound produced in Step A (7 g) was dissolved in water/acetonitrile (1:1), followed by the addition of lithium hydroxide (4 g). The reaction was allowed to stir at 25° C., and monitored by HPLC. After complete hydrolysis (4–6 hours) 10% aqueous HCl was added until pH=2. The product was filtered to give a white solid (7 g) which was dried in a vacuum oven at 70° C. for 16 hours. MS and H-NMR were consistent with the proposed structure.

Step C

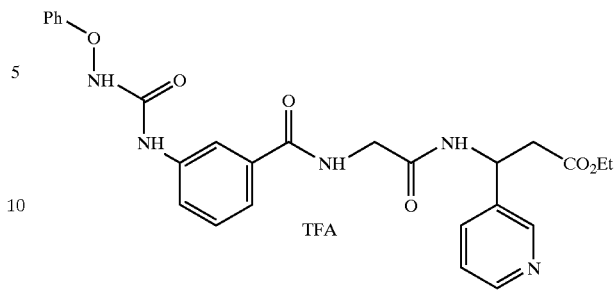

N,N'-disuccinimidyl carbonate (DSC) (1.4 g, 0.5 mmol) was added to the carboxylic acid-urea of O-phenyl hydroxyl amine produced in Step B and 3-ethoxycarbonyl phenylisocyanate [(A13)in Scheme V] (1.0 g, 0.5 mmol) in dry dimethylformamide (20 mL) followed by addition of dimethylaminopyridine (100 mg). After a period of 1 hour gly-DL-ethyl 3-amino-3-(pyridyl)propionate hydrochloride (2.2 g, 0.7 mmol) in DMF/NMM (1:1) (5.0 mL) was added in one portion. After complete reaction the product was purified by reverse phase chromatography (water/acetonitrile) to result in a white solid (0.8 g). MS and H-NMR were consistent with the proposed structure.

Step D

The compound produced in Step C (300 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 500 mg of the title compound as a white solid. MS and H-NMR were consistent with the proposed structure.

EXAMPLE 281

Preparation of β-[[2-[[[3-[[[(phenylamino)amino]carbonyl]amino]phenyl]carbonyl]amino]acetyl]amino]pyridine-3-propanoic acid, trifluoroacetate salt

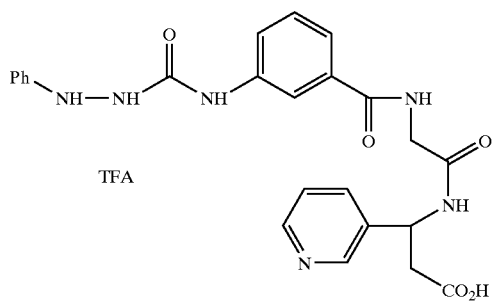

Step A

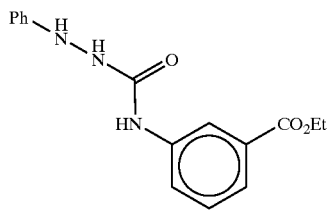

To phenyl hydrazine hydrochloride (Aldrich) (3.5 g) in acetonitrile was added 3-ethoxycarbonyl phenylisocyante (Lancaster) (5 g) and NMM (1 equivalents). The reaction was stirred for 1 hour at 70° C. After complete reaction the solvent was removed under reduced pressure to give a solid mass. Water was added and the tan solid filtered (8.7 g). MS and H-NMR were consistent with the proposed structure.

Step B

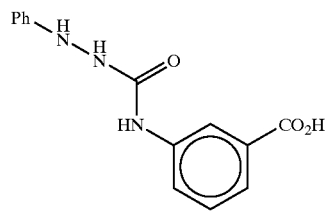

The compound produced in Step A (5 g) was dissolved in water/acetonitrile (1:1), followed by the addition of sodium hydroxide (3 g). The reaction was allowed to stir at 25° C., and monitored by HPLC. After complete hydrolysis (4–6 hours) 10% aqueous HCl was added until pH=4. The product was filtered to give a yellow solid (3.2 g) and dried in a vacuum oven at 70° C. for 16 hours. MS and H-NMR were consistent with the proposed structure.

Step C

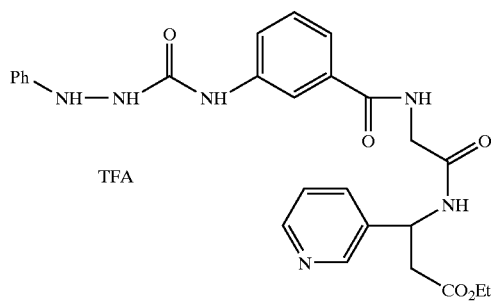

N,N'-disuccinimidyl carbonate (DSC) (500 mg, 0.5 mmol) was added to the compound produced in Step B and 3-ethoxycarbonyl phenylisocyanate (1.0 g, 0.5 mmol) in dry dimethylformamide (20 mL) followed by addition of dimethylaminopyridine (100 mg). After a period of 1 hour glycine-DL-ethyl 3-amino-3-(pyridyl)propionate hydrochloride (1.0 g, 0.7 mmol) in DMF/NMM (1:1) (5.0 mL) was added in one portion. After complete reaction the product was purified by reverse phase chromatography (water/acetonitrile) to result in a white solid (0.8 g). MS and H-NMR were consistent with the proposed structure.

Step D

The compound produced in Step C (300 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 500 mg of the title compound as a white solid. MS and H-NMR were consistent with the proposed structure.

EXAMPLE 282

Preparation of β-[[2-[[[3-[(5-amino-1,2,4-triazol-3-yl)amino]phenyl]carbonyl]amino]acetyl]amino]-3,5-dichlorobenzenepropanoic acid, trifluoroacetate salt

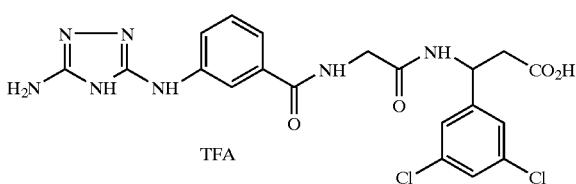

Step A

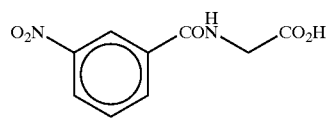

Glycine (20 g, 266 mmol) was added to water (200 mL), followed by addition of potassium hydroxide (20 g, 357 mmol) and the mixture cooled to 0° C. in an ice bath. To this mixture 3-nitrobenzoyl chloride (Aldrich) (20 g, 108 mmol) was added in acetonitrile (20 mL) drop-wise over a 10 minute period. After complete reaction (3–4 hours) concentrated hydrochloric acid was added until pH=1 followed by addition of saturated aqueous NaCl (75 mL). The product was filtered, washed with water and air dried (22 g, 90% yield).

Step B

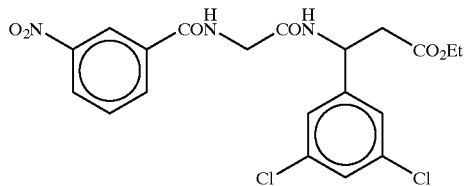

N,N$_3$-disuccinimidyl carbonate (DSC) (1.5 g, 0.7 mmol) was added to the compound produced in Step A (1.0 g, 0.4 mmol) in dry dimethylformamide (6 mL) followed by addition of dimethylaminopyridine (100 mg). After a period of 20 minutes DL ethyl-3-amino-3-(3,5-dichlorophenyl) propionate hydrochloride (1.1 g, 0.5 mmol) was added followed by addition of NMM (2.0 mL). After complete reaction (1–16 hours) the product was isolated by adding water/aqueous HCl (5 ml) and filtering product to result in a white solid (0.9 g). MS and H-NMR were consistent with the proposed structure.

Step C

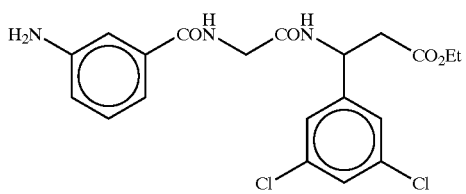

The compound produced in Step B was subjected to the conditions described in Tetrahedron Letters, Vol. 25 1984, 839–842 for the reduction of the nitro group. The reduction was preformed on 2 g of nitro compound.

Step D

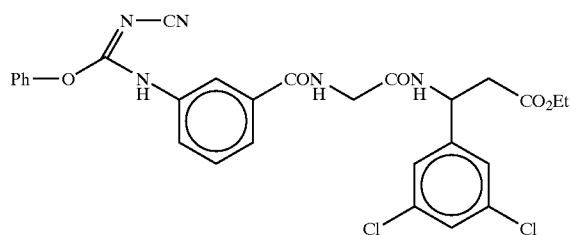

To the compound produced in Step C (2 g) isopropanol (20 mL) was added followed by addition of diphenoxycyanamine (1 g) (Aldrich). The reaction was stirred for 1 hour at 70° C. After complete reaction the solvent was removed under reduced pressure to give a solid mass. Ether was added and the tan solid filtered (3.2 g). MS and H-NMR were consistent with the proposed structure.

Step B

To the compound produced in Step D (1 g) ethanol (10 mL) was added followed by addition of hydrazine (1.5 mL) (Aldrich). The reaction was stirred for 1 hour at 25° C. After complete reaction the solvent was removed under reduced pressure to give a solid mass. After complete reaction (1 hour) the product was purified by reverse phase chromatography (water/acetonitrile) to result in a white solid (0.7 g). MS and H-NMR were consistent with the proposed structure.

Step F

The compound produced in Step E (300 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 430 mg of the title compound as a white solid. MS and H-NMR were consistent with the proposed structure.

EXAMPLE 283

Preparation of β-[[2-[[[3-[(1,2,3,4-tetrahydro-2,4-dioxopyrimidin-6-yl)amino]phenyl]carbonyl]amino]acetyl]amino]pyridine-3-propanoic acid, trifluoroacetate salt

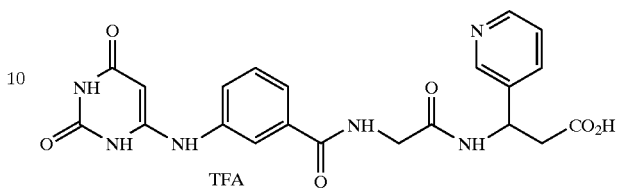

Step A

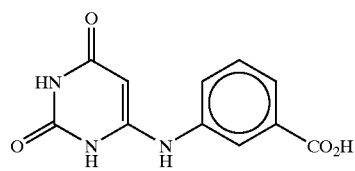

3-Aminobenzoic acid (4 g) was added to ethoxyethanol (4 mL), followed by 6-chloro uracil (4 g), and heated to 125° C. for 3–4 hours. The product was filtered, washed with ether and air dried (4.5 g) to give a tan solid. MS and H-NMR were consistent with the proposed structure.

Step B

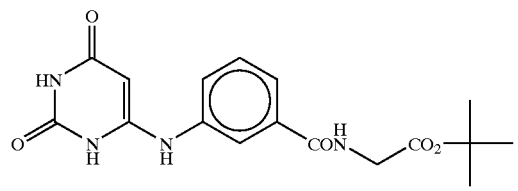

N,N'-disuccinimidyl carbonate (DSC) (2 g, 0.7 mmol) was added to the compound produced in Step A (2.0 g, 0.4 mmol) in dry dimethylformamide (6 mL) followed by addition of dimethylaminopyridine (100 mg). After a period of 20 minutes tert-butyl glycine hydrochloride (1.1 g, 0.5 mmol) was added followed by addition of DIEA (2.0 mL). After complete reaction (2–3 hours) the product was isolated by extraction in ethyl acetate, washed with aqueous HCl, saturated $K_2CO_3$, brine and dried over $Na_2SO_4$ to result in a yellow oil (3 g). MS and H-NMR were consistent with the proposed structure.

Step C

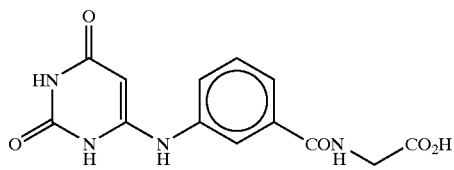

The compound produced in Step B (2 g) was dissolved in methylene chloride (50 mL). To this mixture TFA (20 mL) was added. The mixture was stirred for 12 hours. The solvent was removed under reduced pressure followed by addition of ether. The solid (1.8 g) was filtered and dried in a vacuum for 1–2 hours. MS and H-NMR were consistent with the proposed structure.

Step D

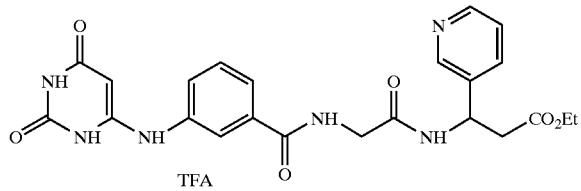

N,N'-disuccinimidyl carbonate (DSC) (1.5 g, 0.7 mmol) was added to the compound produced in Step C of Example 283 (1.0 g, 0.4 mmol) in dry dimethylformamide (6 &L) followed by addition of dimethylaminopyridine (100 mg). After a period of 20 minutes, DL ethyl-3-amino-3-(3-pyridyl)propionate hydrochloride (1.1 g, 0.5 mmol) was added followed by addition of NMM (2.0 mL). After complete reaction (1–16 hours) the product was purified by reverse phase chromatography (water/acetonitrile) to result in a white solid (0.9 g). MS and H-NMR were consistent with the proposed structure.

Step E

The compound produced in Step D (300 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 430 mg of the title compound as a white solid. MS and H-NMR were consistent with the proposed structure.

EXAMPLE 284

Preparation of 3,5-dichloro-β-[[2-[[[3-[[1,2,3,4-tetrahydro-2,4-dioxopyrimidin-6-yl)amino]phenyl]carbonyl]amino]acetyl]amino]benzenepropanoic acid

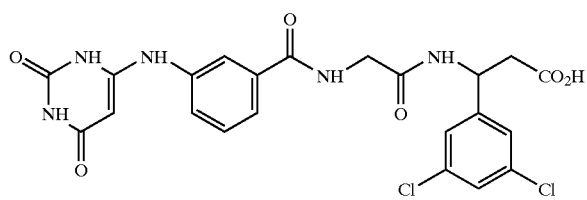

Step A

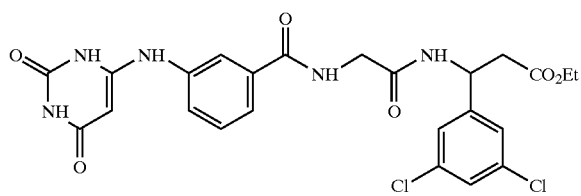

N,N'-disuccinimidyl carbonate (DSC) (0.6 g) was added to the compound from Step C of Example 283 (0.6 g) in dry dimethylformamide (6 mL) followed by addition of dimethylaminopyridine (100 mg). After a period of 20 minutes DL ethyl-3-amino-3-(3,5-dichlorophenyl)propionate hydrochloride (1.1 g, 0.5 mmol) was added followed by addition of NMM (2.0 mL). After complete reaction (1–16 hours) the product was purified by reverse phase chromatography (water/acetonitrile) to result in a white solid (0.9 g). MS and H-NMR were consistent with the proposed structure.

Step B

The compound produced in Step A (200 mg) was dissolved in water/acetonitrile (1:1), followed by addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 105 mg of the title compound as a white solid. MS and H-NMR were consistent with the proposed structure.

EXAMPLE 285

Preparation of 3,5-dichloro-β-[[2-[[[3-[[imino(1-piperidinyl)methyl]amino]phenyl]carbonyl]amino]acetyl]amino]benzenepropanoic acid, trifluoroacetate salt

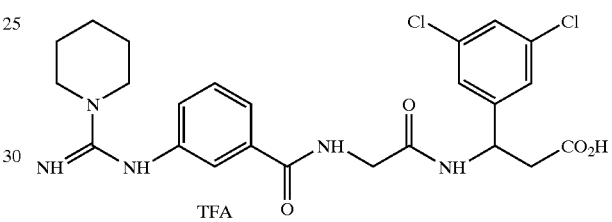

Step A

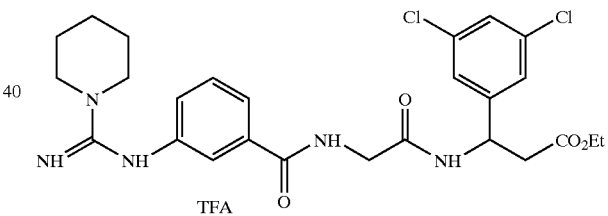

The above compound was prepared according to methodology of Example 24, substituting one equivalent of piperidine for benzylamine in Example 23, Step B, and an equivalent amount of DL ethyl-3-amino-3-(3,5-dichlorophenyl)propionate hydrochloride for DL ethyl-3-amino-3-(3-pyridyl)propionate dihydrochloride in Example 1, Step C and further used in Example 1, Step D as described in Example 23, Step C. MS and H-NMR were consistent with the proposed structure.

Step B

The compound prepared in Step A (200 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 105 mg of the title compound as a white solid. MS and H-NMR were consistent with the proposed structure.

EXAMPLE 286

Preparation of β-[[2-[[[3-[[benzoxazol-2-yl)amino]phenyl]carbonyl]amino]acetyl]amino]pyridine-3-propanoic acid, trifluoroacetate salt

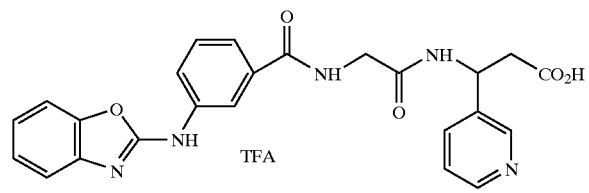

Step A

The compound prepared in Example 104 (2.0 g) was added to absolute ethanol (60 mL) in a Parr jar. Palladium on carbon 5% (500 mg) was added and the mixture was hydrogenolyzed under 50 psi in a Parr apparatus for a period of 2.5 hours. After complete reaction the palladium catalyst was removed by filtration through a plug of celite. The solvent was removed under reduced pressure and the sample dried in vacuo.

Step B

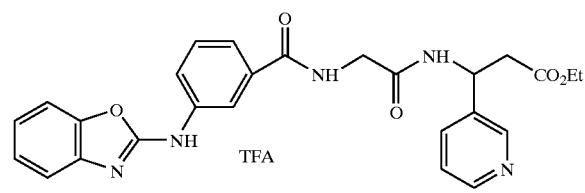

The compound prepared in Step A was dissolved in DMF (20 mL). To this mixture 2-chlorobenzoxazole (Aldrich) (2 g) and $K_2CO_3$ (4 g) was added. The mixture was heated to 70° C. until the aniline was consumed. After complete reaction, the product was purified by reverse phase chromatography (water/acetonitrile) to result in 215 mg of the title compound as a white solid. MS and H-NMR were consistent with the proposed structure.

Step C

The compound prepared in Step B (200 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 185 mg of the title compound as a white solid. MS and H-NMR were consistent with the proposed structure.

EXAMPLE 287

Preparation of β-[[2-[[[3-[[5-phenyl-1H-imidazol-2-yl)amino]phenyl]carbonyl amino]acetyl]amino]pyridine-3-propanoic acid, trifluoroacetate salt

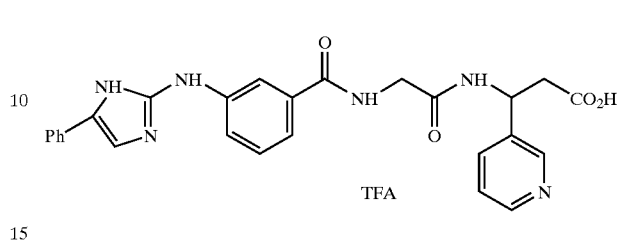

Step A

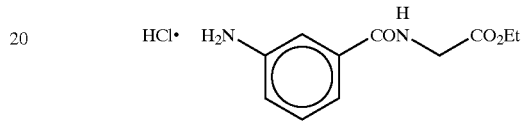

The compound prepared in Example M, Step B (5 g) was added to ethanol (100 mL) followed by dry HCl in dioxane (10 mL). The mixture was heated to reflux for 2 hours. The solvent was removed under reduced pressure to give the ethyl ester (5.6 g). MS and H-NMR were consistent with the proposed structure.

Step B

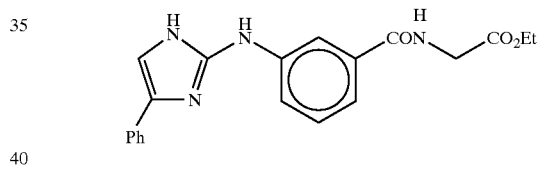

To the product of Step A (3 g) acetonitrile (50 mL) was added followed by addition of bromoacetophenone (2.7 g) and DIEA (2 mL). The mixture was heated for 2 hours and the solvent removed under reduced pressure. The product was isolated by extraction into ethyl acetate and dried over $Na_2SO_4$ to give a dark red solid (5 g). MS and H-NMR were consistent with the proposed structure.

Step C

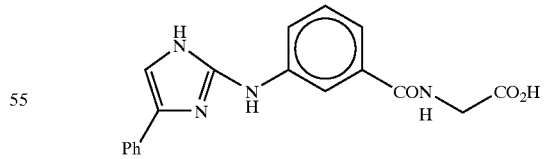

The compound produced in Step B (2 g) was dissolved in water/acetonitrile (1:1), followed by the addition of lithium hydroxide (100 mg). The reaction was allowed to stir at 25° C., and monitored by HPLC. After complete hydrolysis (1–2 hours) aqueous HCl was added until pH=7. The product was filtered and dried in an oven to result in 2.6 g of a tan solid. MS and H-NMR were consistent with the proposed structure.

Step D

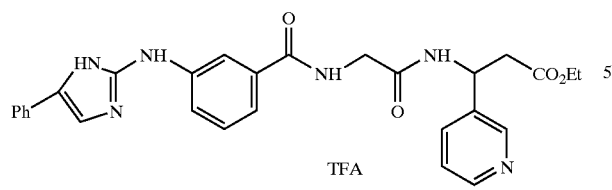

N,N'-disuccinimidyl carbonate (DSC) (0.3 g, 0.7 mmol) was added to the compound produced in Step C (0.5 g, 0.4 mmol) in dry dimethylformamide (5 mL) followed by addition of dimethylaminopyridine (100 mg). After a period of 20 minutes, DL ethyl-3-amino-3-(3-pyridyl)propionate hydrochloride (1.1 g, 0.5 mmol) was added followed by addition of NMM (2.0 mL). After complete reaction (1–16 hours) the product was purified by reverse phase chromatography (water/acetonitrile) to result in a white solid (0.9 g). MS and H-NMR were consistent with the proposed structure.

Step E

The compound produced in Step D (250 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 110 mg of the title compound as a white solid. MS and H-NMR were consistent with the proposed structure.

EXAMPLE 288

Preparation of 3-[[2-[[[3-[(aminoiminomethyl)amino]phenyl]carbonyl]amino]acetyl]amino)-5-[(3,5-dichlorophenyl)amino]-5-oxopentanoic acid, trifluoroacetate salt

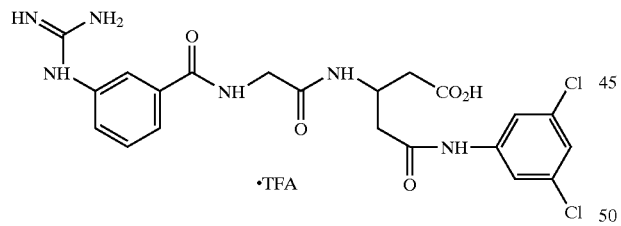

Step A

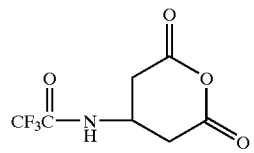

A mixture of β-amino glutaric acid (Sigma) (5 g) and trifluroacetic anhydride (Sigma) (20 mL) was stirred for 1–2 hours at 25° C. The solvent was removed under reduced pressure to leave an oil. To the oil was added ether (50 mL) and the product filtered (5 g). MS and H-NMR were consistent with the proposed structure.

Step B

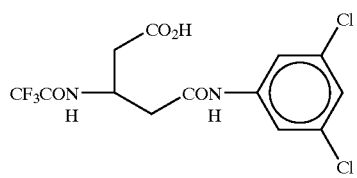

A DMF (20 mL) mixture of the product from Step A and 3,5 dichloroaniline (6 g) was stirred for 16 hours. After complete reaction aqueous HCl (100 mL) and ethyl acetate (100 mL) were added and the mixture, shaken and separated. The organic layer was washed with brine and dried over $Na_2SO_4$ to give the acid amide (4 g). MS and H-NMR were consistent with proposed structure.

Step C

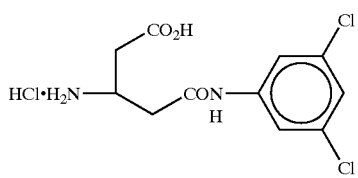

The trifluoroacetate group of the product of Step B was removed by heating the compound produced in Step B with dilute ammonium hydroxide (10 mL in 50 mL water). After complete reaction the mixture was acidified with 10% HCl and the product (2.5 g) was filtered. MS and H-NMR were consistent with the proposed structure.

Step D

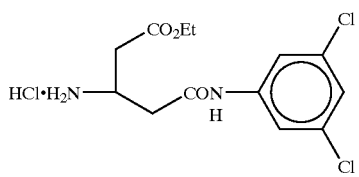

The compound produced in Step C (2 g) was added to ethanol (100 mL) followed by dry HCl in dioxane (10 mL). The mixture was heated to reflux for 2 hours. The solvent was removed under reduced pressure to give the ethyl ester (1.9 g). MS and H-NMR were consistent with the proposed structure.

Step E

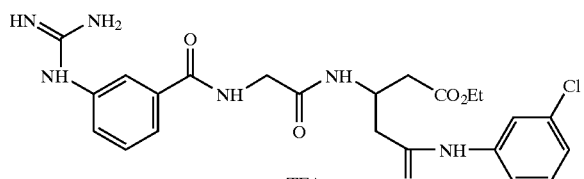

N,N-disuccinimidyl carbonate (DSC) (0.6 g, 0.7 mmol) was added to the compound produced in Example M, Step A (0.6 g, 0.4 mmol) in dry dimethylformamide (5 mL) followed by addition of dimethylaminopyridine (100 mg). After a period of 20 minutes the compound produced in Step D of Example 288 (0.7 g, 0.5 mmol) was added followed by addition of NMM (2.0 mL). After complete reaction (1–16 hours) the product was purified by reverse phase chromatography (water/acetonitrile) to result in a white solid (0.51 g). MS and H-NMR were consistent with the proposed structure.

Step F

The compound produced in Step E (250 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 110 mg of the title compound as a white solid. MS and H-NMR were consistent with the proposed structure.

EXAMPLE 289

Preparation of β-[[2-[[[3-[(aminoiminomethyl)amino]-5-carboxyphenyl]carbonyl]amino]acetyl]amino]pyridine-3-propanoic acid, bis (trifluoroacetate)salt

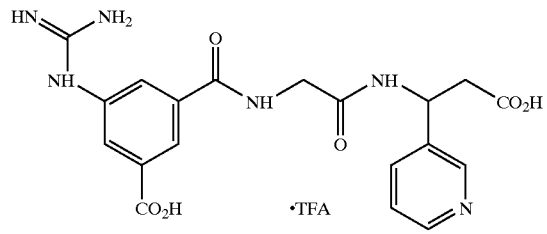

Step A

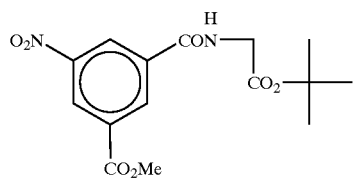

N,N'-disuccinimidyl carbonate (DSC) (6.5 g) was added to methyl hydrogen 5-nitroisophthalate (5 g) in dry dimethylformamide (10 mL) followed by addition of dimethylaminopyridine (200 mg). After a period of 20 minutes tert-butyl β-glycine (2.6 g) was added followed by addition of NMM (2.0 mL). After complete reaction (4 hours) the product was isolated by extraction into ethyl acetate and dried over $Na_2SO_4$ to result in a white solid (5.1 g). MS and H-NMR were consistent with the proposed structure.

Step B

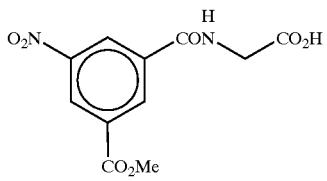

The compound produced in Step A (5 g) was dissolved in dioxane (50 mL). To this mixture dry HCl (20 mL, 4N) was added. The mixture was stirred for 1–2 hours. The solvent was removed under reduced pressure followed by addition of ether and removal of the solvent under reduced pressure. The solid was filtered to result in a white solid (4 g) and dried in a vacuum oven. MS and H-NMR were consistent with the proposed structure.

Step C

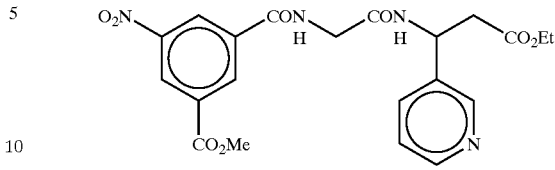

N,N-disuccinimidyl carbonate (DSC) (2 g) was added to the compound produced in Step B (2 g) in dry dimethylformamide (10 mL) followed by addition of dimethylaminopyridine (200 mg). After a period of 20 minutes, DL ethyl-3-amino-3-(3-pyridyl)propionate hydrochloride (1.6 g) was added followed by addition of NMM (2.0 mL). After complete reaction (4 hours) the product was isolated by extraction into ethyl acetate and dried over $Na_2SO_4$ to result in an oil (3 g). MS and H-NMR were consistent with the proposed structure.

Step D

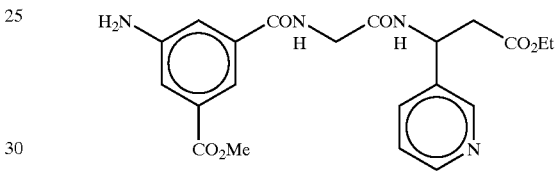

The compound produced in Step C was subjected to the conditions described in Tetrahedron Letters, Vol. 25, 1984, 839–842 to reduce the nitro group. The reduction was performed on 2 g of nitro compound to give 1 g of product. MS and H-NMR were consistent with the proposed structure.

Step E

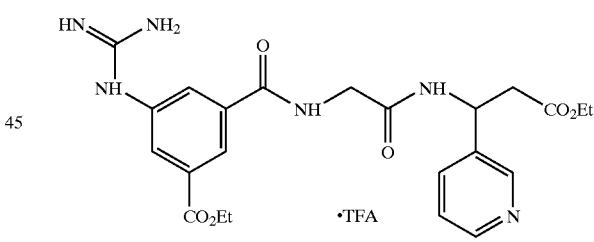

The compound produced in Step D was guanidated according to the method in Example M on a 1 g scale and purified by reverse phase chromatography (water/acetonitrile) to result in 110 mg of the title compound as a white solid. MS and H-NMR were consistent with the proposed structure.

Step F

The compound produced in Step E (100 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 110 mg of the title compound as a white solid. MS and H-NMR were consistent with the proposed structure.

EXAMPLE 290

Preparation of β-[[2-[[[3-[(aminoiminomethyl)amino]-5-carboxyphenyl]carbonyl]amino]acetyl]amino]-3,5-dichlorobenzenepropanoic acid, trifluoroacetate salt

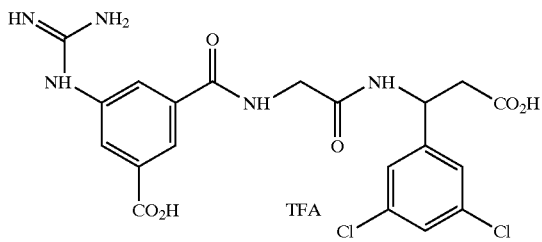

Step A

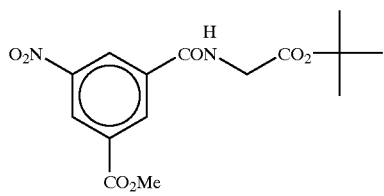

N,N-disuccinimidyl carbonate (DSC) (65 g) was added to methyl hydrogen 5-nitroisophthalate (5 g) in dry dimethylformamide (10 mL) followed by addition of dimethylaminopyridine (200 mg). After a period of 20 minutes tert-butyl β-glycine (2.6 g) was added followed by addition of NMM (2.0 mL). After complete reaction (4 hours) the product was isolated by extraction into ethyl acetate and dried over Na$_2$SO$_4$ to result in a white solid (5.1 g). MS and H-NMR were consistent with the proposed structure.

Step B

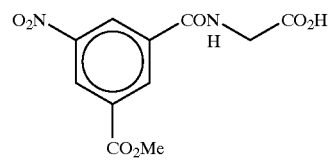

The compound produced in Step A (5 g) was dissolved in dioxane (50 mL). To this mixture dry HCl (20 mL, 4N) was added. The mixture was stirred for 12 hours. The solvent was removed under reduced pressure followed by addition of ether and removal of the solvent under reduced pressure. The solid was filtered to result in a white solid (4 g) and dried in a vacuum oven. MS and H-NMR were consistent with the proposed structure.

Step C

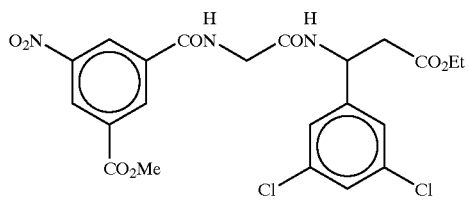

N,N'-disuccinimidyl carbonate (DSC) (2 g) was added to the compound produced in Step B (2 g) in dry dimethylformamide (10 mL) followed by addition of dimethylaminopyridine (200 mg). After a period of 20 minutes DL-ethyl 3-amino-3-(3,5-dichlorophenyl)propionate hydrochloride (1.6 g) was added followed by addition of NMM (2.0 mL). After complete reaction (4 hours) the product was isolated by extraction into ethyl acetate and dried over Na$_2$SO$_4$ to result in an oil (3 g). MS and H-NMR were consistent with the proposed structure.

Step D

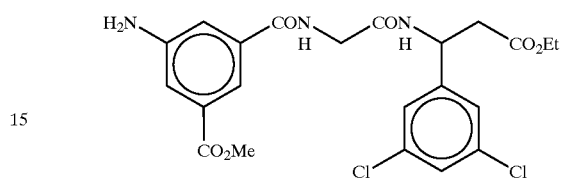

The compound produced in Step C was subjected to the conditions described in Tetrahedron Letters, Vol. 25, 1984, 839–842 to reduce the nitro group. The reduction was performed on 2 g of nitro compound to give 1 g of product.

Step E

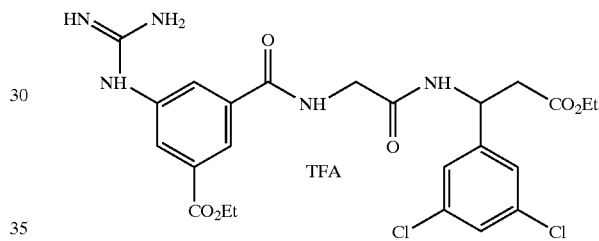

The compound produced in Step D was guanidated according to the method in Example M on a 1 g scale and purified by reverse phase chromatography (water/acetonitrile) to result in 110 mg of the title compound as a white solid. MS and H-NMR were consistent with the proposed structure.

Step F

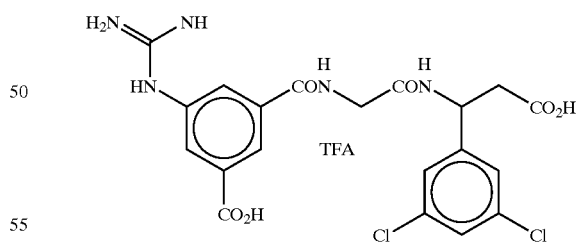

The compound produced in Step E (100 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 25 mg of the title compound as a white solid. MS and H-NMR were consistent with the proposed structure.

EXAMPLE 291

Preparation of β-[[2-[[[3,5-bis[(aminoiminomethyl)amino]phenyl]carbonyl)amino]acetyl]amino]-3,5-dichlorobenzenepropanoic acid, bis(trifluoroacetate) salt

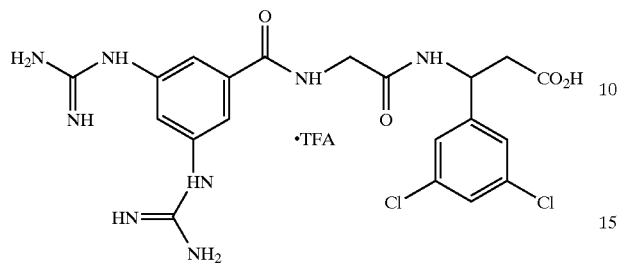

Step A

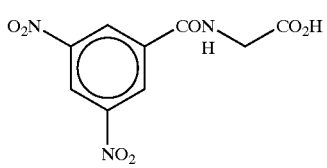

Glycine (20 g, 266 mmol) was added to water (200 mL), followed by addition of potassium hydroxide (20 g, 357 mmol) and cooled to 0° C. in an ice bath. To this mixture 3,5-dinitrobenzoyl chloride (20 g, 108 mmol) was added in acetonitrile (20 mL) drop-wise over a 10 minute period. After complete reaction (3–4 hours) concentrated hydrochloric acid was added until pH=1. The product was filtered, washed with water and air dried (20 g). MS and H-NMR were consistent with the proposed structure.

Step B

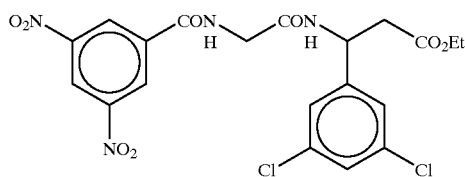

N,N'-disuccinimidyl carbonate (DSC) (1.2 g) was added to the compound produced in Step A (2 g) in dry dimethylformamide (10 mL) followed by addition of dimethylaminopyridine (200 mg). After a period of 20 minutes, DL ethyl 3-amino-3-(3,5 dichlorophenyl)propionate hydrochloride (1.2 g) was added followed by addition of NMM (2.0 mL). After complete reaction (4 hours) the product was isolated by extraction into ethyl acetate and dried over $Na_2SO_4$ to result in an yellow oil (2.1 g). MS and H-NMR were consistent with the proposed structure.

Step C

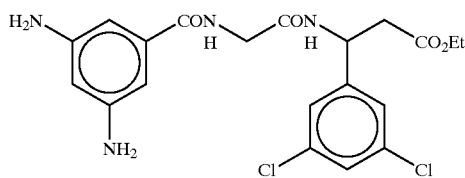

The compound produced in Step B was subjected to the conditions described in Tetrahedron Letters, Vol. 25, 1984, 839–842 to reduce of the nitro group. The reduction was performed on 2.5 g of nitro compound to give 2.1 g of the 3,5-dianilino derivative. MS and H-NMR were consistent with the proposed structure.

Step D

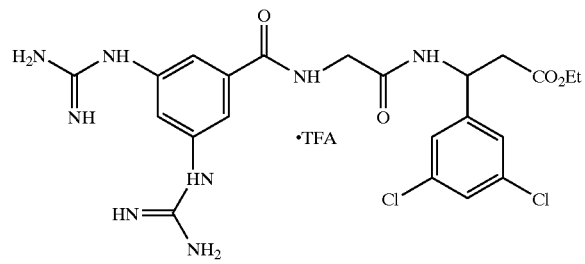

The compound produced in Step C was guanidated according to the method in Example N on a 2 g scale (using 4 g of the guanidating agent) and purified by reverse phase chromatography (water/acetonitrile) to result in 800 mg of a white solid. MS and H-NMR were consistent with the proposed structure.

Step E

The compound produced in Step D (500 mg) was dissolved in water/acetonitrile (1:1), followed by addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 450 mg of the title compound as a white solid. MS and H-NMR were consistent with the proposed structure.

EXAMPLE 292

Preparation of β-[[2-[[[3-[(aminoiminomethyl)amino]-5-(trifluoroacetyl)amino]phenyl]carbonyl]amino]acetyl]amino]-3,5-dichlorobenzenepropanoic acid, trifluoroacetate salt

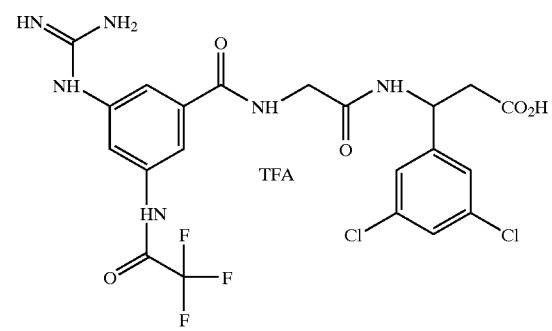

Step A

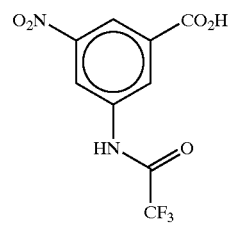

A mixture of 5-amino-3-nitro benzoic acid (Lancaster) (3 g) and trifluroacetic anhydride (Sigma) (20 mL) in methylene chloride was stirred for 2 days at 25° C. The solvent was removed under reduced pressure to leave an oil. To the oil was added water (50 mL) and the product filtered (4.5 g). The product was dried in an oven at 70° C. for 16 hours. MS and H-NMR were consistent with the proposed structure.

Step B

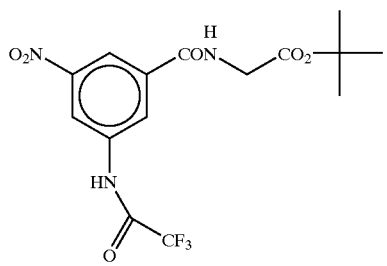

N,N'-disuccinimidyl carbonate (DSC) (3 g) was added to the compound produced in Step A (2.7 g) in dry dimethylformamide (4 mL) followed by addition of dimethylaminopyridine (200 mg). After a period of 20 minutes, tert-butyl glycine hydrochloride (2.7 g) was added followed by addition of NMM (2.0 mL). After complete reaction (4 hours) the product was isolated by extraction into ethyl acetate and dried over $Na_2SO_4$ to result in an yellow oil (3.3 g). MS and H-NMR were consistent with the proposed structure.

Step C

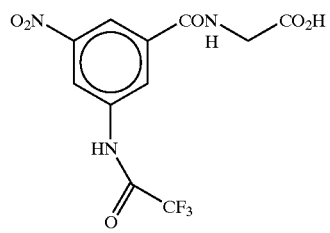

The compound produced in Step B (3 g) was dissolved in methylene chloride (50 mL). To this mixture TFA (20 mL) was added. The mixture was stirred for 12 hours. The solvent was removed under reduced pressure followed by addition of ether. The solid (2.7 g) was filtered and dried in a vacuum oven for 1–2 hours. MS and H-NMR were consistent with the proposed structure.

Step D

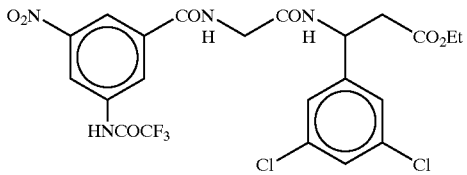

N,N'-disuccinimidyl carbonate (DSC) (1.5 g) was added to the product of Step C (1.2 g) in dry dimethylformamide (10 mL) followed by addition of dimethylaminopyridine (200 mg). After a period of 20 minutes DL ethyl 3-amino-3-(3,5 dichlorophenyl)propionate hydrochloride (1.7 g) was added followed by addition of NMM (2.0 mL). After complete reaction (4 hours) the product was isolated by extraction into ethyl acetate and dried over $Na_2SO_4$ to result in an yellow oil (2.1 g). MS and H-NMR were consistent with the proposed structure.

Step E

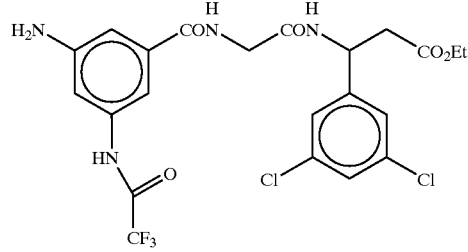

The compound produced in Step D was subjected to the conditions described in Tetrahedron Letters, Vol. 25, 1984, 839–842 to reduce the nitro group. The reduction was performed on 1.8 g of nitro compound to give 1.8 g of the 3-anilino derivative. MS and H-NMR were consistent with the proposed structure.

Step F

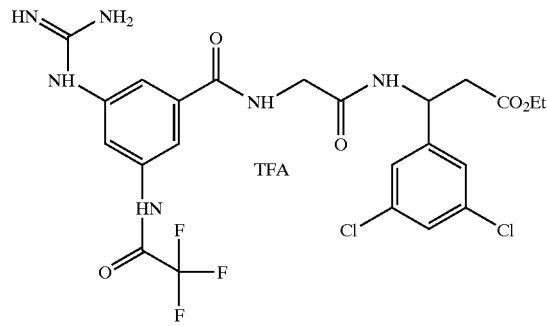

The compound produced in Step E was guanidated according to the method in Example M on a 1.5 g scale (using 3 g of the guanidating agent) and purified by reverse phase chromatography (water/acetonitrile) to result in 750 mg of the above compound as a white solid. MS and H-NMR were consistent with the proposed structure.

Step G

The compound produced in Step F (500 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 300 mg of the title compound as a white solid. MS and H-NMR were consistent with the proposed structure.

EXAMPLE 293

Preparation of β-[[2-[[[3-(acetylamino)-5-[(aminoiminomethyl)amino]phenyl]carbonyl]amino] acetyl]amino]-3,5-dichlorobenzenepropanoic acid, trifluoroacetate salt

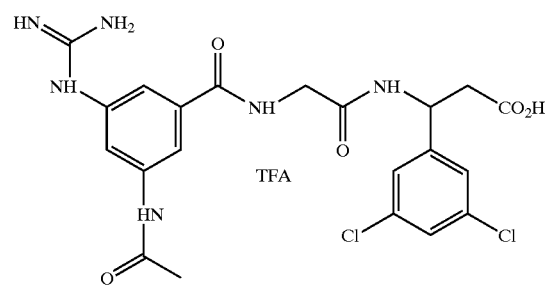

Step A

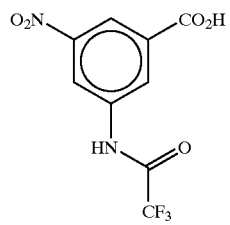

A mixture of 5-amino-3-nitro benzoic acid (Lancaster) (5 g) and acetic anhydride (Sigma) (10 mL) in methylene chloride was stirred for 2 days at 25° C. The solvent was removed under reduced pressure to leave an oil. To the oil was added water (50 mL) and the product filtered (4.5 g). The product was dried in an oven at 70° C. for 16 hours. MS and H-NMR were consistent with the proposed structure.

Step B

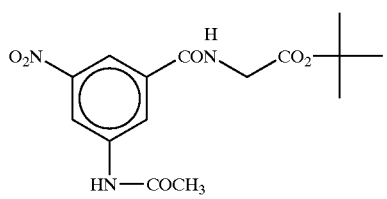

N,N'-disuccinimidyl carbonate (DSC) (3 g) was added to the compound produced in Step A (3 g) in dry dimethylformamide (6 mL) followed by addition of dimethylaminopyridine (200 mg). After a period of 20 minutes tert-butyl glycine hydrochloride (2.1 g) was added followed by addition of NMM (2.0 mL). After complete reaction (4 hours) the product was isolated by extraction into ethyl acetate and dried over $Na_2SO_4$ to result in an yellow oil (3.3 g). MS and H-NMR were consistent with the proposed structure.

Step C

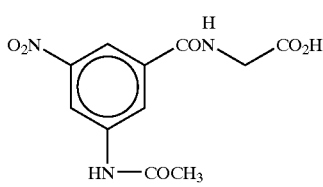

The compound produced in Step B (3 g) was dissolved in methylene chloride (10 mL). To this mixture TFA (10 mL) was added. The mixture was stirred for 12 hours. The solvent was removed under reduced pressure followed by addition of addition of ether. The solid (3 g) was filtered and dried in a vacuum oven for 1–2 hours. MS and H-NMR were consistent with the proposed structure.

Step D

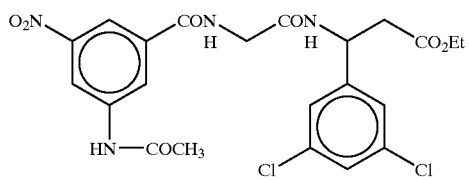

N,N'-disuccinimidyl carbonate (DSC) (1.5 g) was added to the product from Step C (1.2 g) in dry dimethylformamide (10 mL) followed by addition of dimethylaminopyridine (200 mg). After a period of 20 minutes DL ethyl 3-amino-3-(3,5 dichlorophenyl)propionate hydrochloride (1.7 g) was added followed by addition of NMM (2.0 mL). After complete reaction (4 hours) the product was isolated by extraction into ethyl acetate and dried over $Na_2SO_4$ to result in a tan solid (2 g). MS and H-NMR were consistent with the proposed structure.

Step E

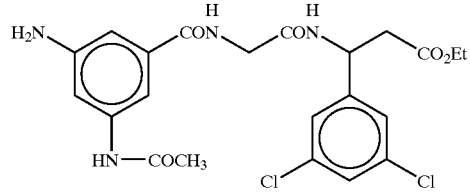

The compound produced in Step D was subjected to the conditions described in Tetrahedron Letters, Vol. 25, 1984, 839–842 to reduce the nitro group. The reduction was performed on 1.5 g of nitro compound to give 1.5 g of the 3-anilino derivative. MS and H-NMR were consistent with the proposed structure.

Step F

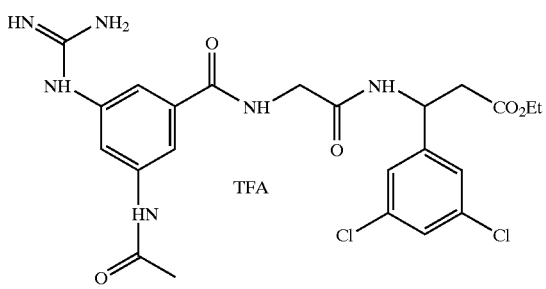

The compound produced in Step E was guanidated according to the method in Example N on a 1.4 g scale (using 2 g of the guanidating agent) and purified by reverse phase chromatography (water/acetonitrile) to result in 750 mg of the above compound as a white solid. MS and H-NMR were consistent with the proposed structure.

Step G

The compound produced in Step F (300 mg) was dissolved in water/acetonitrile (1:1), followed by the addition of lithium hydroxide (100 mg). The reaction was allowed to stir at 25° C., and monitored by HPLC. After complete hydrolysis (1–2 hours) trifluoroacetic acid was added until pH=2. The product was purified by reverse phase chromatography (water/acetonitrile) to result in 200 mg of the title compound as a white solid. MS and H-NMR were consistent with the proposed structure.

EXAMPLES 294–296

Step A

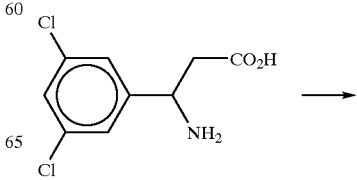

-continued

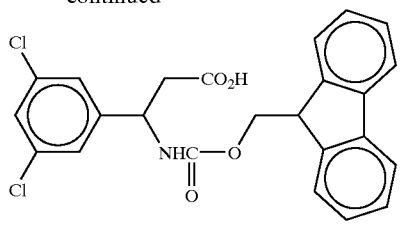

To a 2 L-3-neck round bottom flask equipped with mechanical stirrer was added β-amino-3,5-dichlorobenzenepropanoic acid (52.78 g, 0.2255 mol). The β-amino-3,5-dichlorobenzenepropanoic acid was dissolved in 900 mL of acetone and 300 mL of water and sodium carbonate was added (3.0 eq., 71.70 g, 0.6765 mol). The pH=10. The FMOC succinimidyl carbonate (Sigma Chemical Co., 1.0 eq., 76.06 g, 0.2255 mol) was dissolved in 600 mL of acetone and added slowly to the basic aqueous solution via addition funnel over 45 minutes. The reaction was stirred for 16 hours at room temperature. HPLC analysis (Waters, C18, reverse phase, 25 cm column, 50–90% acetonitrile in water over 30 minutes) indicated that the β-amino-3,5-dichlorobenzenepropanoic acid was consumed. The acetone was removed from the reaction mixture in vacuo. The basic aqueous phase was acidified to pH=3 using 3.0 N hydrochloric acid. In a 2 L separatory funnel the acid layer was washed with 1 L of ethyl acetate, the water layer was removed and the organic layer was washed (2×250 mL water, 2×250 mL saturated sodium chloride). The organic layer was dried (magnesium sulfate), filtered and concentrated in vacuo to 300 mL. Petroleum ether was added (300 mL) and a white flocculent solid precipitated. After 24 hours of air drying, isolated 38.49 g as a first crop (38% yield). The mother liquor was saved for future use. NMR (DMSO): 2.62–2.72 (m, 2H), 4.15–4.32 (m, 1H), 7.21–7.40 (m, 5H), 7.45 (s, 1H), 7.60–7.70 (m, 2H), 7.85 (d, j=7 Hz, 2H), 7.99 (d, j=7 Hz, 1H). MS (FAB) m/e (relative intensity): 456.2 (20), 179 (100).

Step B

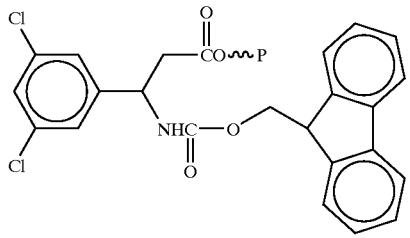

Wang resin (25.0 g, 28.0 mmol) was placed in a 1 L 3-neck round bottom flask fitted with an overhead stirrer and nitrogen inlet. The resin was swelled with 250 mL of methylene chloride for 15 minutes then drained. The FMOC protected amino acid produced in Step A (25.66 g, 56.0 mmol) was activated in a separate 500 mL round bottom flask by dissolving in methylene chloride/dimethylformamide (4:1, 125 mL) and adding diisopropylcarbodiimide (DIC, 8.77 mL, 56.0 mmol) via syringe, followed by addition of dimethylaminopyridine (DMAP, 0.342 g, 2.8 mmol). The solution was stirred at 25° C. for 15 minutes, then added to the preswelled Wang resin. The slurry was stirred for 2 hours at 25° C. The reaction was drained and washed with methanol (3×250 mL), methylene chloride (3×250 mL) and diethyl ether (3×250 mL). The resin was then swelled in 250 mL of methylene chloride and drained. The activated product of Step A (12.83 g, 28.0 mmol, DIC, 4.36 mL, 28.0 mmol, DMAP, 0.170 g, 1.4 mmol in 100 mL methylene chloride/dimethylformamide 4:1) was added to the swelled resin. The slurry was stirred at 25° C. for 1 hour. The resin was drained and washed as before. Elemental analysis calculated for resin bound material: Calculated: C, 81.31; H, 6.30; H, 1.05; Cl, 5.33. Found: C, 79.03; H, 6.37; N, 1.16; Cl, 5.74.

Step C

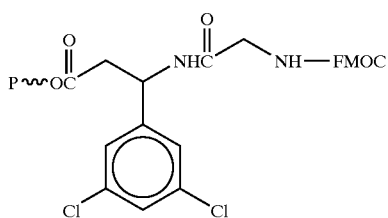

The product of Step B (28.0 mmol) was preswelled in a 1 L 3-neck round bottom flask equipped with overhead stirrer and nitrogen inlet using 250 mL of methylene chloride for 15 minutes. The solvent was drained and a 20% piperidine/dimethylformamide solution (125 mL) was added and the slurry was stirred at 25° C. for 2 hours. The resin was drained and washed with dimethylformamide (3×100 mL), methanol (3×100 mL) methylene chloride (3×100 mL) and diethyl ether (3×100 mL). The resin was dried using house vacuum for 1 hour. An activated solution of FMOC-Glycine (20.81 g, 70.0 mmol, DIC, 10.95 mL, 70.0 mmol, DMAP, 0.85 g, 7.0 mmol. In 150 mL methylene chloride/dimethylformamide, 4:1) was added to the preswelled resin via syringe and stirred at 25° C. for 2 hours. The resin was drained and washed (methylene chloride, methanol and diethyl ether, each 3×100 mL). The resin was preswelled with 250 mL of methylene chloride for 15 minutes, drained and a solution of activated FMOC-Glycine (10.45 g, 35.0 mmol, DIC, 5.42 mL, 35.0 mmol, DMAP, 0.42 g, 3.5 mmol in 100 mL methylene chloride/dimethylformamide 4:1) was added to the swelled resin via syringe. The slurry was stirred at 25° C. for 1 hour. The resin was drained and washed (methylene chloride, methanol, diethyl ether, 3×100 mL each). The resin was vacuum dried for 1 hour. The Kaiser test (Kaiser, E., Color Test for Detection of Free Terminal Amino Groups in the Solid-Phase Synthesis of Peptides. Anal. Biochem. 1970, 34, 595–598) indicated coupling was complete.

Step D

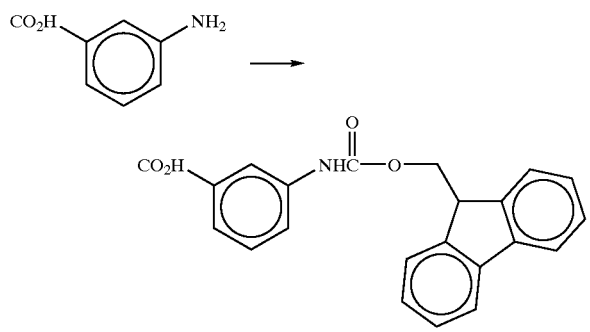

In a 500 mL bottom flask equipped with magnetic stirrer, 3-amino-benzoic acid (Aldrich, 10.0 g, 50.8 mmol) was dissolved in 50 mL of dioxane and 133 mL of 10% sodium carbonate. The stirred solution was cooled to 0° C. (ice/water) and a solution of fluorenylmethyl chloroformate (13.78 g, 53.3 mmol, in 50 mL dioxane) was added dropwise over 15 minutes. The reaction was warmed to 25° C. overnight. HPLC analysis (as described earlier) indicated that the starting material was consumed. 500 mL of water was added to the reaction mixture and a white precipitate formed immediately. The solid was collected, washed with 10% citric acid and dried under vacuum. Isolated 15.23 g, (83.4% yield) of a white flocculent solid. NMR (DMSO): 4.18–4.25 (m, 3H), 7.25–7.41 (m, 6H), 7.62–7.72 (m, 3H), 7.89–7.90 (m, 3H). MS (FAB): product ion M+H observed at m/z 360.

Step E

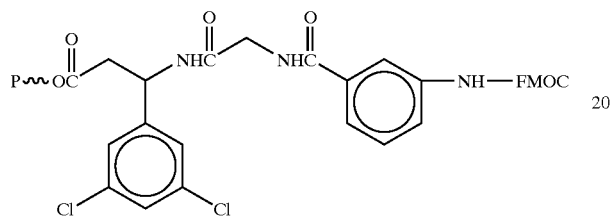

20.0 g of the product of Step C (22.4 mmol) was preswelled in 500 mL of methylene chloride for 30 minutes. The solvent was drained and 250 mL of 20% piperidine/dimethyl formamide was added and allowed to stir at 25° C. for 40 minutes. The resin was drained and washed with dimethyl formamide, methanol, methylene chloride, and diethyl ether (each solvent, 3×150 mL). The Kaiser test indicated the deprotection was complete. The resin was dried using house vacuum for 45 minutes. The resin was then preswelled using 250 mL of methylene chloride, drained and the activated product of Step D (13.54 g, 35.5 mmol, DIC, 5.55 mL, 35.5 mmol, DMAP, 0.88 g, 7.2 mmol, in 100 mL methylene chloride/dimethyl formamide 4:1) was added to the preswelled resin. The reaction was stirred for 16 hours at 25° C. The resin was drained and washed as previously described. The Kaiser test indicated that the reaction was not complete. The coupling reaction was repeated, the resin was drained and washed. A repeat Kaiser test indicated that the coupling reaction was complete. A small portion of the resin was FMOC deprotected (30 minutes with 20% piperidine/dimethyl formamide) then cleaved off resin (1 hour with 95% trifluoroacetic acid/water) for NMR analysis. NMR (DMSO): 2.68–2.78 (m, 2H), 3.88 (d, j=7 Hz, 2H), 5.06–5.20 (m, 1H), 7.32–7.69 (m, 4H), 7.54 (t, j=8 Hz, 1H), 7.76 (s, 1H), 7.83 (d, j=8 Hz, 1H), 8.57 (d, j=9 Hz, 1H), 8.87 (t, j=9 Hz, 1H).

Step F

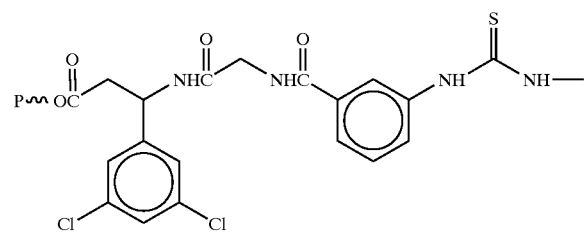

The resin of Step E (2.0 g, 2.0 mmol) in a 100 mL round bottom flask, was preswelled with 20 mL of dimethyl formamide, drained, then treated with 20 mL of 20% piperidine/dimethyl formamide for 40 minutes at 25° C. The resin was filtered and washed with dimethyl formamide, methanol, methylene chloride and diethyl ether (3×10 mL, each). The Kaiser test was inconclusive, and the deprotection step and washings were repeated. The repeat Kaiser test was still inconclusive, and the material used as is. The 2.0 g of resin was split into two 1.0 g portions and placed into 2 dram glass vials. Dimethyl formamide (4.0 mL/vial) was added, followed by methyl isothiocyanate (1.4622 g, 20 mmol). The vials were tightly capped and heated to 80° C. for 4 hours. The resin was filtered and washed with dimethyl formamide, methanol, methylene chloride, and diethyl ether (3×10 mL, each). The resin was dried in vacuo.

Step G

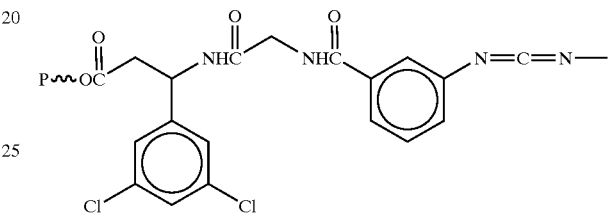

The resin product from Step F was transferred to a fritted, 100 mL reaction vessel. The resin was swelled with methylene chloride (3×10 mL) and drained. In a separate vial 2-chloro-1-methylpyridiniumiodide (Aldrich, 0.405 g, 1.58 mmol) was dissolved in 5 mL of dimethylformamide/methylene chloride 4:1 and added to the preswelled resin, followed by triethylamine (0.441 mL, 3.17 mmol). The reaction slurry was stirred for 8 hours at 25° C. The resin was drained, and washed with dimethylformamide and methylene chloride (3×10 mL each). The resin was dried in vacuo.

Step H

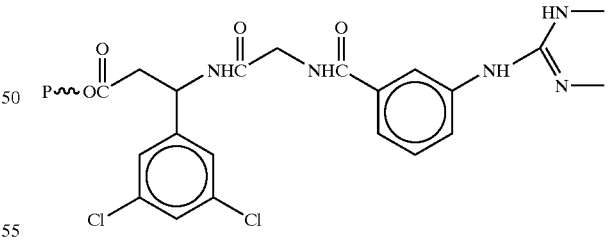

The resin product from Step G (0.666 g, 0.7 mmol) was transferred to a 15 mL fritted vessel and suspended in 3.5 mL of dimethylformamide/methylene chloride (1:1). Methylamine (2.0 M in tetrahydrofuran, 4.4 mL, 8.8 mmol) was added to the resin slurry and allowed to stir at 25° C. for 16 hours. The resin was drained, and washed with dimethylformamide, methanol, methylene chloride and diethyl ether (3×10 mL each). The resin was dried in vacuo for 1 hour.

Step I

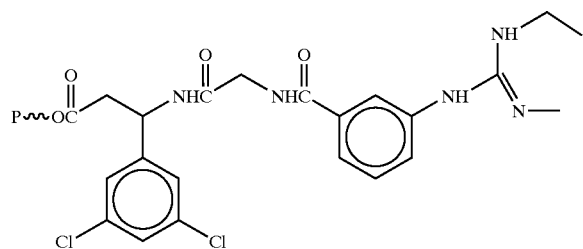

The resin product from Step G (0.666 g, 0.7 mmol) was transferred to a 15 mL fritted vessel and suspended in 3.5 mL dimethylformamide/methylene chloride (1:1). Ethylamine (2.0 M in tetrahydrofuran, 4.4 mL, 8.8 mmol) was added to the resin slurry and allowed to stir at 25° C. for 16 hours. The resin was drained, and washed with dimethylformamide, methanol, methylene chloride and diethyl ether (3×10 mL each). The resin was dried in vacuo for 1 hour.

Step J

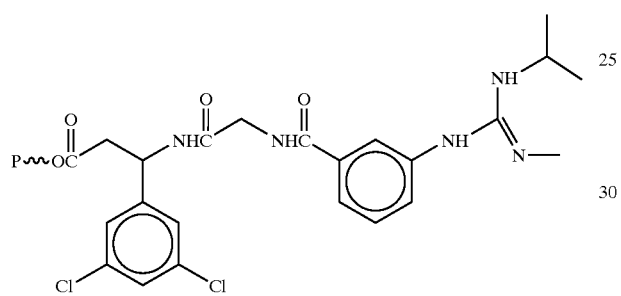

The resin product from Step G (0.666 g, 0.7 mmol) was transferred to a 15 mL fritted vessel and suspended in 3.5 mL dimethylformamide/methylene chloride (1:1). Isopropylamine (0.749 mL, 8.8 mmol) was added to the resin slurry and allowed to stir at 25° C. for 16 hours. The resin was drained, and washed with dimethylformamide, methanol, methylene chloride and diethyl ether (3×10 mL each). The resin was dried in vacuo for 1 hour.

EXAMPLE 294

Preparation of (±)3,5-dichloro-β-[[2-[[[3-[[(methylamino)(methylimino)methyl]amino]phenyl]carbonyl]amino]acetyl]amino]benzenepropanoic acid, trifluoroacetate salt

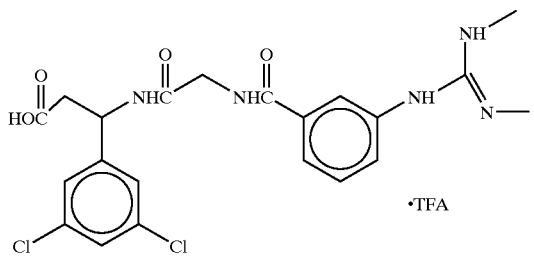

The resin product from Step H was treated with 2.5 mL of 95% trifluoroacetic acid/water for 1 hour at 25° C. The filtrate was collected. The resin was washed with 2×1 mL of 50% trifluoroacetic acid/methylene chloride and the filtrate collected. The resin was washed once more with 1 mL of methylene chloride, All filtrates were combined into a tared 2 dram vial and concentrated under nitrogen flow. Toluene (1 mL) was added to aid in removing excess trifluoroacetic acid, and the sample was concentrated again under nitrogen. Lastly methylene chloride (1 mL) was added and the sample was reconcentrated to give 198.3 mg of a golden oil. HPLC (as described earlier, 220 nM) shows a 91% pure major peak. NMR (DMSO): 2.72 (d, j=7 Hz, 2H), 2.79 (s, 6H), 3.87 (d, j=7 Hz, 2H), 5.11–5.20 (m, 1H), 7.30–7.58 (m, 5H), 7.70–7.80 (m, 4H), 8.55 (d, j=8 Hz, 1H), 8.76 (t, j=3 Hz, 1H), 9.39 (s, 1H). MS(ES): product ion observed at m/z 480.

EXAMPLE 295

Preparation of (±)3,5-dichloro-β-[[2-[[[3-[[(ethylamino)(methylimino)methyl]amino]phenyl]carbonyl]amino]acetyl]amino]benzenepropanoic acid, trifluoroacetate salt

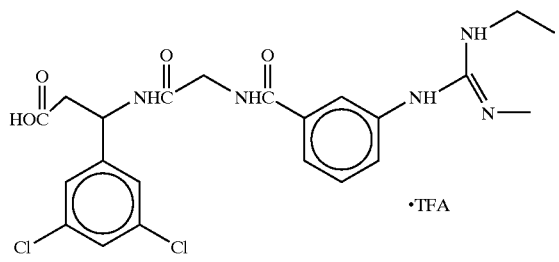

The resin product from Step I was treated with 2.5 mL of 95% trifluoroacetic acid/water for 1 hour at 25° C. The filtrate was collected. The resin was washed with 2×1 mL of 50% trifluoroacetic acid/methylene chloride and the filtrate collected. The resin was washed once more with 1 mL of methylene chloride. All filtrates were combined into a tared 2 dram vial and concentrated under nitrogen flow. Toluene (1 mL) was added to aid in removing excess trifluoroacetic acid, and the sample was concentrated again under nitrogen. Lastly methylene chloride (1 mL) was added and the sample was-reconcentrated to give 261.2 mg of a golden oil. HPLC (as described earlier, 220 nM) shows a 94% pure major peak. NMR (DMSO): 1.11 (t, j=7 Hz, 3H), 2.72 (d, J=7 HZ, 2H), 2.79 (s, 3H), 3.25–3.60 (m, 2H), 3.87 (d, j=7 Hz, 2H), 5.02–5.20 (m, 1H), 7.30–7.58 (m, 5H), 7.70–7.85 (m, 4H), 8.55 (d, j=8 Hz, 1H), 8.76 (t, j=3 Hz, 1H), 9.40 (s, 1H). MS(ES): product ion observed at m/z 494.

EXAMPLE 296

Preparation of (±)3,5-dichloro-β-[[2-[[[3-[[[(1-methylethyl)amino](methylimino)methyl]amino]phenyl]carbonyl]amino]acetyl]amino]benzenepropanoic acid, trifluoroacetate salt

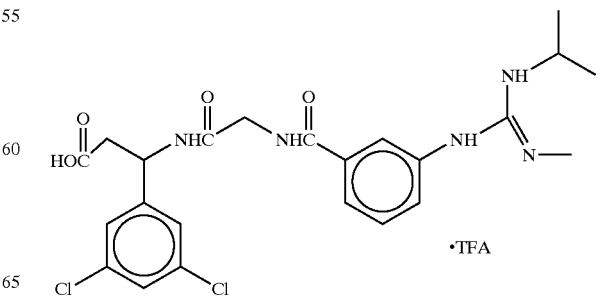

The resin product from Step J was treated with 2.5 mL of 95% trifluoroacetic acid/water for 1 hour at 25° C. The filtrate was collected. The resin was washed with 2×1 mL of 50% trifluoroacetic acid/methylene chloride and the filtrate collected. The resin was washed once more with 1 mL of methylene chloride. All filtrates were combined into a tared 2 dram vial and concentrated under nitrogen flow. Toluene (1 mL) was added to aid in removing excess trifluoroacetic acid, and the sample was concentrated again under nitrogen. Lastly methylene chloride (1 mL) was added and the sample was reconcentrated to give 330.3 mg of a golden oil. HPLC (as described earlier, 220 nM) shows an 89% pure major peak. NMR (DMSO): 1.15 (d, j=7 Hz, 6H), 2.72 (d, j=7 Hz, 2H), 2.79 (d, j=7 Hz, 3H), 3.79–3.92 (m, 3H), 5.05–5.20 (m, 1H), 7.30–7.50 (m, 5H), 7.60–7.78 (m, 4H), 8.55 (d, j=8 Hz, 1H), 8.76 (t, j=3 Hz, 1H), 9.40 (s, 1H). MS(ES): product ion observed at m/z 508.

EXAMPLES 297–299

Step A

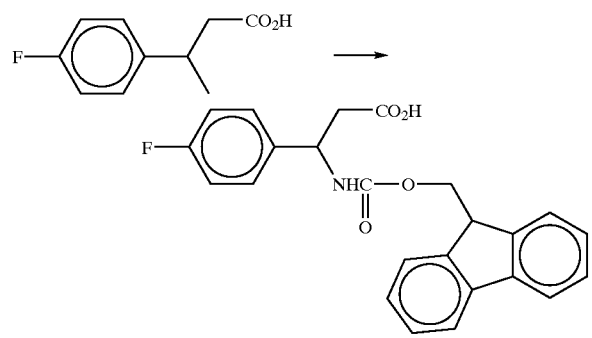

To a 50 mL round bottom flask equipped magnetic stirrer was added 3-amino-3-(4-fluoro-phenyl)-propionic acid, (0.300 g, 1.64 mmol). The propionic acid was dissolved in 1 mL of acetone and 6 mL of water and sodium carbonate was added (0.53 g, 4.92 mmol). The pH=10. The FMOC succinimidyl carbonate (sigma Chemical Co., 0.553 g, 1.64 mmol) was dissolved in 6 mL of acetone and added slowly to the basic aqueous solution via addition funnel over 20 minutes. The reaction was stirred for 16 hours at room temperature. HPLC analysis (Waters, C18, reverse phase, 25 cm column, 50–90% acetonitrile in water over 30 minutes) indicated that the starting material was consumed. The acetone was removed from the reaction mixture in vacuo. The basic aqueous phase was acidified to pH=3 using 3.0 N hydrochloric acid. In a 50 mL separatory funnel the acid layer was washed with 15 mL of ethyl acetate, the water layer was removed and the organic layer was washed (2×30 mL water, 2×30 mL saturated sodium chloride). The organic layer was dried (magnesium sulfate), filtered and concentrated in vacuo. Petroleum ether was added (10 mL) and a white flocculent solid precipitated. After 24 hours of air drying, isolated 0.582 g as a first crop (87.5% yield). The mother liquor was saved for future use. NMR (DMSO): 2.55–2.75 (m, 2H), 4.10–4.30 (m, 3H), 4.85–4.95 (m, 1H), 7.12 (t, j=8 Hz, 2H), 7.24–7.42 (m, 5H), 7.64 (d, J=8 Hz, 2H), 7.82–7.94 (m, 3H). MS (FAB): product ion M+Li observed at m/z 412.

Step B

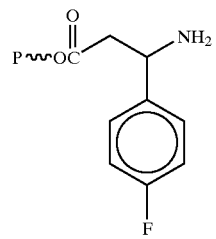

Wang resin (0.60 g, 0.36 mmol) was placed in a 100 mL round bottom flask. The resin was swelled with 8 mL of methylene chloride for 15 minutes then drained. The FMOC protected amino acid of Step A (0.365 g, 0.9 mmol) was activated in a separate 25 mL round bottom flask by dissolving in methylene chloride/dimethylformamide (4:1, 19 mL) and adding diisopropylcarbodiimide (DIC, 0.141 mL, 0.90 mmol) via syringe, followed by the addition of dimethylaminopyridine (DMAP, 22 mg, 0.18 mmol). The solution was stirred at 25° C. for 15 minutes, then added to the preswelled Wang resin. The slurry was stirred for 2 hours at 25° C. The reaction was drained and washed with methanol (3×10 mL), methylene chloride (3×10 mL) and diethyl ether (3×10 mL). To ensure complete reaction, the coupling sequence was repeated. After drying in vacuo the resin was swelled with 8 mL of methylene chloride, drained and 8 mL of 20% piperidine/dimethylformamide was added and the slurry was stirred for 30 minutes. The resin was drained and washed as described previously. The resin was dried in vacuo for 1 hour. Elemental analysis calculated for resin bound material: Calculated: C, 88.23; H, 7.36; N, 0.76; F, 1.03. Found: C, 87.13; H, 7.31; N, 0.79; F, 1.06.

Step C

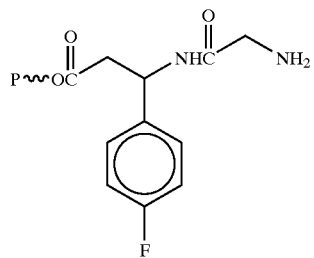

The resin product from Step B was swelled with 8 mL of methylene chloride, then drained. An activated solution of FMOC-Glycine (0.267 g, 0.90 mmol, DIC, 0.140 mL, 0.90 mmol, DMAP, 22 mg, 0.18 mmol. In 10 mL methylene chloride/dimethylformamide, 4:1) was added to the preswelled resin via syringe and stirred at 25° C. for 2 hours. The resin was drained and washed (methylene chloride, methanol and diethyl ether, each 3×10 mL). The resin was preswelled with 20 mL of methylene chloride for 15 minutes, drained and the coupling reaction was repeated to ensure complete reaction. The Kaiser test (Kaiser, E., Color Test for Detection of Free Terminal Amino Groupos in the Solid-Phase Synthesis of Peptides. Anal. Biochem. 1970, 34, 595–598) indicated the coupling was complete. The resin was then suspended in 8 mL of 20% piperidine/dimethylformamide for 30 minutes, drained and washed with dimethylformamide, methanol, methylene chloride, and diethyl ether (3×10 ml, each). The resin was dried in vacuo for 1 hour.

Step D

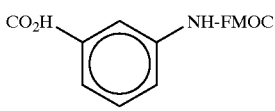

In a 500 mL round bottom flask equipped with magnetic stirrer, 3-amino-benzoic acid (Aldrich, 10.0 g, 50.8 mmol) was dissolved in 50 mL of dioxane and 133 mL of 10% sodium carbonate. The stirred solution was cooled to 0° C. (ice/water) and a solution of fluorenylmethyl chloroformate (13.78 g, 53.3 mmol, in 50 mL dioxane) was added dropwise over 15 minutes. The reaction warmed to 25° C. overnight. HPLC analysis (as described earlier) indicated that the starting material was consumed. 500 mL of water was added to the reaction mixture and a white precipitate formed immediately. The solid was collected, washed with 10% citric acid and dried under vacuum. Isolated 15.23 g, (83.4% yield) of a white flocculent solid. NMR (DMSO): 4.18–4.25 (m, 3H), 7.25–7.41 (m, 6H), 7.62–7.72 (m, 3H), 7.80–7.90 (m, 3H). MS (FAB): product ion M+H observed at m/z 360.

Step E

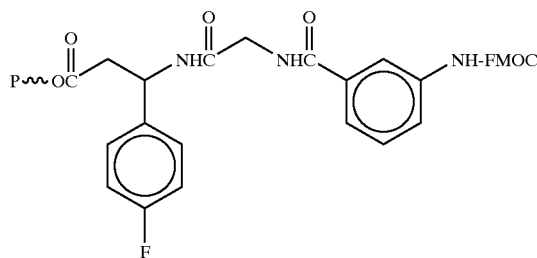

The resin product from Step C was then preswelled using 10 mL of methylene chloride, drained and the activated product of Step D (0.343 g, 0.90 mmol, DIC, 0.141 mL, 0.90 mmol, DMAP, 22 mg, 0.18 mmol, in 5 mL methylene chloride/dimethylformamide 4:1) was added to the preswelled resin. The reaction was stirred for 16 hours at 25° C. The resin was drained and washed as previously described. The Kaiser test indicated that the reaction was not complete. The coupling reaction was repeated, the resin was drained and washed. A repeat Kaiser test indicated that the coupling reaction was complete. The resin was dried in vacuo for 1 hour.

Step F

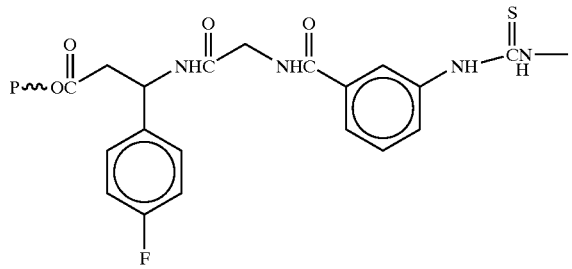

The resin product from Step E was placed in a 100 mL round bottom flask, was preswelled with 10 mL of dimethylformamide, drained, then treated with 20 mL of 20% piperidine/dimethylformamide for 10 minutes at 25° C. The resin was drained and the procedure was repeated. The resin was filtered and washed with dimethylformamide, methanol, methylene chloride and diethyl ether (3×10 mL, each). The Kaiser test indicated that the deprotection step was complete. The resin was placed into a glass 2 dram vial with dimethylformamide (8.0 mL), followed by methyl isothiocyanate (0.526 g, 7.2 mmol). The vial was tightly capped and heated to 80° C. for 4 hours. The resin was filtered and washed with dimethylformamide, methanol, methylene chloride, and diethyl ether (3×10 mL, each). The resin was dried in vacuo. Elemental analysis calculated for resin bound material: Calc'd: C, 83.56; H, 6.46; N, 2.19; F, 1.03; S, 1.35. Found: C, 82.32; H, 6.67; N, 2.53; F, 1.02; S, 1.44.

Step G

The resin product from Step F (100 mg, 0.06 mmol) was transferred to a 2 dram glass vial. The resin was swelled with methylene chloride (3×1 mL) and drained. In a separate vial 2-chloro-1-methylpyridiniumiodide (Aldrich, 18.4 mg, 0.072 mmol) was dissolved in 3 mL of dimethylformamide/methylene chloride 4:1 and added to the preswelled resin, followed by triethylamine (20.1 uL, 0.144 mmol). The reaction slurry was stirred for 16 hours at 25° C. The resin was drained, and washed with dimethylformamide, methanol, methylene chloride, and diethyl ether (3×4 mL, each). The resin was dried in vacuo for 3 hours. The resin was treated with 95% trifluoroacetic acid (1.5 mL) for 1 hour. The resin was filtered and washed with 50% trifluoroacetic acid/methylene chloride (2×1.0 ml) followed by methylene chloride (1×1.0 mL). The filtrates were combined and dried in vacuo in tared 2 dram glass vials.

EXAMPLE 297

Preparation of (±)β-[[2-[[[3-[[(ethylamino)(methylimino)methyl]amino]phenyl]carbonyl]amino]acetyl]amino]-4-fluorobenzenepropanoic acid, trifluoroacetate salt

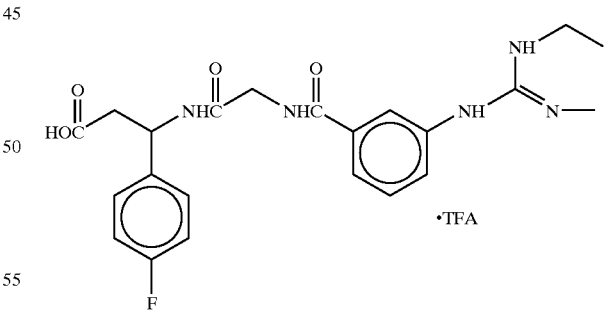

Isolated 28.1 mg of a golden oil. NMR (DMSO): 1.13 (t, j=7 Hz, 3H), 2.65–2.75 (m, 2H), 2.76–2.85 (m, 3H), 3.25 (t, j=3 Hz, 2H), 3.80–3.95 (m, 2H), 5.10–5.21 (m, 1H), 7.13 (t, J=S Hz, 2H), 7.30–7.40 (m, 3H), 7.52 (t, j=8 Hz, 1H), 7.65–7.85 (m, 3H), 8.49 (d, j=8 Hz, 1H), 8.71 (t, j=8 Hz, 1H), 9.40 (s, 1H). HPLC (as described earlier, 220 nM) 90.15% pure. MS (ES): product ion observed at m/z 444.

EXAMPLE 298

Preparation of (±)4-fluoro-β-[[2-[[[3-[[[(1-methylethyl)amino](methylimino)methyl]amino]phenyl]carbonyl]amino]acetyl]amino]benzenepropanoic acid, trifluoroacetate salt

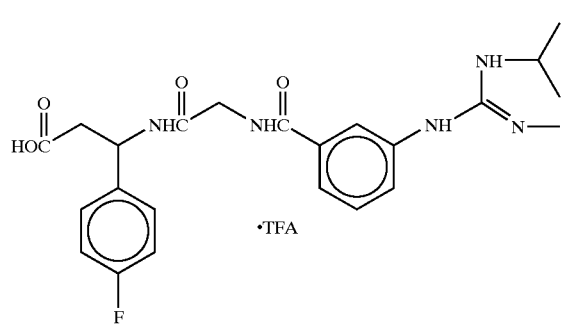

Isolated 44.9 mg of a golden oil. NMR (DMSO): 1.16 (d, j=7 Hz, 6H), 2.61–2.70 (m, 2H), 2.73–2.80 (m, 3H), 3.75–3.90 (m, 3H), 5.10–5.21 (m, 1H), 7.11 (t, j=8 Hz, 2H), 7.25–7.37 (m, 3H), 7.49 (t, j=8 Hz, 1H), 7.59–7.82 (m, 3H), 8.49 (d, j=8 Hz, 1H), 8.70 (t, j=3 Hz, 1H), 9.40 (s, 1H). HPLC (as described earlier, 220 nM) 98% pure. MS (ES): product ion observed at m/z 458.

EXAMPLE 299

Preparation of (±)4-fluoro-β-[[2-[[[3-[[[(4-pyridinylmethyl)amino](methylimino)methyl]amino]phenyl]carbonyl]amino]acetyl]amino]benzenepropanoic acid, trifluoroacetate salt

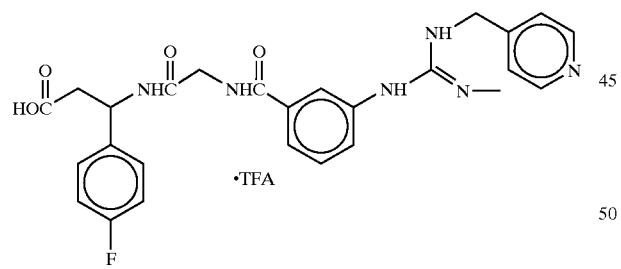

Isolated 31.6 mg of a golden oil. NMR (DMSO): 2.60–2.72 (m, 2H), 2.81–2.89 (d, j=7 Hz, 3H), 3.80–3.95 (m, 2H), 4.61–4.80 (bs, 2H), 5.10–5.21 (m, 1H), 7.01–7.22 (m, 4H), 7.29–7.44 (m, 3H), 7.50 (t, j=8 Hz, 1H), 7.65–7.85 (m, 3H), 8.40–8.50 (d, j=8 Hz, 1H), 8.70–8.85 (m, 3H), 9.73 (s, 1H). HPLC (as described earlier, 220 nM) 98% pure. MS(ES): product ion observed at m/z 507.

The following compounds are prepared according to analogous solid-phase synthetic methods described in Examples 294–299.

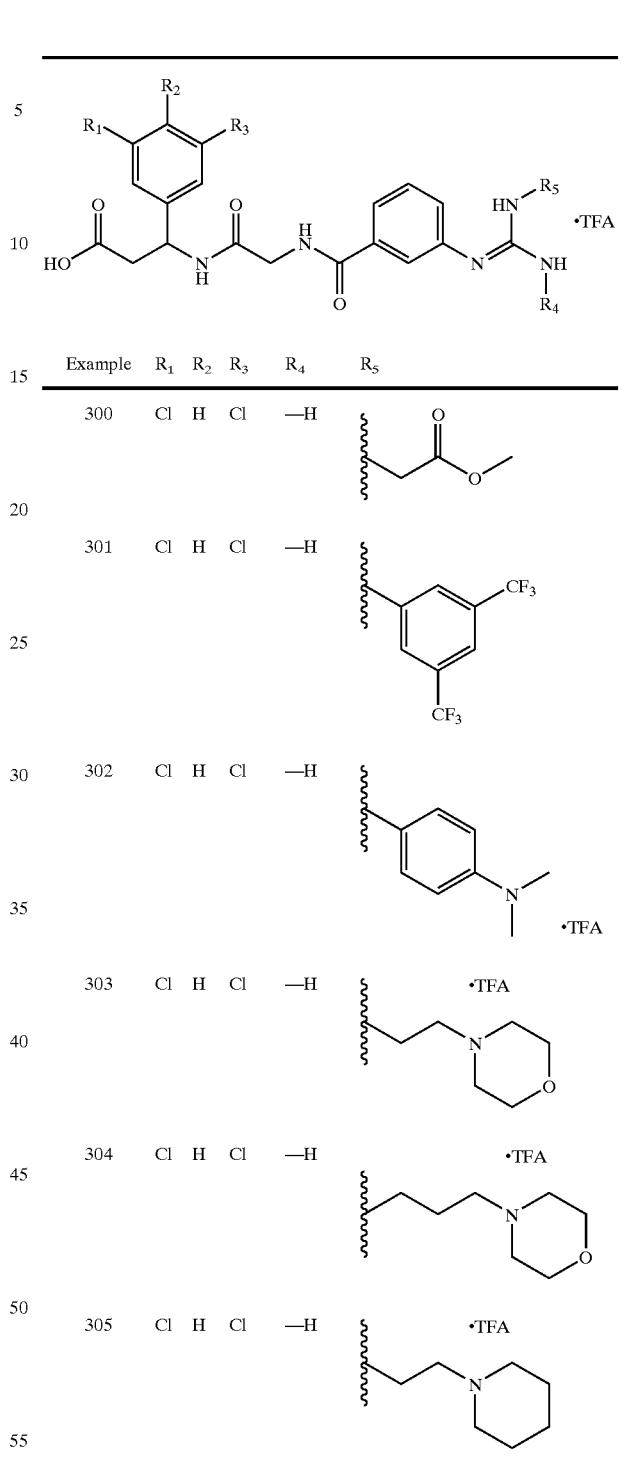

| Example | $R_1$ | $R_2$ | $R_3$ | $R_4$ | $R_5$ |
|---|---|---|---|---|---|
| 300 | Cl | H | Cl | —H | -CH2C(O)OCH3 |
| 301 | Cl | H | Cl | —H | 3,5-bis(CF3)phenyl |
| 302 | Cl | H | Cl | —H | 4-(N,N-dimethylamino)phenyl ·TFA |
| 303 | Cl | H | Cl | —H | -(CH2)2-morpholinyl ·TFA |
| 304 | Cl | H | Cl | —H | -(CH2)3-morpholinyl ·TFA |
| 305 | Cl | H | Cl | —H | -(CH2)2-piperidinyl ·TFA |
| 306 | Cl | H | Cl | —H | —CH2CH3 |
| 307 | Cl | H | Cl | —H | —CH2CH2CH3 |
| 308 | Cl | H | Cl | —H | 4-(CF3)phenyl |

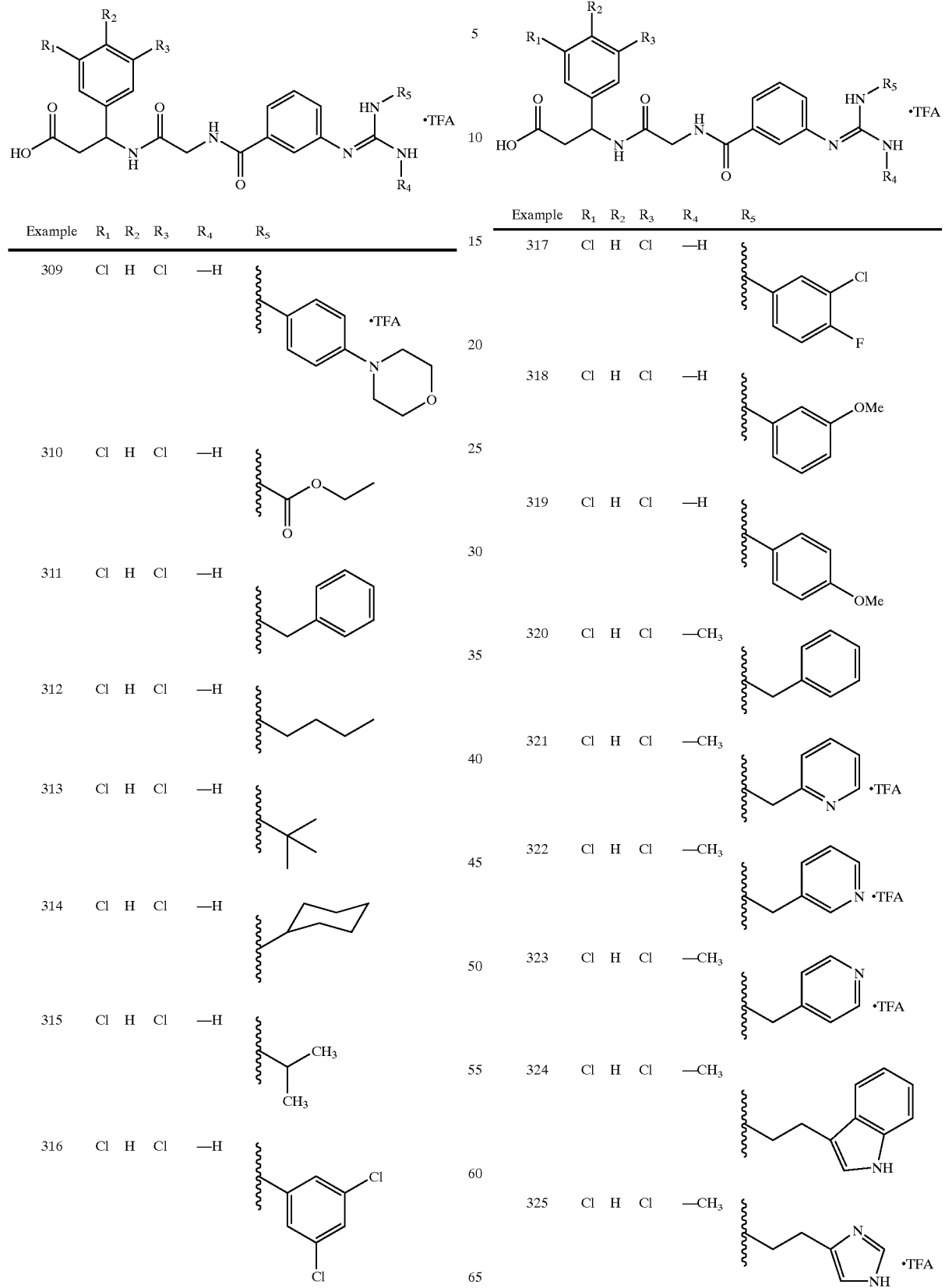

-continued

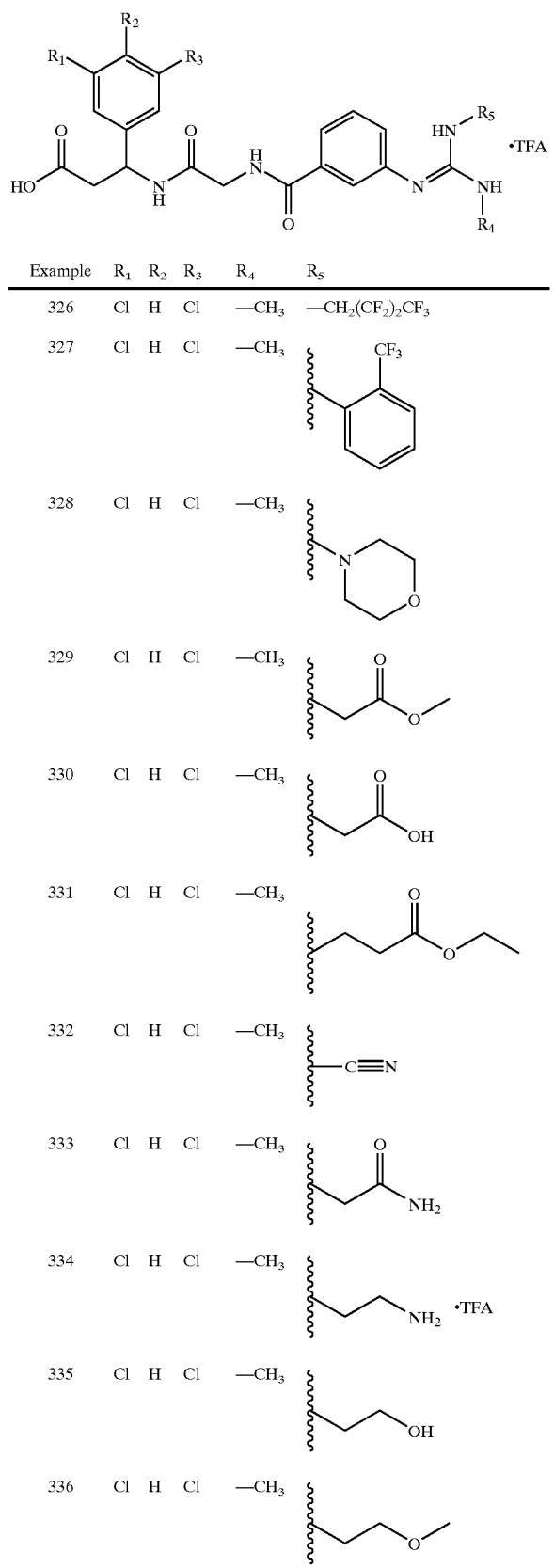

| Example | R₁ | R₂ | R₃ | R₄ | R₅ |
|---|---|---|---|---|---|
| 326 | Cl | H | Cl | —CH₃ | —CH₂(CF₂)₂CF₃ |
| 327 | Cl | H | Cl | —CH₃ | (2-CF₃-phenyl) |
| 328 | Cl | H | Cl | —CH₃ | (morpholinyl) |
| 329 | Cl | H | Cl | —CH₃ | —CH₂C(O)OCH₃ |
| 330 | Cl | H | Cl | —CH₃ | —CH₂C(O)OH |
| 331 | Cl | H | Cl | —CH₃ | —(CH₂)₂C(O)OEt |
| 332 | Cl | H | Cl | —CH₃ | —C≡N |
| 333 | Cl | H | Cl | —CH₃ | —CH₂C(O)NH₂ |
| 334 | Cl | H | Cl | —CH₃ | —(CH₂)₃NH₂ •TFA |
| 335 | Cl | H | Cl | —CH₃ | —(CH₂)₃OH |
| 336 | Cl | H | Cl | —CH₃ | —(CH₂)₂OCH₃ |

-continued

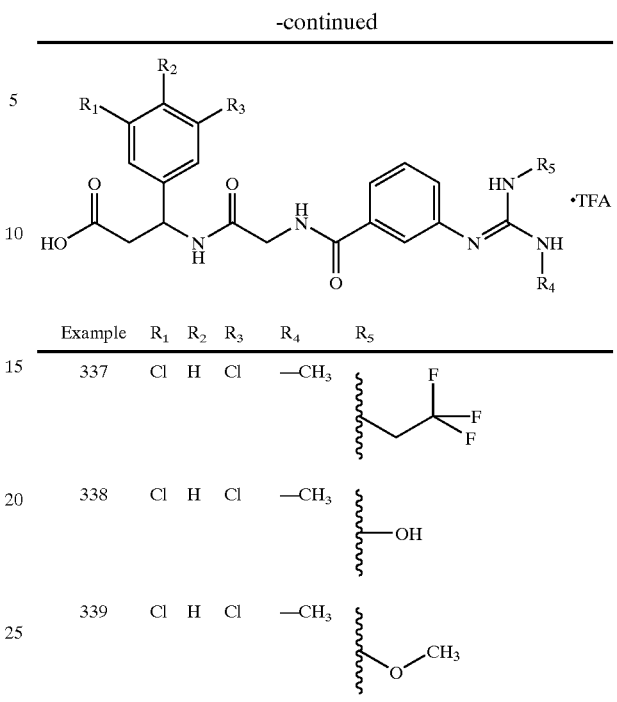

| Example | R₁ | R₂ | R₃ | R₄ | R₅ |
|---|---|---|---|---|---|
| 337 | Cl | H | Cl | —CH₃ | —CH₂CHF₂ (CH₂CF₂F) |
| 338 | Cl | H | Cl | —CH₃ | —OH |
| 339 | Cl | H | Cl | —CH₃ | —OCH₃ |

EXAMPLE 361

Preparation of (±)ethyl 3,5-dichloro-β-[[2-[[[3-[(1,4,5,6-tetrahydro-5,5-dimethylpyrimidin-2-yl)amino]phenyl]carbonyl]amino]acetyl]amino]benzenepropanoate, trifluoroacetate salt Step A

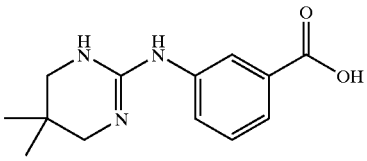

To a suspension of the 1-(3-carboxyphenyl)-2-thiourea (produced in Example 236, Step A) (10.00 g, 0.051 mol) in ethanol (100 mL) was added iodomethane (3.5 mL) and heated at 70° C. under nitrogen atmosphere for 2.5 hours. The reaction mixture was concentrated under reduced pressure, the residue was triturated with ether containing 10% EtOAc (2×100 mL) and the supernatent decanted. The resulting solid was dried in vacuo for 2 hours, dissolved in DMF (75 mL) and added dropwise to a solution of 2,2 dimethyl-1,3 propanediamine (42 g, 0.41 mol) in DMF (20 mL) over a period of 1 hour. The resulting mixture was heated at 80° C. under nitrogen atmosphere for 16 hours with simultaneous trapping of the methylmercaptan in 5% sodium hypochlorite solution. DMF was distilled in vacuo, the residue was dissolved in water (50 mL) and washed with diethyl ether (3×25 mL). The aqueous phase was acidified with 2N HCl to pH 4.0 when a white precipitate was obtained. It was filtered, washed with water and ether and dried to give the desired product 8.0 g (63%) as a white powder. ¹H-NMR and MS were consistent with the structure.

Step B

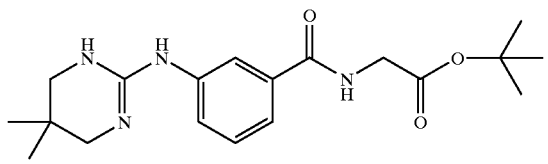

To a suspension of the HCl salt of Step A (1.0 g, 0.0035 mol) in DMF (15 ml), was added N-methylmorpholine (0.46 mL) and cooled to −10° C. in an ice-salt bath. This reaction mixture was then treated with isobutyl chloroformate (0.45 mL), stirred at −10° C. for 30 minutes, and a solution of the amine generated by the addition of N-methylmorpholine (0.46 mL) to a solution of t-butylglycinate hydrochloride (0.6 g) in DMF (5 mL) at 0° C. The resulting reaction mixture was stirred at −10° C. for 1 hour and at room temperature for 16 hours under argon atmosphere. DMF was distilled in vacuo, the residue was treated with 5% sodium bicarbonate (25 mL) and EtOAc (25 mL) and stirred at room temperature for 30 minutes. A white precipitate was obtained. The precipitate was filtered, washed with water (2×20 mL), and EtOAc (2×20 mL), and dried to give the desired compound, 0.58 g (46%). $^1$H-NMR and MS were consistent with the structure.

Step C

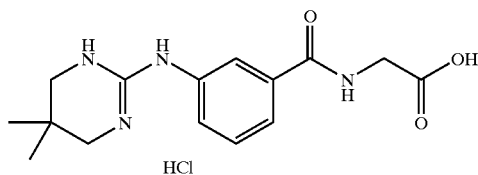

The product of Step B (0.6 g, 0.0017 mol) was suspended in dioxane (2.0 mL) and treated with 4N HCl in dioxane (0.9 mL) and stirred overnight at room temperature. The reaction mixture was diluted with diethyl ether, filtered, and the residue washed with diethyl ether (3×20 mL). The resulting pale yellow solid was dried in a desiccator over NaOH pallets and used as such in the following step, without purification.

Step D

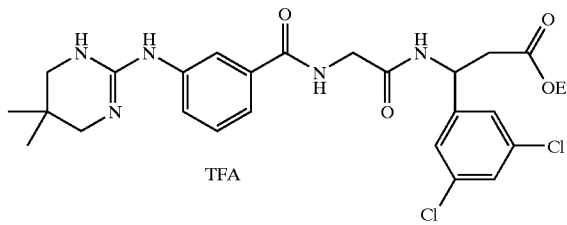

To a suspension of HCl salt as prepared in Step C in DMF (10 mL), was added N-methylmorpholine (0.21 mL) and cooled to −10° C. in an ice-salt bath. This reaction mixture was then treated with isobutylchloroformate (0.24 mL), stirred at −10° C. for 30 minutes, and a solution of the amine generated by the addition of N-methylmorpholine (0.46 mL) to a solution of ethyl DL-3-amino-3-(3,5-dichlorophenyl) propionate (produced as in Example 1, Steps A and B substituting 3,5-dichlorobenzaldehyde for 3-pyridine carboxaldehyde) (0.6 g, 0.002 mol) in DMF (5 mL) at 0° C.

The resulting reaction mixture was stirred at −10° C. for 1 hour and at room temperature for 16 hours under argon atmosphere. DMF was distilled in vacuo, the residue was triturated with ether (2×25 mL) and the supernatant decanted. The insoluble residue was purified by reverse phase HPLC using a 30 minute gradient of 5–70% CH$_3$CN in water at a flow rate of 70 mL/minute. The appropriate fractions were combined and freeze dried to afford the desired TFA salt, as a pale yellow powder. $^1$H-NMR and MS were consistent with the structure.

EXAMPLE 362

Preparation of (±)3,5-dichloro-2-hydroxy-β-[[2-[[[3-[(1,4,5,6-tetrahydro-5,5-dimethylpyrimidin-2-yl)amino]phenyl]carbonyl]amino]acetyl]amino]benzenepropanoic acid, trifluoroacetate salt

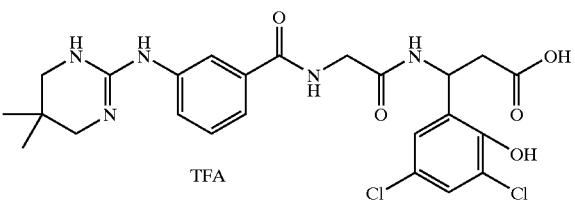

The above compound was prepared by coupling the product of Step C in Example 361 with the product of Example 440, Step A, as described in Example 361. The desired product was isolated by reverse-phase HPLC using a 30 minute gradient of 5–70% CH$_3$CN in water at a flow rate of 70 mL/minute. The appropriate fractions were combined and freeze dried to afford the desired TFA salt. $^1$H-NMR and MS were consistent with the structure.

EXAMPLE 363

Preparation of β-[[2-[[[3-[(aminoiminomethyl)amino]phenyl]carbonyl]amino]acetyl]amino]-4-fluorobenzenepropanoic acid, trifluoroacetate salt

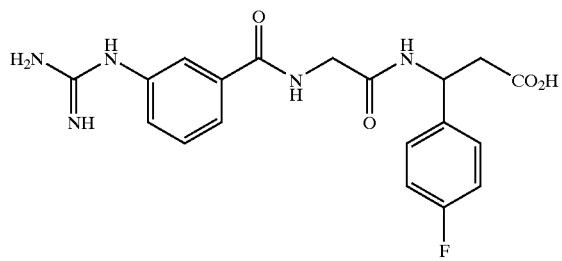

Step A

A mixture of 4-fluorophenyl bromide (10.0 g, 0.057 mol), tert-butylacrylate (9.52 g, 0.074 mol), palladium acetate (0.13 g, 0.00057 mol), tri-para-tolyphosphine (0.87 g, 0.0029 mol) and triethylamine (5.78 g, 0.057 mol) in 30 mL of DMF was heated at 120° C. for 16 hours. The mixture was cooled and treated with 500 mL of water. The aqueous phase was extracted with ethyl acetate (3×200 mL) and the organic layer was washed with brine, dried over magnesium sulfate and filtered. The filtrate was concentrated and the residue was purified by chromatography on silica gel (ethyl acetate/hexane, 1:9) to give 10.13 g of product as a yellow oil (80%). The NMR was consistent with the proposed structure.

Analysis Calc'd. for $C_{13}H_{15}FO_2$: C, 70.25; H, 6.80. Found: C, 69.77; H, 7.08.

Step B

The product from Step A (8.7 g, 0.039 mol) was treated with tert-butanol saturated with ammonia and 3 mL of acetic acid at 110° C. and 900 psi in a Parr shaker for 48 hours. The mixture was filtered and concentrated. The residue was dissolved with 200 mL of cold 1N HCl and extracted with ethyl acetate. The aqueous phase was then basified with potassium carbonate and extracted with methylene chloride (2×200 mL). The combined extracts were washed with brine, dried over magnesium sulfate and filtered. The filtrate was concentrated to give 4.23 g of a yellow oil (41%). The structural assignment was supported by the NMR spectrum.

Step C

To a solution of the compound of Example M (1.0 g, 0.0037 mol) in 10 mL of DMF was added N-methylpiperidine (0.42 g, 0.0037 mol) rapidly. The mixture was stirred at room temperature for 20 minutes, then treated with isobutyl chloroformate at 0° C. After 15 minutes, a solution of the product from Step B in 3 mL of DMF was added. The reaction mixture was allowed to warm to room temperature and stirred overnight. Dimethylformamide was removed in vacuo and the residue was purified by reverse phase HPLC [acetonitrile/water (containing 0.5% of TFA)) to give 0.97 g of a pale yellow solid (44%):

Analysis Calc'd. for $C_{23}H_{27}N_5O_4F.1.0\ H_2O.1.0$ TFA: C, 50.93; H, 5.30; N, 11.88. Found: C, 50.61; H, 4.92; N, 11.74.

Step D

To a suspension of the product from Step C in 10 mL of methylene chloride at 0° C. was added 6 mL of TFA. The mixture was stirred at room temperature for 4 hours. Solvent was removed and the residue was purified by reverse phase HPLC [acetonitrile/water (containing 0.5% of TFA)]to give 0.75 g of the title compound as a white solid (75%):

Analysis Calc'd. for $C_{19}H_{20}N_5O_4F.1.5$ TFA: C, 46.16; H, 3.79; N, 12.23. Found: C, 45.86; H, 3.68; N, 12.23.

EXAMPLE 364

Preparation of (±)β-[[2-[[[3-[(aminoiminomethyl) amino]phenyl]carbonyl]amino]acetyl]amino]-1H-imidazole-2-propanoic acid, tris(trifluoroacetate)salt

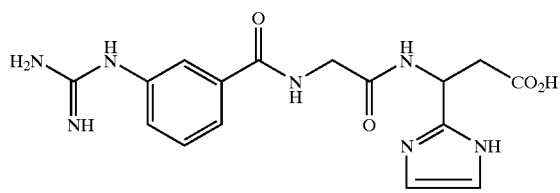

Step A

A solution of 2-imidazolecarboxaldehyde (6.0 g, 0.063 mol) and (tert-butylcarbonylmethylene)triphenylphosphorane (29.4 g, 0.078 mol) in 150 mL of tetrahydrofuran was heated at 55° C. overnight. The clear solution was cooled and concentrated in vacuo. The residue was purified by chromatography on silica gel (ethyl acetate/hexane, 8:2) to give 9.7 g of product (1:1 E/Z mixture) as a white solid (79%): Analysis Calc'd. for $C_{10}H_{14}N_2O_2$: C, 61.84; H, 7.27; N, 14.42. Found: C, 61.52; H, 7.39; N, 14.21.

Step B

To a suspension of prewashed sodium hydride (0.62 g, 0.026 mol) in 40 mL of dry dimethylformamide was added the product from Step A slowly. After 30 minutes, 2-(trimethylsilyl)ethoxymethyl chloride was added and the reaction mixture was stirred at room temperature for 2 hours. Water was added and the aqueous phase was extracted with ethyl acetate. The organic layer was washed with brine, dried over magnesium sulfate and filtered. The filtrate was concentrated and the residue purified by chromatography on silica gel (ethyl acetate/hexane, 1:1) to give 3.54 g of E isomer as a colorless oil and 2.66 g of Z isomer as a white solid (73%). Analysis Calc'd. for $C_{16}H_{28}N_2O_3Si$: C, 59.22; H, 8.70; N, 8.63. Found: C, 58.94; H, 9.12; N, 8.53.

Step C

To a solution of N-benzyl(trimethylsilyl)amine (2.16 g, 0.012 mol) in 30 mL of dry tetrahydrofuran at −78° C. was added n-butyllithium (0.012 mol) slowly. After 30 minutes, a solution of the product of Step B (2.6 g, 0.008 mol) in 15 mL of tetrahydrofuran was added and the reaction mixture was stirred at this temperature for 2.5 hours. The reaction was then quenched with a solution of acetic acid in tetrahydrofuran, followed by addition of saturated sodium bicarbonate to pH 9. The aqueous phase was extracted with ethyl acetate and the organic layer was washed with brine, dried over magnesium sulfate and filtered. The filtrate was concentrated and purified by chromatography on silica gel (ethyl acetate/hexane, 6:4) to give 1.96 g of product as a clear oil (60%).

Analysis Calc'd. for $C_{23}H_{37}N_3O_3Si$: C, 64.00; H, 8.64; N, 9.73. Found: C, 63.72; H, 8.85; N, 9.73.

Step D

To a solution of the product from Step C (5.4 g, 0.0125 mol) and ammonium formamide (7.89 g, 0.125 mol) in 150 mL of methanol was added Pd/C (170 mg). The mixture was stirred at reflux for 3 hours. The catalyst was filtered through celite and the filtrate was concentrated. The residue was dissolved in 400 mL of water, saturated with potassium carbonate, extracted with ethyl acetate. The organic layer was washed with brine, dried over magnesium sulfate and filtered. The filtrate was concentrated to give 3.9 g of product as a colorless oil (91%). The NMR spectrum indicated that the compound was of sufficient purity for the next step.

Step E

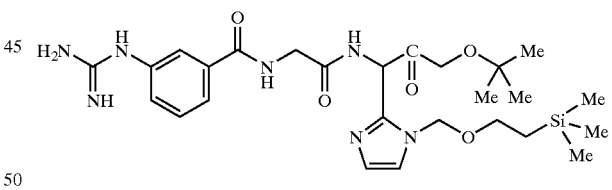

The above compound was synthesized under the same conditions as described in Step C of Example 363. The crude product was purified by reverse phase HPLC [acetonitrile/water (containing 0.5% of TFA)]to give 1.5 g of product as a yellow solid (60%):

Analysis Calc'd. for $C_{26}H_{41}N_7O_5Si.2.5$ TFA: C, 44.07; H, 5.19; N, 11.61. Found: C, 44.24; H, 5.14; N, 11.91.

Step F

The title compound was obtained from the product of Step E following the procedure described in Step D of Example 363. The crude product was purified by reverse phase HPLC [acetonitrile/water (containing 0.5% of TFA)] to give 0.35 g of the title compound as a yellow solid (24%):

Analysis Calc'd. for $C_{16}H_{19}N_7O_4.3.0$ TFA: C, 36.93; H, 3.10; N, 13.70. Found: C, 37.76; H, 2.95; N, 14.22.

EXAMPLE 365

Preparation of (±)β-[[2-[[[3-[(aminoiminomethyl)amino]phenyl]carbonyl]amino]acetyl]amino]-2,3,5,6-tetrafluorobenzenepropanoic acid, trifluoroacetate salt

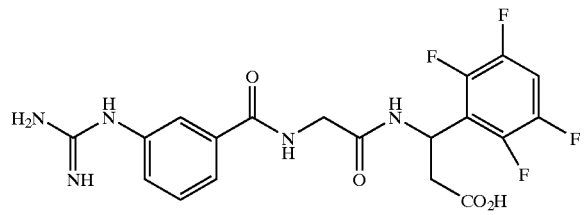

The above compound was made by following the reaction sequence described in Example 364 Step A and Step C to Step F. The structure was confirmed by the NMR spectrum.

Analysis Calc'd. for $C_{19}H_{17}N_5O_4F_4$·1.5 TFA: C, 42.18; H, 2.98; N, 11.18. Found: C, 42.24; H, 3.07; N, 11.12.

EXAMPLE 366

Preparation of β-[[2-[[[3-[(aminoiminomethyl)amino]phenyl]carbonyl]amino]acetyl]amino]-5-bromothiophene-2-propanoic acid, trifluoroacetate salt, monohydrate

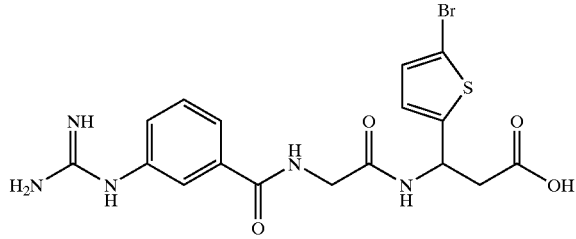

A solution of the product of t-butyl ester of the above compound (prepared according to analoguous methodology as described herein) (1.0 g, 1.91 mmol) and trifluoroacetic acid (14.8 g, 10.0 ml, 13.0 mmol) in dichloromethane (25 ml) was stirred at 0° C. for 30 minutes. The reaction mixture was allowed to warm to room temperature and stirred for 6 hours. The solvent was removed under reduced pressure. The crude product was purified by HPLC (acetonitrile, water, trifluoroacetic acid) to give pure title compound (0.43 g, 38%) as a white solid.

Analysis Calc'd. for $C_{17}H_{18}N_5O_4SBr·CF_3COOH·H_2O$: C, 38.01; H, 3.53; N, 11.67; S, 5.34; Found: C, 38.07; H, 3.23; N, 11.48; S, 4.99.

EXAMPLE 367

Preparation of (±)3,5-dichloro-β-[[2-[[[3-[(1,4,5,6-tetrahydro-5,5-dimethylpyrimidin-2-yl)amino]phenyl]carbonyl]amino]acetyl]amino]benzenepropanoic acid, trifluoroacetate salt

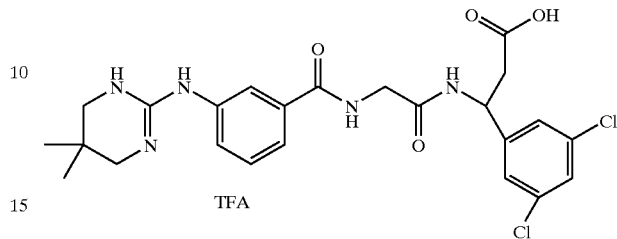

The ethyl ester prepared in Example 361, Step D (0.22 g) was hydrolyzed to the acid using 1M LiOH, (1.8 mL) in acetonitrile (0.2 mL), followed by acidification and purification by reverse-phase HPLC to give 0.18 g of the acid as pale yellow powder. $^1$H NMR and MS were consistent with the structure.

EXAMPLE 368

Preparation of (±)3-bromo-5-dichloro-2-hydroxy-β-[[2-[[[3-[(1,4,5,6-tetrahydro-5,5-dimethylpyrimidin-2-yl)amino]phenyl]carbonyl]amino]acetyl]amino]benzenepropanoic acid, trifluoroacetate salt

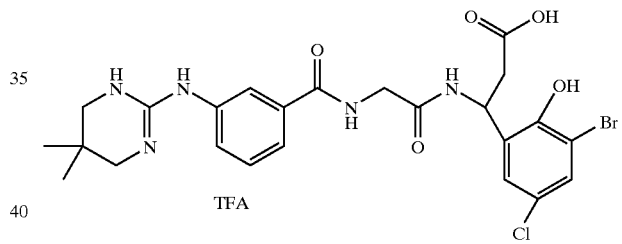

The above compound was prepared by coupling the acid prepared in Example 361, Step C, (0.6 g) with the product of Example 233, Step B (0.5 g) according to the procedure described in Example 361. The desired product was isolated by reverse-phase HPLC to give 0.38 g of the above compound as a pale yellow powder. $^1$H NMR and MS were consistent with the structure.

EXAMPLE 370

Synthesis of β-[[2-[[[3-[(aminoiminomethyl)amino]phenyl]carbonyl]amino]acetyl]amino]-2-mercaptobenzenepropanoic acid, lithium salt

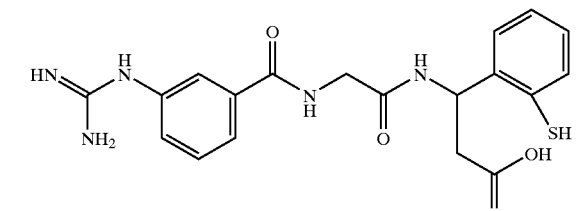

Step A
Synthesis of S-Phenyl Thiocinnamate: A solution of cinnamoyl chloride (14.6 g, 87.68 mmol) in dichloromethane (100 mL) was added to a solution of thiophenol (9.55 g, 86.68 mmol) and pyridine (7 mL) in dichloromethane (150 mL) in an ice-water bath. After 18 hours at room temperature, the reaction mixture was washed with dilute hydrochloric acid (100 mL, 1N), brine (100 mL), dried ($MgSO_4$) and was concentrated to afford 19.0 g (91%) of the desired thioester as a crystalline solid.

Step B
Synthesis of Thiocoumarin: A mixture of S-phenyl thiocinnamate (14.0 g, 58.25 mmol) and aluminum chloride (39 g) was stirred and heated at 85° C. for 3 hours. The hot reaction mixture was poured carefully over ice, then was extracted with ethyl acetate (3×300 mL), washed with brine (200 mL), dried ($MgSO_4$) and was concentrated. The residue was recrystallized from hexane-ethyl acetate to afford 5.2 g (52%) of the desired product as pale yellow crystals.

Step C
Synthesis of 4-Amino-3,4-Dihydrothiocoumarin Hydrochloride Salt: Lithium hexamethyldisilazane (10.22 ml, 1N, 10.22 mmol) was added slowly to a solution of thiocoumarin (1.41 g, 8.52 mmol) in tetrahydrofuran (20 mL) at −78° C. After 45 minutes, the reaction mixture was warmed up to 0° C., then was quenched with glacial acetic acid (0.511 g). After 10 minutes, the reaction mixture was partitioned between ethyl acetate (100 mL) and sodium bicarbonate (100 mL). The organic layer was dried ($MgSO_4$) and was concentrated. The residue obtained was dissolved in ether (100 mL) and dioxane/HCl (20 mL, 4N) was added. The precipitate formed was filtered and the solid was dried in vacuo to afford (0.50 g, 27%) of the desired product as a yellow powder.

Step D
A solution of m-guanidinohippuric acid (0.506 g, 1.855 mmol) in dimethylformamide (5 mL) and N-methylmorpholine (0.187 g, 1.855 mmol) was cooled to 0° C. and was stirred for 15 minutes. Isobutylchloroformate (0.253 g, 1.855 mmol) was added in three portions. After 10 minutes, 4-amino-3,4-dihydrothiocoumarin hydrochloride (0.404 g, 1.855 mmol) was added in one portion followed by N-methylmorpholine (0.187 g, 1.855 mmol). The reaction mixture was stirred for 18 hours at room temperature. The reaction mixture was concentrated and the residue was dissolved in tetrahydrofuran/water (1:1, 5 mL) and was chromatographed (reverse phase, 95:5 water:acetonitrile over 60 minutes to 30:70 water:acetonitrile containing 0.1% TFA). The eluents were lyophilized to afford 0.300 g of the title compound as a pale yellow powder.

Proton NMR and MS were consistent with the desired product.

EXAMPLE 371

Preparation of (±)β-2-[[[3-[(aminoiminomethyl)amino]phenyl]carbonyl)amino]acetyl]amino]-5-chloro-2-mercaptobenzenepropanoic acid, dilithium salt Step A
Synthesis of S-(4-Chlorophenyl)Thiocinnamate: A solution of cinnamoyl chloride (26.0 g, 156.3 mmol) in dichloromethane (100 mL) was added to a solution of thiophenol (22.6 g, 156.3 mmol) and pyridine (12.6 mL) in dichloromethane (200 mL) in an ice-water bath. After 18 hours at room temperature, the reaction mixture was washed with dilute hydrochloric acid (100 mL, 1N), brine (100 mL), dried ($MgSO_4$) and was concentrated to afford 41.0 g (96%) of the desired thioester as a crystalline solid.

Step A
Synthesis of 6-Chlorothiocoumarin: A powdered mixture of S-(4-chlorophenyl)thiocinnamate (19.4 g) and aluminum chloride (52 g) was stirred and heated at 125° C. for 3 hours. The hot reaction mixture was poured carefully over ice/water, then was extracted with ethyl acetate (3×300 ml), washed with brine (200 mL), dried ($MgSO_4$) and was concentrated. The residue was triturated with hexane/ethyl acetate to afford 2.0 g (14%) of the desired product as pale yellow crystals.

Step C
Synthesis of 4-amino-6-chloro-3,4-dihydrothiocoumarin hydrochloride salt: Lithium hexamethyldisilazane (6.4 mL, 1N, 6.4 mmol) was added slowly to a solution of 6-chlorothiocoumarin (1.05 g, 5.345 mmol) in tetrahydrofuran (20 mL) at −78° C. After 45 minutes, the reaction mixture was warmed up to 0° C., then was quenched with glacial acetic acid (0.321 g). After 10 minutes, the reaction mixture was partitioned between ethyl acetate (100 mL) and sodium bicarbonate (100 mL). The organic layer was dried ($MgSO_4$) and was concentrated. The residue obtained was dissolved in ether (100 mL) and dioxane/HCl (20 mL, 4N) was added. The precipitate formed was filtered and the solid was dried in vacuo to afford (0.80 g, 60%) of the desired product as a yellow powder.

Step D
A solution of m-guanidinohippuric acid (0.548 g, 2.0 mmol) in dimethylformamide (5 mL) and N-methylmorpholine (0.220 mL, 2.0 mmol) was cooled to 0° C. and was stirred for 15 min. Isobutylchloroformate (0.260 mL, 2.0 mmol) was added in three portions. After 10 minutes, 4-amino-6-chloro-3,4-dihydrothiocoumarin hydrochloride (0.50 g, 2.0 mmol) was added in one portion followed by N-methylmorpholine (0.220 mL, 2.0 mmol). The reaction mixture was stirred for 18 hours at room temperature. The reaction mixture was concentrated and the residue was dissolved in tetrahydrofuran/water (1:1, 5 mL) and was chromatographed (reverse phase, 95:5 water:acetonitrile over 60 minutes to 30:70 water:acetonitrile containing 0.1% TFA). The eluents were basified with an aqueous solution of lithium hydroxide and then was lyophilized to afford 0.300 g of the title compound as a pale yellow powder.

MS and NMR were consistent with the proposed structure.

EXAMPLE 372

The following compounds are prepared according to the methodology described in Examples 370–371.

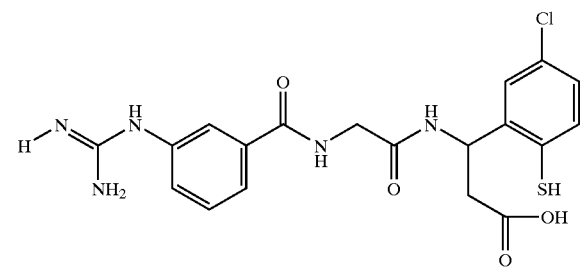

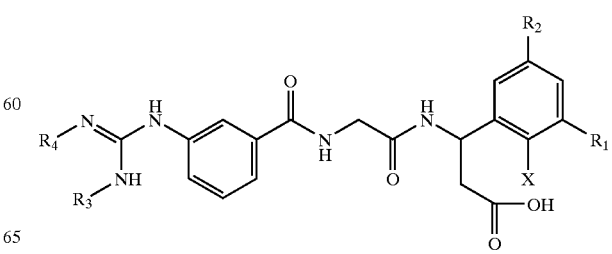

X=SH; R₁,R₂=Cl; R₃,R₄=H

X=SH; R₁,R₂=F; R₃,R₄=H

X=SH; R₁,R₂=Me; R₃,R₄=H

X=SH; R₁,R₂=CF₃; R₃,R₄=H

X=SH; R₁,R₂=Br; R₃,R₄=H

X=SH; R₁=H, R₂=F; R₃,R₄=H

X=SH; R₁=H, R₂=Br; R₃,R₄=H

X=SH; R₁=H, R₂=CF₃; R₃,R₄=H

X=SH; R₁=H, R₂=CH₃; R₃,R₄=H and the above compounds wherein R₃ and R₄ together are (CH₂)₃ or (CH₂)₂.

EXAMPLE 374

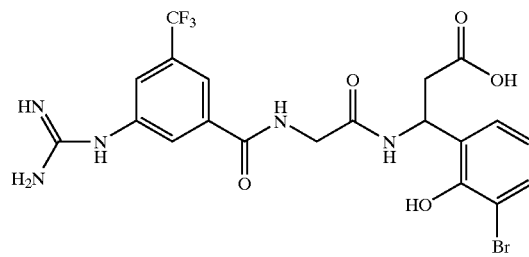

The above compound is prepared by reacting the compound prepared in Example 233, Step B with 3-guanidino-5-trifluoromethylhippuric acid (prepared according to the procedure of Example 38) using substantially the proportions and procedure of Example N, Step 3 and substituting 3-guanidino-5-trifluoromethylhippuric acid hydrochloride for GIHA HCl. The desired product is isolated by C-18 RPHPLC.

EXAMPLE 375

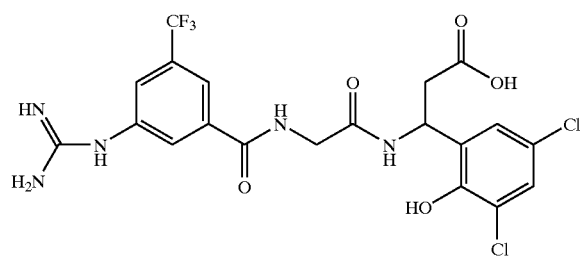

The above compound is prepared using the procedure of Example 374 and substituting (RS)-4-amino-6,8-dichlorohydrocoumarin hydrochloride prepared in Example 237 for the compound of Example 233, Step B. The desired product is isolated by C-18 RPHPLC.

EXAMPLE 376

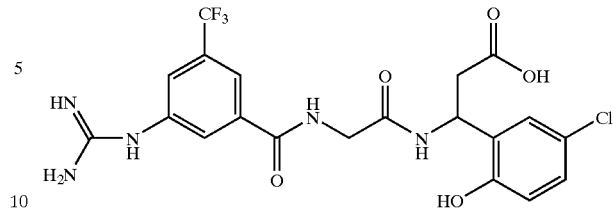

The above compound is prepared using the procedure of Example 374 and substituting (RS)-4-amino-6-chlorohydrocoumarin hydrochloride prepared in Example 231 for the compound of Example 233, Step B. The desired product is isolated by C-18 RPHPLC.

EXAMPLE 377

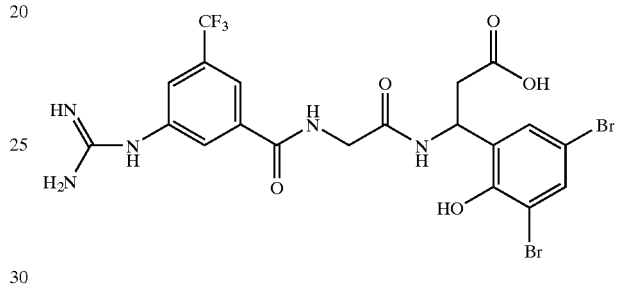

The above compound is prepared using the procedure of Example compound prepared in Example compound of Example 233, Step B. The desired product is isolated by C-18 RPHPLC.

EXAMPLE 378

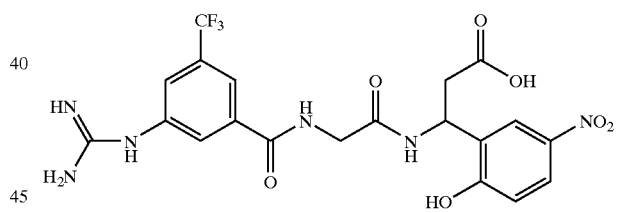

The above compound is prepared using the procedure of Example 374 and substituting (RS)-4-amino-6-nitrohydrocoumarin hydrochloride prepared in Example 226 for the compound prepared in Example 233, Step B. The desired product is isolated by C-18 RPHPLC.

EXAMPLE 379

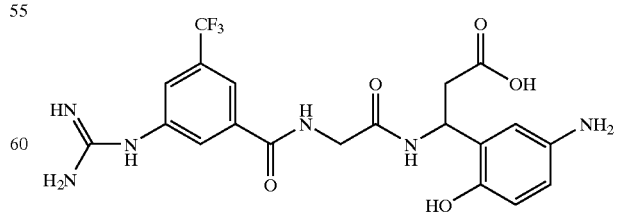

The above compound is prepared from the product of Example 378 using the conditions of Example 234. The desired product is isolated by C-18 RPHPLC.

EXAMPLE 380

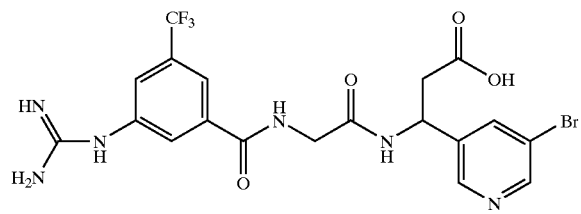

The above compound is prepared using the procedure of Example 374 and substituting the compound prepared in Example 235, Steps A–C and two equivalents of NMM in the coupling step for the compound prepared in Example 233, Step B and one equivalent of NMM. The desired product is isolated by C-18 RPHPLC.

EXAMPLE 381

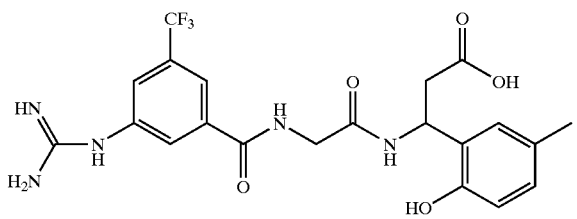

The above compound is prepared using the procedure of Example 374 and substituting (RS)-4-amino-6-methylhydrocoumarin hydrochloride (prepared in Example 88) for the compound prepared in Example 233, Step B. The desired product is isolated by C-18 RPHPLC.

EXAMPLE 382

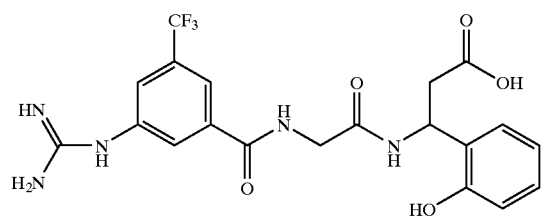

The above compound is prepared using the procedure of Example 374 and substituting (RS)-4-amino-hydrocoumarin hydrochloride (prepared in Example 87) for the compound prepared in Example 233, Step B. The desired product is isolated by C-18 RPHPLC.

EXAMPLE 383

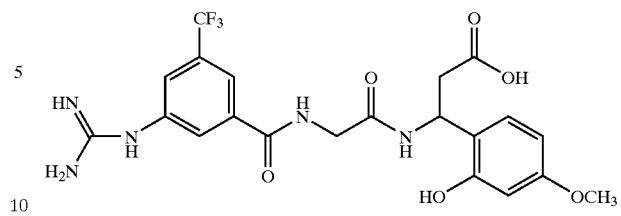

The above compound is prepared using the procedure of Example 374 and substituting (RS)-4-amino-7-methoxyhydrocoumarin hydrochloride (prepared in Example 222) for the compound prepared in Example 233, Step B. The desired product is isolated by C-18 RPHPLC.

EXAMPLE 384

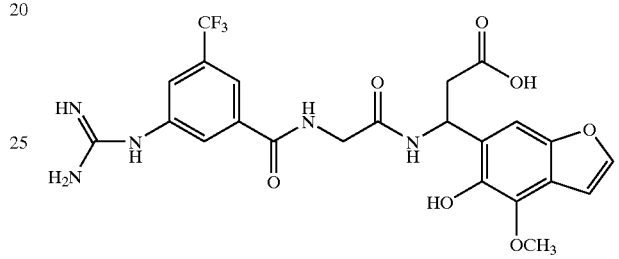

The above compound is prepared using the procedure of Example 374 and substituting (RS)-4-amino-7-methoxyhydropsoralen hydrochloride (prepared in Example 223) for the compound prepared in Example 233, Step B. The desired product is isolated by C-18 RPHPLC.

EXAMPLE 385

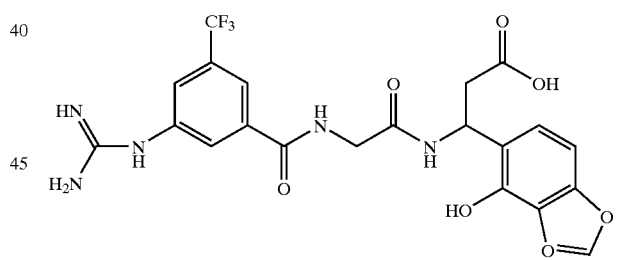

Step A
Preparation of

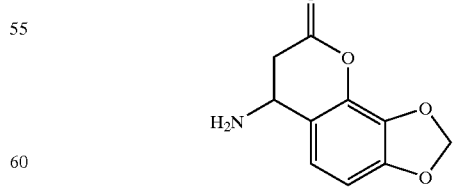

The above compound is prepared from 7,8-methylenedioxy-coumarin (which may be prepared from 7,8-dihydroxy-chromen-2-one according to P. Castillo, J. C. Rodriguez-Ubis, and F. Rodriguez, Synthesis, 10, 839–840 (1986)) using the procedure of Example 233, Steps A and B.

Step B

The above Example compound is prepared using the procedure of Example 374, substituting the hydrochloride salt of the product of Step A for the compound prepared in Example 233, Step B. The desired product is isolated by C-18 RPHPLC.

EXAMPLE 386

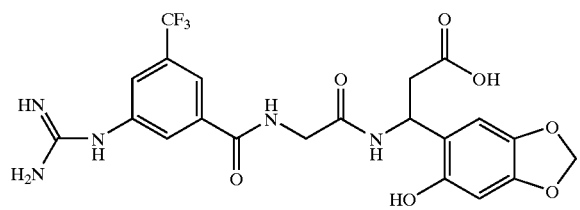

Step A

Preparation of

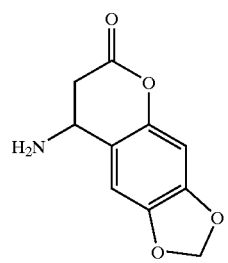

The above compound is prepared from 6,7-methylenedioxy-coumarin [which may be prepared from 6,7-dihydroxy-chromen-2-one according to Spaeth, et al., Chem. Ber., 70, 702 (1937)] using the procedure of Example 233, Steps A and B.

Step B

The above Example compound is prepared using the procedure of Example 374 and substituting the hydrochloride salt of the product of Step A for the compound prepared in Example 233, Step B. The desired product is isolated by C-18 RPHPLC.

EXAMPLE 387

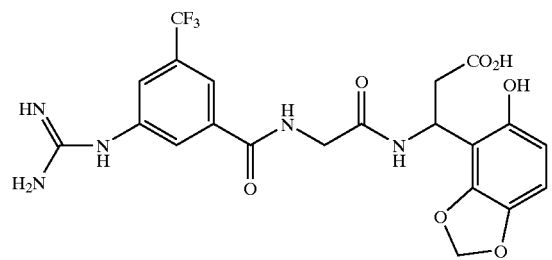

Step A

Preparation of

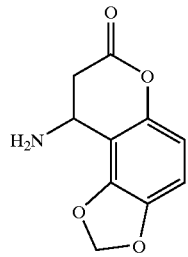

The above compound is prepared from 5,6-methylenedioxy-coumarin [prepared from 5,6-dihydroxychromen-2-one according to P. Castillo, J. C. Rodriguez-Ubis, and F. Rodriguez, Synthesis 10, 839–840 (1986)] using the procedure of Example 233, Steps A and B.

Step B

The above Example compound is prepared using the procedure of Example 374, substituting the hydrochloride salt of the hydrochloride salt of the product of Step A for the compound prepared in Example 233, Step B. The desired product is isolated by C-18 RPHPLC.

EXAMPLE 388

Step A

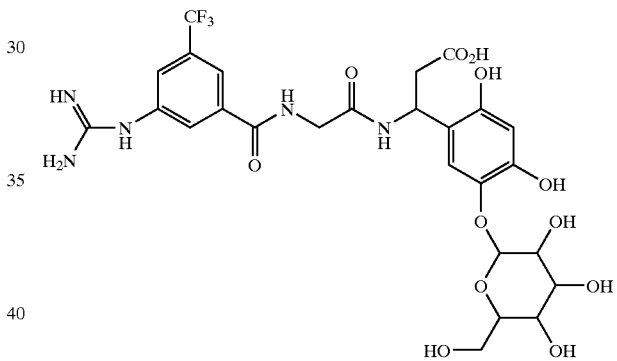

Preparation of

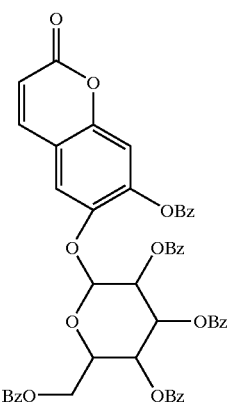

The above compound may be prepared by reacting esculin (Aldrich, rendered substantially free from water of hydration by storage of $P_2O_5$ in a vacuum dessicator) according substantially to the procedure of S. Kato, et al., Bull. Chem. Soc. Jap., 54, 6, 1981, 1895–1896, for the conversion of phenyl-α-D-glucoparanoside to phenyl 2,3,4,6-tetra-O- benzyl-α-D-glucoparanoside and substituting the appropriate molar quantities of reagents to effect complete conversion of esculin to the above compound. The desired product may be isolated by standard silica gel chromatography or by preparative C-18 RPHPLC.

Step B

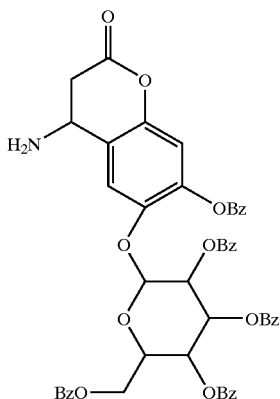

The above compound is prepared using the procedure of Example 233, Step B and substituting the product of Step A for the product of Example 233, Step A.

Step C

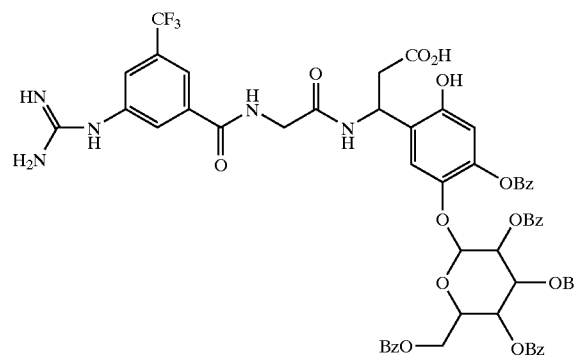

The above compound is prepared using the procedure of Example 374, substituting the hydrochloride salt of the product of Step B for the compound prepared in Example 233, Step B. The desired product is isolated by C-18 RPHPLC.

Step D

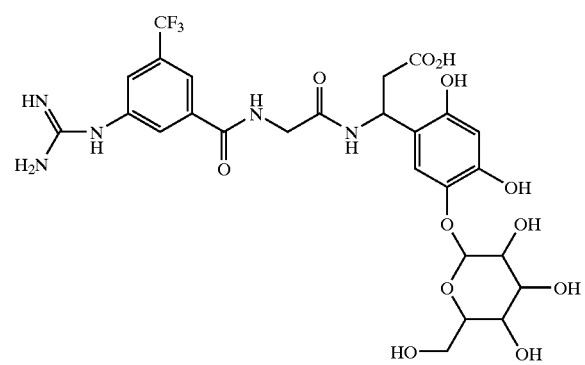

The above compound is prepared by taking the product of Step C, dissolving in a suitable solvent (e.g. aqueous ethanol), transferring to a Fischer-Porter pressure bottle equipped with an inlet and outlet valve, pressure gauge and pressure relief valve and removing the benzyl groups by standard catalytic hydrogenolysis procedure: 5% Pd on carbon catalyst and hydrogen atmosphere until the debenzylation reaction is substantially complete. The desired product is isolated by C-18 RPHPLC.

EXAMPLE 389

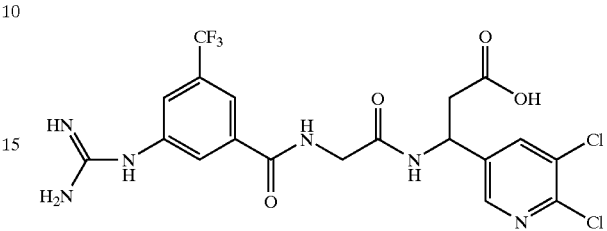

Step A
Preparation of

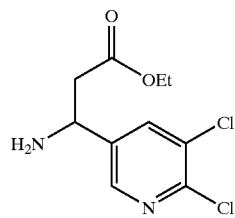

The above compound is prepared using substantially the procedure of Example 235, Steps A–C.

Step B

The above Example compound is prepared using substantially the procedure of Example 235, Steps D and E and is isolated using preparative C-18 RPHPLC.

EXAMPLE 390

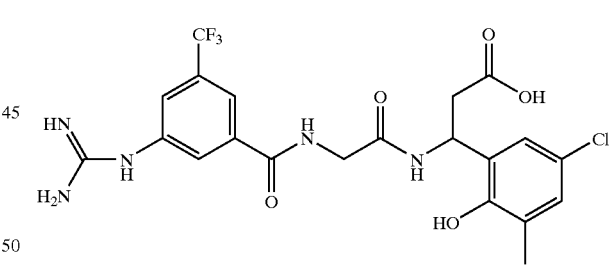

Step A
Preparation of 4-chloro-2-iodophenol

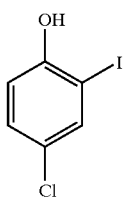

The above compound is prepared according to the procedure of K. J. Edgar and S. N. Falling, *J. Org. Chem.*, 55, 16, 1990, 5287–5291.

Step B

Preparation of 5-chloro-3-iodosalicylaldehyde

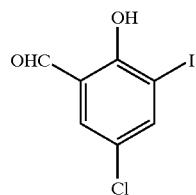

4-chloro-2-iodophenol prepared in Step A is converted to the salicylaldehyde using the procedure of G. Casiraghi, et al., J. C. S. Perkin I, 1978, 318–321.

Step C

Preparation of 6-chloro-5-iodocoumarin

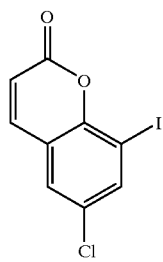

5-chloro-3-iodosalicylaldehyde is converted into the corresponding coumarin, 6-chloro-8-iodocoumarin, using substantially the procedure of Example 233, Step A and substituting 5-chloro-3-iodo-salicylaldehyde for 3-bromo-5-chlorosalicylaldehyde. The desired product may be isolated by standard silica gel chromatography or distillation.

Step D

Preparation of (R,S)-4-amino-6-chloro-8-iodo-hydrocoumarin

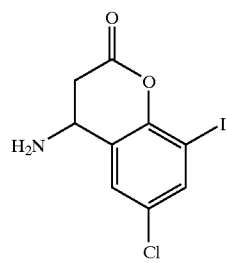

The above compound is prepared using substantially the procedure of Example 233, Step B and substituting the product of Step C for 3-bromo-5-chlorosalicylaldehyde to give the product as substantially pure hydrochloride salt.

Step E

The above Example compound is prepared using the procedure of Example 274 and substituting the product of Step D for the compound prepared in Example 233, Step B. The desired product is isolated by C-18 RPHPLC.

EXAMPLE 391

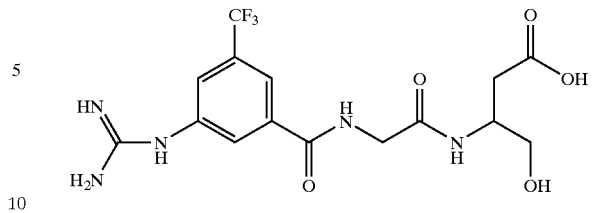

The above compound is prepared using substantially the procedure of Example 86, Step D, substituting 3-guanidino-5-trifluoromethylhippuric acid hydrochloride for GIHA HCl. The desired product is isolated by C-18 RPHPLC.

EXAMPLE 392

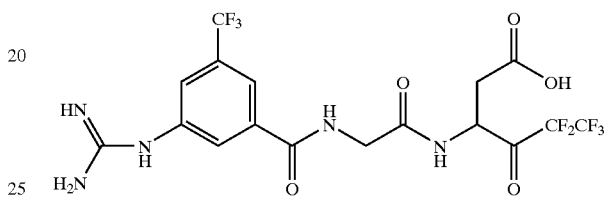

Step A
Preparation of

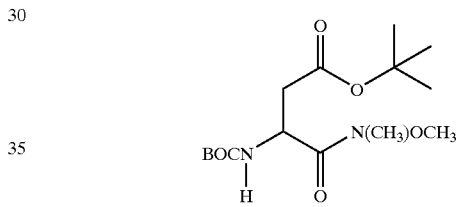

The above compound is prepared using substantially the procedure of Example 235, Step A, substituting BOC-L-aspartic acid-4-tert-butyl ester (Fluka) for 5-bromonicotinic acid.

Step B
Preparation of

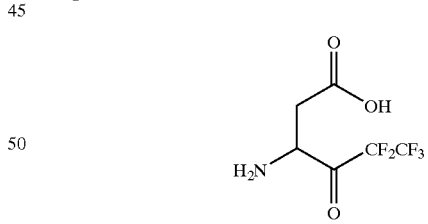

The above compound is prepared according to substantially the procedure of M. R. Angelastro, et al., J. Med. Chem., 1994, 37, 4538–4554, substituting the product of Step A for Reference compound 2 {(S)-[1-(methoxymethylamino)carbonyl]-2-methylpropyl}carbamic acid, 1,1-dimethylethyl ester} and deprotecting according to substantially the procedure employed for obtaining reference compound 3 to obtain the above compound as the HCl salt.

Step C

The above Example compound is prepared using substantially the procedure of Example 85, Step A, substituting the product of Step B for glycine t-butyl ester and substituting 3-guanidino-5-trifluoromethylhippuric acid hydrochloride for GIHA HCl. The desired product may be obtained by C-18 RPHPLC.

EXAMPLE 393

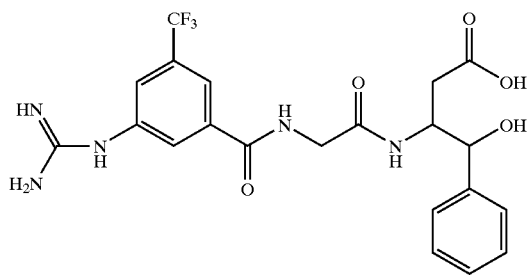

Step A
Preparation of 3-N-t-Boc-amino-4-hydroxy-(3S)-butyric acid benzyl ester

N-t-Boc-L-aspartic acid, β-benzyl ester (10.0 mmole) was dissolved in 10 mL of THF and added dropwise over a period of 30 minutes to a 0° C. solution of $BH_3$-THF (20 mL, 20.0 mmole), under argon. After the mixture was stirred for an additional 1–2 hours at 0° C., the reaction was quenched by dropwise addition of 10% acetic acid in methanol and the solvent evaporated. The oil residue was dissolved in ethyl acetate and extracted with 1N HCl, water, and 1M $NH_4HCO_3$. The ethyl acetate layer was dried ($Na_2SO_4$) and volatiles evaporated to give an oil was crystallized from isopropanol/hexane (mp 56–57° C.): $^1$H NMR, $CDCl_3$, δ, 1.45 (s, 9H), 2.65 (d, 2H), 3.68 (d, 2H), 5.12 (s, 2H), 5.25 (m, 1H), 7.35 (m, 5H).

Step B
Preparation of

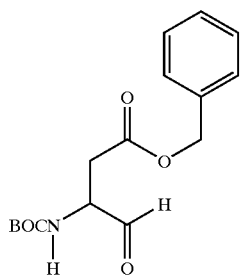

The 3-N-t-Boc-amino-4-hydroxy-butyric acid benzyl ester prepared in Step A was oxidized to the corresponding aldehyde using the following Swern oxidation conditions: oxalyl chloride (6.40 g, 20.72 mmole) was dissolved in dry $CH_2Cl_2$ (25 mL) under argon and cooled to −63° C. using a dry ice/chloroform bath. Dry DMSO (g, 41.4 mmole) dissolved in $CH_2Cl_2$ (12 mL) was added in a dropwise fashion over 15 minutes. The alcohol (6.40 g, 20.7 mmole), dissolved in methylene chloride (50 mL) was then added over 10 minutes. After stirring the reaction mixture for an additional 10 minutes, $Et_3N$ (11.6 mL, 82.9 mmole, 4.0 equivalents) in $CH_2Cl_2$ (25 mL) was added over 15 minutes. The resulting mixture was stirred for 15 minutes and quenched by addition of water (31 mL). The resulting slurry was poured onto hexanes (250 mL) and the organic layer washed with aqueous $KHSO_4$. The aqueous layer was extracted with diethyl ether and the combined organic extracts were washed with saturated $NaHCO_3$, dried ($Na_2SO_4$) and evaporated to give 5.8 g of a light yellow oil which was substantially the desired aldehyde. A small portion was purified by flash chromatography (hexane: ethyl acetate, Merck 60 silica gel): $^1$H NMR (300 MHz), $CDCl_3$, δ, 1.46 (s, 9H), 2.95 (m, 2H), 4.37 (m, 1H), 5.13 (s, 2H), 5.62 (m, 1H), 7.38 (m, 5H), 9.65 (s, 1H), MS (FAB+) 314.3 (M+Li).

Step C
Preparation of 3-N-t-Boc-amino-4-hydroxy-4-phenyl-(3S)-butyric acid benzyl ester To a diethyl ether (150 mL) solution of aldehyde (5.0 g, 15 mmole) prepared in Step B at −40° C. (acetonitrile/dry ice bath) was added in a dropwise fashion a 3.0 M solution of phenyl magnesium bromide in diethyl ether (10.8 mL, 32.6 mmole, 2 equivalents). The resulting mixture was stirred for 15 minutes and warmed to room temperature. After several minutes the mixture was poured into 1 M $K_2HPO_4$. The aqueous layer was extracted again with ether, the combined ether layers washed with aqueous $NaHCO_3$, dried ($Na_2SO_4$) and evaporated to give an oil (5.66 g) that was used in the next step without further purification: $^1$H NMR (300 MHz), $CDCl_3$, δ, 1.4 (multiple singlets, 9H), 2.65 (m, 2H), 4.18 (m, 1H), 5.15 (m, 2H), 7.4 (m, 10H); MS (FAB+) 392.4 (M+Li+).

Step D
Preparation of 2-phenyl-3-N-t-Boc-amino-5-oxo-3S-furan

The hydroxy-ester product of Step C (5.31 g, 13.8 mmole) was taken up in benzene (100 mL) a catalytic amount of camphor sulfonic acid was added and the solution refluxed (Dean-Stark) for five hours and the solvent removed. Conversion to lactone was 50% so the reaction was reconstituted and refluxed for a further 6 hours. Solvent was removed and the resulting oil taken up in ethyl acetate. The organic layer was washed with aqueous saturated $NaHCO_3$, dried ($Na_2SO_4$) and evaporated to give a mixture of the desired diastereomeric lactones as a viscous oil in a 2:1 ratio and benzyl alcohol: $^1$H NMR (300 MHz), $CDCl_3$, δ, 1.35, 1.45 (s, 2:1, 9H), 2.75 (m, 2H), 4.5, 4.75 (m, 2:1, 1H), 4.7 (s, 2H), 5.1 (m, 1H), 5.7 (d, 1H), 7.35 (m, 10H); MS (FAB+) 284.6 (M+Li+).

Step E
Preparation of 2-phenyl-3-amino-5-oxo-3S-furane, hydrochloride

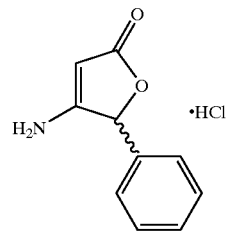

The lactone (0.94 g, 3.4 mmole) prepared in Step D was treated with 4 N HCl in dioxane (20 mL) at room temperature until gas evolution ceased. Excess HCl was removed by evaporation and the desired amino lactone isolated as a white crystalline solid that was dessicated (0.48 g, 66%): $^1$H NMR (300 MHz), $d_6$ DMSO, δ, 3.05 (m, 2H), 4.4 (m, 1H), 5.85 (d, 1H), 7.4 (s, 5H), 8.2 (bs, 3H); MS (FAB+) 178 (M+H+).

Step F

Preparation of

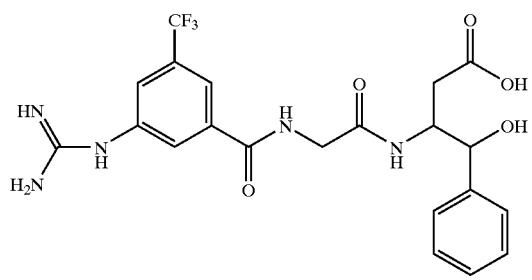

The above compound is prepared using substantially the procedure of Example 374, substituting the product of Step E for the compound prepared in Example 233, Step B. The desired product is isolated by C-18 RPHPLC.

EXAMPLE 394

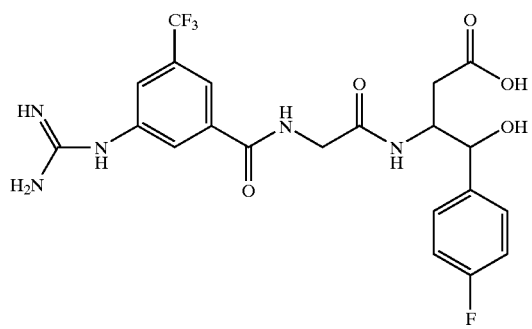

The above compound is prepared following substantially the procedure of Example 393, substituting 4-fluorophenyl magnesium bromide for phenyl magnesium bromide in Step C.

EXAMPLE 395

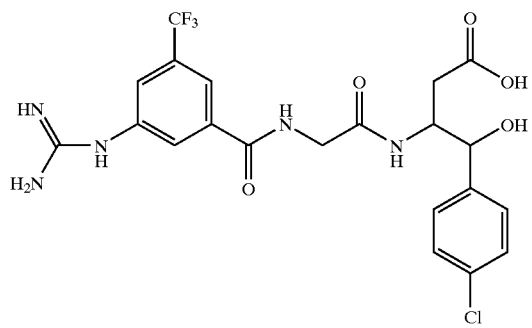

The above compound is prepared following substantially the procedure of Example 393, substituting 4-chlorophenyl magnesium bromide for phenyl magnesium bromide in Step C.

EXAMPLE 396

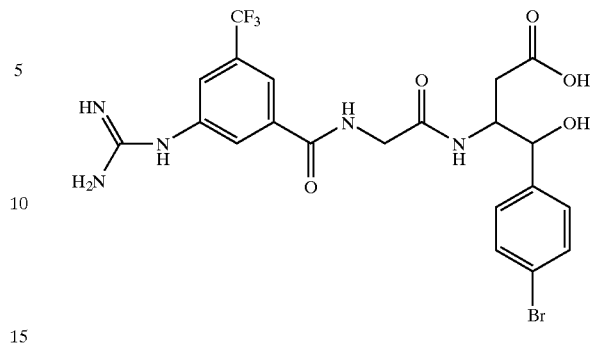

The above compound is prepared following substantially the procedure of Example 393, substituting 4-bromophenyl magnesium bromide for phenyl magnesium bromide in Step C.

EXAMPLE 397

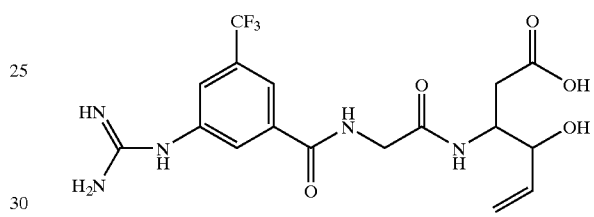

The above compound is prepared following substantially the procedure of Example 393, substituting vinyl magnesium bromide for phenyl magnesium bromide in Step C.

EXAMPLE 398

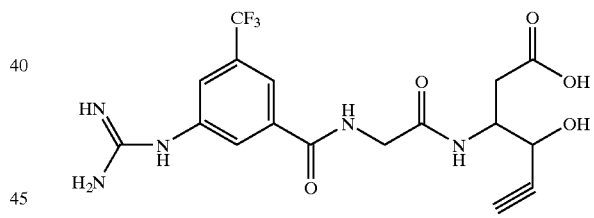

The above compound is prepared following substantially the procedure of Example 393, substituting ethynylmagnesium bromide for phenyl magnesium bromide in Step C.

EXAMPLE 399

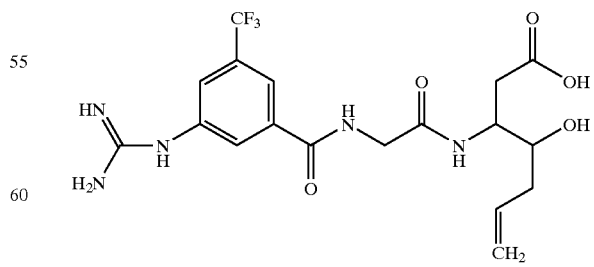

The above compound is prepared following substantially the procedure of Example 393, substituting allylmagnesium bromide for phenyl magnesium bromide in Step C.

EXAMPLE 400

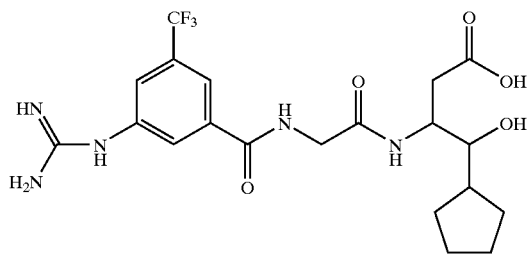

The above compound is prepared following substantially the procedure of Example 393, substituting cyclopentylmagnesium bromide for phenyl magnesium bromide in Step C.

EXAMPLE 401

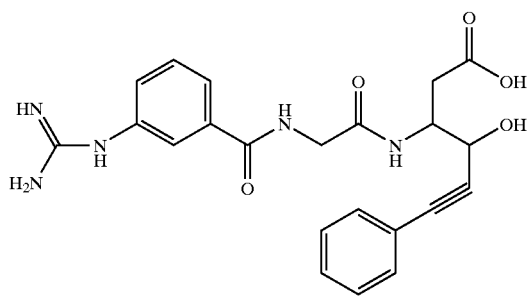

The above compound is prepared following substantially the procedure of Example 393, substituting phenylethynylmagnesium bromide for phenyl magnesium bromide in Step C.

EXAMPLE 402

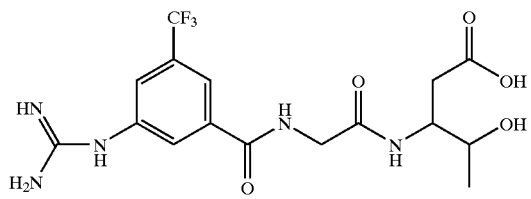

The above compound is prepared following substantially the procedure of Example 393, substituting methylmagnesium bromide for phenyl magnesium bromide in Step C.

EXAMPLE 403

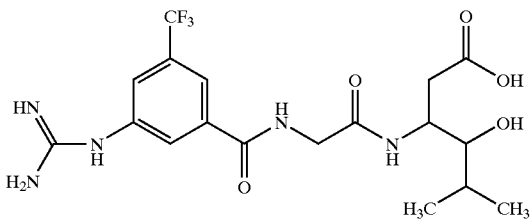

The above compound is prepared following substantially the procedure of Example 393, substituting isopropylmagnesium bromide for phenyl magnesium bromide in Step C.

EXAMPLE 404

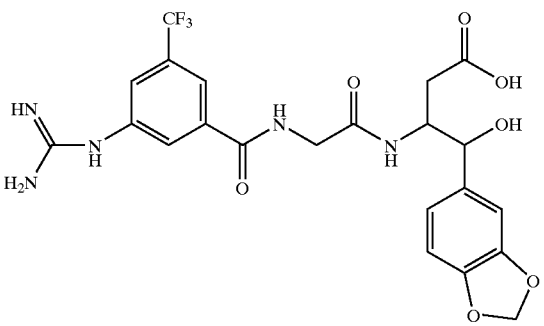

Step A

Preparation of 4-bromomagnesium-1,2-(methylenedioxy)benzene

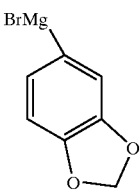

To 1.74 gm (0.072 mole) freshly-ground magnesium in 100 mL dry THF in a 250 mL round bottom flask was added in a dropwise fashion 13.1 gm (0.062 mole) 4-bromo-1,2-(methylenedioxy)benzene in 50 mL dry THF. The reaction mixture was sonicated during the addition and the reaction temperature maintained below 50° C. by use of a water bath. Upon completion of reaction the mixture was filtered and used in the next step.

Step B

Preparation of

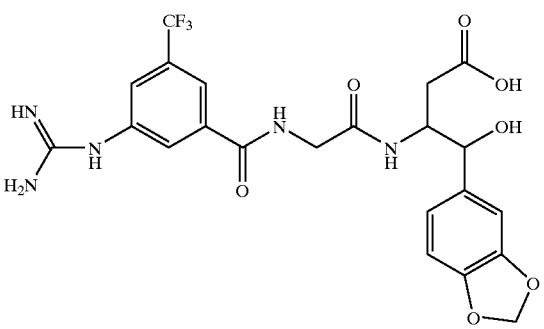

The above compound is prepared following substantially the procedure of Example 393, substituting the grignard of Step A for phenyl magnesium bromide in Example 393, Step C.

EXAMPLE 405

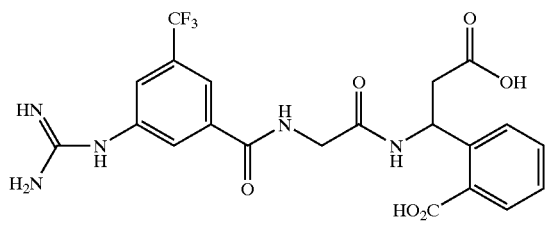

Step A

Preparation of

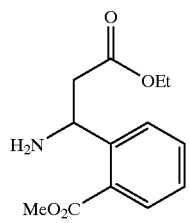

The above compound is prepared according to the procedure of Example 55, Step A, substituting methyl-2-formylbenzoate for 2-furancarboxaldehyde.

Step B

Preparation of

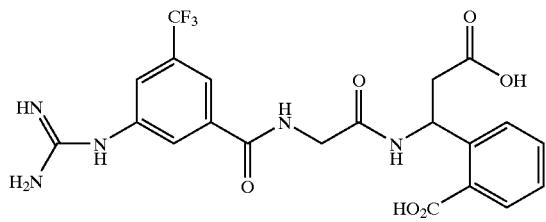

The above compound is prepared according to the procedure of Example 55, Steps B and C, substituting the product of Step A for the product of Example 55, Step A.

EXAMPLE 406

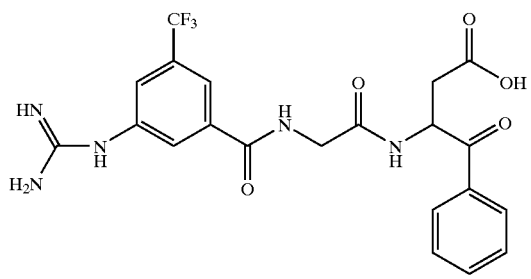

Step A

Preparation of

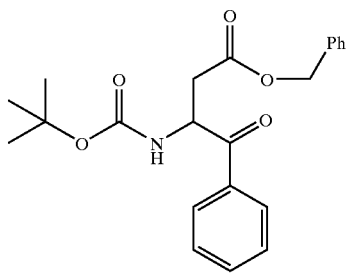

The product of Example 393, Step C is oxidized to the above ketone using the procedure of Example 393, Step B.

Step B

Preparation of

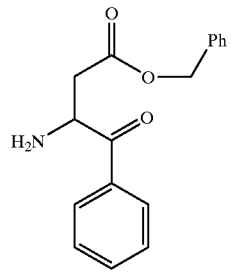

The above product is prepared using the procedure of Example 393, Step E using the product of Step A above.

Step C

Preparation of

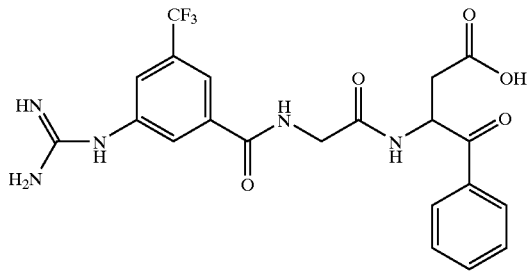

The Example compound is prepared using substantially the procedure of Example 374, substituting the product of Step B for the compound prepared in Example 233, Step B. The desired product is obtained by converting the benzyl ester to the corresponding carboxylic acid by hydrolysis using substantially the procedure of Example 4 and isolating the desired product by C-18 RPHPLC.

EXAMPLES 407–414

Using the procedure of Example 406, substituting the appropriate protected aspartyl alcohols prepared in Examples 394–403 for the aspartyl alcohol of Example 406, Step A, the following representative compounds are prepared:

Ex. 407

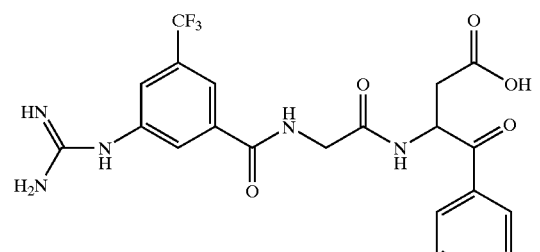

Ex. 408

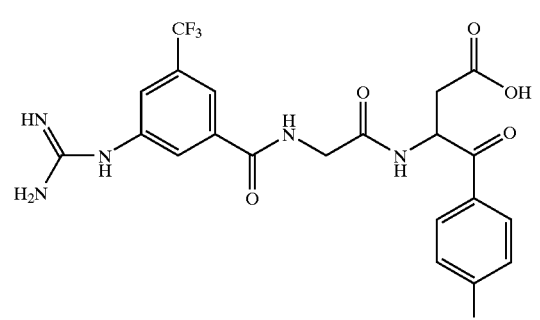

Ex. 409

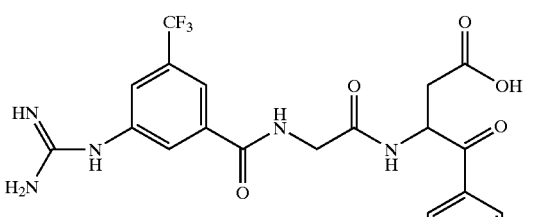

Ex. 410

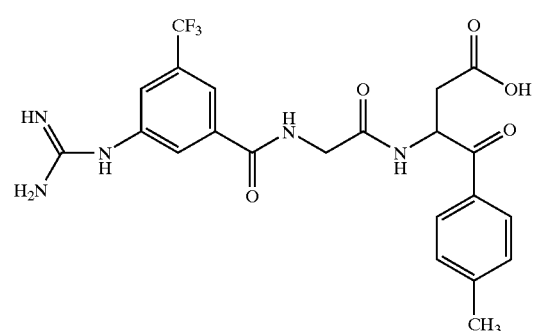

Ex. 411

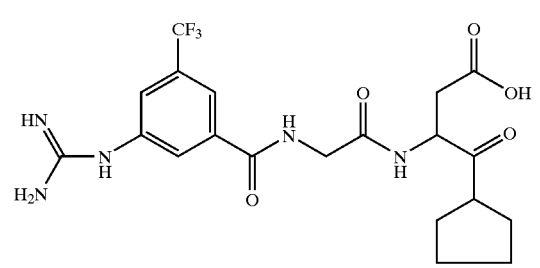

-continued

Ex. 412

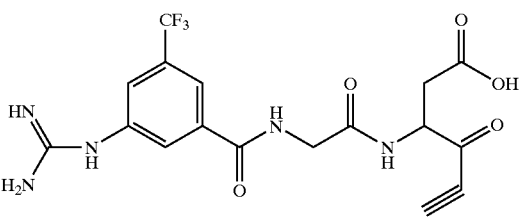

Ex. 413

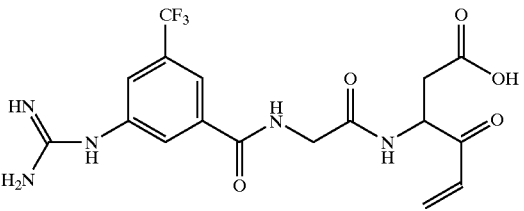

Ex. 414

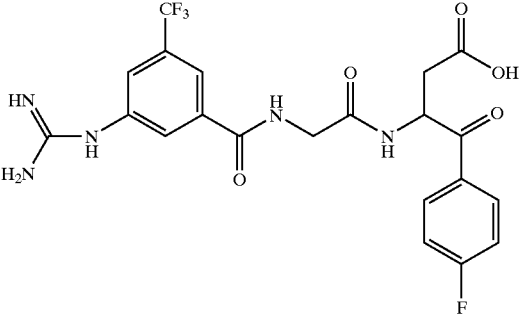

EXAMPLE 415

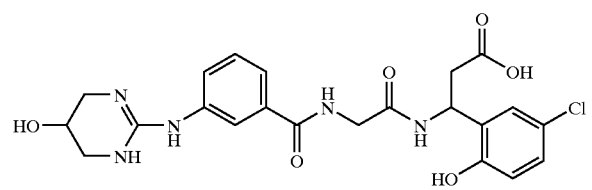

Preparation of

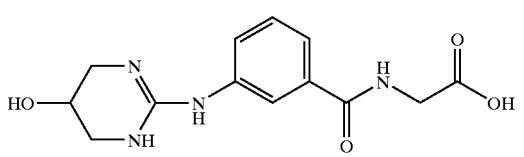

Step A

To the product of Example 23, Step A in DMF is added excess 1,3-diamino-2-hydroxypropane and catalytic DMAP and the solution heated until substantially complete conversion of the starting S-methylisothiouronium salt is achieved. The desired product may be isolated by precipitation of the zwitterion or by preparative C-18 RPHPLC (for a related procedure see U.S. Pat. No. 2,899,426). After drying to remove water, the hydrochloride salt is formed by stirring the zwitterion in excess 4N HCl in dioxane (Aldrich) and isolating the HCl salt by filtration.

Step B

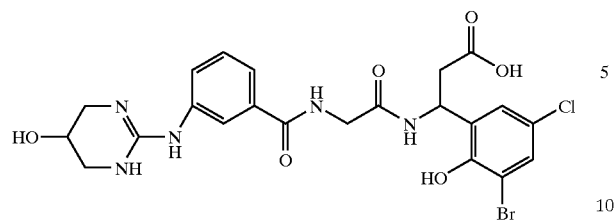

The above compound is prepared using substantially the procedure of Example 233, substituting the product of Step A for GHIA hydrochloride in Example 233, Step C.

EXAMPLE 416–439

Using substantially the procedure of Example 415, substituting the appropriate amine for (RS)-4-amino-6-chloro-8-bromo-hydrocoumarin hydrochloride the following representative compounds may be prepared:

Ex. 416

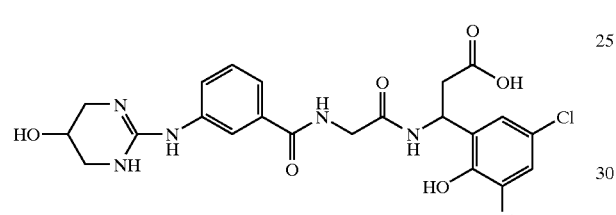

Ex. 417

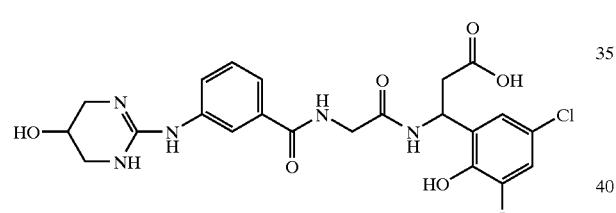

Ex. 418

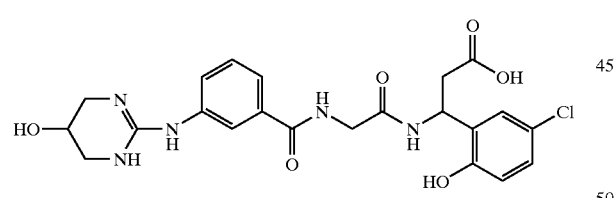

Ex. 419

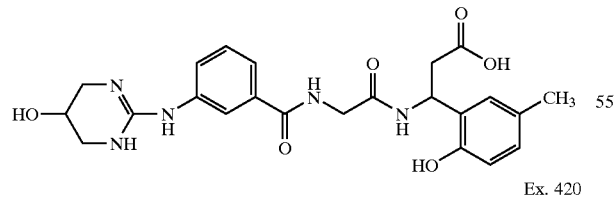

Ex. 420

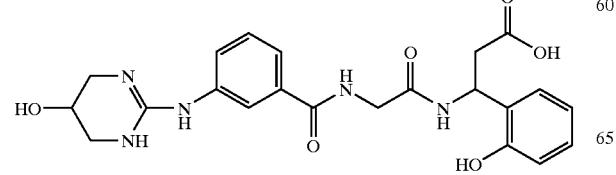

Ex. 421

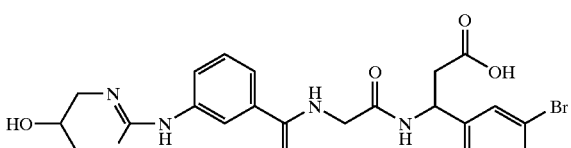

Ex. 422

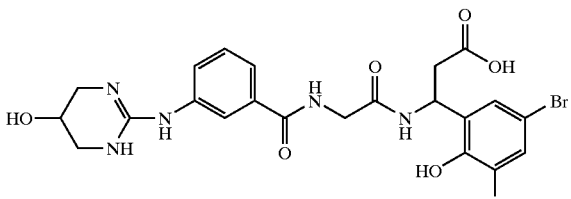

Ex. 423

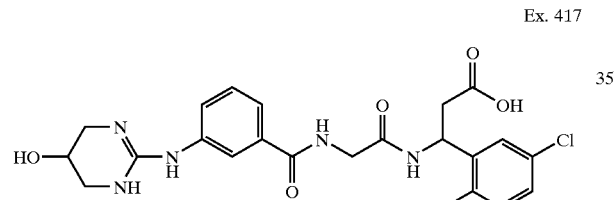

Ex. 424

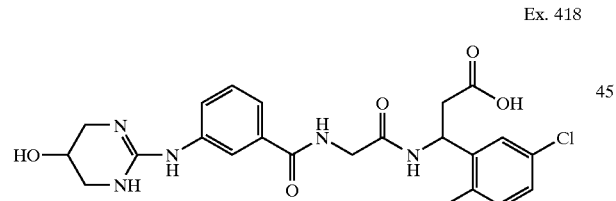

Ex. 425

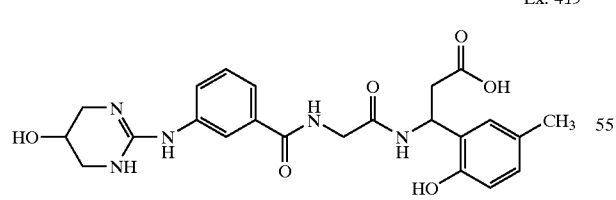

Ex. 426

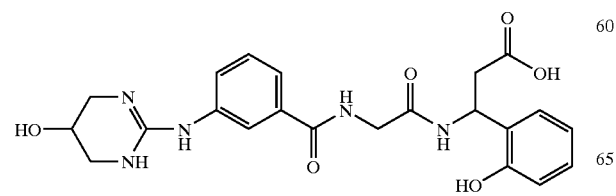

Ex. 427

Ex. 428
Ex. 429
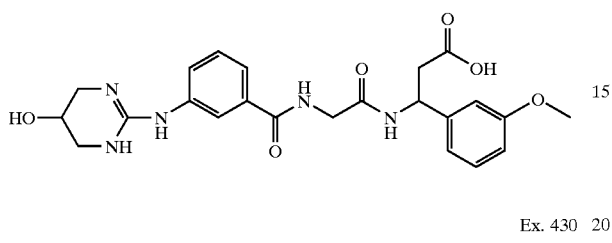
Ex. 430
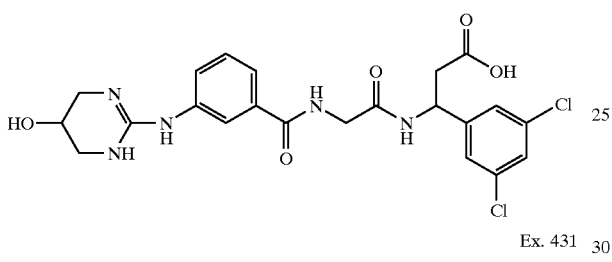
Ex. 431
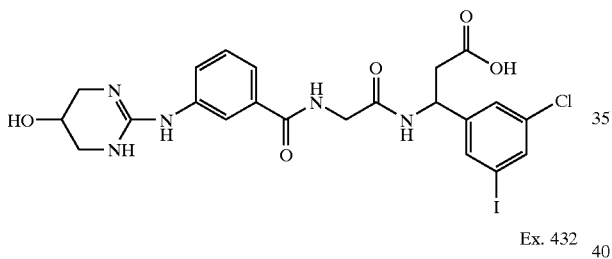
Ex. 432
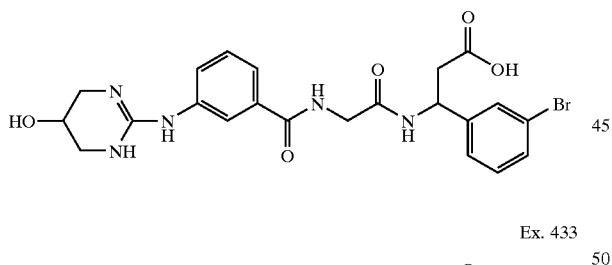
Ex. 433
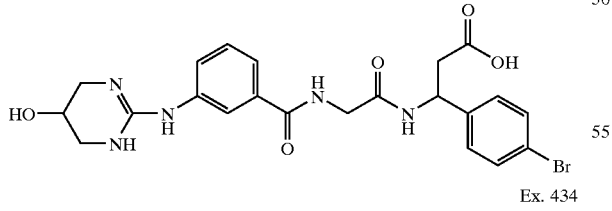
Ex. 434
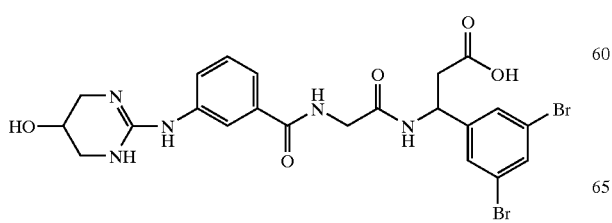
Ex. 435
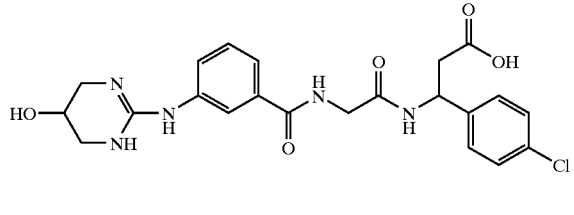
Ex. 436
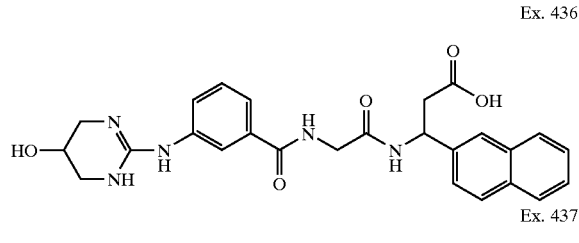
Ex. 437
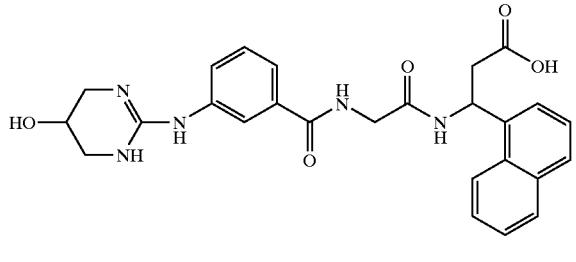
Ex. 438
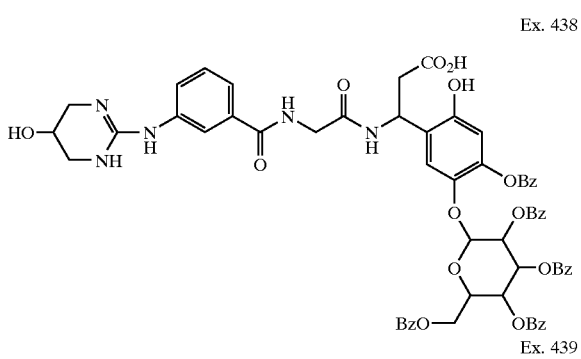
Ex. 439
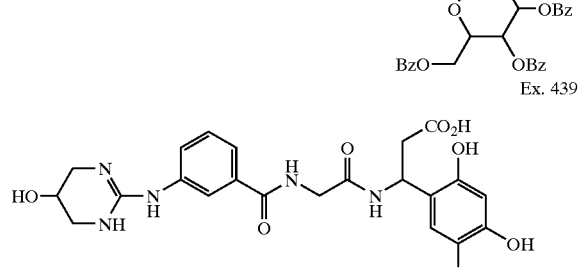
EXAMPLE 440
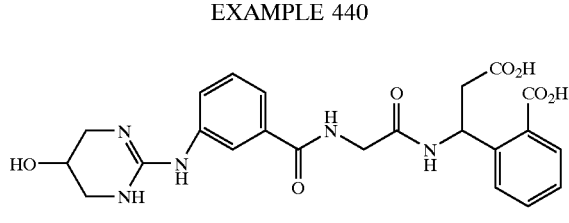

Step A

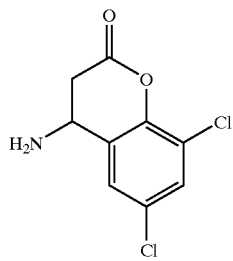

The above compound was prepared using the procedure of Example 233, Steps A and B, substituting 3,5-dichlorosalicylaldehyde for 3-bromo-5-chlorosalicylaldehyde in Step A. NMR and MS were consistent with the proposed structure (HCl salt).

Step B

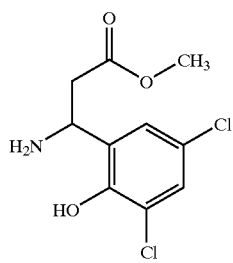

The above compound is prepared by treating the product of Step A with dry HCl gas in methanol in a suitable reactor while maintaining vigorous stirring. Upon completion of reaction excess HCl is removed under vacuum and the solution concentrated to dryness. The crude product is used in the next step. Alternatively, the product may be isolated by C-18 RPHPLC and lyophilized to obtain substantially pure material.

Step C

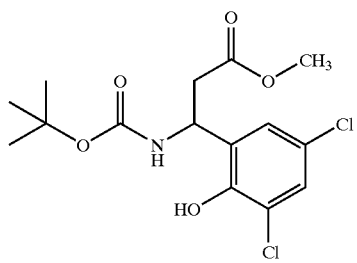

The above compound is prepared by taking the product of Step B and dissolving in DMF. To the stirred solution is added an equimolar amount of both di-tert butyl dicarbonate and triethylamine with a catalytic amount of DMAP. Upon completion of the reaction volatiles are removed under vacuum and the product partitioned between dilute aqueous hydrochloric acid and ethyl acetate. The organic layer is washed with water, dried ($Na_2SO_4$) and concentrated to provide substantially the above compound that may be employed in the next step without further purification. Alternatively, the product may be isolated by C-18 RPHPLC and lyophilized to obtain substantially pure material.

Step D

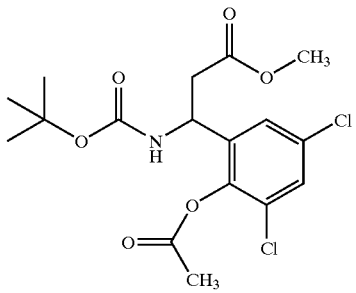

The above compound is prepared by adding under an inert atmosphere an equivalent of acetic anhydride or acetyl chloride and an equivalent of triethylamine to a stirred solution of the product from Step C in DMF. Upon completion of reaction volatiles are removed under vacuum and the reaction residue partitioned between dilute aqueous hydrochloric acid and ethyl acetate. The organic layer is washed with aqueous sodium bicarbonate, dried ($Na_2SO_4$) and concentrated to provide substantially the above compound that may be employed in the next step without further purification. Alternatively, the product may be isolated by C-18 RPHPLC and lyophilized to obtain substantially pure Material.

Step E

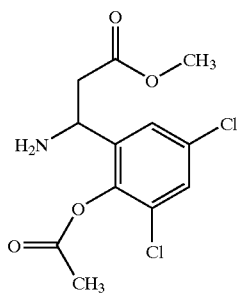

The above compound is prepared by treating the product of Step D with 4 N HCl in dioxane with vigorous stirring. Shortly after cessation of gas evolution excess HCl gas is removed in vacuo and the reaction mixture concentrated at less than about 40° C. The product is triturated with diethyl ether to obtain substantially the desired product. Alternatively, the product may be isolated by C-18 RPHPLC and lyophilized to obtain substantially pure mater.

Step F

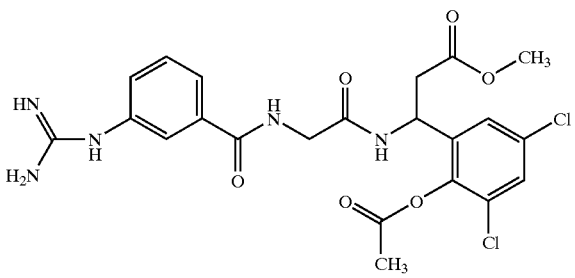

The above compound is prepared according to the procedure of Example 230, Step B, substituting the product of Step E for the product of Example 230, Step A.

EXAMPLE 441

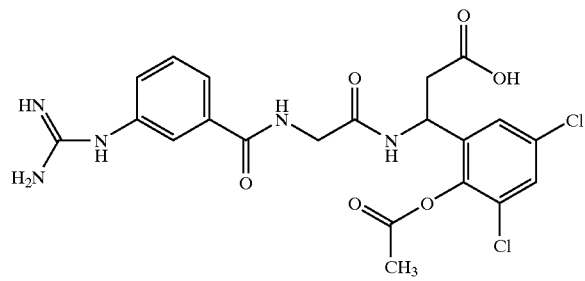

The above compound is prepared by treating a DMF mixture of the compound of Example 225 with two equivalents of N-methylmorpholine and one equivalent of acetic anhydride or acetyl chloride. Upon completion of the reaction the desired product may be isolated by C-18 RPHPLC and lyophilization.

EXAMPLE 442

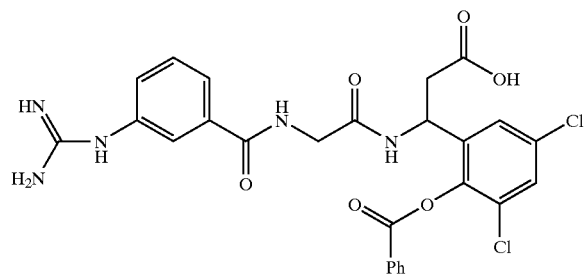

The above compound is prepared by treating a DMF mixture of the compound of Example 225 with two equivalents of N-methylmorpholine and one equivalent of benzoic anhydride or benzoyl chloride. Upon completion of the reaction the desired product may be isolated by C-18 RPHPLC and lyophilization.

EXAMPLE 443–452

Using substantially the procedure of Example 230, Step B and substituting the appropriate amine for the product of Example 230, Step A, the following representative compounds may be prepared:

Ex. 443

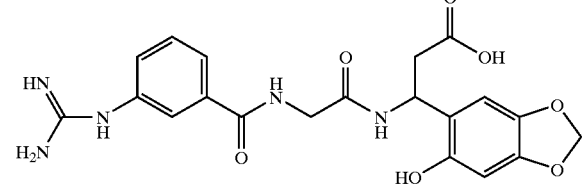

Ex. 444

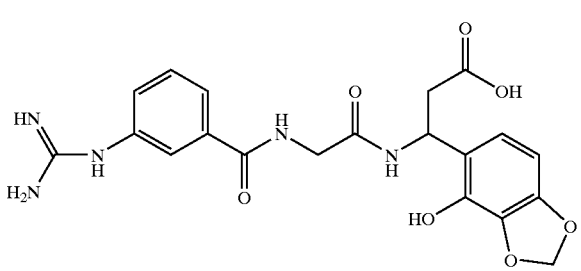

Ex. 445

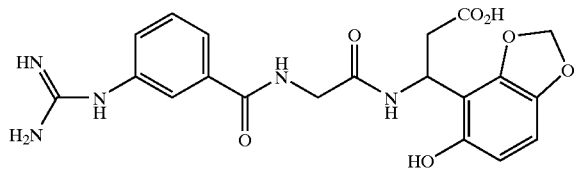

Ex. 446

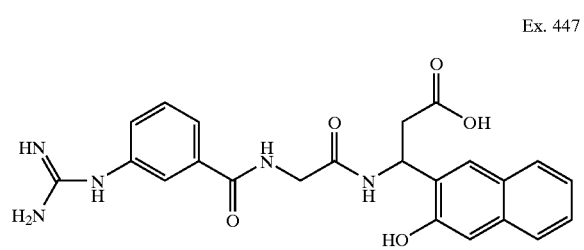

Ex. 447

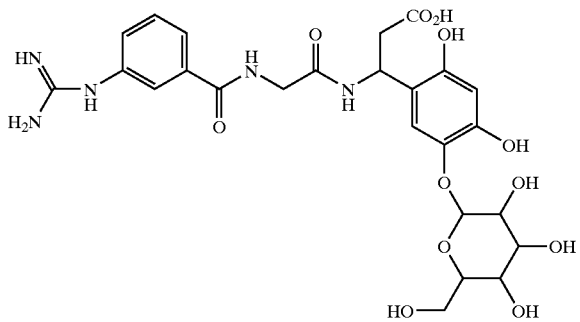

Ex. 448

Ex. 449
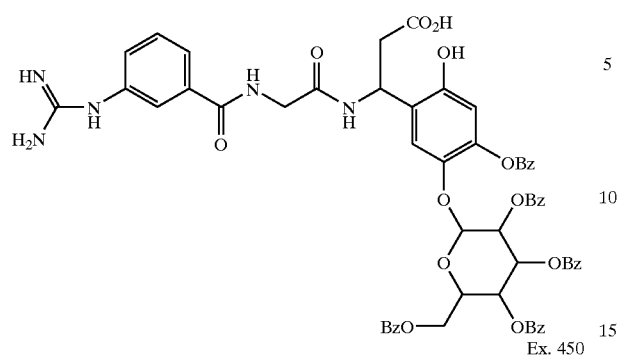
Ex. 454
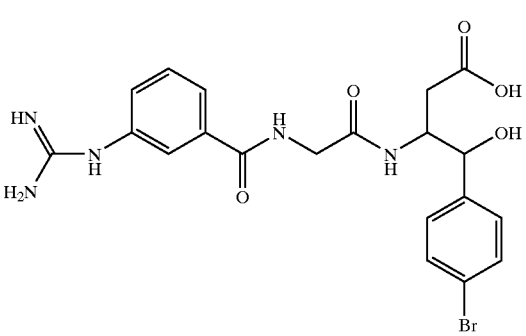
Ex. 450
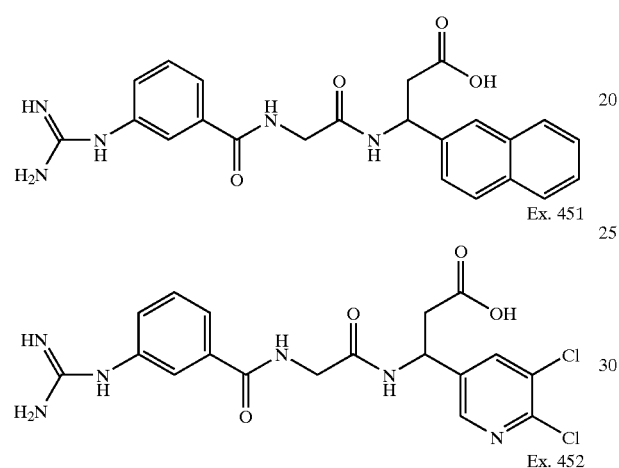
Ex. 455
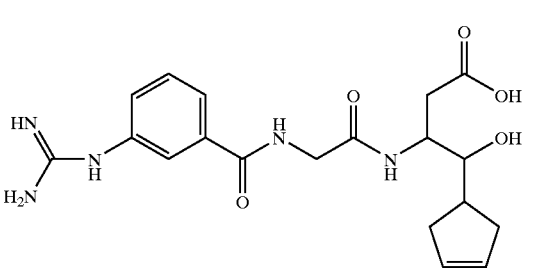
Ex. 451
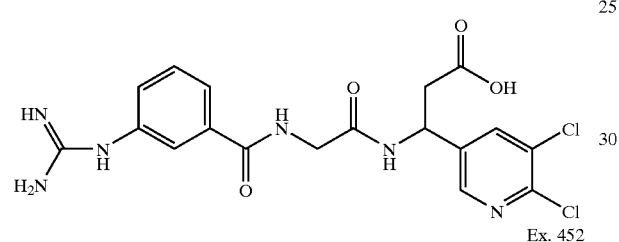
Ex. 456
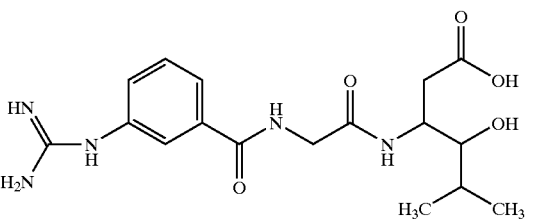
Ex. 452
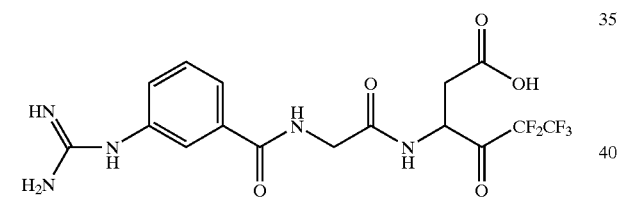
Ex. 457
EXAMPLE 453–460
Using the procedure of Example 393, substituting the appropriate amine hydrochloride for the product of Step E in Step F and substituting GIHA HCl for 3-guanidino-5-trifluoromethylhippuric acid in Step F the following representative compounds may be prepared:
Ex. 453
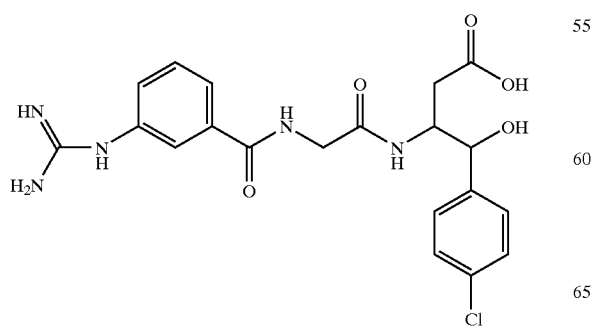
Ex. 458
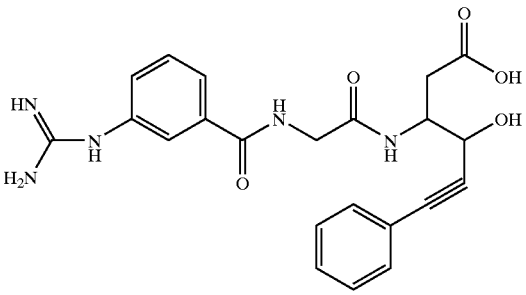

Ex. 459
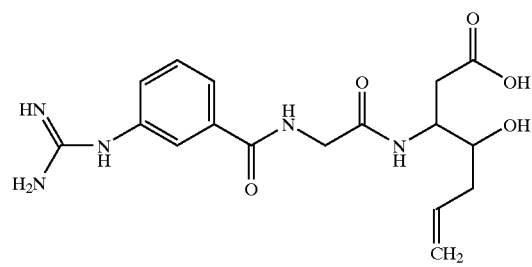
Ex. 460
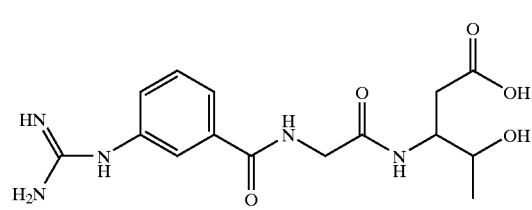
EXAMPLE 461
Using the procedure of Example 406, substituting the appropriate protected aspartyl alcohol prepared in Examples 394–403 for the aspartyl alcohol of Example 406, Step A, and substituting GIHA HCl for 3-guanidino-5-trifluoromethylhippuric acid in Example 393, Step F the following representative compounds may be prepared:
Ex. 461
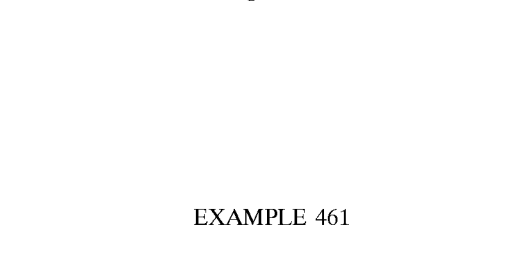
Ex. 462
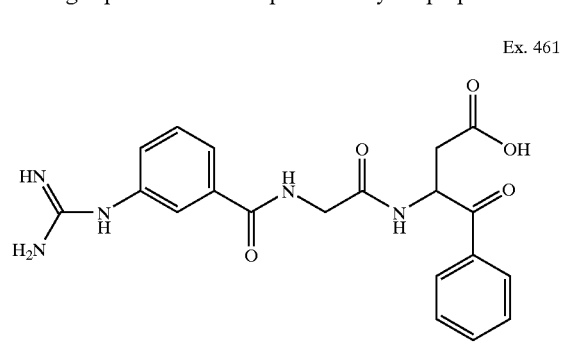
Ex. 463
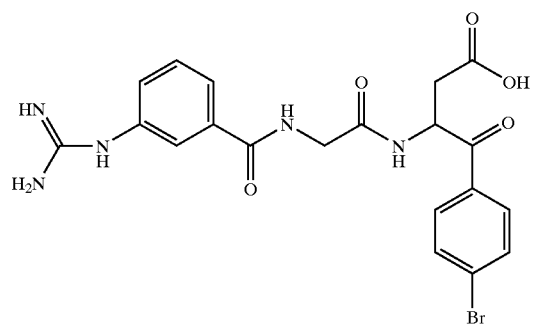
Ex. 464
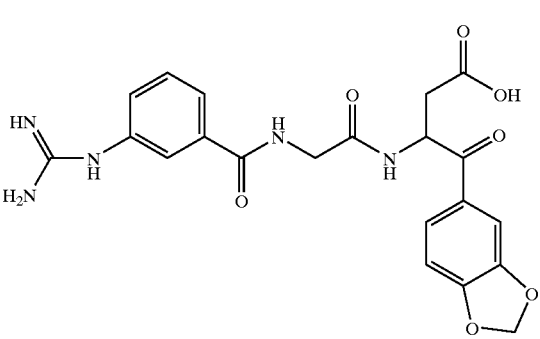
Ex. 465
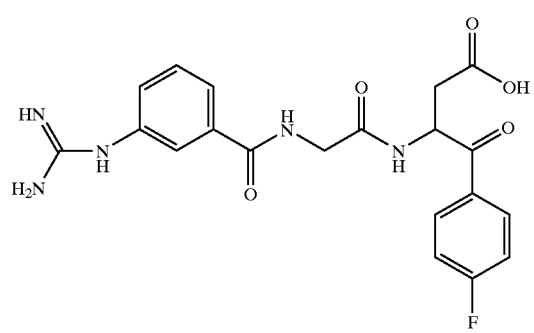
Ex. 466
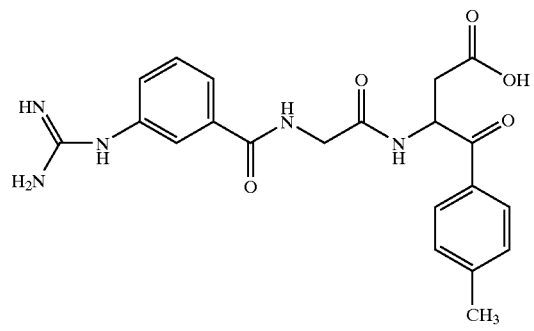

Ex. 467

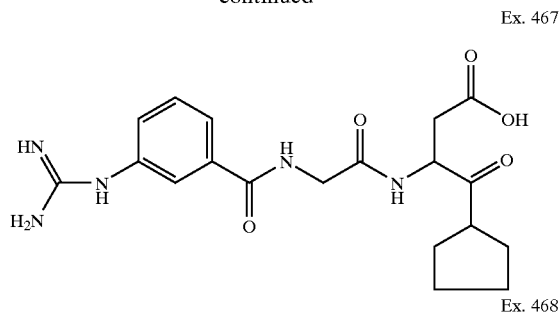

Ex. 468

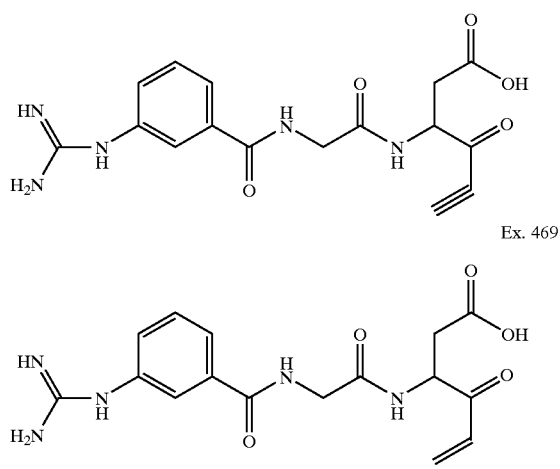

Ex. 469

EXAMPLE 470

Preparation of

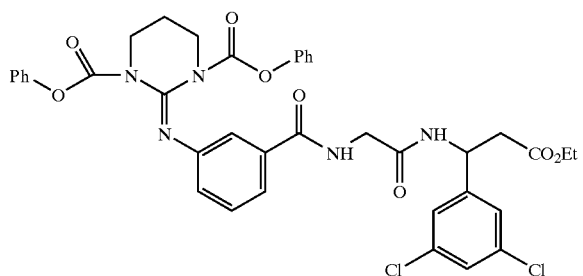

Step A

To 3,4,5,6-tetrahydro-2-pyrimidinethiol (Aldrich) (5.0 g, 0.043 mole) and triethylamine (8.7 g, 0.086 mole) in $CH_2Cl_2$ (50 mL) was added dropwise and at ice bath temperature, phenylchloroformate [(Aldrich) 13.5 g, 0.086 mole)]. The reaction was then stirred overnight at room temperature. The precipitate was filtered and washed with $CH_2Cl_2$. The $CH_2Cl_2$ filtrate was washed with $H_2O$ (3x), dried over $MgSO_4$ and removed under vacuum. The residue was recrystallized from 50% EtOAc/Hexane to yield 9.03 g of 3,4,5,6-tetrahydro-2-pyrimidinethione-N,N'-diphenylcarbamate as a yellow solid.

MS and NMR are consistent with the desired structure.

Step B

To the product from Example 282, Step C (200 mg, 0.00042 mole), the product from Step A above (150 mg, 0.00042 mole) and triethylamine (142 mg, 0.0014 mole) in 3 mL DMF was added 250 mg (0.00046 mole) $HgCl_2$ at ice bath temperature. The reaction was stirred at ice bath temperature for ½ hour and at room temperature for 2 hours. 100 mg additional $HgCl_2$ was added and the reaction was stirred overnight at 60° C. Excess ethyl acetate was added and the slurry was filtered through celite. The filtrate was washed with $H_2O$ (3x), passed through a pad of silica gel and the product isolated by silica gel chromatography to yield the above compound (110 mg) as a white solid.

MS and NMR were consistent with the desired structure.

EXAMPLE 471

Preparation of

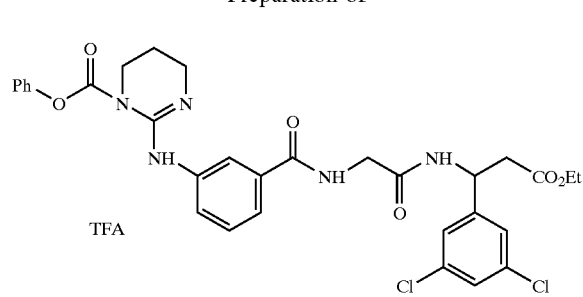

Step A

To 3,4,5,6-tetrahydro-2-pyrimidinethiol (Aldrich) (10 g, 0.086 mole) in absolute ethanol (75 mL) is added methyl iodide (12.2 g, 0.086 mole). The reaction was stirred at reflux for 2.5 hours. The solvent was removed under vacuum and the residue dried to yield 3,4,5,6-tetrahydro-2-methylthiopyrimidine.HI (22 g) as a white solid.

MS and NMR were consistent with the desired structure.

Step B

To the product from Step A above (5.16 g, 0.02 mole) and triethylamine (4.1 g, 0.04 mole) in $CH_2Cl_2$ (25 mL) was added phenylchloroformate (Aldrich) (3.13 g, 0.02 mole) dropwise at ice bath temperature. The reaction was then stirred overnight at room temperature. The precipitate was filtered and washed with $CH_2Cl_2$. The $CH_2Cl_2$ from the filtrate was washed with $H_2O$ (3x), dried over $MgSO_4$ and removed under vacuum to yield 3,4,5,6-tetrahydro-2-methylthiopyrimidine-N-phenylcarbamate (4.8 g) as a white solid.

MS and NMR were consistent with the desired structure.

Step C

To the product from Step B above (2 g, 0.008 mole) in $CH_2CN$ (12 mL) was added the product of Example M, Step B (1.84 g, 0.008 mole). The reaction was stirred at reflux overnight and the product isolated by RPHPLC to yield 3,4,5,6-tetrahydro-N-phenylcarbamyl-2-pyrimidine-m-aminohippuric acid.TFA (1 g) as a white solid.

Step D

The above compound was prepared according to the methodology of Example 174, substituting an equivalent amount of 3,5-dichlorobenzaldehyde for 3,4-dichlorobenzaldehyde in Example 174, Step A and substituting an equivalent amount of the product from Step C above for m-guanidinohippuric acid.HCl in Example 174, Step B.

MS and NMR were consistent with the desired structure.

EXAMPLE 472

Preparation of

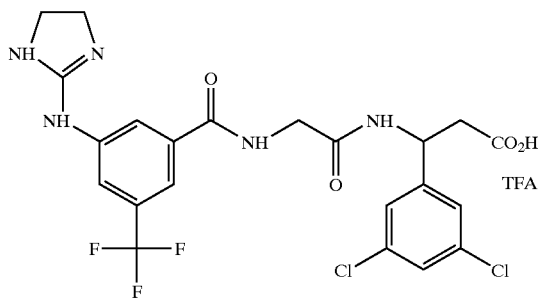

Step A

To 2-methylthio-2-imidazoline.HI (Aldrich) (10 g, 0.041 male) and triethylamine (4.14 g, 0.041 mole) in $CH_2Cl_2$ (50 mL) was added BOC anhydride (Aldrich) (8.94 g, 0.041 mole) at ice bath temperature. The reaction was stirred overnight at room temperature. The $CH_2Cl_2$ was washed with $H_2O$ (3×), dried over $MgSO_4$, washed with $H_2O$ (3×), dried over $MgSO_4$ and removed under vacuum to yield N-BOC-2-methylthio-2-imidazoline (8.1 g) as a clear liquid which turned to a white solid upon standing. MS and NMR were consistent with the desired structure.

Step B To the product of Step A above (2.7 g, 0.0124 mole) in $CH_3CN$ (6 mL) was added 3-amino-5-trifluoromethylbenzoic acid (synthesized by catalytic hydrogenation (Pd/C) of 3-nitro-5-trifluorobenzoic acid (Lancaster) followed by treatment with HCl) (3 g, 0.0124 mole). The reaction was stirred at 35–40° C. for 10 days. After cooling to room temperature, the precipitate was filtered, washed with $CH_3CN$ and dried to yield 3-(N-BOC-4,5-dihydroimidazol-2-yl)amino-5-trifluoromethylbenzoic acid HCl (3.2 g) as a white solid. MS and NMR were consistent with the desired structure.

Step C

The above compound was prepared according to the methodology of Example 200, substituting an equivalent amount of the product from Step B above for the product from Step A in Example 199, Step B and by additionally treating the intermediate ethyl ester, N-BOC derivative with TFA for 1 hour to remove the BOC protecting group.

MS and NMR were consistent with the desired structure.

EXAMPLE 473

Preparation of

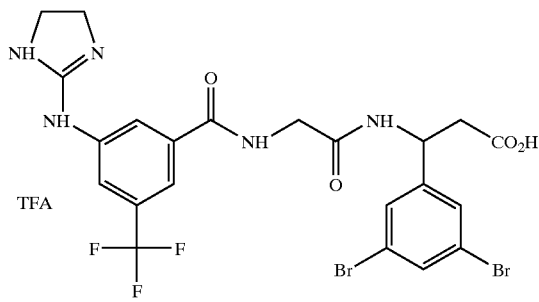

Step A

To 3-amino-5-trifluoromethylhippuric acid hydrochloride [prepared according to Example M, Steps A and B substituting 3-nitro-5-trifluoromethylbenzoyl chloride (prepared from 3-nitro-5-trifluoromethylbenzoic acid (Lancaster) and thionyl chloride for M-nitrobenzoyl chloride in Example M, Step A] (3 g, 0.01 mole) in $CH_3CN$ (5 mL) was added the product from Example 472, Step A (2.2 g, 0.01 mole). The reaction was stirred at 35° C. for 3 days then at reflux for 4 hours. After cooling, the $CH_3CN$ was decanted off, the residue slurried several times in ether (ether decanted off) and then dried to yield 3-(4,5-dihydro-1H-imidazol-2-yl)amino-5-trifluoromethylhippuric acid.HCl (2.5 g) as a white solid.

MS and NMR were consistent with the desired structure.

Step B

The above compound was prepared according to the methodology of Example 210, substituting an equivalent amount of the product from Step A above for m-guanidinohippuric acid.HCl in Example 174, Step B.

MS and NMR were consistent with the desired structure.

EXAMPLE 474

Preparation of

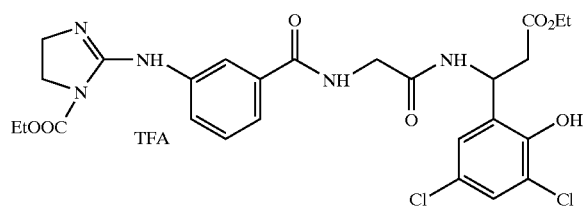

Step A

To 2-methylthio-2-imidazoline.HI (Aldrich) (10 g, 0.041 mole) and triethylamine (8.3 g, 0.0082 mole) in $CH_2Cl_2$ (50 mL) was added ethylchloroformate (Aldrich) (4.5 g, 0.041 mole) dropwise at ice bath temperature. The reaction was stirred overnight at room temperature. The precipitate was filtered and washed with $CH_2Cl_2$. The $CH_2Cl_2$ from the filtrate was washed with $H_2O$ (3×), dried over $MgSO_4$ and removed under vacuum to yield 2-methylthio-2-imidazoline-N-ethylcarbamate (7.1 g) as a clear yellow oil.

MS and NMR were consistent with the desired H structure.

Step B

To the product from Step A above (5.73 g, 0.0305 mole) in $CH_3CN$ (12 mL) was added m-aminohippuric acid.HCl (Example M, Step B) (7.02 g, 0.0305 mole). The reaction was stirred overnight at room temperature then at 50° C. for 6 hours and at 80° C. for 2 hours. After cooling to room temperature and stirring at room temperature overnight, the precipitate was filtered, washed with $CH_3CN$ and dried to yield 3-(4,5-dihydro-N-ethylcarbamate-imidazol-2-yl) aminohippuric acid.HCl (9.6 g) as a white solid.

MS and NMR were consistent with the desired structure.

Step C

The above compound was prepared according to the methodology of Example 174, substituting an equivalent amount of the product from Step B above for m-aminohippuric acid in Example 174, Step B and an equivalent amount of the product from Example 230, Step A for the product from Example 174, Step A in Example 174, Step B.

MS and NMR were consistent with the desired structure.

EXAMPLE 475

Preparation of

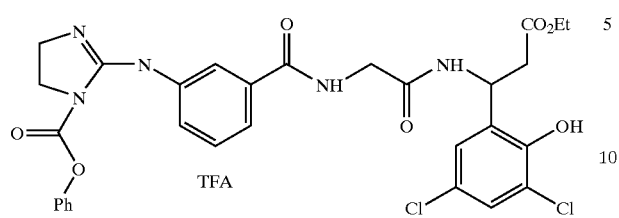

TFA

The above compound was prepared according to the methodology of Example 474, substituting an equivalent amount of phenylchloroformate (Aldrich) for ethylchloroformate in Example 474, Step A and by heating the reaction mixture at 70° C. for 8 hours then room temperature for 2 days in Example 474, Step B.

MS and NMR were consistent with the desired structure.

Using the methodologies, reagents and conditions exemplified in the schemes and examples of this disclosure (or the synthesis of reagents from readily available starting materials via methodologies known to those skilled in the art), the following compounds of the present invention are synthesized:

EXAMPLES 476–517

Ex. 476

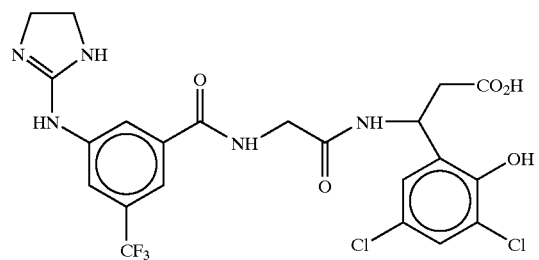

Ex. 477

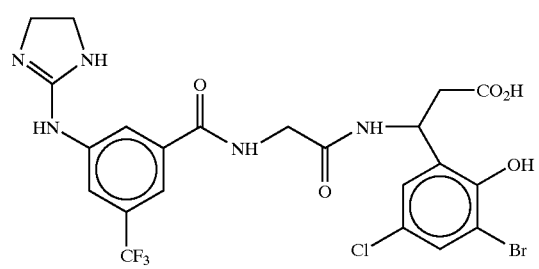

Ex. 478

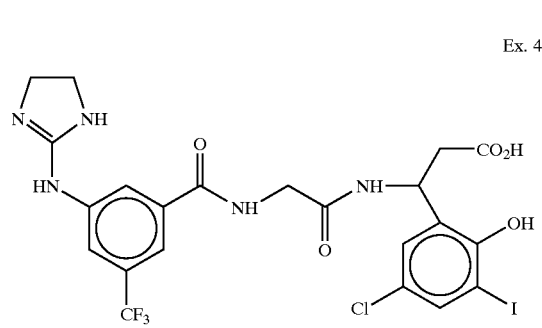

Ex. 479

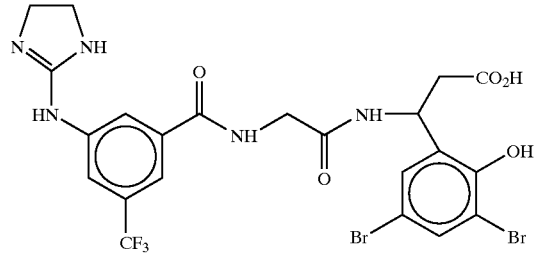

Ex. 480

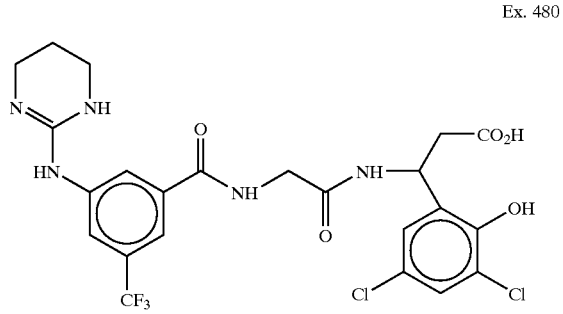

Ex. 481

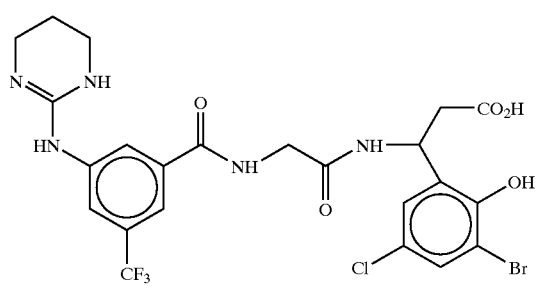

Ex. 482

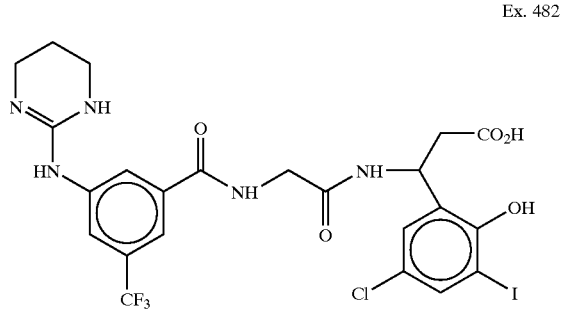

Ex. 483

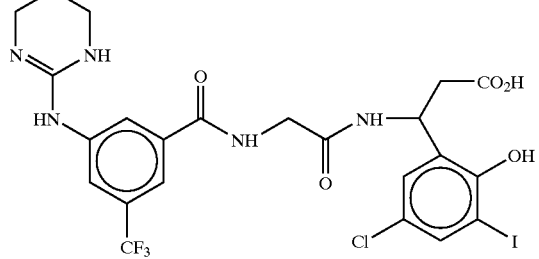

Ex. 484
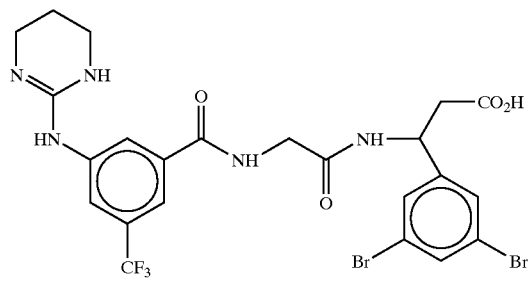
Ex. 485
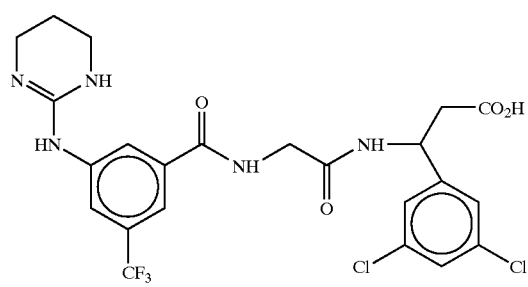
Ex. 486
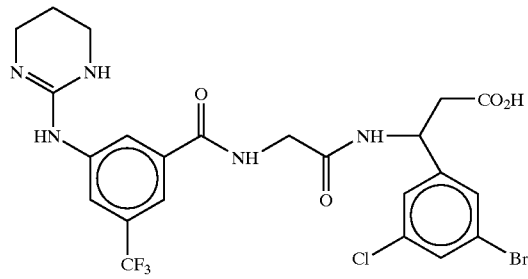
Ex. 487
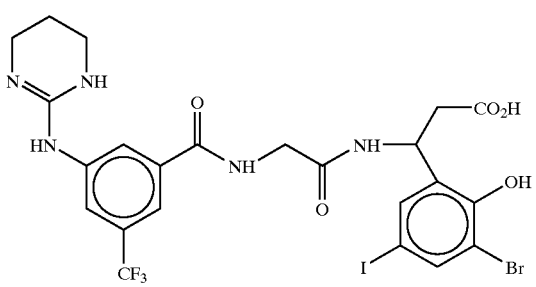
Ex. 488
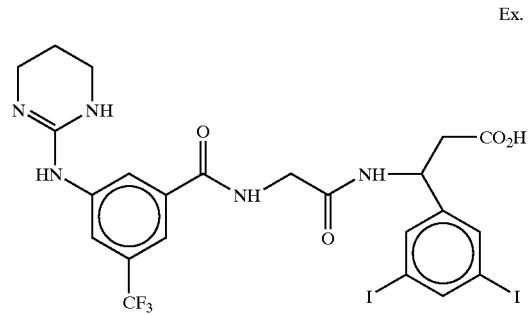
Ex. 489
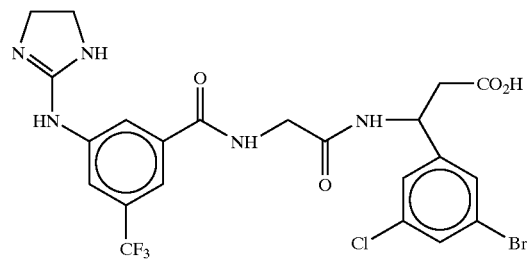
Ex. 490
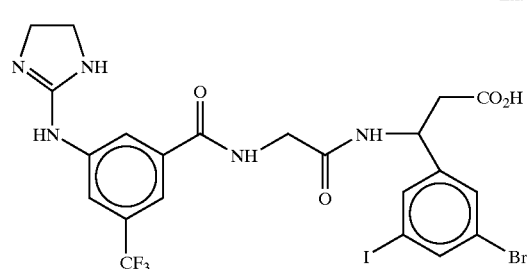
Ex. 491
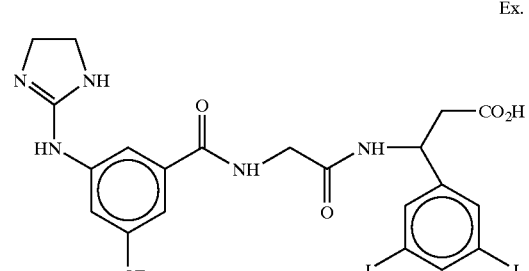
Ex. 492
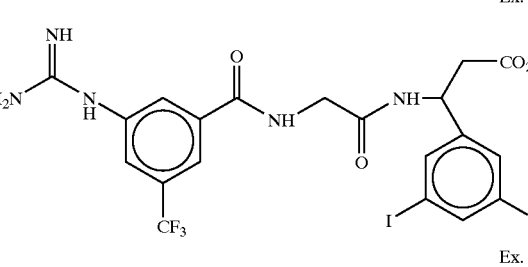
Ex. 493
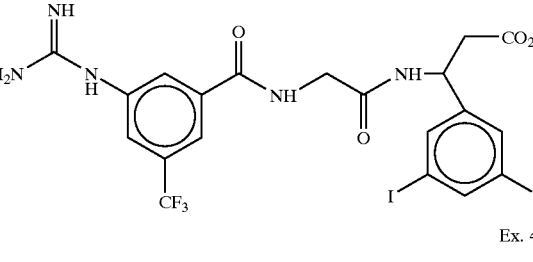
Ex. 494
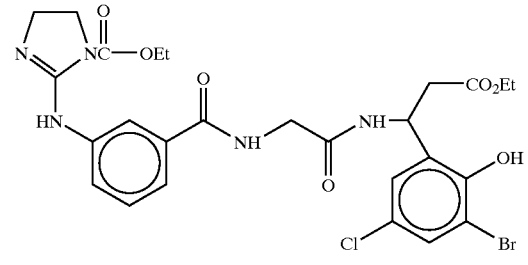

Ex. 495
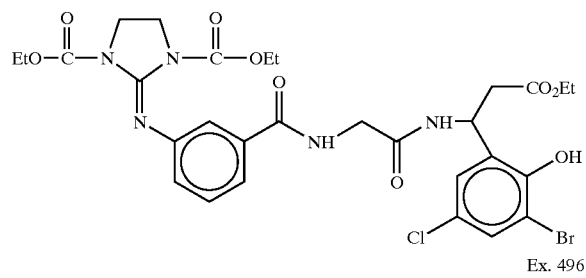
Ex. 496
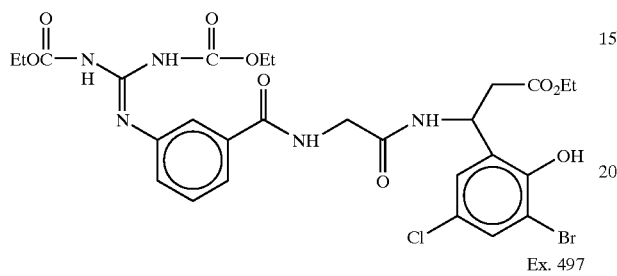
Ex. 497
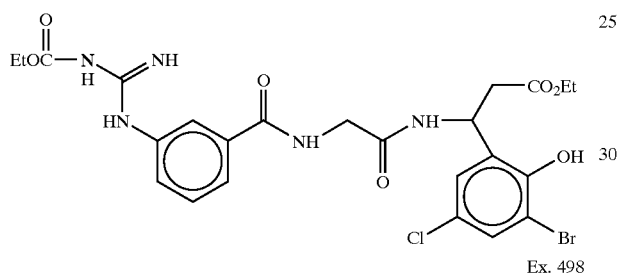
Ex. 498
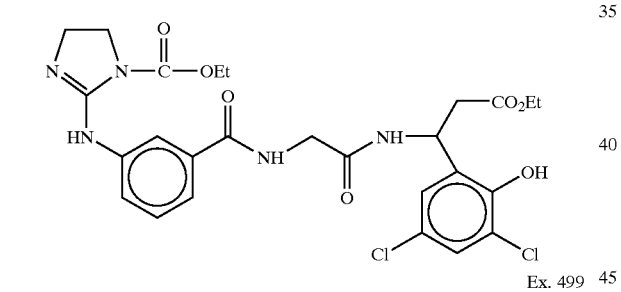
Ex. 499
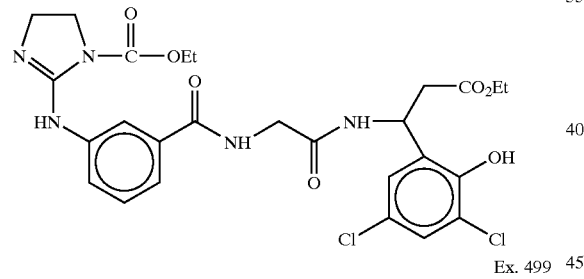
Ex. 500
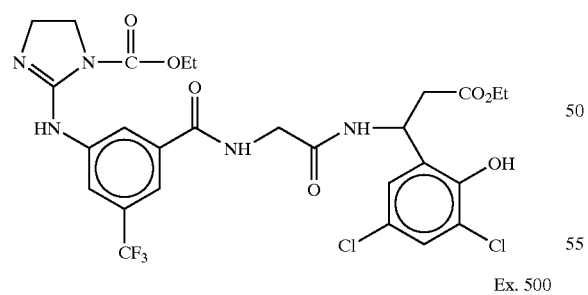
Ex. 501
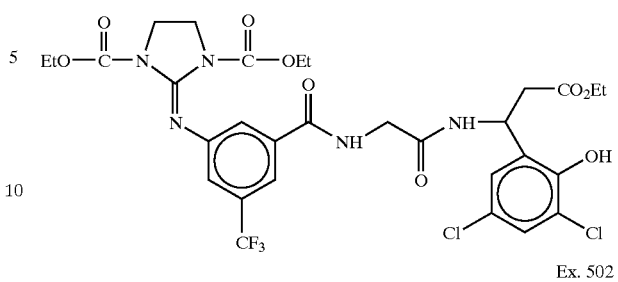
Ex. 502
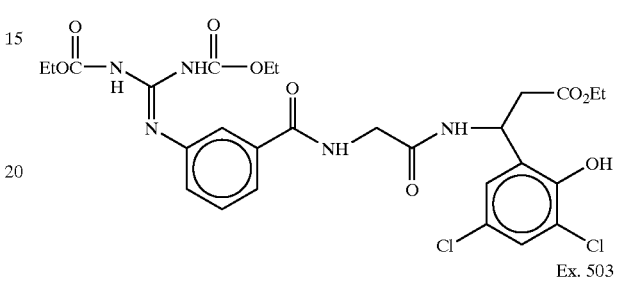
Ex. 503
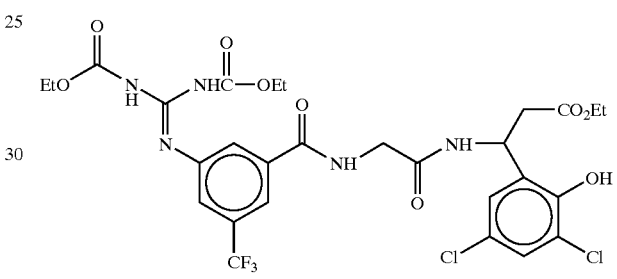
Ex. 504
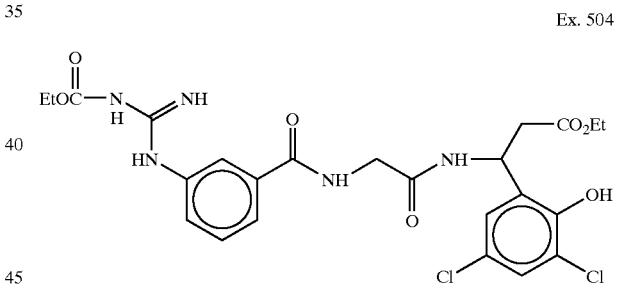
Ex. 505
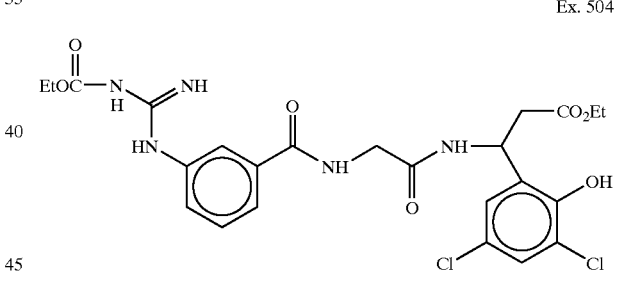
Ex. 506
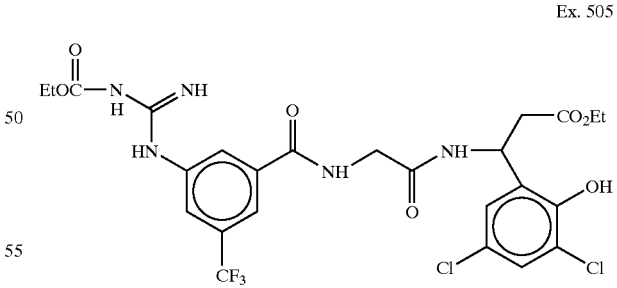

Ex. 507
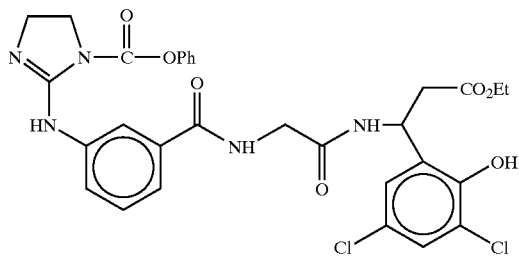
Ex. 512
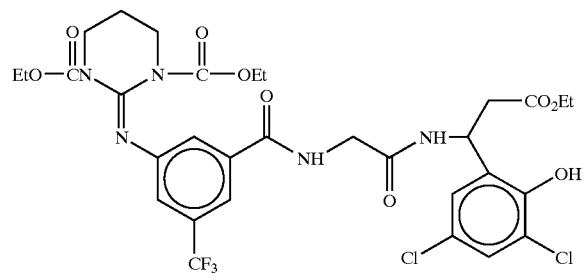
Ex. 508
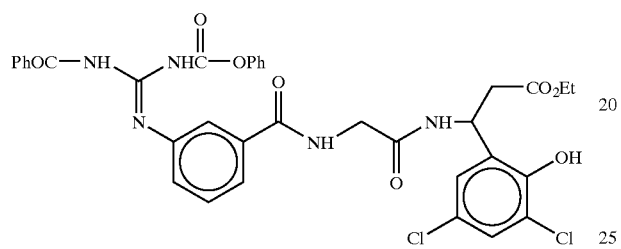
Ex. 513
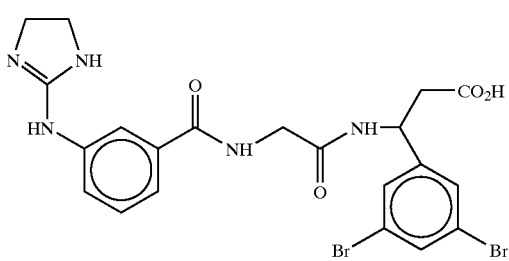
Ex. 509
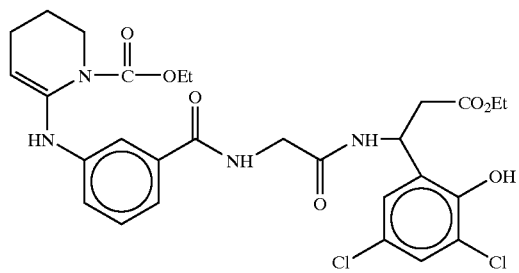
Ex. 514
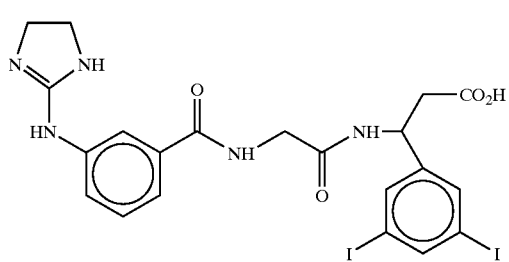
Ex. 510
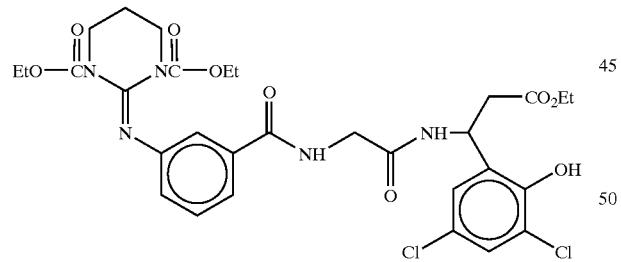
Ex. 515
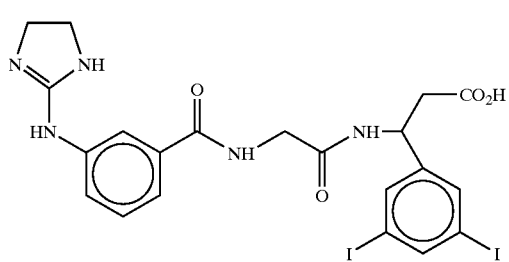
Ex. 511
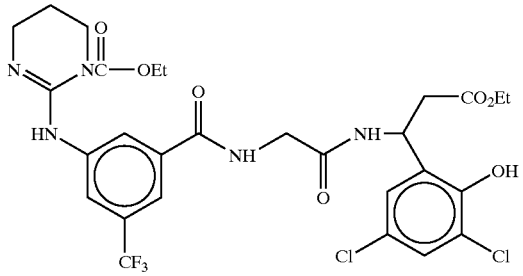
Ex. 516
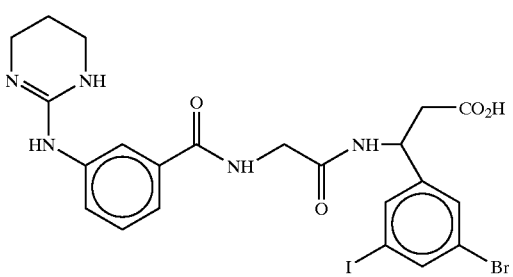

Ex. 517

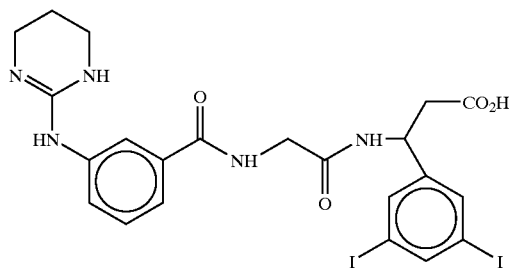

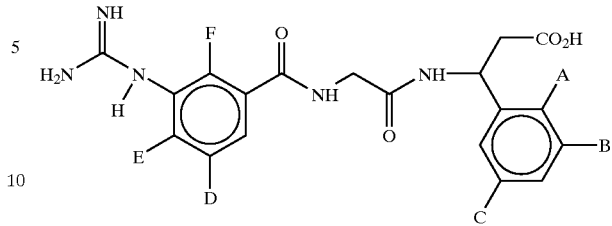

| Example # | A | B | C | D | E | F |
|---|---|---|---|---|---|---|
| 546 | OH | Br | Cl | H | Br | H |
| 547 | OH | Br | Cl | Cl | OH | H |
| 548 | OH | Br | Cl | Br | OH | H |
| 549 | OH | Br | Cl | I | OH | H |

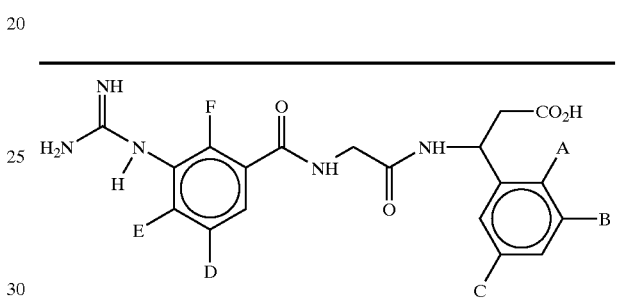

| Example # | A | B | C | D | E | F |
|---|---|---|---|---|---|---|
| 518 | OH | Cl | Cl | Br | H | H |
| 519 | OH | Cl | Cl | OH | H | H |
| 520 | OH | Cl | Cl | NO$_2$ | H | H |
| 521 | OH | Cl | Cl | I | H | H |
| 522 | OH | Cl | Cl | Cl | H | H |
| 523 | OH | Cl | Cl | Cl | H | Cl |
| 524 | OH | Cl | Cl | OMe | H | H |
| 525 | OH | Cl | Cl | H | CF$_3$ | H |
| 526 | OH | Cl | Cl | H | OH | H |
| 527 | OH | Cl | Cl | H | OMe | H |
| 528 | OH | Cl | Cl | H | Cl | H |
| 529 | OH | Cl | Cl | H | Cl | Cl |
| 530 | OH | Cl | Cl | H | Br | H |
| 531 | OH | Cl | Cl | Cl | OH | H |
| 532 | OH | Cl | Cl | Br | OH | H |
| 533 | OH | Cl | Cl | I | OH | H |

| Example # | A | B | C | D | E | F |
|---|---|---|---|---|---|---|
| 550 | OH | I | Cl | Br | H | H |
| 551 | OH | I | Cl | OH | H | H |
| 552 | OH | I | Cl | NO$_2$ | H | H |
| 553 | OH | I | Cl | I | H | H |
| 554 | OH | I | Cl | Cl | H | H |
| 555 | OH | I | Cl | Cl | H | Cl |
| 556 | OH | I | Cl | OMe | H | H |
| 557 | OH | I | Cl | H | CF$_3$ | H |
| 558 | OH | I | Cl | H | OH | H |
| 559 | OH | I | Cl | H | OMe | H |
| 560 | OH | I | Cl | H | Cl | H |
| 561 | OH | I | Cl | H | Cl | Cl |
| 562 | OH | I | Cl | H | Br | H |
| 563 | OH | I | Cl | CF$_3$ | H | H |
| 564 | OH | I | Cl | Cl | OH | H |
| 565 | OH | I | Cl | Br | OH | H |
| 566 | OH | I | Cl | I | OH | H |

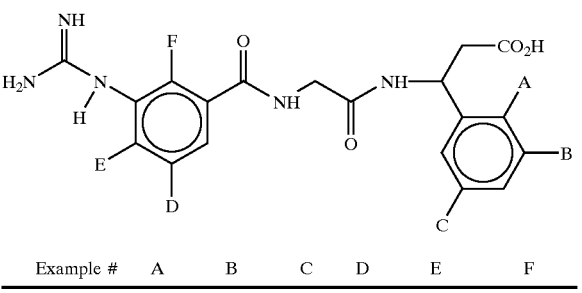

| Example # | A | B | C | D | E | F |
|---|---|---|---|---|---|---|
| 534 | OH | Br | Cl | Br | H | H |
| 535 | OH | Br | Cl | OH | H | H |
| 536 | OH | Br | Cl | NO$_2$ | H | H |
| 537 | OH | Br | Cl | I | H | H |
| 538 | OH | Br | Cl | Cl | H | H |
| 539 | OH | Br | Cl | Cl | H | Cl |
| 540 | OH | Br | Cl | OMe | H | H |
| 541 | OH | Br | Cl | H | CF$_3$ | H |
| 542 | OH | Br | Cl | H | OH | H |
| 543 | OH | Br | Cl | H | OMe | H |
| 544 | OH | Br | Cl | H | Cl | H |
| 545 | OH | Br | Cl | H | Cl | Cl |

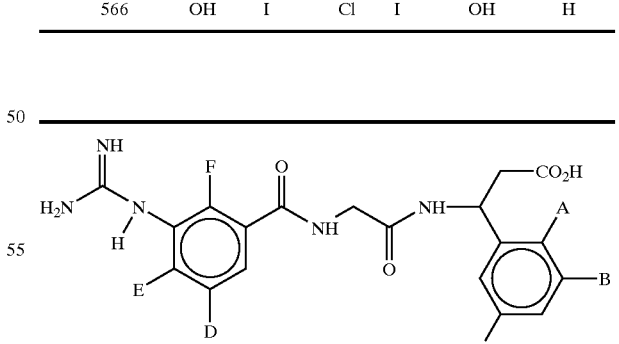

| Example # | A | B | C | D | E | F |
|---|---|---|---|---|---|---|
| 567 | H | Br | Cl | Br | H | H |
| 568 | H | Br | Cl | OH | H | H |
| 569 | H | Br | Cl | NO$_2$ | H | H |
| 570 | H | Br | Cl | I | H | H |
| 571 | H | Br | Cl | Cl | H | H |
| 572 | H | Br | Cl | Cl | H | Cl |

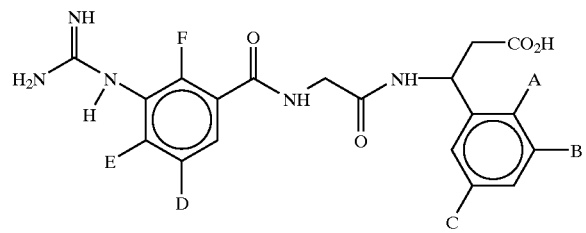

| Example # | A | B | C | D | E | F |
|---|---|---|---|---|---|---|
| 573 | H | Br | Cl | OMe | H | H |
| 574 | H | Br | Cl | H | CF3 | H |
| 575 | H | Br | Cl | H | OH | H |
| 576 | H | Br | Cl | H | OMe | H |
| 577 | H | Br | Cl | H | Cl | H |
| 578 | H | Br | Cl | H | Cl | Cl |
| 579 | H | Br | Cl | H | Br | H |
| 580 | H | Br | Cl | Cl | OH | H |
| 581 | H | Br | Cl | Br | OH | H |
| 582 | H | Br | Cl | I | OH | H |

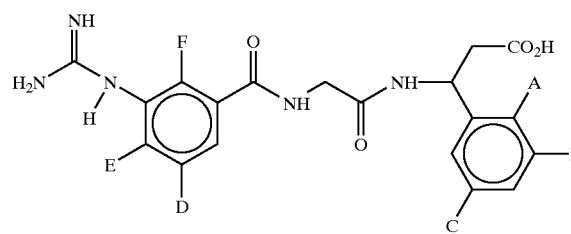

| Example # | A | B | C | D | E | F |
|---|---|---|---|---|---|---|
| 583 | H | Br | Br | Br | H | H |
| 584 | H | Br | Br | OH | H | H |
| 585 | H | Br | Br | NO2 | H | H |
| 586 | H | Br | Br | I | H | H |
| 567 | H | Br | Br | Cl | H | H |
| 588 | H | Br | Br | Cl | H | Cl |
| 589 | H | Br | Br | OMe | H | H |
| 590 | H | Br | Br | H | CF3 | H |
| 591 | H | Br | Br | H | OH | H |
| 592 | H | Br | Br | H | OMe | H |
| 593 | H | Br | Br | H | Cl | H |
| 594 | H | Br | Br | H | Cl | Cl |
| 595 | H | Br | Br | H | Br | H |
| 596 | H | Br | Br | Cl | OH | H |
| 597 | H | Br | Br | Br | OH | H |
| 598 | H | Br | Br | I | OH | H |

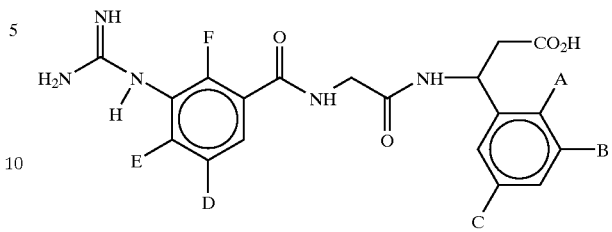

| Example # | A | B | C | D | E | F |
|---|---|---|---|---|---|---|
| 599 | H | Br | I | Br | H | H |
| 600 | H | Br | I | OH | H | H |
| 601 | H | Br | I | NO2 | H | H |
| 602 | H | Br | I | I | H | H |
| 603 | H | Br | I | Cl | H | H |
| 604 | H | Br | I | Cl | H | Cl |
| 605 | H | Br | I | OMe | H | H |
| 606 | H | Br | I | H | CF3 | H |
| 607 | H | Br | I | H | OH | H |
| 608 | H | Br | I | H | OMe | H |
| 609 | H | Br | I | H | Cl | H |
| 610 | H | Br | I | H | Cl | Cl |
| 611 | H | Br | I | H | Br | H |
| 612 | H | Br | I | Cl | OH | H |
| 613 | H | Br | I | Br | OH | H |
| 614 | H | Br | I | I | OH | H |

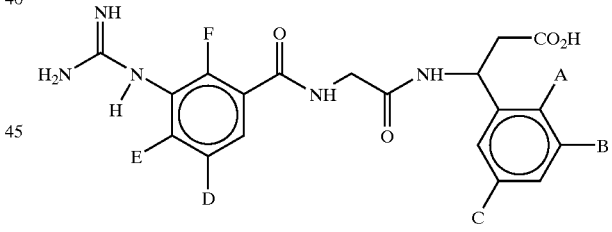

| Example # | A | B | C | D | E | F |
|---|---|---|---|---|---|---|
| 615 | H | I | I | Br | H | H |
| 616 | H | I | I | OH | H | H |
| 617 | H | I | I | NO2 | H | H |
| 618 | H | I | I | I | H | H |
| 619 | H | I | I | Cl | H | H |
| 620 | H | I | I | Cl | H | Cl |
| 621 | H | I | I | OMe | H | H |
| 622 | H | I | I | H | CF3 | H |
| 623 | H | I | I | H | OH | H |
| 624 | H | I | I | H | OMe | H |
| 625 | H | I | I | H | Cl | H |
| 626 | H | I | I | H | Cl | Cl |
| 627 | H | I | I | H | Br | H |
| 628 | H | I | I | Cl | OH | H |
| 629 | H | I | I | Br | OH | H |
| 630 | H | I | I | I | OH | H |

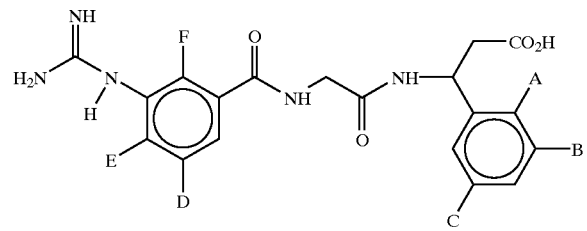

| Example # | A | B | C | D | E | F |
|---|---|---|---|---|---|---|
| 631 | H | Cl | Cl | Br | H | H |
| 632 | H | Cl | Cl | OH | H | H |
| 633 | H | Cl | Cl | $NO_2$ | H | H |
| 634 | H | Cl | Cl | I | H | H |
| 635 | H | Cl | Cl | Cl | H | H |
| 636 | H | Cl | Cl | Cl | H | Cl |
| 637 | H | Cl | Cl | OMe | H | H |
| 638 | H | Cl | Cl | H | $CF_3$ | H |
| 639 | H | Cl | Cl | H | OH | H |
| 640 | H | Cl | Cl | H | OMe | H |
| 641 | H | Cl | Cl | H | Cl | H |
| 642 | H | Cl | Cl | H | Cl | Cl |
| 643 | H | Cl | Cl | H | Br | H |
| 644 | H | Cl | Cl | Cl | OH | H |
| 645 | H | Cl | Cl | Br | OH | H |
| 646 | H | Cl | Cl | I | OH | H |

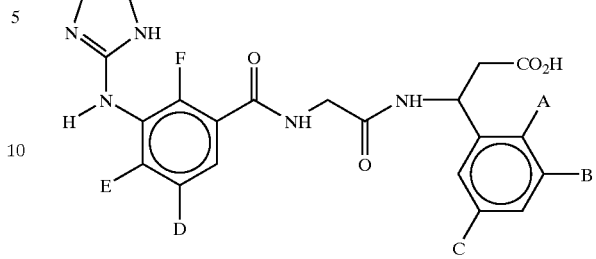

| Example # | A | B | C | D | E | F |
|---|---|---|---|---|---|---|
| 663 | OH | Br | Cl | Br | H | H |
| 664 | OH | Br | Cl | OH | H | H |
| 665 | OH | Br | Cl | $NO_2$ | H | H |
| 666 | OH | Br | Cl | I | H | H |
| 667 | OH | Br | Cl | Cl | H | H |
| 668 | OH | Br | Cl | Cl | H | Cl |
| 669 | OH | Br | Cl | OMe | H | H |
| 670 | OH | Br | Cl | H | $CF_3$ | H |
| 671 | OH | Br | Cl | H | OH | H |
| 672 | OH | Br | Cl | H | OMe | H |
| 673 | OH | Br | Cl | H | Cl | H |
| 674 | OH | Br | Cl | H | Cl | Cl |
| 675 | OH | Br | Cl | H | Br | H |
| 676 | OH | Br | Cl | Cl | OH | H |
| 677 | OH | Br | Cl | Br | OH | H |
| 678 | OH | Br | Cl | I | OH | H |

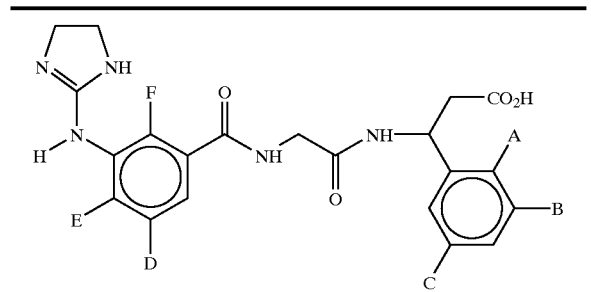

| Example # | A | B | C | D | E | F |
|---|---|---|---|---|---|---|
| 647 | OH | Cl | Cl | Br | H | H |
| 648 | OH | Cl | Cl | OH | H | H |
| 649 | OH | Cl | Cl | $NO_2$ | H | H |
| 650 | OH | Cl | Cl | I | H | H |
| 651 | OH | Cl | Cl | Cl | H | H |
| 652 | OH | Cl | Cl | Cl | H | Cl |
| 653 | OH | Cl | Cl | OMe | H | H |
| 654 | OH | Cl | Cl | H | $CF_3$ | H |
| 655 | OH | Cl | Cl | H | OH | H |
| 656 | OH | Cl | Cl | H | OMe | H |
| 657 | OH | Cl | Cl | H | Cl | H |
| 658 | OH | Cl | Cl | H | Cl | Cl |
| 659 | OH | Cl | Cl | H | Br | H |
| 660 | OH | Cl | Cl | Cl | OH | H |
| 661 | OH | Cl | Cl | Br | OH | H |
| 662 | OH | Cl | Cl | I | OH | H |

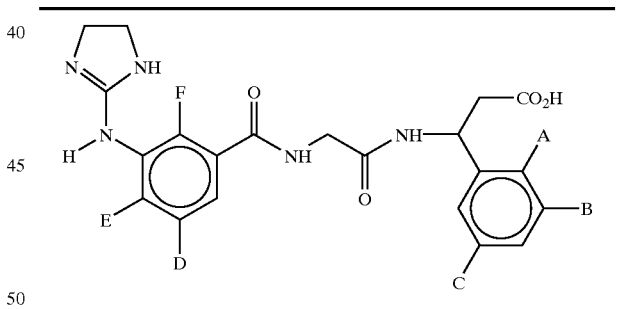

| Example # | A | B | C | D | E | F |
|---|---|---|---|---|---|---|
| 679 | OH | I | Cl | Br | H | H |
| 680 | OH | I | Cl | OH | H | H |
| 681 | OH | I | Cl | $NO_2$ | H | H |
| 682 | OH | I | Cl | I | H | H |
| 683 | OH | I | Cl | Cl | H | H |
| 684 | OH | I | Cl | Cl | H | Cl |
| 685 | OH | I | Cl | OMe | H | H |
| 686 | OH | I | Cl | H | $CF_3$ | H |
| 687 | OH | I | Cl | H | OH | H |
| 688 | OH | I | Cl | H | OMe | H |
| 689 | OH | I | Cl | H | Cl | H |
| 690 | OH | I | Cl | H | Cl | Cl |
| 691 | OH | I | Cl | H | Br | H |
| 692 | OH | I | Cl | Cl | OH | H |
| 693 | OH | I | Cl | Br | OH | H |
| 694 | OH | I | Cl | I | OH | H |

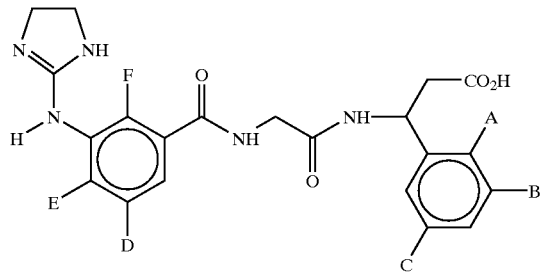

| Example # | A | B | C | D | E | F |
|---|---|---|---|---|---|---|
| 695 | H | Cl | Cl | Br | H | H |
| 696 | H | Cl | Cl | OH | H | H |
| 697 | H | Cl | Cl | NO$_2$ | H | H |
| 698 | H | Cl | Cl | I | H | H |
| 699 | H | Cl | Cl | Cl | H | H |
| 700 | H | Cl | Cl | Cl | H | Cl |
| 701 | H | Cl | Cl | OMe | H | H |
| 702 | H | Cl | Cl | H | CF$_3$ | H |
| 703 | H | Cl | Cl | H | OH | H |
| 704 | H | Cl | Cl | H | OMe | H |
| 705 | H | Cl | Cl | H | Cl | H |
| 706 | H | Cl | Cl | H | Cl | Cl |
| 707 | H | Cl | Cl | H | Br | H |
| 708 | H | Cl | Cl | Cl | OH | H |
| 709 | H | Cl | Cl | Br | OH | H |
| 710 | H | Cl | Cl | I | OH | H |

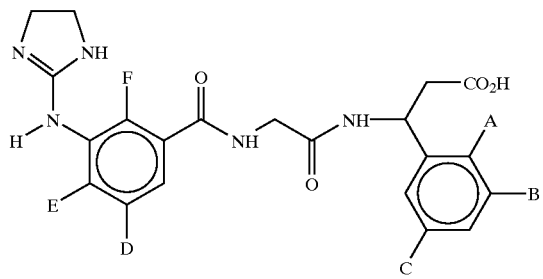

| Example # | A | B | C | D | E | F |
|---|---|---|---|---|---|---|
| 727 | H | Br | Br | Br | H | H |
| 728 | H | Br | Br | OH | H | H |
| 729 | H | Br | Br | NO$_2$ | H | H |
| 730 | H | Br | Br | I | H | H |
| 731 | H | Br | Br | Cl | H | H |
| 732 | H | Br | Br | Cl | H | Cl |
| 733 | H | Br | Br | OMe | H | H |
| 734 | H | Br | Br | H | CF$_3$ | H |
| 735 | H | Br | Br | H | OH | H |
| 736 | H | Br | Br | H | OMe | H |
| 737 | H | Br | Br | H | Cl | H |
| 738 | H | Br | Br | H | Cl | Cl |
| 739 | H | Br | Br | H | Br | H |
| 740 | H | Br | Br | Cl | OH | H |
| 741 | H | Br | Br | Br | OH | H |
| 742 | H | Br | Br | I | OH | H |

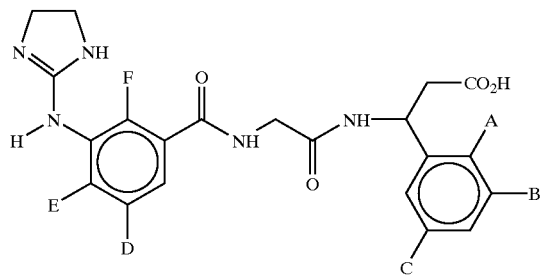

| Example # | A | B | C | D | E | F |
|---|---|---|---|---|---|---|
| 711 | H | Br | Cl | Br | H | H |
| 712 | H | Br | Cl | OH | H | H |
| 713 | H | Br | Cl | NO$_2$ | H | H |
| 714 | H | Br | Cl | I | H | H |
| 715 | H | Br | Cl | Cl | H | H |
| 716 | H | Br | Cl | Cl | H | Cl |
| 717 | H | Br | Cl | OMe | H | H |
| 718 | H | Br | Cl | H | CF$_3$ | H |
| 719 | H | Br | Cl | H | OH | H |
| 720 | H | Br | Cl | H | OMe | H |
| 721 | H | Br | Cl | H | Cl | H |
| 722 | H | Br | Cl | H | Cl | Cl |
| 723 | H | Br | Cl | H | Br | H |
| 724 | H | Br | Cl | Cl | OH | H |
| 725 | H | Br | Cl | Br | OH | H |
| 726 | H | Br | Cl | I | OH | H |

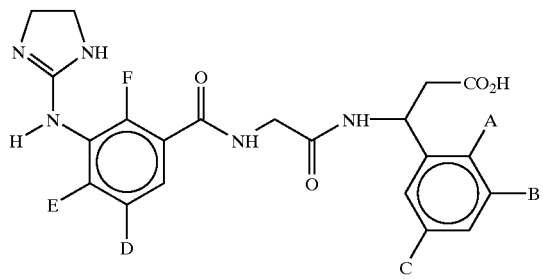

| Example # | A | B | C | D | E | F |
|---|---|---|---|---|---|---|
| 743 | H | Br | I | Br | H | H |
| 744 | H | Br | I | OH | H | H |
| 745 | H | Br | I | NO$_2$ | H | H |
| 746 | H | Br | I | I | H | H |
| 747 | H | Br | I | Cl | H | H |
| 748 | H | Br | I | Cl | H | Cl |
| 749 | H | Br | I | OMe | H | H |
| 750 | H | Br | I | H | CF$_3$ | H |
| 751 | H | Br | I | H | OH | H |
| 752 | H | Br | I | H | OMe | H |
| 753 | H | Br | I | H | Cl | H |
| 754 | H | Br | I | H | Cl | Cl |
| 755 | H | Br | I | H | Br | H |
| 756 | H | Br | I | Cl | OH | H |
| 757 | H | Br | I | Br | OH | H |
| 758 | H | Br | I | I | OH | H |

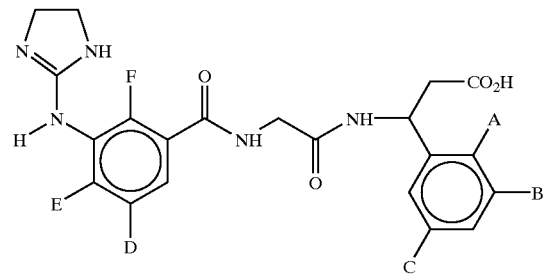

| Example # | A | B | C | D | E | F |
|---|---|---|---|---|---|---|
| 759 | H | I | I | Br | H | H |
| 760 | H | I | I | OH | H | H |
| 761 | H | I | I | NO2 | H | H |
| 762 | H | I | I | I | H | H |
| 763 | H | I | I | Cl | H | H |
| 764 | H | I | I | Cl | H | Cl |
| 765 | H | I | I | OMe | H | H |
| 766 | H | I | I | H | CF3 | H |
| 767 | H | I | I | H | OH | H |
| 768 | H | I | I | H | OMe | H |
| 769 | H | I | I | H | Cl | H |
| 770 | H | I | I | H | Cl | Cl |
| 771 | H | I | I | H | Br | H |
| 772 | H | I | I | Cl | OH | H |
| 773 | H | I | I | Br | OH | H |
| 774 | H | I | I | I | OH | H |

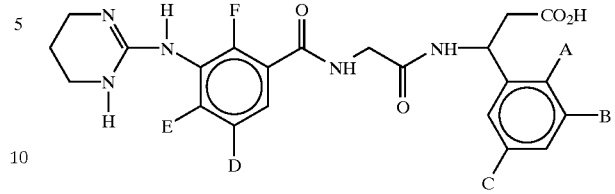

| Example # | A | B | C | D | E | F |
|---|---|---|---|---|---|---|
| 791 | OH | Br | Cl | Br | H | H |
| 792 | OH | Br | Cl | OH | H | H |
| 793 | OH | Br | Cl | NO2 | H | H |
| 794 | OH | Br | Cl | I | H | H |
| 795 | OH | Br | Cl | Cl | H | H |
| 796 | OH | Dr | Cl | Cl | H | Cl |
| 797 | OH | Br | Cl | OMe | H | H |
| 798 | OH | Br | Cl | H | CF3 | H |
| 799 | OH | Br | Cl | H | OH | H |
| 800 | OH | Br | Cl | H | OMe | H |
| 801 | OH | Br | Cl | H | Cl | H |
| 802 | OH | Br | Cl | H | Cl | Cl |
| 803 | OH | Br | Cl | H | Br | H |
| 804 | OH | Br | Cl | Cl | OH | H |
| 805 | OH | Br | Cl | Br | OH | H |
| 806 | OH | Br | Cl | I | OH | H |

| Example # | A | B | C | D | E | F |
|---|---|---|---|---|---|---|
| 775 | OH | Cl | Cl | Br | H | H |
| 776 | OH | Cl | Cl | OH | H | H |
| 777 | OH | Cl | Cl | NO2 | H | H |
| 778 | OH | Cl | Cl | I | H | H |
| 779 | OH | Cl | Cl | Cl | H | H |
| 780 | OH | Cl | Cl | Cl | H | Cl |
| 781 | OH | Cl | Cl | OMe | H | H |
| 782 | OH | Cl | Cl | H | CF3 | H |
| 783 | OH | Cl | Cl | H | OH | H |
| 784 | OH | Cl | Cl | H | OMe | H |
| 785 | OH | Cl | Cl | H | Cl | H |
| 786 | OH | Cl | Cl | H | Cl | Cl |
| 787 | OH | Cl | Cl | H | Br | H |
| 788 | OH | Cl | Cl | Cl | OH | H |
| 789 | OH | Cl | Cl | Br | OH | H |
| 790 | OH | Cl | Cl | I | OH | H |

| Example # | A | B | C | D | E | F |
|---|---|---|---|---|---|---|
| 807 | OH | I | Cl | Br | H | H |
| 808 | OH | I | Cl | OH | H | H |
| 809 | OH | I | Cl | NO2 | H | H |
| 810 | OH | I | Cl | I | H | H |
| 811 | OH | I | Cl | Cl | H | H |
| 812 | OH | I | Cl | Cl | H | Cl |
| 813 | OH | I | Cl | OMe | H | H |
| 814 | OH | I | Cl | H | CF3 | H |
| 815 | OH | I | Cl | H | OH | H |
| 816 | OH | I | Cl | H | OMe | H |
| 817 | OH | I | Cl | H | Cl | H |
| 818 | OH | I | Cl | H | Cl | Cl |
| 819 | OH | I | Cl | H | Br | H |
| 820 | OH | I | Cl | Cl | OH | H |
| 821 | OH | I | Cl | Br | OH | H |
| 822 | OH | I | Cl | I | OH | H |

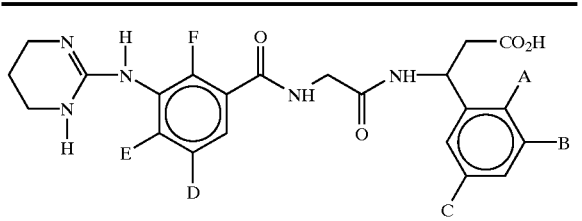

| Example # | A | B | C | D | E | F |
|---|---|---|---|---|---|---|
| 823 | H | Cl | Cl | Br | H | H |
| 824 | H | Cl | Cl | H | H | H |
| 825 | H | Cl | Cl | NO$_2$ | H | H |
| 826 | H | Cl | Cl | I | H | H |
| 827 | H | Cl | Cl | Cl | H | H |
| 828 | H | Cl | Cl | Cl | H | Cl |
| 829 | H | Cl | Cl | OMe | H | H |
| 830 | H | Cl | Cl | H | CF$_3$ | H |
| 831 | H | Cl | Cl | H | OH | H |
| 832 | H | Cl | Cl | H | OMe | H |
| 833 | H | Cl | Cl | H | Cl | H |
| 834 | H | Cl | Cl | H | Cl | Cl |
| 835 | H | Cl | Cl | H | Br | H |
| 836 | H | Cl | Cl | Cl | OH | H |
| 837 | H | Cl | Cl | Br | OH | H |
| 838 | H | Cl | Cl | I | OH | H |

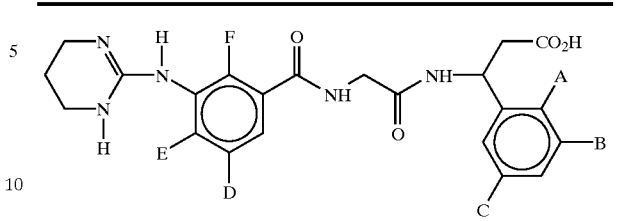

| Example # | A | B | C | D | E | F |
|---|---|---|---|---|---|---|
| 856 | H | Br | Br | Br | H | H |
| 857 | H | Br | Br | OH | H | H |
| 858 | H | Br | Br | NO$_2$ | H | H |
| 859 | H | Br | Br | I | H | H |
| 860 | H | Br | Br | Cl | H | H |
| 861 | H | Br | Br | Cl | H | Cl |
| 862 | H | Br | Br | OMe | H | H |
| 863 | H | Br | Br | H | CF$_3$ | H |
| 864 | H | Br | Br | H | OH | H |
| 865 | H | Br | Br | H | OMe | H |
| 866 | H | Br | Br | H | Cl | H |
| 867 | H | Br | Br | H | Cl | Cl |
| 868 | H | Br | Br | H | Br | H |
| 869 | H | Br | Br | Cl | OH | H |
| 870 | H | Br | Br | Br | OH | H |
| 871 | H | Br | Br | I | OH | H |

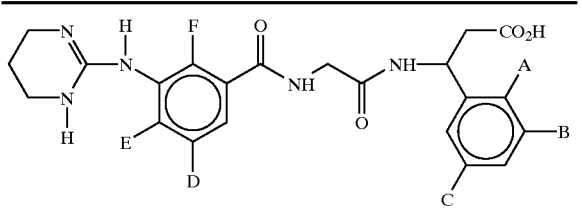

| Example # | A | B | C | D | E | F |
|---|---|---|---|---|---|---|
| 839 | H | Br | Cl | Br | H | H |
| 840 | H | Br | Cl | OH | H | H |
| 841 | H | Br | Cl | NO$_2$ | H | H |
| 842 | H | Br | Cl | I | H | H |
| 843 | H | Br | Cl | Cl | H | H |
| 845 | H | Br | Cl | Cl | H | Cl |
| 846 | H | Br | Cl | OMe | H | H |
| 847 | H | Br | Cl | H | CF$_3$ | H |
| 848 | H | Br | Cl | H | OH | H |
| 849 | H | Br | Cl | H | OMe | H |
| 850 | H | Br | Cl | H | Cl | H |
| 851 | H | Br | Cl | H | Cl | Cl |
| 852 | H | Br | Cl | H | Br | H |
| 853 | H | Br | Cl | Cl | OH | H |
| 854 | H | Br | Cl | Br | OH | H |
| 855 | H | Br | Cl | I | OH | H |

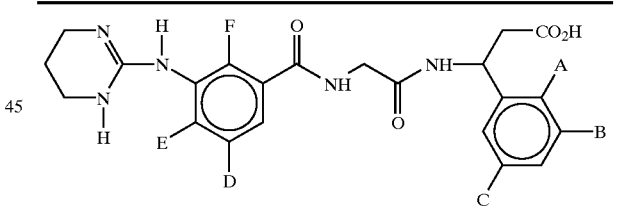

| Example # | A | B | C | D | E | F |
|---|---|---|---|---|---|---|
| 872 | H | Br | I | Br | H | H |
| 873 | H | Br | I | OH | H | H |
| 874 | H | Br | I | NO$_2$ | H | H |
| 875 | H | Br | I | I | H | H |
| 876 | H | Br | I | Cl | H | H |
| 877 | H | Br | I | Cl | H | Cl |
| 878 | H | Br | I | OMe | H | H |
| 879 | H | Br | I | H | CF$_3$ | H |
| 880 | H | Br | I | H | OH | H |
| 881 | H | Br | I | H | OMe | H |
| 882 | H | Br | I | H | Cl | H |
| 883 | H | Br | I | H | Cl | Cl |
| 884 | H | Br | I | H | Br | H |
| 885 | H | Br | I | Cl | OH | H |
| 886 | H | Br | I | Br | OH | H |
| 887 | H | Br | I | I | OH | H |

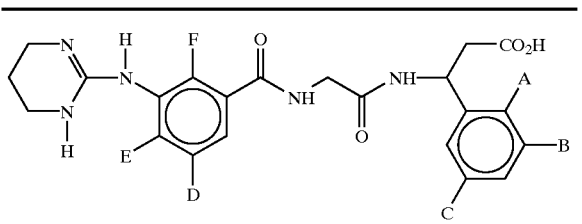

| Example # | A | B | C | D | E | F |
|---|---|---|---|---|---|---|
| 888 | H | I | I | Br | H | H |
| 889 | H | I | I | OH | H | H |
| 890 | H | I | I | NO2 | H | H |
| 891 | H | I | I | I | H | H |
| 892 | H | I | I | Cl | H | H |
| 893 | H | I | I | Cl | H | Cl |
| 894 | H | I | I | OMe | H | H |
| 895 | H | I | I | H | CF3 | H |
| 896 | H | I | I | H | OH | H |
| 897 | H | I | I | H | OMe | H |
| 898 | H | I | I | H | Cl | H |
| 899 | H | I | I | H | Cl | Cl |
| 900 | H | I | I | H | Br | H |
| 901 | H | I | I | Cl | OH | H |
| 902 | H | I | I | Br | OH | H |
| 903 | H | I | I | I | OH | H |

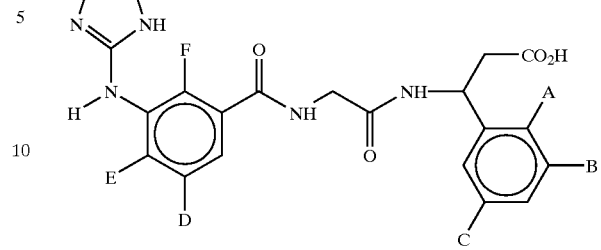

| Example # | A | B | C | D | E | F |
|---|---|---|---|---|---|---|
| 922 | H | CF3 | Br | Br | H | H |
| 923 | H | CF3 | Br | OH | H | H |
| 924 | H | CF3 | Br | NO2 | H | H |
| 925 | H | CF3 | Br | I | H | H |
| 926 | H | CF3 | Br | Cl | H | H |
| 927 | H | CF3 | Br | Cl | H | Cl |
| 928 | H | CF3 | Br | OMe | H | H |
| 929 | H | CF3 | Br | H | CF3 | H |
| 930 | H | CF3 | Br | H | OH | H |
| 931 | H | CF3 | Br | H | OMe | H |
| 932 | H | CF3 | Br | H | Cl | H |
| 933 | H | CF3 | Br | H | Cl | Cl |
| 934 | H | CF3 | Br | H | Br | H |
| 935 | H | CF3 | Br | CF3 | H | H |
| 936 | H | CF3 | Br | H | H | H |
| 937 | H | CF3 | Br | Cl | OR | H |
| 938 | H | CF3 | Br | Br | OH | H |
| 939 | H | CF3 | Br | I | OH | H |

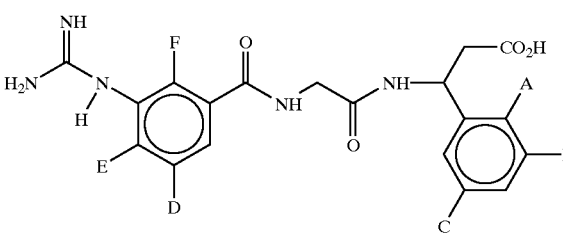

| Example # | A | B | C | D | E | F |
|---|---|---|---|---|---|---|
| 904 | H | CF3 | Br | Br | H | H |
| 905 | H | CF3 | Br | OH | H | H |
| 906 | H | CF3 | Br | NO2 | H | H |
| 907 | H | CF3 | Br | I | H | H |
| 908 | H | CF3 | Br | Cl | H | H |
| 909 | H | CF3 | Br | Cl | H | Cl |
| 910 | H | CF3 | Br | OMe | H | H |
| 911 | H | CF3 | Br | H | CF3 | H |
| 912 | H | CF3 | Br | H | OH | H |
| 913 | H | CF3 | Br | H | OMe | H |
| 914 | H | CF3 | Br | H | Cl | H |
| 915 | H | CF3 | Br | H | Cl | Cl |
| 916 | H | CF3 | Br | H | Br | H |
| 917 | H | CF3 | Br | CF3 | H | H |
| 918 | H | CF3 | Br | H | H | H |
| 919 | H | CF3 | Br | Cl | OH | H |
| 920 | H | CF3 | Br | Br | OH | H |
| 921 | H | CF3 | Br | I | OH | H |

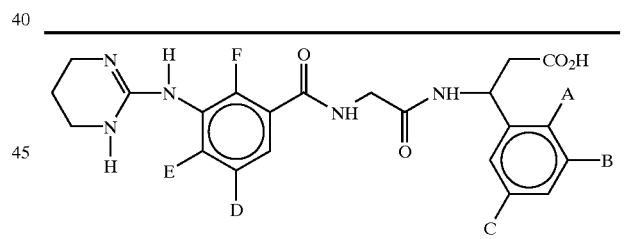

| Example # | A | B | C | D | E | F |
|---|---|---|---|---|---|---|
| 940 | H | CF3 | Br | Br | H | H |
| 941 | H | CF3 | Br | OH | H | H |
| 942 | H | CF3 | Br | NO2 | H | H |
| 943 | H | CF3 | Br | I | H | H |
| 944 | H | CF3 | Br | Cl | H | H |
| 945 | H | CF3 | Br | Cl | H | Cl |
| 946 | H | CF3 | Br | OMe | H | H |
| 947 | H | CF3 | Br | H | CF3 | H |
| 948 | H | CF3 | Br | H | OH | H |
| 949 | H | CF3 | Br | H | OMe | H |
| 950 | H | CF3 | Br | H | Cl | H |
| 951 | H | CF3 | Br | H | Cl | Cl |
| 952 | H | CF3 | Br | H | Br | H |
| 953 | H | CF3 | Br | CF3 | H | H |
| 954 | H | CF3 | Br | H | H | H |
| 955 | H | CF3 | Br | Cl | OH | H |
| 956 | H | CF3 | Br | Br | OH | H |
| 957 | H | CF3 | Br | I | OH | H |

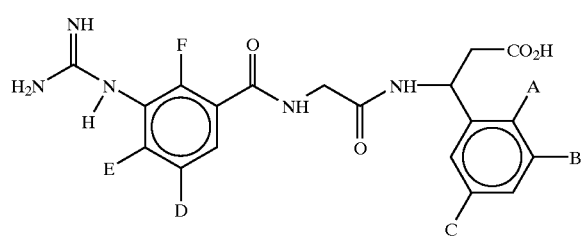

| Example # | A | B | C | D | E | F |
|---|---|---|---|---|---|---|
| 958 | H | CF₃ | I | Br | H | H |
| 959 | H | CF₃ | I | OH | H | H |
| 960 | H | CF₃ | I | NO₂ | H | H |
| 961 | H | CF₃ | I | I | H | H |
| 962 | H | CF₃ | I | Cl | H | H |
| 963 | H | CF₃ | I | Cl | H | Cl |
| 964 | H | CF₃ | I | OMe | H | H |
| 965 | H | CF₃ | I | H | CF₃ | H |
| 966 | H | CF₃ | I | H | OH | H |
| 967 | H | CF₃ | I | H | OMe | H |
| 968 | H | CF₃ | I | H | Cl | H |
| 969 | H | CF₃ | I | H | Cl | Cl |
| 970 | H | CF₃ | I | H | Br | H |
| 971 | H | CF₃ | I | CF₃ | H | H |
| 972 | H | CF₃ | I | H | H | H |
| 973 | H | CF₃ | I | Cl | OH | H |
| 974 | H | CF₃ | I | Br | OH | H |
| 975 | H | CF₃ | I | I | OH | H |

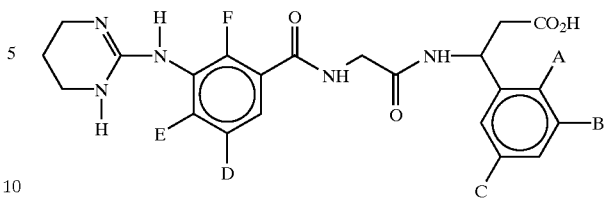

| Example # | A | B | C | D | E | F |
|---|---|---|---|---|---|---|
| 994 | H | CF₃ | I | Br | H | H |
| 995 | H | CF₃ | I | OH | H | H |
| 996 | H | CF₃ | I | NO₂ | H | H |
| 997 | H | CF₃ | I | I | H | H |
| 998 | H | CF₃ | I | Cl | H | H |
| 999 | H | CF₃ | I | Cl | H | Cl |
| 1000 | H | CF₃ | I | OMe | H | H |
| 1001 | H | CF₃ | I | H | CF₃ | H |
| 1002 | H | CF₃ | I | H | OH | H |
| 1003 | H | CF₃ | I | H | OMe | H |
| 1004 | H | CF₃ | I | H | Cl | H |
| 1005 | H | CF₃ | I | H | Cl | Cl |
| 1006 | H | CF₃ | I | H | Br | H |
| 1007 | H | CF₃ | I | CF₃ | H | H |
| 1008 | H | CF₃ | I | H | H | H |
| 1009 | H | CF₃ | I | Cl | OH | H |
| 1010 | H | CF₃ | I | Br | OH | H |
| 1011 | H | CF₃ | I | I | OH | H |

The activity of the compounds of the present invention was tested in the following assays. The results of testing in the assays are tabulated in Table 1.

VITRONECTIN ADHESION ASSAY

Materials

Human vitronectin receptor ($\alpha_v\beta_3$) was purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay was essentially the same as previously reported [Niiya et al., *Blood*, 70:475–483 (1987)]. The purified human vitronectin receptor ($\alpha_v\beta_3$) was diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in $TBS^{+++}$ ($TBS^{+++}$/BSA) were added to block exposed plastic surfaces. Following a 2 hour incubation, the assay plates were washed with $TBS^{+++}$ using

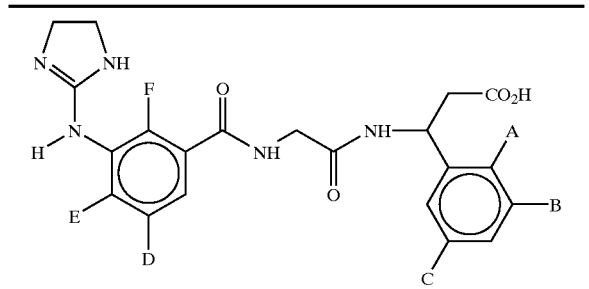

| Example # | A | B | C | D | E | F |
|---|---|---|---|---|---|---|
| 976 | H | CF₃ | I | Br | H | H |
| 977 | H | CF₃ | I | OH | H | H |
| 978 | H | CF₃ | I | NO₂ | H | H |
| 979 | H | CF₃ | I | I | H | H |
| 980 | H | CF₃ | I | Cl | H | H |
| 981 | H | CF₃ | I | Cl | H | Cl |
| 982 | H | CF₃ | I | OMe | H | H |
| 983 | H | CF₃ | I | H | CF₃ | H |
| 984 | H | CF₃ | I | H | OH | H |
| 985 | H | CF₃ | I | H | OMe | H |
| 986 | H | CF₃ | I | H | Cl | H |
| 987 | H | CF₃ | I | H | Cl | Cl |
| 988 | H | CF₃ | I | H | Br | H |
| 989 | H | CF₃ | I | CF₃ | H | H |
| 990 | H | CF₃ | I | H | H | H |
| 991 | H | CF₃ | I | Cl | OH | H |
| 992 | H | CF₃ | I | Br | OH | H |
| 993 | H | CF₃ | I | I | OH | H | a 96 well plate washer. Logarithmic serial dilution of the test compound and controls were made starting at a stock concentration of 2 mM and using 2 nM biotinylated vitronectin in TBS$^{+++}$/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was $1.0 \times 10^{-4}$ M. The competition occurred for two hours after which all wells were washed with a plate washer as before. Affinity purified horseradish peroxidase labeled goat anti-biotin antibody was diluted 1:3000 in TBS$^{+++}$/BSA and 125 µL were added to each well. After 30 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

PURIFIED IIb/IIIa RECEPTOR ASSAY

Materials

Human fibrinogen receptor ($\alpha_{IIb}\beta_3$) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods
Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor ($\alpha_{IIb}\beta_3$) was diluted from stock solutions to 1.0 µg/mL in Tris-buffered saline containing 1.0 mM Ca$^{++}$, Mg$^{++}$, and Mn$^{++}$, pH 7.4 (TBS$^{+++}$). The diluted receptor was immediately transferred to Linbro microtiter plates at 100 µL/well (100 ng receptor/well). The plates were sealed and incubated overnight at 4° C. to allow the receptor to bind to the wells. All remaining steps were at room temperature. The assay plates were emptied and 200 µL of 1% RIA grade BSA in TBS$^{+++}$ (TBS$^{+++}$/BSA) were added to block exposed plastic surfaces. Following a 2 hour incubation, the assay plates were washed with TBS$^{+++}$ using a 96 well plate washer. Logarithmic serial dilution of the test compound and controls were made starting at a stock concentration of 2 mM and using 2 nM biotinylated vitronectin in TBS$^{+++}$/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was $1.0 \times 10^{-4}$ M. The competition occurred for two hours after which all wells were washed with a plate washer as before. Affinity purified horseradish peroxidase labeled goat anti-biotin antibody was diluted 1:3000 in TBS$^{+++}$/BSA and 125 µL were added to each well. After 30 minutes, the plates were washed and incubated with ODD/$H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm, [Robard et al., *Int. Atomic Energy Agency, Vienna*, pp 469 (1977)], plotted on a semi-log scale, and the 15 computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

Human Platelet Rich Plasma Assays

Healthy aspirin free donors were selected from a pool of volunteers. The harvesting of platelet rich plasma and subsequent ADP induced platelet aggregation assays were performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood was transferred to a 50 mL conical polyethylene tube. The blood was centrifuged at room temperature for 12 minutes at 200×g to sediment non-platelet cells. Platelet rich plasma was removed to a polyethylene tube and stored at room temperature until used. Platelet poor plasma was obtained from a second centrifugation of the remaining blood at 2000×g for 15 minutes. Platelet counts are typically 300,000 to 500,000 per microliter. Platelet rich plasma (0.45 mL) was aliquoted into siliconized cuvettes and stirred (1100 rpm) at 37° C. for 1 minute prior to adding 50 uL of pre-diluted test compound. After 1 minute of mixing, aggregation was initiated by the addition of 50 uL of 200 uM ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. All compounds were tested in duplicate and the concentration of half-maximal inhibition (IC$_{50}$) was calculated graphically from the dose response curve for those compounds which exhibited 50% or greater inhibition at the highest concentration tested; otherwise, the IC$_{50}$ is reported as being greater than the highest concentration tested.

M21 MELANOMA CELL ADHESION ASSASY

This assay involves an $\alpha_v\beta_3$-dependent adhesion of M21 human melanoma cells to human fibrinogen-coated plastic tissue culture dishes.

Fibrinogen was purified from human plasma. Fibronectin and plasminogen were eliminated from the preparation by passing the sample over gelatin-sepharose 4B and lysine-sepharose 4B resins, respectively. The fibrinogen is diluted to 10 μg/mL in coating buffer (20 GM Tris-HCl, 150 mM NaCl, pH 7.4). 100 μL of diluted fibrinogen is added to each well of a 96-well Immulon 2 microtiter plate (Dynatech; Chantilly, Va.) and allowed to coat overnight at 4° C. Plates are blocked with 1% BSA (Miles/Pentex; Kankakee, Ill.) in adhesion buffer (Hank's balanced salt solution without Ca$^{++}$ or Mg$^{++}$ [HBSS--], 50 mM Hepes, 1 mg/mL BSA, pH 7.4) for 1 hour at 37° C.

M21 human melanoma cells were provided by Dr. J. Smith, La Jolla Cancer Research Institute. M21 cells are harvested from tissue culture flasks by washing with HBSS-- and adding cell dissociation solution (Sigma) and incubating for 5 minutes at 37° C. Harvested cells are washed 3 times with adhesion assay buffer containing 200 μM Mn$^{++}$. Cells are counted and suspended to a density of 2×10$^6$/mL in adhesion assay buffer containing 200 μM Mn$^{++}$. M21 cells are pre-incubated with antagonists of $\alpha_v\beta_3$ for 30 minutes at room temperature. Following the pre-incubation, the solutions containing a mixture of cells and antagonists are added to each well of the microtiter plate and allowed to bind for 30 minutes at 37° C.

Following adhesion, plates are gently washed 3 times with 200 μL of wash buffer (50 mM Tris-HCl, 150 mM NaCl, pH 7.4) using large bore pipet tips. Plates are briefly blotted dry and 100 μL of cell lysis buffer (50 mM sodium acetate, pH 5.0, 0.5% Triton X-100, 0.3 mg/mL p-nitrophenyl phosphate [Sigma] is added to each well. Plates are incubated for 60 minutes at 37° C. and 50 μL of 1N NaOH is added to stop the reaction. The absorbance of the wells at 412 nM is read using an automatic plate reader.

TABLE I

| Example | AvB3 IC50 (nM) | IIb/IIIa IC50 (nM) | M21 Melanoma Cells IC50 (nM) | Human PRP (μM) |
|---|---|---|---|---|
| 1 | 76.9 | 8350 | | >200 |
| 2 | 0.54 | 51.2 | 0.25 | 200 |
| 3 | 498 | 72900 | 3050 | |
| 4 | 3.17 | 473 | 3.3 | >200 |
| 5 | 227 | 3150 | | |
| 6 | 1.04 | 15.9 | | 80 |
| 8 | 0.69 | 9.83 | 0.28 | 73.3 |
| 10 | 0.92 | 54.4 | 1.82 | >200 |
| 12 | 1.1 | 595 | 9.32 | >200 |
| 14 | 1.62 | 139 | 5.42 | >200 |
| 15 | 10.2 | 3830 | 202 | >200 |
| 17 | 2.66 | 137 | 3.64 | >200 |
| 19 | 303 | 72000 | | |
| 21 | 2.44 | 1910 | | >200 |
| 22 | 1.37 | 280 | | >200 |
| 24 | 0.91 | 58.6 | 12.7 | >200 |
| 26 | 14.2 | 809 | | >200 |
| 27 | 1.53 | 178 | | >200 |
| 30 | 1.75 | 424 | 320 | >200 |
| 34 | 94.3 | 269 | | >200 |
| 35 | 57.1 | 6.21 | | 69.5 |
| 36 | 14.6 | 1580 | 143 | >200 |
| Step B 37 | 0.88 | 13.9 | | >20.0 |
| 39 | 12.2 | 1540 | | >20.0 |
| 40 | 10.3 | 834 | | >200 |
| 41 | 12.1 | 830 | | >200 |
| 42 | 124 | 9800 | | |
| 43 | 28.3 | 1640 | 188 | >200 |
| 44 | 0.33 | 998 | | >20.0 |
| 45 | 0.69 | 39.5 | 2.54 | 167 |
| 46 | 5.34 | 1680 | 147 | >200 |
| 47 | 0.86 | 4270 | 1.18 | >200 |
| 51 | 9730 | >100000 | | |
| 52 | 3.62 | 139 | 11.7 | >200 |
| 53 | 54.6 | 930 | | >200 |
| 54 | 10.7 | 175 | | >200 |
| 55 | 4.77 | 117 | | >200 |
| 56 | 3.12 | 65.3 | 6.87 | >200 |
| 57 | 1340 | 15300 | | |
| 58 | 162 | 5740 | | |
| 59 | 2.35 | 172 | 24.3 | >200 |
| 60(B) | 1.21 | 72.7 | | >200 |
| 60(C) | 0.73 | 16.4 | 0.74 | >200 |
| 61 | 1.76 | 192 | 228 | >200 |
| 62 | 1.42 | 28.4 | | >200 |
| 65 | 9.7 | 170 | 13.8 | >200 |
| 66 | 1.44 | 73.7 | 2.51 | >100 |
| 67 | 2.05 | 92.3 | 4.08 | >200 |
| 68 | 5.48 | 125 | | >200 |
| 69 | 0.92 | 33.6 | 0.95 | >200 |
| 70 | 63 | 3240 | 924 | >200 |
| 71 | 20.4 | 202 | 1040 | >200 |
| 72 | 1.21 | 152 | | >200 |
| 80 | 9.49 | 4.35 | | 30 |
| 82 | 334 | 353 | | |
| 83 | 3.39 | 97.7 | 11 | >200 |
| 84 | 2800 | 246 | | |
| 85 | 6.65 | 8.07 | | |
| 86 | 8.79 | 246 | | >200 |
| 87 | 6.35 | 732 | | >200 |
| 88 | 8.44 | 945 | 52.3 | >200 |
| 89 | 1240 | 9830 | | |
| 94 | 1.16 | 101 | 1 | >200 |
| 95 | 1.43 | 25.4 | | >200 |
| 96 | 1810 | 5400 | | |
| 97 | 26.9 | 1170 | 163 | |
| 98 | 146 | 500 | | |
| 99 | 0.38 | 1.89 | 0.49 | 57.5 |
| 100 | 8560 | >100000 | | |
| 101 | 1680 | 65700 | | |
| 103 | 16.6 | 19100 | | >20.0 |
| 106 | 0.79 | 3140 | 0.81 | >200 |
| 107 | 6400 | 18700 | | |
| 108 | 25.2 | 4870 | | >200 |
| 109 | 575 | >100000 | | |
| 110 | 4.5 | 1860 | 177 | >200 |
| 112 | 284 | 6340 | | |

TABLE I-continued

| Example | AvB3 IC50 (nM) | IIb/IIIa IC50 (nM) | M21 Melanoma Cells IC50 (nM) | Human PRP (μM) |
|---|---|---|---|---|
| 113 | 276 | 100000 | | |
| 114 | 3.26 | 2940 | 200 | >200 |
| 116 | 15500 | >100000 | | |
| 117 | 60.1 | 20100 | | >200 |
| 119 | 3.61 | 11100 | 90.4 | >20.0 |
| 121 | 2840 | >100000 | | |
| 122 | 0.79 | 420 | | >20.0 |
| 123 | 11800 | 85500 | | |
| 124 | 22 | 317 | | >20.0 |
| 126 | 2.48 | 2010 | | >200 |
| 127 | 0.51 | 461 | | >200 |
| 129 | 68.9 | 9460 | | >200 |
| 130 | 47 | 2690 | | >200 |
| 131 | 3.82 | 1760 | | >20.0 |
| 135 | 50700 | >100000 | | |
| 136 | 54.4 | 14200 | | >20.0 |
| 137 | 16.2 | 6500 | | >200 |
| 138 | 36.9 | 5820 | | >200 |
| 139 | 23.8 | 16100 | | >200 |
| 140 | 4590 | >100000 | | |
| 141 | 3.09 | 125 | | >200 |
| 143 | 6700 | >100000 | | |
| 144 | 55.3 | 5830 | | >200 |
| 145 | 2720 | >100000 | | |
| 146 | 14.3 | 879 | | >200 |
| 150 | 5.74 | 631 | | >200 |
| 155 | 5.05 | 81.1 | | >200 |
| 158 | 10.1 | 547 | | |
| 160 | 25.6 | 10400 | | |
| 162 | 4.62 | 1340 | | >200 |
| 166 | 13000 | 45900 | | |
| 168 | 2.29 | 269 | | |
| 171 | 0.35 | 83.2 | | |
| 173 | 0.5 | 17.4 | | |
| 175 | 2.12 | 205 | | |
| 177 | 0.58 | 137 | | >20.0 |
| 179 | 2.72 | 927 | | |
| 181 | 132 | 22800 | | |
| 183 | 1.58 | 258 | | |
| 185 | 1.47 | 166 | | |
| 187 | 1.31 | 264 | | |
| 189 | 4.03 | 1980 | | |
| 191 | 0.49 | 70.3 | | >20.0 |
| 193 | 2.56 | 209 | | >20.0 |
| 195 | 1.09 | 98 | | |
| 198 | 114 | 37800 | | |
| 200 | 0.48 | 1100 | | >200 |
| 201 | 58.1 | 10800 | | |
| 203 | 3.56 | 650 | | |
| 205 | 1.68 | 1240 | | |
| 206 | 78.5 | 22000 | | |
| 207 | 0.9 | 148 | | |
| 208 | 1.15 | 277 | | |
| 209 | 0.83 | 140 | | |
| 210 | 2.62 | 343 | | |
| 211 | 0.47 | 607 | | |
| 212 | 1.93 | 306 | | |
| 213 | 2.93 | 334 | | |
| 214 | 2.35 | 454 | | |
| 215 | 0.41 | 656 | | |
| 216 | 1 | 326 | | |
| 217 | 74.8 | 78900 | | |
| 219 | 2.29 | 253 | | |
| 221 | 70.5 | 23.7 | | >200 |
| 222 | 2.02 | 112 | | >200 |
| 223 | 4.36 | 293 | | >200 |
| 224 | 0.71 | 25.9 | | |
| 225 | 2.76 | 471 | | >20.0 |
| 226 | 7.07 | 2910 | | >200 |
| 227 | 14.1 | 2640 | | >200 |
| 228 | 3.36 | 583 | | >200 |
| 229 | 39.1 | 10600 | | |
| 231 | 2.99 | 424 | | |
| 232 | 19.1 | 12100 | | >200 |
| 233 | 3.31 | 647 | | >200 |
| 234 | 89.3 | 830 | | |
| 235 | 0.54 | 29.9 | | |
| 236 | 0.53 | 1250 | | |
| 237 | 0.57 | 1950 | | |
| 238 | 0.92 | 646 | | |
| 239 | 0.83 | 673 | | |
| 240 | 49400 | 76400 | | |
| 241 | 557 | 17200 | | |
| 242 | 2.28 | 533 | | |
| 243 | 0.35 | 23.6 | | |
| 244 | 17.6 | 4560 | | |
| 245 | 0.96 | 134 | | |
| 246 | 7.24 | 802 | | |
| 247 | 1.24 | 417 | | |
| 248 | 12300 | 21000 | | |
| 249 | 5.31 | 244 | | |
| 251(B) | 3.49 | 280 | | |
| 251(C) | 0.76 | 124 | | |
| 252 | 1.52 | 213 | | |
| 253 | 0.84 | 109 | | |
| 254 | 16.5 | 6910 | | |
| 255 | 28.4 | 6050 | | |
| 256 | 0.58 | 22 | | |
| 257 | 49.2 | 4660 | | |
| 259 | 0.81 | 86.7 | | |
| 260 | 0.74 | 65.3 | | |
| 261 | 6.47 | 4710 | | |
| 262 | 1.24 | 172 | | |
| 263 | 4.19 | 2760 | | |
| 264 | 2.18 | 574 | | |
| 265 | 6.19 | 706 | | |
| 266 | 0.77 | 1810 | | |
| 267 | 131 | 43900 | | |
| 268 | 0.67 | 7430 | | |
| 269 | 209 | 25400 | | |
| 270 | 5.51 | 9160 | | |
| 271 | 29.9 | 4610 | | |
| 272 | 893 | 8210 | | |
| 273 | 12.9 | 4160 | | |
| 274 | 31.1 | 21200 | | |
| 275 | 6.98 | 1200 | | |
| 276 | 1.25 | 111 | | |
| 277 | 1.41 | 198 | | |
| 278 | 0.45 | 150 | | |
| 279 | 7.12 | 637 | | |
| 281 | 4.16 | 11500 | | |
| 282 | 864 | 9770 | | |
| 284 | 195 | 18400 | | |
| 285 | 229 | 3170 | | |
| 286 | 413 | 8090 | | |
| 287 | 49.7 | 41.1 | | |
| 288 | 8.62 | 1060 | | |
| 289 | 0.9 | 621 | | |
| 290 | 1.62 | 1020 | | |
| 291 | 1.24 | 37.4 | | |
| 292 | 3.55 | 337 | | |
| 294 | 173 | 1990 | | |
| 295 | 144 | 4560 | | |
| 296 | 404 | 9450 | | |
| 297 | 89.8 | 3920 | | |
| 298 | 252 | 5560 | | |
| 299 | 109 | 927 | | |
| 362 | 0.84 | 7260 | | |
| 363 | 2.12 | 509 | | |
| 364 | 3.58 | 223 | | |
| 365 | 16.9 | 8470 | | |
| 366 | 0.44 | 91.3 | | |
| 367 | 0.35 | 1540 | | |

What is claimed is:

1. A compound of the formula

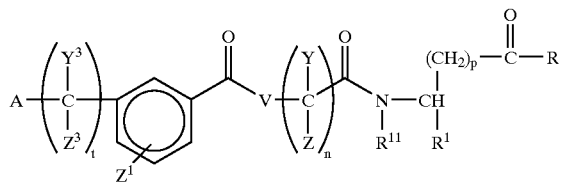

or a pharmaceutically acceptable salt thereof, wherein
A is

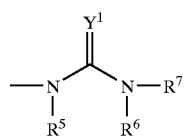

wherein $Y^1$ is N—$R^2$;

$R^2$ taken together with $R^7$ forms a 6 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl;

$R^5$ is selected from the group consisting of H, alkyl, alkenyl, alkynyl, benyl, and phenethyl;

$R^8$ and $R^{8'}$ are independently selected from the group consisting of H, alkyl, alkenyl, alkynyl, aralkyl, amino, alkylamino, hydroxy, alkoxy, arylamino, amido, alkylcarbonyl, arylcarbonyl, alkoxycarbonyl, aryloxycarbonyl, haloalkylcarbonyl, aryloxy, haloalkoxycarbonyl, alkylthiocarbonyl, arylthiocarbonyl, acyloxymethoxycarbonyl, cycloalkyl, bicycloalkyl, aryl, acyl, benzolyl, alkyl optionally substituted with one or more substituent selected from lower alkyl, halogen, hydroxy, haloalkyl, cyano, nitro, carboxyl, derivatives, amino, alkoxy, thio, alkylthio, sulfonyl, aryl, arylkyl, aryl optionally substituted with one or more substituent selected from halogen, haloalkyl, lower alkyl, alcoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, aryl optionally substituted with one or more substituent selected from halogen, haloalkyl, lower alkyl, alkoxy, alkylthio, haloalkylthio, thio hydroxy, cyano, nitro, carboxyl derivatives aryloxy, amido, acylamino, amino, alkylamino, dialkylamino, trifluoroalkyoxy, trifluoromethylsulfonyl, alkylsulfonyl, sulfonic acid, sulfonamide, aryl, fused aryl, $SO_2R^{10}$ wherein $R^{10}$ is selected from the group consisting of alkyl and, aryl and

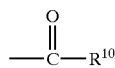

wherein $R^{10}$ is selected from the group consisting of alkyl and aryl;

$Z^1$ is one or more substituent selected from the group consisting of H; alkyl; hydroxy; alkoxy; aryloxy; halogen; haloalkyl; haloalkoxy; nitro; amino; alkylamino; acylamino; dialkylamino; cyano; alkylthio; alkylsulfonyl; carboxyl derivatives; trihaloacetamide; acetamide; aryl; fused aryl; cycloalkyl; thio;

V is selected from the group consisting of —N—($R^6$)— wherein $R^6$ is selected from the group consisting of H; lower alkyl; cycloalkyl; aralkyl; and aryl;

Y, $Y^3$, Z and $Z^3$ are independently selected from the group consisting of hydrogen; alkyl; aryl; and cycloalkyl; or Y and Z taken together form a cycloalkyl; or $Y^3$ and $Z^3$ taken together form a cycloalkyl;

n is an integer 1, 2, or 3;

t is 0;

p is an integer 0, 1, 2, or 3;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; polyalkylethers; alkylamido; alkyl N,N-dialkylamido; pivaloyloxymethyl; and in the case of the free acid, all pharmaceutically acceptable salts thereof;

$R^1$ is selected from the group consisting of hydrogen; alkyl; alkenyl; alkynyl; aryl; carboxyl derivatives; haloalkyl;

alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, alkylcarbonyl, haloalkylcarbonyl, and arylcarbonyl;

aryl optionally substituted in one or more positions with halo, haloalkyl, alkyl, alkoxy, aryloxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, and

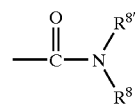

wherein $R^{8'1\ and\ R8}$ are as defined above;
and $R^{11}$ is selected from the group consisting of H, alkyl, aralkyl, alkenyl, alkynyl, haloalkyl or haloalkynyl.

2. A compound according to claim 1 wherein A is

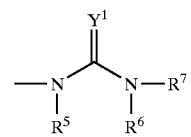

wherein $Y^1$ is N—$R^2$; $R^2$ taken together with $R^7$ forms a 4–12 membered ring; and $R^5$ and $R^8$ are independently selected from the group consisting of H, alkyl, alkenyl, alkynyl, cycloalkyl, bicycloalkyl substituted alkyl, arylalkyl, aryloxy, hydroxy, alkoxy, amino, alkylamino, arylamino, amide, alkylcarbonyl, arylcarbonyl, alkoxycarbonyl, aryloxycarbonyl, haloalkylcarbonyl, haloalkoxycarbonyl, alkylthiocarbonyl, arylthiocarbonyl, acyloxymethoxycarbonyl, substituted phenyl, arylacyl, monocyclic and bicyclic heterocycles, monocyclic and bicyclic heterocyclicalkyl and —SO$_2$R$^{10}$ wherein R$^{10}$ is selected from the group consisting of alkyl, amino and aryl which are all optionally substituted with one or more substituent selected from the group consisting of acylamino, amino, carbonyl cyano, nitro, alkoxy, halo, alkyl, trifluoroalkyl, amido, alkylaminosulfonyl, alkysulfonyl, alkylsulfonylamino, alkylamino, dialkylamino, aryloxy, thio, trifluoromethylthio, trifluoroalkoxy, and trifluoromethylsulfonyl or —NR$^7$ and R$^8$ taken together form a 4–12 membered ring wherein said ring optionally contains a heteroatom selected from the group consisting of O, N, and S wherein said ring is optionally substituted.

3. A compound according to claim 2 wherein
V is —N(R$^6$)— wherein R$^6$ is selected from the group consisting of H and lower alkyl;
n is 1;
t is 0; and
p is 1.

4. A pharmaceutical composition comprising a therapeutically effective amount of a compound of the formula

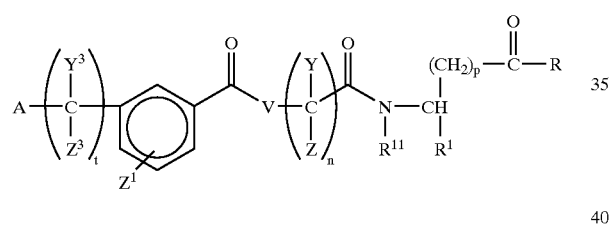

or a pharmaceutically acceptable salt thereof, wherein A is

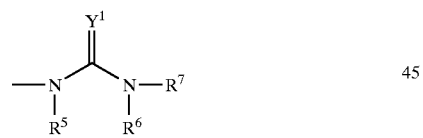

wherein Y$^1$ is N—R$^2$;
R$^2$ taken together with R$^7$ forms a 6 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl;
R$^5$ is selected from the group consisting of H, alkyl, alkenyl, alkynyl, benyl, and phenethyl;
R$^8$ and R$^{8"}$ are independently selected from the group consisting of H, alkyl, alkenyl, alkynyl, aralkyl, amino, alkylamino, hydroxy, alkoxy, arylamino, amido, alkylcarbonyl, arylcarbonyl, alkoxycarbonyl, aryloxycarbonyl, haloalkylcarbonyl, aryloxy, haloalkoxycarbonyl, alkylthiocarbonyl, arylthiocarbonyl, acyloxymethoxycarbonyl, cycloalkyl, bicycloalkyl, aryl, acyl, benzolyl, alkyl optionally substituted with one or more substituent selected from lower alkyl, halogen, hydroxy, haloalkyl, cyano, nitro, carboxyl, derivatives, amino, alkoxy, thio, alkylthio, sulfonyl, aryl, arylkyl, aryl optionally substituted with one or more substituent selected from halogen, haloalkyl, lower alkyl, alcoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, aryl optionally substituted with one or more substituent selected from halogen, haloalkyl, lower alkyl alkoxy, alkylthio, haloalkylthio, thio hydroxy, cyano, nitro, carboxyl derivatives aryloxy, amido, acylamino, amino, alkylamino, dialkylamino, trifluoroalkyoxy, trifluoromethylsulfonyl, alkylsulfonyl, sulfonic acid, sulfonamide, aryl, fused aryl, SO$_2$R$^{10}$ wherein R$^{10}$ is selected from the group consisting of alkyl and, aryl and

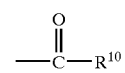

wherein R$^{10}$ is selected from the group consisting of alkyl and aryl;
Z$^1$ is one or more substituent selected from the group consisting of H; alkyl; hydroxy; alkoxy; aryloxy; halogen; haloalkyl; haloalkoxy; nitro; amino; alkylamino; acylamino; dialkylamino; cyano; alkylthio; alkylsulfonyl; carboxyl derivatives; trihaloacetamide; acetamide; aryl; fused aryl; cycloalkyl; thio;
V is selected from the group consisting of —N—(R$^6$— wherein R$^6$ is selected from the group consisting of H; lower alkyl; cycloalkyl; aralkyl; and aryl;
Y, Y$^3$, Z and Z$^3$ are independently selected from the group consisting of hydrogen; alkyl; aryl; and cycloalkyl; or Y and Z taken together form a cycloalkyl; or Y$^3$ and Z$^3$ taken together form a cycloalkyl;
n is an integer 1, 2, or 3;
t is 0;
p is an integer 0, 1, 2, or 3;
R is X—R$^3$ wherein X is selected from the group consisting of O, S and NR$^4$, wherein R$^3$ and R$^4$ are independently selected from the group consisting of hydrogen; alkyl; alkenyl; alkynyl; haloalkyl; aryl; arylalkyl; polyalkylethers; alkylamido; alkyl N,N-dialkylamido; pivaloyloxymethyl; and in the case of the free acid, all pharmaceutically acceptable salts thereof;
R$^1$ is selected from the group consisting of hydrogen; alkyl; alkenyl; alkynyl; aryl; carboxyl derivatives; haloalkyl; alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, alkylcarbonyl, haloalkylcarbonyl, and arylcarbonyl;

aryl optionally substituted in one or more positions with halo, haloalkyl, alkyl, alkoxy, aryloxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, and

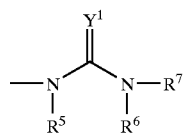

wherein $R^{8"}$ and $R^8$ are as defined above; and $R^{11}$ is selected from the group consisting of H, alkyl, aralkyl, alkenyl, alkynyl, haloalkyl or haloalkynyl and a pharmaceutically acceptable carrier.

5. A pharmaceutical composition according to claim 4 wherein
A is

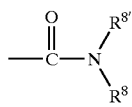

wherein $Y^1$ is N—$R^2$ taken together with $R^7$ forms a 4–12 membered ring; and $R^8$ is selected from the group consisting of H, alkyl, alkenyl, alkynyl, cycloalkyl, bicycloalkyl substituted alkyl, arylalkyl, aryloxy, hydroxy, alkoxy, amino, alkylamino, arylamino, amido, alkylcarbonyl, arylcarbonyl, alkoxycarbonyl, aryloxycarbonyl, haloalkylcarbonyl, haloalkoxycarbonyl, alkylthiocarbonyl, arylthiocarbonyl, acyloxymethoxycarbonyl, substituted phenyl, arylacyl, monocyclic and bicyclic heterocycles, monocyclic and bicyclic heterocyclicalkyl and —$SO_2R^{10}$ wherein $R^{10}$ is selected from the group consisting of alkyl, amino and aryl which are all optionally substituted with one or more substituent selected from the group consisting of acylamino, amino, carbonyl cyano, nitro, alkoxy, halo, alkyl, trifluoroalkyl, amido, alkylaminosulfonyl, alkylsulfonyl, alkysulfonylamino, alkylamino, dialkylamino, aryloxy, thio, trifluoromethylthio, trifluoroalkoxy, and trifluoromethylsulfonyl or —$NR^7$ and $R^8$ taken together form a 4–12 membered ring wherein said ring optionally contains a heteroatom selected from the group consisting of O, N, and S wherein said ring is optionally substituted.

6. A pharmaceutical composition according to claim 5 wherein

V is —N($R^6$)— wherein $R^6$ is selected from the group consisting of H and lower alkyl;

n is 1;

t is 0; and p is 1.

7. A method for treating conditions mediated by the $\alpha_v\beta_3$ integrin in a mammal in need of such treatment comprising administering an effective $\alpha_v\beta_3$ inhibiting amount of a compound of the formula

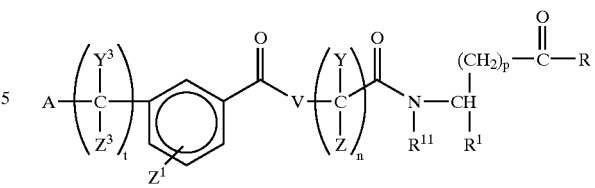

or a pharmaceutically acceptable salt thereof, wherein A is

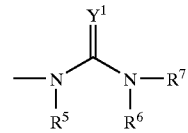

wherein $Y^1$ is N—$R^2$;

$R^2$ taken together with $R^7$ forms a 6 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl;

$R^5$ is selected from the group consisting of H, alkyl, alkenyl, alkynyl, benyl, and phenethyl;

$R^8$ and $R^{8"}$ are independently selected from the group consisting of H, alkyl, alkenyl, alkynyl, aralkyl, amino, alkylamino, hydroxy, alkoxy, arylamino, amido, alkylcarbonyl, arylcarbonyl, alkoxycarbonyl, aryloxycarbonyl, haloalkylcarbonyl, aryloxy, haloalkoxycarbonyl, alkylthiocarbonyl, arylthiocarbonyl, acyloxymethoxycarbonyl, cycloalkyl, bicycloalkyl, aryl, acyl, benzolyl, alkyl optionally substituted with one or more substituent selected from lower alkyl, halogen, hydroxy, haloalkyl, cyano, nitro, carboxyl, derivatives, amino, alkoxy, thio, alkylthio, sulfonyl, aryl, arylkyl, aryl optionally substituted with one or more substituent selected from halogen, haloalkyl, lower alkyl, alcoxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, aryl optionally substituted with one or more substituent selected from halogen, haloalkyl, lower alkyl, alkoxy, alkylthio, haloalkylthio, thio hydroxy, cyano, nitro, carboxyl derivatives aryloxy, amido, acylamino, amino, alkylamino, dialkylamino, trifluoroalkyoxy, trifluoromethylsulfonyl, alkylsulfonyl, sulfonic acid, sulfonamide, aryl, fused aryl, $SO_2R^{10}$ wherein $R^{10}$ is selected from the group consisting of alkyl and, aryl and

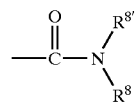

wherein $R^{10}$ is selected from the group consisting of alkyl and aryl;

$Z^1$ is one or more substituent selected from the group consisting of H; alkyl; hydroxy; alkoxy, aryloxy; halogen; haloalkyl; haloalkoxy; nitro; amino; alkylamino;

acylamino; dialkylamino; cyano; alkylthio; alkylsulfonyl; carboxyl derivatives; trihaloacetamide; acetamide; aryl; fused aryl; cycloalkyl; thio;

V is selected from the group consisting of —N—(R⁶)— wherein R⁶ is selected from the group consisting of H; lower alkyl; cycloalkyl; aralkyl; and aryl;

Y, Y³, Z and Z³ are independently selected from the group consisting of hydrogen; alkyl; aryl; and cycloalkyl; or Y and Z taken together form a cycloalkyl; or Y³ and Z³ taken together form a cycloalkyl;

n is an integer 1, 2, or 3;

t is 0;

p is an integer 0, 1, 2, or 3;

R is X—R³ wherein X is selected from the group consisting of O, S and NR⁴, wherein R³ and R⁴ are independently selected from the group consisting of hydrogen; alkyl; alkenyl; alkynyl; haloalkyl; aryl; arylalkyl; polyalkylethers; alkylamido; alkyl N,N-dialkylamido; pivaloyloxymethyl; and in the case of the free acid, all pharmaceutically acceptable salts thereof;

R¹ is selected from the group consisting of hydrogen; alkyl; alkenyl; alkynyl; aryl; carboxyl derivatives; haloalkyl; alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, alkylcarbonyl, haloalkylcarbonyl, and arylcarbonyl;

aryl optionally substituted in one or more positions with halo, haloalkyl, alkyl, alkoxy, aryloxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, and

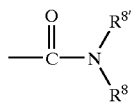

wherein R⁸" and R⁸ are as defined above; and

R¹¹ is selected from the group consisting of H, alkyl, aralkyl, alkenyl, alkynyl, haloalkyl or haloalkynyl.

8. A method according to claim 7 wherein the condition treated is tumor metastasis.

9. A method according to claim 7 wherein the condition treated is solid tumor growth.

10. A method according to claim 7 wherein the condition treated is angiogenesis.

11. A method according to claim 7 wherein the condition treated is osteoporosis.

12. A method according to claim 7 wherein the condition treated is humoral hypercalcemia of malignancy.

13. A method according to claim 7 wherein the condition treated is smooth muscle cell migration.

14. A method according to claim 13 wherein restenosis is inhibited.

15. A method according to claim 7 wherein the condition treated is reumatoid arthritis.

16. A compound according to claim 3, selected from the group consisting of (±)ethyl 3,5-dichloro-β-[[2-[[[3-[(1,4,5,6-tetrahydropyrimidin-2-yl)amino]phenyl]carbonyl]amino]acetyl]amino]benzenepropanoate;

(±)3,5-dichloro-β-[[2-[[[3-[(1,4,5,6-tetrahydropyrimidin-2-yl)amino]phenyl]carbonyl]amino]acetyl]amino]benzenepropanoic acid;

(±)3,5-dichloro-β-[[2-[[[3-[(1,4,5,6-tetrahydropyrimidin-2-yl)amino]phenyl]carbonyl]amino]acetyl]amino]benzenepropanoic acid;

(±)3-bromo-5-chloro-β-[[2-[[[3-[(1,4,5,6-tetrahydropyrimidin-2-yl)amino]phenyl]carbonyl]amino]acetyl]amino]benzenepropanoic acid;

(±)[2-[2-[2-(2-hydroxyethoxy)ethoxy]ethoxy]ethyl]3,5-dichloro-β-[[2-[[[3-[(1,4,5,6-tetrahydropyrimidin-2-yl)amino]phenyl]carbonyl]amino]acetyl]amino]benzenepropanoate;

(±)[2-[2-(2-hydroxyethoxy)ethoxy]ethoxy]ethyl]3,5-dichloro-β-[[2-[[[3-[(1,4,5,6-tetrahydropyrimidin-2-yl)amino]phenyl]carbonyl]amino]acetyl]amino]benzenepropanoate;

(±)3-bromo-5-chloro-2-hydroxy-β-[[2-[[[3-[(1,4,5,6-tetrahydropyrimidin-2-yl)amino]phenyl]carbonyl]amino]acetyl]amino]benzenepropanoic acid;

ethyl(±)3-bromo-5-chloro-2-hydroxy-β-[[2-[[[3-[(1,4,5,6-tetrahydropyrimidin-2-yl)amino]phenyl]carbonyl]amino]acetyl]amino]benzenepropanoate;

(±)3,5-dichloro-2-hydroxy-β-[[2-[[[3-[(1,4,5,6-tetrahydropyrimidin-2-yl)amino]phenyl]carbonyl]amino]acetyl]amino]benzenepropanoic acid, (±)ethyl 3,5-dichloro-β-[[2-[[[3-[(1,4,5,6-tetrahydro-5,5-dimethylpyrimidin-2-yl)amino]phenyl]carbonyl]amino]acetyl]amino]benzenepropanoate;

(±)3,5-dichloro-β-[[2-[[[3-[(1,4,5,6-tetrahydro-5,5-dimethylpyrimidin-2-yl)amino]phenyl]carbonyl]amino]acetyl]amino]benzenepropanoic acid;

Ethyl(±)3,5-dichloro-2-hydroxy-β-[[2-[[[3-[1,4,5,6-tetrahydro-5,5-dimethylpyrimidin-2-yl)amino]phenyl]carbonyl]amino]acetyl]amino]benzenepropanoate;

(±)3-bromo-5-dichloro-2-hydroxy-β-[[2-[[[3-[(1,4,5,6-tetrahydro-5,5-dimethylpyrimidin-2-yl)amino]phenyl]carbonyl]amino]acetyl]amino]benzenepropanoic acid and ethyl(±)3-bromo-5-dichloro-2-hydroxy-β-[[2-[[[3-[(1,4,5,6-tetrahydro-5,5-dimethylpyrimidin-2-yl)amino]phenyl]carbonyl]amino]acetyl]amino]benzenepropanoate.

17. A compound according to claim 1 of the formula

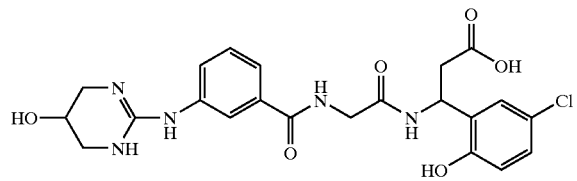

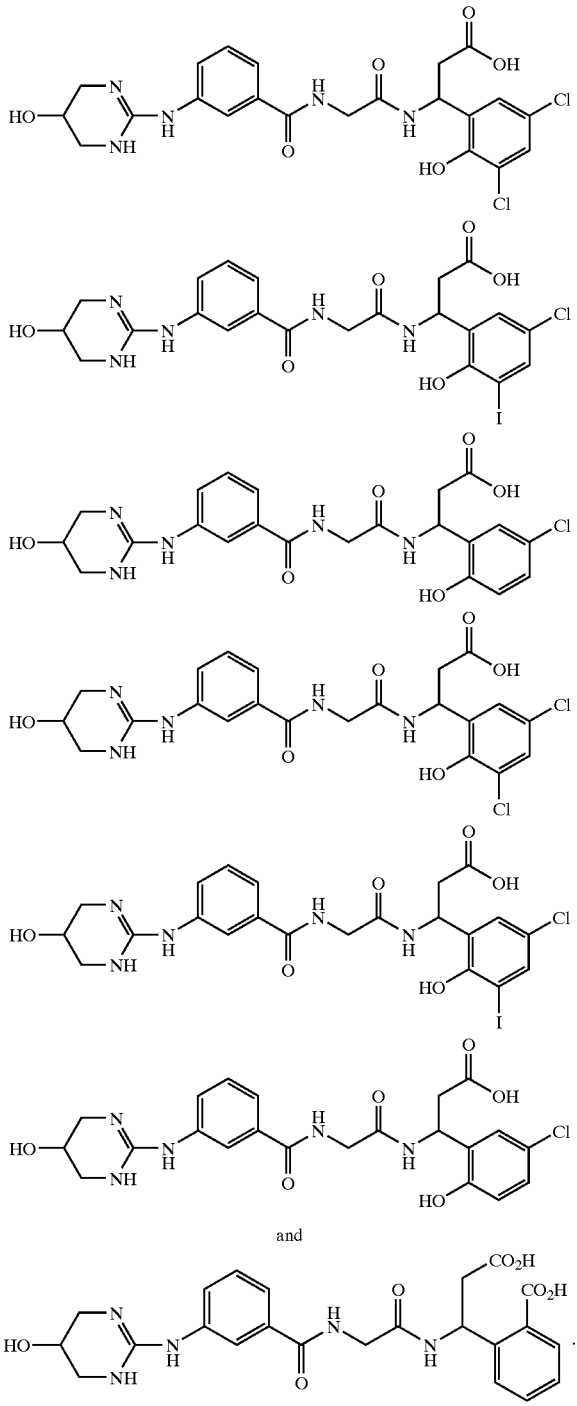

and

18. A pharmaceutical composition according to claim 6 wherein compound is selected from the group consisting of (±)ethyl 3,5-dichloro-β-[[2-[[[3-[(1,4,5,6-tetrahydropyrimidin-2-yl)amino]phenyl]carbonyl]amino]acetyl]amino]benzenepropanoate;

(±)3,5-dichloro-β-[[2-[[[3-[(1,4,5,6-tetrahydropyrimidin-2-yl)amino]phenyl]carbonyl]amino]acetyl]amino]benzenepropanoic acid;

(±)3,5-dibromo-β-[[2-[[[3-[(1,4,5,6-tetrahydropyrimidin-2-yl)amino]phenyl]carbonyl]amino]acetyl]amino]benzenepropanoic acid;

(±)3-bromo 5-chloro β-[[2-[[[3-[(1,4,5,6-tetrahydropyrimidin-2-yl)amino]phenyl]carbonyl]amino]acetyl]amino]benzenepropanoic acid;

(±)[2-[2-[2-(2-hydroxyethoxy)ethoxy]ethoxy]ethyl]3,5-dichloro-β-[[2-[[[3-[(1,4,5,6-tetrahydropyrimidin-2-yl)amino]phenyl]carbonyl]amino]acetyl]amino]benzenepropanoate;

(±)[2-[2-(2-hydroxyethoxy)ethoxy]ethoxy]ethyl]3,5-dichloro-β-[[2-[[[3-[(1,4,5,6-tetrahydropyrimidin-2-yl)amino]phenyl]carbonyl]amino]acetyl]amino]benzenepropanoate;

(±)3-bromo-5-chloro-2-hydroxy-β-[[2-[[[3-[(1,4,5,6-tetrahydropyrimidin-2-yl)amino]phenyl]carbonyl]amino]acetyl]amino]benzenepropanoic acid;

ethyl(±)3-bromo-5-chloro-2-hydroxy-β-[[2-[[[3-[(1,4,5,6-tetrahydropyrimidin-2-yl)amino]phenyl]carbonyl]amino]acetyl]amino]benzenepropanoate;

(±)3,5-dichloro-2-hydroxy-β-[[2-[[[3-[(1,4,5,6-tetrahydropyrimidin-2-yl)amino]phenyl]carbonyl]amino]acetyl]amino]benzenepropanoic acid;

(±)ethyl 3,5-dichloro-β-[[2-[[[3-[(1,4,5,6-tetrahydro-5,5-dimethylpyrimidin-2-yl)amino]phenyl]carbonyl]amino]acetyl]amino]benzenepropanoate;

(±)3,5-dichloro-β-[[2-[[[3-[(1,4,5,6-tetrahydro-5,5-dimethylpyrimidin-2-yl)amino]phenyl]carbonyl]amino]acetyl]amino]benzenepropanoic acid.

19. A pharmaceutical composition according to claim 4 wherein compound is selected from the group consisting of

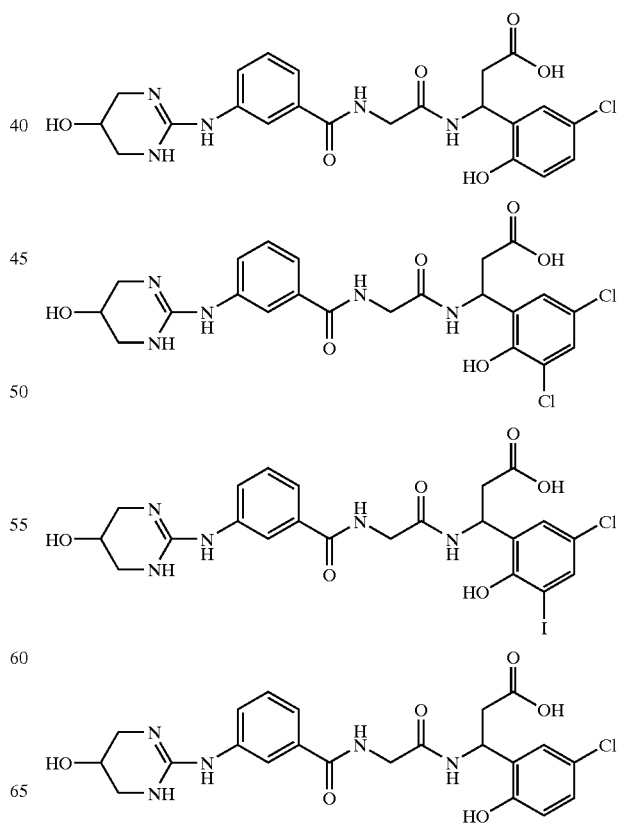

-continued

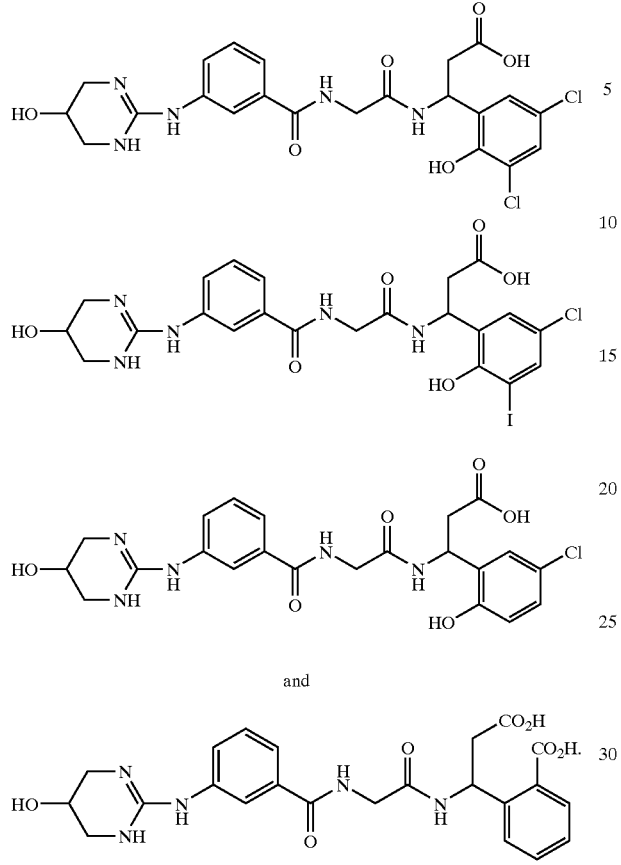

and

20. A method according to claim 7 wherein the compound is selected from
(±)ethyl 3,5-dichloro-β-[[2-[[[3-[(1,4,5,6-tetrahydropyrimidin-2-yl)amino]phenyl]carbonyl]amino]acetyl]amino]benzenepropanoate;
(±)3,5-dichloro-β-[[2-[[[3-[(1,4,5,6-tetrahydropyrimidin-2-yl)amino]phenyl]carbonyl]amino]acetyl]amino]benzenepropanoic acid;
(±)3,5-dibromo-β-[[2-[[[3-[(1,4,5,6-tetrahydropyrimidin-2-yl)amino]phenyl]carbonyl]amino]acetyl]amino]benzenepropanoic acid;
(±)3-bromo-5-chloro-β-[[2-[[[3-[(1,4,5,6-tetrahydropyrimidin-2-yl)amino]phenyl]carbonyl]amino]acetyl]amino]benzenepropanoic acid;
(±)[2-[2-[2-(2-hydroxyethoxy)ethoxy]ethoxy]ethyl]3,5-dichloro-β-[[2-[[[3-[(1,4,5,6-tetrahydropyrimidin-2-yl)amino]phenyl]carbonyl]amino]acetyl]amino]benzenepropanoate;
(±)[2-[2-(2-hydroxyethoxy)ethoxy]ethyl]3,5-dichloro-β-[[2-[[[3-[(1,4,5,6-tetrahydropyrimidin-2-yl)amino]phenyl]carbonyl]amino]acetyl]amino]benzenepropanoate;
(±)3-bromo-5-chloro-2-hydroxy-β-[[2-[[[3-[(1,4,5,6-tetrahydropyrimidin-2-yl)amino]phenyl]carbonyl]amino]acetyl]amino]-benzenepropanoic acid;
ethyl(±)3-bromo-5-chloro-2-hydroxy-β-[[2-[[[3-[(1,4,5,6-tetrahydropyrimidin-2-yl)amino]phenyl]carbonyl]amino]-acetyl]amino]benzenepropanoate;
(±)3,5-dichloro-2-hydroxy-β-[[2-[[[3-[(1,4,5,6-tetrahydropyrimidin-2-yl)amino]phenyl]carbonyl]amino]acetyl]amino]benzenepropanoic acid;
(±)ethyl 3,5-dichloro-β-[[2-[[[3-[(1,4,5,6-tetrahydro-5,5-dimethylpyrimidin-2-yl)amino]phenyl]carbonyl]amino]acetyl]amino]benzenepropanoate:
(±)3,5-dichloro-β-[[2-[[[3-[(1,4,5,6-tetrahydro-5,5-dimethylpyrimidin-2-yl)amino]phenyl]carbonyl]-amino]acetyl]amino]benzenepropanoic acid;
ethyl(±)3,5-dichloro-2-hydroxy-β-[[2-[[[3-[(1,4,5,6-tetrahydro-5,5-dimethylpyrimidin-2-yl)amino]phenyl]carbonyl]amino]acetyl]amino]benzenepropanoate;
(±)3-bromo-5-dichloro-2-hydroxy-β[[2-[[[3-[(1,4,5,6-tetrahydro-5,5-dimethylpyrimidin-2-yl)amino]phenyl]carbonyl]amino]acetyl]amino]benzenepropanoic acid; and
ethyl(±)3-bromo-5-dichloro-2-hydroxy-β-[[2-[[[3-[(1,4,5,6-tetrahydro-5,5-dimethylpyrimidin-2-yl)amino]phenyl]carbonyl]amino]acetyl]-amino]benzenepropanoate.

* * * * *